US007888477B2

(12) United States Patent
Bangur et al.

(10) Patent No.: US 7,888,477 B2
(45) Date of Patent: *Feb. 15, 2011

(54) OVARIAN CANCER-ASSOCIATED ANTIBODIES AND KITS

(75) Inventors: Chaitanya S Bangur, Seattle, WA (US); Marc W Retter, Carnation, WA (US); Gary R Fanger, Mill Creek, WA (US); Paul Hill, Everett, WA (US)

(73) Assignee: Corixa Corporation, Seattle, WA (US)

( * ) Notice: Subject to any disclaimer, the term of this patent is extended or adjusted under 35 U.S.C. 154(b) by 363 days.

This patent is subject to a terminal disclaimer.

(21) Appl. No.: 10/860,790

(22) Filed: Jun. 2, 2004

(65) Prior Publication Data

US 2005/0031634 A1 Feb. 10, 2005

Related U.S. Application Data

(63) Continuation of application No. 10/198,053, filed on Jul. 17, 2002, now Pat. No. 6,858,710, which is a continuation-in-part of application No. 09/907,969, filed on Jul. 17, 2001, now abandoned, which is a continuation-in-part of application No. 09/884,441, filed on Jun. 18, 2001, now abandoned, which is a continuation-in-part of application No. 09/827,271, filed on Apr. 4, 2001, now Pat. No. 6,962,980, which is a continuation-in-part of application No. 09/667,857, filed on Sep. 20, 2000, now Pat. No. 6,699,664, which is a continuation-in-part of application No. 09/636,801, filed on Aug. 10, 2000, now Pat. No. 7,202,334, which is a continuation-in-part of application No. 09/617,747, filed on Jul. 17, 2000, now abandoned.

(51) Int. Cl.
C07K 16/00 (2006.01)
C12P 21/08 (2006.01)

(52) U.S. Cl. .............. 530/387.1; 530/387.7; 530/388.1; 435/7; 435/230

(58) Field of Classification Search ........................ None
See application file for complete search history.

(56) References Cited

U.S. PATENT DOCUMENTS

| 5,480,795 | A | 1/1996 | Kurihara et al. | ............ 435/91.4 |
| 6,284,487 | B1 | 9/2001 | Stahl et al. | ................. 435/69.1 |

FOREIGN PATENT DOCUMENTS

| EP | 1033401 A2 | 9/2000 |
| WO | WO 99/25877 | 5/1999 |
| WO | WO 99/31117 | 6/1999 |
| WO | WO 99/63088 | 12/1999 |
| WO | WO 00/12758 | 3/2000 |
| WO | WO 00/36107 | 6/2000 |
| WO | WO 00/55629 | 9/2000 |
| WO | WO 00/73454 | 12/2000 |
| WO | WO 00/76531 | 12/2000 |
| WO | WO 01/16318 | 3/2001 |
| WO | WO 01/18542 | 3/2001 |
| WO | WO 01/40269 | 6/2001 |
| WO | WO 01/57272 | 8/2001 |
| WO | WO 01/94641 | 12/2001 |
| WO | WO 02/02587 | 1/2002 |
| WO | WO 02/02624 | 1/2002 |
| WO | WO 02/10187 | 2/2002 |
| WO | WO 02/16429 | 2/2002 |
| WO | WO 02/16581 | 2/2002 |

OTHER PUBLICATIONS

Bookman et al., "Biological therapy of ovarian cancer: Current directions," *Seminars in Oncology*, 25(3):381-396, 1998.
Frankel, A.E. et al., "Targeted Toxins," *Clinical Cancer Research* 6 : 326-334, Feb. 2000.
GenBank Database, Accession No. AA075632, Dec. 23, 1997. Available at www.ncbi.nlm.nih.gov/entrz.
GenBank Database, Accession No. AA404225, Aug. 8, 1997. Available at www.ncbi.nlm.nih.gov/entrz.
GenBank Database, Accession No. U97694, Aug. 27, 1997. Available at www.ncbi.nlm.nih.gov/entrz.
Geneseq Database (Thomson Derwent), Accession No. AAT23436, Aug. 8, 1996.
Gillespie et al., "Mage, Bage and Gage: Tumour antigen expression in benign and malignant ovarian tissue," *British Journal of Cancer*, 78(6):816-821, Sep. 1998.
Heller et al., "Discovery and analysis of inflammatory disease-related genes using cDNA microarrays," *Proc. Natl. Acad. Sci. USA* 94:2150-2155, Mar. 1997.
Hovig, E. et al., "CA 125: The End of the Beginning," *Tumor Biology* 22: 345-347, 2001.
Ishikawa et al., "Prediction of the coding sequence of unidentified human genes. The complete sequence of 100 new cDNA clones from brain which can code for large proteins in vitro," *DNA Res.*, 5:169-176, 1998.
Jin et al., "Human T cell leukemia virus type 1 oncoprotein tax targets the human mitotic checkpoint protein MAD1," *Cell* 93:81-91, Apr. 3, 1998.
Köhler et al., "Immunotherapy of Ovarian Carcinoma with the Monoclonal Anti-Idiotype Antibody ACA125—Results of the Phase LB Study," *Gebrutshilfe and Fraenheilkunde*, 58(4):180-186, Apr. 1998 + (English Abstract).
Ma et al., "Use of encapsulated single chain antibodies for induction of anti-idiotypic humoral and cellular immune responses," *Journal of Pharmaceutical Sciences*, 87(11):1375-1378, Nov. 1998.

(Continued)

*Primary Examiner*—Shubo (Joe) Zhou
(74) *Attorney, Agent, or Firm*—Seed IP Law Group PLLC

(57) ABSTRACT

Compositions and methods for the therapy and diagnosis of cancer, particularly ovarian cancer, are disclosed. Illustrative compositions comprise one or more ovarian tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly ovarian cancer.

9 Claims, 101 Drawing Sheets

OTHER PUBLICATIONS

O'Brien, T.J. et al., "The CA 125 Gene: A Newly Discovered Extension of the Glycosylated N-Terminal Domain Doubles the Size of This Extracellular Superstructure," *Tumor Biology* 23: 154-169, 2002.

O'Brien, T.J. et al., "The CA 125 Gene: An Extracellular Superstructure Dominated by Repeat Sequences," *Tumor Biology* 22: 348-366, 2001.

Parker et al., "Scheme for ranking potential HLA-A2 binding peptides based on independent binding of individual peptide sidechains," *The Journal of Immunology* 152(1):163-175, Jan. 1, 1994.

Peoples et al., "Ovarian cancer-associated lymphocyte recognition of folate binding protein peptides," *Annals of Surgical Oncology*, 5(8):743-750, Dec. 1998.

Schena et al., "Parallel human genome analysis: Microarray-based expression monitoring of 1000 genes," *Proc. Natl. Acad. Sci.*, 93:10614-10619, Oct. 1996.

Schummer, M. et al., "Comparative hybridization of an array of 21 500 ovarian cDNAs for the discovery of genes overexpressed in ovarian carcinomas," *Gene* 238: 375-385, 1999.

Whitehouse, C. et al., "NBR1 interacts with fasciculation and elongation protein zeta-1 (FEZ1) and calcium and integrin binding protein (CIB) and shows developmentally restricted expression in the neural tube," *Eur. J. Biochem.* 269: 538-545, 2002.

Yin and Lloyd, "Molecular Cloning of the CA125 Ovarian Cancer Antigen. Identification as a new mucin, MUC16," *Journal of Biological Chemistry* 276 (29): 27371-27375, Jul. 20, 2001.

Yin, B.W.T. et al., "Ovarian cancer antigen CA125 is encoded by the *MUC16* mucin gene," *International Journal of Cancer* 98: 737-740, 2002.

Durbaka et al., "B7S1, a Novel B7 Family Member That Negatively Regulates T Cell Activation," *Immunity* 18(6): 863-873, Jun. 1, 2003.

Salceda et al., "The Immunomodulatory Protein B7-H4 is Overexpressed in Breast and Ovarian Cancers and Promotes Epithelial Cell Transformation," *Experimental Cell Research* 306(1): 128-141, May 15, 2005.

Sica et al., "B7-H4, a Molecule of the B7 Family, Negatively Regulates T Cell Immunity," *Immunity* 18(6): 849-861, Jun. 1, 2003.

Zang et al., "B7X: A Widely Expressed B7 Family Member That Inhibits T Cell Activation," *Proceedings of the Nat'l Acad. of Sciences* 100(18): 10388-10392, Sep. 2, 2003.

11729.1 contg (SEQ ID NO:1)

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC

11729-45.21.21.cons1 (SEQ ID NO:2)

TAGGATGTGTTGGACCCTCTGTGTCAAAAAAAACCTCACAAAGAATCCCCTGCTCATTACAGAAGAAGATGCATTT
AAAATATGGGTTATTTTCAACTTTTTATCTGAGGACAAGTATCCATTAATTATTGTGTCAGAAGAGATTGAATACC
TGCTTAAGAAGCTTACAGAAGCTATGGGAGGAGGTTGGCAGCAAGAACAATTTGAACATTATAAAATCAACTTTGA
TGACAGTAAAAATGGCCTTTCTGCATGGGAACTTATTGAGCTTATTGGAAATGGACAGTTTAGCAAAGGCATGGAC
CGGCAGACTGTGTCTATGGCAATTAATGAAGTCTTTAATGAACTTATATTAGATGTGTTAAAGCAGGGTTACATGA
TGAAAAAGGGCCACAGACGGAAAAACTGGACTGAAAGATGGTTTGTACTAAAACCCAACATAATTTCTTACTATGT
GAGTGAGGATCTGAAGGATAAGAAAGGAGACATTCTCTTGGATGAAAATTGCTGTGTAGAGTCCTTGCCTGACAAA
GATGGAAA

11729-45.21.21.cons2 (SEQ ID NO:3)

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC

11731.1contig (SEQ ID NO:4)

TCTTTTTCTTTCGATTTCCTTCAATTTGTCACGTTTGATTTTATGAAGTTGTTCAAGGGCTAACTGCTGTGTATTA
TAGCTTTCTCTGAGTTCCTTCAGCTGATTGTTAAATGAATCCATTTCTGAGAGCTTAGATGCAGTTTCTTTTTCAA
GAGCATCTAATTGTTCTTTAAGTCTTTGGCATAATTCTTCCTTTTCTGATGACTTTTTATGAAGTAAACTGATCCC
TGAATCAGGTGTGTTACTGAGCTGCATGTTTTAATTCTTTCGTTTAATAGCTGCTTCTCAGGGACCAGATAGATA
AGCTTATTTTGATATTCCTTAAGCTCTTGTTGAAGTTGTTTGATTTCCATAATTTCCAGGTCACACTGTTTATCCA
AAACTTCTAGCTCAGTCTTTTGTGTTTGCTTTCTGATTTGGACATCTTGTAGTCTGCCTGAGATCTGCTGATGXTT
TCCATTCACTGCTTCCAGTTCCAGGTGGAGACTTTXCTTTCTGGAGCTCAGCCTGACAATGCCTTCTTGXTCCCT

*Fig. 1A*

11731.2contig (SEQ ID NO:5)

AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTA

11734.1contig (SEQ ID NO:6)

AATAGATTTAATGCAGAGTGTCAACTTCAATTGATTGATAGTGGCTGCCTAGAGTGCTGTGTTGAGTAGGTTTCTG
AGGATGCACCCTGGCTTGAAGAGAAAGACTGGCAGGATTAACAATATCTAAAATCTCACTTGTAGGAGAAACCACA
GGCACCAGAGCTGCCACTGGTGCTGGCACCAGCTCCACCAAGGCCAGCGAAGAGCCCAAATGTGAGAGTGGCGGTC
AGGCTGGCACCAGCACTGAAGCCACCACTGGTGCTGGCACTGGCACTGGCACTGTTATTGGTACTGGTACTGGCAC
CAGTGCTGGCACTGCCACTCTCTTGGGCTTTGGCTTTAGCTTCTGCTCCCGCCTGGATCCGGGCTTTGGCCCAGGG
TCCGATATCAGCTTCGTCCCAGTTGCAGGGCCCGGCAGCATTCTCCGAGCCGAGCCCAATGCCCATTCGAGCTCTA
ATCTCGGCCCTAGCCTTGGCTTCAGCTGCAGCCTCAGCTGCAGCCTTCAAATCCGCTTCCATCGCCTCTCGGTAC

11734.2contig (SEQ ID NO:7)

GCCAAGAAAGCCCGAAAGGTGAAGCATCTGGATGGGGAAGAGGATGGCAGCAGTGATCAGAGTCAGGCTTCTGGAA
CCACAGGTGGCCGAAGGGTCTCAAAGGCCCTAATGGCCTCAATGGCCCGCAGGGCTTCAAGGGGTCCCATAGCCTT
TTGGGCCCGCAGGGCATCAAGGACTCGGTTGGCTGCTTGGGCCCGGAGAGCCTTGCTCTCCCTGAGATCACCTAAA
GCCCGTAGGGGCAAGGCTCGCCGTAGAGCTGCCAAGCTCCAGTCATCCCAAGAGCCTGAAGCACCACCACCTCGGG
ATGTGGCCCTTTTGCAAGGGAGGGCAAATGATTTGGTGAAGTACCTTTTGGCTAAAGACCAGACGAAGATTCCCAT
CAAGCGCTCGGACATGCTGAAGGACATCATCAAAGAATACACTGATGTGTACCCCGAAATCATTGAACGAGCAGGC
TATTCCTTGGAGAAGGTATTTGGGATTCAATTGAAGGAAATTGATAAGAATGACCACTTGTACATTCTTCTCAGC

11736.1contg (SEQ ID NO:8)

GAGGTCTCACTATGTTGCCCAGGCTGTTCTTGAACTCCTGGGATCAAGCAATCCACCCATGTTGGTCTCCAAAAGT
GCTGGGATCATAGGCGTGAGCCACCTCACCCAGCCACCAATTTTCAATCAGGAAGACTTTTTCCTTCTTCAAGAAG
TGAAGGGTTTCCAGAGTATAGCTACACTATTGCTTGCCTGAGGGTGACTACAAAATTGCTTGCTAAAAGGTTAGGA
TGGGTAAAGAATTAGATTTTCTGAATGCAAAAATAAAATGTGAACTAATGAACTTTAGGTAATACATATTCATAAA
ATAATTATTCACATATTTCCTGATTTATCACAGAAATAATGTATGAAATGCTTTGAGTTTCTTGGAGTAAACTCCA
TTACTCATCCCAAGAAACCATATTATAAGTATCACTGATAATAAGAACAACAGGACCTTGTCATAAATTCTGGATA
AGAGAAATAGTCTCTGGGTGTTTGXTCTTAATTGATAAAATTTACTTGTCCATCTTTTAGTTCAGAATCACAAAA

*Fig. 1B*

11736.2contig (SEQ ID NO:9)

```
AAGCGGAAATGAGAAAGGAGGGAAAATCATGTGGTATTGAGCGGAAAACTGCTGGATGACAGGGCTCAGTCCTGTT
GGAGAACTCTGGGTGGTGCTGTAGAACAGGGCCACTCACAGTGGGGTGCACAGACCAGCACGGCTCTGTGACCTGT
TTGTTACAGGTCCATGATGAGGTAAACAATACACTGAGTATAAGGGGTTGGTTTAGAAACTCTTACAGCAATTTGAC
AAAGTAATCTTCTGTGCAGTGAATCTAAGAAAAAAATTGGGGCTGTATTTGTATGTTCCTTTTTTTCATTTCATGT
TCTGAGTTACCTATTTTTATTGCATTTTACAAAAGCATCCTTCCATGAAGGACCGGAAGTTAAAAACAAAGCAGGT
CCTTTATCACAGCACTGTCGTAGAACACAGTTCAGAGTTATCCACCCAAGGAGCCAGGGAGCTGGGCTAAACCAAA
GAATTTTGCTTTTGGTTAATCATCAGGTACTTGAGTTGGAATTGTTTTAATCCCATCATTACCAGGCTGGAXGTG
```

11739-1&2 (SEQ ID NO:10)

```
CCGCGGCTCCTGTCCAGACCCTGACCCTCCCTCCCAAGGCTCAACCGTCCCCCAACAACCGCCAGCCTTGTACTGA
TGTCGGCTGCGAGAGCCTGTGCTTAAGTAAGAATCAGGCCTTATTGGAGACATTCAAGCAAAGGTTGGACAACTAC
TTTTCCAGAACAGAAAGGAAACTCATGCATCAGAAAAGGTGACTAATAAAGGTACCAGAAGAATATGGCTGCACAA
ATACCAGAATCTGATCAGATAAAACAGTTTAAGGAATTTCTGGGGACCTACAATAAACTTACAGAGACCTGCTTTT
TGGACTGTGTTAGAGACTTCACAACAAGAGAAGTAAAACCTGAAGAGACCACCTGTTCAGAACATTGCTTACAGAA
ATATTTAAAAATGACACAAAGAATATCCATGAGATTTCAGGAATATCATATTCAGCAGAATGAAGCCCTGGCAGCC
AAAGCAGGACTCCTTGGCCAACCACGATAGAGAAGTCCTGATGGATGAACTTTTGATGAAAGATTGCCAACAGCTG
CTTTATTGGAAATGAGGACTCATCTGATAGAATCCCCTGAAAGCAGTAGCCACCATGTTCAACCATCTGTCATGAC
TGTTTGGCAAATGGAAACCGCTGGAGAAACAAAATTGCTATTTACCAGGAATAATCACAATAGAAGGTCTTATTGT
TCAGTGAAATAATAAGATGCAACATTTGTTGAGGCCTTATGATTCAGCAGCTTGGTCACTTGATTAGAAAAATAAA
CCATTGTTTCTTCAATTGTGACTGTTAATTTTAAAGCAACTTATGTGTTCGATCATGTATGAGATAGAAAAATTTT
TATTACTCAAAGTAAAATAAATGGA
```

11740.1.contig (SEQ ID NO:11)

```
GAAAAAAAATATAAAACACACTTTTGCGAAAACGGTGGCCCTAAAAGAGGAAAAGAATTTCACCAATATAAATCCA
ATTTTATGAAAACTGACAATTTAATCCAAGAATCACTTTTGTAAATGAAGCTAGCAAGTGATGATATGATAAAATA
AACGTGGAGGAAATAAAAACACAAGACTTGGCATAAGATATATCCACTTTTGATATTAAACTTGTGAAGCATATTC
TTCGACAAATTGTGAAAGCGTTCCTGATCTTGCTTGTTCTCCATTTCAAATAAGGAGGCATATCACATCCCAAGAG
TAACAGAAAAAGAAAAAAGACATTTTTGCATTTTGAGATGAACCAAAGACACAAAACAAAACGAACAAAGTGTCAT
GTCTAATTCTAGCCTCTGAAATAAACCTTGAACATCTCCTACAAGGCACCGTGATTTTTGTAATTCTAACCTGAAG
AAATGTGATGACTTTTGTGGACATGAAAATCAGATGAGAAAACTGTGGTCTTTCCAAAGCCTGAACTCCCCTGAAA
ACCTTTGCA
```

*Fig. 1C*

11766.1.contig (SEQ ID NO:12)

```
CTGGGATCATTTCTCTTGATGTCATAAAAGACTCTTCTTCTTCCTCTTCATCCTCTTCTTCATCCTCTTCTGTACA
GTGCTGCCGGGTACAACGGCTATCTTTGTCTTTATCCTGAGATGAAGATGATGCTTCTGTTTCTCCTACCATAACT
GAAGAAATTTCGCTGGAAGTCGTTTGACTGGCTGTTTCTCTGACTTCACCTTCTTTGTCAAACCTGAGTCTTTTTA
CCTCATGCCCCTCAGCTTCCACAGCATCTTCATCTGGATGTTTATTTTTCAAAGGGCTCACTGAGGAAACTTCTGA
TTCAGAGGTCGAAGAGTCACTGTGATTTTTCTCCTCATTTTGCTGCAAATTTGCCTCTTTGCTGTCTGTGCTCTCA
GGCAACCCATTTGTTGTCATGGGGGCTGACAAAGAAACCTTTGGTCGATTAAGTGGCCTGGGTGTCCCAGGCCCAT
TTATATTAGACCTCTCAGTATAGCTTGGTGAATTTCCAGGAAACATAACACCATTCATTCGATTTAAACTATTGGA
ATTGGTTTT
```

11766.2.contig (SEQ ID NO:13)

```
GAGGGTTGGTGGTAGCGGCTTGGGGAGGTGCTCGCTCTGTCGGTCTTGCTCTCTCGCACGCTTCCCCCGGCTCCCT
TCGTTTCCCCCCCCGGTCGCCTGCGTGCCGGAGTGTGTGCGAGGGAGGGGGAGGGCGTCGGGGGGGTGGGGGGAG
GCGTTCCGGTCCCCAAGAGACCCGCGGAGGGAGGCGGAGGCTGTGAGGGACTCCGGGAAGCCATGGACGTCGAGAG
GCTCCAGGAGGCGCTGAAAGATTTTGAGAAGAGGGGGAAAAAGGAAGTTTGTCCTGTCCTGGATCAGTTTCTTTGT
CATGTAGCCAAGACTGGAGAAACAATGATTCAGTGGTCCCAATTTAAAGGCTATTTTATTTTCAAACTGGAGAAAG
TGATGGATGATTTCAGAACTTCAGCTCCTGAGCCAAGAGGTCCTCCCAACCCTAATGTCGA
```

11773.2.contig (SEQ ID NO:14)

```
AAGCAGGCGGCTCCCGCGCTCGCAGGGCCGTGCCACCTGCCCGCCCGCCCGCTCGCTCGCTCGCCCGCCGCGCCGC
GCTGCCGACCGCCAGCATGCTGCCGAGAGTGGGCTGCCCCGCGCTGCCGXTGCCG
```

11775-1&2 (SEQ ID NO:15)

```
ATCTCTTGTATGCCAAATATTTAATATAAATCTTTGAAACAAGTTCAGATGAAATAAAAATCAAAGTTTGCAAAAA
CGTGAAGATTAACTTAATTGTCAAATATTCCTCATTGCCCCAAATCAGTATTTTTTTATTTCTATGCAAAAGTAT
GCCTTCAAACTGCTTAAATGATATATGATATGATACACAAACCAGTTTTCAAATAGTAAAGCCAGTCATCTTGCAA
TTGTAAGAAATAGGTAAAAGATTATAAGACACCTTACACACACACACACACACACGTGTGCACGCCAATGAC
AAAAAACAATTTGGCCTCTCCTAAAATAAGAACATGAAGACCCTTAATTGCTGCCAGGAGGGAACACTGTGTCACC
CCTCCCTACAATCCAGGTAGTTTCCTTTAATCCAATAGCAAATCTGGGCATATTTGAGAGGAGTGATTCTGACAGC
CACGTTGAAATCCTGTGGGGAACCATTCATGTCCACCCACTGGTGCCCTGAAAAAATGCCAATAATTTTTCGCTCC
CACTTCTGCTGCTGtCTCTTCCACATCCTCACATAGACCCCAGACCCGCTGGCCCCTGGCTGGGCATCGCATTGCT
GGTAGAGCAAGTCATAGGTCTCGTCTTTGACGTCACAGAAGCGATACACCAAATTGCCTGGTCGGTCATTGTCATA
ACCAGAGA
```

*Fig. 1D*

11777.1&2.cons (SEQ ID NO:16)

```
CAGACGGGGTTTCACTATGTTGGCTAGGCTGGTCTTGAACTCCTGACTTCAGGTGATCTGCCTGCCTTGGCCTCCC
AAAGTGCTGGGATTACAGGCATAAGCCACTGCGCCCGGCTGATCTGATGGTTTCATAAGGCTTTTCCCCCTTTTGC
TCAGCACTTCTCCTTCCTGCCGCCATGTGAAGAAGGACATGTTTGCTTCCCCTTCCACCACGATTGTAAGTTGTTT
CCTGAGGCCTCCCCGGCCATGCTGAACTGTGAGTCAATTAAACCTCTTTCCTTTATAAATTATCCAGTTTTGGGTA
TGTCTTTATTAGTAGAATGAGAACAGACTAATACAACCCTTAAAGGAGACTGACGGAGAGGATTCTTCCTGGATCC
CAGCACTTCCTCTGAATGCTACTGACATTCTTCTTGAGGACTTTAAACTGGGAGATAGAAAACAGATTCCATGGCT
CAGCAGCCTGAGAGCAGGGAGGGAGCCAAGCTATAGATGACATGGGCAGCCTCCCCTGAGGCCAGGTGTGGCCGAA
CCTGGGCAGTGCTGCcACCCACCCCACCAGGGCCAAGTCCTGTCCTTGGAGAGCCAAGCCTCAATCACTGCTAGCC
TCAAGTGTCCCCAAGCCACAGTGGCTAGGGGGACTCAGGGAACAGTTCCCAGTCTGCCCTACTTCTCTTACCTTTA
CCCCTCATACCTCCAAAGTAGACCATGTTCATGAGGTCCAAAGG
```

11779.2.contig (SEQ ID NO:17)

```
AAGCGAGGAAGCCACTGCGGCTCCTGGCTGAAAAGCGGCGCCAGGCTCGGGAACAGAGGGAACGCGAAGAACAGGA
GCGGAAGCTGCAGGCTGAAAGGGACAAGCGAATGCGAGAGGAGCAGCTGGCCCGGGAGGCTGAAGCCCGGGCTGAA
CGTGAGGCCGAGGCGCGGAGACGGGAGGAGCAGGAGGCTCGAGAGAAGGCGCAGGCTGAGCAGGAGGAGCAGGAGC
GACTGCAGAAGCAGAAAGAGGAAGCCGAAGCCCGGTCCCGGGAAGAAGCTGAGCGCCAGCGCCAGGAGCGGGAAAA
GCACTTTCAGAAGGAGGAACAGGAGAGACAAGAGCGAAGAAAGCGGCTGGAGGAGATAATGAAGAGGACTCGGAAA
TCAGAAGCCGCCGAAACCAAGAAGCAGGATGCAAAGGAGACCGCAGCTAACAATTCCGGCCCAGACCCTTGTGAAA
GCTGTAGAGACTCGGCCCTCTGGGCTTCCAGAAAGGATTCTATTGCAGAAAGGAAGGAGCTXGGCCCCCCAXGGA
```

11781 & 37.cons (SEQ ID NO:18)

```
CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACXTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAAT
```

*Fig. 1E*

11781-76-87-37 (SEQ ID NO:19)

```
CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACCTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAATTA
```

11784-1 & 2 (SEQ ID NO:20)

```
GGACGACAAGGCCATGGCGATATCGGATCCGAATTCAAGCCTTTGGAATTAAATAAACCTGGAACAGGGAAGGTGA
AAGTTGGAGTGAGATGTCTTCCATATCTATACCTTTGTGCACAGTTGAATGGGAACTGTTTGGGTTTAGGGCATCT
TAGAGTTGATTGATGGAAAAAGCAGACAGGAACTGGTGGGAGGTCAAGTGGGGAAGTTGGTGAATGTGGAATAACT
TACCTTTGTGCTCCACTTAAACCAGATGTGTTGCAGCTTTCCTGACATGCAAGGATCTACTTTAATTCCACACTCT
CATTAATAAATTGAATAAAAGGGAATGTTTTGGCACCTGATATAATCTGCCAGGCTATGTGACAGTAGGAAGGAAT
GGTTTCCCCTAACAAGCCCAATGCACTGGTCTGACTTTATAAATTATTTAATAAAATGAACTATTATC
```

11785.2.contig (SEQ ID NO:21)

```
GGCAGTGACATTCACCATCATGGGAACCACCTTCCCTTTTCTTCAGGATTCTCTGTAGTGGAAGAGAGCACCCAGT
GTTGGGCTGAAAACATCTGAAAGTAGGGAGAAGAACCTAAAATAATCAGTATCTCAGAGGGCTCTAAGGTGCCAAG
AAGTCTCACTGGACATTTAAGTGCCAACAAAGGCATACTTTCGGAATCGCCAAGTCAAAACTTTCTAACTTCTGTC
TCTCTCAGAGACAAGTGAGACTCAAGAGTCTACTGCTTTAGTGGCAACTACAGAAAACTGGTGTTACCCAGAAAAA
CAGGAGCAATTAGAAATGGTTCCAATATTTCAAAGCTCCGCAAACAGGATGTGCTTTCCTTTGCCCATTTAGGGTT
TCTTCTCTTTCCTTTCTCTTTATTAACCACT
```

*Fig. 1F*

11718-1&2 cons (SEQ ID NO:22)

```
TGCGCTGAAAACAACGGCCTCCTTTACTGTTAAAATGCAGCCACAGGTGCTTAGCCGTGGGCATCTCAACCACCAG
CCTCTGTGGGGGGCAGGTGGGCGTCCCTGTGGGCCTCTGGGCCCACGTCCAGCCTCTGTCCTCTGCCTTCCGTTCT
TCGACAGTGTTCCCGGCATCCCTGGTCACTTGGTACTTGGCGTGGGCCTCCTGTGCTGCTCCAGCAGCTCCTCCAG
GXGGTCGGCCCGCTTCACCGCAGCCTCATGTTGTGTCCGGAGGCTGCTCACGGCCTCCTCCTTCCTCGCGAGGGCT
GTCTTCACCCTCCGGXGCACCTCCTCCAGCTCCAGCTGCTGGCGGGCCTGCAGCGTGGCCAGCTCGGCCTTGGCCT
GCCGCGTCTCCTCCTCARAGGCTGCCAGCCGGTCCTCGAACTCCTGGCGGATCACCTGGGCCAGGTTGCTGCGCTC
GCTAGAAAGCTGCTCGTTCACCGCCTGCGCATCCTCCAGCGCCCGCTCCTTCTGCCGCACAAGGCCCTGCAGACGC
AGATTCTCGCCCTCGGCcTCCCCAAGCTGGCCCTTCAGCTCCGAGCACCGCTCCTGAAGCTTCCGCTCCGACTGCT
CCAGCTCGGAGAGCTCGGCCTCGTACTTGTCCCGTAAGCGCTTGATGCGGCTCTCGGCAGCCTTCTCACTCTCCTC
CTTGGCCAGCGCCATGTCGGCCTCCAGCCGGTGAATGACCAGCTCAATCTCCTTGTCCCGGCCTTTCCGGATTTCT
TCCCTCAGCTCCTGTTCCCGGTTCAGCAGCCACGCCTCCTCCTTCCTGGTGCGGCCGGCCTCCCACGCCTGCCTCT
CCAGCTCCAGCTGCTGCTTCAGGGTATTCAGCTCCATCTGGCGGGCCTGCAGCGTGGCCA
```

13690.4 (SEQ ID NO:23)

```
CAACTTATTACTTGAAATTATAATATAGCCTGTCCGTTTGCTGTTTCCAGGCTGTGATATATTTTCCTAGTGGTTT
GACTTTAAAAATAAATAAGGTTTAATTTTCTCCCC
```

13693.1 (SEQ ID NO:24)

```
TGCAAGTCACGGGAGTTTATTTATTTAATTTTTTTCCCCAGATGGAGACTCTGTCGCCCAGGCTGGAGTGCAATGG
TGTGATCTTGGCTCACTGCAACCTCCACCTCCTGGGTTCAAGCGATTCTCCTGCCACAGCCTCCCGAGTAGCTGGG
ATTACAGGTGCCCGCCACCACACCCAGCTAATTTTTATATTTTTAGTAAAGACAGGGTTTCCCCATGTTGGCCAGG
CTGGTCTTGAACTTCTGACCTCAGGTGATCCACCTGCCTCGGCCTCCCAAAGTGTTGGGATTACAGGCGTGAGCTA
CCCGTGCCTGGCCAGCCACTGGAGTTTAAAGGACAGTCATGTTGGCTCCAGCCTAAGGCGGCATTTTCCCCCATCA
GAAAGCCCGCGGCTCCTGTACCTCAAAATAGGGCACCTGTAAAGTCAGTCAGTGAAGTCTCTGCTCTAACTGGCCA
CCCGGGGCCATTGGCNTCTGACACAGCCTTGCCAGGANGCCTGCATCTGCAAAAGAAAAGTTCACTTCCTTTCCG
```

13694.1 (SEQ ID NO:25)

```
CAGAGAATCTKAGAAAGATGTCGCGTTTTCTTTTAATGAATGAGAGAAGCCCATTTGTATCCCTGAATCATTGAGA
AAAGGCGGCGGTGGCGACAGCGGCGACCTAGGGATCGATCTGGAGGGACTTGGGGAGCGTGCAGAGACCTCTAGCT
CGAGCGCGAGGGACCTCCCGCCGGGATGCCTGGGGAGCAGATGGACCCTACTGGAAGTCAGTTGGATTCAGATTTC
TCTCAGCAAGATACTCCTTGCCTGATAATTGAAGATTCTCAGCCTGAAAGCCAGGTTCTAGAGGATGATTCTGGTT
CTCACTTCAGTATGCTATCTCGACACCTTCCTAATCTCCAGACGCACAAAGAAAATCCTGTGTTGGATGTTGNGTC
CAATCCTTGAACAAACAGCTGGAGAAGAACGAGGAGACCGGTAATAGTGGGTTCAATGAACATTTGAAAGAAAACC
AGGTTGCAGACCCTG
```

*Fig. 1G*

13694.2 (SEQ ID NO:26)
GACTGTCCTGAACAAGGGACCTCTGACCAGAGAGCTGCAGGAGATGCAGAGTGGTGGCAGGAGTGGAAGCCAAAGA
ACACCCACCTTCCTCCCTTGAAGGAGTAGAGCAACCATCAGAAGATACTGTTTTATTGCTCTGGTCAAACAAGTCT
TCCTGAGTTGACAAAACCTCAGGCTCTGGTGACTTCTGAATCTGCAGTCCACTTTCCATAAGTTCTTGTGCAGACA
ACTGTTCTTTTGCTTCCATAGCAGCAACAGATGCTTTGGGGCTAAAAGGCATGTCCTCTGACCTTGCAGGTGGTGG
ATTTTGCTCTTTTACAACATGTACATCCTTACTGGGCTGTGCTGTCACAGGGATGTCCTTGCTGGACTGTTCTGCT
ATGGGGATATCTTCGTTGGACTGTTCTTCATGCTTAATTGCAGTATTAGCATCCACATCAGACAGCCTGGTATAAC
CAGAGTTGGTGGTTACTGATTGTAGCTGCTCTTTGTCCACTTCATATGGCACAAGTATTTTCCTCAACATCCTGGC
TCTGGGAAG

13695.1 (SEQ ID NO:27)
GAAATGTATATTTAATCATTCTCTTGAACGATCAGAACTCTRAAATCAGTTTTCTATAACARCATGTAATACAGTC
ACCGTGGCTCCAAGGTCCAGGAAGGCAGTGGTTAACACATGAAGAGTGTGGGAAGGGGGCTGGAAACAAAGTATTC
TTTTCCTTCAAAGCTTCATTCCTCAAGGCCTCAATTCAAGCAGTCATTGTCCTTGCTTTCAAAAGTCTGTGTGTGC
TTCATGGAAGGTATATGTTTGTTGCCTTAATTTGAATTGTGGCCAGGAAGGGTCTGGAGATCTAAATTCAGAGTAA
GAAAACCTGAGCTAGAACTCAGGCATTTCTCTTACAGAACTTGGCTTGCAGGGTAGAATGAANGGAAAGAAACTTA
GAAGCTCAACAAGCTGAAGATAATCCCATCAGGCATTTCCCATAGGCCTTGCAACTCTGTTCACTGAGAGATGTTA
TCCTG

13695.2 (SEQ ID NO:28)
AGTCTGGAGTGAGCAAACAAGAGCAAGAAACAARRAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGAGTGATAAGTAA
AATGCACGTGGAGACAAGTGCATCCCCAGATCTCAGGGACCTCCCCCTGCCTGTCACCTGGGGAGTGAGAGGACAG
GATAGTGCATGTTCTTTGTCTCTGAATTTTTAGTTATATGTGCTGTAATGTTGCTCTGAGGAAGCCCCTGGAAAGT
CTATCCCAACATATCCACATCTTATATTCCACAAATTAAGCTGTAGTATGTACCCTAAGACGCTGCTAATTGACTG
CCACTTCGCAACTCAGGGGCGGCTGCATTTTAGTAATGGGTCAAATGATTCACTTTTTATGATGCTTCCCAAGGTG
CCTTGGCTTCTCTTCCCAACTGACAAATGCCCAAGTTGAGAAAAATGATCATAATTTTAGCATAAACCGAGCAATC
GGCGACCCC

13697.1 (SEQ ID NO:29)
TAGCTGTCTTCCTCACTCTTATGGCAATGACCCCATATCTTAATGGATTAAGATAATGAAAGTGTATTTCTTACAC
TCTGTATCTATCACCAGAAGCTGAGGTGATAGCCCGCTTGTCATTGTCATCCATATTCTGGGACTCAGGCGGGAAC
TTTCTGGAATATTGCCAGGGAGCATGGCAGAGGGGCACAGTGCATTCTGGGGGAATGCACATTGGCTCAGCCTGGG
TAATGAGTGATATACATTACCTCTGTTCACAACTCATTGCCCAGCACCAGTCACAAGGCCCCACCCAAATACCAGAG
CCCAAGAAATGTAGTCCTGTTGATATGGTTTTGCTGTGTCCCAACCCAAATCTCATCTTGAATTGTAAGCTCCCAT
AATTCCCATGTGTTGTGGGAGGGACCTGGTG

*Fig. 1H*

13697.2 (SEQ ID NO:30)

```
ATCATGAGGATGTTACCAAAGGGATGGTACTAAACCATTTGTATTCGTCTGTTTTCACACTGCTTTGAAGATACTA
CCTGAGACTGGGTAATTTATAAACAAAAGAGATTTAATTGACTCACAGTTCTGCATGGCTGAAGAGGCCTCAGGAA
ACTTACAGTCATGGTGGAAGGCAAAGGAGGAGCAAGGCATGTCTTACATGTCAGTAGGAGAGAGAGCGAGAGCAGG
AGAACCTGCCACTTATAAACCATTCAGATCTCATAACTCCCTATCATGAGAAAAACATGGAGGAAACCACCCTCAT
GATCCAATCACCTCCCGCCAGGTCCCTCCCTCGACACGTGGGGATTATAATTCAGGATTAGAGGGACACAGAGACA
AACCATATCATCATTCATGAGAAATCCACCCTCATAGTCCAATCAGCTCCTACCAGGCCCCACCTCCAACACTGGG
GATTGCAATTCAACATGAGATTTGGATGGGGACACAGATTCAAACCATATCATAC
```

13699.1&2 (SEQ ID NO:31)

```
CATGGCCTTTCTCCTTAGAGGCCAGAGGTGCTGCCCTGGCTGGGAGTGAAGCTCCAGGCACTACCAGCTTTCCTGA
TTTTCCCGTTTGGTCCATGTGAAGAGCTACCACGAGCCCCAGCCTCACAGTGTCCACTCAAGGGCAGCTTGGTCCT
CTTGTCCTGCAGAGGCAGGCTGGTGTGACCCTGGGAACTTGACCCGGGAACAACAGGTGGCCCAGAGTGAGTGTGG
CCTGGCCCCTCAACCTAGTGTCCGTCCTCCTCTCTCCTGGAGCCAGTCTTGAGTTTAAAGGCATTAAGTGTTAGAT
ACAAGCTCCTTGTGGCTGGAAAAACACCCCTCTGCTGATAAAGCTCAGGGGGCACTGAGGAAGCAGAGGCCCCTTG
GGGGTGCCCTCCTGAAGAGAGCGTCAGGCCATCAGCTCTGTCCCTCTGGTGCTCCCACGTCTGTTCCTCACCCTCC
ATCTCTGGGAGCAGCTGCACCTGACTGGCCACGCGGGGGCAGTGGAGGCACAGGCTCAGGGTGGCCGGGCTACCTG
GCACCCTATGGCTTACAAAGTAGAGTTGGCCCAGTTTCCTTCCACCTGAGGGGAGCACTCTGACTCCTAACAGTCT
TCCTTGCCCTGCCATCATCTGGGGTGGCTGGCTGTCAAGAAAGGCCGGGCATGCTTTCTAAACACAGCCACAGGAG
GCTTGTAGGGCATCTTCCAGGTGGGGAAACAGTCTTAGATAAGTAAGGTGACTTGCCTAAGGCCTCCCAGCACCCT
TGATCTTGGAGTCTCACAGCAGACTGCATGTSAACAACTGGAACCGAAAACATGCCTCAGTATAAAA
```

13703.3 (SEQ ID NO:32)

```
CCAGAACCTCCTTCTCTTTGGAGAATGGGGAGGCCTCTTGGAGACACAGAGGGTTTCACCTTGGATGACCTCTAGA
GAAATTGCCCAAGAAGCCCACCTTCTGGTCCCAACCTGCAGACCCCACAGCAGTCAGTTGGTCAGGCCCTGCTGTA
GAAGGTCACTTGGCTCCATTGCCTGCTTCCAACCAATGGGCAGGAGAGAAGGCCTTTATTTCTCGCCCACCCATTC
TCCTGTACCAGCACCTCCGTTTTCAGTCAGYGTTGTCCAGCAACGGTACCGTTTACACAGTCA
```

13705.1 (SEQ ID NO:33)

```
TGCATGTAGTTTTATTTATGTGTTTTSGTCTGGAAAACCAAGTGTCCCAGCAGCATGACTGAACATCACTCACTTC
CCCTACTTGATCTACAAGGCCAACGCCGAGAGCCCAGACCAGGATTCCAAACACACTGCACGAGAATATTGTGGAT
CCGCTGTCAGGTAAGTGTCCGTCACTGACCCARACGCTGTTACGTGGCACATGACTGTACAGTGCCACGTAACAGC
ACTGTACTTTTCTCCCATGAACAGTTACCTGCCATGTATCTACATGATTCAGAACATTTTGAACAGTTAATTCTGA
CACTTGAATAATCCCATCAAAAACCGTAAAATCACTTTGATGTTTGTAACGACAACATAGCATCACTTTACGACAG
AATCATCTGGAAAAACAGAACAACGAATACATACATCTTAAAAAAATGCTGGGGTGGGCCAGGCACAGCTTCACGCC
TGTAATCCCAGCACTTTGGGAGGCTTAAGCGGGTG
```

*Fig. 1I*

13705.2 (SEQ ID NO:34)

TGGGGCGGAAAGAAGCCAAGGCCAAGGAGCTGGTGCGGCAGCTGCAGCTGGAGGCCGAGGAGCAGAGGAAGCAGAA
GAAGCGGCAGAGTGTGTCGGGCCTGCACAGATACCTTCACTTGCTGGATGGAAATGAAAATTACCCGTGTCTTGTG
GATGCAGACGGTGATGTGATTTCCTTCCCACCAATAACCAACAGTGAGAAGACAAAGGTTAAGAAAACGACTTCTG
ATTTGTTTTTGGAAGTAACAAGTGCCACCAGTCTGCAGATTTGCAAGGATGTCATGGATGCCCTCATTCTGAAAAT
GGCAAGAAATGAAAAAGTACACTTTAGAAAATAAAGAGGAAGGATCACTCTCAGATACTGAAGCCGATGCAGTCTC
TGGACAACTTCCAGATCCCACAACGAATCCCAGTGCTGGAAAGGACGGGCCCTTCCTTCTGGTGGTGGAACANGTC
CCGGTGGTGGATCTTGGAANGGAACCTGAANGTGGTGTACCCCGTCCAAGGCCGACCTTGGCCAC

13707.4 (SEQ ID NO:35)

TCCCGCGCTCGCAGGGCNCGTGCCACCTGCCYGTCCGCCCGCTCGCTCGCTCGCCCGCCGCGCCGCGCTGCCGACC
GYCAGCATGCTGCCGAGAGTGGGCTGCCCCGCGCTGCCGCTGCCGCCGCCGCCGCTGCTGCCGCTGCTGCCGCTGC
TGCTGCTGC

13708.1&2 (SEQ ID NO:36)

GGCGGGTAGGCATGGAACTGAGAAGAACGAAGAAGCTTTCAGACTACGTGGGGAAGAATGAAAAAACCAAAATTAT
CGCCAAGATTCAGCAAAGGGGACAGGGAGCTCCAGCCCGAGAGCCTATTATTAGCAGTGAGGAGCAGAAGCAGCTG
ATGCTGTACTATCACAGAAGACAAGAGGAGCTCAAGAGATTGGAAGAAAATGATGATGATGCCTATTTAAACTCAC
CATGGGCGGATAACACTGCTTTGAAAAGACATTTTCATGGAGTGAAAGACATAAAGTGGAGACCAAGATGAAGTTC
ACCAGCTGATGACACTTCCAAAGAGATTAGCTCACCT

13709.1 (SEQ ID NO:37)

TCTGAAGGTTAAATGTTTCATCTAAATAGGGATAATGRTAAACACCTATAGCATAGAGTTGTTTGAGATTAAATGA
GATAATACATGTAAAATTATGTGCCTGGCATACAGCAAGATTGTTGTTGTTGTTGATGATGATGATGATGATGATA
ATATTTTTCTATCCCCAGTGCACAACTGCTTGAACCTATTAGATAATCAATACATGTTTCTTGAACTGAGATCAAT
TTCCCCATGTTGTCTGACTGATGAAGCCCTACATTTTCTTCTAGAGGAGATGACATTTGAGCAAGATCTTAAAGAA
AATCAGATGCCTTCACCTGACCACTGCTTGGTGATCCCATGGCACTTTGTACATCTCTCCATTAGCTCTCATCTCA
CCAGCCCATCATTATTGTATGTGCTGCCTTCTGAAGCTTGCAGCTGGCTACCATCMGGTAGAATAAAAATCATCCT
TTCATAAAATAGTGACCCTCCTTTTTTATTTGCATTTCCCAAAGCCAAGCACCGTGGGANGGTAG

*Fig. 1J*

13709.2 (SEQ ID NO:38)

```
TATGAAGAAGGGAAAAGAAGATAATTTGTGAAAGAAATGGGTCCAGTTACTAGTCTTTGAAAAGGGTCAGTCTGTA
GCTCTTCTTAATGAGAATAGGCAGCTTTCAGTTGCTCAGGGTCAGATTTCCTTAGTGGTGTATCTAATCACAGGAA
ACATCTGTGGTTCCCTCCAGTCTCTTTCTGGGGGACTTGGGCCCACTTCTCATTTCATTTAATTAGAGGAAATAGA
ACTCAAAGTACAATTTACTGTTGTTTAACAATGCCACAAAGACATGGTTGGGAGCTATTTCTTGATTTGTGTAAAA
TGCTGTTTTTGTGTGCTCATAATGGTTCCAAAAATTGGGTGCTGGCCAAAGAGAGATACTGTTACAGAAGCCAGCA
AGAAGACCTCTGTTCATTCACACCCCCGGGGATATCAGGAATTGACTCCAGTGTGTGCAAATCCAGTTTGGCCTAT
CTTCT
```

13712.1&2 (SEQ ID NO:39)

```
TGAGGGACTGATTGGTTTGCTCTCTGCTATTCAATTCCCCAAGCCCACTTGTTCCTGCAGCGTCCTCCTTCTCATT
CCCTTTAGTTGTACCCTCTCTTTCATCTGAGACCTTTCCTTCTTGATGTCGCCTTTTCTTCTTCTTGCTTTTTCTG
ATGTTCTGCTCAGCATGTTCTGGGTGCTTCTCATCTGCATCATTCCTTTCAGATGCTGTAGCTTCTTCCTCCTCTT
TCTGCCTCCTTTTCTTTTTCTTTTTTTTGGGGGGCTTGCTCTCTGACTGCAGTTGAGGGGCCCCAGGGTCCTGGCC
TTTGAGACGAGCCAGGAAGGCCTGCTCCTGGGCCTCTAGGCGAGCAAGCTTGGCCTTCATTGTGATCCCAAGACGG
GCAGCCTTGTGTGCTGTTCGCCCCTCACAGGCTTGGAGCAGCATCTCATCAGTCAGAATCTTTGGGGACTTGGACC
CCTGGTTGTCGTCATCACTGCAGCTCTCCAAGTCTTTGTTTGGCTTCTCTCCACCTGAAGTCAATGTAGCCATCTT
CACAAACTTCTGATACAGCAAGTTGGGCTTGGGATGATTATAACGGGTGGTCTCCTTAGAAAGGCTCCTTATCTGT
ACTCCATCCTGCCCAGTTTCCACTACCAAGTTGGCCGCAGTCTTGTTGAAGAGCTCATTCCACCAGTGGTTTGTGA
ACTCCTTGGCAGGGTCATGTCCTACCCCATGAGTGTCTTGCTTCAGYGTCACCCTGAGAGCCTGAGTGATACCATT
CTCCTTCCG
```

13714.1&2 (SEQ ID NO:40)

```
GACAACATGAAATAAATCCTAGAGGACAAAATTAAACTCAATAGAGTGTAGTCTAGTTAAAAACTCGAAAAATGAG
CAAGTCTGGTGGGAGTGGAGGAAGGGCTATACTATAAATCCAAGTGGGCCTCCTGATCTTAACAAGCCATGCTCAT
TATACACATCTCTGAACTGGACATACCACCTTTACGCAGGAAACAGGGCTTGGAACTTCTAAGGGAAATTAACATG
CACCACCCACATCTAACCTACCTGCCGGGTAGGTACCATCCCTGCTTCGCTGAAATCAGTGCTC
```

13716.1&2 (SEQ ID NO:41)

```
TTGGAATTAAATAAACCTGGAACAGGGAAGGTGAAAGTTGGAGTGAGATGTCTTCCATATCTATACCTTTGTGCAC
AGTTGAATGGGAACTGTTTGGGTTTAGGGCATCTTAGAGTTGATTGATGGAAAAAGCAGACAGGAACTGGTGGGAG
GTCAAGTGGGGAAGTTGGTGAATGTGGAATAACTTACCTTTGTGCTCCACTTAAACCAGATGTGTTGCAGCTTTCC
TGACATGCAAGGATCTACTTTAATTCCACACTCTCATTAATAAATTGAATAAAAGGGAATGTTTTGGCACCTGATA
TAATCTGCCAGGCTATGTGACAGTAGGAAGGAATGGTTTCCCCTAACAAGCCCAATGCACTGGTCTGACTTTATAA
ATTATTTAATAAAATGAACTATTATC
```

*Fig. 1K*

13718.2 (SEQ ID NO:42)

AAACTGGACCTGCAACAGGGACATGAATTTACTGCARGGTCTGAGCAAGCTCAGCCCCTCTACCTCAGGGCCCCAC
AGCCATGACTACCTCCCCCAGGAGCGGGAGGGTGAAGGGGGCCTGTCTCTGCAAGTGGAGCCAGAGTGGAGGAATG
AGCTCTGAAGACACAGCACCCAGCCTTCTCGCACCAGCCAAGCCTTAACTGCCTGCCTGACCCTGAACCAGAACCC
AGCTGAACTGCCCCTCCAAGGGACAGGAAGGCTGGGGGAGGGAGTTTACAACCCAAGCCATTCCACCCCCTCCCCT
GCTGGGGAGAATGACACATCAAGCTGCTAACAATTGGGGGAAGGGGAAGGAAGAAAACTCTGAAAACAAAATCTTG
T

13722.3 (SEQ ID NO:43)

CATGCGTTTCACCACTGTTGGCCAGGCTGGTCTCGAACTCCTGGCCTCAAGCAATCCACCCGCCTCAGCCTCCAAA
AGTGCTGGGATTACAGATGTGAGCCATGGCACCATGCCAAAAGGCTATATTCCTGGCTCTGTGTTTCCGAGACTGC
TTTTAATCCCAACTTCTCTACATTTAGATTAAAAAATATTTTATTCATGGTCAATCTGGAACATAATTACTGCATC
TTAAGTTTCCACTGATGTATATAGAAGGCTAAAGGCACAATTTTTATCAAATCTAGTAGAGTAACCAAACATAAAA
TCATTAATTACTTTCAACTTAATAACTAATTGACATTCCTCAAAAGAGCTGTTTTCAATCCTGATAGGTTCTTTAT
TTTTTCAAAATATATTTGCCATGGGATGCTAATTTGCAATAAGGCGCATAATGAGAATACCCCAAACTGGA

13722.4 (SEQ ID NO:44)

GTTGGACCCCCAGGGACTGGAAAGACACTTCTTGCCCGAGCTGTGGCGGGAGAAGCTGATGTTCCTTTTTATTATG
CTTCTGGATCCGAATTTGATGAGATGTTTGTGGGTGTGGGAGCCAGCCGTATCAGAAATCTTTTTAGGGAAGCAAA
GGCGAATGCTCCTTGTGTTATATTTATTGATGAATTAGATTCTGTTGGTGGGAAGAGAATTGAATCTCCAATGCAT
CCATATTCAAGGCAGACCATAAATCAACTTCTTGCTGAAATGGATGGTTTTAAACCCAATGAAGGAGTTATCATAA
TAGGAGCCACAAACTTCCCAGAGGCATTAGATAATGCCTTAATACCGTCCTGGTCGTTTTGACATGCAAGTTACAG
TTCCAAGGCCAGATGTAAAAGGTCGAACAGAAATTTTGAAATGGTATCTCAATAAAATAAAGTTTGATCAATCCCG
TTGATCCAGAAATTATAGCCTCGAGGTACTGGTGGCTTTTCCGGAAGCAGAGTTGGGAGAATCTT

13724-13698-13748 (SEQ ID NO:45)

GCCTACAACATCCAGAAAGAGTCTACCCTGCACCTGGTGCTSCGTCTCAGAGGTGGGATGCAGATCTTCGTGAAGA
CCCTGACTGGTAAGACCATCACTCTCGAAGTGGAGCCGAGTGACACCATYGAGAACGTCAAAGCAAAGATCCARGA
CAAGGAAGGCRTYCCTCCTGACCAGCAGAGGTTGATCTTTGCCGGAAAGCAGCTGGAAGATGGDCGCACCCTGTCT
GACTACAACATCCAGAAAGAGTCYACCCTGCACCTGGTGCTCCGTCTCAGAGGTGGGATGCARATCTTCGTGAAGA
CCCTGACTGGTAAGACCATCACCCTCGAGGTGGAGCCCAGTGACACCATCGAGAATGTCAAGGCAAAGATCCAAGA
TAAGGAAGGCATCCCTCCTGATCAGCAGAGGTTGATCTTTGCTGGGAAACAGCTGGAAGATGGACGCACCCTGTCT
GACTACAACATCCAGAAAGAGTCCACTCTGCACTTGGTCCTGCGCTTGAGGGGGGGTGTCTAAGTTTCCCCTTTTA
AGGTTTCMACAAATTTCATTGCACTTTCCTTTCAATAAAGTTGTTGCATTCCC

*Fig. 1L*

13730.1 (SEQ ID NO:46)

```
GAACTGGGCCCTGAGCCCAAGTCATGCCTTGTGTCCGCATCTGCCGTGTCACCTCTGTKCCTGCCCCTCACCCCTC
CCTCCTGGTCTTCTGAGCCAGCACCATCTCCAAATAGCCTATTCCTTCCTGCAAATCACACACACATGCGGGCCAC
ACATACCTGCTGCCCTGGAGATGGGGAAGTAGGAGAGATGAATAGAGGCCCATACATTGTACAGAAGGAGGGGCAG
GTGCAGATAAAAGCAGCAGACCCAGCGGCAGCTGAGGTGCATGGAGCACGGTTGGGGCCGGCATTGGGCTGAGCAC
CTGATGGGCCTCATCTCGTGAATCCTCGAGGCAGCGCCACAGCAGAGGAGTTAAGTGGCACCTGGGCCGAGCAGAG
CAGGAGACTGAGGGTCAGAGTGGAGGCTAAGCTGCCCTGGAACTCCTCAATCTTGCCTGCCCCCTAGTATGAAGCC
CCCTTCCTGCCCCTACAATTCCTGA
```

13732.1 (SEQ ID NO:47)

```
ATGGATCTTACTTTGCCACCCAGGTTGGAGTGCAGTGCTGCAATCTTGGCTCACTGCAGCCTTAACCTCCCAGGCT
CAAGCTATCCTCCTGCCAAAGCCTTCCACATAGCTGGGACTACAGGTACACNGCCACCACACCCAGCTAAAATTTT
TGTATTTTTTGTAGAGACGGGATCTCGCCACGTTGCCCAGGCTGGTCCCATCCTGACCTCAAGCAGATCTGCCCAC
CTCAGCCCCCAACGTGCTAGGATTACAGGCGTGAGCCACCGCACCCAGCCTTTGTTTTGCTTTTAATGGAATCAC
CAGTTCCCCTCCGTGTCTCAGCAGCAGCTGTGAGAAATGCTTTGCATCTGTGACCTTTATGAAGGGGAACTTCCAT
GCTGAATGAGGGTAGGATTACATGCTCCTGTTTCCCGGGGGTCAAGAAAGCCTCAGACTCCAGCATGATAAGCAGG
GTGAG
```

13732.2 (SEQ ID NO:48)

```
ATAGGGGCTTTAAGGAGGGAATTCAGGTTCAATGAGGTCGTAAGGCCAGGGCTCTTATCCAGTAAGACTGGGGTCC
TTAGATGAGAAAGAGACACCCGAGGTCCTTCTCTCTGCCGTGTGAGGATGCATCAAGAAGGCGGCCGTCTGCAAGC
GAAGGAGAGGCCGCACCAGAAACCGACACCTTCATCTTGGACTTGCAGCCTCTAGAACTGAGAAAATAACTGTCTG
TTGGTTAAGCCACCCAGTTTGTAGTATTCTCTTATGGCTTCCTAAGCAGACTAACAAACAAACACCCAAAATTAAC
TGATGGCTTCGCTGTCTTCTGTAAAAATTGCTATGAGAGAACTTTTCACTCACTGTTTTGCAGTTTCTCCCTCAGT
CCCTGGTTCTTTCTTCTCACATAATCCCAATTTCAATTTATAGTTCATGGCCCAGGCAGAGTCATTCATCACGGCA
TCTCCTGAGCTAAACCAGCACCTGCTCTGCTCACTTCTTGACTGGCTGCTCATCATCAGCCCTCTTGCAGAGATTT
CATTTCCTCCCGTGCCAGGTACTTCACGCACCAAGCTCA
```

*Fig. 1M*

13735.1 (SEQ ID NO:49)

```
GGATAATGAAGTTGTTTTATTTAGCTTGGACAAAAAGGCATATTCCTCTATTTTCTTATACAACAAATATCCCCAA
AATAAAGCAAGCATATATATCTTGAATGTGTAATAATCCAGTGATAAACAAGAGCAGTACTTTAAAAGAAAAAAAA
ATATGTATTTCTGTCAGGTTAAAATGAGAATCAAAACCATTTACTCTGCTAACTCATTATTTTTTGCTTTCTTTTT
GGTTAAGAGAGGCAATGCAATACACTGAAAAAGGTTTTTATCTTATCTGGCATTGGAATTAGACATATTCAAACCC
CAGCCCCCATTTCCAAACTTTAAGACCACAAACAAGTAATTTACTTTTCTGAACATTGGTTTTTTCTGGAAAATGG
GAATTATAAAATAGACTTTGCAGACTCTTATGAGATTAAATAAGATAATGTATGAAATTCTTTCTTCTTTTTTACT
TCTTTTTCCTTTTTGAGATGGAGTCTCACCCCGTCACCCAGGCTGGAGTACAGTG
```

13735.2 (SEQ ID NO:50)

```
CCACTGCACTCCAGCCTGGGTGACGGAGTGAGACTCTGTCTCAAAAAAACAAACAAACAAACAAACAAAAAACTGA
AAAGGAAATAGAGTTCCTCTTTCCTCATATATGAATATATTATTTCAACAGATTGTTGATCACCTACCATATGCTT
GGTATTGTTCTAATTGCTGGGGATACAGCAAGAGGTTCTGCAGAACTTCATGGAGCATGAAAGTAAATAAACAAAG
TTAATTTCAAGGCCAGGCATGGTTGCTCACACCTTTAGTCCCAGCACTTTGGGAGGCTGAGGCAGGTGGATCACTT
GGGCCCAGGAGTTCAAGGCTGCAGTGAGCCAAGATTGTGCCACTACTCTCCAGGCTGGGCAACAGAGCAAGACCCT
GTCTCAGGGGGAACAAAAAGTTAATTTCAGATTTTGTTAAGTGCTGTAAAGGAAGTAAATAGGTTGATATTCAAGA
GAGCACCTGAAGGCCAGGCGTGGTGGCTCACGCCTGTGGTCTAACGCTTTGGGAAGCCCGAGCGGGCGGATCACAA
GGTCAGGAGAATTTTGGCCAGGCATGGTG
```

13736.1 (SEQ ID NO:51)

```
AGAATCCATTTATTGGGTTTTAAACTAGTTACACAACTGAAATCAGTTTGGCACTACTTTATACAGGGATTACGCC
TGTGTATGCCGACACTTAAATACTGTACCAGGACCACTGCTGTGCTTAGGTCTGTATTCAGTCATTCAGCATGTAG
ATACTAAAAATATACTGTAGTGTTCCTTTAAGGAAGACTGTACAGGGTGTGTTGCAAGATGACATTCACCAATTTG
TGAATTATTTCAACCCAGAAGATACCTTTCACTCTATAAACTTGTCATAGGCAAACATGTGGTGTTAGCATTGAGA
GATGCACACAAAAATGTTACATAAAAGTTCAGACATTCTAATGATAAGTGAACTGAAAAAAAAAAAAACCCCACAT
CTCAATTTTTGTAACAAGATAAAGAAAATAATTTAAAAACACAAAAAATGGCATTCAGTGGGTACAAAGCC
```

13737.1&2 (SEQ ID NO:52)

```
CAAATATTTAATATAAATCTTTGAAACAAGTTCAGAKGAAATAAAAATCAAAGTTTGCAAAAACGTGAAGATTAAC
TTAATTGTCAAATATTCCTCATTGCCCCAAATCAGTATTTTTTTTATTTCTATGCAAAAGTATGCCTTCAAACTGC
TTAAATGATATATGATATGATACACAAACCAGTTTTCAAATAGTAAAGCCAGTCATCTTGCAATTGTAAGAAATAG
GTAAAAGATTATAAGACACCTTACACACACACACACACACACACACACGTGTGCACcGCCAATGACAAAAAACA
ATTTGGCCTCTCCTAAAATAAGAACATGAAGACCCTTAATTGCTGCCAGGAGGGAACACTGTGTCACCCCTCCCTA
CAATCCAGGTAGTTTCCTTTAATCCAATAGCAAATCTGGGCATATTTGAGAGGAGTGATTCTGACAGCCACSGTTG
AAATCCTGTGGGGAACCATTCATGTCCACCCACTGGTGCCCTGAAAAAATGCCAATAATTTTTCGCTCCCACTTCT
GCTGCTGTCTCTTCCACATCCTCACATAGACCCCAGACCCGCTGGCCCCTGGCTGGGCATCGCATTGCTGGTAGAG
CAAGTCATAGGTCTCGTCTTTGACGTCACAGAAGCGATACACCAAATTGCCTGGTCGGTCATTGTCATAACCAG
```

*Fig. 1N*

13738.1 (SEQ ID NO:53)

```
TTTGACTTTAGTAGGGGTCTGAACTATTTATTTTACTTTGCCMGTAATATTTARACCYTATATATCTTTCATTATG
CCATCTTATCTTCTAATGBCAAGGGAACAGWTGCTAAMCTGGCTTCTGCATTWATCACATTAAAAATGGCTTTCTT
GGAAAATCTTCTTGATATGAATAAAGGATCTTTTAVAGCCATCATTTAAAGCMGGNTTCTCTCCAACACGAGTCTG
CTSASGGGGGGKGAGCTGTGAACTCTGGCTGAAGGCTTTCCCATACACACTGCAATGACMTGGTTTCTGACCAGBG
TGAGTTA
```

13738.2 (SEQ ID NO:54)

```
AGAGAAGCCCCATAAATGCAATCAGTGTGGGAAGGCCTTCAGTCAGAGCTCAAGCCTTTTCCTCCATCATCGGGTT
CATACTGGAGAGAAACCCTATGTATGTAATGAATGCGGCAGAGCCTTTGGTTTTAACTCTCATCTTACTGAACACG
TAAGGATTCACACAGGAGAAAAACCCTATGTTTGTAATGAGTGCGGCAAAGCCTTTCGTCGGAGTTCCACTCTTGT
TCAGCATCGAAGAGTTCACACTGGGGAGAAGCCCTACCAGTGCGTTGAATGTGGGAAAGCTTTCAGCCAGAGCTCC
CAGCTCACCCTACATCAGCCGAGTTCACACTGGAGAGAAGCCCTATGACTGTGGTGACTGTGGGAAGGCCTTCAGC
CGGAGGTCAACCCTCATTCAGCATCAGAAAGTTCACAGCGGAGAGACTCGTAAGTGCAGAAAACATGGTCCAGCCT
TTGTTCATGGCTCCAGCCTCACAGCAGATGGACAGATTCCCACTGGAGAGAAGCACGGCAGAACCTTTAACCATGG
TGCAAATCTCATTCTGCGCTGGACAGTTC
```

13739.1&2 (SEQ ID NO:55)

```
GAGACAGGGTCTCACTTTGTCACCCAGGCTGGAATGCAGTGGTGCGATCTTACGTAGCTCACTGCAGCCCTGACCT
CCTGGACTCAAACAATTCTCCTGCCTCAGCCCTGCAAGTAGCTGGGACTGTGGGTGCATGCCACCATGCCTGGCTA
ACTTTTGTAGTTTTTGTAAAGATGGGGTTTTGCCATGTTGCACATGCTGGTCTTGAACTCCTGAGCTCAAACGATC
TGCCCACCTCGGCCTCCCAGAATGTTGGGATTACAGGGGTAAACCACCACGCCTGGCCCATTAGGGTATTCTTAG
CATCCACTTGCTCACTGAGATTAATCATAAGAGATGATAAGCACTGGAAGAAAAAAATTTTTACTAGGCTTTGGAT
ATTTTTTTCCTTTTTCAGCTTTATACAGAGGATTGGATCTTTAGTTTTCCTTTAACTGATAATAAAACATTGAAAG
GAAATAAGTTTACCTGAGATTCACAGAGATAACCGGCATCACTCCCTTGCTCAATTCCAGTCTTTACCACATCAAT
TATTTTCAGAGGTGCAGGATAAAGGCCTTTAGTCTGCTTTCGCACTTTTTCTTCCACTTTTTTGTAAACCTGTTGC
CTGACAAATGGAATTGACAGCGTATGCCATGACTATTCCATTTGTCAGGCATACGCTGTCAATTTTTCCACCAATC
CCTTGTCTCTCTTTGGAGAGATCTTCTTATCAGCTAGTCCTTTGGCAAAAGTAATTGCAACTTCTTCTAGGTATTC
TATTGTCCGTTCCACTGGTGGAACCCCTGGGACCAGGACTAAAACCTCCAG
```

13741.1 (SEQ ID NO:56)

```
ATCTCATATATATATTTCTTCCTGACTTTATTTGCTTGCTTCTGNCACGCATTTAAAATATCACAGAGACCAAAAT
AGAGCGGCTTTCTGGTGGAACGCATGGCAGTCACAGGACAAAATACAAAACTAGGGGGCTCTGTCTTCTCATACAT
CATACAATTTTCAAGTATTTTTTTTATGTACAAAGAGCTACTCTATCTGAAAAAAAATTAAAAAATAAATGAGACA
AGATAGTTTATGCATCCTAGGAAGAAAGAATGGGAAGAAAGAACGGGGCAGTTGGGTACAGATTCCTGTCCCCTGT
TCCCAGGGACCACTACCTTCCTGCCACTGAGTTCCCCCACAGCCTCACCCATCATGTCACAGGGCAAGTGCCAGGG
TAGGTGGGGACCAGTGGAGACAGGAACCAGCAACATACTTTGGCCTGGAAGATAAGGAGAAAGTCTCAGAAACACA
CTGGTGGGAAGCAATCCCACNGGCCGTGCCCCANGAGCTTCCCACCTGCTGCTGGCTCCCTGGGTGGCTTTGGGAA
CAGCTTGGGCAGGCCCTTTTGGGTGGGGNCCAACTGGGCCTTTGGGCCCGTGTGGAAAG
```

*Fig. 10*

13742.1 (SEQ ID NO:57)

```
AAACATTGAGATGGAATGATAGGGTTTCCCAGAATCAGGTCCATATTTTAACTAAATGAAAATTATGATTTATAGC
CTTCTCAAATACCTGCCATACTTGATATCTCAACCAGAGCTAATTTTACCTCTTTACAAATTAAATAAGCAAGTAA
CTGGATCCACAATTTATAATACCTGTCAATTTTTTCTGTATTAAACCTCTATCATAGTTTAAGCCTATTAGGGTAC
TTAATCCTTACAAATAAACAGGTTTAAAATCACCTCAATAGGCAACTGCCCTTCTGGTTTTCTTCTTTGACTAAAC
AATCTGAATGCTTAAGATTTTCCACTTTGGGTGCTAGCAGTACACAGTGTTACACTCTGTATTCCAGACTTCTTAA
ATTATAGAAAAAGGAATGTACACTTTTTGTATTCTTTCTGAGCAGGGCCGGGAGGCAACATCATCTACCATGGTAG
GGACTTGTATGCATGGACTACTTTA
```

14351.1 (SEQ ID NO:58)

```
ACTCTGTCGCCCAGGCTGGAGCCCABTGGMGCGATCTCGACTCCCTGCAAGCTMCGCCTCACAGGWTCATGCCATT
CTCCTGCCTCAGCATCTGGAGTAGCTGGGACTACAGGCGCCAGCCACCATGCCCAGCTAATTTTT
```

14351.2 (SEQ ID NO:59)

```
ACCTTAAAGACATAGGAGAATTTATACTGGGAGAGAAAGCTTACAAATGTAAGGTTTCTGACAAGACTTGGGAGTG
ATTCACACCTGGAACAACATACTGGACTTCACACTGGABAGAAACCTTACAAGTGTAATGAGTGTGGCAAAGCCTT
TGGCAAGCAGTCAACACTTATTCACCATCAGGCAATTCA
```

14354.2 (SEQ ID NO:60)

```
AGTCAGGATCATGATGGCTCAGTTTCCCACAGCGATGAATGGAGGGCCAAATATGTGGGCTATTACATCTGAAGAA
CGTACTAAGCATGATAAACAGTTTGATAACCTCAAACCTTCAGGAGGTTACATAACAGGTGATCAAGCCCGTACTT
TTTTCCTACAGTCAGGTCTGCCGGCCCCGGTTTTAGCTGAAATATGGGCCTTATCAGATCTGAACAAGGATGGGAA
GATGGACCAGCAAGAGTTCTCTATAGCTATGAAACTCATCAAGTTAAAGTTGCAGGGCCAACAGCTGCCTGTAGTC
CTCCCTCCTATCATGAAACAACCCCCTATGTTCTCTCCACTAATCTCTGCTCGTTTTGGGATGGGAAGCATGCCCA
ATCTGTCCATTCATCAGCCATTGCCTCCAGTTGCACCTATAGCAACACCCTTGTCTTCTGCTACTTCAGGGACCAG
TATTCCTCCCTAATGATGCCTGCT
```

14354.1 (SEQ ID NO:61)

```
CTTTCGATTTCCTTCAATTTGTCACGTTTGATTTTATGAAGTTGTTCAAGGGCTAACTGCTGTGTATTATAGCTTT
CTCTGAGTTCCTTCAGCTGATTGTTAAATGAATCCATTTCTGAGAGCTTAGATGCAGTTTCTTTTTCAAGAGCATC
TAATTGTTCTTTAAGTCTTTGGCATAATTCTTCCTTTTCTGATGACTTTCTATGAAGTAAACTGATCCCTGAATCA
GGTGTGTTACTGAGCTGCATGTTTTTAATTCTTTCGTTTAATAGCTGCTTCTCAGGGACCAGATAGATAAGCTTAT
TTTGATATTCCTTAAGCTCTTGGTGAAGTTGTTCGATTTCCATAATTTCCAGGTCACACTGGTTATCCCAAACTTC
T
```

*Fig. 1P*

16431.1.2 (SEQ ID NO:62)

```
TGGAGGTGAAACGGAGGCAAGAAAGGGGGCTACCTCAGGAGCGAGGGACAAAGGGGGCGTGAGGCACCTAGGCCGC
GGCACCCCGGCGACAGGAAGCCGTCCTGAACCGGGCTACCGGGTAGGGGAAGGGCCCGCGTAGTCCTCGCAGGGCC
CCAGAGCTGGAGTCGGCTCCACAGCCCCGGGCCGTCGGCTTCTCACTTCCTGGACCTCCCCGGCGCCCGGGCCTGA
GGACTGGCTCGGCGGAGGGAGAAGAGGAAACAGACTTGAGCAGCTCCCCGTTGTCTCGCAACTCCACTGCCGAGGA
ACTCTCATTTCTTCCCTCGCTCCTTCACCCCCCACCTCATGTAGAAAGGTGCTGAAGCGTCCGGAGGGAAGAAGAA
CCTGGGCTACCGTCCTGGCCTTCCCMCCCCCTTCCCGGGGCGCTTTGGTGGGCGTGGAGTTGGGGTTGGGGGGGTG
GGTGGGGGTTCTTTTTTGGAGTGCTGGGGAACTTTTTTCCCTTCTTCAGGTCAGGGGAAAGGGAATGCCCAATTCA
GAGAGACATGGGGGCAAGAAGGACGGGAGTGGAGGAGCTTCTGGAACTTTGCAGCCGTCATCGGGAGGCGGCAGCT
CTAACAGCAGAGAGCGTCACCGCTTGGTATCGAAGCACAAGCGGCATAAGTCCAAACACTCCAAAGACATGGGGTT
GGTGACCCCGAAGCAGCATCCCTGGGCACAGTTATCAAACCTTTGGTGGAGTATGATGATATCAGCTCTGATTCC
GACACCTTCTCCGATGACATGGCCTTCAAACTAGACCGAAGGGAGAACGACGAACGTCGTGGATCAGATCGGAGCG
ACCGCCTGCACAAACATCGTCACCACCAGCACAGGCGTTCCCGGGACTTACTAAAAGCTAAACAGACCG
```

16432-1 (SEQ ID NO:63)

```
GACATGTTTGCCTGCAGGGGACCAGAGACAATGGGATTAGCCAGTGCTCACTGTTCTTTATGCTTCCAGAGAGGAT
GGGGACAGCTCTCAGGTCAGAATCCAGGCTGAGAAGGCCATGCTGGTTGGGGGCCCCCGGAAGCACGGTCCGGATC
CTCCCTGGCATCAGCGTAGACCCGCTGCTCAGGCTTGGGGTACCAAACTCATGCTCTGTACTGTTTTGGCCCCATG
CGGTGAGAGGAAAACCTAGAAAAAGATTGGTCGTGCTAAGGAATCAGCTGCCCCCTCATCCTCCGCATCCAATGCT
GGTGACAACATATTCCCTCTCCCAGGACACAGACTCGGTGACTCCACACTGGGCTGAGTGGCCTCTGGAGGCTCGT
GGCCTAAGGCAGGGCTCCGTAAGGCTGATCGGCTGAACTGGGTGGGGTGAGGGTTTCTGACCCTTCGCTTCCCATC
CCATAACCGCTGTCAATGAGCTCACACTGTGGTCA
```

16432-2 (SEQ ID NO:64)

```
GATGGCATGGTCGTTGCTAATGTGCCTGCTGGGATGGAGCACTTCCTCCTGTGAGCCCAGGGGACCCGCCTGTCCC
TGGAGCTTGGGGCAAGGAGGGAAGAGTGATACCAGGAAGGTGGGGCTGCAGCCAGGGGCCAGAGTCAGTTCAGGGA
GTGGTCCTCGGCCCTCAAAGCTCCTCCGGGGACTGCTCAGGAGTGATGGTGCCCTGGAGTTTGCCCCAACTTCCCT
GGCCACCCTGGAAGGTGCCTGGCTGCTCCAGGCCTCTAGGCTGGGCTGATGGGTTTCTCCAGGACACAAGTATCAT
TAAAGCCACCCTCTCCTCAGCTTGTCAGGCCGCACATGTGGGACAGGCTGTGCTCACAACCCCCTCGCCTGCCCTG
CCCTCCATCAGGAGGAGCCAGTGGAACCTTCGGAAAGCTCCCAGCATCTCAGCAGCCCTCAAAAGTCGTCCTGGGG
CAAGCTCTGGTTCTCCTGACTGGAGGTCATCTGGGCTTGGCCTGCTCTCTCTCGC
```

17184.3 (SEQ ID NO:65)

```
TAAAAAAGTGTAACAAAGGTTTATTTAGACTTTCTTCATGCCCCCAGATCCAGGATGTCTATGTAAACCGTTATCT
TACAAAGAAAGCACAATATTTGGTATAAACTAAGTCAGTGACTTGCTTAACTGAAATAGCGTCCATCCAAAAGTGG
GTTTAAGGTAAAACTACCTGACGATATTGGCGGGGATCCTGCAGTTTGGACTGCTTGCCGGGTTTGTCCAGGGTTC
CGGGTCTGTTCTTGGCACTCATGGGGACAGGCATCCTGCTCGTCTGTGGGGCCCCGCTGGAGCCCTTACGTGAAGC
TGAAGGTATCGACCSTAGGGGGCTCTAGGGCAGTGGGACCTTCATCCGGAACTAACAAGGGTCGGGGAGAGGCCTC
TTGGGCTATGTGGG
```

*Fig. 1Q*

17184.4 (SEQ ID NO:66)

```
CAAGCGTTCCTTTATGGATGTAAATTCAAACAGTCATGCTGAGCCATCCCGGGCTGACAGTCACGTTWAAGACACT
AGGTCGGGCGCCACAGTGCCACCCAAGGAGAAGAAGAATTTGGAATTTTTTCCATGAAGATGTACGGAAATCTGATG
TTGAATATGAAAATGGCCCCCAAATGGAATTCCAAAAGGTTACCACAGGGGCTGTAAGACCTAGTGACCCTCCTAA
GTGGGAAAGAGGAATGGAGAATAGTATTTCTGATGCATCAAGAACATCAGAATATAAAACTGAGATCATAATGAAG
GAAAATTCCATATCCAATATGAGTTTACTCAGAGACAGTAGAAACTATTCCCAGG
```

17185.1 (SEQ ID NO:67)

```
TAGGAATAACAAATGTTTATTCAGAAATGGATAAGTAATACATAATCACCCTTCATCTCTTAATGCCCCTTCCTCT
CCTTCTGCACAGGAGACACAGATGGGTAACATAGAGGCATGGGAAGTGGAGGAGGACACAGGACTAGCCCACCACC
TTCTCTTCCCGGTCTCCCAAGATGACTGCTTATAGAGTGGAGGAGGCAAACAGGTCCCCTCAATGTACCAGATGGT
CACCTATAGCACCAGCTCCAGATGGCCACGTGGTTGCAGCTGGACTCAATGAAACTCTGTGACAACCAGAAGATAC
CTGCTTTGGGATGAGAGGGAGGATAAAGCCATGCAGGGAGGATATTTACCATCCCTACCCTAAGCACAGTGCAAGC
AGTGAGCCCCCGGCTCCCAGTACCTGAAAAACCAAGGCCTACTGNCTTTTGGATGCTCTCTTGGGCCACG
```

17188.2 (SEQ ID NO:68)

```
AAGCCTCCTGCCCTGGAAATCTGGAGCCCCTTGGAGCTGAGCTGGACGGGGCAGGGAGGGGCTGAGAGGCAAGACC
GTCTCCCTCCTGCTGCAGCTGCTTCCCCAGCAGCCACTGCTGGGCACAGCAGAAACGCCAGCAGAGAAAATGGGAG
CCGAGAGTCCTTAGCCCTGGAGCTGAGGCTGCCTCTGGGCTGACCCGCTGGCTGTACGTGGCCAGAACTGGGGTTG
GCATCTGGCATCCATTTGAGGCCAGGGTGGAGGAAAGGGAGGCCAACAGAGGAAAACCTATTCCTGCTGTGACAAC
ACAGCCCTTGTCCCACGCAGCCTAAGTGCAGGGAGCGTGATGAAGTCAGGCAGCCAGTCGGGGAGGACGAGGTAAC
TCAGCAGCAATGTCACCTTGTAGCCTATGCGCTCAATGGCCCGGAGGGGCAGCAACCCCCCGCACACGTCAGCCAA
CAGCAGTGCCTCTGCAGGCACCAAGAGAGCGATGATGGACTTGAGCGCCGTGTTC
```

17190.1 (SEQ ID NO:69)

```
GTTTGGCAGAAGACATGTTTAATAACATTTTCATATTTAAAAAATACAGCAACAATTCTCTATCTGTCCACCATCT
TGCCTTGCCCTTCCTGGGGCTGAGGCAGACAAAGGAAAGGTAATGAGGTTAGGGCCCCCAGGCGGGCTAAGTGCTA
TTGGCCTGCTCCTGCTCAAAGAGAGCCATAGCCAGCTGGGCACGGCCCCCTAGCCCCTCCAGGTTGCTGAGGCGGC
AGCGGTGGTAGAGTTCTTCACTGAGCCGTGGGCTGCAGTCTCGCAGGGAGAACTTCTGCACCAGCCCTGGCTCTAC
GGCCCCGAAAGAGGTGGAGCCCTGAGAACCGGAGGAAAACATCCATCACCTCCAGCCCCTCCAGGGCTTCCTCCTCT
TCCTGGCCTGCCAGTTCACCTGCCAGCCGGGCTCGGGCCGCCAGGTAGTCAGCGTTGTAGAAGCAGCCCTCCGCAG
AAGCCTGCCGGTCAAATCTCCCCGCTATAGGAGCCCCCCGGGAGGGGTCAGCACC
```

*Fig. 1R*

17190.2 (SEQ ID NO:70)

CAAGTTGAACGTCAGGCTTGGCAGAGGTGGAGTGTAGATGAAAACAAAGGTGTGATTATGAAGAGGATGTGAGTCC
TTTGGGTGTAGGAGAGAAAGGCTGTTGAGCTTCTATTTCAAGATACTTTTACCTGTGCAAAAAGCACATTTTCCAC
CTCCTTCTCATGGCATTTGTGTAAGGTGAGTATGATTCCTATTCCATCTGCATTTTAGAGGTGAAGAATAACGTAC
AAGGGATTCAGTGATTAGCAAGGGACCCCTCACTAAGTGTTGATGGAGTTAGGACAGAGCTCAGCTGTTTGAATCT
CAGAGCCCAGGCAGCTGGAGCTGGGTAGGATCCTGGAGCTGGCACTAATGTGAGGTGCATTCCCTCCAACCCAGGC
TCAGATCCGGAACCTGACCGTGCTGACCCCCGAAGGGGAGGCAGGGCTGAGCTGGCCCGTTGGGCTCCCTGCTCCT
TTCACACCACACTCTCGCTTTGAGGTGCTGGGCTGGGACTACTTCACAGAGCAGC

17191.2&89.2 (SEQ ID NO:71)

TGGCCTGGGCAGGATTGGGAGAGAGGTAGCTACCCGGATGCAGTCCTTTGGGATGAAGACTATAGGGTATGACCCC
ATCATTTCCCCAGAGGTCTCGGCCTCCTTTGGTGTTCAGCAGCTGCCCCTGGAGGAGATCTGGCCTCTCTGTGATT
TCATCACTGTGCACACTCCTCTCCTGCCCTCCACGACAGGCTTGCTGAATGACAACACCTTTGCCCAGTGCAAGAA
GGGGGTGCGTGTGGTGAACTGTGCCCGTGGAGGGATCGTGGACGAAGGCGCCCTGCTCCGGGCCCTGCAGTCTGGC
CAGTGTGCCGGGGCTGCACTGGACGTGTTTACGGAAGAGCCGCCACGGGACCGGGCCTTGGTGGACCATGAGAATG
TCATCAGCTGTCCCCACCTGGGTGCCAGCACCAAGGAGGCTCAGAGCCGCTGTGGGGAGGAAATTGCTGTTCAGTT
CGTGGACATGGTGAAGGGGAAATCTCTCACGGGGGTTGTGAATGCCCAGGCCCTT

*Fig. 1S*

```
AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTAC
ATCCTCATTACCAAATGGAACTGCCAGTCTCATTCAGCCTTTATCCATTCCTTATTCTTCTTCAACATTGCCTCAT
GCATCATCTTACAGCCTGATGATGGGAGGATTTGGTGGTGCTAGTATCCAGAAGGCCCAGTCTCTGATTGATTTAG
GATCTAGTAGCTCAACTTCCTCAACTGCTTCCCTCTCAGGGAACTCACCTAAGACAGGGACCTCAGAGTGGGCAGT
TCCTCAGCCTTCAAGATTAAAGTATCGGCAAAAATTTAATAGTCTAGACAAAGGCATGAGCGGATACCTCTCAGGT
TTTCAAGCTAGAAATGCCCTTCTTCAGTCAAATCTCTCTCAAACTCAGCTAGCTACTATTTGGACTCTGGCTGACA
TCGATGGTGACGGACAGTTGAAAGCTGAAGAATTTATTCTGGCGATGCACCTCACTGACATGGCCAAAGCTGGACA
GCCACTACCACTGACGTTGCCTCCCGAGCTTGTCCCTCCATCTTTCAGAGGGGGAAAGCAAGTTGATTCTGTTAAT
GGAACTCTGCCTTCATATCAGAAAACACAAGAAGAAGAGCCTCAGAAGAAACTGCCAGTTACTTTTGAGGACAAAC
GGAAAGCCAACTATGAACGAGGAAACATGGAGCTGGAGAAGCGACGCCAAGTGTTGATGGAGCAGCAGCAGAGGGA
GGCTGAACGCAAAGCCCAGAAAGAGAAGGAAGAGTGGGAGCGGAAACAGAGAGAACTGCAAGAGCAAGAATGGAAG
AAGCAGCTGGAGTTGGAGAAACGCTTGGAGAAACAGAGAGAGCTGGAGAGACAGCGGGAGGAAGAGAGGAGAAAGG
AGATAGAAAGACGAGAGGCAGCAAAACAGGAGCTTGAGAGACAACGCCGTTTAGAATGGGAAAGACTCCGTCGGCA
GGAGCTGCTCAGTCAGAAGACCAGGGAACAAGAAGACATTGTCAGGCTGAGCTCCAGAAAGAAAAGTCTCCACCTG
GAACTGGAAGCAGTGAATGGAAAACATCAGCAGATCTCAGGCAGACTACAAGATGTCCAAATCAGAAAGCAAACAC
AAAAGACTGAGCTAGAAGTTTTGGATAAACAGTGTGACCTGGAAATTATGGAAATCAAACAACTTCAACAAGAGCT
TAAGGAATATCAAAATAAGCTTATCTATCTGGTCCCTGAGAAGCAGCTATTAAACGAAAGAATTAAAAACATGCAG
CTCAGTAACACACCTGATTCAGGGATCAGTTTACTTCATAAAAAGTCATCAGAAAAGGAAGAATTATGCCAAAGAC
TTAAAGAACAATTAGATGCTCTTGAAAAAGAAACTGCATCTAAGCTCTCAGAAATGGATTCATTTAACAATCAGCT
GAAGGAACTCAGAGAAAGCTATAATACACAGCAGTTAGCCCTTGAACAACTTCATAAAATCAAACGTGACAAATTG
AAGGAAATCGAAAGAAAAAGATTAGAGCAAAAAAAAAAAAAA
```

*Fig. 2A*

```
ATGGCAGTGACATTCACCATCATGGGAACCACCTTCCCTTTTCTTCAGGATTCTCTGTAGTGGAAGAGAGCACCCA
GTGTTGGGCTGAAAACATCTGAAAGTAGGGAGAAGAACCTAAAATAATCAGTATCTCAGAGGGCTCTAAGGTGCCA
AGAAGTCTCACTGGACATTTAAGTGCCAACAAAGGCATACTTTCGGAATCGCCAAGTCAAAACTTTCTAACTTCTG
TCTCTCTCAGAGACAAGTGAGACTCAAGAGTCTACTGCTTTAGTGGCAACTACAGAAAACTGGTGTTACCCAGAAA
AACAGGAGCAATTAGAAATGGTTCCAATATTTCAAAGCTCCGCAAACAGGATGTGCTTTCCTTTGCCCATTTAGGG
TTTCTTCTCTTTCCTTTCTCTTTATTAACCACTA
```

*Fig. 2B*

```
ATATCTAGAAGTCTGGAGTGAGCAAACAAGAGCAAGAAACAAAAAGAAGCCAAAAGCAGAAGGCTCCAATATGAAC
AAGATAAATCTATCTTCAAAGACATATTAGAAGTTGGGAAAATAATTCATGTGAACTAGACAAGTGTGTTAAGAGT
GATAAGTAAAATGCACGTGGAGACAAGTGCATCCCCAGATCTCAGGGACCTCCCCCTGCCTGTCACCTGGGGAGTG
AGAGGACAGGATAGTGCATGTTCTTTGTCTCTGAATTTTTAGTTATATGTGCTGTAATGTTGCTCTGAGGAAGCCC
CTGGAAAGTCTATCCCAACATATCCACATCTTATATTCCACAAATTAAGCTGTAGTATGTACCCTAAGACGCTGCT
AATTGACTGCCACTTCGCAACTCAGGGGCGGCTGCATTTTAGTAATGGGTCAAATGATTCACTTTTTATGATGCTT
CCAAAGGTGCCTTGGCTTCTCTTCCCAACTGACAAATGCCAAAGTTGAGAAAAATGATCATAATTTTAGCATAAAC
AGAGCAGTCGGCGACACCGATTTTATAAATAAACTGAGCACCTTCTTTTTAAACAAACAAATGCGGGTTTATTTCT
CAGATGATGTTCATCCGTGAATGGTCCAGGGAAGGACCTTTCACCTTGACTATATGGCATTATGTCATCACAAGCT
CTGAGGCTTCTCCTTTCCATCCTGCGTGGACAGCTAAGACCTCAGTTTTCAATAGCATCTAGAGCAGTGGGACTCA
GCTGGGGTGATTTCGCCCCCCATCTCCGGGGGAATGTCTGAAGACAATTTTGTTACCTCAATGAGGGAGTGGAGGA
GGATACAGTGCTACTACCAACTAGTGGATAAAGGCCAGGGATGCTGCTCAACCTCCTACCATGTACAGGACGTCTC
CCCATTACAACTACCCAATCCGAAGTGTCAACTGTGTCAGGACTAAGAAACCCTGGTTTTGAGTAGAAAAGGGCCT
GGAAAGAGGGGAGCCAACAAATCTGTCTGCTTCCTCACATTAGTCATTGGCAAATAAGCATTCTGTCTCTTTGGCT
GCTGCCTCAGCACAGAGAGCCAGAACTCTATCGGGCACCAGGATAACATCTCTCAGTGAACAGAGTTGACAAGGCC
TATGGGAAATGCCTGATGGGATTATCTTCAGCTTGTTGAGCTTCTAAGTTTCTTTCCCTTCATTCTACCCTGCAAG
CCAAGTTCTGTAAGAGAAATGCCTGAGTTCTAGCTCAGGTTTTCTTACTCTGAATTTAGATCTCCAGACCCTTCCT
GGCCACAATTCAAATTAAGGCAACAAACATATACCTTCCATGAAGCACACACAGACTTTTGAAAGCAAGGACAATG
ACTGCTTGAATTGAGGCCTTGAGGAATGAAGCTTTGAAGGAAAAGAATACTTTGTTTCCAGCCCCCTTCCCACACT
CTTCATGTGTTAACCACTGCCTTCCTGGACCTTGGAGCCACGGTGACTGTATTACATGTTGTTATAGAAAACTGAT
TTTAGAGTTCTGATCGTTCAAGAGAATGATTAAATATACATTTCCTA
```

```
TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT
```

Fig. 4

```
TAGCGYGGTCGCGGCCGAGGYCTGCTTYTCTGTCCAGCCCAGGGCCTGTGGGGTCAGGGCGGTGGGTGCAGATGGC
ATCCACTCCGGTGGCTTCCCCATCTTTCTCTGGCCTGAGCAAGGTCAGCCTGCAGCCAGAGTACAGAGGGCCAACA
CTGGTGTTCTTGAACAAGGGCCTTAGCAGGCCCTGAAGGRCCCTCTCTGTAGTGTTGAACTTCCTGGAGCCAGGCC
ACATGTTCTCCTCATACCGCAGGYTAGYGATGGTGAAGTTGAGGGTGAAATAGTATTMANGRAGATGGCTGGCARA
CCTGCCCGGGCGGCCGCTCSAAATCC
```

*Fig. 5*

```
AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA
```

TTGGGGNTTTMGAGCGGCCGCCCGGGCAGGTACCGGGGTGGTCAGCGAGGAGCCATTCACACTGAACTTCACCATC
AACAACCTGCGGTATGAGGAGAACATGCAGCACCCTGGCTCCAGGAAGTTCAACACCACGGAGAGGGTCCTTCAGG
GCCTGCTCAGGTCCCTGTTCAAGAGCACCAGTGTTGGCCCTCTGTACTCTGGCTGCAGACTGACTTTGCTCAGACT
TGAGAAACATGGGGCAGCCACTGGAGTGGACGCCATCTGCACCCTCCGCCTTGATCCCACTGGTCCTGGACTGGAC
AGAGAGCGGCTATACTGGGAGCTGAGCCAGTCCTCTGGCGGNGACNCCNCTT

Fig. 7B

AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 7A and 7B*

```
TGTGGTGTTGAACTTCCTGGAGNCAGGGTGACCCATGTCCTCCCCATACTGCAGGTTGGTGATGGTGAAGTTGAGG
GTGAATGGTACCAGGAGAGGGCCAGCAGCCATAATTGTSGRGCKGSMGMSSGAGGMWGGWGTYYCWGAGGTTCYRA
RRTCCACTGTGGAGGTCCCAGGAGTGCTGGTGGTGGGCACAGAGSTCYGATGGGTGAAACCATTGACATAGAGACT
GTTCCTGTCCAGGGTGTAGGGGCCCAGCTCTTYRATGYCATTGGYCAGTTKGCTYAGCTCCCAGTACAGCCRCTCT
CKGYYGMGWCCAGSGCTTTTGGGGTCAAGATGATGGATGCAGATGGCATCCACTCCAGTGGCTGCTCCATCCTTCT
CGGACCTGAGAGAGGTCAGTCTGCAGCCAGAGTACAGAGGGCCAACACTGGTGTTCTTTGAATA
```

*Fig. 8*

```
TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG
```

*Fig. 9*

| Gene Name | Bal Exp | Probe 1 Name | P1 | | P2 | Probe 2 Name | GEM ID | Probe1 Value | Probe2 Value | Probe1 B/B | Probe1 A% | Probe2 B/B | Probe2 A% |
|---|---|---|---|---|---|---|---|---|---|---|---|---|---|
| 42100188 [D3] | +7.0 | 205A Ovary T | | | | 270A Liver N | 422Q0606 | 8620 | 1240 | 57.7 | 65 | 2.2 | 65 |
| 42100188 [D3] | +5.9 | S23 Ovary T | | | | S56 Spinal Cord N | 422G0628 | 5894 | 1002 | 35.3 | 89 | 3.9 | 89 |
| 42100188 [D3] | +5.7 | 385A Ovary T | | | | S91 Fetal tissue | 422X0607 | 12151 | 2121 | 54.3 | 73 | 2.8 | 73 |
| 42100188 [D3] | +5.1 | 426A Ovary T (met) | | | | 415A Aorta N | 422X0611 | 7487 | 1480 | 53.0 | 73 | 9.7 | 73 |
| 42100188 [D3] | +3.5 | 263A Ovary T | | | | S73 Breast N | 422H0623 | 7302 | 2116 | 39.2 | 84 | 4.5 | 84 |
| 42100188 [D3] | +3.3 | 381A Ovary T (met) | | | | I1 Colon N | 422B0609 | 3714 | 1113 | 20.4 | 83 | 2.6 | 83 |
| 42100188 [D3] | +3.0 | 9334 Ovary T (SCID) | | | | I2 Skin N | 422R0601 | 2435 | 814 | 12.1 | 75 | 2.1 | 75 |
| 42100188 [D3] | +2.6 | 384A Ovary T (met) | | | | 272A Dendritic cell | 42240608 | 4578 | 1754 | 25.0 | 69 | 2.3 | 69 |
| 42100188 [D3] | +2.2 | 264A Ovary T | | | | S2 Pancreas N | 422N0629 | 7904 | 3596 | 38.5 | 81 | 5.6 | 81 |
| 42100188 [D3] | +2.0 | 386A Ovary T | | | | S40 PBMC (activat | 42210605 | 2191 | 1081 | 14.0 | 90 | 2.9 | 90 |
| 42100188 [D3] | +2.0 | S115 Ovary T (mets) | | | | CT10 Small intestin | 422C0604 | 1979 | 971 | 10.4 | 80 | 2.7 | 80 |
| 42100188 [D3] | +2.0 | 265A Ovary T | | | | CT5 Heart N | 422O0624 | 1911 | 964 | 13.9 | 93 | 3.4 | 93 |
| 42100188 [D3] | +2.0 | 335A Ovary T | | | | S7 Ovary N | 42220626 | 1666 | 817 | 9.8 | 100 | 3.0 | 100 |
| 42100188 [D3] | -1.9 | 428A Ovary T (met) | | | | 243A Esophagus N | 42240612 | 1827 | 3480 | 13.4 | 97 | 9.5 | 97 |
| 42100188 [D3] | +1.6 | 261A Ovary T | | | | S10 Skeletal muscl | 42230621 | 5914 | 3653 | 30.4 | 86 | 6.0 | 86 |
| 42100188 [D3] | +1.6 | 266A Ovary T | | | | S27 Ovary N | 42250603 | 2039 | 1274 | 11.9 | 50 | 2.6 | 50 |
| 42100188 [D3] | +1.6 | S22 Ovary T | | | | C19 Kidney N | 42290627 | 1736 | 1072 | 11.0 | 92 | 4.0 | 92 |
| 42100188 [D3] | +1.4 | 9485 OT-1-P (SCID) | | | | 9485 OT-5-P (SCID) | 422Y0602 | 4204 | 3074 | 23.0 | 93 | 7.7 | 93 |
| 42100188 [D3] | +1.4 | 262A Ovary T | | | | 334A Large Intestin | 422A0622 | 3002 | 2101 | 16.6 | 89 | 4.0 | 89 |
| 42100188 [D3] | +1.3 | S25 Ovary T | | | | CT4 Bone Marrow | 422H0619 | 1643 | 1297 | 9.6 | 90 | 3.1 | 90 |
| 42100188 [D3] | +1.2 | 429A Ovary T (met) | | | | 364A Ovary N | 42210614 | 2521 | 2084 | 22.0 | 65 | 23.9 | 65 |
| 42100188 [D3] | +1.2 | 382A Ovary T | | | | CT19 Brain N | 422Q0610 | 2072 | 1663 | 10.9 | 88 | 2.3 | 88 |
| 42100188 [D3] | +1.2 | 288A Ovary T | | | | CT12 Lung N | 422V0625 | 1840 | 1473 | 10.7 | 87 | 3.8 | 87 |
| 42100188 [D3] | +1.1 | 201A Ovary T | | | | S6 Stomach N | 422W0620 | 1329 | 1204 | 9.1 | 90 | 3.5 | 90 |

Fig. 10

| Gene Name | Bal Exp | Probe 1 Name | P1 | P2 | Probe 2 Name | QEM ID | Probe1 Value | Probe2 Value | Probe1 S/B | Probe1 A% | Probe2 S/B | Probe2 A% |
|---|---|---|---|---|---|---|---|---|---|---|---|---|
| 421B0181 (C3) | +18.8 | 385A Ovary T | | | S91 Fetal tissue | 422X0607 | 26711 | 1424 | 103.3 | 54 | 2.0 | 54 |
| 421B0181 (C3) | +11.5 | S23 Ovary T | | | S56 Spinal Cord N | 422G0628 | 13559 | 1179 | 65.3 | 68 | 3.9 | 68 |
| 421B0181 (C3) | +11.1 | 426A Ovary T | | | 415A Aorta N | 422X0611 | 14125 | 1273 | 67.3 | 61 | 5.6 | 61 |
| 421B0181 (C3) | +10.8 | 205A Ovary T | | | 270A Liver N | 422Q0606 | 16121 | 1488 | 93.1 | 43 | 2.3 | 43 |
| 421B0181 (C3) | +5.1 | 263A Ovary T | | | S73 Breast N | 422H0623 | 11326 | 2235 | 58.2 | 68 | 4.4 | 68 |
| 421B0181 (C3) | +4.6 | 384A Ovary T (mets) | | | 272A Dendritic cells | 42240608 | 6583 | 1424 | 24.5 | 40 | 2.1 | 40 |
| 421B0181 (C3) | +4.4 | 264A Ovary T | | | S2 Pancreas N | 422N0629 | 9865 | 2245 | 40.9 | 64 | 3.6 | 64 |
| 421B0181 (C3) | +4.4 | 429A Ovary T (mets) | | | 364A Ovary N | 42210614 | 2803 | 638 | 22.6 | 60 | 7.4 | 60 |
| 421B0181 (C3) | +4.2 | 261A Ovary T | | | S10 Skeletal muscle N | 42230621 | 8271 | 1949 | 39.5 | 68 | 3.6 | 68 |
| 421B0181 (C3) | +3.8 | S115 Ovary T (mets) | | | CT10 Small intestine N | 22C0604 | 2281 | 607 | 11.6 | 60 | 2.1 | 60 |
| 421B0181 (C3) | +2.5 | 265A Ovary T | | | CT5 Heart N | 422O0624 | 3192 | 1293 | 19.2 | 68 | 4.0 | 68 |
| 421B0181 (C3) | -2.3 | S22 Ovary T | | | CT9 Kidney N | 422Y0627 | 565 | 1276 | 3.6 | 70 | 3.9 | 70 |
| 421B0181 (C3) | +2.2 | 266A Ovary T | | | S27 Ovary N | 42250603 | 2774 | 1260 | 14.3 | 46 | 2.7 | 46 |
| 421B0181 (C3) | +2.1 | 9334 Ovary T (SCID) | | | I2 Skin N | 422R0601 | 1774 | 837 | 8.4 | 56 | 2.1 | 56 |
| 421B0181 (C3) | +1.9 | 9485 OT 1-P (SCID) | | | 9485 OT 5-P (SCID) | 422Y0602 | 6967 | 3726 | 41.5 | 70 | 9.2 | 70 |
| 421B0181 (C3) | +1.6 | 382A Ovary T | | | CT19 Brain N | 422Q0610 | 2313 | 1471 | 6.2 | 50 | 1.9 | 50 |
| 421B0181 (C3) | +1.6 | 288A Ovary T | | | CT12 Lung N | 422V0625 | 1657 | 1054 | 9.7 | 69 | 2.9 | 69 |
| 421B0181 (C3) | -1.5 | S25 Ovary T | | | CT4 Bone Marrow N | 422H0619 | 848 | 1243 | 4.5 | 65 | 2.7 | 65 |
| 421B0181 (C3) | +1.4 | 262A Ovary T | | | 334A Large Intestine | 422A0622 | 3171 | 2214 | 16.8 | 69 | 3.8 | 69 |
| 421B0181 (C3) | +1.2 | 386A Ovary T | | | S40 PBMC (activated) | 42210605 | 630 | 544 | 4.2 | 53 | 1.9 | 53 |
| 421B0181 (C3) | -1.2 | 335A Ovary T | | | S7 Ovary T | 42220626 | 592 | 730 | 3.7 | 75 | 2.6 | 75 |
| 421B0181 (C3) | -1.0 | 201A Ovary T | | | S6 Stomach N | 422W0620 | 1197 | 1237 | 7.8 | 65 | 3.5 | 65 |
| 421B0181 (C3) | -1.0 | 428A Ovary T (mets) | | | 243A Esophagus N | 42240612 | 783 | 797 | 4.5 | 95 | 2.4 | 95 |
| 421B0181 (C3) | | 383A Ovary T (mets) | | | I1 Colon N | 422B0609 | 3470 | 862 | 8.9 | 24 | 1.7 | 24 |

*Fig. 11*

| Gene Name | Bal Exp | Probe 1 Name | P1 | | | Probe 2 Name | P2 | GEM ID | Probe1 Value | Probe2 Value | Probe1 S/B | Probe1 A% | Probe2 S/B | Probe2 A% |
|---|---|---|---|---|---|---|---|---|---|---|---|---|---|---|
| 42110182 (H7) | +16.7 | 426A Ovary T (met) | | | | 415A Aorta N | | 422X0611 | 7706 | 462 | 46.3 | 75 | 3.5 | 75 |
| 42110182 (H7) | +10.7 | 205A Ovary T | | | | 270A Liver N | | 422Q0606 | 10171 | 950 | 61.2 | 41 | 1.8 | 41 |
| 42110182 (H7) | +9.9 | 385A Ovary T | | | | S91 Fetal tissue | | 422X0607 | 14415 | 1459 | 62.1 | 48 | 2.2 | 48 |
| 42110182 (H7) | +8.8 | S23 Ovary T | | | | S56 Spinal Cord N | | 422H0628 | 7781 | 880 | 47.3 | 73 | 3.4 | 73 |
| 42110182 (H7) | +6.4 | 383A Ovary T | | | | I1 Colon N | | 422B0609 | 4807 | 748 | 27.6 | 47 | 2.2 | 47 |
| 42110182 (H7) | +5.1 | 263A Ovary T | | | | S73 Breast N | | 422H0623 | 9815 | 1909 | 57.1 | 74 | 4.2 | 74 |
| 42110182 (H7) | +4.9 | 429A Ovary T (met) | | | | 364A Ovary N | | 422I0614 | 2661 | 543 | 20.3 | 61 | 6.7 | 61 |
| 42110182 (H7) | +3.5 | 264A Ovary T | | | | S2 Pancreas N | | 422N0629 | 7934 | 2274 | 38.8 | 71 | 3.9 | 71 |
| 42110182 (H7) | -2.9 | S25 Ovary T | | | | CT4 Bone Marrow | | 422H0619 | 480 | 1375 | 3.5 | 80 | 3.0 | 80 |
| 42110182 (H7) | +2.8 | 261A Ovary T | | | | S10 Skeletal muscle | | 422J0621 | 8993 | 3245 | 34.6 | 69 | 5.1 | 69 |
| 42110182 (H7) | +2.5 | S115 Ovary T (mets) | | | | CT10 Small intestine | | 422C0604 | 1864 | 738 | 8.1 | 67 | 2.2 | 67 |
| 42110182 (H7) | +2.3 | 9334 Ovary T (SCID) | | | | I2 Skin N | | 422R0601 | 2552 | 1113 | 12.7 | 41 | 2.6 | 41 |
| 42110182 (H7) | -2.3 | S22 Ovary T | | | | C19 Kidney N | | 422Q0627 | 386 | 889 | 3.2 | 69 | 3.4 | 69 |
| 42110182 (H7) | +2.2 | 384A Ovary T (met) | | | | 272A Dendritic cell | | 422O0608 | 3516 | 1567 | 18.7 | 55 | 2.2 | 55 |
| 42110182 (H7) | -2.2 | 382A Ovary T | | | | CT19 Brain N | | 422Q0610 | 608 | 1320 | 4.2 | 60 | 2.3 | 60 |
| 42110182 (H7) | +1.9 | 265A Ovary T | | | | CT5 Heart N | | 422O0624 | 2063 | 1080 | 13.6 | 87 | 3.5 | 87 |
| 42110182 (H7) | +1.8 | 266A Ovary T | | | | S27 Ovary N | | 422J0603 | 1550 | 847 | 7.0 | 58 | 2.1 | 58 |
| 42110182 (H7) | +1.5 | 262A Ovary T | | | | 334A Large Intestine | | 422A0622 | 2559 | 1651 | 13.2 | 73 | 3.2 | 73 |
| 42110182 (H7) | -1.4 | 386A Ovary T | | | | S40 PBMC (activat) | | 422J0605 | 534 | 738 | 3.9 | 62 | 2.2 | 62 |
| 42110182 (H7) | -1.3 | 288A Ovary T | | | | CT12 Lung N | | 422V0625 | 893 | 1120 | 5.3 | 66 | 3.1 | 66 |
| 42110182 (H7) | -1.3 | 335A Ovary T | | | | S7 Ovary N | | 422O0626 | 440 | 567 | 3.3 | 60 | 2.2 | 60 |
| 42110182 (H7) | +1.2 | 9485 OT 1-P (SCID) | | | | 9485 OT S-P (SCID) | | 422Y0602 | 4188 | 3529 | 21.6 | 66 | 9.5 | 66 |
| 42110182 (H7) | +1.1 | 428A Ovary T (met) | | | | 243A Esophagus N | | 422J0612 | 725 | 689 | 6.2 | 65 | 2.8 | 65 |
| 42110182 (H7) | -1.0 | 201A Ovary T | | | | S6 Stomach N | | 422W0620 | 1008 | 1018 | 7.4 | 62 | 3.2 | 62 |

Fig. 12

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421V0189_[D1] | +33.2 | 426A Ovary T (mets) | | | 415A Aorta N | 422X0611 | 8072 | 243 | 55.2 | 67 | 2.4 | 67 |
| 421V0189_[D1] | +13.7 | S23 Ovary T | | | S56 Spinal Cord N | 422G0628 | 7367 | 537 | 42.6 | 69 | 2.5 | 69 |
| 421V0189_[D1] | +12.6 | 429A Ovary T (mets) | | | 364A Ovary N | 422I0614 | 2850 | 227 | 21.7 | 64 | 3.5 | 64 |
| 421V0189_[D1] | +8.0 | 385A Ovary T | | | S91 Fetal tissue | 422X0607 | 11711 | 1469 | 54.0 | 58 | 2.2 | 58 |
| 421V0189_[D1] | +7.3 | 263A Ovary T | | | S73 Breast N | 422H0623 | 6949 | 952 | 37.8 | 69 | 2.6 | 69 |
| 421V0189_[D1] | -5.8 | S25 Ovary T | | | CT4 Bone Marrow N | 422H0619 | 208 | 1210 | 2.1 | 44 | 2.9 | 44 |
| 421V0189_[D1] | +5.0 | 205A Ovary T | | | 270A Liver N | 422Q0606 | 8676 | 1737 | 52.3 | 57 | 2.6 | 57 |
| 421V0189_[D1] | +4.5 | 383A Ovary T (mets) | | | I1 Colon N | 422B0609 | 3149 | 707 | 17.4 | 57 | 2.0 | 57 |
| 421V0189_[D1] | +4.4 | 261A Ovary T | | | S10 Skeletal muscle | 422J0621 | 6332 | 1443 | 29.1 | 77 | 2.9 | 77 |
| 421V0189_[D1] | +4.2 | 264A Ovary T | | | S2 Pancreas N | 422N0629 | 7612 | 1809 | 38.1 | 79 | 3.3 | 79 |
| 421V0189_[D1] | -3.2 | 382A Ovary T | | | CT19 Brain N | 422Q0610 | 468 | 1508 | 3.4 | 60 | 2.3 | 60 |
| 421V0189_[D1] | +2.9 | 9334 Ovary T (SCID) | | | I2 Skin N | 422R0601 | 2500 | 860 | 12.3 | 51 | 2.1 | 51 |
| 421V0189_[D1] | +2.5 | S115 Ovary T (mets) | | | CT10 Small intestine N | 422C0604 | 1424 | 569 | 6.7 | 61 | 2.1 | 61 |
| 421V0189_[D1] | +2.4 | 265A Ovary T | | | CT5 Heart N | 422O0624 | 1742 | 723 | 11.8 | 70 | 2.8 | 70 |
| 421V0189_[D1] | +2.3 | 384A Ovary T (mets) | | | 272A Dendritic cells | 422J0608 | 3083 | 1342 | 17.0 | 62 | 2.0 | 62 |
| 421V0189_[D1] | +1.9 | 266A Ovary T | | | S27 Ovary N | 422S0603 | 1370 | 732 | 8.0 | 47 | 2.0 | 47 |
| 421V0189_[D1] | -1.9 | 386A Ovary T | | | S40 PBMC (activated) | 422J0605 | 307 | 580 | 2.6 | 41 | 2.0 | 41 |
| 421V0189_[D1] | +1.7 | 202A Ovary T | | | 334A Large Intestine N | 422A0622 | 2097 | 1202 | 11.2 | 86 | 2.7 | 86 |
| 421V0189_[D1] | -1.3 | 335A Ovary T | | | S7 Ovary N | 422O0626 | 373 | 470 | 2.9 | 47 | 2.0 | 47 |
| 421V0189_[D1] | -1.1 | 288A Ovary T | | | CT12 Lung N | 422V0625 | 969 | 1094 | 5.6 | 72 | 2.9 | 72 |
| 421V0189_[D1] | +1.1 | 201A Ovary T | | | S6 Stomach N | 422W0620 | 750 | 672 | 5.6 | 62 | 2.4 | 62 |
| 421V0189_[D1] | +1.1 | 428A Ovary T (mets) | | | 243A Esophagus N | 422J0610 | 498 | 446 | 4.2 | 73 | 2.1 | 73 |
| 421V0189_[D1] | -1.0 | 9485 OT 1-P (SCID) | | | 9485 OT 5-P (SCID) | 422Y0602 | 3117 | 3174 | 16.7 | 91 | 8.2 | 91 |
| 421V0189_[D1] | | S22 Ovary T | | | C19 Kidney N | 422O0627 | 224 | 409 | 2.3 | 48 | 2.3 | 48 |

*Fig. 13*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421H0187 [E11] | +20.2 | 426A Ovary T (met) | | | 415A Aorta N | 422X0611 | 5441 | 270 | 36.3 | 50 | 2.3 | 50 |
| 421H0187 [E11] | +10.0 | S23 Ovary T | | | S56 Spinal Cord N | 422G0628 | 5318 | 533 | 27.1 | 56 | 2.3 | 56 |
| 421H0187 [E11] | +8.3 | 429A Ovary T (met) | | | 364A Ovary N | 422I0614 | 1252 | 150 | 10.1 | 58 | 2.5 | 58 |
| 421H0187 [E11] | +5.7 | 385A Ovary T | | | S91 Fetal tissue | 422X0607 | 9507 | 1668 | 35.8 | 45 | 2.1 | 45 |
| 421H0187 [E11] | +4.4 | 205A Ovary T | | | 270A Liver N | 422Q0606 | 5456 | 1235 | 31.1 | 50 | 2.0 | 50 |
| 421H0187 [E11] | +4.2 | 265A Ovary T | | | CT5 Heart N | 422O0624 | 1834 | 438 | 11.9 | 48 | 2.0 | 48 |
| 421H0187 [E11] | -4.1 | 382A Ovary T | | | CT19 Brain N | 422Q0610 | 309 | 1259 | 2.6 | 48 | 2.0 | 48 |
| 421H0187 [E11] | +3.6 | 261A Ovary T | | | S10 Skeletal muscle | 422230621 | 3733 | 1036 | 17.7 | 55 | 2.3 | 55 |
| 421H0187 [E11] | +3.4 | 263A Ovary T | | | S73 Breast N | 422H0623 | 4163 | 1239 | 23.0 | 62 | 3.0 | 62 |
| 421H0187 [E11] | +2.5 | S115 Ovary T (met) | | | CT10 Small intestin | 422C0604 | 1565 | 627 | 8.8 | 47 | 2.1 | 47 |
| 421H0187 [E11] | +2.1 | 264A Ovary T | | | S2 Pancreas N | 422N0629 | 3455 | 1630 | 14.9 | 60 | 3.0 | 60 |
| 421H0187 [E11] | +2.1 | 384A Ovary T (met) | | | 272A Dendritic cell | 422240608 | 2667 | 1270 | 13.4 | 44 | 1.9 | 44 |
| 421H0187 [E11] | -2.1 | S22 Ovary T | | | CT9 Kidney N | 42290627 | 291 | 605 | 2.4 | 51 | 2.5 | 51 |
| 421H0187 [E11] | -1.7 | 386A Ovary T | | | S40 PBMC (activat | 42210605 | 410 | 687 | 3.2 | 47 | 2.0 | 47 |
| 421H0187 [E11] | +1.6 | 9334 Ovary T (SCII | | | I2 Skin N | 422R0601 | 1622 | 984 | 7.9 | 44 | 2.2 | 44 |
| 421H0187 [E11] | +1.5 | 262A Ovary T | | | 334A Large Intestir | 422A0622 | 1892 | 1245 | 10.1 | 50 | 2.6 | 50 |
| 421H0187 [E11] | -1.5 | 288A Ovary T | | | CT12 Lung N | 422V0625 | 604 | 908 | 4.1 | 62 | 2.6 | 62 |
| 421H0187 [E11] | -1.4 | 428A Ovary T (met) | | | 243A Esophagus N | 422240612 | 236 | 325 | 2.7 | 78 | 1.9 | 78 |
| 421H0187 [E11] | -1.3 | 335A Ovary T | | | S7 Ovary N | 422O0626 | 382 | 501 | 2.9 | 58 | 2.0 | 58 |
| 421H0187 [E11] | -1.2 | 201A Ovary T | | | S6 Stomach N | 422W0620 | 558 | 677 | 4.2 | 58 | 2.3 | 58 |
| 421H0187 [E11] | +1.0 | 9485 OT 5-P (SCID | | | 9485 OT 5-P (SCID | 422Y0602 | 2582 | 2493 | 15.1 | 57 | 6.3 | 57 |
| 421H0187 [E11] | | 383A Ovary T (met) | | | I1 Colon N | 422B0609 | 2261 | 562 | 12.5 | 38 | 1.7 | 38 |
| 421H0187 [E11] | | 266A Ovary T | | | S27 Ovary N | 42250603 | 1739 | 965 | 9.7 | 36 | 2.2 | 36 |
| 421H0187 [E11] | | S25 Ovary T | | | CT4 Bone Marrow | 422H0619 | 283 | 845 | 2.2 | 44 | 2.2 | 44 |

ACGGTTTCAATGGACACTTTTATTGTTTACTTAATGGATCATCAATTTTGTCTCACTACCTACAAATGGAATTTCA
TCTTGTTTCCATGCTGAGTAGTGAAACAGTGACAAAGCTAATCATAATAACCTACATCAAAAGAGAACTAAGCTAA
CACTGCTCACTTTCTTTTTAACAGGCAAAATATAAATATATGCACTCTAXAATGCACAATGGTTTAGTCACTAAAA
AATTCAAATGGGATCTTGAAGAATGTATGCAAATCCAGGGTGCAGTGAAGATGAGCTGAGATGCTGTGCAACTGTT
TAAGGGTTCCTGGCACTGCATCTCTTGGCCACTAGCTGAATCTTGACATGGAAGGTTTTAGCTAATGCCAAGTGGA
GATGCAGAAAATGCTAAGTTGACTTAGGGGCTGTGCACAGGAACTAAAAGGCAGGAAAGTACTAAATATTGCTGAG
AGCATCCACCCCAGGAAGGACTTTACCTTCCAGGAGCTCCAAACTGGCACCACCCCCAGTGCTCACATGGCTGACT
TTATCCTCCGTGTTCCATTTGGCACAGCAAGTGGCAGTG

11721-2

AAGGCTGGTGGGTTTTTGATCCTGCTGGAGAACCTCCGCTTTCATGTGGAGGAAGAAGGGAAGGGAAAAGATGCTT
CTGGGAACAAGGTTAAAGCCGAGCCAGCCAAAATAGAAGCTTTCCGAGCTTCACTTTCCAAGCTAGGGGATGTCTA
TGTCAATGATGCTTTTGGCACTGCTCACAGAGCCCACAGCTCCATGGTAGGAGTCAATCTGCCACAGAAGGCTGGT
GGGTTTTTGATGAAGAAGGAGCTGAACTACTTTGCAAAGGCCTTGGAGAGCCCAGAGCGACCCTTCCTGGCCATCC
TGGGCGGAGCTAAAGTTGCAGACAAGATCCAGCTCATCAATAATATGCTGGACAAAGTCAATGAGATGATTATTGG
TGGTGGAATGGCTTTTACCTTCCTTAAGGTGCTCAACAACATGGAGATTGGCACTTCTCTGTTTGATGAAGAGGGA
GCCAAGATTGTCAAAGACCTAATGTCCAAAGCTGAGAAGAATGGTGTGAAGATTACCTTGCCTGTTGACTTTGTCA
CTGCTGACAAGTTTGATGA

11724-1

TTTGTTCCTTACATTTTTCTAAAGAGTTACTTAAATCAGTCAACTGGTCTTTTGAGACTCTTAAGTTCTGATTCCAA
CTTAGCTAATTCATTCTGAGAACTGTGGTATAGGTGGCGTGTCTCTTCTAGCTGGGACAAAAGTTCTTTGTTTTCC
CCCTGTAGAGTATCACAGACCTTCTGCTGAAGCTGGACCTCTGTCTGGGCCTTGGACTCCCAAATCTGCTTGTCAT
GTTCAAGCCTGGAAATGTTAATCTTTAATTCTTCCATATGGATGGACATCTGTCTAAGTTGATCCTTTAGAACACT
GCAATTATCTTCTTTGAGTCTAATTTCTTCTTCTTTGCTTTGAATCGCATCACTAAACTTCCTCTCCCATTTCTTA
GCTTCATCTATCACCCTGTCACGATCATCCTGGAGGGAAGACATGCTCTTAGTAAAGGCTGCAAGCTGGGTCACAG
TACTGTCCAAGTTTTCCTGAAGTTGCTGAACTTCCTTGTCTTTCTTGTTCAAAGTAACCTGAATCTCTCCAATTGT
CTCTTCCAAGTGGACTTTTTCTCTGCGCAAAGCATCCAG

11724-2

TCATTGCCTGTGATGGCATCTGGAATGTGATGAGCAGCCAGGAAGTTGTAGATTTCATTCAATCAAAGGATTCAGC
ATGTGGTGGAAGCTGTGAGGCAAGAGAAACAAGAACTGTATGGCAAGTTAAGAAGCACAGAGGCAAACAAGAAGGA
GACAGAAAAGCAGTTGCAGGAAGCTGAGCAAGAAATGGAGGAAATGAAAGAAAAGATGAGAAAGTTTGCTAAATCT
AAACAGCAGAAAATCCTAGAGCTGGAAGAAGAGAATGACCGGCTTAGGGCAGAGGTGCACCCTGCAGGAGATACAG
CTAAAGAGTGTATGGAAACACTTCTTTCTTCCAATGCCAGCATGAAGGAAGAACTTGAAAGGGTCAAAATGGAGTA
TGAAACCCTTTCTAAGAAGTTTCAGTCTTTAATGTCTGAGAAAGACTCTCTAAGTGAAGAGGTTCAAGATTTAAAG
CATCAGATAGAAGGTAATGTATCTAAACAAGCTAACCTAGAGGCCACCGAGAAACATGATAACCAAACGAATGTCA
CTGAAGAGGGAACACAGTCTATACCAGGT

AAGCCAATAATCACCATTTATTACTTAATATATGCCAACCACTGTACTTGGCAGTTCACAAATTCTCACCGTTACA
ACAACCCCATGAGGTATTTATTCCCATTCTATAGATAGGGAAACCACAGCTCAAGTAAGTTAGGAAACTGAGCCAA
GTATACACAGAATACGAAGTGGCAAAACTAGAAGGAAAGACTGACACTGCTATCTGCTGGCCTCCAGTGTCCTGGC
TCTTTTCACACGGGtTCAATGTCTCCAGCGCTGCTGCTGCTGCTGCATTACCATGCCCTCATTGTTTTTCTTCCTC
TGGTGTTCAACTGCATCCTTCAAAGAATCTAACTCATTCCAGAGACCACTTATTTCTTTCTCTCTTTCTGAAATTA
CTTTTAATAATTCTTCATGAGGGGGAAAAGAAGATGCCTGTTGGTAGTTTTGTTGTTTAAGCTGCTCAATTTGGGA
CTTAAACAATTTGTTTTCATCTTGTACATCCTGTAACAGCTGTGTTTTGCTAGAAAGATCACTCTCCCTCTCTTTT
AGCATGGCTTCTAACCTCTTCAATTCATTTTCCTTTTCTTTCAACACAATCTCAAGTTCTTCAAACTGTGATGCAG
AAGAGGCCTCTTTCAAGTTATGTTGTGCTACTTCCTGAACATGTGCTTTTAAAGATTCATTTTCTTCTTGAAGATC
CTGTAACCACTTCCCTGTATTGGCTAGGTCTTTCTCTTTCTCTTCCAAAACAGCCTTCATGGTATTCATCTGTTCC
TCTTTTCCTTTTAATAAGTTCAGGAGCTTCAGAAC

11726-1&2

CAAGCTTTTTTTTTTTTTTAAAAAGTGTTAGCATTAATGTTTTATTGTCACGCAGATGGCAACTGGGTTTATGTC
TTCATATTTTATATTTTTGTAAATTAAAAAAATTACAAGTTTTAAATAGCCAATGGCTGGTTATATTTTCAGAAAA
CATGATTAGACTAATTCATTAATGGTGGCTTCAAGCTTTTCCTTATTGGCTCCAGAAAATTCACCCACCTTTTGTC
CCTTCTTAAAAAACTGGAATGTTGGCATGCATTTGACTTCACACTCTGAAGCAACATCCTGACAGTCATCCACATC
TACTTCAAGGAATATCACGTTGGAATACTTTTCAGAGAGGGAATGAAAGAAAGGCTTGATCATTTTGCAAGGCCCA
CACCACGTGGCTGAGAAGTCAACTACTACAAGTTTATCACCTGCAGCGTCCAAGGCTTCCTGAAAAGCAGTCTTGC
TCTCGATCTGCTTCACCATCTTGGCTGCTGGAGTCTGACGAGCGGCTGTAAGGACCGATGGAAATGGATCCAAAGC
ACCAAACAGAGCTTCAAGACTCGCTGCTTGGCTTGAATTCGGATCCGATATCGCCATGGCCT

11727-1&2

AAGTGTTAGCATTAATGTTTTATTGTCACGCAGATGGCAACTGGGTTTATGTCTTCATATTTTATATTTTTGTAAA
TTAAAAAAATTMCAAGTTTTAAATAGCCAATGGCTGGTTATATTTTCAGAAAACATGATTAGACTAATTCATTAAT
GGTGGCTTCAAGCTTTTCCTTATTGGCTCCAGAAAATTCACCCACCTTTTGTCCCTTCTTAAAAAACTGGAATGTT
GGCATGCATTTGACTTCACACTCTGAAGCAACATCCTGACAGTCATCCACATCTACTTCAAGGAATATCACGTTGG
AATACTTTTCAGAGAGGGAATGAAAGAAAGGCTTGATCATTTTGCAAGGCCCACACCACGTGGCTGAGAAGTCAAC
TACTACAAGTTTATCACCTGCAGCGTCCAAGGCTTCCTGAAAAGCAGTCTTGCTCTCGATCTGCTTCACCATCTTG
GCTGCTGGAGTCTGACGAGCGGCTGTAAGGACCGATGGAAATGGATCCAAAGCACCAAACAGAGCTTCAAGACTCG
CTGCTTGGCATGAATTCGGATCCGA

```
TACAAACTTTATTGAAACGCACACGCGCACACACACAAACACCCCTGTGGATAGGGAAAAGCACCTGGCCACAGGG
TCCACTGAAACGGGGAGGGGATGGCAGCTTGTAATGTGGCTTTTGCCACAACCCCCTTCTGACAGGGAAGGCCTTA
GATTGAGGCCCCACCTCCCATGGTGATGGGGAGCTCAGAATGGGGTCCAGGGAGAATTTGGTTAGGGGGAGGTGCT
AGGGAGGCATGAGCAGAGGGCACCCTCCGAGTGGGGTCCCGAGGGCTGCAGAGTCTTCAGTACTGTCCCTCACAGC
AGCTGTCTCAAGGCTGGGTCCCTCAAAGGGGCGTCCCAGCGCGGGGCCTCCCTGCGCAAACACTTGGTACCCCTGG
CTGCGCAGCGGAAGCCAGCAGGACAGCAGTGGCGCCGATCAGCACAACAGACGCCCTGGCGGTAGGGACAGCAGGC
CCAGCCCTGTCGGTTGTCTCGGCAGCAGGTCTGGTTATCATGGCAGAAGTGTCCTTCCCACACTTCACGTCCTTCA
CACCCACGTGAXGGCTACXGGCCAGGAAG
```

11728.2.40.19.19

```
CCCGTGGGTGCCATCCACGGAGTTGTTACCTGATCTTTGGAAGCAGGATCGCCCGTCTGCACTGCAGTGGAAGCCC
CGTGGGCAGCAGTGATGGCCATCCCCGCATGCCACGGCCTCTGGGAAGGGGCAGCAACTGGAAGTCCCTGAGACGG
TAAAGATGCAGGAGTGGCCGGCAGAGCAGTGGGCATCAACCTGGCAGGGGCCACCCAGATGCCTGCTCAGTGTTGT
GGGCCATTTGTCCAGAAGGGGACGGCAGCAGCTGTAGCTGGCTCCTCCGGGGTCCAGGCAGCAGGCCACAGGGCAG
AACTGACCATCTGGGCACCGCGTTCCAGCCACCAGCCCTGCTGTTAAGGCCACCCAGCTCACCAGGGTCCACATGG
TCTGCCTGCGTCCGACTCCGCGGTCCTTGGGCCCTGATGGTTCTACCTGCTGTGAGCTGCCCAGTGGGAAGTATGG
CTGCTGCCAATGCCCAACGCCACCTGCTGCTCCGATCACCTGCACTGCTGCCCCAAGACACTGTGTGTGACCTGAT
CCAGAGTAAGTGCCTCTCCAAGGAGAACG
```

11730-1

```
GAATCACCTTTCTGGTTTAGCTAGTACTTTGTACAGAACAATGAGGTTTCCCACAGCGGAGTCTCCCTGGGCTCTG
TTTGGCTCTCGGTAAGGCAGGCCTACACCTTTTCCTCTCCTCTATGGAGAGGGGAATATGCATTAAGGTGAAAAGT
CACCTTCCAAAAGTGAGAAAGGGATTCGATTGCTGCTTCAGGACTGTGGAATTATTTGGAATGTTTTACAAATGGT
TGCTACAAAACAACAAAAAAGGTAATTACAAAATGTGTACATCACAACATGCTTTTTAAAGACATTATGCATTGTG
CTCACATTCCCTTAAATGTTGTTTCCAAAGGTGCTCAGCCTCTAGCCCAGCTGGATTCTCCGGGAAGAGGCAGAGA
CAGTTTGGCGAAAAAGACACAGGGAAGGAGGGGGTGGTGAAAGGAGAAAGCAGCCTTCCAGTTAAAGATCAGCCCT
CAGTTAAAGGTCAGCTTCCCGCAXGCTGGCCTCAXGCGGAGTCTGGGTCAGAGGGAGGAGCAGCAGCAGGGTGGGA
CTGGGGCGT
```

11730-2

```
AACCGGAGCGCGAGCAGTAGCTGGGTGGGCACCATGGCTGGGATCACCACCATCGAGGCGGTGAAGCGCAAGATCC
AGGTTCTGCAGCAGCAGGCAGATGATGCAGAGGAGCGAGCTGAGCGCCTCCAGCGAGAAGTTGAGGGAGAAAGGCG
GGCCCGGGAACAGGCTGAGGCTGAGGTGGCCTCCTTGAACCGTAGGATCCAGCTGGTTGAAGAAGAGCTGGACCGT
GCTCAGGAGCGCCTGGCCACTGCCCTGCAAAAGCTGGAAGAAGCTGAAAAAGCTGCTGATGAGAGTGAGAGAGGTA
TGAAGGTTATTGAAAACCGGGCCTTAAAAGATGAAGAAAAGATGGAACTCCAGGAAATCCAACTCAAAGAAGCTAA
GCACATTGCAGAAGAGGCAGATAGGAAGTATGAAGAGGTGGCTCGTAAGTTGGTGATCATTGAAGGAGACTTGGAA
CGCACAGAGGAACGAGCTGAGCTGGCAGAGTCCCGTTGCCGAGAGATGGATGAGCAGATTAGACTGATGGACCAGA
ACCTGAAGTGTCTGAGTGC
```

*Fig. 15C*

11732.1contig

```
GAGAACTTGGCCTTTATTGTGGGCCCAGGAGGGCACAAAGGTCAGGAGGCCCAAGGGAGGGATCTGGTTTTCTGGA
TAGCCAGGTCATAGCATGGGTATCAGTAGGAATCCGCTGTAGCTGCACAGGCCTCACTTGCTGCAGTTCCGGGGAG
AACACCTGCACTGCATGGCGTTGATGACCTCGTGGTACACGACAGAGCCATTGGTGCAGTGCAAGGGCACGCGCAT
GGGCTCCGTCCTCGAGGGCAGGCAGCAGGAGCATTGCTCCTGCACATCCTCGATGTCAATGGAGTACACAGCTTTG
CTGGCACACTTTCCCTGGCAGTAATGAATGTCCACTTCCTCTTGGGACTTACAATCTCCCACTTTGATGTACTGCA
CCTTGGCTGTGATGTCTTTGCAATCAGGCTCCTCACATGTGTCACAGCAGGTGCCTGGAATTTTCACGATTTTGCC
TCCTTCAGCCAGACACTTGTGTTCATCAAATGGTGGGCAGCCCGTGACCCTCTTCTCCCAGATGTACTCTCCTCT
```

11732.2contig

```
GCCTGGACCTTGCCGGATCAGTGCCACACAGTGACTTGCTTGGCAAATGGCCAGACCTTGCTGCAGAGTCATCGTG
TCAATTGTGACCATGGACCCCGGCCTTCATGTGCCAACAGCCAGTCTCCTGTTCGGGTGGAGGAGACGTGTGGCTG
CCGCTGGACCTGCCCTTGTGTGTGCACGGGCAGTTCCACTCGGCACATCGTCACCTTCGATGGGCAGAATTTCAAG
CTTACTGGTAGCTGCTCCTATGTCATCTTTCAAAACAAGGAGCAGGACCTGGAAGTGCTCCTCCACAATGGGGCCT
GCAGCCCCGGGGCAAAACAAGCCTGCATGAAGTCCATTGAGATTAAGCATGCTGGCGTCTCTGCTGAGCTGCACAG
TAACATGGAGATGGCAGTGGATGGGAGACTGGTCCTTGCCCCGTACGTTGGTGAAAACATGGAAGTCAGCATCTAC
GGCGCTATCATGTATGAAGTCAGGTTTACCCATCTTGGCCACATCCTCACATACACCGCCXCAAAACAACGAGTT
```

11735-1-2

```
AGATCAACCTCTGCTGGTCAGGAGGAATGCCTTCCTTGTCTTGGATCTTTGCTTTGACGTTCTCGATAGTRWCAaC
TKKRYTSRAMSKMAAGKGYRATGRWMTTKSYWGWRASYKTMWWMRSGRARAYTTaGaCAYCCCMCCTCWgAGaCGS
AGKACCARGTGCAgAgGTGGACTCTTTCTGGATGTTGTAGTCAGACAGGGTGCGTCCATCTTCCAGCTGTTTCCCA
GCAAAGATCAACCTCTGCTGATCAGGAGGGATGCCTTCCTTATCTTGGATCTTTGCCTTGACATTCTCGATGGTGT
CACTGGGCTCCACCTCGAGGGTGATGGTCTTACCAGTCAGGGTCTTCACGAAGATYTGCATCCCACCTCTGAGACG
GAGCACCAGGTGCAGGGTRGACTCTTTCTGGATGTTGTAGTCAGACAGGGTGCGYCCATCTTCCAGCTGcTTTCCS
aGCAAAGATCAACCTCTGCTGGTCAGGAGGRATGCCTTCCTTGTCYTGGATCTTTGCYTTGACRTTCTCRATGGTG
TCACTCGGCTCCACTTCGAGAGTGATGGTCTTACCAGTCAGGGTCTTCACGAAGATCTGCATCCCACCTCTAA
```

11740.2.contig

```
AAGTCACAAACAGACAAAGATTATTACCAGCTGCAAGCTATATTAGAAGCTGAACGAAGAGACAGAGGTCATGATT
CTGAGATGATTGGAGACCTTCAAGCTCGAATTACATCTTTACAAGAGGAGGTGAAGCATCTCAAACATAATCTCGA
AAAAGTGGAAGGAGAAAGAAAAGAGGCTCAAGACATGCTTAATCACTCAGAAAAGGAAAAGAATAATTTAGAGATA
GATTTAAACTACAAACTTAAATCATTACAACAACGGTTAGAACAAGAGGTAAATGAACACAAAGTAACCAAAGCTC
GTTTAACTGACAAACATCAATCTATTGAAGAGGCAAAGTCTGTGGCAATGTGTGAGATGGAAAAAAAGCTGAAAGA
AGAAAGAGAAGCTCGAGAGAAGGCTGAAAATCGGGTTGTTCAGATTGAGAAACAGTGTTCCATGCTAGACGTTGAT
CTGAAGCAATCTCAGCAGAAACTAGAACATTTGACTGGAAATAAAGAAAGGATGGAGGATGAAGTTAAGAATCTA
```

*Fig. 15D*

11765.2&64.2.contig

CGCCTCCACCATGTCCATCAGGGTGACCCAGAAGTCCTACAAGGTGTCCACCTCTGGCCCCCGGGCCTTCAGCAGC
CGCTCCTACACGAGTGGGCCCGGTTCCCGCATCAGCTCCTCGAGCTTCTCCCGAGTGGGCAGCAGCAACTTTCGCG
GTGGCCTGGGCGGCGGCTATGGTGGGGCCAGCGGCATGGGAGGCATCACCGCAGTTACGGTCAACCAGAGCCTGCT
GAGCCCCCTTGTCCTGGAGGTGGACCCCAACATCCAGGCCGTGCGCACCCAGGAGAAGGAGCAGATCAAGACCCTC
AACAACAAGTTTGCCTCCTTCATAGACAAGGTACGGTTCCTGGAGCAGCAGAACAAGATGCTGGAGACCAAGTGGA
GCCTCCTGCAGCAGCAGAAGACGGCTCGAAGCAACATGGACAACATGTTCGAGAGCTACATCAACACRCCTTAGGCG
GCAGCTGGAGACTCTGGGCCAGGAGAAGCTGAAGCTGGAGGCGGAGCTTGGCAACATGCAGGGGCTGGTGGAGGAC
TTCAAGAACAAGTATGAGGATGAGATCAATAAGCGTACAGAGATGGAGAACGAATTTGTCCTCATCAAGAAGGATG
TGGATGAAGCTTACATGAACAAGGTAGAGCTGGAGTCTCGCCTGGAAGGGCTGACCGACGAGATCAACTTCCTCAG
GCAGCTGTATGAAGAGGAGATCCGGGAGCTGCAGTCCCAGATCTCGGACACATCTGTGGTGCTGTCCATGGACAAC
AGCCGCTCCCTGGACATGGACAGCATCATTGCTGAGGTCAAGGCACAGTACGAGGATATTGCCAACCGCAGCCGGG
CTGAGGCTGAGAGCATGTACCAGGTCAAGTATGAGGAGCTGCAGAGCCTGGCTGGGAAGCACGGGGATGACCTGCG
GCGCACAAAGACTGAGATCTCTGAGATGAACCCGGAACATCAGCCCGGCTXCAGGCTGAGATTGAGGGCCTCAAAG
GCCAGAXGGCTTXCCTGGAXGXCCGCCAT

11767.2.contig

CCCGGAGCCAGCCAACGAGCGGAAAATGGCAGACAATTTTTCGCTCCATGATGCGTTATCTGGGTCTGGAAACCCA
AACCCTCAAGGATGGCCTGGCGCATGGGGGAACCAGCCTGCTGGGGCAGGGGGCTACCCAGGGGCTTCCTATCCTG
GGGCCTACCCCGGGCAGGCACCCCCAGGGGCTTATCCTGGACAGGCACCTCCAGGCGCCTACCCTGGAGCACCTGG
AGCTTATCCCGGAGCACCTGCACCTGGAGTCTACCCAGGGCCACCCAGCGGCCCTGGGGCCTACCCATCTTCTGGA
CAGCCAAGTGCCACCGGAGCCTACCCTGCCACTGGCCCCTATGGCGCCCCTGCTGGGCCACTGATTGTGCCTTATA
ACCTGCCTTTGCCTGGGGGAGTGGTGCCTCGCATGCTGATAACAATTCTGGGCACGGTGAAGCCCAATGCAAACAG
AATTGCTTTAGATTTCCAAAGAGGGAATGATGTTGCCTTCCACTTTAACCCACGCTTCAATGAGAACAACAGGAGA
GTCATTGGTTGCAATACAAAGCTGGATAA

11768-1&2

GGGAATGCAACAACTTTATTGAAAGGAAAGTGCAATGAAATTTGTTGAAACCTTAAAAGGGGAAACTTAGACACCC
CCCCTCRAgCGMAGKACCARgTGCARAgGTGGACTCTTTCTGGATGTTGTAGTCAGACAGGGTRCGWCCATCTTCC
AGCTGTTTYCCRGCAAAGATCAACCTCTGCTGATCAGGAGGRATGCCTTCCTTATCTTGGATCTTTGCCTTGACAT
TCTCGATGGTGTCACTGGGCTCCACCTCGAGGGTGATGGTCTTACCAGTCAGGGTCTTCACGAAGATYTGCATCCC
ACCTCTGAGACGGAGCACCAGGTGCAGGGTRGACTCTTTCTGGATGTTGTAGTCAGACAGGGTGCGYCCATCTTCC
AGCTGcTTTCCSaGCAAAGATCAACCTCTGCTGGTCAGGAGGRATGCCTTCCTTGTCYTGGATCTTTGCYTTGACR
TTCTCAATGGTGTCACTCGGCTCCACTTCGAGAGTGATGGTCTTACCAGTCAGGGTCTTCACGAAGATCTGCATCC
CACCTCTAAGACGGAGCACCAGGTGCAGGGTGGACTCTTTCTGGATGgTTGTAGTCAGACAGGGTGCGTCCATCTT
CCAGCTGTTTCCCAGCAAAGATCAACCT

```
AGGTTGATCTTTGCTGGGAAACAGCTGGAAGATGGACGCACCCTGTCTGACTACAAcCATCCAGAAAGAGTCCACC
CTGCACCTGGTGCTCCGTCTTAGAGGTGGGATGCAGATCTTCGTGAAGACCCTGACTGGTAAGACCATCACTCTCG
AAGTGGAGCCGAGTGACACCATTGAGAAYGTCAARGCAAAGATCCARGACAAGGAAGGCATYCCTCCTGACCAGCA
GAGGTTGATCTTTGCtSGGAAAgCAGCTGGAAGATGGRCGCACCCTGTCTGACTACAACATCCAGAAAGAGTCYAC
CCTGCACCTGGTGCTCCGTCTCAGAGGTGGGATGCARATCTTCGTGAAGACCCTGACTGGTAAGACCATCACCCTC
GAGGTGGAGCCCAGTGACACCATCGAGAATGTCAAGGCAAAGATCCAAGATAAGGAAGGCATCCCTCCTGATCAGC
AGAGGTTGATCTTTGCTGGGAAACAGCTGGAAGATGGACGCACCCTGTCTGACTACAACATCCAGAAAGAGTCCAC
cTYTGCACYTGGTMCTBCGtCTYaGAGGKGGGRTGcaaaTCTWMGTKWagaCaCtCaCTKKYAAGRYYaTCAMCMW
tgAKKTCgAKYSCASTKWCaCTWTCRAKAAMGTYRWWGCAWagaTCCMAGACAAGGAAGGCATTCCTCCTGACCAG
CAGAGGTTGATCT
```

11769.1.contig

```
ATGGAGTCTCACTCTGTCGACCAGGCTGGAGCGCTGTGGTGCGATATCGGCTCACTGCAGTCTCCACTTCCTGGGT
TCAAGCGATCCTCCTGCCTCAGCCTCCCGAGTAGCTGGGACTACAGGCAGGCGTCACCATAATTTTTGTATTTTTA
GTAGAGACATGGTTTCGCCATGTTGGCTGGGCTGGTCTCGAACTCCTGACCTCAAGTGATCTGTCCTGGCCTCCCA
AAGTGTTGGGATTACAGGCGAAAGCCAACGCTCCCGGCCAGGGAACAACTTTAGAATGAAGGAAATATGCAAAAGA
ACATCACATCAAGGATCAATTAATTACCATCTATTAATTACTATATGTGGGTAATTATGACTATTTCCCAAGCATT
CTACGTTGACTGCTTGAGAAGATGTTTGTCCTGCATGGTGGAGAGTGGAGAAGGGCCAGGATTCTTAGGTT
```

11769.2.contig

```
AGCGCGGTCTTCCGGCGCGAGAAAGCTGAAGGTGATGTGGCCGCCCTCAACCGACGCATCCAGCTCGTTGAGGAGG
AGTTGGACAGGGCTCAGGAACGACTGGCCACGGCCCTGCAGAAGCTGGAGGAGGCAGAAAAAGCTGCAGATGAGAG
TGAGAGAGGAATGAAGGTGATAGAAAACCGGGCCATGAAGGATGAGGAGAAGATGGAGATTCAGGAGATGCAGCTC
AAAGAGGCCAAGCACATTGCGGAAGAGGCTGACCGCAAATACGAGGAGGTAGCTCGTAAGCTGGTCATCCTGGAGG
GTGAGCTGGAGAGGGCAGAGGAGCGTGCGGAGGTGTCTGAACTAAAATGTGGTGACCTGGAAGAAGAACTCAAGAA
TGTTACTAACAATCTGAAATCTCTGGAGGCTGCATCTGAAAAGTATTCTGAAAAGGAGGACAAATATGAAGAAGAA
ATTAAACTTCTGTCTGACAAACTGAAAGAGGCTGAGACCCGTGCTGAATTTGCAGAGAGAACGGTTGCAAAACTGG
AAAAGACAATTGATGACCTGGAAGAGAAACTTGCCCAGC
```

11770.1.contig

```
GTGCACAGGTCCCATTTATTGTAGAAAATAATAATAATTACAGTGATGAATAGCTCTTCTTAAATTACAAAACAGA
AACCACAAAGAAGGAAGAGGAAAAACCCCAGGACTTCCAAGGGTGAAGCTGTCCCCTCCTCCCTGCCACCCTCCCA
GGCTCATTAGTGTCCTTGGAAGGGGCAGAGGACTCAGAGGGGATCAGTCTCCAGGGGCCCTGGGCTGAAGCGGGTG
AGGCAGAGAGTCCTGAGGCCACAGAGCTGGGCAACCTGAGCCGCCTCTCTGGCCCCCTCCCCCACCACTGCCCAAA
CCTGTTTACAGCACCTTCGCCCCTCCCCTCTAAACCCGTCCATCCACTCTGCACTTCCCAGGCAGGTGGGTGGGCC
AGGCCTCAGCCATACTCCTGGGCGCGGGTTTCGGTGAGCAAGGCACAGTCCCAGAGGTGATATCAAGGCCT
```

*Fig. 15F*

11770.2.contig

```
GCAAGGAACTGGTCTGCTCACACTTGCTGGCTTGCGCATCAGGACTGGCTTTATCTCCTGACTCACGGTGCAAAGG
TGCACTCTGCGAACGTTAAGTCCGTCCCCAGCGCTTGGAATCCTACGGCCCCCACAGCCGGATCCCCTCAGCCTTC
CAGGTCCTCAACTCCCGTGGACGCTGAACAATGGCCTCCATGGGGCTACAGGTAATGGGCATCGCGCTGGCCGTCC
TGGGCTGGCTGGCCGTCATGCTGTGCTGCGCGCTGCCCATGTGGCGCGTGACGGCCTTCATCGGCAGCAACATTGT
CACCTCGCAGACCATCTGGGAGGGCCTATGGATGAACTGCGTGGTGCAGAGCACCGGCCAGATGCAGTGCAAGGTG
TACGACTCGCTGCTGGCACTGCCGCAGGACCTGCAGGCGGCCCGCGCCCTCGTCATCATCA
```

11773.1.contig

```
TGCAAAAGGGACACAGGGGTTCAAAAATAAAAATTTCTCTTCCCCCTCCCCAAACCTGTACCCCAGCTCCCCGACC
ACAACCCCCTTCCTCCCCCGGGGAAAGCAAGAAGGAGCAGGTGTGGCATCTGCAGCTGGGAAGAGAGAGGCCGGGG
AGGTGCCGAGCTCGGTGCTGGTCTCTTTCCAAATATAAATACXTGTGTCAGAACTGGAAAATCCTCCAGCACCCAC
CACCCAAGCACTCTCCGTTTTCTGCCGGTGTTTGGAGAGGGGCGGGGGGCAGGGGCGCCAGGCACCGGCTGGCTGC
GGTCTACTGCATCCGCTGGGTGTGCACCCCGCGAGCCTCCTGCTGCTCATTGTAGAAGAGATGACACTCGGGGTCC
CCCCGGATGGTGGGGGCTCCCTGGATCAGCTTCCCGGTGTTGGGGTTCACACACCAGCACTCCCCACGCTGCCCGT
TCAGAGACATCTTGCACTGTTTGAGGTTGTACAGGCCATGCTTGTCACAGTTG
```

11778.1.contig

```
GGGTTGGAGGGACTGGTTCTTTATTTCAAAAAGACACTTGTCAATATTCAGTATCAAAACAGTTGCACTATTGATT
TCTCTTTCTCCCAATCGGCCCCAAAGAGACCACATAAAAGGAGAGTACATTTTAAGCCAATAAGCTGCAGGATGTA
CACCTAACAGACCTCCTAGAAACCTTACCAGAAAATGGGGACTGGGTAGGGAAGGAAACTTAAAAGATCAACAAAC
TGCCAGCCCACGGACTGCAGAGGCTGTCACAGCCAGATGGGGTGGCCAGGGTGCCACAAACCCAAAGCAAAGTTTC
AAAATAATATAAAATTTAAAAAGTTTTGTACATAAGCTATTCAAGATTTCTCCAGCACTGACTGATACAAAGCACA
ATTGAGATGGCACTTCTAGAGACAGCAGCTTCAAACCCAGAAAAGGGTGATGAGATGAGTTTCACATGGCTAAATC
AGTGGCAAAAACACAGTCTTCTTTCTTTCTTTCTTTCAAGGAGGCAGGAAAGCAATTAAGTGGTCACCTCAACATA
AGGGGGACATGATCCATTCTGTAAGCAGTTGTGAAGGGG
```

11778-2&30-2

```
CAGGAACCGGAGCGCGAGCAGTAGCTGGGTGGGCACCATGGCTGGGATCACCACCATCGAGGCGGTGAAGCGCAAG
ATCCAGGTTCTGCAGCAGCAGGCAGATGATGCAGAGGAGCGAGCTGAGCGCCTCCAGCGAGAAGTTGAGGGAGAAA
GGCGGGCCCGGGAACAGGCTGAGGCTGAGGTGGCCTCCTTGAACCGTAGGATCCAGCTGGTTGAAGAAGAGCTGGA
CCGTGCTCAGGAGCGCCTGGCCACTGCCCTGCAAAAGCTGGAAGAAGCTGAAAAAGCTGCTGATGAGAGTGAGAGA
GGTATGAAGGTTATTGAAAACCGGGCCTTAAAAGATGAAGAAAAGATGGAACTCCAGGAAATCCAACTCAAAGAAG
CTAAGCACATTGCAGAAGAGGCAGATAGGAAGTATGAAGAGGTGGCTCGTAAGTTGGTGATCATTGAAGGAGACTT
GGAACGCACAGAGGAACGAGCTGAGCTGGCAGAGTCCCGTTGCCGAGAGATGGATGAGCAGATTAGACTGATGGAC
CAGAACCTGAAGTGTCTGAGTGC
```

*Fig. 15G*

11782.1.contig

```
ATCTACGTCATCAATCAGGCTGGAGACACCATGTTCAATCGAGCTAAGCTGCTCAATATTGGCTTTCAAGAGGCCT
TGAAGGACTATGATTACAACTGCTTTGTGTTCAGTGATGTGGACCTCATTCCGATGGACGACCGTAATGCCTACAG
GTGTTTTTCGCAGCCACGGCACATTTCTGTTGCAATGGACAAGTTCGGGTTTAGCCTGCCATATGTTCAGTATTTT
GGAGGTGTCTCTGCTCTCAGTAAACAACAGTTTCTTGCCATCAATGGATTCCCTAATAATTATTGGGGTTGGGGAG
GAGAAGATGACGACATTTTTAACAGATTAGTTCATAAAGGCATGTCTATATCACGTCCAAATGCTGTAGTAGGGAG
GTGTCGAATGATCCGGCATTCAAGAGACAAGAAAAATGAGCCCAATCCTCAGAGGTTTGACCGGATCGCACATACA
AAGGAAACGATGCGCTTCGATGGTTTGAACTCACTTACCTACAAGGTGTTGGATGTCAGAGATACCCGTTATATAC
CCAAATCAC
```

11782.2.contig

```
CTAGACCTCTAATTAAAAGGCACAATCATGCTGGAGAATGAACAGTCTGACCCCGAGGGCCACAGCGAATTTTAGG
GAAGGAGGCAAAGAGGTGAGAAGGGAAAGGAAAGAAGGAAGGAAGGAGAACAATAAGAACTGGAGACGTTGGGTGG
GTCAGGGAGTGTGGTGGAGGCTCGGAGAGATGGTAAACAAACCTGACTGCTATGAGTTTTCAACCCCATAGTCTAG
GGCCATGAGGGCGTCAGTTCTTGGTGGCTGAGGGTCCTTCCACCCAGCCCACCTGGGGGAGTGGAGTGGGGAGTTC
TGCCAGGTAAGCAGATGTTGTCTCCCAAGTTCCTGACCCAGATGTCTGGCAGGATAACGCTGACCTGTTCCCTCAA
CAAGGGACCTGAAAGTAATTTTGCTCTTTAC
```

11783-1 & 2

```
CCGAATTCAAGCGTCAACGATCCYTCCCTTACCATCAAATCAATTGGCCACCAATGGTACTGAACCTACGAGTACA
CCGACTACgGGCGGACTAATCTTCAACTCCTACATACTTCCCCCATTATTCCTAGAACCAGGCGACCTGCGACTCC
TTGACGTTGACAATCGAGTAGTACTCCCGATTGAAGCCCCCATTCGTATAATAATTACATCACAAGACGTCTTGCA
CTCATGAGCTGTCCCCACATTAGGCTTAAAAACAGATGCAATTCCCGGACGTCTAAGCCAAACCACTTTCACCGCT
ACACGACCGGGGGTATACTACGGTCAATGCTCTGAAATCTGTGGAGCAAACCACAGTTTCATGCCCATCGTCCTAG
AATTAATTCCCCTAAAAATCTTTGAAATAGGGCCCGTATTTACCCTATAGCACCCCCTCTACCCCCTCTAG
```

11786.1.contig

```
GCTCTTCACACTTTTATTGTTAATTCTCTTCACATGGCAGATACAGAGCTGTCGTCTTGAAGACCACCACTGACCA
GGAAATGCCACTTTTACAAAATCATCCCCCCTTTTCATGATTGGAACAGTTTTCCTGACCGTCTGGGAGCGTTGAA
GGGTGACCAGCACATTTGCACATGCAAAAAAGGAGTGACCCCAAGGCCTCAACCACACTTCCCAGAGCTCACCATG
GGCTGCAGGTGACTTGCCAGGTTTGGGGTTCGTGAGCTTTCCTTGCTGCTGCGGTGGGGAGGCCCTCAAGAACTGA
GAGGCCGGGGTATGCTTCATGAGTGTTAACATTTACGGGACAAAAGCGCATCATTAGGATAAGGAACAGCCACAGC
ACTTCATGCTTGTGAGGGTTAGCTGTAGGAGCGGGTGAAAGGATTCCAGTTTATGAAAATTTAAAGCAAACAACGG
TTTTTAGCTGGGTGGGAAACAGGAAAACTGTGATGTCGGCCAATGACCACCATTTTTCTGCCCATGTGAAGGTCCC
CATGAAACC
```

*Fig. 15H*

11786.2.contig

CAAGCGCTTGGCGTTTGGACCCAGTTCAGTGAGGTTCTTGGGTTTTGTGCCTTTGGGGATTTTGGTTTGACCCAGG
GGTCAGCCTTAGGAAGGTCTTCAGGAGGAGGCCGAGTTCCCCTTCAGTACCACCCCTCTCTCCCCACTTTCCCTCT
CCCGGCAACATCTCTGGGAATCAACAGCATATTGACACGTTGGAGCCGAGCCTGAACATGCCCCTCGGCCCCAGCA
CATGGAAAACCCCCTTCCTTGCCTAAGGTGTCTGAGTTTCTGGCTCTTGAGGCATTTCCAGACTTGAAATTCTCAT
CAGTCCATTGCTCTTGAGTCTTTGCAGAGAACCTCAGATCAGGTGCACCTGGGAGAAAGACTTTGTCCCCACTTAC
AGATCTATCTCCTCCCTTGGGAAGGGCAGGGAATGGGGACGGTGTATGGAGGGGAAGGGATCTCCTGCGCCCTTCA
TTGCCACACTTGGTGGGACCATGAACATCTTTAGTGTCTGAGCTTCTCAAATTACTGCAATAGGA

13691.1&2

AGCGTCAAATCAGAATGGAAAAGACTCAAAACCATCATCAACACCAAGATCAAAAGGACAAGRATCCTTCAAGAAA
CAGGAAAAAACTCCTAAAACACCAAAAGGACCTAGTTCTGTAGAAGACATTAAAGCAAAAATGCAAGCAAGTATAG
AAAAAGGTGGTTCTCTTCCCAAAGTGGAAGCCAAATTCATCAATTATGTGAAGAATTGCTTCCGGATGACTGACCA
AGAGGCTATTCAAGATCTCTGGCAGTGGAGGAAGTCTCTTTAAGAAAATAGTTTAAACAATTTGTTAAAAAATTTT
CCGTCTTATTTCATTTCTGTAACAGTTGATATCTGGCTGTCCTTTTTATAATGCAGAGTGAGAACTTTCCCTACCG
TGTTTGATAAATGTTGTCCAGGTTCTATTGCCAAGAATGTGTTGTCCAAAATGCCTGTTTAGTTTTTAAAGATGGA
ACTCCACCCTTTGCTTGGTTTTAAGTATGTATGGAATGTTATGATAGGACATAGTAGTAGCGGTGGTCAGACATGG
AAATGGTGGGSMGACAAAAATATACATGTGAAATAA

13692.1&2

TCCGAATTCCAAGCGAATTATGGACAAACGATTCCTTTTAGAGGATTACTTTTTTTCAATTTCGGTTTTAGTAATCT
AGGCTTTGCCTGTAAAGAATACAACGATGGATTTTAAATACTGTTTGTGGAATGTGTTTAAAGGATTGATTCTAGA
ACCTTTGTATATTTGATAGTATTTCTAACTTTCATTTCTTTACTGTTTGCAGTTAATGTTCATGTTCTGCTATGCA
ATCGTTTATATGCACGTTTCTTTAATTTTTTTAGATTTTCCTGGATGTATAGTTTAAACAACAAAAAGTCTATTTA
AAACTGTAGCAGTAGTTTACAGTTCTAGCAAAGAGGAAAGTTGTGGGGTTAAACTTTGTATTTTCTTTCTTATAGA
GGCTTCTAAAAAGGTATTTTTATATGTTCTTTTTAACAAATATTGTGTACAACCTTTAAAACATCAATGTTTGGAT
CAAAACAAGACCCAGCTTATTTTCTGC

13693.2

TGTGGTGGCGCGGGCTGAGGTGGAGGCCCAGGACTCTGACCCTGCCCCTGCCTTCAGCAAGGCCCCCGGCAGCGCC
GGCCACTACGAACTGCCGTGGGTTGAAAAATATAGGCCAGTAAAGCTGAATGAAATTGTCGGGAATGAAGACACCG
TGAGCAGGCTAGAGGTCTTTGCAAGGGAAGGAAATGTGCCCAACATCATCATTGCGGGCCCTCCAGGAACCGGCAA
GACCACAAGCATTCTGTGCTTGGCCCGGGCCCTGCTGGGCCCAGCACTCAAAGATGCCATGTTGGAACTCAATGCT
TCAAATGACAGGGGCATTGACGTTGTGAGGAATAAAATTAAAATGTTTGCTCAACAAAAAGTCACTCTTCCCAAAG
GCCGACATAAGATCATCATTCTGGATGAAGCAGACAGCATGACCGACGGAGCCCAGCAAGCCTTGAGGAGAACCAT
GGAAATCTACTCTAAAACCACTCGTTCGCCCTTGCTTGTAATGCTTCGGATAAGATCATCGAGCC

```
CTTTGCAAAGCTTTTATTTCATGTCTGCGGCATGGAATCCACCTGCACATGGCATCTTAGCTGTGAAGGAGAAAGC
AGTGCACGAGAAGGAATGAGTGGGCGGAACCAACGGCCTCCACAAGCTGCCTTCCAGCAGCCTGCCAAGGCCATGG
CAGAGAGAGACTGCAAACAAACACAAGCAAACAGAGTCTCTTCACAGCTGGAGTCTGAAAAGCTCATAGTGGCATGT
GTGAATCTGACAAAATTAAAAGTGTGCATAGTCCATTACATGCATAAAACACTAATAATAATCCTGTTTACACGTG
ACTGCAGCAGGCAGGTCCAGCTCCACCACTGCCCTCCTGCCACATCACATCAAGTGCCATGGTTTAGAGGGTTTTT
CATATGTAATTCTTTTATTCTGTAAAAGGTAACAAAATATACAGAACAAAACTTTCCCTTTTTAAAACTAATGTTA
CAAATCTGTATTATCACTTGGATATAAATAGTATATAAGCTGATC
```

13700.1

```
CAAGGGATATATGTTGAGGGTACRGRGTGACACTGAACAGATCACAAAGCACGAGAAACATTAGTTCTCTCCCTCC
CCAGCGTCTCCTTCGTCTCCCTGGTTTTTCCGATGTCCACAGAGTGAGATTGTCCCTAAGTAACTGCATGATCAGAG
TGCTGKCTTTATAAGACTCTTCATTCAGCGTATCCAATTCAGCAATTGCTTCATCAAATGCCGTTTTTGCCAGGCT
ACAGGCCTTTTCAGGAGAGTTTAGAATCTCATAGTAAAAGACTGAGAAATTTAGTGCCAGACCAAGACGAATTGGG
TGTGTAGGCTGCATTNCTTTCTTACTAATTTCAAATGCTTCCTGGTAAGCCTGCTGGGAGTTCGACACAAGTGGTT
TGTTTGTTGCTCCAGATGCCACTTCAGAAAGATACCTAAAATAATCTCCTTTCATTTTCAAAGTAGAACAC
```

13700.2

```
TCCGGAGCCGGGGTAGTCGCCGCCGCCGCCGCCGGTGCAGCCACTGCAGGCACCGCTGCCGCCGCCTGAGTAGTGG
GCTTAGGAAGGAAGAGGTCATCTCGCTCGGAGCTTCGCTCGGAAGGGTCTTTGTTCCCTGCAGCCCTCCCACGGGA
ATGACAATGGATAAAAGTGAGCTGGTACAGAAAGCCAAACTCGCTGAGCAGGCTGAGCGATATGATGATATGGCTG
CAGCCATGAAGGCAGTCACAGAACAGGGGCATGAACTCTCCAACGAAGAGAGAAATCTGCTCTCTGTTGCCTACAA
GAATGTGGTAAGGCCGCCCGCCGCTCTTCCTGGCGTGTCATCTCCAGCATTGAGCAGAAAACAGAGAGGAATGAGA
AGAAGCAGCAGATGGGCAAAGAGTACCGTGAGAAGATAGAGGCAGAACTGCAGGACATCTGCAATGATGTTCTGGA
GCTTGTTGGACAAATATCTTATTCCAATGCTACACAACCCAGAAA
```

13701.1

```
AAAAAGCAGCARGTTCAACACAAAATAGAAATCTCAAATGTAGGATAGAACAAAACCAAGTGTGTGAGGGGGGAAG
CAACAGCAAAAGGAAGAAATGAGATGTTGCAAAAAAGATGGAGGAGGGTTCCCCTCTCCTCTGGGGACTGACTCAA
ACACTGATGTGGCAGTATACACCATTCCAGAGTCAGGGGTGTTCATTCTTTTTTGGGAGTAAGAAAAGGTGGGGAT
TAAGAAGACGTTTCTGGAGGCTTAGGGACCAAGGCTGGTCTCTTTCCCCCCCTCCCAACCCCCTTGATCCCTTTCTC
TGATCAGGGGAAAGGAGCTCGAATGAGGGAGGTAGAGTTGGAAAGGGAAAGGATTCCACTTGACAGAATGGGACAG
ACTCCTTCCCA
```

TGGCAATAGCACAGCCATCCAGGAGCTCTTCARGCGCATCTCGGAGCAGTTCACTGCCATGTTCCGCCGGAAGGCC
TTCCTCCACTGGTACACAGGCGAGGGCATGGACGAGATGGAGTTCACCGAGGCTGAGAGCAACATGAACGACCTCG
TCTCTGAGTATCAAGCAGTACCAGGATGCCACCGCAGAAGAGGAGGAGGATTTCGGTGAGGAGGCCGAAGAGGAGG
CCTAAGGCAGAGCCCCCATCACCTCAGGCTTCTCAGTTCCCTTAGCCGTCTTACTCAACTGCCCCTTTCCTCTCCC
TCAGAATTTGTGTTTGCTGCCTCTATCTTGTTTTTTGTTTTTTCTTCTGGGGGGGTCTAGAACAGTGCCTGGCACA
TAGTAGGCGCTCAATAAATACTTGGTTGNTGAATGTCTCCT

13702.2

AGCTGGCGCTAGGGCTCGGTTGTGAAATACAGCGTRGTCAGCCCTTGCGCTCAGTGTAGAAACCCACGCCTGTAAG
GTCGGTCTTCGTCCATCTGCTTTTTTCTGAAATACACTAAGAGCAGCCACAAAACTGTAACCTCAAGGAAACCATA
AAGCTTGGAGTGCCTTAATTTTTAACCAGTTTCCAATAAAACGGTTTACTACCT

13704.2-13740.2

GGAGATGAAGATGAGGAAGCTGAGTCAGCTACGGGCARGCGGGCAGCTGAAGATGATGAGGATGACGATGTCGATA
CCAAGAAGCAGAAGACCGACGAGGATGACTAGACAGCAAAAAAGGAAAAGTTAAA

13706.1

GATGAAAATTAAATACTTAAATTAATCAAAAGGCACTACGATACCACCTAAAACCTACTGCCTCAGTGGCAGTAKG
CTAAKGAAGATCAAGCTACAGSACATYATCTAATATGAATGTTAGCAATTACATAKCARGAAGCATGTTTGCTTTC
CAGAAGACTATGGNACAATGGTCATTWGGGCCCAAGAGGATATTTGGCCNGGAAAGGATCAAGATAGATNAANGTA
AAG

13706.2

GAGTAGCAACGCAAAGCGCTTGGTATTGAGTCTGTGGGSGACTTCGGTTCCGGTCTCTGCAGCAGCCGTGATCGCT
TAGTGGAGTGCTTAGGGTAGTTGGCCAGGATGCCGAATATCAAAATCTTCAGCAGGCAGCTCCCACCAGGACTTAT
CTCASAAAATTGCTGACCGCCTGGGCCTGGAGCTAGGCAAGGTGGTGACTAAGAAATTCAGCAACCAGGAGACCTG
TGTGGAAATTGGTGAAAGTGTACCGTGGAGAGGATGTCTACATTGTTCAGAGTGGNTGTGGCGAAATCAATGACAA
TTTAATGGAGCTTTTGATCATGATTAATGCCTGCAAGATTGCTTCAGCCAGCCGGGTTACTGCAGTCATCCCATGC
TTCCCTTATGCCCCGGCAGGATAAGAAAGATNAGAGCCGGGCCGCCAATCTCAGCCAAGCTTGGTGCAAATATGCT
ATCTGTAGCAGTGCAGATCATATTATCACCATGGACCTACATGCTTCTCAAATTCANGGCTTTTT

ATGCAAAAGGGGACACAGGGGGTTCAAAAATAAAAATTTCTCTTCCCCCTCCCCAAACCTGTACCCCAGCTCCCCG
ACCACAACCCCCTTCCTCCCCCGGGGAAAGCAAGAAGGAGCAGGTGTGGCATCTGCAGCTGGGAAGAGAGAGGCCG
GGGAGGTGCCGAGCTCGGTGCTGGTCTCTTTCCAAATATAAATACGTGTGTCAGAACTGGAAAATCCTCCAGCACC
CACCACCCAAGCACTCTCCGTTTTCTGCCGGTGTTTGGAGAGGGGCGGNGGGCAGGGGCGCCAGGCACCGGCTGGC
TGCGGTCTACTGCATCCGCTGGGTGTGCACCCCGCGA 13710.2

AGGTTGGAGAAGGTCATGCAGGTGCAGATTGTCCAGGSKCAGCCACAGGGTCAAGCCCAACAGGCCCAGAGTGGCA
CTGGACAGACCATGCAGGTGATGCAGCAGATCATCACTAACACAGGAGAGATCCAGCAGATCCGGTGCAGCTGAA
TGCCGGCCAGCTGCAGTATATCCGCTTAGCCCAGCCTGTATCAGGCACTCAAGTTGTGCAGGGACAGATCCAGACA
CTTGCCACCAATGCTCAACAGATTACACAGACAGAGGTCCAGCAAGGACAGCAGCAGTTCAAGCCAGTTCACAAGA
TGGACAGCAGCTCTACCAGATCCAGCAAGTCACCATGCCTGCGGGCCANGACCTCGCCAGCCCATGTTCATCCAGT
CAAGCCAACCAGCCCTTCNACGGGCAGGCCCCCCAGGTGACCGGCGACTGAAGGGCCTGAGCTGGCAAGGCCAANG
ACACCCAACACAATTTTTGCCATACAGCCCCCAGGCAATGGGCACAGCCTTTCTTCCCAGAGGAC 13710-1

TGAGATTTATTGCATTTCATGCAGCTTGAAGTCCATGCAAAGGRGACTAGCACAGTTTTTAATGCATTTAAAAAAT
AAAAGGGAGGTGGGCAGCAAACACACAAAGTCCTAGTTTCCTGGGTCCCTGGGAGAAAAGAGTGTGGCAATGAATC
CACCCACTCTCCACAGGGAATAAATCTGTCTCTTAAATGCAAAGAATGTTTCCATGGCCTCTGGATGCAAATACAC
AGAGCTCTGGGGTCAGAGCAAGGGATGGGGAGAGGACCACGAGTGAAAAAGCAGCTACACACATTCACCTAATTCC
ATCTGAGGGCAAGAACAACGTGGCAAGTCTTGGGGGTAGCAGCTGTT 13711.1

TCCAGACATGCTCCTGTCCTAGGCGGGGAGCAGGAACCAGACCTGCTATGGGAAGCAGAAAGAGTTAAGGGAAGGT
TTCCTTTCATTCCTGTTCCTTCTCTTTTGCTTTTGAACAGTTTTTAAATATACTAATAGCTAAGTCATTTGCCAGC
CAGGTCCCGGTGAACAGTAGAGAACAAGGAGCTTGCTAAGAATTAATTTTGCTGTTTTTCACCCCATTCAAACAGA
GCTGCCCTGTTCCCTGATGGAGTTCCATTCCTGCCAGGGCACGGCTGAGTAACACGAAGCCATTCAAGAAAGGCGG
GTGTGAAATCACTGCCACCCCATGGACAGACCCCTCACTCTTCCTTCTTAGCCGCAGCGCTACTTAATAAATATAT
TTATACTTTGAAATTATGATAACCGATTTTTCCCATGCGGCATCCTAAGGGCACTTGCCAGCTCTTATCCGGACAG
TCAAGCACTGTTGTTGGACAACAGATAAAGGAAAAGAAAAAGAAGAAAACAACCGCAACTTCTGT

TGAGACGGACCACTGGCCTGGTCCCCCCTCATKTGCTGTCGTAGGACCTGACATGAAACGCAGATCTAGTGGCAGA
GAGGAAGATGATGAGGAACTTCTGAGACGTCGGCAGCTTCAAGAAGAGCAATTAATGAAGCTTAACTCAGGCCTGG
GACAGTTGATCTTGAAAGAAGAGATGGAGAAAGAGAGCCGGGAAAGGTCATCTCTGTTAGCCAGTCGCTACGATTC
TCCCATCAACTCAGCTTCACATATTCCATCATCTAAAACTGCATCTCTCCCTGGCTATGGAAGAAATGGGCTTCAC
CGGCCTGTTTCTACCGACTTCGCTCAGTATAACAGCTATGGGGATGTCAGCGGGGGAGTGCGAGATTACCAGACAC
TTCCAGATGGCCACATGCCTGCAATGAGAATGGACCGAGGAGTGTCTATGCCCAACATGTTGGAACCAAAGATATT
TCCATATGAAATGCTCATGGTGACCAACAGAGGGCCGAAACCAAATCTCAGAGAGGTGGACAGAA 13713.1&2

TCACTTTATTTTTCTTGTATAAAAACCCTATGTTGTAGCCACAGCTGGAGCCTGAGTCCGCTGCACGGAGACTCTG
GTGTGGGTCTTGACGAGGTGGTCAGTGAACTCCTGATAGGGAGACTTGGTGAATACAGTCTCCTTCCAGAGGTCGG
GGGTCAGGTAGCTGTAGGTCTTAGAAATGGCATCAAAGGTGGCCTTGGCGAAGTTGCCCAGGGTGGCAGTGCAGCC
CCGGGCTGAGGTGTAGCAGTCATCGATACCAGCCATCATGAG 13715.4

CTGGAATATAGACCCGTGATCGACAAAACTTTGAACGAGGCTGACTGTGCCACCGTCCCGCCAGCCATTCGCTCCT
ACTGATGAGACAAGATGTGGTGATGACAGAATCAGCTTTTGTAATTATGTATAATAGCTCATGCATGTGTCCATGT
CATAACTGTCTTCATACGCTTCTGCACTCTGGGGAAGAAGGAGTACATTGAAGGGAGATTGGCACCTAGTGGCTGG
GAGCTTGCCAGGAACCCAGTGGCCAGGGAGCGTGGCACTTACCTTTGTCCCTTGCTTCATTCTTGTGAGATGATAA
AACTGGGCACAGCTCTTAAATAAAATATAAATGAACA 13717.1&2

TGAATGGGGAGGAGCTGACCCAGGAAATGGAGCTTGNGGAGACCAGGCCTGCAGGGGATGGAACCTTCCAGAAGTG
GGCATCTGTGGTGGTGCCTCTTGGGAAGGAGCAGAAGTACACATGCCATGTGGAACATGAGGGGCTGCCTGAGCCC
CTCACCCTGAGATGGGGCAAGGAGGAGCCTCCTTCATCCACCAAGACTAACACAGTAATCATTGCTGTTCCGGTTG
TCCTTGGAGCTGTGGTCATCCTTGGAGCTGTGATGGCTTTTGTGATGAAGAGGAGGAGAAACACAGGTGGAAAAGG
AGGGGACTATGCTCTGGCTCCAGGCTCCCAGAGCTCTGATATGTCTCTCCCAGATTGTAAAGTGTGAAGACAGCTG
CCTGGTGTGGACTTGGTGACAGACAATGTCTTCACACATCTCCTGTGACATCCAGAGACCTCAGTTCTCTTTAGTC
AAGTGTCTGATGTTCCCTGTGAGTCTGCGGGCTCAAAGTGAAGAACTGTGGAGCCCAGTCCACCCCTGCACACCAG
GACCCTATCCCTGCACTGCCCTGTGTTCCCTTCCACAGCCAACCTTGCTGCTCCAGCCAAACATTGGTGGACATCT
GCAGCCTGTCAGCTCCATGCTACCCTGACCTTCAACTCCTCACTTCCACACTGAGAATAATAATTTGAATGTGGGT
GGCTGGAGAGATGGCTCAGCGCTGACTGCTCTTCCAAAGGTCCTGAGTTCAAATCCCAGCAACCACATGGTGGCTC
ACAACCATCTGTAATGGGATCTAATACCCTCTTCTGCAGTGTCTGAAGACASCTACAGTGTACTTACATATAATAA
TAAATAAG

```
GGCCGGGCGCGCGCGCCCCCGCCACACGCACGCCGGGCGTGCCAGTTTATAAAGGGAGAGAGCAAGCAGCGAGTCT
TGAAGCTCTGTTTGGTGCTTTGGATCCATTTCCATCGGTCCTTACAGCCGCTCGTCAGACTCCAGCAGCCAAGATG
GTGAAGCAGATCGAGAGCAAGACTGCTTTTCAGGAAGCCTTGGACGCTGCAGGTGATAAACTTGTAGTAGTTGACT
TCTCAGCCACGTGGTGTGGGCCTTGCAAAATGATCAAGCCTTTCTTTCATTCCCTCTCTGAAAAGTATTCCAACGT
GATATTCCTTGAAGTAGATGTGGATGACTGTCAGGATGTTGCTTCAGAGTGTGAAGTCAAATGCATGCCAACATTC
CAGTTTTTTAAGAAGGGACAAAAGGTGGGTGAATTTTCTGGAGCCAATAAGGAAAAGCTTGAAGCCACCATTAATG
AATTAGTCTAATCATGTTTTCTGAAAATATAACCAGCCATTGGCTATTTAAAACTTGTAATTTTTTTAATTTACAA
AAATATAAAATATGAAGACATAAACCCMGTTGCCATCTGCGTGACAATAAAACATTAATGCTAACACTT
```

13721.1

```
TCACATAAGAAATTTAAGCAAGTTACRCTATCTTAAAAAACACAACGAATGCATTTTAATAGAGAAACCCTTCCCT
CCCTCCACCTCCCTCCCCCACCCTCCTCATGAATTAAGAATCTAAGAGAAGAAGTAACCATAAAACCAAGTTTTGT
GGAATCCATCATCCAGAGTGCTTACATGGTGATTAGGTTAATATTGCCTTCTTACAAAATTTCTATTTTAAAAAAA
ATTATAACCTTGATTGCTTATTACAAAAAAATTCAGTACAAAAGTTCAATATATTGAAAAATGCTTTTCCCCTCCC
TCACAGCACCGTTTTATATATAGCAGAGAATAATGAAGAGATTGCTAGTCTAGATGGGGCAATCTTCAAATTACAC
CAAGACGCACAGTGGTTTATTTACCCTCCCCTTCTCATAAG
```

13721.2

```
GGAAAGGATTCAAGAATTAGAGGACTTGCTTGCTRRAGAAAAAGACAACTCTCGTCGCATGCTGACAGACAAAGAG
AGAGAGATGGCGGAAATAAGGGATCAAATGCAGCAACAGCTGAATGACTATGAACAGCTTCTTGATGTAAAGTTAG
CCCTGGACATGGAAATCAGTGCTTACAGGAAACTCTTAGAAGGCGAAGAAGAGAGGTTGAAGCTGTCTCCAAGCCC
TTCTTCCCGTGTGACAGTATCCCGAGCATCCTCAAGTCGTAGTGTACCGTACAACTAGAGGAAAGCGGAAGAGGGT
TGATGTGGAAGAATCAGAGGCGAAGTAGTAGTGTTAGCATCTCTCATTCCGCCTCAACCACTGGAAATGTTTGCAT
CGAAGAAATTGATGTTGATGGGAAATTTATCCCGCTTGAAGAACACTTCTGAACAGGATCAACCAATGGGAAGGCT
TGGGAGATGATCAGAAAAATTGGAGACACATCAGTCAGTTATAAATATACCTCAA
```

13723.1

```
CATGGGTTTCACCAGGTTGGCCAGGCTGCTCTTGAACTSCTGACCTCAGGTGATCCACCCGCCTCGGCCTCCCAAA
GTGCTGGGATTACAGGCGTGAGCCACCACGCCCGGCCCCCAAAGCTGTTTCTTTTGTCTTTAGCGTAAAGCTCTCC
TGCCATGCAGTATCTACATAACTGACGTGACTGCCAGCAAGCTCAGTCACTCCGTGGTCTTTTTCTCTTTCCAGTT
CTTCTCTCTCTCTTCAAGTTCTGCCTCAGTGAAAGCTGCAGGTCCCCAGTTAAGTGATCAGGTGAGGGTTCTTTGA
ACCTGGTTCTATCAGTCGAATTAATCCTTCATGATGG
```

GATGTGTTGGACCCTCTGTGTCAAAAAAAACCTCACAAAGAATCCCCTGCTCATTACAGAAGAAGATGCATTTAAA
ATATGGGTTATTTTCAACTTTTTATCTGAGGACAAGTATCCATTAATTATTGTGTCAGAAGAGATTGAATACCTGC
TTAAGAAGCTTACAGAAGCTATGGGAGGAGGTTGGCAGCAAGAACAATTTGAACATTATAAAATCAACTTTGATGA
CAGTAAAAATGGCCTTTCTGCATGGGAACTTATTGAGCTTATTGGAAATGGACAGTTTAGCAAAGGCATGGACCGG
CAGACTGTGTCTATGGCAATTAATGAAGTCTTTAATGAACTTATATTAGATGTGTTAAAGCAGGGTTACATGATGA
AAAAGGGCCACAGACGGAAAAACTGGACTGAAAGATGGTTTGTACTAAAACCCAACATAATTTCTTACTATGTGAG
TGAGGATCTGAAGGATAAGAAAGGAGACATTCTCTTGGATGAAAATTGCTGTGTAGAAGTCCTTGCCTGACAAAAG
ATGGAAAGAAATGCCTTTT

13725.1

GACTGGTTCTTTATTTCAAAAAGACACTTGTCAATATTCAGTRTCAAAACAGTTGCACTATTGATTTCTCTTTCTC
CCAATCGGCCCCAAAGAGACCACATAAAAGGAGAGTACATTTTAAGCCAATAAGCTGCAGGATGTACACCTAACAG
ACCTCCTAGAAACCTTACCAGAAAATGGGGACTGGGTAGGGAAGGAAACTTAAAAGATCAACAAACTGCCAGCCCA
CGGACTGCAGAGGCTGTCACAGCCAGATGGGGTGGCCAGGGTGCCACAAACCCAAAGCAAAGTTTCAAAATAATAT
AAAATTTAAAAAGTTTTGTACATAAGCTATTCAAGATTTCTCCAGCACTGACTGATACAAAGCACAATTGAGATGG
CACTTCTAGAGACAGCAGCTTCAAACCCAGAAAAGGGTGATGAGATGAAGTTTCACATGGCTAAATCAGTGGCAAA
AACACAGTCTTCTTTCTTTCTTTCAAGGANGCAGGAAAGCAATTAAGTGGTCACCTTAACATAAGGGGGAC

13725.2

TGGGTGGGCACCATGGCTGGGATCACCACCATCGAGGCGGTGAAGCGCAAGATCCAGGTTCTGCAGCAGCAGGCAG
ATGATGCAGAGGAGCGAGCTGAGCGCCTCCAGCGAGAAGTTGAGGGAGAAAGGCGGGCCCGGGAACAGGCTGAGGC
TGAGGTGGCCTCCTTGAACCGTAGGATCCAGCTGGTTGAAGAAGAGCTGGACCGTGCTCAGGAGCGCCTGGCCACT
GCCCTGCAAAAGCTGGAAGAAGCTGAAAAAGCTGCTGATGAGAGTGAGAGAGGTATGAAGGTTATTGAAAACCGGG
CCTTAAAAGATGAAGAAAAGATGGAACTCCAGGAAATCCAACTCAAAGAAGCTAAGCACATTGCAGAAGAGGCAGA
TAGGAAGTATGAAGAGGTGGCTCGTAAGTTGGTGATCATTGAAGGAGACTTGGAACCGCACAGAAGGAACGAGCTT
GAGCTTGGCAAAAGTCCCGTTGCCCAGAGATGGGATGAACCAGATTAGACTGATGGACCANAACC

13726.1&2

AGGGGCNGCGGGTGCGTGGGCCACTGGGTGACCGACTTAGCCTGGCCAGACTCTCAGCACCTGGAAGCGCCCCGAG
AGTGACAGCGTGAGGCTGGGAGGGAGGACTTGGCTTGAGCTTGTTAAACTCTGCTCTGAGCCTCCTTGTCGCCTGC
ATTTAGATGGCTCCCGCAAAGAAGGGTGGCGAGAAGAAAAAGGGCCGTTCTGCCATCAACGAAGTGGTAACCCGAG
AATACACCATCAACATTCACAAGCGCATCCATGGAGTGGGCTTCAAGAAGCGTGCACCTCGGGCACTCAAAGAGAT
TCGGAAATTTGCCATGAAGGAGATGGGAACTCCAGATGTGCGCATTGACACCAGGCTCAACAAAGCTGTCTGGGCC
AAAGGAATAAGGAATGTGCCATACCGAATCCGGTGTGCGGCTGTCCAGAAAACGTAATGAGGATGAAGATTCACCA
AATAAGCTATATACTTTGGTTACCTATGTACCTGTTACCACTTTCAAAAATCTACAGACAGTCAATGTGGATGAGA
ACTAATCGCTGATCGTCAGATCAAATAAAGTTATAAAAT

```
TCGGGAGCCACACTTGGCCCTCTTCCTCTCCAAAGSGCCAGAACCTCCTTCTCTTTGGAGAATGGGGAGGCCTCTT
GGAGACACAGAGGGTTTCACCTTGGATGACCTCTAGAGAAATTGCCCAAGAAGCCCACCTTCTGGTCCCAACCTGC
AGACCCCACAGCAGTCAGTTGGTCAGGCCCTGCTGTAGAAGGTCACTTGGCTCCATTGCCTGCTTCCAACCAATGG
GCAGGAGAGAAGGCCTTTATTTCTCGCCCACCCATTCCTCCTGTACCAGCACCTCCGTTTTCAGTCAGTGTTGTCC
AGCAACGGTACCGTTTACACAGTCACCTCAGACACACCATTTCACCTCCCTTGCCAAGCTGTTAGCCTTAGAGTGA
TTGCAGTGAACACTGTTTACACACCGTGAATCCATTCCCATCAGTCCATTCCAGTTGGCACCAGCCTGAACCATTT
GGTACCTGGTGTTAACTGGAGTCCTGTTTACAAGGTGGAGTCGGGGCTTGCTGACTTCTCTTCATTTGAGGGCAC
```

13727.2

```
ACCTAGACAGAAGGTGGGTGAGGGAGGACTGGTAGGAGGCTGAGGCAATTCCTTGGTAGTTTGTCCTGAAACCCTA
CTGGAGAAGTCAGCATGAGGCACCTACTGAGAGAAGTGCCCAGAAACTGCTGACTGCATCTGTTAAGAGTTAACAG
TAAAGAGGTAGAAGTGTGTTTCTGAATCAGAGTGGAAGCGTCTCAAGGGTCCCACAGTGGAGGTCCCTGAGCTACC
TCCCTTCCGTGAGTGGGAAGAGTGAAGCCCATGAAGAACTGAGATGAAGCAAGGATGGGGTTCCTGGGCTCCAGGC
AAGGGCTGTGCTCTCTGCAGCAGGGAGCCCCACGAGTCAGAAGAAAAGAACTAATCATTTGTTGCAAGAAACCTTG
CCCGGATACTAGCGGAAAACTGGAGGCGGNGGTGGGGGCACAGGAAAGTGGAAGTGATTTGATGGAGAGCAGAGAA
GCCTATGCACAGTGGCCGAGTCCACTTGTAAAGTG
```

13728.1&2

```
TTCAAGCAATTGTAACAAGTATATGTAGATTAGAGTGAGCAAAATCATATACAATTTTCATTTCCAGTTGCTATTT
TCCAAATTGTTCTGTAATGTCGTTAAAATTACTTAAAAATTAACAAAGCCAAAAATTATATTTATGACAAGAAAGC
CATCCCTACATTAATCTTACTTTTCCACTCACCGGCCCATCTCCTTCCTCTTTTTCCTAACTATGCCATTAAAACT
GTTCTACTGGGCCGGGCGTGTGGCTCATGCCTGTAATCCCAGCATTTTGGGAGGCCAAGGCAGGCGGATCATGAGG
TCAAGAGATTGAGACCATCCTGGCCAACATGGTGAAACCCCGCCTCGACTAAGAATACAAAAATTAGCTGGGCATG
GTGGCGCATGCCTGTAGTCTCAGCTACTCGGGAGGCTGAGGCAGAAGAATCGCTTGAACCCGGGAGGCAGAGGATG
CAGTGAGCCCCGATCGCGCCACTGCACTCTAGCCTGGGCGACAGACTGAGACTCTGCTC
```

13731.1&2

```
TGTGCCAGTCTACAGGCCTATCAGCAGCGACTCCTTCAGCAACAGATGGGGTCCCCTGTTCAGCCCAACCCCATGA
GCCCCCAGCAGCATATGCTCCCAAATCAGGCCCAGTCCCCACACCTACAAGGCCAGCAGATCCCTAATTCTCTCTC
CAATCAAGTGCGCTCTCCCCAGCCTGTCCCTTCTCCACGGCCACAGTCCCAGCCCCCCCACTCCAGTCCTTCCCCA
AGGATGCAGCCTCAGCCTTCTCCACACCACGTTTCCCCACAGACAAGTTCCCCACATCCTGGACTGGTAGTTGCCC
AGGCCAACCCCATGGAACAAGGGCATTTTGCCAGCC
```

```
TGTAAAAACTTGTTTTTAATTTTGTATAAAATAAAGGTGGTCCATGCCCACGGGGGCTGTAGGAAATCCAAGCAGACCA
GCTGGGGTGGGGGGATGTAGCCTACCTCGGGGGACTGTCTGTCCTCAAAACGGGCTGAGAAGGCCCGTCAGGGGCCCAG
GTCCCACAGAGAGGCCTGGGATACTCCCCCAACCCGAGGGGCAGACTGGGCAGTGGGGAGCCCCCATCGTGCCCCAGAG
GTGGCCACAGGCTGAAGGAGGGGCCTGAGGCACCGCAGCCTGCAACCCCCAGGGCTGCAGTCCACTAACTTTTTACAGA
ATAAAAGGAACATGGGGATGGGGAAAAAAGCACCAGGTCAGGCAGGGCCCGAGGGCCCCAGATCCCAGGAGGGCCAGGA
CTCAGGATGCCAGCACCACCCTAGCAGCTCCCACAGCTCCTGGCACAGGAGGCCGCCACGGATTGGCACAGGCCGCTGC
TGGCCATCACGCCACATTTGGAGAACTTGTCCCGACAGAGGTCAGCTCGGAGGAGCTCCTCGTGGGCACACACTGTACG
AACACAGATCTCCTTGTTAATGACGTACACACGGCGGAGGCTGCGGGGACAGGGCACGGGAGGTCTCAGCCCCACTT
```

13736.2

```
ATGGCTGCTGGATTTAGGTGGTAATAGGGGCTGTGGGCCATAAATCTGAAGCCTTGAGAACCTTGGGTCTGGAGAGCCA
TGAAGAGGGAAGGAAAAGAGGGCAAGTCCTGAACCTAACCAATGACCTGATGGATTGCTCGACCAAGACACAGAAGTGA
AGTCTGTGTCTGTGCACTTCCCACAGACTGGAGTTTTTGGTGCTGAATAGAGCCAGTTGCTAAAAAATTGGGGGTTTGG
TGAAGAAATCTGATTGTTGTGTGTATTCAATGTGTGATTTTAAAAATAAACAGCAACAACAATAAAAACCCTGACTGGC
TGTTTTTTCCCTGTATTCTTTACAACTATTTTTTGACCCTCTGAAAATTATTATACTTCACCTAAATGGAAGACTGCTG
TGTTTGTGGAAATTTTGTAATTTTTTAATTTATTTTATTCTCTCTCCTTTTTATTTTGCCTGCAGAATCCGTTGAGAGA
CTAATAAGGCTTAATATTTAATTGATTTGTTTAATATGTATATAAAT
```

13744.2-13696.2

```
GGCATGCGAGCGCACTCGGCGGACGCAAGGGCGGCGGGGAGCACACGGAGCACTGCAGGCGCCGGGTTGGGACAGCGTC
TTCGCTGCTGCTGGATAGTCGTGTTTTCGGGGATCGAGGATACTCACCAGAAACCGAAAATGCCGAAACCAATCAATGT
CCGAGTTACCACCATGGATGCAGAGCTGGAGTTTGCAATCCAGCCAAATACAACTGGAAAACAGCTTTTTGATCAGGTG
GTAAAGACTATCGGCCTCCGGGAAGTGTGGTACTTTGGCCTCCACTATGTGGATAATAAAGGATTTCCTACCTGGCTGA
AGCTGGATAAGAAGGTGTCTGCCCAGGAGGTCAGGAAGGAGAATCCCCTCCAGTTCAAGTTCCGGGCCAAaGTTCTACC
CTGAAGATGTGGCTGAGGAGCTCATCCAGGACATCACCCAGAAACTTTTCTTCCTTCAAGTGAAGGAAGGAATCCTTAG
CGATGAGATCTACTGCCCCCCTTGARACTGCCGTGCTCTTGGGGTCCTACGCTTGTGCATGCCAAGTTTGGGGACTACC
ACCAAGAAG
```

13746.1&2-13720.1&2

```
GAAGGAGTCGGGATACTCAGCATTGATGCACCCCAATTTCAAAGCGGCATTCTTCGGCAGGTCTCTGGGACAATCTCTA
GGGTCACTACCTGGAAACTCGTTAGGGTACAACTGAATGCTGAAAGGAAAGAACACCTGCAGAACCGGACAGAAATTCA
CCCCGGCGATCAGCTGATTGATCTCGGTCGACCAGAAGTCATGGCTAAAGATGACGAGGACGTTGTCAATTCCCTGGGC
TTTTCGAAGTGAGTCCAGCAGCAGTCTGAGGTATTCGGGCCGGTTATGCACCTGGACCACCAGCACCAGCTCCCGGGGG
GCCCAGGTGCCAGCCTTATCTACATTCCTCAGGGTCTGATCAAAGTTCAGCTGGTACACCAGGGACCGGTACCGCAGCG
TCAGGTTGTCCGCTCGGGCTGGGGGACCGCCGGGACCAGGGAAGCCGCCGACACGTTGGAGACCCTGCGGATGCCCACA
GCCACAGAGGGGTGGTCCCCACCGCGGCCGCCGGCACCCCGCGCGGGTTCGGCGTCCAGCAACGGTGGGGCGAGGGCCT
CGTTCTTCCTTTGTCGCCCATTGCTGCTCCAGAGGACGAAGCCGCAGGCGGCCACCACGAGCGTCAGGATTAGCACCTT
CCGTTTGTAGATGCGGAACCTCATGGTCTCCAGGGCCGGGAGCGCAGCTACAGCTCGAGCGTCGGCGCCGCCGCTAGGA
GCCGCGGCTCGGCTTCGTCTCCGTCCTCTCCATTCAGCACCACGGGTCCCGGAAAAAGCTCAGCCSCGGTCCCAACCGC
ACCCTAGCTTCGTTACCTGCGCCTCGCTTG
```

```
CAGATTTTTATTTGCAGTCGTCACTGGGGCCGTTTCTTGCTGCTTATTTGTCTGCTAGCCTGCTCTTCCAGCTGCA
TGGCCAGGCGCAAGGCCTTGATGACATCTCGCAGGGCTGAGAAATGCTTGGCTTGCTGGGCCAGAGCAGATTCCGC
TTTGTTCACAAAGGTCTCCAGGTCATAGTCTGGCTGCTCGGTCATCTCAGAGAGCTCAAGCCAGTCTGGTCCTTGC
TGTATGATCTCCTTGAGCTCTTCCATAGCCTTCTCCTCCAGCTCCCTGATCTGAGTCATGGCTTCGTTAAAGCTGG
ACATCTGGGAAGACAGTTCCTCCTCTTCCTTGGATAAATTGCCTGGAATCAGCGCCCCGTTAGAGCAGGCTTCCAT
CTCTTCTGTTTCCATTTGAATCAACTGCTCTCCACTGGGCCCACTGTGGGGGCTCAGCTCCTTGACCCTGCTGCAT
ATCTTAAGGGTGTTTAAAGGATATTCACAGGAGCTTATGCCTGGT
```

14347.2

```
CTCCTCTTGGTACATGAACCCAAGTTGAAAGTGGACTTAACAAAGTATCTGGAGAACCAAGCATTCTGCTTTGACT
TTGCATTTGATGAAACAGCTTCGAATGAAGTTGTCTACAGGTTCACAGCAAGGCCACTGGTACAGACAATCTTTGA
AGGTGGAAAAGCAACTTGTTTTGCATATGGCCAGACAGGAAGTGGCAAGACACATACTATGGGCGGAGACCTCTCT
GGGAAAGCCCAGAATGCATCCAAAGGGATCTATGCCATGGCCTTCCGGGACGTCTTCTTCTGAAGAATCAACCCTG
CTACCGGAAGTTGGGCCTGGAAGTCTATGTGACATTCTTCGAGATCTACAATGGGAAGCTGTTTGACCTGCTCAAC
AAGAAGGCCAAGCTTGCGCGTGCTGGAAGACGGCAAGCAACAGGTGCAAGTGGTGGGGGCTTGCAGGAACATCTGG
NTAACTCTGCTTGATGATGGCANTCAAGATGATCGACATGGGCAGCGCCTGCAGA
```

14348.2&14350.1&2

```
TCCCGAATTCAAGCGACAAATTGGAWAGTGAAATGGAAGATGCCTATCATGAACATCAGGCAAATCTTTTGCGCCA
AGATCTGATGAGACGACAGGAAGAATTAAGACGCATGGAAGAACTTCACAATCAAGAAATGCAGAAACGTAAAGAA
ATGCAATTGAGGCAAGAGGAGGAACGACGTAGAAGAGAGGAAGAGATGATGATTCGTCAACGTGAGATGGAAGAAC
AAATGAGGCGCCAAAGAGAGGAAAGTTACAGCCGAATGGGCTACATGGATCCACGGGAAAGAGACATGCGAATGGG
TGGCGGAGGAGCAATGAACATGGGAGATCCCTATGGTTCAGGAGGCCAGAAATTTCCACCTCTAGGAGGTGGTGGT
GGCATAGGTTATGAAGCTAATCCTGGCGTTCCACCAGCAACCATGAGTGGTTCCATGATGGGAAGTGACATGCGTA
CTGAGCGCTTTGGGCAGGGAGGTGCGGGGCCTGTGGGTGGACAGGGTCCTAGAGGAATGGGGCCTGGAACTCCAGC
AGGATATGGTAGAGGGAGAGAAGAGTACGAAGGC
```

14349.1&2

```
TTCGTGAAGACCCTGACTGGTAAGACCATCACTCTCGAAGTGGAGCCCGAGTGACACCATTGAGAATGTCAAGGCA
AAGATCCAAGACAAGGAAGGCATCCCTCCTGACCAGCAKAGGTTGATCTTTGCTGGGAAACAGCTGGAAGATGGAC
GCACCCTGTCTGACTACAACATCCAGAAAGAGTCCACCCTGCACCTGGTGCTCCGTCTCAGAGGTGGGATGCAAAT
CTTCGTGAAGACCCTGACTGGTAAGACCATCACCCTCGAGGTGGAGCCCAGTGACACCATCGAGAATGTCAAGGCA
AAGATCCAAGATAAGGAAGGCATCCCTCCTGATCAGCAGAGGTTGATCTTTGCTGGGAAACAGCTGGAAGATGGAC
GCACCCTGTCTGACTACAACATCCAGAAAGAGTCCACTCTGCACTTGGTCCTGCGCTTGAGGGGGGGTGTCTAAGT
TTCCCCTTTTAAGGTTTCAACAAATTTCATTGCACTTTCCTTTCAATAAAGTTGTTGCATTC
```

```
GCGCGGGTGCGTGGGCCACTGGGTGACCGACTTAGCCTGGCCAGACTCTCAGCACCTGGAAGCGCCCCGAGAGTGA
CAGCGTGAGGCTGGGAGGGAGGACTTGGCTTGAGCTTGTTAAACTCTGCTCTGAGCCTCCTTGTCGCCTGCATTTA
GATGGCTCCCGCAAAGAAGGGTGGCGAGAAGAAAAAGGGCCGTTCTGCCATCAACGAAGTGGTAACCCGAGAATAC
ACCATCAACATTCACAAGCGCATCCATGGAGTGGGCTTCAAGAAGCGTGCACCTCGGGCACTCAAAGAGATTCGGA
AATTTGCCATGAAGGAGATGGGAACTCCAGATGTGCGCATTGACACCAGGCTCAACAAAGCTGTCTGGGCCAAAGG
AATAAGGAATGTGCCATACCGAATCCGTGTGCGGCTGTCCAGAAAACGTAATGAGGATGAAGATTCACCAAATAAG
CTATATACTTTGGTTACCTATGTACCTGTTACCACTTTCAAAAATCTACAGACAGTCAATGTGGATGAGAACTAAT
CGCTGATCGT
```

14353.1

```
AATTCTTTATTTAAATCAACAAACTCATCTTCCTCAAGCCCCAGACCATGGTAGGCAGCCCTCCCTCTCCATCCCC
TCACCCCACCCCTTAGCCACAGTGAAGGGAATGGAAAATGAGAAGCCACGAGGGCCCCTGCCAGGGAAGGCTGCCC
CAGATGTGTGGTGAGCACAGTCAGTGCAGCTGTGGCTGGGGCAGCAGCTGCCACAGGCTCCTCCCTATAAATTAAG
TTCCTGCAGCCACAGCTGTGGGAGAAGCATACTTGTAGAAGCAAGGCCAGTCCAGCATCAGAAGGCAGAGGCAGCA
TCAGTGACTCCCAGCCATGGAATGAACGGAGGACACAGAGCTCAGAGACAGAACAGGCCAGGGGGAAGAAGGAGAG
ACAGAATAGGCCAGGGCATGGCGGTGAGGGA
```

14353.2

```
TGATGAATCTGGGTGGGCTGGCAGTAGCCCGAGATGATGGGCTCTTCTCTGGGGATCCCAACTGGTTCCCTAAGAA
ATCCAAGGAGAATCCTCGGAACTTCTCGGATAACCAGCTGCAAGAGGGCAAGAACGTGATCGGGTTACAGATGGGC
ACCAACCGCGGGGCGTCTCANGCAGGCATGACTGGCTACGGGATGCCACGCCAGATCCTCTGATCCCACCCCAGGC
CTTGCCCCTGCCCTCCCACGAATGGTTAATATATATGTAGATATATATTTTAGCAGTGACATTCCCAGAGAGCCCC
AGAGCTCTCAAGCTCCTTTCTGTCAGGGTGGGGGGTTCAAGCCTGTCCTGTCACCTCTGAAGTGCCTGCTGGCATC
CTCTCCCCCATGCTTACTAATACATTCCCTTCCCCATAGCC
```

17182.1&2

```
AGCGGAGCTCCCTCCCCTGGTGGCTACAACCCACACACGCCAGGCTCAGGCATCGAGCAGAACTCCAGCGACTGGG
TAACCACTGACATTCAGGTGAAGGTGCGGGACACCTACCTGGATACACAGGTGGTGGGACAGACAGGTGTCATCCG
CAGTGTCACGGGGGGCATGTGCTCTGTGTACCTGAAGGACAGTGAGAAGGTTGTCAGCATTTCCAGTGAGCACCTG
GAGCCTATCACCCCCACCAAGAACAACAAGGTGAAAGTGATCCTGGGCGAGGATCGGGAAGCCACGGGCGTCCTAC
TGAGCATTGATGGTGAGGATGGCATTGTCCGTATGGACCTTGATGAGCAGCTCAAGATCCTCAACCTCCGCTTCCT
GGGGAAGCTCCTGGAAGCCTGAAGCAGGCAGGGCCGGTGGACTTCGTCGGATGAAGAGTGATCCTCCTTCCTTCCC
TGGCCCTTGGCTGTGACACAAGATCCTCCTGCAGGGCTAGGCGGATTGTTCTGGATTTCCTTTTGTTTTTCCTTTT
AGGTTTCCATCTTTTCCCTCCCTGGTGCTCATTGGAATCTGAGTAGAGTCTGGGGGAGGGTCCCCACCTTCCTGTA
CCTCCTCCCCACAGCTTGCTTTTGTTGTACCGTCTTTCAATAAAAAGAAGCTGTTTGGTCTA
```

```
GGTTCACAGCACTGCTGCTTGTGTGTTGCCGGCCAGGAATTCCAGGCTCACAAGGCTATCTTAGCAGCTCGTTCTC
CGGTTTTTAGTGCCATGTTTGAACATGAAATGGAGGAGAGCAAAAAGAATCGAGTTGAAATCAATGATGTGGAGCC
TGAAGTTTTTAAGGAAATGATGTGCTTCATTTACACGGGGAAGGCTCCAAACCTCGACAAAATGGCTGATGATTTG
CTGGCAGCTGCTGACAAGTATGCCCTGGAGCGCTTAAAGGTCATGTGTGAGGATGCCCTCTGCAGTAACCTGTCCG
TGGAGAACGCTGCAGAAATTCTCATCCTGGCCGACCTCCACAGTGCAGATCAGTTGAAAACTCAGGCAGTGGATTT
CATCAACTATCATGCTTCGGATGTCTTGGAGACCTCTTGGG
```

17186.1&2

```
TCGTAGCCATTTTTCTGCTTCTTTGGAGAATGACGCCACACTGACTGCTCATTGTCGTTGGTTCCATGCCAATTGG
TGAAATAGAACCTCATCCGGTAGTGGAGCCGGAGGGACATCTTGTCATCAACGGTGATGGTGCGATTTGGAGCATA
CCAGAGCTTGGTGTTCTCGCCATACAGGGCAAAGAGGTTGTGACAAAGAGGAGAGATACGGCATGCCTGTGCAGCC
CTGATGCACAGTTCCTCTGCTGTGTACTCTCCACTGCCCAGCCGGAGGGGCTCCCTGTCCGACAGATAGAAGATCA
CTTCCACCCCTGGCTTG
```

17187.1&2

```
TGGCACACTGCTCTTAAGAAACTATGAWGATCTGAGATTTTTTGTGTATGTTTTTGACTCTTTTGAGTGGTAATC
ATATGTGTCTTTATAGATGTACATACCTCCTTGCACAAATGGAGGGGAATTCATTTTCATCACTGGGAGTGTCCTT
AGTGTATAAAAACCATGCTGGTATATGGCTTCAAGTTGTAAAAATGAAAGTGACTTTAAAAGAAAATAGGGGATGG
TCCAGGATCTCCACTGATAAGACTGTTTTTAAGTAACTTAAGGACCTTTGGGTCTACAAGTATATGTGAAAAAAAT
GAGACTTACTGGGTGAGGAAATTCATTGTTTAAAGATGGTCGTGTGTGTGTGTGTGTGTGTGTTGTGTTGTG
TTTTGTTTTTTAAGGGAGGGAATTTATTATTTACCGTTGCTTGAAATTACTGKGTAAATATATGTYTGATAATGAT
TTGCTYTTTGVCMACTAAAATTAGGVCTGTATAAGTWCTARATGCMTCCCTGGGKGTTGATYTTCCMAGATATTGA
TGATAMCCCTTAAAATTGTAACCYGCCTTTTTCCCTTTGCTYTCMATTAAAGTCTATTCMAAAG
```

17191.1&89.1

```
GGGGGTAGGCTCTTTATTAGACGGTTATTGCTGTACTACAGGGTCAGAGTGCAGTGTAAGCAGTGTCAGAGGCCCG
CGTTCAGCCCAAGAATGTGGATTTTCTCTCCCTATTGATCACAGTGGGTGGGTTTCTTCAGAAAAGCCCCAGAGGC
AGGGACCAGTGAGCTCCAAGGTTAGAAGTGGAACTGGAAGGCTTCAGTCACATGCTGCTTCCACGCTTCCAGGCTG
GGCAGCAAGGAGGAGATGCCCATGACGTGCCAGGTCTCCCCATCTGACACCAGTGAAGTCTGGTAGGACAGCAGCC
GCACGCCTGCCTCTGCCAGGAGGCCAATCATGGTAGGCAGCATTGCAGGGTCAGAGGTCTGAGTCCGGAATAGGAG
CAGGGGCAGGTCCCTGCGGAGAGGCACTTCTGGCCTGAAGACAGCTCCATTGAGCCCCTGCAGTACAGGYGTAGTG
CCTTGGACCAAGCCCACAGCCTGGTAAGGGGCGCCTGCCAGGGCCACGGCCAGGAGGCA
```

```
TAATTTCTTAGTCGTTTGGAATCCTTAAGCATGCAAAAGCTTTGAACAGAAGGGTTCACAAAGGAACCAGGGTTGT
CTTATGGCATCCAGTTAAGCCAGAGCTGGGAATGCCTCTGGGTCATCCACATCAGGAGCAGAAGCACTTGACTTGT
CGGTCCTGCTGCCACGGTTTGGGCGCCCACCACGCCCACGTCCACCTCGTCCTCCCCTGCCGCCACGTCCTGGGCG
GCCAAGGTCTCCAAAATTGATCTCCAGCTGAGACGTTATATCATTTGCTGGCTTCCGGAAATGATGGTCCATAACC
GAATCTTCAGCATGAGCCTCTTCACTCTTTGATTTATGAAGAACAAATCCCTTCTTCCACTGCCCATCAGCACCTT
CATTTGGTTTTCGGATATTAAATTCTACTTTTGCCCGGTCCTTATTTTGAATAGCCTTCCACTCATCCAAAGTCAT
CTCTTTTGGACCCTCCTCTTTTACCTCTTCAACTTCATTCTCCTTATTTTCAGTGTCTGCCACTGGATGATGTTCT
TCACCTTCAGGTGTTTCCTCAGTCACATTTGATTGATCCAAGTCAGTTAATTCGTCTTTGACAGTTCCCCAGTTGT
GAGATCCGCTACCTCCACGTTTGTCCTCGTGCTTCAGGCCAGATCTATCACTTCCACTATGCCTATCAAATTCACG
TTTGCCACGAGAATCAAATCCATCTCCTCGGCCCATTCCACGTCCACGGCCCCCTCGACCTCTTCCAAGACCACCA
CGACCTCGAATAGGTCGGTCAATAATCGGTCTATCAACTGAAAATTCGCCTCCTTCACCCTTTTCTTCAAGTGGCT
TTTCGAATCTTCGTTCACGAGGTGGTCGCCTTTCTGGTCTTCTATCAATTATTTTCCCTTCACCCTGAAGTTGTTG
ATCAGGTCTTCTTCCAACTCGTGC
```

17193

```
AAGCGGATGGACCTGAGTCAGCCGAATCCTAGCCCCTTCCCTTGGGCCTGCTGTGGTGCTCGACATCAGTGACAGA
CGGAAGCAGCAGACCATCAAGGCTACGGGAGGCCCGGGGCGCTTGCGAAGATGAAGTTTGGCTGCCTCTCCTTCCG
GCAGCCTTATGCTGGCTTTGTCTTAAATGGAATCAAGACTGTGGAGACGCGCTGGCGTCCTCTGCTGAGCAGCCAG
CGGAACTGTACCATCGCCGTCCACATTGCTCACAGGGACTGGGAAGGCGATGCCTGTCGGGAGCTGCTGGTGGAGA
GACTCGGGATGACTCCTGCTCAGATTCAGGCCTTGCTCAGGAAAGGGGAAAAGTTTGGTCGAGGAGTGATAGCGGG
ACTCGTTGACATTGGGGAAACTTTGCAATGCCCCGAAGACTTAACTCCCGATGAGGTTGTGGAACTAGAAAATCAA
GCTGCACTGACCAACCTGAAGCAGAAGTACCTGACTGTGATTTCAAACCCCAGGTGGTTACTGGAGCCCATACCTA
GGAAAGGAGGCAAGGATGTATTCCAGGTAGACATCCCAGAGCACCTGATCCCTTTGGGGCATGAAGTGTGACAAGT
GTGGGCTCCTGAAAGGAATGTTCCRGAGAAACCAGCTAAATCATGGCACCTTCAATTTGCCATCGTGACGCAGACC
TGTATAAATTAGGTTAAAGATGAATTTCCACTGCTTTGGAGAGTCCCACCCACTAAGCACTGTGCATGTAAACAGG
TTCCTTTGCTCAGATGAAGGAAGTAGGGGGTGGGGCTTTCCTTGTGTGATGCCTCCTTAGGCACACAGGCAATGTC
TCAAGTACTTTGACCTTAGGGTAGAAGGCAAAGCTGCCAGTAAATGTCTCAGCATTGCTGCTAATTTTGGTCCTGC
TAGTTTCTGGATTGTACAAATAAATGTGTTGTAGATGA
```

*Fig. 15U*

16443.1.edit

```
TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAACCAGTCCTGGTGCANGAC
GGTGAGGACGCTNACCACACGGTACGNGCTGGTGTACTGCTCCTCCCGCGGCTTTGTCTTGGCATTATGCACCTCC
ACGCCGTCCACGTACCAATTGAACTTGACCTCAGGGTCTTCGTGGCTCACGTCCACCACCACGCATGTAACCTCAA
ANCTCGGNCGCGANCACGC
```

16443.2.edit

```
AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGCGACA
TCGCCCGTGGAGTGGGAGAGCAATGGGCAGCCGGAGAACAACTACAAGACCACGCCTCCCGTGCTGGACTCCGACA
CCTGCCGGGCGGCCGCTCGA
```

16444.2.edit

```
AGCGTGGTTNCGGCCGAGGTCCCAACCAAGGCTGCANCCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGNCGCTCGA
```

16445.1.edit

```
AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGCCGCTCGA
```

*Fig. 15V*

16445.2.edit

```
TCGAGCGGTCGCCCGGGCAGGTCCACATCGGCAGGGTCGGAGCCCTGGCCGCCATACTCGAACTGGAATCCATCGG
NCATGCTCTCGCCGAACCAGACATGCCTCTTGNCCTTGGGGTTCTTGCTGATGTACCAGNTCTTCTGGGCCACACT
GGGCTGAGTGGGGTACACGCAGGTCTCACCANTCTCCATGTTGCANAAGACTTTGATGGCATCCAGGTTGCAGCCT
TGGTTGGGGTCAATCCAGTACTCTCCACTCTTCCAGACAGAGTGGCACATCTTGAGGTCACGGCAGGTGCGGGCGG
GGTTCTTGACCTCGGTCGCGACCACGCT
```

16446.1.edit

```
TCGAGCGGCCGCCCGGGCAGGTCCTCCTCAGAGCGGTAGCTGTTCTTATTGCCCCGGCAGCCTCCATAGATNAAGT
TATTGCANGAGTTCCTCTCCACGTCAAAGTACCAGCGTGGGAAGGATGCACGGCAAGGCCCAGTGACTGCGTTGGC
GGTGCAGTATTCTTCATAGTTGAACATATCGCTGGAGTGGACTTCAGAATCCTGCCTTCTGGGAGCACTTGGGACA
GAGGAATCCGCTGCATTCCTGCTGGTGGACCTCGGCCGCGACCACGCT
```

16446.2.edit

```
AGCGTGGTCGCGGCCGAGGTCCACCAGCAGGAATGCAGCGGATTCCTCTGTCCCAAGTGCTCCCAGAAGGCAGGAT
TCTGAAGACCACTCCAGCGATATGTTCAACTATGAAGAATACTGCACCGCCAACGCAGTCACTGGGCCTTGCCGTG
CATCCTTCCCACGCTGGTACTTTGACGTGGAGAGGAACTCCTGCAATAACTTCATCTATGGAGGCTGCCGGGGCAA
TAAGAACAGCTACCGCTCTGAGGAGGACCTGCCCGGGCGGCCGCTCGA
```

16447.1.edit

```
TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGCCAGAATGGCACATCTTGAGGTCACGGCANGTGCGGGCGG
GGTTCTTGACCTCGGCCGCGACCACGCT
```

*Fig. 15W*

16447.2.edit

```
AGCGTGGTCGCGGCCGAGGTCAAGAAACCCCGCCCGCACCTGCCGTGACCTCAAGATGTGCCACTCTGGCTGGAAG
AGTGGAGAGTACTGGATTGACCCCAACCAAGGCTGCAACCTGGATGCCATCAAAGTCTTCTGCAACATGGAGACTG
GTGAGACCTGCGTGTACCCCACTCAGCCCAGTGTGGCCCAGAAGAACTGGTACATCAGCAAGAACCCCAAGGACAA
GAGGCATGTCTGGCTCGGCGAGAGCATGACCGATGGATTCCAGTTCGAGTATGGCGGCCAGGGCTCCGACCCTGCC
GATGTGGACCTGCCCGGGCGGCCGCTCGA
```

16449.1.edit

```
AGCGTGGTCGCGGCCGAGGTCCTGTCAGAGTGGCACTGGTAGAAGNTCCAGGAACCCTGAACTGTAAGGGTTCTTC
ATCAGTGCCAACAGGATGACATGAAATGATGTACTCAGAAGTGTCCTGNAATGGGGCCCATGANATGGTTGNCTGA
GAGAGAGCTTCTTGTCCTACATTCGGCGGGTATGGTCTTGGCCTATGCCTTATGGGGGTGGCCGTTGNGGGCGGTG
NGGTCCGCCTAAAACCATGTTCCTCAAAGATCATTTGTTGCCCAACACTGGGTTGCTGACCANAAGTGCCAGGAAG
CTGAATACCATTTCCAGTGTCATACCCAGGGTGGGTGACGAAAGGGGTCTTTTGAACTGTGGAAGGAACATCCAAG
ATCTCTGNTCCATGAAGATTGGGGTGTGGAAGGGTTACCAGTTGGGGAAGCTCGCTGTCTTTTTCCTTCCAATCAN
GGGCTCGCTCTTCTGAATATTCTTCAGGGCAATGACATAAATTGTATATTCGGTTCCCGGTTCCAGGCCAG
```

16450.1.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGANGAACATGGNTTT
AGGCGGACCACACCGGCCACAACGGGCACCCCCATAAGGCATAGGCCAAGAACATACCCGNCGAATGTAGGACAAG
AAGCTCTNTCTCANACAANCATCTCATGGGCCCCATTCCANGACACTTCTGAGTACATCANTTCATGGCATCCTGG
TGGCACTGATAAAAACCCTTACAGTTA
```

16450.2.edit

```
AGCGTGGTCGCGGGCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
NGGGCTCGCTCTTCTGATTATTCTTCAGGGCAATGACATAAATTGTATATTCGGNTCCCGGGTNCAGCCAATAATA
ATAACCCTCTGTGACACCANGGCGGGGCCGAAGGANCACT
```

*Fig. 15X*

16451.1.edit

```
AGCGTGGTCGCGGCCGAGGTCCTCACCAGAGGTACCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA
```

16451.2.edit

```
TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGNTGACAGAGTTGCCCACGGTAACAACCTCTTCCCGAACCTTATGCCTCTGCTGG
TCTTTCAGTGCCTCCACTATGATGTTGTAGGTGGTACCTCTGGTGAGGACCTCGGCCGCGACCACGCT
```

16452.1.edit

```
AGCGTGGCCGCGGCCGAGGTCCATTGGCTGGAACGGCATCAACTTGGAAGCCAGTGATCGTCTCAGCCTTGGTTCT
CCAGCTAATGGTGATGGNGGTCTCAGTAGCATCTGTCACACGAGCCCTTCTTGGTGGGCTGACATTCTCCAGAGTG
GTGACAACACCCTGAGCTGGTCTGCTTGTCAAAGTGTCCTTAAGAGCATAGACACTCACTTCATATTTGGCGNCCA
CCATAAGTCCTGATACAACCACGGAATGACCTGTCAGGAAC
```

16452.2.edit

```
TCGAGCGGCCGCCCGGGCAGGTCCTCAGACCGGGTTCTGAGTACACAGTCAGTGTGGTTGCCTTGCACGATGATAT
GGAGAGCCAGCCCCTGATTGGAACCCAGTCCACAGCTATTCCTGCACCAACTGACCTGAAGTTCACTCAGGTCACA
CCCACAAGCCTGAGCGCCCAGTGGACACCACCCAATGTTCAGCTCACTGGATATCGAGTGCGGGTGACCCCCAAGG
AGAAGACCGGACCAATGAAAGAAATCAACCTTGCTCCTGACAGCTCATCCGTGGTTGTATCAGGACTTATGGCGGC
CACCAAATATGAAGTGAGTGTCTATGCTCTTAAGGACACTTTGACAAGCAGACCAGCTCAGGGTGTTGTCACCACT
CTGGAGAATGTCAGCCCACCAAGAAGGGCTCGTGTGACAGATGCTACTGAGACCACCATCACCATTAGCTGGAGAA
CCAAGACTGAGACGATCACTGGCTTCCAAGTTGATGCCGTTCCAGCCAATGGACCTCGGCCGCGACCACGCTT
```

*Fig. 15Y*

16453.1.edit

AGCGTGGTCGCGGCCGAGGTCTGGCCGAACTGCCAGTGTACAGGGAAGATGTACATGTTATAGNTCTTCTCGAAGT
CCCGGGCCAGCAGCTCCACGGGGTGGTCTCCTGCCTCCAGGCGCTTCTCATTCTCATGGATCTTCTTCACCCGCAG
CTTCTGCTTCTCAGTCAGAAGGTTGTTGTCCTCATCCCTCTCATACAGGGTGACCAGGACGTTCTTGAGCCAGTCC
CGCATGCGCAGGGGGAATTCGGTCAGCTCAGAGTCCAGGCAAGGGGGGATGTATTTGCAAGGCCCGATGTAGTCCA
AGTGGAGCTTGTGGCCCTTCTTGGTGCCCTCCAAGGTGCACTTTGTGGCAAAGAAGTGGCAGGAAGAGTCGAAGGT
CTTGTTGTCATTGCTGCACACCTTCTCAAACTCGCCAATGGGGGCTGGGCAGACCTGCCCGGGCGGCCGCTCGA

16453.2.edit

TCGAGCGGCCGCCCGGGCAGGTCTGCCCAGCCCCCATTGGCGAGTTTGAGAAGGNGTGCAGCAATGACAACAAGAC
CTTCGACTCTTCCTGCCACTTCTTTGCCACAAAGTGCACCCTGGAGGGCACCAAGAAGGGCCACAAGCTCCACCTG
GACTACATCGGGCCTTGCAAATACATCCCCCCTTGCCTGGACTCTGAGCTGACCGAATTCCCCCTGCGCATGCGGG
ACTGGCTCAAGAACGTCCTGGTCACCCTGTATGAGAGGGATGAGGACAACAACCTTCTGACTGAGAAGCANAAGCT
GCGGGTGAAGAANATCCATGAGAATGANAAGCGCCTGNAGGCANGAGACCACCCCGTGGAGCTGCTGGCCCGGGAC
TTCGAGAAGAACTATAACATGTACATCTTCCCTGTACACTGGCAGTTCGGCCAGACCTCGGCCGCGACCACGCT

16454.1.edit

AGCGTGGNTGCGGACGACGCCCACAAAGCCATTGTATGTAGTTTTANTTCAGCTGCAAANAATACCNCCAGCATCC
ACCTTACTAACCAGCATATGCAGACA

16454.2.edit

TCGAGCGGTCGCCCGGGCAGGTCTGGGCGGATAGCACCGGGCATATTTTGGAATGGATGAGGTCTGGCACCCTGAG
CAGCCCAGCGAGGACTTGGTCTTAGTTGAGCAATTTGGCTAGGAGGATAGTATGCAGCACGGTTCTGAGTCTGTGG
GATAGCTGCCATGAAGNAACCTGAAGGAGGCGCTGGCTGGTANGGGTTGATTACAGGGCTGGGAACAGCTCGTACA
CTTGCCATTCTCTGCATATACTGGNTAGTGAGGCGAGCCTGGCGCTCTTCTTTGCGCTGAGCTAAAGCTACATACA
ATGGCTTTGNGGACCTCGGCCGCGACCACGCTT

*Fig. 15Z*

16455.1.edit

TCGAGCGGCCGCCCGGGCAGGTCCATTTTCTCCCTGACGGTCCCACTTCTCTCCAATCTTGTAGTTCACACCATTG
TCATGACACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAAGTTGCCCACGGTAACAACCTCTTCCCGAACCTTATGCCTCTGCTG
GTCTTTCAAGTGCCTCCACTATGATGTTGTAGGTGGCACCTCTGGTGAGGACCTCGGCCGCGACCACGCT

16455.2.edit

AGCGTGGTTTGCGGCCGAGGTCCTCACCANAGGTGCCACCTACAACATCATAGTGGAGGCACTGAAAGACCAGCAG
AGGCATAAGGTTCGGGAAGAGGTTGTTACCGTGGGCAACTCTGTCAACGAAGGCTTGAACCAACCTACGGATGACT
CGTGCTTTGACCCCTACACAGNTTCCCATTATGCCGTTGGAGATGAGTGGGAACGAATGTCTGAATCAGGCTTTAA
ACTGTTGTGCCAGTGCTTANGCTTTGGAAGTGGTCATTTCAGATGTGATTCATCTANATGGTGTCATGACAATGGT
GNGAACTACAAGATTGGAGAGAAGTGGNACCGTCAGGGGANAAAATGGACCTGCCCGGGCGGCNCGCTCGA

16456.1.edit

AGCGTGGTCGCGGCCGAGGTCTGGCTTNCTGCTCANGTGATTATCCTGAACCATCCAGGCCAAATAAGCGCCGGCT
ATGCCCCTGNATTGGATTGCCACACGGCTCACATTGCATGCAAGTTTGCTGAGCTGAAGGAAAAGATTGATC

16456.2.edit

TCGAGCGGCCGCCCGGGCAGGTCCAATTGAAACAAACAGTTCTGAGACCGTTCTTCCACCACTGATTAAGAGTGGG
GNGGCGGGTATTAGGGATAATATTCATTTAGCCTTCTGAGCTTTCTGGGCAGACTTGGTGACCTTGCCAGCTCCAG
CAGCCTTCTGGTCCACTGCTTTGATGACACCCACCGCAACTGTCTGTCTCATATCACGAACAGCAAAGCGACCCAA
AGGTGGATAGTCTGAGAAGCTCTCAACACACATGGGCTTGCCAGGAACCATATCAACAATGGGCAGCATCACCAGA
CTTCAAGAATTTAAGGGGCCATCTTCCAGCTTTTTACCAGAACGGCGATCAATCTTTTCCTTCAGCTCAGCAAACTT
GCATGCAATGTGAGCCG

*Fig. 15A-1*

16459.1.edit

TCGAGCGGCCGCCCGGGCAGGTCCAGAGGGCTGTGCTGAAGTTTGCTGCTGCCACTGGAGCCACTCCAATTGCTGG
CCGCTTCACTCCTGGAACCTTCACTAACCAGATCCAGGCAGCCTTCCGGGAGCCACGGCTTCTTGTGGNTACTGAC
CCCAGGGCTGACCACCAGCCTCTCACGGAGGCATCTTATGTTAACCTACCTACCATTGCGCTGTGTAACACAGATT
CTCCTCTGCGCTATGTGGACATTGCCATCCCATGCAACAACAAGGGAGCTCACTCAGNGGGGTTTGATGTGGTGGA
TGCTGGCTCGGGAAGTTCTGCGCATGCGTGGCACCATTTCCCGTGAACACCCATGGGANGNCATGCCTGATCTGGA
CTTCTACAGAGATCCTGAAGAGATTGAAAAAGAAGAACAGGCTGNTTGCTGANAAAGCAAGTGACCAAGGANGAAA
TTTCANGGGTGAAANGGACTGCTCCCGCTCCTGAATTCACTGCTACTCAACCTGANGNTGCAGACTGGTCTTGAAG
GNGNACANGGGCCCTCTGGGCCTATTTAAGCANCTTCGGTCGCGAACACGNT

16459.2.edit

AGCGTGNGTCGCGGCCGAGGTGCTGAATAGGCACAGAGGGCACCTGTACACCTTCAGACCAGTCTGCAACCTCAGG
CTGAGTAGCAGTGAACTCAGGAGCGGGAGCAGTCCATTCACCCTGAAATTCCTCCTTGGNCACTGCCTTCTCAGCA
GCAGCCTGCTCTTCTTTTTCAATCTCTTCAGGATCTCTGTAGAAGTACAGATCAGGCATGACCTCCCATGGGTGTT
CACGGGAAATGGTGCCACGCATGCGCAGAACTTCCCGAGCCAGCATCCACCACATCAAACCCACTGAGTGAGCTCC
CTTGTTGTTGCATGGGATGGGCAATGTCCACATAGCGCAGAGGAGAATCTGTGTTACACAGCGCAATGGTAGGTAG
GTTAACATAAGATGCCTCCGCGAGAAGCTGGTGGTCAGCCCTGGGGTCAAGTAACCACAAGAAGCCGTGGCTCCCG
GAAGGCTGCCTGGATCTGGTTAGTGAAGGNTCCAGGAGTGAAGCGGCCAACAATTGGAGTGGCTTCAGTGGCAAGC
AGCAAACTTCAGCACAAGCCCTCTGGACCTGCCCGGCGGCCGCTCGA

16460.1.edit

TCGAGCGGCCGCCCGGGCAGGTCCATTTTCTCCCTGACGGNCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCNTCCCCGAACCTTATGCCTCTGCTG
GGCTTTCAGNGCCTCCACTATGATGNTGTAGGGGGGCACCTCTGGNGANGACCTCGGCCGCGACCACGCT

16460.2.edit

AGCGTGGTCGCGGCCGAGGTCCTCACCAGAGGTGCCACCTACAACATCATAGTGGAGGCACTGAAAGACCAGCAGA
GGCATAAGGCTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGGTCATTTCAGATGTGATTCATCTAGATGGTGCCATGACAATGGN
GNGAACTACAAGATTGGAGAGAAGTGGNACCGNCAGGGAGAAAATGGACCTGCCCGGGCGGCCGCTCGA

*Fig. 15B-1*

16461.1.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGNTGCAACCTTG
GTTGGGGTCAATCCAGTACTCTCCACTCTTCCAGCCAGAGTGGCACATCTTGAGGTCACGGCAGGTGCGGNCGGGG
GNTTTTGCGGCTGCCCTCTGGNCTTCGGNTGTNCTCNATCTGCTGGCTCA
```

16461.2.edit

```
TCGAGCGGCCGCCCGGGCAGGTCTCGCGGTCGCACTGGTGATGCTGGTCCTGTTGGTCCCCCCGGCCCTCCTGGAC
CTCCTGGCCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGNCGCAAGAACCCCGCCCGCACCTGCCGTG
ACCTCAAGATGTGCCACTCTGACTGGAAGAGTGGAGAGTACTGGATTGACCCCAACCAAGCTGCAACCTGGATGCC
ATCAAAGTCTTCTGCAACATGGAGACTGGTGAGACCTGCGTGTACCCCACTCAGCCCAGTGTGGCCCAAAAGAACT
GGTACATCAGCAAGAACCCCAAGGACAAGAAGCATGTCTGGTTCGGCGAGAACATGACCGATGGATTCCAGTTCGA
GTATGGCGGGCAGGGCTCCGACCCTGCCGATGGGGACCTTGGCCGCGAACACGCT
```

16463.1.edit

```
AGCGTGGNNGCGGCCGAGGTATAAATATCCAGNCCATATCCTCCCTCCACACGCTGANAGATGAAGCTGTNCAAAG
ATCTCAGGGTGGANAAAACCAT
```

16463.2.edit

```
TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT
```

*Fig. 15C-1*

16464.1.edit

CGAGCGGGCGACCGGGCAGGTNCAGACTCCAATCCANANAACCATCAAGCCAGATGTCAGAAGCTACACCATCACA
GGTTTACAACCAGGCACTGACTACAAGANCTACCTGCACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGTACATCATCNAGTATGANAAGCCTGGGCCTCCTCCCAGAGAAGNGG
TCCCTCGGCCCCGCCCTGNTGTCCCANAGGNTACTATTACTGNGCCNGCAACCGGCAACCGATATCNATTTTGNCA
TTGGCCTTCAACAATAATTA

16464.2.edit

AGCGTGGTTCGCGGCCGANGTCCTGTCAGAGTGGCACTGGTAGAAGTTCCAGGAACCCTGAACTGTAAGGGTTCTT
CATCAGNGCCAACAGGATGACATGAAATGATGTACTCAGAAGTGTCCTGGAATGGGGCCCATGAGATGGTTGTCTG
AGAGAGAGCTTCTTGNCCTGTCTTTTTCCTTCCAATCAGGGGCTCGCTCTTCTGATTATTCTTCAGGGCAATGACA
TAAATTGTATATTCGGGTCCCGGNTCCAGGCCAGTAATAGTANCCTCTGTGACACCAGGGCGGNGCCGAGGGACCA
CTTCTCTGGGAGGAGACCCAGGCTTCTCATACTTGATGATGTAACCGGTAATCCTGGCACGTGGCGGCTGCCATGA
TACCAGCAAGGAATTGGGGTGTGGTGGCCAGGAAACGCAGGTTGGATGGNGCATCAATGGCAGTGGAGGCCGTCGA
TGACCACAGGGGGAGCTCCGACATTGTCATTCAAGGTG

16465.1.edit

AGCGTGGNCGCGGCCGAGGTGCAGCGCGGGCTGTGCCACCTTCTGCTCTCTGCCCAACGATAAGGAGGGTNCCTGC
CCCCAGGAGAACATTAACTNTCCCCAGCTCGGCCTCTGCCGG

16465.2.edit

TCGAGCGGCCGCCCGGGCAGGTTTTTTTTGCTGAAAGTGGNTACTTTATTGGNTGGGAAAGGGAGAAGCTGTGGTC
AGCCCAAGAGGGAATACAGAGNCCCGAAAAAGGGGAGGGCAGGTGGGCTGGAACCAGACGCAGGGCCAGGCAGAAA
CTTTCTCTCCTCACTGCTCAGCCTGGTGGTGGCTGGAGCTCANAAATTGGGAGTGACACAGGACACCTTCCCACAG
CCATTGCGGCGGCATTTCATCTGGCCAGGACACTGGCTGTCCACCTGGCACTGGTCCCGACAGAAGCCCGAGCTGG
GGAAAGTTAATGTTCACCTGGGGGCAGGAACCCTCCTTATCATTGNGCAGAGAGCAGAAGGTGGCACAGCCCGCGC
TGCACCTCGGCCGCGACCACGCT

16466.2.edit

TCGAGCGGCCGCCCGGGCAGGTCCACCATAAGTCCTGATACAACCACGGATGAGCTGTCAGGAGCAAGGTTGATTT
CTTTCATTGGTCCGGNCTTCTCCTTGGGGGNCACCCGCACTCGATATCCAGTGAGCTGAACATTGGGTGGCGTCCA
CTGGGCGCTCAGGCT

16467.2.edit

TCGAGCGGTTCGCCCGGGCAGGTCCACCACACCCAATTCCTTGCTGGTATCATGGCAGCCGCCACGTGCCAGGATT
ACCGGCTACATCATCAAGTATGAGAAGCCTGGGTCTCCTCCCAGAGAAGCGGTCCCTCGGCCCCGCCCTGGTGTCA
CAGAGGCTACTATTACTGGCCTGGAACCGGGAACCGAATATACAATTTATGTCATTGNCCTGAAGAATAATCANNA
ANAGCGANCCCCTGATTGGAAGGA

*Fig. 15D-1*

01_16469.edit

AGCGTGGTCGCGGCCGAGGTTGTACAAGCTTTTTTTTTTTTTTTTTTTTTTTTTTTTTTTTTTTTTTTTTTTTT
TTTTTTTTTTTTTTTT

02_16469.edit

TCGAGCGGNCGCCCGGGCAGGTCTGCCAACACCAAGATTGGCCCCCGCCGCATCCACACAGTCCGTGTGCGGGGAG
GTAACAAGAAATACCGTGCCCTGAGGTTGGACGTGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATCGACAGCACACCGTACCGACAGTGGTACGAGTCCCACTATGCGCTGCCCCTGGGCCGCAAGAAGGGAG
CCAAGCTGACTCCTGAGGAAGAAGAGATTTTAAACAAAAAACGATCTAANAAAAAAAAAAACAAT

03_16470.edit

AGCGTGGTCGCGGCCGAGGTGAAATGGTATTCAGCTTCCTGGCACTTCTGGTCAGCAACCCAGTGTTGGGCAACAA
ATGATCTTTGAGGAACATGGTTTTAGGCGGACCACACCGCCCACAACGGCCACCCCCATAAGGCATAGGCCAAGAC
CATACCCGCCGAATGTAGGACAAGAAGCTCTCTCTCAGACAACCATCTCATGGGCCCCATTCCAGGACACTTCTGA
GTACATCATTTCATGTCATCCTGTTGGCACTGATGAAGAACCCTTACAGTTCAGGGTTCCTGGAACTTCTACCAGT
GCCACTCTGACAGGACCTGCCCGGGCGGCCGCTCGA

04_16470.edit

TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCACCTCGGCCGCGACCACGCTA

05_16471.edit

TCGAGCGGCCGCCCGGGCAGGTCTCCCTTCTTGCGGCCCAGGGGCAGCGCATAGTGGGACTCGTACCACTGTCGGT
ACGGTGTGCTGTCGATGAGCACGATGCAATTCTTCACCAGGGTCTTGGTACGAACCAGCTCGTTATTAGATGCATT
GTAGACAACATCGATGATCCTTGTTTTACGAGTACAACACTCTGAGCCCCAGGAGAAATTCCCCACGTCCAACCTC
AGGGCACGGTATTTCTTGTTACCTCCCCGCACACGGACTGTGTGGATGCGGCGGGGGCCAAGCTGACTCCTGAGGA
AGAAGAGATTTTAAACAAAAAACGATCTAAAAAAATTCAGAAGAAATATGATGAAAGGAAAAAGAATGCCAAAATC
AGCAGTCTCCTGGAGGAGCAGTTCCAGCAGGGCAAGCTTCTTGCGTGCATCGCTTCAAGGCCGGGACAGTGTGACC
GAGCAGATGGCTATGTGCTAGAGGGCAAAGAAGTGGAGTTCTATCTTAAGAAAATCAGGGCCCAGAATGGTGNGTC
TTCAACTAATCCAAAGGGGAGTTTCAGACCAGTGCAATCAGCAAAAACATTGATACTGNTGGCCAAATTTATTGGT
GCAGGGCTTGCACANTANGANNGGCTGGGTCTTGGGGCTTGGATTGGNACAAGCTTTGGCAGCCTTTTCTTTGGTT
TTGCCAAAAACCTTTTGNTGAAGANGANACCTNGGGCGGACCCCTTAACCGATTCCACNCCNGGNGGCGTTCTANG
GNCCCNCTTG

*Fig. 15E-1*

06_16471.edit

```
AGCGTGGTCGCGGCCGAGGTCTGCTGCTTCAGCGAAGGGTTTCTGGCATAACCAATGATAAGGCTGCCAAAGACTG
TTCCAATACCAGCACCAGAACCAGCCACTCCTACTGTTGCAGCACCTGCACCAATAAATTTGGCAGCAGTATCAAT
GTCTCTGCTGATTGCACTGGTCTGAAACTCCCTTTGGATTAGCTGAGACACACCATTCTGGGCCCTGATTTTCCTA
AGATAGAACTCCAACTCTTTGCCCTCTAGCACATAGCCATCTGCTCGGTCACACTGTCCCGGCCTTGAAGCGATGC
ACGCAAGAAGCTTGCCCTGCTGGAACTGCTCCTCCAGGAGACTGCTGATTTTGGCATTCTTTTTCCTTTCATCATA
TTTCTTCTGAATTTTTTTAGATCGTTTTTTGTTTAAAATCTCTTCTTCCTCAGGAGTCAGCTTGGCCCCCGCCGCA
TCCACACAGTCCGTGTGCGGGGAGGTAACAAGAAATACCGTGCCCTGAGGTTGGACGTGGGGAATTTCTCCTGGGG
CTCAGAGTGGTGTACTCGTAAAACAAGGATCATCGATGGTGNCTACAATGCATCTAATAACGAGCTGGGTCGGACC
CAAAGAACCTGGNGAANAAATGGATCGNCTCATCGACAGGACACCGTACCCGACAGGGGNACGANTCCCACTATGC
GCTTGCCCCTGGGCCGCAANAAAGGAAAACTGCCCGGGCGGCCNTCGAAAGCCCAATTNTGGAAAAAATCCATCAC
ACTGGGNGGCCNGTCGAGCATGCATNTANAGGGGCCCATTCCCCCTNANN
```

07_16472.edit

```
TCGAGCGGCCGCCCGGGCAGGTCCCCAACCAAGGCTGCAACCTGGATGCCATCAAAGTCTTCTGCAACATGGAGAC
TGGTGAGACCTGCGTGTACCCCACTCAGCCCAGTGTGGCCCAGAAGAACTGGTACATCAGCAAGAACCCCAAGGAC
AAGAGGCATGTCTGGTTCGGCGAGAGCATGACCGATGGATTCCAGTTCGAGTATGGCGGCCAGGGCTCCGACCCTG
CCGATGTGGACCTCGGCCGCGACCACGCT
```

08_16472.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGACCTGCCCGGGCGGCCGCTCGA
```

09_16473.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGNTTT
AGGCGGACCACACCGCCCACAACGGCCACCCCCATAAGGCATAGGCCAAGACCATACCCGCCGAATGTAGGACAAG
AAGCTNTNTNTCANACACCATNTNATGGGCCCCATTCCAGGACACTTCTGAGTACATCATTTATGNCATCTGTGGC
ACTTGATGAAAACCCTTACAGTTCAGGGTTCTGGAACTTTTACCAGGCCTNTTACAGGACTNGGCCGGACNCCTTA
AGCCNATTNCACCCTGGGGCGTTCTANGGTCCCACTCGNNCACTGGNGAAAATGGCTACTGTN
```

*Fig. 15F-1*

11_16474.edit

```
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGNGAAACTCCNAGGACANGAGGGCTAAATTCCATGAAGTTTGTGGATGGCCTGATGATCCACAAT
CGGAGACCCTGTTAACTACTACCGTCTNACCNCCTGCTGTNCNCCCCCNTTTCTGCTNAANACATNGGGNTNNTNC
TTGNCCNTCCTTGGGTNGAANATNNAATNGCCTNCCCNTTCNTANCNCTACTNGNTCCANANTTGGCCTTTAAANA
ATCCNCCTTGCCTTNNNCACTGTTCANNTNTTTNNTCGTAAACCCTATNANTTNNATTANATNNTNNNNNNCTCAC
CCCCCTCNTCATTNANCCNATANGCTNNNAANTCCTTNANNCCTCCCNCCCNNTNCNCTCNTACTNANTNCTTCTN
NCCCATTACNNAGCTCTTTCNTTTAANATAATGNNGCCNNGCTCTNCATNTCTACNATNTGNNNAATNCCCCCNCC
CCCNANCGNNTTTTTGACCTNNNAACCTCCTTTCCTCTTCCCTNCNNAAAATTNCNNANTTCCNCNTTCCNNCNTTT
CGGNTNNTCCCATNCTTTCCANNNCTTCANTCTANCNCNCTNCAACTTATTTTCCTNTCATCCCTTNTTCTTTACA
NNCCCCCTNNTCTACTCNNCNNTTNCATTANATTTGAAACTNCCACNNCTANTTNCCTCNCTCTACNNTTTTATTT
TNCGNTCNCTCTACNTAATANTTTAATNANTTNTCN
```

12_16474.edit

```
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAAGCAGTGTCAACGTAGTAAGTTAACAGGGTCTCCGCTGTGGATCA
TCAGGCCATCCACAAACTTCATGGATTTAGCCCTCTGTCCTCGGAGTTTCCCAGACACCACAACCTCGCAGCCTTT
GGCCCCACTCTCCATGATGAACCGCAGCACACCATAGCAGGCCCTCCGCACAAGCAAGCCCTCCTAAGAATTTGTA
ACGCANANACTCTGCTGGCAATGGCACACAAACCTCTAGTGGACCTCGGNCGCGACCACGC
```

13_16475.edit

```
TCGAGCGGCCGCCCGGGCAGGTCTGGTCCAGGATAGCCTGCGAGTCCTCCTACTGCTACTCCAGACTTGACATCAT
ATGAATCATACTGGGGAGAATAGTTCTGAGGACCAGTAGGGCATGATTCACAGATTCCAGGGGGGCCAGGAGAACC
AGGGGACCCTGGTTGTCCTGGAATACCAGGGTCACCATTTCTCCCAGGAATACCAGGAGGGCCTGGATCTCCCTTG
GGGCCTTGAGGTCCTTGACCATTAGGAGGGCGAGTAGGAGCAGTTGGAGGCTGTGGGCAAACTGCACAACATTCTC
CAAATGGAATTTCTGGGTTGGGGCAGTCTAATTCTTGATCCGTCACATATTATGTCATCGCAGAGAACGGATCCTG
AGTCACAGACACATATTTGGCATGGTTCTGGCTTCCAGACATCTCTATCCGNCATAGGACTGACCAAGATGGGAAC
ATCCTCCTTCAACAAGCTTNCTGTTGTGCCAAAAATAATAGTGGGATGAAGCAGACCGAGAAGTANCCAGCTCCCC
TTTTTGCACAAAGCNTCATCATGTCTAAATATCAGACATGAGACTTCTTTGGGCAAAAAAGGAGAAAAAGAAAAAG
CAGTTCAAAGTANCCNCCATCAAGTTGGTTCCTTGCCCNTTCAGCACCCGGGCCCCGTTATAAAACACCTNGGGCC
GGACCCCCCTT
```

*Fig. 15G-1*

14_16475.edit

AGCGTGGTCGCGGCCGAGGTGTTTTATGACGGGCCCGGTGCTGAAGGGCAGGGAACAACTTGATGGTGCTACTTTG
AACTGCTTTTCTTTTCTCCTTTTTGCACAAAGAGTCTCATGTCTGATATTTAGACATGATGAGCTTTGTGCAAAAG
GGGAGCTGGCTACTTCTCGCTCTGCTTCATCCCACTATTATTTTGGCACAACAGGAAGCTGTTGAAGGAGGATGTT
CCCATCTTGGTCAGTCCTATGCGGATAGAGATGTCTGGAAGCCAGAACCATGCCAAATATGTGTCTGTGACTCAGG
ATCCGTTCTCTGCGATGACATAATATGTGACGATCAAGAATTAGACTGCCCCAACCCAGAAATTCCATTTGGAGAA
TGTTGTGCAGTTTGCCCACAGCCTCCAACTGCTCCTACTCGCCCTCCTAATGGTCAAGGACCTCAAGGCCCCAAGG
GAGATCCAGGCCCTCCTGGTATTCCTGGGAGAAATGGTGACCCTGGTATTCCAGGACAACCAGGGTCCCCTGGTTC
TCCTGGCCCCCCTGGAATCNGGNGAATCATGCCCTACTGGTCCTCAAACTATTCTCCCANATGATTCATATGATGT
CAAGTCTGGGATAGCNAGTANGGANGGACTCGCAGGCTATTCTGGACCANACCTGCCGGGGGGGCGTTCGAAAGCC
CGAATCTGCANANNTNCNTTCACACTGGCGGCCGTCGAGCTGCTTTAAAAGGGCCATTCCNCCTTTAGNGNGGGGG
ANTACAATTACTNGGCGGCGTTTTANANCGCGNGNCTGGGAAAT

15_16476.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAGGCTCTTGAGGGTGGTGTCCACCTCGA
GGTCACGGTCACGAACCACATTGGCATCATCAGCCCGGTAGTAGCGGCCACCATCGTGAGCCTTCTCTTGANGTGG
CTGGGGCAGGAACTGAAGTCGAAACCAGCGCTGGGAGGACCAGGGGGACCAANAGGTCCAGGAAGGGCCCGGGGGG
GACCAACAGGACCAGCATCACCAAGTGCGACCCGCGAGAACCTGCCCGGCCGNCCGCTCGAA

16_16476.edit

TCGAGCGNNCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGCCGCAAGAACCCCGCCCGCACCTGCCGTG
ACCTCAAGATGTGCCACTCTGACTGGAAGAGTGGGAGAGTACTGGATTGACCCCAACCAAGGCTGCAACCTGGATGC
CATCAAAGTCTTCTGCAACATGGAGACTGGTGAGACCTGCGTGTACCCCACTCAGCCCAGTGTGGCCCAGAAGAAC
TGGTACATCAGCAAGAACCCCAAGGACAAGAGGCATGTCTGGTTCGGCGAGAGCATGACCGATGGATTCCAGTTCG
AGTATGGCGGCCAGGGCTCCCACCCTGCCGATGTGGACCTCCGGCCGCGACCACCCTT

*Fig. 15H-1*

17_16477.edit

```
TNGAGCGGCCGCCCGGGCAGGNTGNNAACGCTGGTCCTGCTGGTCCTCCTGGCAAGGCTGGTGAAGATGGTCACCC
TGGAAAACCCGGACGACCTGGTGAGAGAGGAGTTGTTGGACCACAGGGTGCTCGTGGTTTCCCTGGAACTCCTGGA
CTTCCTGGCTTCAAAGGCATTAGGGGACACAATGGTCTGGATGGATTGAAGGGACAGCCCGGTGCTCCTGGTGTGA
AGGGTGAACCTGGTGCCCCTGGTGAAAATGGAACTCCAGGTCAAACAGGAGCCCGTGGGCTTCCTGGTGAGAGAGG
ACCGTGTTGGTGCCCCTGGCCCANACCTCGGCCGCGACCACGCTAAGCCCGAATTTCCAGCACACTGGNGGCCGTT
ACTANTGGATCCGAGCTCGGTACCAAGCTTGGCGTAATCATGGTCATAGCTGTTTCCTGNGTGAAATTGTTATCCG
CTCACAATTTCACACANCATACGAAGCCGGAAAGCATAAAGTGTAAAGCCTTGGGGTGCTAATGAGTGAGCTAACT
CNCATTAAATTGCGTTGCGCTCACTGCCCGCTTTTCCANNNGGGAAACCNTGGCNTNGCCNGCTTGCNTTAANTGA
AATCCGCCNACCCCCGGGGAAAAGNCGGTTTGCNGTATTGGGGCNCTTTTTCCCTTTCCTCGGNTTACTTGANTTA
NTGGGCTTTGGNCGNTTCGGGTTGNGGCGANCNGGTTCAACNTCACNCCAAAGGNGGNAANACGGTTTTCCCANAA
TCCGGGGGNTANCCCAANGNAAAACATNNGNCNAANGGGCT
```

18_16477.edit

```
AGCGTGGTTNGCGGCCGAGGTCTGGGCCAGGGGCACCAACACGTCCTCTCTCACCAGGAAGCCCACGGGCTCCTGT
TTGACCTGGAGTTCCATTTTCACCAGGGGCACCAGGTTCACCCTTCACACCAGGAGCACCGGGCTGTCCCTTCAAT
CCATNCAGACCATTGTGNCCCCTAATGCCTTTGAAGCCAGGAAGTCCAGGAGTTCCAGGGAAACCACCGAGCACCC
TGTGGTCCAACAACTCCTCTCTCACCAGGTCGTCCGGGTTTTCCAGGGTGACCATCTTCACCAGCCTTGCCAGGAG
GACCAGCAGGACCAGCGTTACCAACCTGCCCGGGCGGCCGCTCGA
```

21_16479.edit

```
TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT
```

22_16479.edit

```
AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAAGATGTGATTCATCTAGATGGTGCCATGACAATGGT
GTGAACTACAAGATTGGAGAGAAGTGGGACCGTCAGGGAGAAAATGGACCTGCCCGGGCCGGCCGCTCGA
```

*Fig. 151-1*

24_16480.edit

```
TCGAGCGNNCGCCCGGGCAGGTCCAGTAGTGCCTTCGGGACTGGGTTCACCCCCAGGTCTGCGGCAGTTGTCACAG
CGCCAGCCCCGCTGGCCTCCAAAGCATGTGCAGGAGCAAATGGCACCGAGATATTCCTTCTGCCACTGTTCTCCTA
CGTGGTATGTCTTCCCATCATCGTAACACGTTGCCTCATGAGGGTCACACTTGAATTCTCCTTTTCCGTTCCCAAG
ACATGTGCAGCTCATTTGGCTGGCTCTATAGTTTGGGGAAAGTTTGTTGAAACTGTGCCACTGACCTTTACTTCCT
CCTTCTCTACTGGAGCTTTCGTACCTTCCACTTCTGCTGTTGGTAAAATGGTGGATCTTCTATCAATTTCATTGAC
AGTACCCACTTCTCCCAAACATCCAGGGAAATAGTGATTTCAGAGCGATTAGGAGAACCAAATTATGGGGCAGAAA
TAAGGGGCTTTTCCACAGGTTTTCCTTTGGAGGAAGATTTCAGTGGTGACTTTAAAAGAATACTCAACAGTGTCTT
CATCCCCATAGCAAAAGAAGAAACNGTAAATGATGGAANGCTTCTGGAGATGCCNNCATTTAAGGGACNCCCAGAA
CTTCACCATCTACAGGACCTACTTCAGTTTACANNAAGNCACATANTCTGACTCANAAAGGACCCAAGTAGCNCCA
TGGNCAGCACTTTNAGCCTTTCCCCTGGGGAAAANNTTACNTTCTTAAANCCTNGGCCNNGACCCCCTTAAGNCCA
AATTNTGGAAAANTTCCNTNCNNCTGGGGGGCNGTTCNACATGCNTTTNAAGGGCCCAATTNCCCCNT
```

25_16481.edit

```
TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAGCCAGTCCTGGTGCAGGAC
GGTGAGGACGCTGACCACACGGTACGTGCTGTTGTACTGCTCCTCCCGCGGCTTTGTCTTGGCATTATGCACCTCC
ACGCCGTCCACGTACCAGTTGAACTTGACCTCAGGGTCTTCGTGGCTCACGTCCACCACCACGCATGTAACCTCAG
ACCTCGGCCGCGACCACGCT
```

26_16481.edit

```
AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAAGCCCCGAGAACCACAGGTGTACACCCT
GCCCCCATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACA
CCTGCCCGGGCGGCCGCTCGA
```

27_16482.edit

```
TCGAGCGGCCGCCCGGGCAGGTTGAATGGCTCCTCGCTGACCACCCCGGTGCTGGTGGTGGGTACAGAGCTCCGAT
GGGTGAAACCATTGACATAGAGACTGTCCCTGTCCAGGGTGTAGGGGCCCAGCTCAGTGATGCCGTGGGTCAGCTG
GCTCAGCTTCCAGTACAGCCGCTCTCTGTCCAGTCCAGGGCTTTTGGGGTCAGGACGATGGGTGCAGACAGCATCC
ACTCTGGTGGCTGCCCCATCCTTCTCAGGCCTGAGCAAGGTCAGTCTGCAACCAGAGTACAGAGAGCTGACACTGG
TGTTCTTGAACAAGGGCATAAGCAGACCCTGAAGGACACCTCGGCCGCGACCACGCT
```

*Fig. 15J-1*

28_16482.edit

```
AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA
```

29_16483.edit

```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTCCCGGTTCCAGGCCAGTAATA
GTAGCCTCTGTGACACCAGGGCGGGGCCGAGGGACCCTTCTNTTGGAAGAGACCAGCTTCTCATACTTGATGATGA
GNCCGGTAATCCTGGCACGTGGNGGTTGCATGATNCCACCAAGGAAATNGGNGGGGGNGGACCTGCCCGGCGGCCG
TTCNAAAGCCCAATTCCACACACTTGGNGGCCGTACTATGGATCCCACTCNGTCCAACTTGGNGGAATATGGCATA
ACTTTT
```

31_16484.edit

```
TCGAGCGGCCGCCCGGGCAGGTCCTTGACCTTTTCAGCAAGTGGGAAGGTGTAATCCGTCTCCACAGACAAGGCCA
GGACTCGTTTGTACCCGTTGATGATAGAATGGGGTACTGATGCAACAGTTGGGTAGCCAATCTGCAGACAGACACT
GGCAACATTGCGGACACCCTCCAGGAAGCGAGAATGCAGAGTTTCCTCTGTGATATCAAGCACTTCAGGGTTGTAG
ATGCTGCCATTGTCGAACACCTGCTGGATGACCAGCCCAAAGGAGAAGGGGGAGATGTTGAGCATGTTCAGCAGCG
TGGCTTCGCTGGCTCCCACTTTGTCTCCAGTCTTGATCAGACCTCGGCCGCGACCACGCT
```

37_16487.edit

```
AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCCGCATCCCCCTTCCAAACCTGCCCGGGCGGCCGCTCG
```

*Fig. 15K-1*

38_16487.edit

CGAGCGGCCGCCCGGGCAGGTTTGGAAGGGGGATGCGGGGGAAGAGGAAGACTGACGGTCCCCCCAGGAGTTCAGG
TGCTGGGCACGGTGGGCATGTGTGAGTTTTGTCACAAGATTTGGGCTCAACTCTCTTGTCCACCTTGGTGTTGCTG
GGCTTGTGATCTACGTTGCAGGTGTAGGTCTGGGTGCCGAAGTTGCTGGAGGGCACGGTCACCACGCTGCTGAGGG
AGTAGAGTCCTGAGGACTGTAGGACAGACCTCGGCCGCGACCACGCT

39_16488.edit

NGGNNGGTCCGGNCNGNCAGGACCACTCNTCTTCGAAATA

41_16489.edit

AGCGTGGTCGCGGCCGAGGTCCTCACTTGCCTCCTGCAAAGCACCGATAGCTGCGCTCTGGAAGCGCAGATCTGTT
TTAAAGTCCTGAGCAATTTCTCGCACCAGACGCTGGAAGGGAAGTTTGCGAATCAGAAGTTCAGTGGACTTCTGAT
AACGTCTAATTTCACGGAGCGCCACAGTACCAGGACCTGCCCGGGCGGCCGCTCGA

42_16489.edit

TCGAGCGGCCGCCCGGGCAGGTCCTGGTACTGNGGCGCTCCGTGAAATTAGACGTTATCAGAAGTCCACTGAACTT
CTGATTCGCAAACTTCCCTTCCAGCGTCTGGTGCGAGAAATTGCTCAGGACTTTAAAACAGATCTGCGCTTCCAGA
GCGCAGCTATCGGTGCTTTGCAGGAGGCAAGTGAGGACCTCGGCCGCGACCACGCT

45_16491.edit

TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT

*Fig. 15L-1*

46_16491.edit

```
GTGGGNTTGAACCCNTTTNANCTCCGCTTGGTACCGAGCTCGGATCCACTAGTAACGGCCGCCAGTGTGCTGGAAT
TCGGCTTAGCGTGGTCGCGGCCGAGGTCAAGAACCCCGCCCGCACCTGCCGTGACCTCAAGATGTGCCACTCTGAC
TGGAAGAGTGGAGAGTACTGGATTGACCCCAACCAAGGCTGCAACCTGGATGCCATCAAAGTCTTCTGCAACATGG
AGACTGGTGAGACCTGCGTGTACCCCACTCAGCCCAGTGTGGCCCAGAAGAACTGGTACATCAGCAAGAACCCCAA
GGACAAGAGGCATGTCTGGTTCGGCGAGAGCATGACCGATGGATTCCAGTTCGAGTATGGCGGCCAGGGCTCCGAC
CCTGCCGATGTGGACCTGCCCGGGCGGCCGCTCGA
```

47_16492.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAAGTGT
CTATGCTCAGAATCCAAGCGGAGAGAAGTCAGCCTCTGGTTCAGACTGNAAGTAACCAACATTGATCGCCTAAAGG
ACTGGCATTCACTGATGNGGATGCCGATTCCATCAAAATTGNTTGGGAAAACCCACAGGGGCAAGTTTNCANGTCN
AGGNGGACCTACTCGAGCCCTGAGGATGGAATCCTTGACTNTTCCTTNNCCTGATGGGGAAAAAAAACCTTNAAAA
CTTGAAGGACCTGCCCGGGCGGCCGTNCAAAACCCAATTCCACCCCCTTGGGGGCGTTCTATGGGNCCCACTCGGA
CCAAACTTGGGGTAAN
```

48_16492.edit

```
TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGGCATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAGTTTTTGTTGGTCCTGGTCCATTTTTGGGAGTGGTGGTTACTCTGT
AACCAGTAACAGGGGAACTTGAAGGCAGCCACTTGACACTAATGCTGTTGTCCTGAACATCGGTCACTTGCATCTG
GGATGGTTTGTCAATTTCTGTTCGGTAATTAATGGAAATTGGCTTGCTGCTTGCGGGGCTTGTCTCCACGGCCAGT
GACAGCATACACAGTGATGGTATAATCAACTCCAGGTTTAAGCCGCTGATGGTAGCTGAAACTTTGCTCCAGGCAC
AAGTGAACTCCTGACAGGGCTATTTCCTNCTGTTCTCCGTAAGTGATCCTGTAATATCTCACTGGGACAGCAGGAN
GCATTCCAAAACTTCGGGCGNGACCCCCTAAGCCGAATTNTGCAATATNCATCACACTGGCGGGCGCTCGANCATT
CATTAAAAGGCCCAATCNCCCCTATAGGGAGTNTANTACAATTNG
```

*Fig. 15M-1*

49_16493.edit

TCGAGCGGCCGCCCGGGCAGGTCACTTTTGGTTTTTGGTCATGTTCGGTTGGTCAAAGATAAAAACTAAGTTTGAG
AGATGAATGCAAAGGAAAAAAATATTTTCCAAAGTCCATGTGAAATTGTCTCCCATTTTTTTGGCTTTTGAGGGGG
TTCAGTTTGGGTTGCTTGTCTGTTTCCGGGTTGGGGGGAAAGTTGGTTGGGTGGGAGGGAGCCAGGTTGGGATGGA
GGGAGTTTACAGGAAGCAGACAGGGCCAACGTCG

55_16496.edit

AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA

56_16496.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT

59_16498.edit

TCGAGCGGCCGCCCGGGCAGGTCCACCATAAGTCCTGATACAACCACGGATGAGCTGTCAGGAGCAAGGTTGATTT
CTTTCATTGGTCCGGTCTTCTCCTTGGGGGTCACCCGCACTCGATATCCAGTGAGCTGAACATTGGGTGGTGTCCA
CTGGGCGCTCAGGCTTGTGGGTGTGACCTGAGTGAACTTCAGGTCAGTTGGTGCAGGAATAGTGGTTACTGCAGTC
TGAACCAGAGGCTGACTCTCTCCGCTTGGATTCTGAGCATAGACACTAACCACATACTCCACTGTGGGCTGCAAGC
CTTCAATAGTCATTTCTGTTTGATCTGGACCTGCAGTTTTAGTTTTTGTTGGTCCTGGTCCATTTTTGGGAGTGGT
GGTTACTCTGTAACCAGTAACAGGGGAACTTGAAGGCAGCCACTTGACACTAATGCTGTTGTCCTGAACATCGGTC
ACTTGCATCTGGGATGGTTTGNCAATTTCTGTTCGGTAATTAATGGAAATTGGCTTGCTGCTTGCGGGGCTGTCTC
CACGGCCAGTGACAGCATACACAGNGATGGNATNATCAACTCCAAGTTTAAGGCCCTGATGGTAACTTTAAACTTG
CTCCCAGCCAGNGAACTTCCGGACAGGGTATTTCTTCTGGTTTTCCGAAAGNGANCCTGGAATNNTCTCCTTGGAN
CAGAAGGANCNTCCAAAACTTGGGCCGGAACCCCTT

*Fig. 15N-1*

60_16473.edit

```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTTCCCGGTTCCAGGCCAGTAAT
AGTAGCCTCTTGTGACACCAGGCGGGGCCCANGGACCACTTCTCTGGGANGAGACCCAGCTTCTCATACTTGATGA
TGTAACCCGGTAATCCTGCACGTGGCGGCTGNCATGATACCANCAAGGAATTGGGTGNGGNGGACCTGCCCGGCGG
CCCTCNA
```

60_16498.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAGTGTC
TATGCTCAGAATCCAAGCGGAGAGAGTCAGCCTCTGGTTCAGACTGCAGTAACCACTATTCCTGCACCAACTGACC
TGAAGTTCACTCAGGTCACACCCCACAAGCCTGAGCCGCCAGTGGACACCACCCAATGTTCACTCACTGGATATCGA
GTGCGGGTGACCCCCAAGGAGAAGACCCGGACCCATGAAAGAAATCAACCTTGCTCCTGACAGCTCATCCGNGGGT
GTATCAGGACTTATGGGGGACTGCCCCGGCNGGCCGNTCGAAANCGAATTNTGAAATTTCCTTCNCACTGGGNGGC
GNTTCGAGCTTNCTTNTANANGGCCCAATTCNCCTNTAGNGGGTCGTN
```

61_16499.edit

```
AGCGTGGTCGCGGCCGAGGTCNAGG
```

62_16483.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGTTTT
AGGCGGACCACACCGCCCACAACGGGCACCCCCATAAGGNATAGGCCAAGACCATACCCCGCCGAATGTAGGACAA
GAAGCTCTNTCTCAACAACCATCTCATGGGCCCCATTCCAGGACACTTCTGAGTACATCATTTCATGTCATCCTGG
TGGGCACTTGATGAANAACCCTTACAGTTCAGGGTTCCTGGAACTTCTACCAGNGCCACTTCTGACAGGANCTTGG
GCGNGACCACCCT
```

*Fig. 15O-1*

63_16500.edit

```
AGCGTGGTCGCGGCCGAGGTCCATTTTCTCCCTGACGGTCCCACTTCTCTCCAATCTTGTAGTTCACACCATTGTC
ATGGCACCATCTAGATGAATCACATCTGAAATGACCACTTCCAAAGCCTAAGCACTGGCACAACAGTTTAAAGCCT
GATTCAGACATTCGTTCCCACTCATCTCCAACGGCATAATGGGAAACTGTGTAGGGGTCAAAGCACGAGTCATCCG
TAGGTTGGTTCAAGCCTTCGTTGACAGAGTTGCCCACGGTAACAACCTCTTCCCGAACCTTATGCCTCTGCTGGTC
TTTCAGTGCCTCCACTATGATGTTGTAGGTGGCACCTCTGGTGAGGACCTGCCCGGGCGGCCCGCTCGA
```

64_16493.edit

```
AGCGTGGTCGCGGCCGAGGTGTGCCCCAGACCAGGAATTCGGCTTCGACGTTGGCCCTGTCTGCTTCCTGTAAACT
CCCTCCATCCCAACCTGGCTCCCTCCCACCCAACCAACTTTCCCCCCAACCCGGAAACAGACAAGCAACCCAAACT
GAACCCCCTCAAAAGCCAAAAAAATGGGAGACAATTTCACATGGACTTTGGAAAATATTTTTTTCCTTTGCATTCA
TCTCTCAAACTTAGTTTTTATCTTTGACCAACCGAACATGACCAAAAACCAAAAGTGACCTGCCCGGGCGGCCGCT
CGA
```

64_16500.edit

```
TCGAGCGGCCGCCCGGGCAGGTCCTCACCAGAGGTGCCACCTACAACATCATAGTGGAGGCACTGAAAGACCAGCA
GAGGCATAAGGTTCGGGAAGAGGTTGTTACCGTGGGCAACTCTGTCAACGAAGGCTTGAACCAACCTACGGATGAC
TCGTGCTTTGACCCCTACACAGTTTCCCATTATGCCGTTGGAGATGAGTGGGAACGAATGTCTGAATCAGGCTTTA
AACTGTTGTGCCAGTGCTTAGGCTTTGGAAGTGGTCATTTCAGATGTGATTCATCTAGATGGTGCCATGACAATGG
TGTGAACTACAAGATTGGAGAGAAGTGGGACCGTCAGGGAGAAAATGGACCTCGGCCGCGACCACGCT
```

*Fig. 15P-1*

16501.edit

```
TCGAGCGGCCGCCCGGGCAGGTACCGGGGTGGTCAGCGAGGAGCCATTCACACTGAACTTCACCATCAACAACCTG
CGGTATGAGGAGAACATGCAGCACCCTGGCTCCAGGAAGTTCAACACCACGGAGAGGGTCCTTCAGGGCCTGCTCA
GGTCCCTGTTCAAGAGCACCAGTGTTGGCCCTCTGTACTCTGGCTGCAGACTGACTTTGCTCAGACCTGAGAAACA
TGGGGCAGCCACTGGAGTGGACGCCATCTGCACCCTCCGCCTTGATCCCACTGGTNCTGGACTGGACANANAGCGG
CTATACTTGGGAGCTGANCCNAACCTTTGGCGGNGACNCCNCTT
```

16501.2.edit

```
GAGGACTGGCTCAGCTCCCAGTATAGCCGCTCTCTGTCCAGTCCAGGACCAGTGGGATCAAGGCGGAGGGTGCAGA
TGGCGTCCACTCCAGTGGCTGCCCCATGTTTCTCAAGTCTGAGCAAAGNCAGTCTGCAGCCAGAGTACAGAGGGCC
AACACTGGTGCTCTTGAACAGGGACCTGAGCAGGCCCTGAAGGACCCTCTCCGTGGTGTTGAACTTCCTGGAGCCA
GGGTGCTGCATGTTCTCCTCATACCGCAGGTTGTTGATGGTGAAGTTCAGTGTGAATGGCTCCTCGCTGACCACCC
```

16502.1.edit

```
AGCGTGGTCGCGGCCGAGGTCCACCACACCCAATTCCTTGCTGGTATCATGGCAGCCGCCACGTGCCAGGATTACC
GGCTACATCATCAAGTATGAGAAGCCTGGGTCTCCTCCCAGAGAAGTGGTCCCTCGGCCCCGCCCTGGTGTCACAG
AGGCTACTATTACTGGCCTGGAACCGGGAACCGAATATACAATTTATGTCATTGCCCTGAAGAATAATCAGAAGAG
CGAGCCCCTGATTGGAAGGAAAAAGACAGACGAGCTTCCCCAACTGGTAACCCTTCCACACCCCAATCTTCATGGA
CCANANANCTTGGATNGTCCTTTCACNGGTTNAAAAAACCCTTTTCGCCCCCCCACCTTGGGGATTAACCTTGGGA
AANGGGGATTTNACCNTTCC
```

16502.2.edit

```
TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCCAGTGTCATACCCAGGGNGGGTGACCAAAGGGGGTCNTTTNGACCTGGNGAAAGGAACCA
TCCAAAANCTCTGNCCCATG
```

*Fig. 15Q-1*

16503.1.edit

```
AGCGTGGNCGCGGCCGAGGTCTGAGGATGTAAACTCTTCCCAGGGGAAGGCTGAAGTGCTGACCATGGTGCTACTG
GGTCCTTCTGAGTCAGATATGTGACTGATGNGAACTGAAGTAGGTACTGTAGATGGTGAAGTCTGGGTGTCCCTAA
ATGCTGCATCTCCAGAGCCTTCCATCATTACCGTTTCTTCTTTTGCTATGGGATGAGACACTGTTGAGTATTCTCT
AAAGTCACCACTGAAATCTTCCTCCAAAGGAAAAACCTGTGGAAAAGCCCCTTATTTCTGCCCCATAATTTGGTTCT
CCTAATCNCTCTGAAATCACTATTTCCCTGGAANGTTTGGGAAAAAANNGGGCNACCTGNCANTGGAAANTGGATAN
AAAGATCCCACCATTTTACCCAACNAGCAGAAAGTGGGAANGGTACCGAAAAGCTCCAAGTAANAAAAAGGAGGGA
AGTAAAGGTCAAGTGGGCACCAGTTTCAAACAAAACTTTCCCCAAACTATANAACCCA
```

16503.2.edit

```
AAGCGGCCGCCCGGGCAGGNNCAGNAGTGCCTTCGGGACTGGGNTCACCCCCAGGTCTGCGGCAGTTGTCACAGCG
CCAGCCCCGCTGGCCTCCAAAGCATGTGCAGGAGCAAATGGCACCGAGATATTCCTTCTGCCACTGTTCTCCTACG
TGGTATGTCTTCCCATCATCGTAACACGTTGCCTCATGAGGGTCACACTTGAATTCTCCTTTTCCGTTCCCAAGAC
ATGTGCAGCTCATTTGGCTGGCTCTATAGTTTGGGGAAAGTTTGTTGAAACTGTGCCACTGACCTTTACTTCCTCC
TTCTCTACTGGAGCTTTCCGTACCTTCCACTTCTGCTGNTGGNAAAAAGGGNGGAACNTCTTATCAATTTCATTGG
ACAGTANCCCNCTTTCTNCCCAAAACATNCAAGGGAAAATATTGATTNCNAGAGCGGATTAAGGAACAACCCNAAT
TATGGGGGCCAGAAATAAAGGGGGCTTTTCCACAGGTNTTTTCCT
```

16504.1.edit

```
TCGAGCGGCCGCCCGGGCAGGTCTGCAGGCTATTGTAAGTGTTCTGAGCACATATGAGATAACCTGGGCCAAGCTA
TGATGTTCGATACGTTAGGTGTATTAAATGCACTTTTGACTGCCATCTCAGTGGATGACAGCCTTCTCACTGACAG
CAGAGATCTTCCTCACTGTGCCAGTGGGCAGGAGAAAGAGCATGCTGCGACTGGACCTCGGCCGCGACCACGCT
```

16504.2.edit

```
AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA
```

*Fig. 15R-1*

16505.1.edit

```
CGAGCGGCCGCCCGGGCAGGTCCAGACTCCAATCCAGAGAACCACCAAGCCAGATGTCAGAAGCTACACCATCACA
GGTTTACAACCAGGCACTGACTACAAGATCTACCTGTACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGCTACATCATCAAGTATGAGAAGCCTGGGTCTCCTCCCAGAGAAGTG
GTCCCTCGGCCCCGCCCTGGTGNCACAGAAGCTACTATTACTGGCCTGGAACCGGGAACCGAATATACAATTTATG
TCATTGCCCTGAAGAATAATCANAAGAGCGAGCCCCTGATTGGAAGG
```

16505.2.edit

```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTGTCTTTTTCCTTCCAATCAGGGGCTCGCTCTTCTGATTATTCTTCAGGGCAATGACAT
AAATTGTATATTCGGTTCCCGGTTCCAGGCCAGTAATAGTAGCCTCTGTGACACCAGGGCGGGGCCGAGGGACCAC
TTCTCTGGGAGGAGACCCAGGCTTCTCATACTTGATGATGTANCCGGTAATCCTGGCACCGTGGCGGCTGCCATGA
TACCAGCAAGGAATTGGGTGTGGTGGCCAAGAAACGCAGGTTGGATGGTGCATCAATGGCAGTGGAGGCGTCGATN
ACCACAGGGGAGCTCCGANCATTGTCATTCAAGGTGGACAGGTAGAATCTTGTAATCAGGTGCCTGGTTTGTAAAC
CTG
```

16506.1.edit

```
TCGAGCGGCCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGCCCAGAAGAACTGGTACATCAGCAAGAACC
CCAAGGACAAGAAGCATGTCTGGTTCGGCGAAAGCATGACCGATGGATTCCAGTTCGAGTATGGCGGCCAGGGCTC
CGACCCTGCCGATGTGGACCTCGGCCGCGACCACGCTAAGCCCGAATTCCAGCACACTGGCGGCCGTTACTAGTGG
GATCCGAGCTTCGGTACCAAGCTTGGCGTAATCATGGGNCATAGCTGTTTCCTGNGTGAAAATGGTATTCCGCTTC
ACAATTTCCCAC
```

16506.2.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAAGCTCTTGAAGGGTGGTGTCCACCTCG
AGGTCACGGTCACGAAACCTGCCCGGGCGGCCGCTCGA
```

*Fig. 15S 1*

16507.1.edit

```
AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGNGCCGGNCCGCTCGAAAAGCCCNAATTTCCAGNCACACTTGGCCGGCCGTTACTACTG
```

16507.2.edit

```
TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT
```

16508.1.edit

```
CGAGCGGCCGCCCGGGCAGGTCCCCCCCCTTTTTTTTTTTTTTTTTTTTTTTTTTTTTTTTTTTTTTTTTTTTTTT
TTTTTTTTTTTTTTTTTT
```

16508.2.edit

```
AGCGTGGTCGCGGCCGAGGTCTGGCATTCCTTCGACTTCTCTCCAGCCGAGCTTCCCAGAACATCACATATCACTG
CAAAAATAGCATTGCATACATGGATCAGGCCAGTGGAAATGTAAAGAAGGCCCTGAAGCTGATGGGGTCAAATGAA
GGTGAATTCAAGGCTGAAGGAAATAGCAAATTCACCTACACAGTTCTGGAGGATGGTTGCACGAAACACACTGGGG
AATGGAGCAAAACAGTCTTTGAATATCGAACACGCAAGGCTGTGAGACTACCTATTGTAGATATTGCACCCTATGA
CATTGGTGGTCCTGATCAAGAATTTGGTGTGGACGTTGGCCCTGTTTGCTTTTTATAAACCAAACTCTATCTGAAA
TCCCAACAAAAAAAATTTAACTCCATATGTGNTCCTCTTGTTCTAATCTTGGCAACCAGTGCAAGTGACCGACAAA
ATTCCAGTTATTTATTTCCAAAATGTTTGGAAACAGTATAATTTGACAAAGAAAAAAGGATACTTCTCTTTTTTTG
GCTGGTCCACCAAATACAATTCAAAAGGCTTTTTGGTTTTATTTTTTTANCCAATTCCAATTTCAAAATGTCTCAA
TGGNGCTTATAATAAAATAAACTTTCACCCTTNTTTTNTGAT
```

*Fig. 15T-1*

16509.1.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAAGTAACCACCACTCCCAAAAATGGACCAGGACCAACAAAAA
CTAAAACTGCAGGTCCAGATCAAACAGAAAATGGACTATTGAAGGCTTGCAGCCCACAGTGGAAGTATGTGGNTAG
GNGTCTATGCTCAGAATCCCAAGCCGGAGAAAGTCAGCCTTCTGGTTTAGACTGCAGTAACCAACATTGATCGCCC
TAAAGGACTGGNCATTCACTTGGATGGTGGATGTCCAATTC
```

16509.2.edit

```
TCGAGCGGCCGCCCGGGCAGGTCCTTGCAGCTCTGCAGNGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGNGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGGTGGTCCTGNCCCATTTTTGGGAAGTGGGGGGTTACTC
TGTAACCAGTAACAGGGGAACTTGAAGGCAGCCACTTGACACTAATGCTGTTGTCCTGAACATCGGTCACTTGCAT
CTGGGGATGGTTTTGACAATTTCTGGTTCGGCAAATTAATGGAAATTGGCTTGCTGCTTGGCGGGGCTGNCTCCAC
GGGCCAGTGACAGCATAC
```

16510.1.edit

```
TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGTTGGNCCTGNNCCATTTTTGGGGAAGGGGTGGTTACTC
TTGTAACCAGTAACAGGGGAACTTGAAGCAGCCACTTGACACTAATGCTGGTGGCCTGAACATCGGTCACTTGCAT
CTGGGATGGTTTGGTCAATTTCTGTTCGGTAATTAATGGGAAATTGGCTTACTGGCTTGCGGGGGCTGTCTCCACG
GNCAGTGACAAGCATACACAGGNGATGGGTATAATCAACTCCAGGTTTAAGGCCNCTGATGGTA
```

16510.2.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGTAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGGACCAGGACCAACAAAAA
ACTAAAACTGCANGGTCCAGATCAAACAGAAATGACTATTGAAGGCTTGCAGCCCACAGTGGAGTATGTGGGTTAG
TGTCTATGCTCAGAATNCCAAGCGGAGAGAGTCAGCCTCTGGTTCAGACT
```

*Fig. 15U-1*

16511.1.edit

```
TCGAGCGGCCGCCCGGGCAGGTCAGCGCTCTCAGGACGTCACCACCATGGCCTGGGCTCTGCTCCTCCTCACCCTC
CTCACTCAGGGCACAGGGTCCTGGGCCCAGTCTGCCCTGACTCAGCCTCCCTCCGCGTCCGGGTCTCCTGGACAGT
CAGTCACCATCTCCTGCACTGGAACCAGCAGTGACGTTGGTGCTTATGAATTTGTCTCCTGGTACCAACAACACCC
AGGCAAGGCCCCCAAACTCATGATTTCTGAGGTCACTAAGCGGCCCTCAGGGGTCCCTGATCGCTTCTCTGGCTCC
AAGTCTGGCAACACGGCCTCCCTGACCGTCTCTGGGCTCCANGCTGAGGATGANGCTGATTATTACTGGAAGCTCA
TATGCAGGCAACAACAATTGGGTGTTCGGCGGAAGGGACCAAGCTGACCGTNCTAAGGTCAAGCCCAAGGCTTGCC
CCCCTCGGTCACTCTGTTCCCACCCTCCTCTGAAGAAGCTTTCAAGCCAACAANGNCACACTGGGTGTGTCTCATA
AGTGGACTTTCTACCC
```

16511.2.edit

```
AGCGTGGTCGCGGCCGAGGTCTGTAGCTTCTGTGGGACTTCCACTGCTCAGGCGTCAGGCTCAGGTAGCTGCTGGC
CGCGTACTTGTTGTTGCTTTGNTTGGAGGGTGTGGTGGTCTCCACTCCCGCCTTGACGGGGCTGCTATCTGCCTTC
CAGGCCACTGTCACGGCTCCCGGGTAGAAGTCACTTATGAGACACACCAGTGTGGCCTTGTTGGCTTGAAGCTCCT
CAGAGGAGGGTGGGAACAGAGTGACCGAGGGGGCAGCCTTGGGCTGACCTAGGACGGTCAGCTTGGTCCCTCCGCC
GAACACCCAATTGTTGTTGCCTGCATATGAGCTGCAGTAATAATCAGCCTCATCCTCAGCCTGGAGCCCAGAGACN
GTCAAGGGAGGCCCGTGTTTGCCAAGACTTGGAAGCCAGANAAGCGATCAGGGACCCCTGAGGGCCGCTTTACNGA
CCTCAAAAAATCATGAATTTGGGGGGCCTTTGCCTGGGNGTTGGTTGGTNACCAGNAAAACAAAATTTCATAAAGC
ACCAACGTCACTGCTGGTTTCCAGTGCANGAAANATGGTGAACTGAANTGTCC
```

16512.1.edit

```
AGCGTGGTCGCGGCCGAGGTCCAGCATCAGGAGCCCCGCCTTGCCGGCTCTGGTCATCGCCTTTCTTTTTGTGGCC
TGAAACGATGTCATCAATTCGCAGTAGCAGAACTGCCGTCTCCACTGCTGTCTTATAAGTCTGCAGCTTCACAGCC
AATGGCTCCCATATGCCCAGTTCCTTCATGTCCACCAAAGTACCCGTCTCACCATTTACACCCCAGGTCTCACAGT
TCTCCTGGGTGTGCTTGGCCCGAAGGGAGGTAAGTANACGGATGGTGCTGGTCCCACAGTTCTGGATCAGGGTACG
AGGAATGACCTCTAGGGCCTGGGCNACAAGCCCTGTATGGACCTGCCCGGGCGGGCCCGCTCGA
```

16512.2.edit

```
TCGAGCGGCCGCCCGGGCAGGTCCATACAGGGCTGTTGCCCAGGCCCTAGAGGNCATTCCTTGTACCCTGATCCAG
AACTGTGGGACCAGCACCATCCGTCTACTTACCTCCCTTCGGGCCAAGCACACCCAGGAGAACTGTGAGACCTGGG
GTGTAAATGGNGAGACGGGTACTTTGGTGGACATGAAGGAACTGGGCATATGGGAGCCATTGGCTGNGAAGCTGCA
NACTTATAAGACAGCAGTGGAGACGGCAGTTCTGCTACTGCGAATTGATGACATCGTTTCAGGCCACAAAAAGAAA
GGCGATGACCANAGCCGGCAAGGCGGGGCTTCCTGATGCTGGACCTCGGCCGCCGACCACGCTT
```

*Fig. 15V-1*

16514.1.edit

```
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTGCTGTGCGCCACGTGTTGCTCANACAGGGTGTGCTGGGCATCAAGGTG
AAGATCATGCTGCCCTGGGACCCANCTGGCAAAAATGGCCCTTAAAAACCCCTTGCCNTGACCACGTGAACCATTT
GTGNGAACCCCAAGATGAANATACTTGCCCACCACCCCCCATTC
```

16514.2.edit

```
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAGTGTCAACGTAGTAGTTAACAGGGTCTCCGCTGTGGATCATC
AGGCCATCCACAAACTTCATGGATTTAGCCCTCTGTCCTCGGAGTTTCCCAAAACACCACAACCTCGCCAGCCTTT
GGGCCCCACTTCTTCATGAATGAAACCGCAGCACACCATTANCAAGGCCCTTCCGCACAGGNAAGCCCTTCCTAAG
GAGTTTTGTAAACGCAAAAAACTCTTGCCTGGGGCAAATGGGCACACAGACCTNTANTNGGACCTTGGNCCGCGAA
CCACCGCTT
```

16515.1.edit

```
AGCGTGGTCGCGGCCGAGGTCTGGCCCTCCTGGCAAGGCTGGTGAAGATGGTCACCCTGGAAAACCCGGACGACCT
GGTGAGAGAGGAGTTGTTGGACCACAGGGTGCTCGTGGTTTCCCTGGAACTCCTGGACTTCCTGGCTTCAAAGGCA
TTAGGGGACACAATGGTCTGGATGGATTGAAGGGACAGCCCGGTGCTCCTGGTGTGAAGGGTGAACCTGGNGCCCC
TGGTGAAAATGGAACTCCAGGTCAAACAGGAGCCCGNGGGCTTCCTGGNGAGAGAGGACGTGTTGGTGCCCCTGGC
CCANACCTGCCCGGGCGGCCGCTCNAAAAGCCGAAATCCAGNACACTGGCGGCCGNTACTANTGGAATCCGAACTT
CGGTACCAAAGCTTGGCCGTAATCATGGCCATAGCTTGTTCCCTGGGGNGGAAATTGGTATTCCGCTNCCAATTCC
ACACAACATACCGAACCCGGAAAGCATTAAAGTGTAAAAGCCCTGGGGGGGCCTAAATGANGTGAGCNTAACTCNC
ATTTAATTGGCGTTGCGCTTCACTGCCCCGCTTTTCCAGTCCGGGNA
```

16515.2.edit

```
TCGAGCGGCCGCCCGGGCAGGTCTGGGCCAGGGGCACCAACACGTCCTCTCTCACCAGGAAGCCCACGGGCTCCTG
TTTGACCTGGAGTTCCATTTTCACCAGGGGCACCAGGTTCACCCTTCACACCAGGAGCACCGGGCTGTCCCTTCAA
TCCATCCAGACCATTGTGNCCCCTAATGCCTTTGAAGCCAGGAAGTCCAGGAGTTCCAGGGAAACCACGAGCACCC
TGTGGTCCAACAACTCCTCTCTCACCAGGTCGTCCGGGTTTTCCAGGGTGACCATCTTCACCAGCCTTGCCAGGAG
GGCCAGACCTCGGCCGCGACCACGCT
```

*Fig. 15W-1*

16516.1.edit

ANCGTGGTCGCGGCCGAGGTCCTCACCAGAGGTGNCACCTACAACATCATAGTGGAGGCACTGAAAGACCANCAGA
GGCATAAGGTTCGGGAAGAGG

16516.2.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGTCCACGGTAACAACCTCTTCCCGAACCTTATGCCTCTGCTGG
TCTTTCAGTGCCTCCACTATGATGTTGTAGGTGGCACCTCTGGTGAGGACCTCNGNCCNGAACAACGCTTAAGCCC
GNATTCTGCAGAATAATCCCATCACACTTGGCGGCCGCTTCGANCATGCATCNTAAAAGGGGCCCCAATTTCCCCC
TTATAAGNGAANCCGTATTTNCCAATTTCACTGGNCCCGCCGNTTTTACAAACGNCGGTGAACTGGGGAAAAACCC
TGGCGGTTACCCAACTTTAATCGCCNTTGGCAGCACAATCCCCCCTTTTCGNCCANCNTGGGCGTAAATAACCGAA
AA

16517.1.edit

ANCGNGGTCGCGGCCGANGTNTTTTTTCTTNTTTTTTT

16518.1.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GGGNGGTCAGCGTCCTCACCGTCCTGCACCAGAATTGGTTGAATGGCAAGGAGTACAAGNGCAAGGTTTCCAACAA
AGCCNTCCCAGCCCCCNTCGAAAAAACCATTTCCAAAGCCAAAGGGCAGCCCCGAGAACCACAGGTGTACACCCTG
CCCCCATCCCGGGAGGAAAAGANCAANAACCNGGTTCAGCCTTAACTTGCTTGGTCNAANGCTTTTTATCCCAACG
NACTTCCCCCNTGGAANTGGGAAAAACCAATGGGCCAANCCGAAAAACAATTACAANAACCCC

16518.2.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGAACACCTGGGGTTCTCGGGGCTTGCCCTTTGGTTTTGAANATGGTTTTC
TCGATGGGGGCTGGAAGGGCTTTGTTGNAAACCTTGCACTTGACTCCTTGCCATTCACCCAGNCCTGGNGCAGGAC
GGNGAGGACNCTNACCACACGGAACCGGGCTGGTGGACTGCTCC

*Fig. 15X-1*

16519.1.edit

AGCGTGGTCGCGGACGANGTCCTGTCAGAGTGGNACTGGTAGAAGTTCCANGAACCCTGAACTGTAAGGGTTCTTC
ATCAGTGCCAACAGGATGACATGAAATGATGTACTCAGAAGNGNCCTGGAATGGGGCCCATGANATGGTTGCC

16519.2.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGGCACCCCCCCTGGGTATGAACCTGGGAA
AANGGNANTTAANCTTTCCTGGCA

16520.1.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGGTNCCCTGGTACTGGGTTACAGANTAACCACCACTCCCAAAAATGGACCAGGAACCACAAAAA
CTTAAACTGCAGGGTCCAGATCAAAACAGAAATGACTATTGAANGCTTGCAGCCCACAGTGGGAGTATGNGGGTAG
TGNCTATGCTTCAGAATCCAAGCGGAAAAAANGTCAAGCCTTNTGGGTTCAA

16520.2.edit

TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGNCTGAACCAGAGG
CTGACTCTCTCCGCTTGGATTCTGAGCATAGACACTAACCACATACTCCACTGTGGGCTGCAANCCTTCAATAANN
CATTTCTGTTTGATCTGGACC

16521.2.edit

TCGAGCGGCCGCCCGGGCAGGTCTGGTGGGGTCCTGGCACACGCACATGGGGGNGTTGNTCTNATCCAGCTGCCCA
GCCCCCATTGGCGAGTTTGAGAAGGTGTGCAGCAATGACAACAANACCTTCGACTCTTCCTGCCACTTCTTTGCCA
CAAAGTGCACCCTGGAGGGCACCAAGAAGGGCACAAGCTCCACCTGGACTACATCGGGCCTTGCAAATACATCCC
CCCTTGCCTGGACTCTGAGCTGACCGAATTCCCCCTTGCGCATGCGGGACTGGCTCAAGAACCGTCCTGGCACCCT
TGTATGANAGGGATGAAGACACNACCC

*Fig. 15Y-1*

16522.1.edit

AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCGAAAGCCGAATTCCAGCACACTGGCGGCCG
GTACTAGTGGANCCNAACTTGGNANCCAACCTGGNGGAANTAATGGGCATAANCTGTTTCTGGGGGGAAATTGGTA
TCCNGTTTACAATTCCCNCACAACATACGAGCCGGAAGCATAAAAGNGTAAAAGCCTGGGGGNGGCCTANTGAAGT
GAAGCTAAACTCACATTAATTNGCGTTGCCGCTCACTGGCCCGCTTTTCCAGC 16522.2.edit TCGAGCGGCCGCCCGGGCAGGTTTGGAAGGGGGATGCGGGGGAAGAGGAAGACTGACGGTCCCCCCAGGAGTTCAG
GTGCTGGGCACGGTGGGCATGTGTGAGTTTTGTCACAAGATTTGGGCTCAACTCTCTTGTCCACCTTGGTGTTGCT
GGGCTTGTGATCTACGTTGCAGGTGTAGGTCTGGGNGCCGAAGTTGCTGGAGGGCACGGTCACCACGCTGCTGAGG
GAGTAGAGTCCTGAGGACTGTANGACAGACCTCGGCCGNGACCACGCTAAGCCGAATTCTGCAGATATCCATCACA
CTGGCGGCCGCTCCGAGCATGCATTTTAGAGG 16523.1.edit

AGCGTGGNCGCGGACGANGACAACAACCCC 16523.2.edit

TCGAGCGGCCGCCCGGGCAGGNCCACATCGGCAGGGTCGGAGCCCTGGCCGCCATACTCGAACTGGAATCCATCGG
TCATGCTCTTGCCGAACCAGACATGCCTCTTGTCCTTGGGGTTCTTGCTGATGNACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCT 16524.1.edit AGCGTGGTCGCGGCCGAGGTCCAGCCTGGAGATAANGGTGAAGGTGGTGCCCCCGGACTTCCAGGTATAGCTGGAC
CTCGTGGTAGCCCTGGTGAGAGAGGTGAAACTGGCCCTCCAGGACCTGCTGGTTTCCCTGGTGCTCCTGGACAGAA
TGGTGAACCTGGNGGTAAAGGAGAAAGAGGGGCTCCGGNTGANAAAGGTGAAGGAGGCCCTCCTGNATTGGCAGGG
GCCCCANGACTTAGAGGTGGAGCTGGCCCCCCTGGCCCCGAAGGAGGAAAGGGTGCTGCTGGTCCTCCTGGGCCAC
CTGG

*Fig. 15Z-1*

16524.2.edit

TCGAGCGGCCGCCCGGGCAGGTCTGGGCCAGGAGGACCAATAGGACCAGTAGGACCCCTTGGGCCATCTTTCCCTG
GGACACCATCAGCACCTGGACCGCCTGGTTCACCCTTGTCACCCTTTGGACCAGGACTTCCAAGACCTCCTCTTTC
TCCAGGCATTCCTTGCAGACCAGGAGTACCANCAGCACCAGGTGGCCCAGGAGGACCAGCAGCACCCTTTCCTCCT
TCGGGACCAGGGGGACCAGCTCCACCTCTAAGTCCTGGGGCCCCTGCCAATCCAGGAGGGCCTCCTTCACCTTTCT
CACCCGGAGCCCCTCTTTCT 16526.1.edit TCGAGCGGCCGCCCGGGCAGGTCCACCGGGATATTCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGACAACCGGAG
GCTGGAGAGCAAAATCCGGGAGCACTTGGAGAAGAAGGGACCCCAGGTCAGAGACTGGAGCCATTACTTCAAGATC
ATCGAGGACCTGAGGGCTCANATCTTCGCAAATACTGCNGACAATGCCCG 16526.2.edit ATGCGNGGTCGCGGCCGANGACCANCTCTGGCTCATACTTGACTCTAAAGNCNTCACCAGNANTTACGGNCATTGC
CAATCTGCAGAACGATGCGGGCATTGTCCGCANTATTTGCGAAGATCTGAGCCCTCAGGNCCTCGATGATCTTGAA
GTAANGGCTCCAGTCTCTGACCTGGGGTCCCTTCTTCTCCAAGTGCTCCCGGATTTTGCTCTCCAGCCTCCGGTTC
TCGGTCTCCAAGNCTTCTCACTCTGTCCAGGAAAAGAGGCCAGGCGGNCGATCAGGGCTTTTGCATGGACT 16527.1.edit AGCGTGGTCGCGGCCGAGGTTGTACAAGCTTTTTTTTTTTTTTTTTTTTTTTTTTTTTTTTTTTTTTTTTTTTTTT
TTTTTTTTTTTTTTTTTTTTTTTT 16527.2.edit TCGAGCGGCCGCCCGGGCAGGTCTGCCAACACCAAGATTGGCCCCCGCCGCATCCACACAGTTNGTGTGCGGGGAG
GTAACAAGAAATACCGTGCCCTGAGGNTGGACGNGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATNGACAGCACACCGTACCGACAGTGGGTACCGAAGTCCCACTATGCNCCT

*Fig. 15A-2*

16528.1.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAG
```

16528.2.edit

```
AGCGTGNTCNCGGCCGAGGATGGGGAAGCTCGNCTGTCTTTTTCCTTCCAATCAGGGGCTNNNTCTTCTGATTATT
CTTCAGGGCAANGACATAAATTGTATATTCGGNTCCCGGTTCCAGNCCAGTAATAGTAGCCTCTGTGACACCAGGG
CGGGGCCGAGGGACCACTTCTCTGGGAGGAGACCCAGGCTTCTCATACTTGATGATGAAGCCGGTAATCCTGGCAC
GTGGGCGGCTGCCATGATACCACCAANGAATTGGGTGTGGTGGACCTGCCCGGGCGGGCCGCTCGAAAAACCGAAT
TCNTGCAAGAATATCCATCACACTTGGGCGGGCCGNTCGAACCATGCATCNTAAAAGGGCCCCAATTTCCCCCCTA
TTAGGNGAAGCCNCATTTAACAAATTCCACTTGG
```

16529.1.edit

```
TCGAGCGGCCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTTGAGCCAGCAGAATCGAAAACATTCGGAACCCAAGAAGGGCAAGCCCGCAAAGAAACCCCGCCCGCAC
CTGGCCGNGAACCTCCAAGAANGTGCCCACNTCTTGACTGGGAAAAAAAGGGAAAANTACTTGGAATTGGAC
```

16529.2.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAAGTGGCACATCTTGAGGTCACGGCAGGGTGCGGGCGG
GGTTCTTGCGGGCTGCCCTTCTGGGCTCCCGGAATGTTCTNNGAACTTGCTGG
```

*Fig. 15B-2*

16530.1.edit

```
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTTGCTTGTGCGCCACGTGTTGCTCANACANGGGTGGGCTGGGCATCAAG
GNG
```

16530.2.edit

```
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAAGTGTCAACGTAAGTAAGTTAACAGGGTCTCCGCTGTGGATC
ATCAGGCCATCCACAAACTTCATGGATTTAACCCTCTGTCCTCGGAG
```

16531.1.edit

```
TCGAGCGGCCGCCCGGGCAGGTGTTTCAGAGGTTCCAAGGTCCACTGTGGAGGTCCCAGGAGTGCTGGTGGTGGGC
ACAGAGGTCCGATGGGTGAAACCATTGACATAGAGACTGTTCCTGTCCAGGGTGTAGGGGCCCAGCTCTTTGATGC
CATTGGCCAGTTGGCTCAGCTCCCAGTACAGCCGCTCTCTGTTGAGTCCAGGGCTTTTGGGGTCAAGATGATGGAT
GCAGATGGCATCCACTCCAGTGGCTGCTCCATCCTTCTCGGACCTGAGAGAGGTCAGTCTGCAGCCAGAGTACAGA
GGGCCAACACTGGTGTTCTTTGAATA
```

16531.2.edit

```
AGCGTGGTCGCGGCCGAGGTCTGTACTGGGAGCTAAGCAAACTGACCAATGACATTGAAGAGCTGGGCCCCTACAC
CCTGGACAGGAACAGTCTCTATGTCAATGGTTTCACCCATCAGAGCTCTGTGNCCACCACCAGCACTCCTGGGACC
TCCACAGTGGATTTCAGAACCTCAGGGACTCCATCCTCCCTCTCCAGCCCCACAATTATGGCTGCTGGCCCTCTCC
TGGTACCATTCACCCTCAACTTCACCATCACCAACCTGCAGTATGGGGAGGACATGGGTCACCCTGNCTCCAGGAA
GTTCAACACCACA
```

16532.1.edit

```
TCGAGCGGCCGCCCGGACAGGTCTGGGCGGATAGCACCGGGCATATTTTGGAATGGATGAGGTCTGGCACCCTGAG
CAGTCCAGCGAGGACTTGGTCTTAGTTGAGCAATTTGGCTAGGAGGATAGTATGCAGCACGGNTCTGAGNCTGTGG
GATAGCTGCCATGAAGTAACCTGAAGGAGGTGCTGGCTGGTANGGGTTGATTACAGGGTTGGGAACAGCTCGTACA
CTTGCCATTCTCTGCATATACTGGTTAGTGAGGTGAGCCTGGCCCTCTTCTTTTG
```

*Fig. 15C-2*

01_16558.3.edit

AGCGTGGTCGCGGCCGAGGTGAGCCACAGGTGACCGGGGCTGAAGCTGGGGCTGCTGGNCCTGCTGGTCCTG

02_16558.4.edit

CAGCNGCTCCNACGGGGCCTGNGGGACCAACAACACCGTTTTCACCCTTAGGCCCTTTGGCTCCTCTTTCTCCTTT
AGCACCAGGTTGACCAGCAGCNCCANCAGGACCAGCAAATCCATTGGGGCCAGCAGGACCGACCTCACCACGTTCA
CCAGGGCTTCCCCGAGGACCAGCAGGACCAGCAGGACCAGCAGCCCCAGCTTCGCCCCGGTCACCTGTGGCTCACC
TCGGCCGCGACCACGCT

03_16535.1.edit

TCGAGCGGTCGCCCGGGCAGGTCCACCGGGATAGCCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGANAACCGGAG
GCTGGANAGCAAAATCCGGGAGCACTTGGAGAAGAAGGGACCCCAGGTCAAGAGACTGGAGCCATTACTTCAAGAT
CATCGAGGGACCTGGAGG

04_16535.2.edit

AGCGNGGTCGCGGCCGAGGTCCAGCTCTGTCTCATACTTGACTCTAAAGTCATCAGCAGCAAGACGGGCATTGTCA
ATCTGCAGAACGATGCGGGCATTGTCCGCAGTATTTGCGAAGATCTGAGCCCTCAGGTCCTCGATGATCTTGAAGT
AATGGCTCCAGTCTCTGACCTGGGGTCCCTTCTTCTCCAAGTGCTCCCGGATTTTGCTCTCCAGCCTCCGGTTCTC
GGTCTCCAGGCTCCTCACTCTGTCCAGGTAAGAAGGCCCAGGCGGTCGTTCAGGCTTTGCATGGTCTCCTTCTCGT
TCTGGATGCCTCCCATTCCTGCCAGACCC

05_16536.1.edit

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 15D-2*

07_16537.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACCGCAGGTCTCACCAGTCTCCATGTTGCAGAAGACTTTGATGGCATCCAGGTTGCAGCCTT
GGTTGGGGTCAATCCAGTACTCTCCACTCTTCCAGTCAGAAGTGGGCACATCTTGAGGTCACCGGCAGGTGCCGGG
CCGGGGGTTCTTGCGGCTTGCCCTCTGGGCTCCGGATGTTCTCGATCTGCTTGGCTCAGGCTCTTGAGGGTGGGTG
TCCACCTCGAGGTCACGGTCACCGAAACCTGCCCGGGCGGCCCGCTCGA

08_16537.2.edit

TCGAGCGGTCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGGCCCAGAAGAAACTGGTACATCAGCAAGGA
ACCCCAAGGACAAGAGGCATTGTCTTGGTTCGGCGAGNAGCATGACCCGATGGATTCCAGTTTCGAGTATTGGCGG
CCAGGGCTTCCCGACCCTTGCCGATGTGGACCTCGGCCGCGACCACCGCT

*Fig. 15E-2*

O8E Rabbits 01212000

Date:1/21/99

| Antigen on Plate | Sera Sample | Antibody Dilutions | | | | | | | | | | |
|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| O8E (#632-24) | Preimmune sera (#2576L):11/10/99 | 0.13 | 0.09 | 0.08 | 0.07 | 0.07 | 0.07 | 0.07 | 0.06 | 0.07 | 0.07 | 0.07 | 0.07 |
| | | 0.10 | 0.08 | 0.07 | 0.07 | 0.07 | 0.07 | 0.07 | 0.06 | 0.06 | 0.07 | 0.06 | 0.07 |
| | Average | 0.11 | 0.08 | 0.07 | 0.07 | 0.07 | 0.07 | 0.07 | 0.06 | 0.06 | 0.07 | 0.06 | 0.07 |
| | α-O8E (#2576K):1/11/2000 | 2.92 | 2.81 | 2.74 | 2.70 | 2.58 | 2.08 | 1.61 | 1.01 | 0.68 | 0.40 | 0.24 | 0.15 |
| | | 2.93 | 2.77 | 2.74 | 2.69 | 2.48 | 2.08 | 1.57 | 1.00 | 0.66 | 0.40 | 0.23 | 0.16 |
| | Average | 2.93 | 2.79 | 2.74 | 2.69 | 2.53 | 2.08 | 1.59 | 1.00 | 0.67 | 0.40 | 0.23 | 0.16 |
| | Preimmune sera (#2333L):11/10/99 | 0.09 | 0.07 | 0.06 | 0.06 | 0.07 | 0.07 | 0.07 | 0.07 | 0.07 | 0.07 | 0.07 | 0.07 |
| | | 0.08 | 0.07 | 0.06 | 0.07 | 0.10 | 0.08 | 0.07 | 0.07 | 0.07 | 0.07 | 0.07 | 0.07 |
| | Average | 0.08 | 0.07 | 0.06 | 0.06 | 0.08 | 0.07 | 0.07 | 0.07 | 0.07 | 0.07 | 0.07 | 0.07 |
| | α-O8E (#2333L):1/11/2000 | 2.73 | 2.75 | 2.64 | 2.48 | 2.30 | 1.78 | 1.41 | 0.92 | 0.58 | 0.32 | 0.20 | 0.14 |
| | | 2.73 | 2.76 | 2.51 | 2.60 | 2.37 | 1.93 | 1.44 | 0.88 | 0.58 | 0.35 | 0.20 | 0.14 |
| | Average | 2.73 | 2.76 | 2.57 | 2.54 | 2.33 | 1.85 | 1.43 | 0.90 | 0.58 | 0.33 | 0.20 | 0.14 |

*Fig. 23* affi-pure O8E #2576L 739.87A&B

| Antibody Name | O8E polyclonal | |
|---|---|---|
| Rabbit #, Bleed Date | 2576L, 1/11/2000 | |
| Purification Method | affinity | |
| Buffer | PBS | |
| Notebook | #705, p150 | |
| lot # | 739.87A | 739.87B |
| Antibody Concentration | 1.4mg/ml | 1.7mg/ml |
| Initial Amount | 18mg | 3mg |

Date: 5/2/2000

| Antigen on Plate | Sera Sample | Antibody Dilutions | | | | | | | | | | |
|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| O8E #632-24 | preimmune sera (2576L) | 0.15 | 0.11 | 0.09 | 0.08 | 0.08 | 0.07 | 0.07 | 0.07 | 0.07 | 0.08 | 0.07 | 0.08 |
| | | 0.14 | 0.10 | 0.09 | 0.08 | 0.07 | 0.07 | 0.07 | 0.07 | 0.07 | 0.07 | 0.07 | 0.07 |
| | Average | 0.14 | 0.10 | 0.09 | 0.08 | 0.07 | 0.07 | 0.07 | 0.07 | 0.07 | 0.08 | 0.07 | 0.08 |
| | α-O8E (2576K):2/8/2000 | 2.74 | 2.71 | 2.63 | 2.49 | 2.29 | 1.87 | 1.39 | 0.92 | 0.57 | 0.33 | 0.20 | 0.14 |
| | | 2.72 | 2.68 | 2.64 | 2.47 | 2.26 | 1.93 | 1.42 | 0.94 | 0.57 | 0.34 | 0.21 | 0.14 |
| | Average | 2.73 | 2.70 | 2.63 | 2.48 | 2.27 | 1.90 | 1.41 | 0.93 | 0.57 | 0.34 | 0.21 | 0.14 |
| | affinity pure α-O8E poly salt peak 739-87A | 2.69 | 2.60 | 2.50 | 2.21 | 1.83 | 1.34 | 0.99 | 0.64 | 0.38 | 0.22 | 0.15 | 0.11 |
| | | 2.59 | 2.48 | 2.38 | 2.21 | 1.82 | 1.33 | 1.00 | 0.62 | 0.37 | 0.22 | 0.14 | 0.11 |
| | Average | 2.64 | 2.54 | 2.44 | 2.21 | 1.83 | 1.34 | 1.00 | 0.63 | 0.37 | 0.22 | 0.15 | 0.11 |
| | affinity pure α-O8E poly acid peak 739-67B | 2.46 | 2.39 | 2.40 | 2.34 | 2.08 | 1.73 | 1.29 | 0.81 | 0.49 | 0.29 | 0.19 | 0.13 |
| | | 2.65 | 2.66 | 2.61 | 2.45 | 2.14 | 1.76 | 1.30 | 0.82 | 0.48 | 0.29 | 0.19 | 0.13 |
| | Average | 2.56 | 2.53 | 2.51 | 2.39 | 2.11 | 1.74 | 1.30 | 0.81 | 0.49 | 0.29 | 0.19 | 0.13 |

Fig. 24

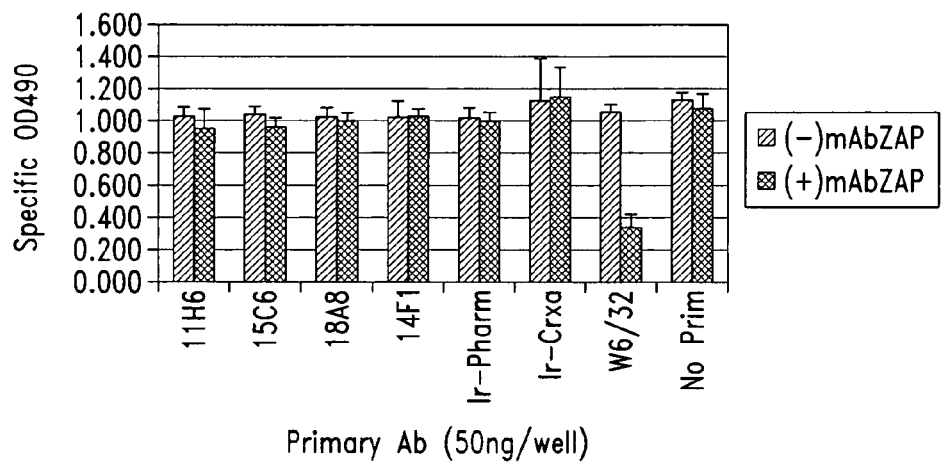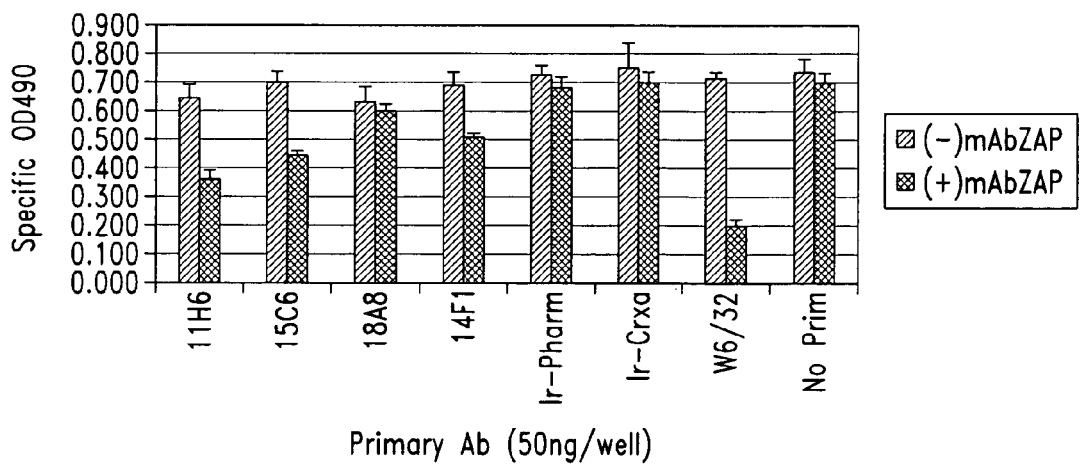
Fig. 25

SEQUENCE LISTING

```
<160> NUMBER OF SEQ ID NOS: 624

<210> SEQ ID NO 1
<211> LENGTH: 461
<212> TYPE: DNA
<213> ORGANISM: Homo sapiens

<400> SEQUENCE: 1
ttagagaggc acagaaggaa gaagagttaa aagcagcaaa gccgggtttt tttgttttgt      60
tttgttttgt tttgttttga gatggagtct cactctgttg cccaagctgg agtacaacgg     120
catgatctca gctcgctgca acctccgcct cccacgttca agtgattctc ctgcctcagc     180
ctcccaagta gctgggatta caggcgcccg ccaccacgct cagctaattt tttttgtatt     240
tttagtagag acagggtttc accaggttgg ccaggctgct cttgaactcc tgacctcagg     300
tgatccaccc gcctcggcct cccaaagtgc tgggattaca ggcgtgagcc accacgcccg     360
gcccccaaag ctgtttcttt tgtctttagc gtaaagctct cctgccatgc agtatctaca     420
taactgacgt gactgccagc aagctcagtc actccgtggt c                          461

<210> SEQ ID NO 2
<211> LENGTH: 540
<212> TYPE: DNA
<213> ORGANISM: Homo sapiens

<400> SEQUENCE: 2
taggatgtgt tggaccctct gtgtcaaaaa aaacctcaca aagaatcccc tgctcattac      60
agaagaagat gcatttaaaa tatgggttat tttcaacttt ttatctgagg acaagtatcc     120
attaattatt gtgtcagaag agattgaata cctgcttaag aagcttacag aagctatggg     180
aggaggttgg cagcaagaac aatttgaaca ttataaaatc aactttgatg acagtaaaaa     240
tggcctttct gcatgggaac ttattgagct tattggaaat ggacagttta gcaaaggcat     300
ggaccggcag actgtgtcta tggcaattaa tgaagtcttt aatgaactta tattagatgt     360
gttaaagcag ggttacatga tgaaaaaggg ccacagacgg aaaaactgga ctgaaagatg     420
gtttgtacta aaacccaaca taatttctta ctatgtgagt gaggatctga aggataagaa     480
aggagacatt ctcttggatg aaaattgctg tgtagagtcc ttgcctgaca aagatggaaa     540
```

<210> SEQ ID NO 3
<211> LENGTH: 461
<212> TYPE: DNA
<213> ORGANISM: Homo sapiens

<400> SEQUENCE: 3

```
ttagagaggc acagaaggaa gaagagttaa aagcagcaaa gccgggtttt tttgttttgt      60
tttgttttgt tttgttttga gatggagtct cactctgttg cccaagctgg agtacaacgg     120
catgatctca gctcgctgca acctccgcct cccacgttca agtgattctc ctgcctcagc     180
ctcccaagta gctgggatta caggcgcccg ccaccacgct cagctaattt ttttgtatt      240 tttagtagag acagggtttc accaggttgg ccaggctgct cttgaactcc tgacctcagg     300
tgatccaccc gcctcggcct cccaaagtgc tgggattaca ggcgtgagcc accacgcccg     360
gcccccaaag ctgtttcttt tgtcttagc gtaaagctct cctgccatgc agtatctaca      420
taactgacgt gactgccagc aagctcagtc actccgtggt c                        461
```

<210> SEQ ID NO 4
<211> LENGTH: 531
<212> TYPE: DNA
<213> ORGANISM: Homo sapiens
<220> FEATURE:
<221> NAME/KEY: misc_feature
<222> LOCATION: 454, 492, 526
<223> OTHER INFORMATION: n = A,T,C or G

<400> SEQUENCE: 4

```
tcttttctt tcgatttcct tcaatttgtc acgtttgatt ttatgaagtt gttcaagggc      60
taactgctgt gtattatagc tttctctgag ttccttcagc tgattgttaa atgaatccat    120
ttctgagagc ttagatgcag tttcttttc aagagcatct aattgttctt taagtctttg    180
gcataattct tccttttctg atgacttttt atgaagtaaa ctgatccctg aatcaggtgt    240
gttactgagc tgcatgtttt taattctttc gtttaatagc tgcttctcag ggaccagata    300
gataagctta ttttgatatt ccttaagctc ttgttgaagt tgtttgattt ccataatttc    360
caggtcacac tgtttatcca aaacttctag ctcagtcttt tgtgtttgct ttctgatttg    420
gacatcttgt agtctgcctg agatctgctg atgntttcca ttcactgctt ccagttccag    480
gtggagactt tncttctgg agctcagcct gacaatgcct tcttgntccc t              531
```

<210> SEQ ID NO 5
<211> LENGTH: 531
<212> TYPE: DNA
<213> ORGANISM: Homo sapiens

<400> SEQUENCE: 5

```
agccagatgg ctgagagctg caagaagaag tcaggatcat gatggctcag tttcccacag     60
cgatgaatgg agggccaaat atgtgggcta ttacatctga agaacgtact aagcatgata   120
aacagtttga taacctcaaa ccttcaggag gttacataac aggtgatcaa gcccgtactt   180
ttttcctaca gtcaggtctg ccggccccgg ttttagctga aatatgggcc ttatcagatc   240
tgaacaagga tgggaagatg gaccagcaag agttctctat agctatgaaa ctcatcaagt   300
taaagttgca gggccaacag ctgcctgtag tcctccctcc tatcatgaaa caacccccta   360
tgttctctcc actaatctct gctcgttttg ggatgggaag catgcccaat ctgtccattc   420
atcagccatt gcctccagtt gcacctatag caacacccct gtcttctgct acttcaggga   480
```

-continued

```
ccagtattcc tcccctaatg atgcctgctc ccctagtgcc ttctgttagt a         531
```

<210> SEQ ID NO 6
<211> LENGTH: 531
<212> TYPE: DNA
<213> ORGANISM: Homo sapiens

<400> SEQUENCE: 6

```
aatagattta atgcagagtg tcaacttcaa ttgattgata gtggctgcct agagtgctgt   60
gttgagtagg tttctgagga tgcaccctgg cttgaagaga aagactggca ggattaacaa  120
tatctaaaat ctcacttgta ggagaaacca caggcaccag agctgccact ggtgctggca  180
ccagctccac caaggccagc gaagagccca atgtgagag tggcggtcag ctggcacca  240
gcactgaagc caccactggt gctggcactg gcactggcac tgttattggt actggtactg  300
gcaccagtgc tggcactgcc actctcttgg gctttggctt tagcttctgc tcccgcctgg  360
atccgggctt tggcccaggg tccgatatca gcttcgtccc agttgcaggg ccggcagca  420
ttctccgagc cgagcccaat gcccattcga gctctaatct cggccctagc cttggcttca  480
gctgcagcct cagctgcagc cttcaaatcc gcttccatcg cctctcggta c          531
```

<210> SEQ ID NO 7
<211> LENGTH: 531
<212> TYPE: DNA
<213> ORGANISM: Homo sapiens

<400> SEQUENCE: 7

```
gccaagaaag cccgaaaggt gaagcatctg gatggggaag aggatggcag cagtgatcag   60
agtcaggctt ctggaaccac aggtggccga agggtctcaa aggccctaat ggcctcaatg  120
gcccgcaggg cttcaagggg tcccatagcc ttttgggccc gcagggcatc aaggactcgg  180
ttggctgctt gggcccggag agccttgctc tccctgagat cacctaaagc ccgtaggggc  240
aaggctcgcc gtagagctgc caagctccag tcatcccaag agcctgaagc accaccacct  300
cgggatgtgg cccttttgca agggagggca aatgatttgg tgaagtacct tttggctaaa  360
gaccagacga agattcccat caagcgctcg gacatgctga aggacatcat caagaatac  420
actgatgtgt accccgaaat cattgaacga gcaggctatt ccttggagaa ggtatttggg  480
attcaattga aggaaattga taagaatgac cacttgtaca ttcttctcag c          531
```

<210> SEQ ID NO 8
<211> LENGTH: 531
<212> TYPE: DNA
<213> ORGANISM: Homo sapiens
<220> FEATURE:
<221> NAME/KEY: misc_feature
<222> LOCATION: 481
<223> OTHER INFORMATION: n = A,T,C or G

<400> SEQUENCE: 8

```
gaggtctcac tatgttgccc aggctgttct tgaactcctg ggatcaagca atccacccat   60
gttggtctcc aaaagtgctg ggatcatagg cgtgagccac ctcacccagc caccaatttt  120
caatcaggaa gactttttcc ttcttcaaga agtgaagggt ttccagagta tagctacact  180
attgcttgcc tgagggtgac tacaaaattg cttgctaaaa ggttaggatg ggtaaagaat  240
tagattttct gaatgcaaaa ataaaatgtg aactaatgaa ctttaggtaa tacatattca  300
taaaataatt attcacatat ttcctgattt atcacagaaa taatgtatga aatgctttga  360
gtttcttgga gtaaactcca ttactcatcc caagaaacca tattataagt atcactgata  420
```

```
ataagaacaa caggaccttg tcataaattc tggataagag aaatagtctc tgggtgtttg      480
ntcttaattg ataaaattta cttgtccatc ttttagttca gaatcacaaa a              531
```

<210> SEQ ID NO 9
<211> LENGTH: 531
<212> TYPE: DNA
<213> ORGANISM: Homo sapiens
<220> FEATURE:
<221> NAME/KEY: misc_feature
<222> LOCATION: 528
<223> OTHER INFORMATION: n = A,T,C or G

<400> SEQUENCE: 9

```
aagcggaaat gagaaggag ggaaaatcat gtggtattga gcggaaaact gctggatgac       60
agggctcagt cctgttggag aactctgggt ggtgctgtag aacagggcca ctcacagtgg     120
ggtgcacaga ccagcacggc tctgtgacct gtttgttaca ggtccatgat gaggtaaaca     180
atacactgag tataagggtt ggtttagaaa ctcttacagc aatttgacaa agtaatcttc     240
tgtgcagtga atctaagaaa aaaattgggg ctgtatttgt atgttccttt ttttcatttc     300
atgttctgag ttacctattt ttattgcatt ttacaaaagc atccttccat gaaggaccgg     360
aagttaaaaa caaagcaggt cctttatcac agcactgtcg tagaaacagag ttcagagtta     420 tccacccaag gagccaggga gctgggctaa accaaagaat tttgcttttg gttaatcatc     480
aggtacttga gttggaattg ttttaatccc atcattacca ggctggangt g             531
```

<210> SEQ ID NO 10
<211> LENGTH: 861
<212> TYPE: DNA
<213> ORGANISM: Homo sapiens

<400> SEQUENCE: 10

```
ccgcggctcc tgtccagacc ctgaccctcc ctcccaaggc tcaaccgtcc cccaacaacc       60
gccagccttg tactgatgtc ggctgcgaga gcctgtgctt aagtaagaat caggccttat     120
tggagacatt caagcaaagg ttggacaact acttttccag aacagaaagg aaactcatgc     180
atcagaaaag gtgactaata aaggtaccag aagaatatgg ctgcacaaat accagaatct     240
gatcagataa aacagtttaa ggaatttctg gggacctaca ataaacttac agagacctgc     300
tttttggact gtgttagaga cttcacaaca agagaagtaa aacctgaaga gaccacctgt     360
tcagaacatt gcttacagaa atatttaaaa atgcacaaaa gaatatccat gagatttcag     420
gaatatcata ttcagcagaa tgaagccctg gcagccaaag caggactcct tggccaacca     480
cgatagagaa gtcctgatgg atgaactttt gatgaaagat tgccaacagc tgctttattg     540
gaaatgagga ctcatctgat agaatcccct gaaagcagta gccaccatgt tcaaccatct     600
gtcatgactg tttggcaaat ggaaccgct ggagaaacaa aattgctatt taccaggaat       660
aatcacaata gaaggtctta tgttcagtg aaataataag atgcaacatt gttgaggcc       720 ttatgattca gcagcttggt cacttgatta gaaaaataaa ccattgtttc ttcaattgtg     780
actgttaatt ttaaagcaac ttatgtgttc gatcatgtat gagatagaaa aatttttatt     840
actcaaagta aaataaatgg a                                              861
```

<210> SEQ ID NO 11
<211> LENGTH: 541
<212> TYPE: DNA
<213> ORGANISM: Homo sapiens

<400> SEQUENCE: 11

```
gaaaaaaaat ataaaacaca cttttgcgaa acggtggcc ctaaaagagg aaaagaattt      60
caccaatata atccaatttt tatgaaaact gacaatttaa tccaagaatc acttttgtaa    120
atgaagctag caagtgatga tatgataaaa taaacgtgga ggaaataaaa acacaagact    180
tggcataaga tatatccact tttgatatta aacttgtgaa gcatattctt cgacaaattg    240
tgaaagcgtt cctgatcttg cttgttctcc atttcaaata aggaggcata tcacatccca    300
agagtaacag aaaagaaaa aagacatttt tgcattttga gatgaaccaa agacacaaaa    360
caaaacgaac aaagtgtcat gtctaattct agcctctgaa ataaaccttg aacatctcct    420
acaaggcacc gtgattttg taattctaac ctgaagaaat gtgatgactt ttgtggacat    480
gaaaatcaga tgagaaaact gtggtctttc caaagcctga actcccctga aaacctttgc    540
a                                                                    541
```

<210> SEQ ID NO 12
<211> LENGTH: 541
<212> TYPE: DNA
<213> ORGANISM: Homo sapiens

<400> SEQUENCE: 12

```
ctgggatcat ttctcttgat gtcataaaag actcttcttc ttcctcttca tcctcttctt      60
catcctcttc tgtacagtgc tgccgggtac aacggctatc tttgtcttta tcctgagatg    120
aagatgatgc ttctgttct cctaccataa ctgaagaaat ttcgctggaa gtcgtttgac    180
tggctgtttc tctgacttca ccttctttgt caaacctgag tctttttacc tcatgcccct    240
cagcttccac agcatcttca tctggatgtt tattttcaa agggctcact gaggaaactt    300
ctgattcaga ggtcgaagag tcactgtgat ttttctcctc attttgctgc aaatttgcct    360
cttttgctgtc tgtgctctca ggcaacccat tgttgtcat gggggctgac aaagaaacct    420
ttggtcgatt aagtggcctg ggtgtcccag gcccatttat attagacctc tcagtatagc    480
ttggtgaatt tccaggaaac ataacaccat tcattcgatt taaactattg gaattggttt    540
t                                                                    541
```

<210> SEQ ID NO 13
<211> LENGTH: 441
<212> TYPE: DNA
<213> ORGANISM: Homo sapiens

<400> SEQUENCE: 13

```
gagggttggt ggtagcggct tggggaggtg ctcgctctgt cggtcttgct ctctcgcacg      60
cttccccgg ctcccttcgt ttccccccc cggtcgcctg cgtgccggag tgtgtgcgag    120
ggaggggag ggcgtcgggg gggtggggg aggcgttccg gtccccaaga gacccgcgga    180
gggaggcgga ggctgtgagg gactccggga agccatggac gtcgagaggc tccaggaggc    240
gctgaaagat tttgagaaga gggggaaaaa ggaagtttgt cctgtcctgg atcagtttct    300
ttgtcatgta gccaagactg gagaaacaat gattcagtgg tcccaattta aaggctattt    360
tattttcaaa ctggagaaag tgatggatga tttcagaact tcagctcctg agccaagagg    420
tcctcccaac cctaatgtcg a                                              441
```

<210> SEQ ID NO 14
<211> LENGTH: 131
<212> TYPE: DNA
<213> ORGANISM: Homo sapiens

```
<220> FEATURE:
<221> NAME/KEY: misc_feature
<222> LOCATION: 126
<223> OTHER INFORMATION: n = A,T,C or G

<400> SEQUENCE: 14
aagcaggcgg ctcccgcgct cgcagggccg tgccacctgc ccgcccgccc gctcgctcgc      60
tcgcccgccg cgccgcgctg ccgaccgcca gcatgctgcc gagagtgggc tgccccgcgc     120
tgccgntgcc g                                                         131

<210> SEQ ID NO 15
<211> LENGTH: 692
<212> TYPE: DNA
<213> ORGANISM: Homo sapiens

<400> SEQUENCE: 15
atctcttgta tgccaaatat ttaatataaa tctttgaaac aagttcagat gaaataaaaa      60
tcaaagtttg caaaaacgtg aagattaact taattgtcaa atattcctca ttgccccaaa     120
tcagtatttt ttttatttct atgcaaaagt atgccttcaa actgcttaaa tgatatatga     180
tatgatacac aaaccagttt tcaaatagta aagccagtca tcttgcaatt gtaagaaata     240
ggtaaaagat tataagacac cttacacaca cacacacaca cacacacgtg tgcacgccaa     300
tgacaaaaaa caatttggcc tctcctaaaa taagaacatg aagacccta attgctgcca     360 ggagggaaca ctgtgtcacc cctccctaca atccaggtag tttcctttaa tccaatagca     420
aatctgggca tatttgagag gagtgattct gacagccacg ttgaaatcct gtggggaacc     480
attcatgtcc acccactggt gccctgaaaa aatgccaata attttcgct cccacttctg      540 ctgctgtctc ttccacatcc tcacatagac cccagaccg ctggcccctg ctgggcatc      600 gcattgctgg tagagcaagt cataggtctc gtctttgacg tcacagaagc gatacaccaa     660
attgcctggt cggtcattgt cataaccaga ga                                  692

<210> SEQ ID NO 16
<211> LENGTH: 728
<212> TYPE: DNA
<213> ORGANISM: Homo sapiens

<400> SEQUENCE: 16
cagacggggt ttcactatgt tggctaggct ggtcttgaac tcctgacttc aggtgatctg      60
cctgccttgg cctcccaaag tgctgggatt acaggcataa gccactgcgc ccggctgatc     120
tgatggtttc ataaggcttt tcccccttt gctcagcact tctccttcct gccgccatgt      180
gaagaaggac atgtttgctt ccccttccac cacgattgta agttgtttcc tgaggcctcc     240
ccggccatgc tgaactgtga gtcaattaaa cctctttcct ttataaatta ccagttttg     300 ggtatgtctt tattagtaga atgagaacag actaatacaa cccttaaagg agactgacgg     360
agaggattct tcctggatcc cagcacttcc tctgaatgct actgacattc ttcttgagga     420
ctttaaactg ggagatagaa aacagattcc atggctcagc agcctgagag cagggaggga     480
gccaagctat agatgacatg gcagcctcc cctgaggcca ggtgtggccg aacctgggca     540
gtgctgccac ccaccccacc agggccaagt cctgtccttg gagagccaag cctcaatcac     600
tgctagcctc aagtgtcccc aagccacagt ggctagggg actcagggaa cagttcccag     660
tctgccctac ttctcttacc tttaccctc atacctccaa agtagaccat gttcatgagg      720
tccaaagg                                                             728
```

<210> SEQ ID NO 17
<211> LENGTH: 531
<212> TYPE: DNA
<213> ORGANISM: Homo sapiens
<220> FEATURE:
<221> NAME/KEY: misc_feature
<222> LOCATION: 518, 528
<223> OTHER INFORMATION: n = A,T,C or G

<400> SEQUENCE: 17

```
aagcgaggaa gccactgcgg ctcctggctg aaaagcggcg ccaggctcgg gaacagaggg      60
aacgcgaaga acaggagcgg aagctgcagg ctgaaaggga caagcgaatg cgagaggagc     120
agctggcccg ggaggctgaa gcccgggctg aacgtgaggc cgaggcgcgg agacgggagg     180
agcaggaggc tcgagagaag gcgcaggctg agcaggagga gcaggagcga ctgcagaagc     240
agaaagagga agccgaagcc cggtcccggg aagaagctga gcgccagcgc caggagcggg     300
aaaagcactt tcagaaggag gaacaggaga gacaagagcg aagaaagcgg ctggaggaga     360
taatgaagag gactcggaaa tcagaagccg ccgaaaccaa gaagcaggat gcaaaggaga     420
ccgcagctaa caattccggc ccagacccct gtgaaagctg tagagactcg gccctctggg     480
cttccagaaa ggattctatt gcagaaagga aggagctngg cccccangg a               531
```

<210> SEQ ID NO 18
<211> LENGTH: 1041
<212> TYPE: DNA
<213> ORGANISM: Homo sapiens
<220> FEATURE:
<221> NAME/KEY: misc_feature
<222> LOCATION: 544
<223> OTHER INFORMATION: n = A,T,C or G

<400> SEQUENCE: 18

```
ctctgtggaa aactgatgag gaatgaattt accattaccc atgttctcat ccccaagcaa      60
agtgctgggt ctgattactg caacacagag aacgaagaag aacttttcct catacaggat     120
cagcagggcc tcatcacact gggctggatt catactcacc ccacacagac cgcgtttctc     180
tccagtgtcg acctacacac tcactgctct taccagatga tgttgccaga gtcagtagcc     240
attgtttgct cccccaagtt ccaggaaact ggattcttta aactaactga ccatggacta     300
gaggagattt cttcctgtcg ccagaaagga tttcatccac acagcaagga tccacctctg     360
ttctgtagct gcagccacgt gactgttgtg gacagagcag tgaccatcac agaccttcga     420
tgagcgtttg agtccaacac cttccaagaa caacaaaacc atatcagtgt actgtagccc     480
cttaatttaa gctttctaga aagctttgga agttttgta gatagtagaa aggggggcat     540
cacntgaaaa agagctgatt ttgtatttca ggtttgaaaa gaaataactg aacatatttt     600
ttaggcaagt cagaaagaga acatggtcac ccaaaagcaa ctgtaactca gaaattaagt     660
tactcagaaa ttaagtagct cagaaattaa gaaagaatgg tataatgaac ccccatatac     720
ccttccttct ggattcacca attgttaaca ttttttttcct ctcagctatc cttctaattt     780
ctctctaatt tcaatttgtt tatatttacc tctgggctca ataagggcat ctgtgcagaa     840
atttggaagc catttagaaa atctttttgga ttttcctgtg gtttatggca atatgaatgg     900
agcttattac tggggtgagg gacagcttac tccatttgac cagattgttt ggctaacaca     960
tcccgaagaa tgattttgtc aggaattatt gttatttaat aaatatttca ggatattttt    1020
cctctacaat aaagtaacaa t                                               1041
```

<210> SEQ ID NO 19
<211> LENGTH: 1043
<212> TYPE: DNA
<213> ORGANISM: Homo sapiens

<400> SEQUENCE: 19

| | | |
|---|---|---|
| ctctgtggaa aactgatgag gaatgaattt accattaccc atgttctcat ccccaagcaa | 60 |
| agtgctgggt ctgattactg caacacagag aacgaagaag aacttttcct catacaggat | 120 |
| cagcagggcc tcatcacact gggctggatt catactcacc ccacacagac cgcgtttctc | 180 |
| tccagtgtcg acctacacac tcactgctct taccagatga tgttgccaga gtcagtagcc | 240 |
| attgtttgct cccccaagtt ccaggaaact ggattcttta aactaactga ccatggacta | 300 |
| gaggagattt cttcctgtcg ccagaaagga tttcatccac acagcaagga tccacctctg | 360 |
| ttctgtagct gcagccacgt gactgttgtg gacagagcag tgaccatcac agaccttcga | 420 |
| tgagcgtttg agtccaacac cttccaagaa caacaaaacc atatcagtgt actgtagccc | 480 |
| cttaattta gctttctaga aagctttgga agttttgta gatagtagaa aggggggcat | 540 |
| cacctgagaa agagctgatt tgtatttca ggtttgaaaa gaataactg aacatatttt | 600 |
| ttaggcaagt cagaaagaga acatggtcac ccaaaagcaa ctgtaactca gaaattaagt | 660 |
| tactcagaaa ttaagtagct cagaaattaa gaaagaatgg tataatgaac ccccatatac | 720 |
| ccttccttct ggattcacca attgttaaca ttttttttcct ctcagctatc cttctaattt | 780 |
| ctctctaatt tcaatttgtt tatatttacc tctgggctca ataagggcat ctgtgcagaa | 840 |
| atttggaagc catttagaaa atcttttgga ttttcctgtg gttatgca atatgaatgg | 900 |
| agcttattac tggggtgagg acagcttac tccatttgac cagattgttt ggctaacaca | 960 |
| tcccgaagaa tgattttgtc aggaattatt gttatttaat aaatatttca ggatattttt | 1020 |
| cctctacaat aaagtaacaa tta | 1043 |

<210> SEQ ID NO 20
<211> LENGTH: 448
<212> TYPE: DNA
<213> ORGANISM: Homo sapiens

<400> SEQUENCE: 20

| | | |
|---|---|---|
| ggacgacaag gccatggcga tatcggatcc gaattcaagc ctttggaatt aaataaacct | 60 |
| ggaacaggga aggtgaaagt tggagtgaga tgtcttccat atctatacct ttgtgcacag | 120 |
| ttgaatggga actgtttggg tttagggcat cttagagttg attgatggaa aaagcagaca | 180 |
| ggaactggtg ggaggtcaag tggggaagtt ggtgaatgtg gaataactta cctttgtgct | 240 |
| ccacttaaac cagatgtgtt gcagctttcc tgacatgcaa ggatctactt taattccaca | 300 |
| ctctcattaa taaattgaat aaaagggaat gttttggcac ctgatataat ctgccaggct | 360 |
| atgtgacagt aggaaggaat ggtttcccct aacaagccca atgcactggt ctgactttat | 420 |
| aaattatta ataaaatgaa ctattatc | 448 |

<210> SEQ ID NO 21
<211> LENGTH: 411
<212> TYPE: DNA
<213> ORGANISM: Homo sapiens

<400> SEQUENCE: 21

| | | |
|---|---|---|
| ggcagtgaca ttcaccatca tgggaaccac cttcccttt cttcaggatt ctctgtagtg | 60 |
| gaagagagca cccagtgttg ggctgaaaac atctgaaagt agggagaaga acctaaaata | 120 |

-continued

| | |
|---|---|
| atcagtatct cagagggctc taaggtgcca agaagtctca ctggacattt aagtgccaac | 180 |
| aaaggcatac tttcggaatc gccaagtcaa aactttctaa cttctgtctc tctcagagac | 240 |
| aagtgagact caagagtcta ctgctttagt ggcaactaca gaaaactggt gttacccaga | 300 |
| aaaacaggag caattagaaa tggttccaat atttcaaagc tccgcaaaca ggatgtgctt | 360 |
| tcctttgccc atttagggtt tcttctcttt cctttctctt tattaaccac t | 411 |

<210> SEQ ID NO 22
<211> LENGTH: 896
<212> TYPE: DNA
<213> ORGANISM: Homo sapiens
<220> FEATURE:
<221> NAME/KEY: misc_feature
<222> LOCATION: 230, 320
<223> OTHER INFORMATION: n = A,T,C or G

<400> SEQUENCE: 22

| | |
|---|---|
| tgcgctgaaa acaacggcct cctttactgt taaaatgcag ccacaggtgc ttagccgtgg | 60 |
| gcatctcaac caccagcctc tgtgggggc aggtgggcgt ccctgtgggc ctctgggccc | 120 |
| acgtccagcc tctgtcctct gccttccgtt cttcgacagt gttcccggca tcctggtca | 180 |
| cttggtactt ggcgtgggcc tcctgtgctg ctccagcagc tcctccaggn ggtcggcccg | 240 |
| cttcaccgca gcctcatgtt gtgtccgag gctgctcacg gcctcctcct tcctcgcgag | 300 |
| ggctgtcttc accctccggn gcacctcctc cagctccagc tgctggcggg cctgcagcgt | 360 |
| ggccagctcg gccttggcct gccgcgtctc tcctcarag gctgccagcc ggtcctcgaa | 420 |
| ctcctggcgg atcacctggg ccaggttgct gcgctcgcta gaaagctgct cgttcaccgc | 480 |
| ctgcgcatcc tccagcgccc gctccttctg ccgcacaagg ccctgcagac gcagattctc | 540 |
| gccctcggcc tccccaagct ggcccttcag ctccgagcac cgctcctgaa gcttccgctc | 600 |
| cgactgctcc agctcggaga gctcggcctc gtacttgtcc cgtaagcgct tgatgcggct | 660 |
| ctcggcagcc ttctcactct cctccttggc cagcgccatg tcggcctcca gccggtgaat | 720 |
| gaccagctca atctccttgt cccggccttt ccggatttct tccctcagct cctgttcccg | 780 |
| gttcagcagc cacgcctcct ccttcctggt gcggccggcc tccacgcct gcctctccag | 840 |
| ctccagctgc tgcttcaggg tattcagctc catctggcgg gcctgcagcg tggcca | 896 |

<210> SEQ ID NO 23
<211> LENGTH: 111
<212> TYPE: DNA
<213> ORGANISM: Homo sapiens

<400> SEQUENCE: 23

| | |
|---|---|
| caacttatta cttgaaatta taatatagcc tgtccgtttg ctgtttccag gctgtgatat | 60 |
| atttttcctag tggtttgact ttaaaaataa ataaggttta attttctccc c | 111 |

<210> SEQ ID NO 24
<211> LENGTH: 531
<212> TYPE: DNA
<213> ORGANISM: Homo sapiens
<220> FEATURE:
<221> NAME/KEY: misc_feature
<222> LOCATION: 472, 494
<223> OTHER INFORMATION: n = A,T,C or G

<400> SEQUENCE: 24

| | |
|---|---|
| tgcaagtcac gggagtttat ttatttaatt ttttccca gatggagact ctgtcgccca | 60 |
| ggctggagtg caatggtgtg atcttggctc actgcaacct ccacctcctg ggttcaagcg | 120 |

```
attctcctgc cacagcctcc cgagtagctg ggattacagg tgcccgccac cacacccagc      180
taatttttat attttagta aagacagggt ttccccatgt tggccaggct ggtcttgaac       240
ttctgacctc aggtgatcca cctgcctcgg cctcccaaag tgttgggatt acaggcgtga      300 gctaccgtg cctggccagc cactggagtt taaaggacag tcatgttggc tccagcctaa       360
ggcggcattt tccccatca gaaagcccgc ggctcctgta cctcaaaata gggcacctgt       420
aaagtcagtc agtgaagtct ctgctctaac tggccacccg gggccattgg cntctgacac      480
agccttgcca ggangcctgc atctgcaaaa gaaaagttca cttcctttcc g               531
```

```
<210> SEQ ID NO 25
<211> LENGTH: 471
<212> TYPE: DNA
<213> ORGANISM: Homo sapiens
<220> FEATURE:
<221> NAME/KEY: misc_feature
<222> LOCATION: 377
<223> OTHER INFORMATION: n = A,T,C or G

<400> SEQUENCE: 25
cagagaatct kagaaagatg tcgcgttttc ttttaatgaa tgagagaagc ccatttgtat       60
ccctgaatca ttgagaaaag gcggcggtgg cgacagcggc gacctaggga tcgatctgga      120
gggacttggg gagcgtgcag agacctctag ctcgagcgcg agggacctcc cgccgggatg      180
cctggggagc agatggaccc tactggaagt cagttggatt cagatttctc tcagcaagat      240
actccttgcc tgataattga agattctcag cctgaaagcc aggttctaga ggatgattct      300
ggttctcact tcagtatgct atctcgacac cttcctaatc tccagacgca caagaaaat      360 cctgtgttgg atgttgngtc caatccttga acaaacagct ggagaagaac gaggagaccg      420
gtaatagtgg gttcaatgaa catttgaaag aaaaccaggt tgcagaccct g               471
```

```
<210> SEQ ID NO 26
<211> LENGTH: 541
<212> TYPE: DNA
<213> ORGANISM: Homo sapiens

<400> SEQUENCE: 26
gactgtcctg aacaagggac ctctgaccag agagctgcag gagatgcaga gtggtggcag       60
gagtggaagc caaagaacac ccaccttcct cccttgaagg agtagagcaa ccatcagaag      120
atactgtttt attgctctgg tcaaacaagt cttcctgagt tgacaaaacc tcaggctctg      180
gtgacttctg aatctgcagt ccactttcca taagttcttg tgcagacaac tgttcttttg      240
cttccatagc agcaacagat gctttggggc taaaaggcat gtcctctgac cttgcaggtg      300
gtggattttg ctcttttaca acatgtacat ccttactggg ctgtgctgtc acagggatgt      360
ccttgctgga ctgttctgct atggggatat cttcgttgga ctgttcttca tgcttaattg      420
cagtattagc atccacatca gacagcctgg tataaccaga gttggtggtt actgattgta      480
gctgctcttt gtccacttca tatggcacaa gtatttcct caacatcctg gctctgggaa      540
g                                                                      541
```

```
<210> SEQ ID NO 27
<211> LENGTH: 461
<212> TYPE: DNA
<213> ORGANISM: Homo sapiens
<220> FEATURE:
<221> NAME/KEY: misc_feature
<222> LOCATION: 367
```

<223> OTHER INFORMATION: n = A,T,C or G

<400> SEQUENCE: 27

```
gaaatgtata tttaatcatt ctcttgaacg atcagaactc traaatcagt tttctataac      60
arcatgtaat acagtcaccg tggctccaag gtccaggaag gcagtggtta acacatgaag     120
agtgtgggaa gggggctgga aacaaagtat tcttttcctt caaagcttca ttcctcaagg     180
cctcaattca agcagtcatt gtccttgctt tcaaaagtct gtgtgtgctt catggaaggt     240
atatgtttgt tgccttaatt tgaattgtgg ccaggaaggg tctggagatc taaattcaga     300
gtaagaaaac ctgagctaga actcaggcat ttctcttaca gaacttggct tgcagggtag     360
aatgaaggga agaaactta gaagctcaac aagctgaaga taatcccatc aggcatttcc      420
cataggcctt gcaactctgt tcactgagag atgttatcct g                        461
```

<210> SEQ ID NO 28
<211> LENGTH: 541
<212> TYPE: DNA
<213> ORGANISM: Homo sapiens

<400> SEQUENCE: 28

```
agtctggagt gagcaaacaa gagcaagaaa caarragaaag ccaaaagcag aaggctccaa     60
tatgaacaag ataaatctat cttcaaagac atattagaag ttgggaaaat aattcatgtg    120
aactagacaa gtgtgttaag agtgataagt aaaatgcacg tggagacaag tgcatcccca    180
gatctcaggg acctcccccct gcctgtcacc tggggagtga gaggacagga tagtgcatgt    240
tctttgtctc tgaatttta gttatatgtg ctgtaatgtt gctctgagga agccccctgga    300
aagtctatcc caacatatcc acatcttata ttccacaaat taagctgtag tatgtaccct    360
aagacgctgc taattgactg ccacttcgca actcaggggc ggctgcattt tagtaatggg    420
tcaaatgatt cacttttat gatgcttccc aaggtgcctt ggcttctctt cccaactgac    480
aaatgcccaa gttgagaaaa atgatcataa ttttagcata aaccgagcaa tcggcgaccc    540
c                                                                    541
```

<210> SEQ ID NO 29
<211> LENGTH: 411
<212> TYPE: DNA
<213> ORGANISM: Homo sapiens

<400> SEQUENCE: 29

```
tagctgtctt cctcactctt atggcaatga ccccatatct taatggatta agataatgaa      60
agtgtatttc ttacactctg tatctatcac cagaagctga ggtgatagcc cgcttgtcat    120
tgtcatccat attctgggac tcaggcggga actttctgga atattgccag ggagcatggc    180
agaggggcac agtgcattct gggggaatgc acattggctc agcctgggta atgagtgata    240
tacattacct ctgttcacaa ctcattgccc agcaccagtc acaaggcccc accaaatacc    300
agagcccaag aaatgtagtc ctgttgatat ggttttgctg tgtcccaacc caaatctcat    360
cttgaattgt aagctcccat aattcccatg tgttgtggga gggacctggt g             411
```

<210> SEQ ID NO 30
<211> LENGTH: 511
<212> TYPE: DNA
<213> ORGANISM: Homo sapiens

<400> SEQUENCE: 30

```
atcatgagga tgttaccaaa gggatggtac taaaccattt gtattcgtct gttttcacac      60
```

```
tgctttgaag atactacctg agactgggta atttataaac aaaagagatt taattgactc      120
acagttctgc atggctgaag aggcctcagg aaacttacag tcatggtgga aggcaaagga      180
ggagcaaggc atgtcttaca tgtcagtagg agagagagcg agagcaggag aacctgccac      240
ttataaacca ttcagatctc ataactccct atcatgagaa aaacatggag gaaaccaccc      300
tcatgatcca atcacctccc gccaggtccc tccctcgaca cgtggggatt ataattcagg      360
attagaggga cacagagaca aaccatatca tcattcatga gaaatccacc ctcatagtcc      420
aatcagctcc taccaggccc cacctccaac actggggatt gcaattcaac atgagatttg      480
gatggggaca cagattcaaa ccatatcata c                                    511
```

<210> SEQ ID NO 31
<211> LENGTH: 827
<212> TYPE: DNA
<213> ORGANISM: Homo sapiens

<400> SEQUENCE: 31

```
catggccttt ctccttagag gccagaggtg ctgccctggc tgggagtgaa gctccaggca       60
ctaccagctt tcctgatttt cccgtttggt ccatgtgaag agctaccacg agccccagcc      120
tcacagtgtc cactcaaggg cagcttggtc ctcttgtcct gcagaggcag gctggtgtga      180
ccctgggaac ttgacccggg aacaacaggt ggcccagagt gagtgtggcc tggcccctca      240
acctagtgtc cgtcctcctc tctcctggag ccagtcttga gtttaaaggc attaagtgtt      300
agatacaagc tccttgtggc tggaaaaaca ccccctctgct gataaagctc aggggggcact      360 gaggaagcag aggcccccttg ggggtgccct cctgaagaga gcgtcaggcc atcagctctg      420
tccctctggt gctcccacgt ctgttcctca ccctccatct ctgggagcag ctgcacctga      480
ctggccacgc gggggcagtg gaggcacagg ctcagggtgg ccgggctacc tggcaccta       540 tggcttacaa agtagagttg gcccagtttc cttccacctg aggggagcac tctgactcct      600
aacagtcttc cttgccctgc catcatctgg ggtggctggc tgtcaagaaa ggccgggcat      660
gctttctaaa cacagccaca ggaggcttgt agggcatctt ccaggtgggg aaacagtctt      720
agataagtaa ggtgacttgc ctaaggcctc ccagcaccct tgatcttgga gtctcacagc      780
agactgcatg tsaacaactg gaaccgaaaa catgcctcag tataaaa                   827
```

<210> SEQ ID NO 32
<211> LENGTH: 291
<212> TYPE: DNA
<213> ORGANISM: Homo sapiens

<400> SEQUENCE: 32

```
ccagaacctc cttctctttg gagaatgggg aggcctcttg gagacacaga gggtttcacc       60
ttggatgacc tctagagaaa ttgcccaaga agcccacctt ctggtcccaa cctgcagacc      120
ccacagcagt cagttggtca ggccctgctg tagaaggtca cttggctcca ttgcctgctt      180
ccaaccaatg ggcaggagag aaggccttta tttctcgccc accattctc ctgtaccagc       240 acctccgttt tcagtcagyg ttgtccagca acggtaccgt ttacacagtc a              291
```

<210> SEQ ID NO 33
<211> LENGTH: 491
<212> TYPE: DNA
<213> ORGANISM: Homo sapiens

<400> SEQUENCE: 33

```
tgcatgtagt tttatttatg tgttttsgtc tggaaaacca agtgtcccag cagcatgact    60
gaacatcact cacttcccct acttgatcta caaggccaac gccgagagcc cagaccagga   120
ttccaaacac actgcacgag aatattgtgg atccgctgtc aggtaagtgt ccgtcactga   180
cccaracgct gttacgtggc acatgactgt acagtgccac gtaacagcac tgtactttc   240 tcccatgaac agttacctgc catgtatcta catgattcag aacattttga acagttaatt   300
ctgacacttg aataatccca tcaaaaaccg taaaatcact ttgatgtttg taacgacaac   360
atagcatcac tttacgacag aatcatctgg aaaaacagaa caacgaatac atacatctta   420
aaaaatgctg gggtgggcca ggcacagctt cacgcctgta atcccagcac tttgggaggc   480
ttaagcgggt g                                                        491
```

<210> SEQ ID NO 34
<211> LENGTH: 521
<212> TYPE: DNA
<213> ORGANISM: Homo sapiens
<220> FEATURE:
<221> NAME/KEY: misc_feature
<222> LOCATION: 453, 476, 487
<223> OTHER INFORMATION: n = A,T,C or G

<400> SEQUENCE: 34

```
tggggcggaa agaagccaag gccaaggagc tggtgcggca gctgcagctg gaggccgagg    60
agcagaggaa gcagaagaag cggcagagtg tgtcgggcct gcacagatac cttcacttgc   120
tggatggaaa tgaaaattac ccgtgtcttg tggatgcaga cggtgatgtg atttccttcc   180
caccaataac caacagtgag aagacaaagg ttaagaaaac gacttctgat ttgttttgg    240 aagtaacaag tgccaccagt ctgcagattt gcaaggatgt catggatgcc ctcattctga   300
aaatggcaag aaatgaaaaa gtacactta gaaaataaag aggaaggatc actctcagat   360
actgaagccg atgcagtctc tggacaactt ccagatccca caacgaatcc cagtgctgga   420
aaggacgggc ccttccttct ggtggtggaa cangtcccgg tggtggatct tggaanggaa   480
cctgaangtg gtgtaccccg tccaaggccg accttggcca c                       521
```

<210> SEQ ID NO 35
<211> LENGTH: 161
<212> TYPE: DNA
<213> ORGANISM: Homo sapiens
<220> FEATURE:
<221> NAME/KEY: misc_feature
<222> LOCATION: 18
<223> OTHER INFORMATION: n = A,T,C or G

<400> SEQUENCE: 35

```
tcccgcgctc gcagggcncg tgccacctgc cygtccgccc gctcgctcgc tcgcccgccg    60
cgccgcgctg ccgaccgyca gcatgctgcc gagagtgggc tgccccgcgc tgccgctgcc   120
gccgccgccg ctgctgccgc tgctgccgct gctgctgctg c                       161
```

<210> SEQ ID NO 36
<211> LENGTH: 341
<212> TYPE: DNA
<213> ORGANISM: Homo sapiens

<400> SEQUENCE: 36

```
ggcgggtagg catggaactg agaagaacga agaagctttc agactacgtg gggaagaatg    60
aaaaaaccaa aattatcgcc aagattcagc aaagggaca gggagctcca gcccgagagc   120
ctattattag cagtgaggag cagaagcagc tgatgctgta ctatcacaga agacaagagg   180
```

```
agctcaagag attggaagaa aatgatgatg atgcctattt aaactcacca tgggcggata    240
acactgcttt gaaaagacat tttcatggag tgaaagacat aaagtggaga ccaagatgaa    300
gttcaccagc tgatgacact tccaaagaga ttagctcacc t                        341
```

<210> SEQ ID NO 37
<211> LENGTH: 521
<212> TYPE: DNA
<213> ORGANISM: Homo sapiens
<220> FEATURE:
<221> NAME/KEY: misc_feature
<222> LOCATION: 516
<223> OTHER INFORMATION: n = A,T,C or G

<400> SEQUENCE: 37

```
tctgaaggtt aaatgtttca tctaaatagg gataatgrta acacctata gcatagagtt     60 gtttgagatt aaatgagata atacatgtaa aattatgtgc ctggcataca gcaagattgt   120
tgttgttgtt gatgatgatg atgatgatga taatatttt ctatcccag tgcacaactg    180 cttgaaccta ttagataatc aatacatgtt tcttgaactg agatcaattt ccccatgttg   240
tctgactgat gaagccctac attttcttct agaggagatg acatttgagc aagatcttaa   300
agaaaatcag atgccttcac ctgaccactg cttggtgatc ccatggcact ttgtacatct   360
ctccattagc tctcatctca ccagcccatc attattgtat gtgctgcctt ctgaagcttg   420
cagctggcta ccatcmggta gaataaaaat catcctttca taaaatagtg accctccttt   480
tttatttgca tttcccaaag ccaagcaccg tgggangggta g                      521
```

<210> SEQ ID NO 38
<211> LENGTH: 461
<212> TYPE: DNA
<213> ORGANISM: Homo sapiens

<400> SEQUENCE: 38

```
tatgaagaag ggaaaagaag ataatttgtg aaagaaatgg gtccagttac tagtctttga    60
aaagggtcag tctgtagctc ttcttaatga gaataggcag ctttcagttg ctcagggtca   120
gatttcctta gtggtgtatc taatcacagg aaacatctgt ggttccctcc agtctctttc   180
tgggggactt gggcccactt tcatttcat ttaattagag gaaatagaac tcaaagtaca    240
atttactgtt gtttaacaat gccacaaaga catggttggg agctatttct tgatttgtgt   300
aaaatgctgt ttttgtgtgc tcataatggt tccaaaaatt gggtgctggc caaagagaga   360
tactgttaca gaagccagca agaagacctc tgttcattca ccccccggg gatatcagga   420 attgactcca gtgtgtgcaa atccagtttg gcctatcttc t                       461
```

<210> SEQ ID NO 39
<211> LENGTH: 769
<212> TYPE: DNA
<213> ORGANISM: Homo sapiens

<400> SEQUENCE: 39

```
tgagggactg attggtttgc tctctgctat tcaattcccc aagcccactt gttcctgcag    60
cgtcctcctt tcattccct ttagttgtac cctctcttc atctgagacc tttccttctt   120
gatgtcgcct tttcttcttc ttgctttttc tgatgttctg ctcagcatgt tctgggtgct   180
tctcatctgc atcattcctt tcagatgctg tagcttcttc ctcctcttc tgcctccttt   240 tctttttctt ttttttgggg ggcttgctct ctgactgcag ttgagggcc ccagggtcct    300
```

```
ggcctttgag acgagccagg aaggcctgct cctgggcctc taggcgagca agcttggcct    360
tcattgtgat cccaagacgg gcagccttgt gtgctgttcg cccctcacag gcttggagca    420
gcatctcatc agtcagaatc tttggggact tggacccctg gttgtcgtca tcactgcagc    480
tctccaagtc tttgtttggc ttctctccac ctgaagtcaa tgtagccatc ttcacaaact    540
tctgatacag caagttgggc ttgggatgat tataacgggt ggtctcctta gaaaggctcc    600
ttatctgtac tccatcctgc ccagtttcca ctaccaagtt ggccgcagtc ttgttgaaga    660
gctcattcca ccagtggttt gtgaactcct tggcagggtc atgtcctacc ccatgagtgt    720
cttgcttcag ygtcaccctg agagcctgag tgataccatt ctccttccg               769

<210> SEQ ID NO 40
<211> LENGTH: 292
<212> TYPE: DNA
<213> ORGANISM: Homo sapiens

<400> SEQUENCE: 40
gacaacatga ataaatcct agaggacaaa attaaactca atagagtgta gtctagttaa     60
aaactcgaaa aatgagcaag tctggtggga gtggaggaag ggctatacta taaatccaag    120
tgggcctcct gatcttaaca agccatgctc attatacaca tctctgaact ggacatacca    180
cctttacgca ggaaacaggg cttggaactt ctaaggaaa ttaacatgca ccacccacat     240
ctaacctacc tgccgggtag gtaccatccc tgcttcgctg aaatcagtgc tc            292

<210> SEQ ID NO 41
<211> LENGTH: 406
<212> TYPE: DNA
<213> ORGANISM: Homo sapiens

<400> SEQUENCE: 41
ttggaattaa ataaacctgg aacagggaag gtgaaagttg gagtgagatg tcttccatat    60
ctataccttt gtgcacagtt gaatgggaac tgtttgggtt tagggcatct tagagttgat   120
tgatggaaaa agcagacagg aactggtggg aggtcaagtg gggaagttgg tgaatgtgga   180
ataacttacc tttgtgctcc acttaaacca gatgtgttgc agctttcctg acatgcaagg   240
atctacttta attccacact ctcattaata aattgaataa aagggaatgt tttggcacct   300
gatataatct gccaggctat gtgacagtag gaaggaatgg tttcccctaa caagcccaat   360
gcactggtct gactttataa attatttaat aaaatgaact attatc                  406

<210> SEQ ID NO 42
<211> LENGTH: 381
<212> TYPE: DNA
<213> ORGANISM: Homo sapiens

<400> SEQUENCE: 42
aaactggacc tgcaacaggg acatgaattt actgcarggt ctgagcaagc tcagcccctc    60
tacctcaggg ccccacagcc atgactacct cccccaggag cgggagggtg aaggggcct    120 gtctctgcaa gtggagccag agtggaggaa tgagctctga agacacagca cccagccttc   180
tcgcaccagc caagccttaa ctgcctgcct gaccctgaac cagaacccag ctgaactgcc   240
cctccaaggg acaggaaggc tggggagggg agtttacaac ccaagccatt ccaccccctc   300
ccctgctggg gagaatgaca catcaagctg ctaacaattg ggggaagggg aaggaagaaa   360
actctgaaaa caaaatcttg t                                             381
```

<210> SEQ ID NO 43
<211> LENGTH: 451
<212> TYPE: DNA
<213> ORGANISM: Homo sapiens

<400> SEQUENCE: 43

```
catgcgtttc accactgttg gccaggctgg tctcgaactc ctggcctcaa gcaatccacc      60
cgcctcagcc tccaaaagtg ctgggattac agatgtgagc catggcacca tgccaaaagg     120
ctatattcct ggctctgtgt ttccgagact gctttaatc ccaacttctc tacatttaga      180
ttaaaaaata ttttattcat ggtcaatctg aacataatt actgcatctt aagtttccac      240
tgatgtatat agaaggctaa aggcacaatt tttatcaaat ctagtagagt aaccaaacat     300
aaaatcatta attactttca acttaataac taattgacat tcctcaaaag agctgttttc     360
aatcctgata ggttctttat tttttcaaaa tatatttgcc atgggatgct aatttgcaat     420
aaggcgcata atgagaatac cccaaactgg a                                    451
```

<210> SEQ ID NO 44
<211> LENGTH: 521
<212> TYPE: DNA
<213> ORGANISM: Homo sapiens

<400> SEQUENCE: 44

```
gttggacccc cagggactgg aaagacactt cttgcccgag ctgtggcggg agaagctgat      60
gttccttttt attatgcttc tggatccgaa tttgatgaga tgtttgtggg tgtgggagcc     120
agccgtatca gaaatctttt tagggaagca aaggcgaatg ctccttgtgt tatatttatt     180
gatgaattag attctgttgg tgggaagaga attgaatctc caatgcatcc atattcaagg     240
cagaccataa atcaacttct tgctgaaatg gatggtttta aacccaatga aggagttatc     300
ataataggag ccacaaactt cccagaggca ttagataatg ccttaatacc gtcctggtcg     360
ttttgacatg caagttacag ttccaaggcc agatgtaaaa ggtcgaacag aaattttgaa     420
atggtatctc aataaaataa agtttgatca atcccgttga tccagaaatt atagcctcga     480
ggtactggtg gcttttccgg aagcagagtt gggagaatct t                         521
```

<210> SEQ ID NO 45
<211> LENGTH: 585
<212> TYPE: DNA
<213> ORGANISM: Homo sapiens

<400> SEQUENCE: 45

```
gcctacaaca tccagaaaga gtctaccctg cacctggtgc tscgtctcag aggtgggatg      60
cagatcttcg tgaagaccct gactggtaag accatcactc tcgaagtgga gccgagtgac     120
accatygaga acgtcaaagc aaagatccar gacaaggaag gcrtycctcc tgaccagcag     180
aggttgatct tgccggaaa gcagctggaa gatggdcgca ccctgtctga ctacaacatc     240
cagaaagagt cyaccctgca cctggtgctc cgtctcagag gtgggatgca ratcttcgtg     300
aagaccctga ctggtaagac catcaccctc gaggtggagc ccagtgacac catcgagaat     360
gtcaaggcaa agatccaaga taaggaaggc atccctcctg atcagcagag gttgatcttt     420
gctgggaaac agctggaaga tggacgcacc ctgtctgact acaacatcca gaaagagtcc     480
actctgcact tggtcctgcg cttgagggg ggtgtctaag tttccccttt taaggtttcm     540
acaaatttca ttgcactttc ctttcaataa agttgttgca ttccc                     585
```

<210> SEQ ID NO 46

<211> LENGTH: 481
<212> TYPE: DNA
<213> ORGANISM: Homo sapiens

<400> SEQUENCE: 46

```
gaactgggcc ctgagcccaa gtcatgcctt gtgtccgcat ctgccgtgtc acctctgtkc      60
ctgcccctca ccctcccctc ctggtcttct gagccagcac catctccaaa tagcctattc     120
cttcctgcaa atcacacaca catgcgggcc acacatacct gctgccctgg agatggggaa     180
gtaggagaga tgaatagagg cccatacatt gtacagaagg aggggcaggt gcagataaaa     240
gcagcagacc cagcggcagc tgaggtgcat ggagcacggt tggggccggc attgggctga     300
gcacctgatg ggcctcatct cgtgaatcct cgaggcagcg ccacagcaga ggagttaagt     360
ggcacctggg ccgagcagag caggagactg agggtcagag tggaggctaa gctgccctgg     420
aactcctcaa tcttgcctgc ccctagtat gaagccccct tcctgcccct acaattcctg      480
a                                                                    481
```

<210> SEQ ID NO 47
<211> LENGTH: 461
<212> TYPE: DNA
<213> ORGANISM: Homo sapiens
<220> FEATURE:
<221> NAME/KEY: misc_feature
<222> LOCATION: 128
<223> OTHER INFORMATION: n = A,T,C or G

<400> SEQUENCE: 47

```
atggatctta ctttgccacc caggttggag tgcagtgctg caatcttggc tcactgcagc      60
cttaacctcc caggctcaag ctatcctcct gccaaagcct tccacatagc tgggactaca     120
ggtacacngc caccacaccc agctaaaatt tttgtatttt ttgtagagac gggatctcgc     180
cacgttgccc aggctggtcc atcctgacc tcaagcagat ctgccacct cagcccccca      240
acgtgctagg attacaggcg tgagccaccg cacccagcct ttgttttgct tttaatggaa     300
tcaccagttc ccctccgtgt ctcagcagca gctgtgagaa atgctttgca tctgtgacct     360
ttatgaaggg gaacttccat gctgaatgag ggtaggatta catgctcctg tttcccgggg     420
gtcaagaaag cctcagactc cagcatgata agcagggtga g                        461
```

<210> SEQ ID NO 48
<211> LENGTH: 571
<212> TYPE: DNA
<213> ORGANISM: Homo sapiens

<400> SEQUENCE: 48

```
atagggcctt taaggaggga attcaggttc aatgaggtcg taaggccagg gctcttatcc      60
agtaagactg gggtccttag atgagaaaga cacccgag gtccttctct ctgccgtgtg       120
aggatgcatc aagaaggcgg ccgtctgcaa gcgaaggaga ggccgcacca gaaaccgaca     180
ccttcatctt ggacttgcag cctctagaac tgagaaaata actgtctgtt ggttaagcca     240
cccagtttgt agtattctct tatggcttcc taagcagact aacaaacaaa cacccaaaat     300
taactgatgg cttcgctgtc ttctgtaaaa attgctatga gagaactttt cactcactgt     360
tttgcagttt ctccctcagt ccctggttct ttcttctcac ataatcccaa tttcaattta     420
tagttcatgg cccaggcaga gtcattcatc acggcatctc ctgagctaaa ccagcacctg     480
ctctgctcac ttcttgactg gctgctcatc atcagccctc ttgcagagat ttcatttcct     540
cccgtgccag gtacttcacg caccaagctc a                                    571
```

<210> SEQ ID NO 49
<211> LENGTH: 511
<212> TYPE: DNA
<213> ORGANISM: Homo sapiens

<400> SEQUENCE: 49

| | |
|---|---|
| ggataatgaa gttgttttat ttagcttgga caaaaaggca tattcctcta ttttcttata | 60 |
| caacaaatat ccccaaaata aagcaagcat atatatcttg aatgtgtaat aatccagtga | 120 |
| taaacaagag cagtacttta aaagaaaaaa aaatatgtat ttctgtcagg ttaaaatgag | 180 |
| aatcaaaacc atttactctg ctaactcatt attttttgct ttcttttttgg ttaagagagg | 240 |
| caatgcaata cactgaaaaa ggttttttatc ttatctggca ttggaattag acatattcaa | 300 |
| accccagccc ccatttccaa actttaagac cacaaacaag taatttactt ttctgaacat | 360 |
| tggttttttc tggaaaatgg gaattataaa atagactttg cagactctta tgagattaaa | 420 |
| taagataatg tatgaaattc tttcttcttt tttacttctt tttccttttt gagatggagt | 480 |
| ctcacccccgt cacccaggct ggagtacagt g | 511 |

<210> SEQ ID NO 50
<211> LENGTH: 561
<212> TYPE: DNA
<213> ORGANISM: Homo sapiens

<400> SEQUENCE: 50

| | |
|---|---|
| ccactgcact ccagcctggg tgacggagtg agactctgtc tcaaaaaaac aaacaaacaa | 60 |
| acaaacaaaa aactgaaaag gaaatagagt tcctctttcc tcatatatga atatattatt | 120 |
| tcaacagatt gttgatcacc taccatatgc ttggtattgt tctaattgct ggggatacag | 180 |
| caagaggttc tgcagaactt catggagcat gaaagtaaat aaacaaagtt aatttcaagg | 240 |
| ccaggcatgg ttgctcacac ctttagtccc agcactttgg gaggctgagg caggtggatc | 300 |
| acttgggccc aggagttcaa ggctgcagtg agccaagatt gtgccactac tctccaggct | 360 |
| gggcaacaga gcaagaccct gtctcagggg gaacaaaaag ttaattttcag attttgttaa | 420 |
| gtgctgtaaa ggaagtaaat aggttgatat tcaagagagc acctgaaggc caggcgtggt | 480 |
| ggctcacgcc tgtggtctaa cgcttttggga agcccgagcg gcggatcac aaggtcagga | 540 |
| gaattttggc caggcatggt g | 561 |

<210> SEQ ID NO 51
<211> LENGTH: 451
<212> TYPE: DNA
<213> ORGANISM: Homo sapiens

<400> SEQUENCE: 51

| | |
|---|---|
| agaatccatt tatttgggttt taaactagtt acacaactga aatcagtttg gcactacttt | 60 |
| atacagggat tacgcctgtg tatgccgaca cttaaatact gtaccaggac cactgctgtg | 120 |
| cttaggtctg tattcagtca ttcagcatgt agatactaaa aatatactgt agtgttcctt | 180 |
| taaggaagac tgtacagggt gtgttgcaag atgacattca ccaatttgtg aattatttca | 240 |
| acccagaaga tacctttcac tctataaact tgtcataggc aaacatgtgg tgttagcatt | 300 |
| gagagatgca cacaaaaatg ttacataaaa gttcagacat tctaatgata agtgaactga | 360 |
| aaaaaaaaaa aaccccacat ctcaattttt gtaacaagat aaagaaaata atttaaaaac | 420 |
| acaaaaaatg gcattcagtg ggtacaaagc c | 451 |

```
<210> SEQ ID NO 52
<211> LENGTH: 682
<212> TYPE: DNA
<213> ORGANISM: Homo sapiens

<400> SEQUENCE: 52
caaatattta atataaatct ttgaaacaag ttcagakgaa ataaaaatca aagtttgcaa      60
aaacgtgaag attaacttaa ttgtcaaata ttcctcattg ccccaaatca gtattttttt     120
tatttctatg caaaagtatg ccttcaaact gcttaaatga tatatgatat gatacacaaa    180
ccagttttca aatagtaaag ccagtcatct tgcaattgta agaaataggt aaaagattat    240
aagacacctt acacacacac acacacacac acacacacgt gtgcaccgcc aatgacaaaa    300
aacaatttgg cctctcctaa aataagaaca tgaagaccct taattgctgc caggagggaa    360
cactgtgtca ccctcccta caatccaggt agtttccttt aatccaatag caaatctggg    420
catatttgag aggagtgatt ctgacagcca csgttgaaat cctgtgggga accattcatg    480
tccacccact ggtgccctga aaaaatgcca ataatttttc gctcccactt ctgctgctgt    540
ctcttccaca tcctcacata gaccccgac ccgctggccc ctggctgggc atcgcattgc    600
tggtagagca agtcataggt ctcgtctttg acgtcacaga agcgatacac caaattgcct    660
ggtcggtcat tgtcataacc ag                                            682

<210> SEQ ID NO 53
<211> LENGTH: 311
<212> TYPE: DNA
<213> ORGANISM: Homo sapiens
<220> FEATURE:
<221> NAME/KEY: misc_feature
<222> LOCATION: 208
<223> OTHER INFORMATION: n = A,T,C or G

<400> SEQUENCE: 53
tttgacttta gtagggtct gaactattta ttttactttg ccmgtaatat ttaraccyta     60 tatatcttc attatgccat cttatcttct aatgbcaagg gaacagwtgc taamctggct    120
tctgcattwa tcacattaaa aatggcttc ttggaaaatc ttcttgatat gaataaagga    180 tctttttavag ccatcattta aagcmggntt ctctccaaca cgagtctgct sasgggggk    240 gagctgtgaa ctctggctga aggctttccc atacacactg caatgacmtg gtttctgacc    300
agbgtgagtt a                                                        311

<210> SEQ ID NO 54
<211> LENGTH: 561
<212> TYPE: DNA
<213> ORGANISM: Homo sapiens

<400> SEQUENCE: 54
agagaagccc cataaatgca atcagtgtgg gaaggccttc agtcagagct caagcctttt    60
cctccatcat cgggttcata ctggagagaa accctatgta tgtaatgaat gcggcagagc   120
ctttggtttt aactctcatc ttactgaaca cgtaaggatt cacacaggag aaaaaccta   180 tgtttgtaat gagtgcggca aagccttcg tcggagttcc actcttgttc agcatcgaag    240
agttcacact ggggagaagc cctaccagtg cgttgaatgt gggaaagctt tcagccagag    300
ctcccagctc accctacatc agccgagttc acactggaga aagccctat gactgtggtg    360 actgtgggaa ggccttcagc cggaggtcaa ccctcattca gcatcagaaa gttcacagcg    420
gagagactcg taagtgcaga aaacatggtc cagcctttgt tcatggctcc agcctcacag   480
```

```
cagatggaca gattcccact ggagagaagc acggcagaac ctttaaccat ggtgcaaatc    540
tcattctgcg ctggacagtt c                                              561

<210> SEQ ID NO 55
<211> LENGTH: 811
<212> TYPE: DNA
<213> ORGANISM: Homo sapiens

<400> SEQUENCE: 55
gagacagggt ctcactttgt cacccaggct ggaatgcagt ggtgcgatct tacgtagctc     60
actgcagccc tgacctcctg gactcaaaca attctcctgc ctcagccctg caagtagctg    120
ggactgtggg tgcatgccac catgcctggc taacttttgt agttttttgta aagatggggt   180 tttgccatgt tgcacatgct ggtcttgaac tcctgagctc aaacgatctg cccacctcgg    240
cctcccagaa tgttgggatt acaggggtaa accaccacgc ctggccccat tagggtattc    300
ttagcatcca cttgctcact gagattaatc ataagagatg ataagcactg gaagaaaaaa    360
atttttacta ggctttggat attttttttcc tttttcagct ttatacagag gattggatct    420
ttagttttcc tttaactgat aataaaacat tgaaaggaaa taagtttacc tgagattcac    480
agagataacc ggcatcactc ccttgctcaa ttccagtctt taccacatca attattttca    540
gaggtgcagg ataaaggcct ttagtctgct ttcgcacttt ttcttccact tttttgtaaa    600
cctgttgcct gacaaatgga attgacagcg tatgccatga ctattccatt tgtcaggcat    660
acgctgtcaa ttttttccacc aatcccttgt ctctctttgg agagatcttc ttatcagcta    720
gtcctttggc aaaagtaatt gcaacttctt ctaggtattc tattgtccgt tccactggtg    780 gaaccctgg gaccaggact aaaacctcca g                                    811

<210> SEQ ID NO 56
<211> LENGTH: 591
<212> TYPE: DNA
<213> ORGANISM: Homo sapiens
<220> FEATURE:
<221> NAME/KEY: misc_feature
<222> LOCATION: 45, 477, 490, 561
<223> OTHER INFORMATION: n = A,T,C or G

<400> SEQUENCE: 56
atctcatata tatatttctt cctgacttta tttgcttgct tctgncacgc atttaaaata     60
tcacagagac caaaatagag cggctttctg gtggaacgca tggcagtcac aggacaaaat    120
acaaaactag ggggctctgt cttctcatac atcatacaat tttcaagtat ttttttttatg   180 tacaaagagc tactctatct gaaaaaaaat taaaaaataa atgagacaag atagtttatg    240
catcctagga agaaagaatg ggaagaaaga acggggcagt tgggtacaga ttcctgtccc    300
ctgttcccag ggaccactac cttcctgcca ctgagttccc ccacagcctc acccatcatg    360
tcacagggca agtgccaggg taggtgggga ccagtggaga caggaaccag caacatactt    420
tggcctggaa gataaggaga aagtctcaga aacacactgg tgggaagcaa tcccacnggc    480
cgtgccccan gagcttccca cctgctgctg gctccctggg tggctttggg aacagcttgg    540
gcaggccctt tgggtgggg nccaactggg cctttgggcc cgtgtggaaa g              591

<210> SEQ ID NO 57
<211> LENGTH: 481
<212> TYPE: DNA
<213> ORGANISM: Homo sapiens
```

```
<400> SEQUENCE: 57
aaacattgag atggaatgat agggtttccc agaatcaggt ccatatttta actaaatgaa      60
aattatgatt tatagccttc tcaaatacct gccatacttg atatctcaac cagagctaat    120
tttacctctt tacaaattaa ataagcaagt aactggatcc acaatttata atacctgtca    180
atttttcctg tattaaacct ctatcatagt ttaagcctat tagggtactt aatccttaca    240
aataaacagg tttaaaatca cctcaatagg caactgccct tctggttttc ttctttgact    300
aaacaatctg aatgcttaag attttccact ttgggtgcta gcagtacaca gtgttacact    360
ctgtattcca gacttcttaa attatagaaa aaggaatgta cacttttgt attctttctg     420 agcagggccg ggaggcaaca tcatctacca tggtagggac ttgtatgcat ggactacttt    480
a                                                                    481

<210> SEQ ID NO 58
<211> LENGTH: 141
<212> TYPE: DNA
<213> ORGANISM: Homo sapiens

<400> SEQUENCE: 58
actctgtcgc ccaggctgga gcccabtggm gcgatctcga ctccctgcaa gctmcgcctc     60
acaggwtcat gccattctcc tgcctcagca tctggagtag ctgggactac aggcgccagc    120
caccatgccc agctaatttt t                                              141

<210> SEQ ID NO 59
<211> LENGTH: 191
<212> TYPE: DNA
<213> ORGANISM: Homo sapiens

<400> SEQUENCE: 59
accttaaaga cataggagaa tttatactgg gagagaaagc ttacaaatgt aaggtttctg     60
acaagacttg ggagtgattc acacctggaa caacatactg gacttcacac tggabagaaa    120
ccttacaagt gtaatgagtg tggcaaagcc tttggcaagc agtcaacact tattcaccat    180
caggcaattc a                                                         191

<210> SEQ ID NO 60
<211> LENGTH: 480
<212> TYPE: DNA
<213> ORGANISM: Homo sapiens

<400> SEQUENCE: 60
agtcaggatc atgatggctc agtttcccac agcgatgaat ggagggccaa atatgtgggc     60
tattacatct gaagaacgta ctaagcatga taaacagttt gataacctca aaccttcagg    120
aggttacata acaggtgatc aagcccgtac ttttttccta cagtcaggtc tgccggcccc    180
ggttttagct gaaatatggg ccttatcaga tctgaacaag gatgggaaga tggaccagca    240
agagttctct atagctatga aactcatcaa gttaaagttg cagggccaac agctgcctgt    300
agtcctccct cctatcatga aacaaccccc tatgttctct ccactaatct ctgctcgttt    360
tgggatggga agcatgccca atctgtccat tcatcagcca ttgcctccag ttgcacctat    420
agcaacaccc ttgtcttctg ctacttcagg gaccagtatt cctccctaat gatgcctgct    480

<210> SEQ ID NO 61
<211> LENGTH: 381
<212> TYPE: DNA
<213> ORGANISM: Homo sapiens
```

<400> SEQUENCE: 61

```
ctttcgattt ccttcaattt gtcacgtttg attttatgaa gttgttcaag ggctaactgc      60
tgtgtattat agctttctct gagttccttc agctgattgt taaatgaatc catttctgag     120
agcttagatg cagtttcttt ttcaagagca tctaattgtt ctttaagtct ttggcataat     180
tcttcctttt ctgatgactt tctatgaagt aaactgatcc ctgaatcagg tgtgttactg     240
agctgcatgt ttttaattct ttcgtttaat agctgcttct cagggaccag atagataagc     300
ttattttgat attccttaag ctcttggtga agttgttcga tttccataat ttccaggtca     360
cactggttat cccaaacttc t                                               381
```

<210> SEQ ID NO 62
<211> LENGTH: 906
<212> TYPE: DNA
<213> ORGANISM: Homo sapiens

<400> SEQUENCE: 62

```
gtggaggtga aacggaggca agaaaggggg ctacctcagg agcgagggac aaaggggggcg     60
tgaggcacct aggccgcggc accccggcga caggaagccg tcctgaaccg ggctaccggg    120
taggggaagg gcccgcgtag tcctcgcagg gccccagagc tggagtcggc tccacagccc    180
cgggccgtcg gcttctcact tcctggacct ccccggcgcc cgggcctgag gactggctcg    240
gcggagggag aagaggaaac agacttgagc agctccccgt tgtctcgcaa ctccactgcc    300
gaggaactct catttcttcc ctcgctcctt cacccccac ctcatgtaga aaggtgctga    360
agcgtccgga gggaagaaga acctgggcta ccgtcctggc cttcccmccc ccttcccggg    420
gcgctttggt gggcgtggag ttggggttgg ggggtgggt ggggttctt ttttggagtg    480
ctggggaact tttttcctt cttcaggtca ggggaaaggg aatgcccaat tcagagagac    540
atgggggcaa gaaggacggg agtggaggag cttctggaac tttgcagccg tcatcgggag    600
gcggcagctc taacagcaga gagcgtcacc gcttggtatc gaagcacaag cggcataagt    660
ccaaacactc caaagacatg gggttggtga ccccgaagc agcatccctg ggcacagtta    720
tcaaaccttt ggtggagtat gatgatatca gctctgattc cgacaccttc tccgatgaca    780
tggccttcaa actagaccga agggagaacg acgaacgtcg tggatcagat cggagcgacc    840
gcctgcacaa acatcgtcac caccagcaca ggcgttcccg ggacttacta aaagctaaac    900
agaccg                                                                906
```

<210> SEQ ID NO 63
<211> LENGTH: 491
<212> TYPE: DNA
<213> ORGANISM: Homo sapiens

<400> SEQUENCE: 63

```
gacatgtttg cctgcagggg accagagaca atgggattag ccagtgctca ctgttctta      60
tgcttccaga gaggatgggg acagctctca ggtcagaatc caggctgaga aggccatgct    120
ggttgggggc ccccggaagc acggtccgga tcctccctgg catcagcgta gacccgctgc    180
tcaggcttgg ggtaccaaac tcatgctctg tactgttttg gccccatgcg gtgagaggaa    240
aacctagaaa aagattggtc gtgctaagga atcagctgcc ccctcatcct ccgcatccaa    300
tgctggtgac aacatattcc ctctcccagg acacagactc ggtgactcca cactgggctg    360
agtggcctct ggaggctcgt ggcctaaggc agggctccgt aaggctgatc ggctgaactg    420
```

```
ggtggggtga gggtttctga cccttcgctt cccatcccat aaccgctgtc aatgagctca      480
cactgtggtc a                                                           491
```

<210> SEQ ID NO 64
<211> LENGTH: 511
<212> TYPE: DNA
<213> ORGANISM: Homo sapiens

<400> SEQUENCE: 64

```
gatggcatgg tcgttgctaa tgtgcctgct gggatggagc acttcctcct gtgagcccag       60
gggacccgcc tgtccctgga gcttggggca aggaggaag agtgatacca ggaaggtggg      120
gctgcagcca ggggccagag tcagttcagg gagtggtcct cggccctcaa agctcctccg      180
gggactgctc aggagtgatg gtgccctgga gtttgcccca acttccctgg ccaccctgga      240
aggtgcctgg ctgctccagg cctctaggct gggctgatgg gtttctccag gacacaagta      300
tcattaaagc caccctctcc tcagcttgtc aggccgcaca tgtgggacag gctgtgctca      360
caaccccctc gcctgccctg ccctccatca ggaggagcca gtggaaacctt cggaaagctc     420 ccagcatctc agcagccctc aaaagtcgtc ctggggcaag ctctggttct cctgactgga      480
ggtcatctgg gcttggcctg ctctctctcg c                                    511
```

<210> SEQ ID NO 65
<211> LENGTH: 394
<212> TYPE: DNA
<213> ORGANISM: Homo sapiens

<400> SEQUENCE: 65

```
taaaaaagtg taacaaaggt ttatttagac tttcttcatg cccccagatc caggatgtct       60
atgtaaaccg ttatcttaca agaaagcac aatatttggt ataaactaag tcagtgactt      120
gcttaactga aatagcgtcc atccaaaagt gggtttaagg taaaactacc tgacgatatt      180 ggcgggatc ctgcagtttg gactgcttgc cgggtttgtc cagggttccg ggtctgttct      240
tggcactcat ggggacaggc atcctgctcg tctgtggggc cccgctggag cccttacgtg      300
aagctgaagg tatcgaccst aggggctct agggcagtgg gaccttcatc cggaactaac      360
aagggtcggg gagaggcctc ttgggctatg tggg                                 394
```

<210> SEQ ID NO 66
<211> LENGTH: 359
<212> TYPE: DNA
<213> ORGANISM: Homo sapiens

<400> SEQUENCE: 66

```
caagcgttcc tttatggatg taaattcaaa cagtcatgct gagccatccc gggctgacag       60
tcacgttwaa gacactaggt cgggcgccac agtgccaccc aaggagaaga agaatttgga     120 attttccat gaagatgtac ggaaatctga tgttgaatat gaaaatggcc cccaaatgga      180
attccaaaag gttaccacag gggctgtaag acctagtgac cctcctaagt gggaaagagg      240 aatgagaat agtatttctg atgcatcaag aacatcagaa tataaaactg agatcataat      300
gaaggaaaat tccatatcca atatgagttt actcagagac agtagaaact attcccagg      359
```

<210> SEQ ID NO 67
<211> LENGTH: 450
<212> TYPE: DNA
<213> ORGANISM: Homo sapiens
<220> FEATURE:
<221> NAME/KEY: misc_feature
<222> LOCATION: 425
<223> OTHER INFORMATION: n = A,T,C or G

<400> SEQUENCE: 67

```
taggaataac aaatgtttat tcagaaatgg ataagtaata cataatcacc cttcatctct      60
taatgcccct tcctctcctt ctgcacagga gacacagatg ggtaacatag aggcatggga     120
agtggaggag gacacaggac tagcccacca ccttctcttc ccggtctccc aagatgactg     180
cttatagagt ggaggaggca aacaggtccc ctcaatgtac cagatggtca cctatagcac     240
cagctccaga tggccacgtg gttgcagctg gactcaatga aactctgtga caaccagaag     300
atacctgctt tgggatgaga gggaggataa agccatgcag ggaggatatt taccatccct     360
accctaagca cagtgcaagc agtgagcccc cggctcccag tacctgaaaa accaaggcct     420
actgnctttt ggatgctctc ttgggccacg                                      450
```

<210> SEQ ID NO 68
<211> LENGTH: 511
<212> TYPE: DNA
<213> ORGANISM: Homo sapiens

<400> SEQUENCE: 68

```
aagcctcctg ccctggaaat ctggagcccc ttggagctga gctggacggg gcagggaggg      60
gctgagaggc aagaccgtct ccctcctgct gcagctgctt cccagcagc cactgctggg     120
cacagcagaa acgccagcag agaaaatggg agccgagagt ccttagccct ggagctgagg     180
ctgcctctgg gctgacccgc tggctgtacg tggccagaac tggggttggc atctggcatc     240
catttgaggc cagggtggag gaaagggagg ccaacagagg aaaacctatt cctgctgtga     300
caacacagcc cttgtcccac gcagcctaag tgcagggagc gtgatgaagt caggcagcca     360
gtcgggagg acgaggtaac tcagcagcaa tgtcaccttg tagcctatgc gctcaatggc     420
ccggaggggc agcaaccccc cgcacacgtc agccaacagc agtgcctctg caggcaccaa     480
gagagcgatg atggacttga gcgccgtgtt c                                    511
```

<210> SEQ ID NO 69
<211> LENGTH: 511
<212> TYPE: DNA
<213> ORGANISM: Homo sapiens

<400> SEQUENCE: 69

```
gtttggcaga agacatgttt aataacattt tcatatttaa aaaatacagc aacaattctc      60
tatctgtcca ccatcttgcc ttgcccttcc tggggctgag gcagacaaag gaaaggtaat     120
gaggttaggg cccccaggcg ggctaagtgc tattggcctg ctcctgctca aagagagcca     180
tagccagctg ggcacggccc cctagcccct ccaggttgct gaggcggcag cggtggtaga     240
gttcttcact gagccgtggg ctgcagtctc gcagggagaa cttctgcacc agccctggct     300
ctacggcccg aaagaggtgg agccctgaga accggaggaa aacatccatc acctccagcc     360
cctccagggc ttcctcctct tcctggcctg ccagttcacc tgccagccgg gctcgggccg     420
ccaggtagtc agcgttgtag aagcagccct ccgcagaagc ctgccggtca aatctccccg     480
ctataggagc ccccgggag gggtcagcac c                                     511
```

<210> SEQ ID NO 70
<211> LENGTH: 511
<212> TYPE: DNA
<213> ORGANISM: Homo sapiens

<400> SEQUENCE: 70

```
caagttgaac gtcaggcttg gcagaggtgg agtgtagatg aaaacaaagg tgtgattatg    60
aagaggatgt gagtcctttg ggtgtaggag agaaaggctg ttgagcttct atttcaagat   120
acttttacct gtgcaaaaag cacattttcc acctccttct catggcattt gtgtaaggtg   180
agtatgattc ctattccatc tgcattttag aggtgaagaa taacgtacaa gggattcagt   240
gattagcaag ggaccctca ctaagtgttg atggagttag acagagctc agctgtttga    300
atctcagagc ccaggcagct ggagctgggt aggatcctgg agctggcact aatgtgaggt   360
gcattccctc caacccaggc tcagatccgg aacctgaccg tgctgacccc cgaagggagg   420
gcagggctga gctggcccgt tgggctccct gctcctttca caccacactc tcgctttgag   480
gtgctgggct gggactactt cacagagcag c                                  511
```

<210> SEQ ID NO 71
<211> LENGTH: 511
<212> TYPE: DNA
<213> ORGANISM: Homo sapiens

<400> SEQUENCE: 71

```
tggcctgggc aggattggga gagaggtagc tacccggatg cagtcctttg ggatgaagac    60
tatagggtat gaccccatca tttcccaga ggtctcggcc tcctttggtg ttcagcagct    120
gccctggag gagatctggc ctctctgtga tttcatcact gtgcacactc ctctcctgcc    180
ctccacgaca ggcttgctga atgacaacac ctttgcccag tgcaagaagg gggtgcgtgt    240
ggtgaactgt gcccgtggag ggatcgtgga cgaaggcgcc ctgctccggg ccctgcagtc    300
tggccagtgt gccggggctg cactggacgt gtttacggaa gagccgccac gggacgggc    360
cttggtggac catgagaatg tcatcagctg tccccacctg ggtgccagca ccaaggaggc    420
tcagagccgc tgtggggagg aaattgctgt tcagttcgtg gacatggtga aggggaaatc    480
tctcacgggg gttgtgaatg cccaggccct t                                  511
```

<210> SEQ ID NO 72
<211> LENGTH: 2017
<212> TYPE: DNA
<213> ORGANISM: Homo sapiens

<400> SEQUENCE: 72

```
agccagatgg ctgagagctg caagaagaag tcaggatcat gatggctcag tttcccacag    60
cgatgaatgg agggccaaat atgtgggcta ttacatctga agaacgtact aagcatgata   120
aacagtttga taacctcaaa ccttcaggag gttacataac aggtgatcaa gcccgtactt   180
ttttcctaca gtcaggtctg ccggcccgg ttttagctga aatatgggcc ttatcagatc    240
tgaacaagga tgggaagatg gaccagcaag agttctctat agctatgaaa ctcatcaagt   300
taaagttgca gggccaacag ctgcctgtag tcctccctcc tatcatgaaa caaccccta    360
tgttctctcc actaatctct gctcgttttg ggatgggaag catgcccaat ctgtccattc   420
atcagccatt gcctccagtt gcacctatag caacacccctt gtcttctgct acttcaggga   480
ccagtattcc tcccctaatg atgcctgctc ccctagtgcc ttctgttagt acatcctcat   540
taccaaatgg aactgccagt ctcattcagc ctttatccat tccttattct tcttcaacat   600
tgcctcatgc atcatcttac agcctgatga tgggaggatt tggtggtgct agtatccaga   660
aggcccagtc tctgattgat ttaggatcta gtagctcaac ttcctcaact gcttccctct    720
cagggaactc acctaagaca gggaccctcag agtgggcagt tcctcagcct tcaagattaa    780
```

| | |
|---|---|
| agtatcggca aaaatttaat agtctagaca aaggcatgag cggatacctc tcaggttttc | 840 |
| aagctagaaa tgcccttctt cagtcaaatc tctctcaaac tcagctagct actatttgga | 900 |
| ctctggctga catcgatggt gacggacagt tgaaagctga agaatttatt ctggcgatgc | 960 |
| acctcactga catggccaaa gctggacagc cactaccact gacgttgcct cccgagcttg | 1020 |
| tccctccatc tttcagaggg ggaaagcaag ttgattctgt taatggaact ctgccttcat | 1080 |
| atcagaaaac acaagaagaa gagcctcaga agaaactgcc agttactttt gaggacaaac | 1140 |
| ggaaagccaa ctatgaacga ggaaacatgg agctggagaa gcgacgccaa gtgttgatgg | 1200 |
| agcagcagca gagggaggct gaacgcaaag cccagaaaga gaaggaagag tgggagcgga | 1260 |
| aacagagaga actgcaagag caagaatgga agaagcagct ggagttggag aaacgcttgg | 1320 |
| agaaacagag agagctggag agacagcggg aggaagagag gagaaggag atagaaagac | 1380 |
| gagaggcagc aaaacaggag cttgagagac aacgccgttt agaatgggaa agactccgtc | 1440 |
| ggcaggagct gctcagtcag aagaccaggg aacaagaaga cattgtcagg ctgagctcca | 1500 |
| gaaagaaaag tctccacctg gaactggaag cagtgaatgg aaaacatcag cagatctcag | 1560 |
| gcagactaca agatgtccaa atcagaaagc aaacacaaaa gactgagcta aagttttgg | 1620 |
| ataaacagtg tgacctggaa attatggaaa tcaaacaact tcaacaagag cttaaggaat | 1680 |
| atcaaaataa gcttatctat ctggtccctg agaagcagct attaaacgaa agaattaaaa | 1740 |
| acatgcagct cagtaacaca cctgattcag ggatcagttt acttcataaa aagtcatcag | 1800 |
| aaaaggaaga attatgccaa agacttaaag aacaattaga tgctcttgaa aaagaaactg | 1860 |
| catctaagct ctcagaaatg gattcattta caatcagct gaaggaactc agagaaagct | 1920 |
| ataatacaca gcagttagcc cttgaacaac ttcataaaat caaacgtgac aaattgaagg | 1980 |
| aaatcgaaag aaaaagatta gagcaaaaaa aaaaaaa | 2017 |

```
<210> SEQ ID NO 73
<211> LENGTH: 414
<212> TYPE: DNA
<213> ORGANISM: Homo sapiens

<400> SEQUENCE: 73
```

| | |
|---|---|
| atggcagtga cattcaccat catgggaacc accttcccctt ttcttcagga ttctctgtag | 60 |
| tggaagagag cacccagtgt tgggctgaaa acatctgaaa gtagggagaa gaacctaaaa | 120 |
| taatcagtat ctcagagggc tctaaggtgc caagaagtct cactggacat ttaagtgcca | 180 |
| acaaaggcat actttcggaa tcgccaagtc aaaactttct aacttctgtc tctctcagag | 240 |
| acaagtgaga ctcaagagtc tactgcttta gtggcaacta cagaaaactg gtgttaccca | 300 |
| gaaaaacagg agcaattaga aatggttcca atatttcaaa gctccgcaaa caggatgtgc | 360 |
| tttcctttgc ccatttaggg tttcttctct ttcctttctc tttattaacc acta | 414 |

```
<210> SEQ ID NO 74
<211> LENGTH: 1567
<212> TYPE: DNA
<213> ORGANISM: Homo sapiens

<400> SEQUENCE: 74
```

| | |
|---|---|
| atatctagaa gtctggagtg agcaaacaag agcaagaaac aaaagaagc caaaagcaga | 60 |
| aggctccaat atgaacaaga taatctatc ttcaaagaca tattagaagt tgggaaaata | 120 |
| attcatgtga actagacaag tgtgttaaga gtgataagta aaatgcacgt ggagacaagt | 180 |

```
gcatccccag atctcaggga cctcccctg cctgtcacct ggggagtgag aggacaggat     240
agtgcatgtt ctttgtctct gaattttag ttatatgtgc tgtaatgttg ctctgaggaa     300
gcccctggaa agtctatccc aacatatcca catcttatat tccacaaatt aagctgtagt    360
atgtacccta agacgctgct aattgactgc cacttcgcaa ctcagggcg gctgcatttt     420 agtaatgggt caaatgattc acttttatg atgcttccaa aggtgccttg gcttctcttc     480
ccaactgaca aatgccaaag ttgagaaaaa tgatcataat tttagcataa acagagcagt    540
cggcgacacc gattttataa ataaactgag caccttcttt ttaaacaaac aaatgcgggt    600
ttatttctca gatgatgttc atccgtgaat ggtccaggga aggacctttc accttgacta    660
tatggcatta tgtcatcaca agctctgagg cttctccttt ccatcctgcg tggacagcta    720
agacctcagt tttcaatagc atctagagca gtgggactca gctggggtga tttcgccccc    780
catctccggg ggaatgtctg aagacaattt tgttacctca atgagggagt ggaggaggat    840
acagtgctac taccaactag tggataaagg ccagggatgc tgctcaacct cctaccatgt    900
acaggacgtc tccccattac aactacccaa tccgaagtgt caactgtgtc aggactaaga    960
aaccctggtt tgagtagaa aagggcctgg aaagaggga gccaacaaat ctgtctgctt     1020
cctcacatta gtcattggca aataagcatt ctgtctcttt ggctgctgcc tcagcacaga    1080
gagccagaac tctatcgggc accaggataa catctctcag tgaacagagt tgacaaggcc    1140
tatgggaaat gcctgatggg attatcttca gcttgttgag cttctaagtt tctttccctt    1200
cattctaccc tgcaagccaa gttctgtaag agaaatgcct gagttctagc tcaggttttc    1260
ttactctgaa tttagatctc cagacccttc ctggccacaa ttcaaattaa ggcaacaaac    1320
atataccttc catgaagcac acacagactt tgaaagcaa ggacaatgac tgcttgaatt     1380
gaggccttga ggaatgaagc tttgaaggaa aagaatactt tgtttccagc cccttccca    1440 cactcttcat gtgttaacca ctgccttcct ggaccttgga gccacggtga ctgtattaca    1500
tgttgttata gaaaactgat tttagagttc tgatcgttca agagaatgat taaatataca    1560
tttccta                                                             1567

<210> SEQ ID NO 75
<211> LENGTH: 240
<212> TYPE: DNA
<213> ORGANISM: Homo sapiens

<400> SEQUENCE: 75
tcgagcggcc gcccgggcag gtccttcaga cttggactgt gtcacactgc caggcttcca     60
gggctccaac ttgcagacgg cctgttgtgg gacagtctct gtaatcgcga aagcaaccat    120
ggaagacctg ggggaaaaca ccatggtttt atccaccctg agatctttga caacttcat    180 ctctcagcgt gcggagggag gctctggact ggatatttct acctcggccg cgaccacgct    240

<210> SEQ ID NO 76
<211> LENGTH: 330
<212> TYPE: DNA
<213> ORGANISM: Homo sapiens
<220> FEATURE:
<221> NAME/KEY: misc_feature
<222> LOCATION: 288
<223> OTHER INFORMATION: n = A,T,C or G

<400> SEQUENCE: 76
tagcgyggtc gcggccgagg yctgcttytc tgtccagccc agggcctgtg gggtcagggc     60
ggtgggtgca gatggcatcc actccggtgg cttccccatc tttctctggc ctgagcaagg    120
```

```
tcagcctgca gccagagtac agagggccaa cactggtgtt cttgaacaag ggccttagca    180
ggccctgaag grccctctct gtagtgttga acttcctgga gccaggccac atgttctcct    240
cataccgcag gytagygatg gtgaagttga gggtgaaata gtattmangr agatggctgg    300
caracctgcc cgggcggccg ctcsaaatcc                                     330
```

<210> SEQ ID NO 77
<211> LENGTH: 361
<212> TYPE: DNA
<213> ORGANISM: Homo sapiens

<400> SEQUENCE: 77

```
agcgtggtcg cggccgaggt gtccttcagg gtctgcttat gcccttgttc aagaacacca    60
gtgtcagctc tctgtactct ggttgcagac tgaccttgct caggcctgag aaggatgggg    120
cagccaccag agtggatgct gtctgcaccc atcgtcctga ccccaaaagc cctggactgg    180
acagagagcg gctgtactgg aagctgagcc agctgaccca cggcatcact gagctgggcc    240
cctacaccct ggacagggac agtctctatg tcaatggttt cacccatcgg agctctgtac    300
ccaccaccag caccggggtg gtcagcgagg agccattcaa cctgcccggg cggccgctcg    360
a                                                                    361
```

<210> SEQ ID NO 78
<211> LENGTH: 356
<212> TYPE: DNA
<213> ORGANISM: Homo sapiens
<220> FEATURE:
<221> NAME/KEY: misc_feature
<222> LOCATION: 7, 346, 350, 353
<223> OTHER INFORMATION: n = A,T,C or G

<400> SEQUENCE: 78

```
ttggggnttt mgagcggccg cccgggcagg taccggggtg gtcagcgagg agccattcac    60
actgaacttc accatcaaca acctgcggta tgaggagaac atgcagcacc ctggctccag    120
gaagttcaac accacggaga gggtccttca gggcctgctc aggtccctgt tcaagagcac    180
cagtgttggc cctctgtact ctggctgcag actgactttg ctcagacttg agaaacatgg    240
ggcagccact ggagtggacg ccatctgcac cctccgcctt gatcccactg gtcctggact    300
ggacagagag cggctatact gggagctgag ccagtcctct ggcggngacn ccnctt       356
```

<210> SEQ ID NO 79
<211> LENGTH: 226
<212> TYPE: DNA
<213> ORGANISM: Homo sapiens

<400> SEQUENCE: 79

```
agcgtggtcg cggccgaggt ccagtcgcag catgctcttt ctcctgccca ctggcacagt    60
gaggaagatc tctgctgtca gtgagaaggc tgtcatccac tgagatggca gtcaaaagtg    120
catttaatac acctaacgta tcgaacatca tagcttggcc caggttatct catatgtgct    180
cagaacactt acaatagcct gcagacctgc ccgggcggcc gctcga                   226
```

<210> SEQ ID NO 80
<211> LENGTH: 444
<212> TYPE: DNA
<213> ORGANISM: Homo sapiens
<220> FEATURE:
<221> NAME/KEY: misc_feature
<222> LOCATION: 23

<223> OTHER INFORMATION: n = A,T,C or G

<400> SEQUENCE: 80

```
tgtggtgttg aacttcctgg agncagggtg acccatgtcc tccccatact gcaggttggt     60
gatggtgaag ttgagggtga atggtaccag gagagggcca gcagccataa ttgtsgrgck    120
gsmgmssgag gmwggwgtyy cwgaggttcy rarrtccact gtggaggtcc caggagtgct    180
ggtggtgggc acagagstcy gatgggtgaa accattgaca tagagactgt tcctgtccag    240
ggtgtagggg cccagctctt yratgycatt ggycagttkg ctyagctccc agtacagccr    300
ctctckgyyg mgwccagsgc ttttgggtgc aagatgatgg atgcagatgg catccactcc    360
agtggctgct ccatccttct cggacctgag agaggtcagt ctgcagccag agtacagagg    420
gccaacactg gtgttctttg aata                                          444
```

<210> SEQ ID NO 81
<211> LENGTH: 310
<212> TYPE: DNA
<213> ORGANISM: Homo sapiens

<400> SEQUENCE: 81

```
tcgagcggcc gcccgggcag gtcaggaagc acattggtct tagagccact gcctcctgga     60
ttccacctgt gctgcggaca tctccaggga gtgcagaagg gaagcaggtc aaactgctca    120
gatcagtcag actggctgtt ctcagttctc acctgagcaa ggtcagtctg cagccagagt    180
acagagggcc aacactggtg ttcttgaaca agggcttgag cagaccctgc agaaccctct    240
tccgtggtgt tgaacttcct ggaaaccagg gtgttgcatg tttttcctca taatgcaagg    300
ttggtgatgg                                                          310
```

<210> SEQ ID NO 82
<211> LENGTH: 571
<212> TYPE: DNA
<213> ORGANISM: Homo sapiens
<220> FEATURE:
<221> NAME/KEY: misc_feature
<222> LOCATION: 202
<223> OTHER INFORMATION: n = A,T,C or G

<400> SEQUENCE: 82

```
acggtttcaa tggacacttt tattgtttac ttaatggatc atcaattttg tctcactacc     60
tacaaatgga atttcatctt gtttccatgc tgagtagtga aacagtgaca aagctaatca    120
taataaccta catcaaaaga gaactaagct aacactgctc actttctttt taacaggcaa    180
aatataaata tatgcactct anaatgcaca atggtttagt cactaaaaaa ttcaaatggg    240
atcttgaaga atgtatgcaa atccaggtgt cagtgaagat gagctgagat gctgtgcaac    300
tgtttaaggg ttcctggcac tgcatctctt ggccactagc tgaatcttga catggaaggt    360
tttagctaat gccaagtgga gatgcagaaa atgctaagtt gacttagggg ctgtgcacag    420
gaactaaaag gcaggaaagt actaaatatt gctgagagca tccacccag gaaggacttt    480
accttccagg agctccaaac tggcaccacc cccagtgctc acatggctga ctttatcctc    540
cgtgttccat ttggcacagc aagtggcagt g                                  571
```

<210> SEQ ID NO 83
<211> LENGTH: 551
<212> TYPE: DNA
<213> ORGANISM: Homo sapiens

<400> SEQUENCE: 83

```
aaggctggtg ggttttgat cctgctggag aacctccgct ttcatgtgga ggaagaaggg      60
aagggaaaag atgcttctgg gaacaaggtt aaagccgagc cagccaaaat agaagctttc     120
cgagcttcac tttccaagct aggggatgtc tatgtcaatg atgcttttgg cactgctcac     180
agagcccaca gctccatggt aggagtcaat ctgccacaga aggctggtgg gttttgatg      240 aagaaggagc tgaactactt tgcaaaggcc ttggagagcc cagagcgacc cttcctggcc     300
atcctgggcg gagctaaagt tgcagacaag atccagctca tcaataatat gctggacaaa     360
gtcaatgaga tgattattgg tggtggaatg gcttttacct tccttaaggt gctcaacaac     420
atggagattg gcacttctct gtttgatgaa gagggagcca agattgtcaa agacctaatg     480
tccaaagctg agaagaatgg tgtgaagatt accttgcctg ttgactttgt cactgctgac     540
aagtttgatg a                                                         551

<210> SEQ ID NO 84
<211> LENGTH: 571
<212> TYPE: DNA
<213> ORGANISM: Homo sapiens

<400> SEQUENCE: 84
tttgttcctt acattttct aaagagttac ttaaatcagt caactggtct ttgagactct      60
taagttctga ttccaactta gctaattcat tctgagaact gtggtatagg tggcgtgtct    120
cttctagctg gacaaaagt tctttgtttt ccccctgtag agtatcacag accttctgct     180
gaagctggac ctctgtctgg gccttggact cccaaatctg cttgtcatgt tcaagcctgg    240
aaatgttaat cttaattct tccatatgga tggacatctg tctaagttga tcctttagaa     300
cactgcaatt atcttctttg agtctaattt cttcttcttt gctttgaatc gcatcactaa    360
acttcctctc ccatttctta gcttcatcta tcaccctgtc acgatcatcc tggagggaag    420
acatgctctt agtaaaggct gcaagctggg tcacagtact gtccaagttt tcctgaagtt    480
gctgaacttc cttgtctttc ttgttcaaag taacctgaat ctctccaatt gtctcttcca    540
agtggacttt ttctctgcgc aaagcatcca g                                   571

<210> SEQ ID NO 85
<211> LENGTH: 561
<212> TYPE: DNA
<213> ORGANISM: Homo sapiens

<400> SEQUENCE: 85
tcattgcctg tgatggcatc tggaatgtga tgagcagcca ggaagttgta gatttcattc      60
aatcaaagga ttcagcatgt ggtggaagct gtgaggcaag agaaacaaga actgtatggc    120
aagttaagaa gcacagaggc aaacaagaag gagacagaaa agcagttgca ggaagctgag    180
caagaaatgg aggaaatgaa agaaaagatg agaaagtttg ctaaatctaa acagcagaaa    240
atcctagagc tggaagaaga gaatgaccgg cttagggcag aggtgcaccc tgcaggagat    300
acagctaaag agtgtatgga aacacttctt tcttccaatg ccagcatgaa ggaagaactt    360
gaaagggtca aaatggagta tgaaaccctt tctaagaagt ttcagtcttt aatgtctgag    420
aaagactctc taagtgaaga ggttcaagat ttaaagcatc agatagaagg taatgtatct    480
aaacaagcta acctagaggc caccgagaaa catgataacc aaacgaatgt cactgaagag    540
ggaacacagt ctataccagg t                                              561

<210> SEQ ID NO 86
```

<211> LENGTH: 795
<212> TYPE: DNA
<213> ORGANISM: Homo sapiens

<400> SEQUENCE: 86

```
aagccaataa tcaccattta ttacttaata tatgccaacc actgtacttg gcagttcaca      60
aattctcacc gttacaacaa ccccatgagg tatttattcc cattctatag atagggaaac     120
cacagctcaa gtaagttagg aaactgagcc aagtatacac agaatacgaa gtggcaaaac     180
tagaaggaaa gactgacact gctatctgct ggcctccagt gtcctggctc ttttcacacg     240
ggttcaatgt ctccagcgct gctgctgctg ctgcattacc atgccctcat tgttttctt      300
cctctggtgt tcaactgcat ccttcaaaga atctaactca ttccagagac cacttatttc     360
tttctctctt tctgaaatta cttttaataa ttccttcatga gggggaaaag aagatgcctg    420
ttggtagttt tgttgtttaa gctgctcaat ttgggactta acaatttgt tttcatcttg      480
tacatcctgt aacagctgtg ttttgctaga aagatcactc tccctctctt ttagcatggc     540
ttctaacctc ttcaattcat tttccttttc tttcaacaca atctcaagtt cttcaaactg     600
tgatgcagaa gaggcctctt tcaagttatg ttgtgctact tcctgaacat gtgcttttaa    660
agattcattt tcttcttgaa gatcctgtaa ccacttccct gtattggcta ggtctttctc     720
tttctcttcc aaaacagcct tcatggtatt catctgttcc tcttttcctt ttaataagtt     780
caggagcttc agaac                                                      795
```

<210> SEQ ID NO 87
<211> LENGTH: 594
<212> TYPE: DNA
<213> ORGANISM: Homo sapiens

<400> SEQUENCE: 87

```
caagcttttt tttttttttt aaaaagtgtt agcattaatg ttttattgtc acgcagatgg      60
caactgggtt tatgtcttca tattttatat ttttgtaaat taaaaaaatt acaagtttta    120
aatagccaat ggctggttat attttcagaa aacatgatta gactaattca ttaatggtgg    180
cttcaagctt ttccttattg ctccagaaa attcacccac cttttgtccc ttcttaaaaa     240
actggaatgt tggcatgcat ttgacttcac actctgaagc aacatcctga cagtcatcca    300
catctacttc aaggaatatc acgttggaat actttcaga gagggaatga aagaaaggct    360
tgatcatttt gcaaggccca caccacgtgg ctgagaagtc aactactaca agtttatcac    420
ctgcagcgtc caaggcttcc tgaaaagcag tcttgctctc gatctgcttc accatcttgg    480
ctgctggagt ctgacgagcg gctgtaagga ccgatggaaa tggatccaaa gcaccaaaca    540
gagcttcaag actcgctgct tggcttgaat tcggatccga tatcgccatg gcct          594
```

<210> SEQ ID NO 88
<211> LENGTH: 557
<212> TYPE: DNA
<213> ORGANISM: Homo sapiens

<400> SEQUENCE: 88

```
aagtgttagc attaatgttt tattgtcacg cagatggcaa ctgggtttat gtcttcatat      60
tttatatttt tgtaaattaa aaaaattmca gttttaaat agccaatggc tggttatatt     120
ttcagaaaac atgattagac taattcatta atggtggctt caagcttttc cttattggct    180
ccagaaaatt cacccacctt ttgtcccttc ttaaaaaact ggaatgttgg catgcatttg    240
acttcacact ctgaagcaac atcctgacag tcatccacat ctacttcaag gaatatcacg    300
```

| | |
|---|---|
| ttggaatact tttcagagag ggaatgaaag aaaggcttga tcattttgca aggcccacac | 360 |
| cacgtggctg agaagtcaac tactacaagt ttatcacctg cagcgtccaa ggcttcctga | 420 |
| aaagcagtct tgctctcgat ctgcttcacc atcttggctg ctggagtctg acgagcggct | 480 |
| gtaaggaccg atggaaatgg atccaaagca ccaaacagag cttcaagact cgctgcttgg | 540 |
| catgaattcg gatccga | 557 |

<210> SEQ ID NO 89
<211> LENGTH: 561
<212> TYPE: DNA
<213> ORGANISM: Homo sapiens
<220> FEATURE:
<221> NAME/KEY: misc_feature
<222> LOCATION: 544, 551
<223> OTHER INFORMATION: n = A,T,C or G

<400> SEQUENCE: 89

| | |
|---|---|
| tacaaacttt attgaaacgc acacgcgcac acacacaaac acccctgtgg atagggaaaa | 60 |
| gcacctggcc acagggtcca ctgaaacggg gaggggatgg cagcttgtaa tgtggctttt | 120 |
| gccacaaccc ccttctgaca gggaaggcct tagattgagg ccccacctcc catggtgatg | 180 |
| gggagctcag aatgggtgtcc agggagaatt tggttagggg gaggtgctag ggaggcatga | 240 |
| gcagagggca ccctccgagt ggggtcccga gggctgcaga gtcttcagta ctgtccctca | 300 |
| cagcagctgt ctcaaggctg gtccctcaa agggcgtcc cagcgcgggg cctccctgcg | 360 |
| caaacacttg gtaccctgg ctgcgcagcg gaagccagca ggacagcagt ggcgccgatc | 420 |
| agcacaacag acgccctggc ggtagggaca gcaggcccag ccctgtcggt tgtctcggca | 480 |
| gcaggtctgg ttatcatggc agaagtgtcc ttcccacact tcacgtcctt cacacccacg | 540 |
| tganggctac nggccaggaa g | 561 |

<210> SEQ ID NO 90
<211> LENGTH: 561
<212> TYPE: DNA
<213> ORGANISM: Homo sapiens

<400> SEQUENCE: 90

| | |
|---|---|
| cccgtgggtg ccatccacgg agttgttacc tgatctttgg aagcaggatc gcccgtctgc | 60 |
| actgcagtgg aagccccgtg ggcagcagtg atggccatcc ccgcatgcca cggcctctgg | 120 |
| gaaggggcag caactggaag tccctgagac ggtaaagatg caggagtggc cggcagagca | 180 |
| gtgggcatca acctggcagg ggccacccag atgcctgctc agtgttgtgg gccatttgtc | 240 |
| cagaagggga cggcagcagc tgtagctggc tcctccgggg tccaggcagc aggccacagg | 300 |
| gcagaactga ccatctgggc accgcgttcc agccaccagc cctgctgtta aggccaccca | 360 |
| gctcaccagg gtccacatgg tctgcctgcg tccgactccg cggtccttgg gccctgatgg | 420 |
| ttctacctgc tgtgagctgc ccagtgggaa gtatggctgc tgccaatgcc caacgccacc | 480 |
| tgctgctccg atcacctgca ctgctgcccc aagacactgt gtgtgacctg atccagagta | 540 |
| agtgcctctc caaggagaac g | 561 |

<210> SEQ ID NO 91
<211> LENGTH: 541
<212> TYPE: DNA
<213> ORGANISM: Homo sapiens
<220> FEATURE:
<221> NAME/KEY: misc_feature
<222> LOCATION: 480, 491

<223> OTHER INFORMATION: n = A,T,C or G

<400> SEQUENCE: 91

```
gaatcacctt tctggtttag ctagtacttt gtacagaaca atgaggtttc ccacagcgga    60
gtctccctgg gctctgtttg gctctcggta aggcaggcct acaccttttc ctctcctcta   120
tggagagggg aatatgcatt aaggtgaaaa gtcaccttcc aaaagtgaga aagggattcg   180
attgctgctt caggactgtg gaattatttg gaatgtttta caaatggttg ctacaaaaca   240
acaaaaaagg taattacaaa atgtgtacat cacaacatgc tttttaaaga cattatgcat   300
tgtgctcaca ttcccttaaa tgttgtttcc aaaggtgctc agcctctagc ccagctggat   360
tctccgggaa gaggcagaga cagtttggcg aaaaagacac agggaaggag ggggtggtga   420
aaggagaaag cagccttcca gttaaagatc agccctcagt taaaggtcag cttcccgcan   480
gctggcctca ngcggagtct gggtcagagg gaggagcagc agcagggtgg gactggggcg   540
t                                                                  541
```

<210> SEQ ID NO 92
<211> LENGTH: 551
<212> TYPE: DNA
<213> ORGANISM: Homo sapiens

<400> SEQUENCE: 92

```
aaccggagcg cgagcagtag ctgggtgggc accatggctg ggatcaccac catcgaggcg    60
gtgaagcgca agatccaggt tctgcagcag caggcagatg atgcagagga gcgagctgag   120
cgcctccagc gagaagttga gggagaaagg cgggcccggg aacaggctga ggctgaggtg   180
gcctccttga accgtaggat ccagctggtt gaagaagagc tggaccgtgc tcaggagcgc   240
ctggccactg ccctgcaaaa gctggaagaa gctgaaaaag ctgctgatga gagtgagaga   300
ggtatgaagg ttattgaaaa ccgggcctta aagatgaag aaaagatgga actccaggaa   360
atccaactca agaagctaa gcacattgca gaagaggcag ataggaagta tgaagaggtg   420
gctcgtaagt tggtgatcat tgaaggagac ttggaacgca cagaggaacg agctgagctg   480
gcagagtccc gttgccgaga gatggatgag cagattagac tgatggacca gaacctgaag   540
tgtctgagtg c                                                       551
```

<210> SEQ ID NO 93
<211> LENGTH: 531
<212> TYPE: DNA
<213> ORGANISM: Homo sapiens

<400> SEQUENCE: 93

```
gagaacttgg cctttattgt gggcccagga gggcacaaag gtcaggaggc ccaagggagg    60
gatctggttt tctggatagc caggtcatag catgggtatc agtaggaatc cgctgtagct   120
gcacaggcct cacttgctgc agttccgggg agaacacctg cactgcatgg cgttgatgac   180
ctcgtggtac acgacagagc cattggtgca gtgcaagggc acgcgcatgg gctccgtcct   240
cgagggcagg cagcaggagc attgctcctg cacatcctcg atgtcaatgg agtacacagc   300
tttgctggca cactttccct ggcagtaatg aatgtccact tcctcttggg acttacaatc   360
tcccactttg atgtactgca ccttggctgt gatgtctttg caatcaggct cctcacatgt   420
gtcacagcag gtgcctggaa ttttcacgat tttgcctcct tcagccagac acttgtgttc   480
atcaaatggt gggcagcccg tgaccctctt ctcccagatg tactctcctc t           531
```

<210> SEQ ID NO 94
<211> LENGTH: 531
<212> TYPE: DNA
<213> ORGANISM: Homo sapiens
<220> FEATURE:
<221> NAME/KEY: misc_feature
<222> LOCATION: 517
<223> OTHER INFORMATION: n = A,T,C or G

<400> SEQUENCE: 94

```
gcctggacct tgccggatca gtgccacaca gtgacttgct tggcaaatgg ccagaccttg      60
ctgcagagtc atcgtgtcaa ttgtgaccat ggaccccggc cttcatgtgc aacagccag     120
tctcctgttc gggtggagga cgtgtggc tgccgctgga cctgcccttg tgtgtgcacg      180
ggcagttcca ctcggcacat cgtcaccttc gatgggcaga atttcaagct tactggtagc   240
tgctcctatg tcatctttca aaacaaggag caggacctgg aagtgctcct ccacaatggg   300
gcctgcagcc ccggggcaaa acaagcctgc atgaagtcca ttgagattaa gcatgctggc   360
gtctctgctg agctgcacag taacatggag atggcagtgg atgggagact ggtccttgcc   420
ccgtacgttg gtgaaaacat ggaagtcagc atctacggcg ctatcatgta tgaagtcagg   480
tttacccatc ttggccacat cctcacatac accgccncaa acaacgagt t             531
```

<210> SEQ ID NO 95
<211> LENGTH: 605
<212> TYPE: DNA
<213> ORGANISM: Homo sapiens

<400> SEQUENCE: 95

```
agatcaacct ctgctggtca ggaggaatgc cttccttgtc ttggatcttt gctttgacgt      60
tctcgatagt rwcaactkkr ytsramskma agkgyratgr wmttksywgw rasyktmwwm    120
rsgraraytt agacayccm cctcwgagac gsagkaccar gtgcagaggt ggactctttc    180
tggatgttgt agtcagacag ggtgcgtcca tcttccagct gtttcccagc aaagatcaac   240
ctctgctgat caggagggat gccttcctta tcttggatct tgccttgac attctcgatg    300
gtgtcactgg gctccacctc gagggtgatg gtcttaccag tcagggtctt cacgaagaty   360
tgcatcccac ctctgagacg gagcaccagg tgcagggtrg actctttctg gatgttgtag   420
tcagacaggt gcgyccatc ttccagctgc tttccsagca aagatcaacc tctgctggtc    480
aggaggratg ccttccttgt cytggatctt tgcyttgacr ttctcratgg tgtcactcgg   540
ctccacttcg agagtgatgg tcttaccagt cagggtcttc acgaagatct gcatcccacc   600
tctaa                                                                605
```

<210> SEQ ID NO 96
<211> LENGTH: 531
<212> TYPE: DNA
<213> ORGANISM: Homo sapiens

<400> SEQUENCE: 96

```
aagtcacaaa cagacaaaga ttattaccag ctgcaagcta tattagaagc tgaacgaaga      60
gacagaggtc atgattctga gatgattgga gaccttcaag ctcgaattac atctttacaa    120
gaggaggtga agcatctcaa acataatctc gaaaagtgg aaggagaaag aaaagaggct    180
caagacatgc ttaatcactc agaaaaggaa agaataatt tagagataga tttaaactac   240
aaacttaaat cattacaaca acggttagaa caagaggtaa atgaacacaa agtaaccaaa   300
gctcgtttaa ctgacaaaca tcaatctatt gaagaggcaa agtctgtggc aatgtgtgag   360
```

| | |
|---|---:|
| atggaaaaaa agctgaaaga agaaagagaa gctcgagaga aggctgaaaa tcgggttgtt | 420 |
| cagattgaga aacagtgttc catgctagac gttgatctga agcaatctca gcagaaacta | 480 |
| gaacatttga ctggaaataa agaaaggatg gaggatgaag ttaagaatct a | 531 |

<210> SEQ ID NO 97
<211> LENGTH: 1017
<212> TYPE: DNA
<213> ORGANISM: Homo sapiens
<220> FEATURE:
<221> NAME/KEY: misc_feature
<222> LOCATION: 963, 995, 1001, 1008, 1010
<223> OTHER INFORMATION: n = A,T,C or G

<400> SEQUENCE: 97

| | |
|---|---:|
| cgcctccacc atgtccatca gggtgaccca gaagtcctac aaggtgtcca cctctggccc | 60 |
| ccgggccttc agcagccgct cctacacgag tgggcccggt tcccgcatca gctcctcgag | 120 |
| cttctcccga gtgggcagca gcaactttcg cggtggcctg gcggcggct atggtggggc | 180 |
| cagcggcatg ggaggcatca ccgcagttac ggtcaaccag agcctgctga ccccccttgt | 240 |
| cctggaggtg gaccccaaca tccaggccgt gcgcacccag gagaaggagc agatcaagac | 300 |
| cctcaacaac aagtttgcct ccttcataga caaggtacgg ttcctggagc agcagaacaa | 360 |
| gatgctggag accaagtgga gcctcctgca gcagcagaag acggctcgaa gcaacatgga | 420 |
| caacatgttc gagagctaca tcaacarcct taggcggcag ctggagactc tgggccagga | 480 |
| gaagctgaag ctggaggcgg agcttggcaa catgcagggg ctggtggagg acttcaagaa | 540 |
| caagtatgag gatgagatca ataagcgtac agagatggag aacgaatttg tcctcatcaa | 600 |
| gaaggatgtg gatgaagctt acatgaacaa ggtagagctg gagtctcgcc tggaagggct | 660 |
| gaccgacgag atcaacttcc tcaggcagct gtatgaagag gagatccggg agctgcagtc | 720 |
| ccagatctcg gacacatctg tggtgctgtc catggacaac agccgctccc tggacatgga | 780 |
| cagcatcatt gctgaggtca aggcacagta cgaggatatt gccaaccgca gccgggctga | 840 |
| ggctgagagc atgtaccagg tcaagtatga ggagctgcag agcctggctg gaagcacgg | 900 |
| ggatgacctg cggcgcacaa agactgagat ctctgagatg aacccggaac atcagcccgg | 960 |
| ctncaggctg agattgaggg cctcaaaggc caganggctt ncctggangn ccgccat | 1017 |

<210> SEQ ID NO 98
<211> LENGTH: 561
<212> TYPE: DNA
<213> ORGANISM: Homo sapiens

<400> SEQUENCE: 98

| | |
|---|---:|
| cccggagcca gccaacgagc ggaaaatggc agacaatttt tcgctccatg atgcgttatc | 60 |
| tgggtctgga aacccaaacc ctcaaggatg gcctggcgca tgggggaacc agcctgctgg | 120 |
| ggcaggggc tacccagggg cttcctatcc tggggcctac cccgggcagg cacccccagg | 180 |
| ggcttatcct ggacaggcac ctccaggcgc ctaccctgga gcacctggag cttatcccgg | 240 |
| agcacctgca cctggagtct acccaggcc acccagcggc cctggggcct acccatcttc | 300 |
| tggacagcca agtgccaccg gagcctaccc tgccactggc ccctatggcg cccctgctgg | 360 |
| gccactgatt gtgccttata acctgccttt gcctggggga gtggtgcctc gcatgctgat | 420 |
| aacaattctg ggcacggtga agcccaatgc aaacagaatt gctttagatt tccaagagg | 480 |
| gaatgatgtt gccttccact ttaacccacg cttcaatgag aacaacagga gagtcattgg | 540 |
| ttgcaataca aagctggata a | 561 |

<210> SEQ ID NO 99
<211> LENGTH: 636
<212> TYPE: DNA
<213> ORGANISM: Homo sapiens

<400> SEQUENCE: 99

```
gggaatgcaa caactttatt gaaaggaaag tgcaatgaaa tttgttgaaa ccttaaaagg      60
ggaaacttag acacccccc tcragcgmag kaccargtgc araggtggac tctttctgga     120
tgttgtagtc agacagggtr cgwccatctt ccagctgttt yccrgcaaag atcaacctct    180
gctgatcagg aggratgcct tccttatctt ggatctttgc cttgacattc tcgatggtgt    240
cactgggctc cacctcgagg gtgatggtct taccagtcag ggtcttcacg aagatytgca    300
tcccacctct gagacggagc accaggtgca gggtrgactc tttctggatg ttgtagtcag    360
acagggtgcg yccatcttcc agctgctttc csagcaaaga tcaacctctg ctggtcagga    420
ggratgcctt ccttgtcytg gatctttgcy ttgacrttct caatggtgtc actcggctcc    480
acttcgagag tgatggtctt accagtcagg gtcttcacga agatctgcat cccacctcta    540
agacggagca ccaggtgcag ggtggactct ttctggatgg ttgtagtcag acagggtgcg    600
tccatcttcc agctgtttcc cagcaaagat caacct                              636
```

<210> SEQ ID NO 100
<211> LENGTH: 697
<212> TYPE: DNA
<213> ORGANISM: Homo sapiens

<400> SEQUENCE: 100

```
aggttgatct tgctgggaa acagctggaa gatggacgca ccctgtctga ctacaaccat      60
ccagaaagag tccaccctgc acctggtgct ccgtcttaga ggtgggatgc agatcttcgt    120
gaagaccctg actggtaaga ccatcactct cgaagtggag ccgagtgaca ccattgagaa    180
ygtcaargca aagatccarg acaaggaagg catycctcct gaccagcaga ggttgatctt    240
tgctsggaaa gcagctggaa gatggrcgca ccctgtctga ctacaacatc cagaaagagt    300
cyaccctgca cctggtgctc cgtctcagag gtgggatgca ratcttcgtg aagaccctga    360
ctggtaagac catcaccctc gaggtggagc ccagtgacac catcgagaat gtcaaggcaa    420
agatccaaga taaggaaggc atccctcctg atcagcagag gttgatcttt gctgggaaac    480
agctggaaga tggacgcacc ctgtctgact acaacatcca gaaagagtcc acctytgcac    540
ytggtmctbc gtctyagagg kgggrtgcaa atctwmgtkw agacactcac tkkyaagryy    600
atcamcmwtg akktcgakys castkwcact wtcrakaamg tyrwwgcawa gatccmagac    660
aaggaaggca ttcctcctga ccagcagagg ttgatct                              697
```

<210> SEQ ID NO 101
<211> LENGTH: 451
<212> TYPE: DNA
<213> ORGANISM: Homo sapiens

<400> SEQUENCE: 101

```
atggagtctc actctgtcga ccaggctgga gcgctgtggt gcgatatcgg ctcactgcag      60
tctccacttc ctgggttcaa gcgatcctcc tgcctcagcc tcccgagtag ctgggactac    120
aggcaggcgt caccataatt tttgtatttt tagtagagac atggtttcgc catgttggct    180
gggctggtct cgaactcctg acctcaagtg atctgtcctg cctcccaaa gtgttgggat    240
```

```
tacaggcgaa agccaacgct cccggccagg gaacaacttt agaatgaagg aaatatgcaa      300
aagaacatca catcaaggat caattaatta ccatctatta attactatat gtgggtaatt      360
atgactattt cccaagcatt ctacgttgac tgcttgagaa gatgtttgtc ctgcatggtg      420
gagagtggag aagggccagg attcttaggt t                                     451

<210> SEQ ID NO 102
<211> LENGTH: 571
<212> TYPE: DNA
<213> ORGANISM: Homo sapiens

<400> SEQUENCE: 102
agcgcggtct tccggcgcga gaaagctgaa ggtgatgtgg ccgccctcaa ccgacgcatc       60
cagctcgttg aggaggagtt ggacagggct caggaacgac tggccacggc cctgcagaag      120
ctggaggagg cagaaaaagc tgcagatgag agtgagagag gaatgaaggt gatagaaaac      180
cgggccatga aggatgagga gaagatggag attcaggaga tgcagctcaa agaggccaag      240
cacattgcgg aagaggctga ccgcaaatac gaggaggtag ctcgtaagct ggtcatcctg      300
gagggtgagc tggagagggc agaggagcgt gcggaggtgt ctgaactaaa atgtggtgac      360
ctggaagaag aactcaagaa tgttactaac aatctgaaat ctctggaggc tgcatctgaa      420
aagtattctg aaaaggagga caaatatgaa gaagaaatta aacttctgtc tgacaaactg      480
aaagaggctg agacccgtgc tgaatttgca gagagaacgg ttgcaaaact ggaaagaca       540 attgatgacc tggaagagaa acttgcccag c                                     571

<210> SEQ ID NO 103
<211> LENGTH: 451
<212> TYPE: DNA
<213> ORGANISM: Homo sapiens

<400> SEQUENCE: 103
gtgcacaggt cccatttatt gtagaaaata ataataatta cagtgatgaa tagctcttct       60
taaattacaa aacagaaacc acaaagaagg aagaggaaaa accccaggac ttccaagggt      120
gaagctgtcc cctcctccct gccaccctcc caggctcatt agtgtccttg aaggggcag       180 aggactcaga ggggatcagt ctccaggggc cctgggctga gcgggtgag gcagagagtc       240 ctgaggccac agagctgggc aacctgagcc gcctctctgg cccctcccc caccactgcc       300 caaacctgtt tacagcacct tcgcccctcc cctctaaacc cgtccatcca ctctgcactt      360
cccaggcagg tgggtgggcc aggcctcagc catactcctg ggcgcgggtt tcggtgagca      420
aggcacagtc ccagaggtga tatcaaggcc t                                     451

<210> SEQ ID NO 104
<211> LENGTH: 441
<212> TYPE: DNA
<213> ORGANISM: Homo sapiens

<400> SEQUENCE: 104
gcaaggaact ggtctgctca cacttgctgg cttgcgcatc aggactggct ttatctcctg       60
actcacggtg caaaggtgca ctctgcgaac gttaagtccg tccccagcgc ttggaatcct      120
acggccccca cagccggatc ccctcagcct tccaggtcct caactcccgt ggacgctgaa      180
caatggcctc catggggcta caggtaatgg gcatcgcgct ggccgtcctg ggctggctgg      240
ccgtcatgct gtgctgcgcg ctgcccatgt ggcgcgtgac ggccttcatc ggcagcaaca      300
ttgtcacctc gcagaccatc tgggagggcc tatggatgaa ctgcgtggtg cagagcaccg      360
```

```
gccagatgca gtgcaaggtg tacgactcgc tgctggcact ccgcaggac ctgcaggcgg    420 cccgcgccct cgtcatcatc a                                             441

<210> SEQ ID NO 105
<211> LENGTH: 509
<212> TYPE: DNA
<213> ORGANISM: Homo sapiens
<220> FEATURE:
<221> NAME/KEY: misc_feature
<222> LOCATION: 195
<223> OTHER INFORMATION: n = A,T,C or G

<400> SEQUENCE: 105
tgcaaaaggg acacaggggt tcaaaaataa aaatttctct tccccctccc caaacctgta    60
ccccagctcc ccgaccacaa ccccctttcct cccccgggga agcaagaag gagcaggtgt    120 ggcatctgca gctgggaaga gagaggccgg ggaggtgccg agctcggtgc tggtctcttt    180
ccaaatataa atacntgtgt cagaactgga aaatcctcca gcacccacca cccaagcact    240
ctccgttttc tgccggtgtt tggagagggg cggggggcag gggcgccagg caccggctgg    300
ctgcggtcta ctgcatccgc tgggtgtgca ccccgcgagc ctcctgctgc tcattgtaga    360
agagatgaca ctcggggtcc ccccggatgg tggggctcc ctggatcagc ttcccggtgt     420
tggggttcac acaccagcac tccccacgct gcccgttcag agacatcttg cactgtttga    480
ggttgtacag gccatgcttg tcacagttg                                      509

<210> SEQ ID NO 106
<211> LENGTH: 571
<212> TYPE: DNA
<213> ORGANISM: Homo sapiens

<400> SEQUENCE: 106
gggttggagg gactggttct ttatttcaaa aagacacttg tcaatattca gtatcaaaac    60
agttgcacta ttgatttctc tttctcccaa tcggccccaa agagaccaca taaaaggaga    120
gtacatttta agccaataag ctgcaggatg tacacctaac agacctccta gaaaccttac    180
cagaaaatgg ggactgggta gggaaggaaa cttaaaagat caacaaactg ccagcccacg    240
gactgcagag gctgtcacag ccagatgggg tggccagggt gccacaaacc caaagcaaag    300
tttcaaaata atataaaatt taaaaagttt tgtacataag ctattcaaga tttctccagc    360
actgactgat acaaagcaca attgagatgg cacttctaga gacagcagct tcaaacccag    420
aaaagggtga tgagatgagt ttcacatggc taaatcagtg gcaaaaacac agtcttcttt    480
ctttctttct ttcaaggagg caggaaagca attaagtggt cacctcaaca taaggggggac    540 atgatccatt ctgtaagcag ttgtgaaggg g                                   571

<210> SEQ ID NO 107
<211> LENGTH: 555
<212> TYPE: DNA
<213> ORGANISM: Homo sapiens

<400> SEQUENCE: 107
caggaaccgg agcgcgagca gtagctgggt gggcaccatg gctgggatca ccaccatcga    60
ggcggtgaag cgcaagatcc aggttctgca gcagcaggca gatgatgcag aggagcgagc    120
tgagcgcctc cagcgagaag ttgagggaga aaggcgggcc cggaacagg ctgaggctga     180 ggtggcctcc ttgaaccgta ggatccagct ggttgaagaa gagctggacc gtgctcagga    240
```

```
gcgcctggcc actgccctgc aaaagctgga agaagctgaa aaagctgctg atgagagtga    300
gagaggtatg aaggttattg aaaaccgggc cttaaaagat gaagaaaaga tggaactcca    360
ggaaatccaa ctcaaagaag ctaagcacat tgcagaagag gcagatagga agtatgaaga    420
ggtggctcgt aagttggtga tcattgaagg agacttggaa cgcacagagg aacgagctga    480
gctggcagag tcccgttgcc gagagatgga tgagcagatt agactgatgg accagaacct    540
gaagtgtctg agtgc                                                    555

<210> SEQ ID NO 108
<211> LENGTH: 541
<212> TYPE: DNA
<213> ORGANISM: Homo sapiens

<400> SEQUENCE: 108
atctacgtca tcaatcaggc tggagacacc atgttcaatc gagctaagct gctcaatatt    60
ggctttcaag aggccttgaa ggactatgat tacaactgct ttgtgttcag tgatgtggac    120
ctcattccga tggacgaccg taatgcctac aggtgttttt cgcagccacg gcacatttct    180
gttgcaatgg acaagttcgg gtttagcctg ccatatgttc agtattttgg aggtgtctct    240
gctctcagta acaacagtt tcttgccatc aatggattcc ctaataatta ttggggttgg    300
ggaggagaag atgacgacat ttttaacaga ttagttcata aaggcatgtc tatatcacgt    360
ccaaatgctg tagtagggag gtgtcgaatg atccggcatt caagagacaa gaaaaatgag    420
cccaatcctc agaggtttga ccggatcgca catacaaagg aaacgatgcg cttcgatggt    480
ttgaactcac ttacctacaa ggtgttggat gtcagagata cccgttatat acccaaatca    540
c                                                                    541

<210> SEQ ID NO 109
<211> LENGTH: 411
<212> TYPE: DNA
<213> ORGANISM: Homo sapiens

<400> SEQUENCE: 109
ctagacctct aattaaaagg cacaatcatg ctggagaatg aacagtctga ccccgagggc    60
cacagcgaat tttagggaag gaggcaaaga ggtgagaagg gaaaggaaag aaggaaggaa    120
ggagaacaat aagaactgga gacgttgggt gggtcaggga gtgtggtgga ggctcggaga    180
gatggtaaac aaacctgact gctatgagtt ttcaacccca tagtctaggg ccatgagggc    240
gtcagttctt ggtggctgag ggtccttcca cccagcccac ctggggagt ggagtgggga    300 gttctgccag gtaagcagat gttgtctccc aagttcctga cccagatgtc tggcaggata    360
acgctgacct gttccctcaa caagggacct gaaagtaatt ttgctctttta c           411

<210> SEQ ID NO 110
<211> LENGTH: 451
<212> TYPE: DNA
<213> ORGANISM: Homo sapiens

<400> SEQUENCE: 110
ccgaattcaa gcgtcaacga tccytcccct accatcaaat caattggcca ccaatggtac    60
tgaacctacg agtacaccga ctacgggcgg actaatcttc aactcctaca tacttccccc    120
attattccta gaaccaggcg acctgcgact ccttgacgtt gacaatcgag tagtactccc    180
gattgaagcc cccattcgta taataattac atcacaagac gtcttgcact catgagctgt    240
ccccacatta ggcttaaaaa cagatgcaat tcccggacgt ctaagccaaa ccactttcac    300
```

```
cgctacacga ccgggggtat actacggtca atgctctgaa atctgtggag caaaccacag    360
tttcatgccc atcgtcctag aattaattcc cctaaaaatc tttgaaatag ggcccgtatt    420
taccctatag cacccctct accccctcta g                                    451
```

<210> SEQ ID NO 111
<211> LENGTH: 541
<212> TYPE: DNA
<213> ORGANISM: Homo sapiens

<400> SEQUENCE: 111

```
gctcttcaca cttttattgt taattctctt cacatggcag atacagagct gtcgtcttga     60
agaccaccac tgaccaggaa atgccacttt tacaaaatca tcccccctt tcatgattgg    120 aacagttttc ctgaccgtct gggagcgttg aagggtgacc agcacatttg cacatgcaaa    180
aaaggagtga ccccaaggcc tcaaccacac ttcccagagc tcaccatggg ctgcaggtga    240
cttgccaggt ttggggttcg tgagctttcc ttgctgctgc ggtggggagg ccctcaagaa    300
ctgagaggcc ggggtatgct tcatgagtgt taacatttac gggacaaaag cgcatcatta    360
ggataaggaa cagccacagc acttcatgct tgtgagggtt agctgtagga gcgggtgaaa    420
ggattccagt ttatgaaaat ttaaagcaaa caacggtttt tagctgggtg ggaaacagga    480
aaactgtgat gtcggccaat gaccaccatt tttctgccca tgtgaaggtc cccatgaaac    540
c                                                                    541
```

<210> SEQ ID NO 112
<211> LENGTH: 521
<212> TYPE: DNA
<213> ORGANISM: Homo sapiens

<400> SEQUENCE: 112

```
caagcgcttg gcgtttggac ccagttcagt gaggttcttg ggttttgtgc ctttggggat     60
tttggtttga cccaggggtc agccttagga aggtcttcag gaggaggccg agttcccctt    120
cagtaccacc cctctctccc cactttccct ctcccggcaa catctctggg aatcaacagc    180
atattgacac gttggagccg agcctgaaca tgcccctcgg ccccagcaca tggaaaaccc    240
ccttccttgc ctaaggtgtc tgagtttctg gctcttgagg catttccaga cttgaaattc    300
tcatcagtcc attgctcttg agtctttgca gagaacctca gatcaggtgc acctgggaga    360
aagactttgt ccccacttac agatctatct cctcccttgg gaaggcagg gaatggggac    420 ggtgtatgga ggggaaggga tctcctgcgc ccttcattgc cacacttggt gggaccatga    480
acatctttag tgtctgagct tctcaaatta ctgcaatagg a                        521
```

<210> SEQ ID NO 113
<211> LENGTH: 568
<212> TYPE: DNA
<213> ORGANISM: Homo sapiens

<400> SEQUENCE: 113

```
agcgtcaaat cagaatggaa aagactcaaa accatcatca acaccaagat caaaaggaca     60
agratccttc aagaaacagg aaaaaactcc taaaacacca aaaggaccta gttctgtaga    120
agacattaaa gcaaaaatgc aagcaagtat agaaaaaggt ggttctcttc ccaaagtgga    180
agccaaattc atcaattatg tgaagaattg cttccggatg actgaccaag aggctattca    240
agatctctgg cagtggagga agtctcttta agaaaatagt ttaaacaatt tgttaaaaaa    300
```

-continued

```
ttttccgtct tatttcattt ctgtaacagt tgatatctgg ctgtcctttt tataatgcag    360
agtgagaact ttccctaccg tgtttgataa atgttgtcca ggttctattg ccaagaatgt    420
gttgtccaaa atgcctgttt agttttaaa gatggaactc cacccttgc ttggttttaa     480 gtatgtatgg aatgttatga taggacatag tagtagcggt ggtcagacat ggaaatggtg    540
ggsmgacaaa aatatacatg tgaaataa                                       568
```

<210> SEQ ID NO 114
<211> LENGTH: 483
<212> TYPE: DNA
<213> ORGANISM: Homo sapiens

<400> SEQUENCE: 114

```
tccgaattcc aagcgaatta tggacaaacg attccttta gaggattact ttttcaatt      60 tcggttttag taatctaggc tttgcctgta aagaatacaa cgatggattt taaatactgt   120
ttgtggaatg tgtttaaagg attgattcta gaacctttgt atatttgata gtatttctaa   180
ctttcatttc tttactgttt gcagttaatg ttcatgttct gctatgcaat cgtttatatg   240
cacgtttctt taattttttt agattttcct ggatgtatag tttaaacaac aaaaagtcta   300
tttaaaactg tagcagtagt ttacagttct agcaaagagg aaagttgtgg ggttaaactt   360
tgtattttct ttcttataga ggcttctaaa aaggtatttt tatatgttct ttttaacaaa   420
tattgtgtac aacctttaaa acatcaatgt ttggatcaaa acaagaccca gcttattttc   480
tgc                                                                  483
```

<210> SEQ ID NO 115
<211> LENGTH: 521
<212> TYPE: DNA
<213> ORGANISM: Homo sapiens

<400> SEQUENCE: 115

```
tgtggtggcg cgggctgagg tggaggccca ggactctgac cctgcccctg ccttcagcaa     60
ggcccccggc agcgccggcc actacgaact gccgtgggtt gaaaaatata ggccagtaaa   120
gctgaatgaa attgtcggga atgaagacac cgtgagcagg ctagaggtct ttgcaaggga   180
aggaaatgtg cccaacatca tcattgcggg ccctccagga accggcaaga ccacaagcat   240
tctgtgcttg gcccgggccc tgctgggccc agcactcaaa gatgccatgt tggaactcaa   300
tgcttcaaat gacaggggca ttgacgttgt gaggaataaa attaaaatgt ttgctcaaca   360
aaaagtcact cttcccaaag gccgacataa gatcatcatt ctggatgaag cagacagcat   420
gaccgacgga gcccagcaag ccttgaggag aaccatggaa atctactcta aaaccactcg   480
ttcgcccttg cttgtaatgc ttcggataag atcatcgagc c                       521
```

<210> SEQ ID NO 116
<211> LENGTH: 501
<212> TYPE: DNA
<213> ORGANISM: Homo sapiens

<400> SEQUENCE: 116

```
ctttgcaaag cttttatttc atgtctgcgg catggaatcc acctgcacat ggcatcttag     60
ctgtgaagga gaaagcagtg cacgagaagg aatgagtggg cggaaccaac ggcctccaca   120
agctgccttc cagcagcctg ccaaggccat ggcagagaga gactgcaaac aaacacaagc   180
aaacagagtc tcttcacagc tggagtctga aagctcatag tggcatgtgt gaatctgaca   240
aaattaaaag tgtgcatagt ccattacatg cataaaacac taataataat cctgtttaca   300
```

```
cgtgactgca gcaggcaggt ccagctccac cactgccctc ctgccacatc acatcaagtg      360
ccatggttta gagggttttt catatgtaat tcttttattc tgtaaaaggt aacaaaatat      420
acagaacaaa actttcccct tttaaaacta atgttacaaa tctgtattat cacttggata      480
taaatagtat ataagctgat c                                                501

<210> SEQ ID NO 117
<211> LENGTH: 451
<212> TYPE: DNA
<213> ORGANISM: Homo sapiens
<220> FEATURE:
<221> NAME/KEY: misc_feature
<222> LOCATION: 320
<223> OTHER INFORMATION: n = A,T,C or G

<400> SEQUENCE: 117
caagggatat atgttgaggg tacrgrgtga cactgaacag atcacaaagc acgagaaaca       60
ttagttctct ccctccccag cgtctccttc gtctccctgg ttttccgatg tccacagagt      120
gagattgtcc ctaagtaact gcatgatcag agtgctgkct ttataagact cttcattcag      180
cgtatccaat tcagcaattg cttcatcaaa tgccgttttt gccaggctac aggccttttc      240
aggagagttt agaatctcat agtaaaagac tgagaaattt agtgccagac caagacgaat      300
tgggtgtgta ggctgcattn ctttcttact aatttcaaat gcttcctggt aagcctgctg      360
ggagttcgac acaagtggtt tgtttgttgc tccagatgcc acttcagaaa gatacctaaa      420
ataatctcct ttcattttca aagtagaaca c                                    451

<210> SEQ ID NO 118
<211> LENGTH: 501
<212> TYPE: DNA
<213> ORGANISM: Homo sapiens

<400> SEQUENCE: 118
tccggagccg gggtagtcgc cgccgccgcc gccggtgcag ccactgcagg caccgctgcc       60
gccgcctgag tagtgggctt aggaaggaag aggtcatctc gctcggagct tcgctcggaa      120
gggtctttgt tccctgcagc cctcccacgg gaatgacaat ggataaaagt gagctggtac      180
agaaagccaa actcgctgag caggctgagc gatatgatga tatggctgca gccatgaagg      240
cagtcacaga acagggcat gaactctcca cgaagagag aaatctgctc tctgttgcct      300
acaagaatgt ggtaaggccg cccgccgctc ttcctggcgt gtcatctcca gcattgagca      360
gaaaacagag aggaatgaga agaagcagca gatgggcaaa gagtaccgtg agaagataga      420
ggcagaactg caggacatct gcaatgatgt tctggagctt gttggacaaa tatcttattc      480
caatgctaca caacccagaa a                                                501

<210> SEQ ID NO 119
<211> LENGTH: 391
<212> TYPE: DNA
<213> ORGANISM: Homo sapiens

<400> SEQUENCE: 119
aaaaagcagc argttcaaca caaaatagaa atctcaaatg taggatagaa caaaaccaag       60
tgtgtgaggg gggaagcaac agcaaaagga agaaatgaga tgttgcaaaa aagatggagg      120
agggttcccc tctcctctgg ggactgactc aaacactgat gtggcagtat acaccattcc      180
agagtcaggg gtgttcattc ttttttggga gtaagaaaag gtgggattaa agaagacgtt      240
```

| | |
|---|---|
| tctggaggct tagggaccaa ggctggtctc tttcccccct cccaacccc ttgatccctt | 300 |
| tctctgatca ggggaaagga gctcgaatga gggaggtaga gttggaaagg gaaaggattc | 360 |
| cacttgacag aatgggacag actccttccc a | 391 |

<210> SEQ ID NO 120
<211> LENGTH: 421
<212> TYPE: DNA
<213> ORGANISM: Homo sapiens
<220> FEATURE:
<221> NAME/KEY: misc_feature
<222> LOCATION: 409
<223> OTHER INFORMATION: n = A,T,C or G

<400> SEQUENCE: 120

| | |
|---|---|
| tggcaatagc acagccatcc aggagctctt cargcgcatc tcggagcagt tcactgccat | 60 |
| gttccgccgg aaggccttcc tccactggta cacaggcgag ggcatggacg agatggagtt | 120 |
| caccgaggct gagagcaaca tgaacgacct cgtctctgag tatcaagcag taccaggatg | 180 |
| ccaccgcaga agaggaggag gatttcggtg aggaggccga agaggaggcc taaggcagag | 240 |
| cccccatcac ctcaggcttc tcagttccct tagccgtctt actcaactgc ccctttcctc | 300 |
| tccctcagaa tttgtgtttg ctgcctctat cttgtttttt gttttttctt ctgggggggt | 360 |
| ctagaacagt gcctggcaca tagtaggcgc tcaataaata cttggttgnt gaatgtctcc | 420 |
| t | 421 |

<210> SEQ ID NO 121
<211> LENGTH: 206
<212> TYPE: DNA
<213> ORGANISM: Homo sapiens

<400> SEQUENCE: 121

| | |
|---|---|
| agctggcgct agggctcggt tgtgaaatac agcgtrgtca gcccttgcgc tcagtgtaga | 60 |
| aacccacgcc tgtaaggtcg gtcttcgtcc atctgctttt ttctgaaata cactaagagc | 120 |
| agccacaaaa ctgtaacctc aaggaaacca taaagcttgg agtgccttaa ttttaacca | 180 |
| gtttccaata aaacggttta ctacct | 206 |

<210> SEQ ID NO 122
<211> LENGTH: 131
<212> TYPE: DNA
<213> ORGANISM: Homo sapiens

<400> SEQUENCE: 122

| | |
|---|---|
| ggagatgaag atgaggaagc tgagtcagct acgggcargc gggcagctga agatgatgag | 60 |
| gatgacgatg tcgataccaa gaagcagaag accgacgagg atgactagac agcaaaaaag | 120 |
| gaaaagttaa a | 131 |

<210> SEQ ID NO 123
<211> LENGTH: 231
<212> TYPE: DNA
<213> ORGANISM: Homo sapiens
<220> FEATURE:
<221> NAME/KEY: misc_feature
<222> LOCATION: 166, 202, 222, 225
<223> OTHER INFORMATION: n = A,T,C or G

<400> SEQUENCE: 123

| | |
|---|---|
| gatgaaaatt aaatacttaa attaatcaaa aggcactacg ataccaccta aaacctactg | 60 |
| cctcagtggc agtakgctaa kgaagatcaa gctacagsac atyatctaat atgaatgtta | 120 |

```
gcaattacat akcargaagc atgtttgctt tccagaagac tatggnacaa tggtcattwg      180
ggcccaagag gatatttggc cnggaaagga tcaagataga tnaangtaaa g              231
```

<210> SEQ ID NO 124
<211> LENGTH: 521
<212> TYPE: DNA
<213> ORGANISM: Homo sapiens
<220> FEATURE:
<221> NAME/KEY: misc_feature
<222> LOCATION: 284, 412, 513
<223> OTHER INFORMATION: n = A,T,C or G

<400> SEQUENCE: 124

```
gagtagcaac gcaaagcgct tggtattgag tctgtgggsg acttcggttc cggtctctgc      60
agcagccgtg atcgcttagt ggagtgctta gggtagttgg ccaggatgcc gaatatcaaa     120
atcttcagca ggcagctccc accaggactt atctcasaaa attgctgacc gcctgggcct     180
ggagctaggc aaggtggtga ctaagaaatt cagcaaccag gagacctgtg tggaaattgg     240
tgaaagtgta ccgtggagag gatgtctaca ttgttcagag tggntgtggc gaaatcaatg     300
acaatttaat ggagcttttg atcatgatta atgcctgcaa gattgcttca gccagccggg     360
ttactgcagt catcccatgc ttcccttatg ccccggcagg ataagaaaga tnagagccgg     420
gccgccaatc tcagccaagc ttggtgcaaa tatgctatct gtagcagtgc agatcatatt     480
atcaccatgg acctacatgc ttctcaaatt canggctttt t                         521
```

<210> SEQ ID NO 125
<211> LENGTH: 341
<212> TYPE: DNA
<213> ORGANISM: Homo sapiens
<220> FEATURE:
<221> NAME/KEY: misc_feature
<222> LOCATION: 277
<223> OTHER INFORMATION: n = A,T,C or G

<400> SEQUENCE: 125

```
atgcaaaagg ggacacaggg ggttcaaaaa taaaaatttc tcttcccct ccccaaacct       60 gtacccagc tccccgacca caacccctt cctccccgg ggaaagcaag aaggagcagg        120
tgtggcatct gcagctggga agagagaggc cggggaggtg ccgagctcgg tgctggtctc     180
tttccaaata taaatacgtg tgtcagaact ggaaaatcct ccagcaccca ccacccaagc     240
actctccgtt ttctgccggt gtttggagag gggcggnggg caggggcgcc aggcaccggc     300
tggctgcggt ctactgcatc cgctgggtgt gcaccccgcg a                         341
```

<210> SEQ ID NO 126
<211> LENGTH: 521
<212> TYPE: DNA
<213> ORGANISM: Homo sapiens
<220> FEATURE:
<221> NAME/KEY: misc_feature
<222> LOCATION: 353, 399, 455
<223> OTHER INFORMATION: n = A,T,C or G

<400> SEQUENCE: 126

```
aggttggaga aggtcatgca ggtgcagatt gtccaggskc agccacaggg tcaagcccaa      60
caggcccaga gtggcactgg acagaccatg caggtgatgc agcagatcat cactaacaca     120
ggagagatcc agcagatccc ggtgcagctg aatgccggcc agctgcagta tatccgctta     180
gcccagcctg tatcaggcac tcaagttgtg cagggacaga tccagacact tgccaccaat     240
```

```
gctcaacaga ttacacagac agaggtccag caaggacagc agcagttcaa gccagttcac      300
aagatggaca gcagctctac cagatccagc aagtcaccat gcctgcgggc cangacctcg      360
ccagcccatg ttcatccagt caagccaacc agcccttcna cgggcaggcc cccaggtga       420 ccggcgactg aagggcctga gctggcaagg ccaangacac ccaacacaat ttttgccata      480
cagcccccag gcaatgggca gcctttct cccagagga c                            521
```

<210> SEQ ID NO 127
<211> LENGTH: 351
<212> TYPE: DNA
<213> ORGANISM: Homo sapiens

<400> SEQUENCE: 127

```
tgagatttat tgcatttcat gcagcttgaa gtccatgcaa aggrgactag cacagttttt      60
aatgcattta aaaataaaa gggaggtggg cagcaaacac acaaagtcct agtttcctgg       120
gtccctggga gaaagagtg tggcaatgaa tccacccact ctccacaggg aataaatctg       180
tctcttaaat gcaagaatg tttccatggc ctctggatgc aaatacacag agctctgggg       240
tcagagcaag ggatggggag aggaccacga gtgaaaaagc agctcacac attcacctaa       300 ttccatctga gggcaagaac aacgtggcaa gtcttggggg tagcagctgt t               351
```

<210> SEQ ID NO 128
<211> LENGTH: 521
<212> TYPE: DNA
<213> ORGANISM: Homo sapiens

<400> SEQUENCE: 128

```
tccagacatg ctcctgtcct aggcggggag caggaaccag acctgctatg ggaagcagaa      60
agagttaagg gaaggtttcc tttcattcct gttccttctc ttttgctttt gaacagtttt      120
taaatatact aatagctaag tcatttgcca gccaggtccc ggtgaacagt agagaacaag      180
gagcttgcta agaattaatt ttgctgtttt tcaccccatt caaacagagc tgccctgttc      240
cctgatggag ttccattcct gccagggcac ggctgagtaa cacgaagcca ttcaagaaag      300
gcgggtgtga atcactgcc accccatgga cagacccctc actcttcctt cttagccgca      360
gcgctactta ataaatatat ttatactttg aaattatgat aaccgatttt tcccatgcgg      420
catcctaagg gcacttgcca gctcttatcc ggacagtcaa gcactgttgt tggacaacag      480
ataaaggaaa agaaaagaa gaaaacaacc gcaacttctg t                          521
```

<210> SEQ ID NO 129
<211> LENGTH: 521
<212> TYPE: DNA
<213> ORGANISM: Homo sapiens

<400> SEQUENCE: 129

```
tgagacggac cactggcctg gtcccccctc atktgctgtc gtaggacctg acatgaaacg      60
cagatctagt ggcagagagg aagatgatga ggaacttctg agacgtcggc agcttcaaga      120
agagcaatta atgaagctta actcaggcct gggacagttg atcttgaaag aagagatgga      180
gaaagagagc cgggaaaggt catctctgtt agccagtcgc tacgattctc ccatcaactc      240
agcttcacat attccatcat ctaaaactgc atctctccct ggctatggaa gaaatgggct      300
tcaccggcct gtttctaccg acttcgctca gtataacagc tatgggatg tcagcggggg      360 agtgcgagat taccagacac ttccagatgg ccacatgcct gcaatgagaa tggaccgagg      420
agtgtctatg cccaacatgt tggaaccaaa gatatttcca tatgaaatgc tcatggtgac      480
```
caacagaggg ccgaaaccaa atctcagaga ggtggacaga a        521

<210> SEQ ID NO 130
<211> LENGTH: 270
<212> TYPE: DNA
<213> ORGANISM: Homo sapiens

<400> SEQUENCE: 130
tcactttatt tttcttgtat aaaaaccta tgttgtagcc acagctggag cctgagtccg     60
ctgcacggag actctggtgt gggtcttgac gaggtggtca gtgaactcct gatagggaga   120
cttggtgaat acagtctcct tccagaggtc gggggtcagg tagctgtagg tcttagaaat   180
ggcatcaaag gtggccttgg cgaagttgcc cagggtggca gtgcagcccc gggctgaggt   240
gtagcagtca tcgataccag ccatcatgag                                    270

<210> SEQ ID NO 131
<211> LENGTH: 341
<212> TYPE: DNA
<213> ORGANISM: Homo sapiens

<400> SEQUENCE: 131
ctggaatata gacccgtgat cgacaaaact tgaacgagg ctgactgtgc caccgtcccg     60
ccagccattc gctcctactg atgagacaag atgtggtgat gacagaatca gcttttgtaa   120
ttatgtataa tagctcatgc atgtgtccat gtcataactg tcttcatacg cttctgcact   180
ctggggaaga aggagtacat tgaagggaga ttggcaccta gtggctggga gcttgccagg   240
aacccagtgg ccagggagcg tggcacttac cttttgtccct tgcttcattc ttgtgagatg  300
ataaaactgg gcacagctct taaataaaat ataaatgaac a                       341

<210> SEQ ID NO 132
<211> LENGTH: 844
<212> TYPE: DNA
<213> ORGANISM: Homo sapiens
<220> FEATURE:
<221> NAME/KEY: misc_feature
<222> LOCATION: 37
<223> OTHER INFORMATION: n = A,T,C or G

<400> SEQUENCE: 132
tgaatgggga ggagctgacc caggaaatgg agcttgngga gaccaggcct gcaggggatg     60
gaaccttcca gaagtgggca tctgtggtgg tgcctcttgg gaaggagcag aagtacacat   120
gccatgtgga acatgagggg ctgcctgagc ccctcaccct gagatggggc aaggaggagc   180
ctccttcatc caccaagact aacacagtaa tcattgctgt tccggttgtc cttggagctg   240
tggtcatcct tggagctgtg atggcttttg tgatgaagag gaggagaaac acaggtggaa   300
aaggagggga ctatgctctg gctccaggct cccagagctc tgatatgtct ctcccagatt   360
gtaaagtgtg aagacagctg cctggtgtgg acttggtgac agacaatgtc ttcacacatc   420
tcctgtgaca tccagagacc tcagttctct ttagtcaagt gtctgatgtt ccctgtgagt   480
ctgcgggctc aaagtgaaga actgtggagc ccagtccacc cctgcacacc aggaccctat   540
ccctgcactg ccctgtgttc ccttccacag ccaaccttgc tgctccagcc aaacattggt   600
ggacatctgc agcctgtcag ctccatgcta ccctgacctt caactcctca cttccacact   660
gagaataata atttgaatgt gggtggctgg agagatggct cagcgctgac tgctcttcca   720
aaggtcctga gttcaaatcc cagcaaccac atggtggctc acaaccatct gtaatgggat   780

```
ctaataccct cttctgcagt gtctgaagac asctacagtg tacttacata taataataaa    840
taag                                                                 844

<210> SEQ ID NO 133
<211> LENGTH: 601
<212> TYPE: DNA
<213> ORGANISM: Homo sapiens

<400> SEQUENCE: 133
ggccgggcgc gcgcgccccc gccacacgca cgccgggcgt gccagtttat aaagggagag     60
agcaagcagc gagtcttgaa gctctgtttg gtgctttgga tccatttcca tcggtcctta    120
cagccgctcg tcagactcca gcagccaaga tggtgaagca gatcgagagc aagactgctt    180
ttcaggaagc cttggacgct gcaggtgata aacttgtagt agttgacttc tcagccacgt    240
ggtgtgggcc ttgcaaaatg atcaagcctt tctttcattc cctctctgaa agtattcca    300 acgtgatatt ccttgaagta gatgtggatg actgtcagga tgttgcttca gagtgtgaag    360
tcaaatgcat gccaacattc cagttttta agaagggaca aaaggtgggt gaattttctg    420
gagccaataa ggaaaagctt gaagccacca ttaatgaatt agtctaatca tgttttctga    480
aaatataacc agccattggc tatttaaaac ttgtaatttt tttaatttac aaaaatataa    540
aatatgaaga cataaacccm gttgccatct gcgtgacaat aaaacattaa tgctaacact    600
t                                                                    601

<210> SEQ ID NO 134
<211> LENGTH: 421
<212> TYPE: DNA
<213> ORGANISM: Homo sapiens

<400> SEQUENCE: 134
tcacataaga aatttaagca agttacrcta tcttaaaaaa cacaacgaat gcattttaat     60
agagaaaccc ttccctccct ccacctccct cccccaccct cctcatgaat taagaatcta    120
agagaagaag taaccataaa accaagtttt gtggaatcca tcatccagag tgcttacatg    180
gtgattaggt taatattgcc ttcttacaaa atttctattt taaaaaaaat tataaccttg    240
attgcttatt acaaaaaaat tcagtacaaa agttcaatat attgaaaaat gcttttcccc    300
tccctcacag caccgtttta tatatagcag agaataatga agagattgct agtctagatg    360
gggcaatctt caaattacac caagacgcac agtggtttat ttaccctccc cttctcataa    420
g                                                                    421

<210> SEQ ID NO 135
<211> LENGTH: 511
<212> TYPE: DNA
<213> ORGANISM: Homo sapiens

<400> SEQUENCE: 135
ggaaaggatt caagaattag aggacttgct tgctrragaa aaagacaact ctcgtcgcat     60
gctgacagac aaagagagag agatggcgga aataagggat caaatgcagc aacagctgaa    120
tgactatgaa cagcttcttg atgtaaagtt agccctggac atggaaatca gtgcttacag    180
gaaactctta gaaggcgaag aagagaggtt gaagctgtct ccaagccctt cttcccgtgt    240
gacagtatcc cgagcatcct caagtcgtag tgtaccgtac aactagagga agcggaaga    300 gggttgatgt ggaagaatca gaggcgaagt agtagtgtta gcatctctca ttccgcctca    360
accactggaa atgtttgcat cgaagaaatt gatgttgatg ggaaatttat cccgcttgaa    420
```

```
gaacacttct gaacaggatc aaccaatggg aaggcttggg agatgatcag aaaaattgga    480
gacacatcag tcagttataa atatacctca a                                  511

<210> SEQ ID NO 136
<211> LENGTH: 341
<212> TYPE: DNA
<213> ORGANISM: Homo sapiens

<400> SEQUENCE: 136
catgggtttc accaggttgg ccaggctgct cttgaactsc tgacctcagg tgatccaccc     60
gcctcggcct cccaaagtgc tgggattaca ggcgtgagcc accacgcccg gcccccaaag   120
ctgtttcttt tgtctttagc gtaaagctct cctgccatgc agtatctaca taactgacgt   180
gactgccagc aagctcagtc actccgtggt cttttctct ttccagttct tctctctctc   240
ttcaagttct gcctcagtga aagctgcagg tccccagtta agtgatcagg tgagggttct   300
ttgaacctgg ttctatcagt cgaattaatc cttcatgatg g                       341

<210> SEQ ID NO 137
<211> LENGTH: 551
<212> TYPE: DNA
<213> ORGANISM: Homo sapiens

<400> SEQUENCE: 137
gatgtgttgg accctctgtg tcaaaaaaaa cctcacaaag aatcccctgc tcattacaga     60
agaagatgca tttaaaatat gggttatttt caacttttta tctgaggaca agtatccatt   120
aattattgtg tcagaagaga ttgaatacct gcttaagaag cttacagaag ctatgggagg   180
aggttggcag caagaacaat tgaacattta aaaatcaac tttgatgaca gtaaaaatgg    240
cctttctgca tgggaactta ttgagcttat tggaaatgga cagtttagca aaggcatgga   300
ccggcagact gtgtctatgg caattaatga agtctttaat gaacttatat agatgtgtt   360 aaagcagggt tacatgatga aaaagggcca cagacggaaa aactggactg aaagatggtt   420
tgtactaaaa cccaacataa tttcttacta tgtgagtgag gatctgaagg ataagaaagg   480
agacattctc ttggatgaaa attgctgtgt agaagtcctt gcctgacaaa agatggaaag   540
aaatgccttt t                                                        551

<210> SEQ ID NO 138
<211> LENGTH: 531
<212> TYPE: DNA
<213> ORGANISM: Homo sapiens
<220> FEATURE:
<221> NAME/KEY: misc_feature
<222> LOCATION: 490
<223> OTHER INFORMATION: n = A,T,C or G

<400> SEQUENCE: 138
gactggttct ttatttcaaa aagcacttg tcaatattca gtrtcaaaac agttgcacta     60
ttgatttctc tttctcccaa tcggccccaa agagaccaca taaaaggaga gtacatttta   120
agccaataag ctgcaggatg tacacctaac agacctccta gaaaccttac cagaaaatgg   180
ggactgggta gggaaggaaa cttaaaagat caacaaactg ccagcccacg gactgcagag   240
gctgtcacag ccagatgggg tggccagggt gccacaaacc caaagcaaag tttcaaaata   300
atataaaatt taaaaagttt tgtacataag ctattcaaga tttctccagc actgactgat   360
acaaagcaca attgagatgg cacttctaga gacagcagct tcaaacccag aaaagggtga   420
```

```
tgagatgaag tttcacatgg ctaaatcagt ggcaaaaaca cagtcttctt tctttctttc    480
tttcaaggan gcaggaaagc aattaagtgg tcaccttaac ataaggggga c             531

<210> SEQ ID NO 139
<211> LENGTH: 521
<212> TYPE: DNA
<213> ORGANISM: Homo sapiens
<220> FEATURE:
<221> NAME/KEY: misc_feature
<222> LOCATION: 517
<223> OTHER INFORMATION: n = A,T,C or G

<400> SEQUENCE: 139
tgggtgggca ccatggctgg gatcaccacc atcgaggcgg tgaagcgcaa gatccaggtt    60
ctgcagcagc aggcagatga tgcagaggag cgagctgagc gcctccagcg agaagttgag   120
ggagaaaggc gggcccggga acaggctgag gctgaggtgg cctccttgaa ccgtaggatc   180
cagctggttg aagaagagct ggaccgtgct caggagcgcc tggccactgc cctgcaaaag   240
ctggaagaag ctgaaaaagc tgctgatgag agtgagagag gtatgaaggt tattgaaaac   300
cgggccttaa aagatgaaga aaagatgaaa ctccaggaaa tccaactcaa agaagctaag   360
cacattgcag aagaggcaga taggaagtat gaagaggtgg ctcgtaagtt ggtgatcatt   420
gaaggagact tggaaccgca cagaaggaac gagcttgagc ttggcaaaag tcccgttgcc   480
cagagatggg atgaaccaga ttagactgat ggaccanaac c                      521

<210> SEQ ID NO 140
<211> LENGTH: 571
<212> TYPE: DNA
<213> ORGANISM: Homo sapiens
<220> FEATURE:
<221> NAME/KEY: misc_feature
<222> LOCATION: 7
<223> OTHER INFORMATION: n = A,T,C or G

<400> SEQUENCE: 140
aggggcngcg ggtgcgtggg ccactgggtg accgacttag cctggccaga ctctcagcac    60
ctggaagcgc cccgagagtg acagcgtgag gctgggaggg aggacttggc ttgagcttgt   120
taaactctgc tctgagcctc cttgtcgcct gcatttagat ggctcccgca agaagggtg    180 gcgagaagaa aaagggccgt tctgccatca acgaagtggt aacccgagaa tacaccatca   240
acattcacaa gcgcatccat ggagtgggct tcaagaagcg tgcacctcgg gcactcaaag   300
agattcggaa atttgccatg aaggagatgg gaactccaga tgtgcgcatt gacaccaggc   360
tcaacaaagc tgtctgggcc aaaggaataa ggaatgtgcc ataccgaatc cggtgtgcgg   420
ctgtccagaa aacgtaatga ggatgaagat tcaccaaata agctatatac tttggttacc   480
tatgtacctg ttaccacttt caaaaatcta cagacagtca atgtggatga aactaatcg    540 ctgatcgtca gatcaaataa agttataaaa t                                 571

<210> SEQ ID NO 141
<211> LENGTH: 531
<212> TYPE: DNA
<213> ORGANISM: Homo sapiens

<400> SEQUENCE: 141
tcgggagcca cacttggccc tcttcctctc caaagsgcca gaacctcctt ctctttggag    60
aatggggagg cctcttggag acacagaggg tttcaccttg gatgacctct agagaaattg   120
cccaagaagc ccaccttctg gtcccaacct gcagacccca cagcagtcag ttggtcaggc   180
```

```
cctgctgtag aaggtcactt ggctccattg cctgcttcca accaatgggc aggagagaag    240
gcctttattt ctcgcccacc cattcctcct gtaccagcac ctccgttttc agtcagtgtt    300
gtccagcaac ggtaccgttt acacagtcac ctcagacaca ccatttcacc tcccttgcca    360
agctgttagc cttagagtga ttgcagtgaa cactgtttac acaccgtgaa tccattccca    420
tcagtccatt ccagttggca ccagcctgaa ccatttggta cctggtgtta actggagtcc    480
tgtttacaag gtggagtcgg ggcttgctga cttctcttca tttgagggca c             531
```

<210> SEQ ID NO 142
<211> LENGTH: 491
<212> TYPE: DNA
<213> ORGANISM: Homo sapiens
<220> FEATURE:
<221> NAME/KEY: misc_feature
<222> LOCATION: 410
<223> OTHER INFORMATION: n = A,T,C or G
<400> SEQUENCE: 142

```
acctagacag aaggtgggtg agggaggact ggtaggaggc tgaggcaatt ccttggtagt    60
ttgtcctgaa accctactgg agaagtcagc atgaggcacc tactgagaga agtgcccaga    120
aactgctgac tgcatctgtt aagagttaac agtaaagagg tagaagtgtg tttctgaatc    180
agagtggaag cgtctcaagg gtcccacagt ggaggtccct gagctacctc ccttccgtga    240
gtgggaagag tgaagcccat gaagaactga gatgaagcaa ggatgggggtt cctgggctcc    300 aggcaagggc tgtgctctct gcagcaggga gccccacgag tcagaagaaa agaactaatc    360
atttgttgca agaaaccttg cccggatact agcggaaaac tggaggcggn ggtggggggca    420 caggaaagtg gaagtgatttt gatggagagc agagaagcct atgcacagtg gccgagtcca    480
cttgtaaagt g                                                         491
```

<210> SEQ ID NO 143
<211> LENGTH: 515
<212> TYPE: DNA
<213> ORGANISM: Homo sapiens
<400> SEQUENCE: 143

```
ttcaagcaat tgtaacaagt atatgtagat tagagtgagc aaaatcatat acaattttca    60
tttccagttg ctatttttcca aattgttctg taatgtcgtt aaaattactt aaaaattaac    120
aaagccaaaa attatattta tgacaagaaa gccatcccta cattaatctt acttttccac    180
tcaccggccc atctccttcc tcttttttcct aactatgcca ttaaaactgt tctactgggc    240
cgggcgtgtg gctcatgcct gtaatcccag cattttggga ggccaaggca ggcggatcat    300
gaggtcaaga gattgagacc atcctggcca acatggtgaa accccgcctc gactaagaat    360
acaaaaatta gctgggcatg gtggcgcatg cctgtagtct cagctactcg ggaggctgag    420
gcagaagaat cgcttgaacc cgggaggcag aggatgcagt gagccccgat cgcgccactg    480
cactctagcc tgggcgacag actgagactc tgctc                               515
```

<210> SEQ ID NO 144
<211> LENGTH: 340
<212> TYPE: DNA
<213> ORGANISM: Homo sapiens
<400> SEQUENCE: 144

```
tgtgccagtc tacaggccta tcagcagcga ctccttcagc aacagatggg gtcccctgtt    60
```

```
cagcccaacc ccatgagccc ccagcagcat atgctcccaa atcaggccca gtccccacac    120
ctacaaggcc agcagatccc taattctctc tccaatcaag tgcgctctcc ccagcctgtc    180
ccttctccac ggccacagtc ccagccccc cactccagtc cttccccaag gatgcagcct     240
cagccttctc cacaccacgt tccccacag acaagttccc cacatcctgg actggtagtt     300
gcccaggcca accccatgga acaagggcat tttgccagcc                          340
```

<210> SEQ ID NO 145
<211> LENGTH: 630
<212> TYPE: DNA
<213> ORGANISM: Homo sapiens

<400> SEQUENCE: 145

```
tgtaaaaact tgttttaat tttgtataaa ataaaggtgg tccatgccca cggggctgt      60 aggaaatcca agcagaccag ctggggtggg gggatgtagc ctacctcggg ggactgtctg    120
tcctcaaaac gggctgagaa ggcccgtcag ggcccaggt cccacagaga ggcctgggat     180
actcccccaa cccgaggggc agactgggca gtggggagcc cccatcgtgc cccagaggtg    240
gccacaggct gaaggagggg cctgaggcac cgcagcctgc aaccccagg gctgcagtcc     300 actaactttt tacagaataa aaggaacatg gggatggga aaaaagcacc aggtcaggca     360
gggcccgagg gccccagatc ccaggagggc caggactcag gatgccagca ccaccctagc    420
agctcccaca gctcctggca caggaggccg ccacggattg gcacaggccg ctgctggcca    480
tcacgccaca tttggagaac ttgtcccgac agaggtcagc tcggaggagc tcctcgtggg    540
cacacactgt acgaacacag atctccttgt taatgacgta cacggcgg aggctgcggg      600 gacagggcac gggaggtctc agccccactt                                     630
```

<210> SEQ ID NO 146
<211> LENGTH: 521
<212> TYPE: DNA
<213> ORGANISM: Homo sapiens

<400> SEQUENCE: 146

```
atggctgctg gatttaggtg gtaataggg ctgtgggcca taaatctgaa gccttgagaa     60
ccttgggtct ggagagccat gaagagggaa ggaaaagagg gcaagtcctg aacctaacca    120
atgacctgat ggattgctcg accaagacac agaagtgaag tctgtgtctg tgcacttccc    180
acagactgga gttttggtg ctgaatagag ccagttgcta aaaaattggg ggtttggtga     240
agaaatctga ttgttgtgtg tattcaatgt gtgatttaa aaataaacag caacaacaat     300
aaaaaccctg actggctgtt ttttccctgt attctttaca actatttttt gaccctctga    360
aaattattat acttcaccta aatggaagac tgctgtgttt gtggaaattt tgtaattttt    420
taatttattt tattctctct ccttttatt ttgcctgcag aatccgttga gagactaata     480
aggcttaata tttaattgat tgtttaata tgtatataaa t                         521
```

<210> SEQ ID NO 147
<211> LENGTH: 562
<212> TYPE: DNA
<213> ORGANISM: Homo sapiens

<400> SEQUENCE: 147

```
ggcatgcgag cgcactcggc ggacgcaagg gcggcgggga gcacacggag cactgcaggc    60
gccgggttgg gacagcgtct tcgctgctgc tggatagtcg tgttttcggg gatcgaggat    120
actcaccaga aaccgaaaat gccgaaacca atcaatgtcc gagttaccac catggatgca    180
```

```
gagctggagt ttgcaatcca gccaaataca actggaaaac agcttttttga tcaggtggta      240 aagactatcg gcctccggga agtgtggtac tttggcctcc actatgtgga taataaagga      300
tttcctacct ggctgaagct ggataagaag gtgtctgccc aggaggtcag gaaggagaat      360
cccctccagt tcaagttccg ggccaaagtt ctaccctgaa gatgtggctg aggagctcat      420
ccaggacatc acccagaaac ttttcttcct tcaagtgaag gaaggaatcc ttagcgatga      480
gatctactgc ccccettgar actgccgtgc tcttggggtc ctacgcttgt gcatgccaag      540
tttggggact accaccaaga ag                                              562
```

```
<210> SEQ ID NO 148
<211> LENGTH: 820
<212> TYPE: DNA
<213> ORGANISM: Homo sapiens

<400> SEQUENCE: 148
gaaggagtcg ggatactcag cattgatgca ccccaatttc aaagcggcat tcttcggcag       60
gtctctggga caatctctag ggtcactacc tggaaactcg ttagggtaca actgaatgct      120
gaaaggaaag aacacctgca gaaccggaca gaaattcacc ccggcgatca gctgattgat      180
ctcggtcgac cagaagtcat ggctaaagat gacgaggacg ttgtcaattc cctgggcttt      240
tcgaagtgag tccagcagca gtctgaggta ttcgggccgg ttatgcacct ggaccaccag      300
caccagctcc cggggggccc aggtgccagc cttatctaca ttcctcaggg tctgatcaaa      360
gttcagctgg tacaccaggg accggtaccg cagcgtcagg ttgtccgctc gggctggggg      420
accgccggga ccagggaagc cgccgacacg ttggagaccc tgcggatgcc cacagccaca      480
gaggggtggt ccccaccgcg gccgccggca ccccgcgcgg gttcggcgtc cagcaacggt      540
ggggcgaggg cctcgttctt cctttgtcgc ccattgctgc tccagaggac gaagccgcag      600
gcggccacca cgagcgtcag gattagcacc ttccgtttgt agatgcggaa cctcatggtc      660
tccagggccg ggagcgcagc tacagctcga gcgtcggcgc cgccgctagg agccgcggct      720
cggcttcgtc tccgtcctct ccattcagca ccacgggtcc cggaaaaagc tcagccscgg      780
tcccaaccgc accctagctt cgttacctgc gcctcgcttg                           820
```

```
<210> SEQ ID NO 149
<211> LENGTH: 501
<212> TYPE: DNA
<213> ORGANISM: Homo sapiens

<400> SEQUENCE: 149 cagatttttta tttgcagtcg tcactggggc cgtttcttgc tgcttatttg tctgctagcc       60
tgctcttcca gctgcatggc caggcgcaag gccttgatga catctcgcag ggctgagaaa      120
tgcttggctt gctgggccag agcagattcc gctttgttca caaaggtctc caggtcatag      180
tctggctgct cggtcatctc agagagctca agccagtctg gtccttgctg tatgatctcc      240
ttgagctctt ccatagcctt ctcctccagc tccctgatct gagtcatggc ttcgttaaag      300
ctggacatct gggaagacag ttcctcctct tccttggata aattgcctgg aatcagcgcc      360
ccgttagagc aggcttccat ctcttctgtt tccatttgaa tcaactgctc tccactgggc      420
ccactgtggg ggctcagctc cttgaccctg ctgcatatct aagggtgtt taaaggatat      480 tcacaggagc ttatgcctgg t                                              501
```

```
<210> SEQ ID NO 150
```

```
<211> LENGTH: 511
<212> TYPE: DNA
<213> ORGANISM: Homo sapiens
<220> FEATURE:
<221> NAME/KEY: misc_feature
<222> LOCATION: 457, 479
<223> OTHER INFORMATION: n = A,T,C or G

<400> SEQUENCE: 150
ctcctcttgg tacatgaacc caagttgaaa gtggacttaa caaagtatct ggagaaccaa      60
gcattctgct ttgactttgc atttgatgaa acagcttcga atgaagttgt ctacaggttc     120
acagcaaggc cactggtaca gacaatcttt gaaggtggaa aagcaacttg ttttgcatat     180
ggccagacag gaagtggcaa gacacatact atgggcggag acctctctgg gaaagcccag     240
aatgcatcca aagggatcta tgccatggcc ttccggacg tcttcttctg aagaatcaac      300
cctgctaccg gaagttgggc ctggaagtct atgtgacatt cttcgagatc tacaatggga     360
agctgtttga cctgctcaac aagaaggcca agcttgcgcg tgctggaaga cggcaagcaa     420
caggtgcaag tggtggggc ttgcaggaac atctggntaa ctctgcttga tgatggcant      480
caagatgatc gacatgggca gcgcctgcag a                                     511

<210> SEQ ID NO 151
<211> LENGTH: 566
<212> TYPE: DNA
<213> ORGANISM: Homo sapiens

<400> SEQUENCE: 151
tcccgaattc aagcgacaaa ttggawagtg aaatggaaga tgcctatcat gaacatcagg      60
caaatctttt gcgccaagat ctgatgagac gacaggaaga attaagacgc atggaagaac     120
ttcacaatca agaaatgcag aaacgtaaag aaatgcaatt gaggcaagag gaggaacgac     180
gtagaagaga ggaagagatg atgattcgtc aacgtgagat ggaagaacaa atgaggcgcc     240
aaagagagga aagttacagc cgaatgggct acatggatcc acgggaaaga gacatgcgaa     300
tgggtggcgg aggagcaatg aacatggag atccctatgg ttcaggaggc cagaaatttc       360
cacctctagg aggtggtggt ggcataggtt atgaagctaa tcctggcgtt ccaccagcaa     420
ccatgagtgg ttccatgatg ggaagtgaca tgcgtactga gcgctttggg cagggaggtg     480
cggggcctgt gggtggacag ggtcctagag gaatggggcc tggaactcca gcaggatatg     540
gtagagggag agaagagtac gaaggc                                           566

<210> SEQ ID NO 152
<211> LENGTH: 518
<212> TYPE: DNA
<213> ORGANISM: Homo sapiens

<400> SEQUENCE: 152
ttcgtgaaga ccctgactgg taagaccatc actctcgaag tggagcccga gtgacaccat      60
tgagaatgtc aaggcaaaga tccaagacaa ggaaggcatc cctcctgacc agcakaggtt     120
gatctttgct gggaaacagc tggaagatgg acgcaccctg tctgactaca acatccagaa     180
agagtccacc ctgcacctgg tgctccgtct cagaggtggg atgcaaatct cgtgaagac      240 cctgactggt aagaccatca ccctcgaggt ggagcccagt gacaccatcg agaatgtcaa     300
ggcaaagatc caagataagg aaggcatccc tcctgatcag cagaggttga tctttgctgg     360
gaaacagctg gaagatggac gcaccctgtc tgactacaac atccagaaag agtccactct     420
gcacttggtc ctgcgcttga ggggggtgt ctaagtttcc ccttttaagg tttcaacaaa      480
```

```
tttcattgca ctttcctttc aataaagttg ttgcattc                            518

<210> SEQ ID NO 153
<211> LENGTH: 542
<212> TYPE: DNA
<213> ORGANISM: Homo sapiens

<400> SEQUENCE: 153
gcgcgggtgc gtgggccact gggtgaccga cttagcctgg ccagactctc agcacctgga    60
agcgccccga gagtgacagc gtgaggctgg gagggaggac ttggcttgag cttgttaaac   120
tctgctctga gcctccttgt cgcctgcatt tagatggctc ccgcaaagaa gggtggcgag   180
aagaaaaagg gccgttctgc catcaacgaa gtggtaaccc gagaatacac catcaacatt   240
cacaagcgca tccatggagt gggcttcaag aagcgtgcac ctcgggcact caaagagatt   300
cggaaatttg ccatgaagga gatgggaact ccagatgtgc gcattgacac caggctcaac   360
aaagctgtct gggccaaagg aataaggaat gtgccatacc gaatccgtgt gcggctgtcc   420
agaaaacgta atgaggatga agattcacca aataagctat atactttggt tacctatgta   480
cctgttacca ctttcaaaaa tctacagaca gtcaatgtgg atgagaacta atcgctgatc   540
gt                                                                  542

<210> SEQ ID NO 154
<211> LENGTH: 411
<212> TYPE: DNA
<213> ORGANISM: Homo sapiens

<400> SEQUENCE: 154
aattctttat ttaaatcaac aaactcatct tcctcaagcc ccagaccatg gtaggcagcc    60
ctccctctcc atcccctcac cccaccccctt agccacagtg aagggaatgg aaaatgagaa   120
gccacgaggg cccctgccag ggaaggctgc cccagatgtg tggtgagcac agtcagtgca   180
gctgtggctg gggcagcagc tgccacaggc tcctccctat aaattaagtt cctgcagcca   240
cagctgtggg agaagcatac ttgtagaagc aaggccagtc cagcatcaga aggcagaggc   300
agcatcagtg actcccagcc atggaatgaa cggaggacac agagctcaga gacagaacag   360
gccaggggga agaaggagag acagaatagg ccagggcatg gcggtgaggg a            411

<210> SEQ ID NO 155
<211> LENGTH: 421
<212> TYPE: DNA
<213> ORGANISM: Homo sapiens
<220> FEATURE:
<221> NAME/KEY: misc_feature
<222> LOCATION: 173
<223> OTHER INFORMATION: n = A,T,C or G

<400> SEQUENCE: 155
tgatgaatct gggtgggctg gcagtagccc gagatgatgg gctcttctct ggggatccca    60
actggttccc taagaaatcc aaggagaatc ctcggaactt ctcggataac cagctgcaag   120
agggcaagaa cgtgatcggg ttacagatgg gcaccaaccg cggggcgtct cangcaggca   180
tgactggcta cgggatgcca cgccagatcc tctgatccca cccaggcct tgcccctgcc    240 ctcccacgaa tggttaatat atatgtagat atatatttta gcagtgacat tcccagagag   300
ccccagagct ctcaagctcc tttctgtcag ggtgggggt tcaagcctgt cctgtcacct   360
ctgaagtgcc tgctggcatc ctctccccca tgcttactaa tacattccct tccccatagc   420
``` c                                                                        421

<210> SEQ ID NO 156
<211> LENGTH: 670
<212> TYPE: DNA
<213> ORGANISM: Homo sapiens

<400> SEQUENCE: 156
agcggagctc cctcccctgg tggctacaac ccacacacgc caggctcagg catcgagcag      60
aactccagcg actgggtaac cactgacatt caggtgaagg tgcgggacac ctacctggat     120
acacaggtgg tgggacagac aggtgtcatc cgcagtgtca cggggggcat gtgctctgtg     180
tacctgaagg acagtgagaa ggttgtcagc atttccagtg agcacctgga gcctatcacc     240
cccaccaaga caacaaggt gaaagtgatc ctgggcgagg atcgggaagc cacgggcgtc      300
ctactgagca ttgatggtga ggatggcatt gtccgtatgg accttgatga gcagctcaag     360
atcctcaacc tccgcttcct ggggaagctc ctggaagcct gaagcaggca gggccggtgg     420
acttcgtcgg atgaagagtg atcctccttc cttccctggc ccttggctgt gacacaagat     480
cctcctgcag ggctaggcgg attgttctgg atttcctttt gttttccctt ttaggtttcc     540
atcttttccc tccctggtgc tcattggaat ctgagtagag tctggggag ggtccccacc      600 ttcctgtacc tcctccccac agcttgcttt tgttgtaccg tctttcaata aaagaagct     660 gtttggtcta                                                              670

<210> SEQ ID NO 157
<211> LENGTH: 421
<212> TYPE: DNA
<213> ORGANISM: Homo sapiens

<400> SEQUENCE: 157
ggttcacagc actgctgctt gtgtgttgcc ggccaggaat tccaggctca caaggctatc      60
ttagcagctc gttctccggt ttttagtgcc atgtttgaac atgaaatgga ggagagcaaa     120
aagaatcgag ttgaaatcaa tgatgtggag cctgaagttt ttaaggaaat gatgtgcttc     180
atttacacgg ggaaggctcc aaacctcgac aaaatggctg atgatttgct ggcagctgct     240
gacaagtatg ccctggagcg cttaaaggtc atgtgtgagg atgccctctg cagtaacctg     300
tccgtggaga acgctgcaga aattctcatc ctggccgacc tccacagtgc agatcagttg     360
aaaactcagg cagtggattt catcaactat catgcttcgg atgtcttgga cctcttggg      420 g                                                                       421

<210> SEQ ID NO 158
<211> LENGTH: 321
<212> TYPE: DNA
<213> ORGANISM: Homo sapiens

<400> SEQUENCE: 158
tcgtagccat tttctgctt ctttggagaa tgacgccaca ctgactgctc attgtcgttg       60
gttccatgcc aattggtgaa atagaacctc atccggtagt ggagccggag ggacatcttg     120
tcatcaacgg tgatggtgcg atttggagca taccagagct tggtgttctc gccatacagg     180
gcaaagaggt tgtgacaaag aggagagata cggcatgcct gtgcagccct gatgcacagt     240
tcctctgctg tgtactctcc actgcccagc cggaggggct ccctgtccga cagatagaag     300
atcacttcca cccctggctt g                                                  321

<210> SEQ ID NO 159
<211> LENGTH: 596
<212> TYPE: DNA
<213> ORGANISM: Homo sapiens

<400> SEQUENCE: 159

```
tggcacactg ctcttaagaa actatgawga tctgagattt ttttgtgtat gttttgact      60
cttttgagtg gtaatcatat gtgtctttat agatgtacat acctccttgc acaaatggag   120
gggaattcat tttcatcact gggagtgtcc ttagtgtata aaaaccatgc tggtatatgg   180
cttcaagttg taaaaatgaa agtgactta aagaaaata ggggatggtc caggatctcc    240
actgataaga ctgttttaa gtaacttaag gacctttggg tctacaagta tatgtgaaaa   300
aaatgagact tactgggtga ggaaattcat tgtttaaaga tggtcgtgtg tgtgtgtgtg   360
tgtgtgtgtg ttgtgttgtg ttttgttttt taagggaggg aatttattat ttaccgttgc   420
ttgaaattac tgkgtaaata tatgtytgat aatgatttgc tytttgvcma ctaaaattag   480
gvctgtataa gtwctaratg cmtccctggg kgttgatytt ccmagatatt gatgatamcc   540
cttaaaattg taaccygcct ttttcccttt gctytcmatt aaagtctatt cmaaag       596
```

<210> SEQ ID NO 160
<211> LENGTH: 515
<212> TYPE: DNA
<213> ORGANISM: Homo sapiens

<400> SEQUENCE: 160

```
gggggtaggc tctttattag acggttattg ctgtactaca gggtcagagt gcagtgtaag    60
cagtgtcaga ggcccgcgtt cagcccaaga atgtggattt tctctcccta ttgatcacag   120
tgggtgggtt tcttcagaaa agccccagag gcagggacca gtgagctcca aggttagaag   180
tggaactgga aggcttcagt cacatgctgc ttccacgctt ccaggctggg cagcaaggag   240
gagatgccca tgacgtgcca ggtctcccca tctgacacca gtgaagtctg gtaggacagc   300
agccgcacgc ctgcctctgc caggaggcca atcatggtag gcagcattgc agggtcagag   360
gtctgagtcc ggaataggag caggggcagg tccctgcgga gaggcacttc tggcctgaag   420
acagctccat tgagcccctg cagtacaggy gtagtgcctt ggaccaagcc cacagcctgg   480
taagggggcgc ctgccagggc cacggccagg aggca                              515
```

<210> SEQ ID NO 161
<211> LENGTH: 936
<212> TYPE: DNA
<213> ORGANISM: Homo sapiens

<400> SEQUENCE: 161

```
taatttctta gtcgtttgga atccttaagc atgcaaaagc tttgaacaga agggttcaca    60
aaggaaccag ggttgtctta tggcatccag ttaagccaga gctgggaatg cctctgggtc   120
atccacatca ggagcagaag cacttgactt gtcggtcctg ctgccacggt ttgggcgccc   180
accacgccca cgtccacctc gtcctcccct gccgccacgt cctgggcggc caaggtctcc   240
aaaattgatc tccagctgag acgttatatc atttgctggc ttccggaaat gatggtccat   300
aaccgaatct tcagcatgag cctcttcact ctttgattta tgaagaacaa atcccttctt   360
ccactgccca tcagcacctt catttggttt tcggatatta aattctactt ttgcccggtc   420
cttattttga atagccttcc actcatccaa agtcatctct tttggaccct cctcttttac   480
ctcttcaact tcattctcct tatttcagt gtctgccact ggatgatgtt cttcaccttc    540
```

```
aggtgtttcc tcagtcacat ttgattgatc caagtcagtt aattcgtctt tgacagttcc    600
ccagttgtga gatccgctac ctccacgttt gtcctcgtgc ttcaggccag atctatcact    660
tccactatgc ctatcaaatt cacgtttgcc acgagaatca aatccatctc ctcggcccat    720
tccacgtcca cggcccctc gacctcttcc aagaccacca cgacctcgaa taggtcggtc    780
aataatcggt ctatcaactg aaaattcgcc tccttcaccc ttttcttcaa gtggcttttc    840
gaatcttcgt tcacgaggtg gtcgcctttc tggtcttcta tcaattattt tccctttcacc   900 ctgaagttgt tgatcaggtc ttcttccaac tcgtgc                              936
```

```
<210> SEQ ID NO 162
<211> LENGTH: 950
<212> TYPE: DNA
<213> ORGANISM: Homo sapiens

<400> SEQUENCE: 162
```

```
aagcggatgg acctgagtca gccgaatcct agccccttcc cttgggcctg ctgtggtgct     60
cgacatcagt gacagacgga agcagcagac catcaaggct acgggaggcc cggggcgctt    120
gcgaagatga agtttggctg cctctccttc cggcagcctt atgctggctt tgtcttaaat    180
ggaatcaaga ctgtggagac gcgctggcgt cctctgctga gcagccagcg gaactgtacc    240
atcgccgtcc acattgctca cagggactgg gaaggcgatg cctgtcggga gctgctggtg    300
gagagactcg ggatgactcc tgctcagatt caggccttgc tcaggaaagg ggaaaagttt    360
ggtcgaggag tgatagcggg actcgttgac attggggaaa cttttgcaatg ccccgaagac   420 ttaactcccg atgaggttgt ggaactagaa aatcaagctg cactgaccaa cctgaagcag    480
aagtacctga ctgtgatttc aaaccccagg tggttactgg agcccatacc taggaaagga    540
ggcaaggatg tattccaggt agacatccca gagcacctga tccctttggg gcatgaagtg    600
tgacaagtgt gggctcctga aaggaatgtt ccrgagaaac cagctaaatc atggcacctt    660
caatttgcca tcgtgacgca gacctgtata aattaggtta aagatgaatt tccactgctt    720
tggagagtcc cacccactaa gcactgtgca tgtaaacagg ttcctttgct cagatgaagg    780
aagtaggggg tggggctttc cttgtgtgat gcctccttag gcacacaggc aatgtctcaa    840
gtactttgac cttagggtag aaggcaaagc tgccagtaaa tgtctcagca ttgctgctaa    900
ttttggtcct gctagtttct ggattgtaca aataaatgtg ttgtagatga                950
```

```
<210> SEQ ID NO 163
<211> LENGTH: 475
<212> TYPE: DNA
<213> ORGANISM: Homo sapiens
<220> FEATURE:
<221> NAME/KEY: misc_feature
<222> LOCATION: 301, 317, 331, 458, 464, 470
<223> OTHER INFORMATION: n = A,T,C or G

<400> SEQUENCE: 163
```

```
tcgagcggcc gcccgggcag gtgtcggagt ccagcacggg aggcgtggtc ttgtagttgt     60
tctccggctg cccattgctc tcccactcca cggcgatgtc gctgggatag aagcctttga    120
ccaggcaggt caggctgacc tggttcttgg tcatctcctc ccgggatggg ggcagggtgt    180
acacctgtgg ttctcgggggc tgcccttttgg ctttggagat ggtttctcg atggggctg    240 ggagggcttt gttggagacc ttgcacttgt actccttgcc attcaaccag tcctggtgca    300
ngacggtgag gacgctnacc acacggtacg ngctggtgta ctgctcctcc cgcggctttg    360
tcttggcatt atgcacctcc acgccgtcca cgtaccaatt gaacttgacc tcagggtctt    420
```

```
cgtggctcac gtccaccacc acgcatgtaa cctcaaanct cggncgcgan cacgc        475

<210> SEQ ID NO 164
<211> LENGTH: 476
<212> TYPE: DNA
<213> ORGANISM: Homo sapiens

<400> SEQUENCE: 164
agcgtggtcg cggccgaggt ctgaggttac atgcgtggtg gtggacgtga gccacgaaga    60
ccctgaggtc aagttcaact ggtacgtgga cggcgtggag gtgcataatg ccaagacaaa   120
gccgcgggag gagcagtaca acagcacgta ccgtgtggtc agcgtcctca ccgtcctgca   180
ccaggactgg ctgaatggca aggagtacaa gtgcaaggtc tccaacaaag ccctcccagc   240
ccccatcgag aaaaccatct ccaaagccaa agggcagccc cgagaaccac aggtgtacac   300
cctgccccca tcccgggagg agatgaccaa gaaccaggtc agcctgacct gcctggtcaa   360
aggcttctat cccagcgaca tcgcccgtgg agtgggagag caatgggcag ccggagaaca   420
actacaagac cacgcctccc gtgctggact ccgacacctg ccgggcggcc gctcga       476

<210> SEQ ID NO 165
<211> LENGTH: 256
<212> TYPE: DNA
<213> ORGANISM: Homo sapiens
<220> FEATURE:
<221> NAME/KEY: misc_feature
<222> LOCATION: 10, 37, 249
<223> OTHER INFORMATION: n = A,T,C or G

<400> SEQUENCE: 165
agcgtggttn cggccgaggt cccaaccaag gctgcancct ggatgccatc aaagtcttct    60
gcaacatgga gactggtgag acctgcgtgt accccactca gcccagtgtg gcccagaaga   120
actggtacat cagcaagaac cccaaggaca agaggcatgt ctggttcggc gagagcatga   180
ccgatggatt ccagttcgag tatggcggcc agggctccga ccctgccgat gtggacctgc   240
ccgggcggnc gctcga                                                   256

<210> SEQ ID NO 166
<211> LENGTH: 332
<212> TYPE: DNA
<213> ORGANISM: Homo sapiens

<400> SEQUENCE: 166
agcgtggtcg cggccgaggt caagaacccc gcccgcacct gccgtgacct caagatgtgc    60
cactctgact ggaagagtgg agagtactgg attgaccccca accaaggctg caacctggat   120
gccatcaaag tcttctgcaa catggagact ggtgagacct gcgtgtaccc cactcagccc   180
agtgtggccc agaagaactg gtacatcagc aagaacccca aggacaagag gcatgtctgg   240
ttcggcgaga gcatgaccga tggattccag ttcgagtatg gcggccaggg ctccgaccct   300
gccgatgtgg acctgcccgg gcggccgctc ga                                 332

<210> SEQ ID NO 167
<211> LENGTH: 332
<212> TYPE: DNA
<213> ORGANISM: Homo sapiens
<220> FEATURE:
<221> NAME/KEY: misc_feature
<222> LOCATION: 77, 109, 136, 184, 198
<223> OTHER INFORMATION: n = A,T,C or G
```

<400> SEQUENCE: 167

```
tcgagcggtc gcccgggcag gtccacatcg gcagggtcgg agccctggcc gccatactcg     60
aactggaatc catcggncat gctctcgccg aaccagacat gcctcttgnc cttggggttc    120
ttgctgatgt accagntctt ctgggccaca ctgggctgag tggggtacac gcaggtctca    180
ccantctcca tgttgcanaa gactttgatg gcatccaggt tgcagccttg gttggggtca    240
atccagtact ctccactctt ccagacagag tggcacatct tgaggtcacg gcaggtgcgg    300
gcggggttct tgacctcggt cgcgaccacg ct                                  332
```

<210> SEQ ID NO 168
<211> LENGTH: 276
<212> TYPE: DNA
<213> ORGANISM: Homo sapiens
<220> FEATURE:
<221> NAME/KEY: misc_feature
<222> LOCATION: 72, 84
<223> OTHER INFORMATION: n = A,T,C or G

<400> SEQUENCE: 168

```
tcgagcggcc gcccgggcag gtcctcctca gagcggtagc tgttcttatt gccccggcag     60
cctccataga tnaagttatt gcangagttc ctctccacgt caaagtacca gcgtgggaag    120
gatgcacggc aaggcccagt gactgcgttg gcggtgcagt attcttcata gttgaacata    180
tcgctggagt ggacttcaga atcctgcctt ctgggagcac ttgggacaga ggaatccgct    240
gcattcctgc tggtggacct cggccgcgac cacgct                              276
```

<210> SEQ ID NO 169
<211> LENGTH: 276
<212> TYPE: DNA
<213> ORGANISM: Homo sapiens

<400> SEQUENCE: 169

```
agcgtggtcg cggccgaggt ccaccagcag gaatgcagcg gattcctctg tcccaagtgc     60
tcccagaagg caggattctg aagaccactc cagcgatatg ttcaactatg aagaatactg    120
caccgccaac gcagtcactg ggccttgccg tgcatccttc ccacgctggt actttgacgt    180
ggagaggaac tcctgcaata acttcatcta tggaggctgc cggggcaata agaacagcta    240
ccgctctgag gaggacctgc ccgggcggcc gctcga                              276
```

<210> SEQ ID NO 170
<211> LENGTH: 332
<212> TYPE: DNA
<213> ORGANISM: Homo sapiens
<220> FEATURE:
<221> NAME/KEY: misc_feature
<222> LOCATION: 294
<223> OTHER INFORMATION: n = A,T,C or G

<400> SEQUENCE: 170

```
tcgagcggcc gcccgggcag gtccacatcg gcagggtcgg agccctggcc gccatactcg     60
aactggaatc catcggtcat gctctcgccg aaccagacat gcctcttgtc cttggggttc    120
ttgctgatgt accagttctt ctgggccaca ctgggctgag tggggtacac gcaggtctca    180
ccagtctcca tgttgcagaa gactttgatg gcatccaggt tgcagccttg gttggggtca    240
atccagtact ctccactctt ccagccagaa tggcacatct tgaggtcacg gcangtgcgg    300
gcggggttct tgacctcggc cgcgaccacg ct                                  332
```

<210> SEQ ID NO 171
<211> LENGTH: 333
<212> TYPE: DNA
<213> ORGANISM: Homo sapiens

<400> SEQUENCE: 171

```
agcgtggtcg cggccgaggt caagaaaccc cgcccgcacc tgccgtgacc tcaagatgtg      60
ccactctggc tggaagagtg gagagtactg gattgacccc aaccaaggct gcaacctgga     120
tgccatcaaa gtcttctgca acatggagac tggtgagacc tgcgtgtacc ccactcagcc     180
cagtgtggcc cagaagaact ggtacatcag caagaacccc aaggacaaga ggcatgtctg     240
gctcggcgag agcatgaccg atggattcca gttcgagtat ggcggccagg gctccgaccc     300
tgccgatgtg gacctgcccg gcggccgct cga                                   333
```

<210> SEQ ID NO 172
<211> LENGTH: 527
<212> TYPE: DNA
<213> ORGANISM: Homo sapiens
<220> FEATURE:
<221> NAME/KEY: misc_feature
<222> LOCATION: 46, 125, 140, 148, 220, 229, 291, 388, 456
<223> OTHER INFORMATION: n = A,T,C or G

<400> SEQUENCE: 172

```
agcgtggtcg cggccgaggt cctgtcagag tggcactggt agaagntcca ggaaccctga      60
actgtaaggg ttcttcatca gtgccaacag gatgacatga aatgatgtac tcagaagtgt     120
cctgnaatgg ggcccatgan atggttgnct gagagagagc ttcttgtcct acattcggcg     180
ggtatggtct tggcctatgc cttatggggg tggccgttgn gggcggtgng gtccgcctaa     240
aaccatgttc ctcaaagatc atttgttgcc caacactggg ttgctgacca naagtgccag     300
gaagctgaat accatttcca gtgtcatacc cagggtgggt gacgaagggg tcttttgaa      360 ctgtggaagg aacatccaag atctctgntc catgaagatt ggggtgtgga agggttacca     420
gttggggaag ctcgctgtct ttttccttcc aatcangggc tcgctcttct gaatattctt     480
cagggcaatg acataaattg tatattcggt tcccggttcc aggccag                   527
```

<210> SEQ ID NO 173
<211> LENGTH: 635
<212> TYPE: DNA
<213> ORGANISM: Homo sapiens
<220> FEATURE:
<221> NAME/KEY: misc_feature
<222> LOCATION: 444, 453, 517, 540, 546, 551, 573, 593
<223> OTHER INFORMATION: n = A,T,C or G

<400> SEQUENCE: 173

```
tcgagcggcc gcccgggcag gtccaccaca cccaattcct tgctggtatc atggcagccg      60
ccacgtgcca ggattaccgg ctacatcatc aagtatgaga agcctgggtc tcctcccaga     120
gaagtggtcc ctcggccccg ccctggtgtc acagaggcta ctattactgg cctggaaccg     180
ggaaccgaat atacaattta tgtcattgcc ctgaagaata atcagaagag cgagcccctg     240
attggaagga aaagacaga cgagcttccc caactggtaa ccttccaca ccccaatctt       300 catgaccag agatcttgga tgttccttcc acagttcaaa agacccctt cgtcacccac       360 cctgggtatg acactggaaa tggtattcag cttcctggca cttctggtca gcaacccagt     420
gttgggcaac aaatgatctt tgangaacat ggntttaggc ggaccacacc ggccacaacg     480
ggcaccccca taaggcatag gccaagaaca tacccgncga atgtaggaca agaagctctn     540
```

| tctcanacaa ncatctcatg ggccccattc cangacactt ctgagtacat canttcatgg | 600 |
| catcctggtg gcactgataa aaaccttac agtta | 635 |

<210> SEQ ID NO 174
<211> LENGTH: 572
<212> TYPE: DNA
<213> ORGANISM: Homo sapiens
<220> FEATURE:
<221> NAME/KEY: misc_feature
<222> LOCATION: 457, 511, 520, 552, 568
<223> OTHER INFORMATION: n = A,T,C or G

<400> SEQUENCE: 174

| agcgtggtcg cgggcgaggt cctgtcagag tggcactggt agaagttcca ggaaccctga | 60 |
| actgtaaggg ttcttcatca gtgccaacag gatgacatga atgatgtac tcagaagtgt | 120 |
| cctggaatgg ggcccatgag atggttgtct gagagagagc ttcttgtcct acattcggcg | 180 |
| ggtatggtct tggcctatgc cttatggggg tggccgttgt gggcggtgtg gtccgcctaa | 240 |
| aaccatgttc ctcaaagatc atttgttgcc caacactggg ttgctgacca gaagtgccag | 300 |
| gaagctgaat accatttcca gtgtcatacc cagggtgggg gacgaaaggg gtcttttgaa | 360 |
| ctgtggaagg aacatccaag atctctggtc catgaagatt ggggtgtgga agggttacca | 420 |
| gttggggaag ctcgtctgtc tttttccttc caatcanggg ctcgctcttc tgattattct | 480 |
| tcagggcaat gacataaatt gtatattcgg ntcccgggtn cagccaataa taataaccct | 540 |
| ctgtgacacc anggcggggc cgaaggganca ct | 572 |

<210> SEQ ID NO 175
<211> LENGTH: 372
<212> TYPE: DNA
<213> ORGANISM: Homo sapiens
<220> FEATURE:
<221> NAME/KEY: misc_feature
<222> LOCATION: 247
<223> OTHER INFORMATION: n = A,T,C or G

<400> SEQUENCE: 175

| agcgtggtcg cggccgaggt cctcaccaga ggtaccacct acaacatcat agtggaggca | 60 |
| ctgaaagacc agcagaggca taaggttcgg gaagaggttg ttaccgtggg caactctgtc | 120 |
| aacgaaggct tgaaccaacc tacgatgac tcgtgctttg accctacac agtttcccat | 180 |
| tatgccgttg gagatgagtg ggaacgaatg tctgaatcag gctttaaact gttgtgccag | 240 |
| tgcttangct ttggaagtgg tcatttcaga tgtgattcat ctagatggtg ccatgacaat | 300 |
| ggtgtgaact acaagattgg agagaagtgg gaccgtcagg gagaaaatgg acctgcccgg | 360 |
| gcggccgctc ga | 372 |

<210> SEQ ID NO 176
<211> LENGTH: 372
<212> TYPE: DNA
<213> ORGANISM: Homo sapiens
<220> FEATURE:
<221> NAME/KEY: misc_feature
<222> LOCATION: 251
<223> OTHER INFORMATION: n = A,T,C or G

<400> SEQUENCE: 176

| tcgagcggcc gcccgggcag gtccatttc tccctgacgg tcccacttct ctccaatctt | 60 |
| gtagttcaca ccattgtcat ggcaccatct agatgaatca catctgaaat gaccacttcc | 120 |
| aaagcctaag cactggcaca acagtttaaa gcctgattca gacattcgtt cccactcatc | 180 |

```
tccaacggca taatgggaaa ctgtgtaggg gtcaaagcac gagtcatccg taggttggtt      240
caagccttcg ntgacagagt tgcccacggt aacaacctct tcccgaacct tatgcctctg      300
ctggtctttc agtgcctcca ctatgatgtt gtaggtggta cctctggtga ggacctcggc      360
cgcgaccacg ct                                                          372
```

```
<210> SEQ ID NO 177
<211> LENGTH: 269
<212> TYPE: DNA
<213> ORGANISM: Homo sapiens
<220> FEATURE:
<221> NAME/KEY: misc_feature
<222> LOCATION: 94, 225
<223> OTHER INFORMATION: n = A,T,C or G

<400> SEQUENCE: 177
agcgtggccg cggccgaggt ccattggctg gaacggcatc aacttggaag ccagtgatcg       60
tctcagcctt ggttctccag ctaatggtga tggnggtctc agtagcatct gtcacacgag      120
cccttcttgg tgggctgaca ttctccagag tggtgacaac ccctgagct ggtctgcttg       180 tcaaagtgtc cttaagagca tagacactca cttcatattt ggcgnccacc ataagtcctg      240
atacaaccac ggaatgacct gtcaggaac                                        269
```

```
<210> SEQ ID NO 178
<211> LENGTH: 529
<212> TYPE: DNA
<213> ORGANISM: Homo sapiens

<400> SEQUENCE: 178
tcgagcggcc gcccgggcag gtcctcagac cgggttctga gtacacagtc agtgtggttg       60
ccttgcacga tgatatggag agccagcccc tgattggaac ccagtccaca gctattcctg      120
caccaactga cctgaagttc actcaggtca caccacaag cctgagcgcc cagtggacac       180
cacccaatgt tcagctcact ggatatcgag tgcgggtgac ccccaaggag aagaccggac      240
caatgaaaga aatcaacctt gctcctgaca gctcatccgt ggttgtatca ggacttatgg      300
cggccaccaa atatgaagtg agtgtctatg ctcttaagga cactttgaca agcagaccag      360
ctcagggtgt tgtcaccact ctggagaatgt tcagcccacc aagaagggct cgtgtgacag      420
atgctactga gaccaccatc accattagct ggagaaccaa gactgagacg atcactggct      480
tccaagttga tgccgttcca gccaatggac ctcggccgcg accacgctt                  529
```

```
<210> SEQ ID NO 179
<211> LENGTH: 454
<212> TYPE: DNA
<213> ORGANISM: Homo sapiens
<220> FEATURE:
<221> NAME/KEY: misc_feature
<222> LOCATION: 64
<223> OTHER INFORMATION: n = A,T,C or G

<400> SEQUENCE: 179
agcgtggtcg cggccgaggt ctggccgaac tgccagtgta cagggaagat gtacatgtta       60
tagntcttct cgaagtcccg ggccagcagc tccacggggt ggtctcctgc ctccaggcgc      120
ttctcattct catggatctt cttcacccgc agcttctgct tctcagtcag aaggttgttg      180
tcctcatccc tctcatacag ggtgaccagg acgttcttga gccagtcccg catgcgcagg      240
gggaattcgg tcagctcaga gtccaggcaa gggggatgt atttgcaagg cccgatgtag      300
```

| | |
|---|---|
| tccaagtgga gcttgtggcc cttcttggtg ccctccaagg tgcactttgt ggcaaagaag | 360 |
| tggcaggaag agtcgaaggt cttgttgtca ttgctgcaca ccttctcaaa ctcgccaatg | 420 |
| ggggctgggc agacctgccc gggcggccgc tcga | 454 |

<210> SEQ ID NO 180
<211> LENGTH: 454
<212> TYPE: DNA
<213> ORGANISM: Homo sapiens
<220> FEATURE:
<221> NAME/KEY: misc_feature
<222> LOCATION: 55, 299, 317, 332, 342, 348
<223> OTHER INFORMATION: n = A,T,C or G

<400> SEQUENCE: 180

| | |
|---|---|
| tcgagcggcc gcccgggcag gtctgcccag cccccattgg cgagtttgag aaggngtgca | 60 |
| gcaatgacaa caagaccttc gactcttcct gccacttctt tgccacaaag tgcaccctgg | 120 |
| agggcaccaa gaagggccac aagctccacc tggactacat cgggccttgc aaatacatcc | 180 |
| cccttgcct ggactctgag ctgaccgaat tcccctgcg catgcgggac tggctcaaga | 240 |
| acgtcctggt caccctgtat gagagggatg aggacaacaa ccttctgact gagaagcana | 300 |
| agctgcgggt gaagaanatc catgagaatg anaagcgcct gnaggcanga gaccaccccg | 360 |
| tggagctgct ggcccgggac ttcgagaaga actataacat gtacatcttc cctgtacact | 420 |
| ggcagttcgg ccagacctcg gccgcgacca cgct | 454 |

<210> SEQ ID NO 181
<211> LENGTH: 102
<212> TYPE: DNA
<213> ORGANISM: Homo sapiens
<220> FEATURE:
<221> NAME/KEY: misc_feature
<222> LOCATION: 8, 47, 60, 67
<223> OTHER INFORMATION: n = A,T,C or G

<400> SEQUENCE: 181

| | |
|---|---|
| agcgtggntg cggacgacgc ccacaaagcc attgtatgta gttttanttc agctgcaaan | 60 |
| aataccncca gcatccacct tactaaccag catatgcaga ca | 102 |

<210> SEQ ID NO 182
<211> LENGTH: 337
<212> TYPE: DNA
<213> ORGANISM: Homo sapiens
<220> FEATURE:
<221> NAME/KEY: misc_feature
<222> LOCATION: 169, 195, 253, 314
<223> OTHER INFORMATION: n = A,T,C or G

<400> SEQUENCE: 182

| | |
|---|---|
| tcgagcggtc gcccgggcag gtctgggcgg atagcaccgg gcatattttg gaatggatga | 60 |
| ggtctggcac cctgagcagc ccagcgagga cttggtctta gttgagcaat ttggctagga | 120 |
| ggatagtatg cagcacggtt ctgagtctgt gggatagctg ccatgaagna acctgaagga | 180 |
| ggcgctggct ggtangggtt gattacaggg ctgggaacag ctcgtacact tgccattctc | 240 |
| tgcatatact ggntagtgag gcgagcctgg cgctcttctt tgcgctgagc taaagctaca | 300 |
| tacaatggct ttgnggacct cggccgcgac cacgctt | 337 |

<210> SEQ ID NO 183
<211> LENGTH: 374
<212> TYPE: DNA
<213> ORGANISM: Homo sapiens

<400> SEQUENCE: 183

```
tcgagcggcc gcccgggcag gtccattttc tccctgacgg tcccacttct ctccaatctt    60
gtagttcaca ccattgtcat gacaccatct agatgaatca catctgaaat gaccacttcc   120
aaagcctaag cactggcaca acagtttaaa gcctgattca gacattcgtt cccactcatc   180
tccaacggca taatgggaaa ctgtgtaggg gtcaaagcac gagtcatccg taggttggtt   240
caagccttcg ttgacagaag ttgcccacgg taacaacctc ttcccgaacc ttatgcctct   300
gctggtcttt caagtgcctc cactatgatg ttgtaggtgg cacctctggt gaggacctcg   360
gccgcgacca cgct                                                     374
```

<210> SEQ ID NO 184
<211> LENGTH: 375
<212> TYPE: DNA
<213> ORGANISM: Homo sapiens
<220> FEATURE:
<221> NAME/KEY: misc_feature
<222> LOCATION: 30, 174, 248, 285, 306, 332, 345, 368
<223> OTHER INFORMATION: n = A,T,C or G

<400> SEQUENCE: 184

```
agcgtggttt gcggccgagg tcctcaccan aggtgccacc tacaacatca tagtggaggc    60
actgaaagac cagcagaggc ataaggttcg ggaagaggtt gttaccgtgg caactctgt    120
caacgaaggc ttgaaccaac ctacggatga ctcgtgcttt gacccctaca cagnttccca   180
ttatgccgtt ggagatgagt gggaacgaat gtctgaatca ggctttaaac tgttgtgcca   240
gtgcttangc tttggaagtg gtcatttcag atgtgattca tctanatggt gtcatgacaa   300
tggtgngaac tacaagattg gagagaagtg gnaccgtcag gggganaaaat ggacctgccc   360
gggcggcncg ctcga                                                    375
```

<210> SEQ ID NO 185
<211> LENGTH: 148
<212> TYPE: DNA
<213> ORGANISM: Homo sapiens
<220> FEATURE:
<221> NAME/KEY: misc_feature
<222> LOCATION: 28, 36, 86
<223> OTHER INFORMATION: n = A,T,C or G

<400> SEQUENCE: 185

```
agcgtggtcg cggccgaggt ctggcttnct gctcangtga ttatcctgaa ccatccaggc    60
caaataagcg ccggctatgc ccctgnattg gattgccaca cggctcacat tgcatgcaag   120
tttgctgagc tgaaggaaaa gattgatc                                      148
```

<210> SEQ ID NO 186
<211> LENGTH: 397
<212> TYPE: DNA
<213> ORGANISM: Homo sapiens
<220> FEATURE:
<221> NAME/KEY: misc_feature
<222> LOCATION: 78
<223> OTHER INFORMATION: n = A,T,C or G

<400> SEQUENCE: 186

```
tcgagcggcc gcccgggcag gtccaattga aacaaacagt tctgagaccg ttcttccacc    60
actgattaag agtggggngg cgggtattag ggataatatt catttagcct tctgagcttt   120
ctgggcagac ttggtgacct tgccagctcc agcagccttg tggtccactg ctttgatgac   180
```

```
acccaccgca actgtctgtc tcatatcacg aacagcaaag cgacccaaag gtggatagtc    240
tgagaagctc tcaacacaca tgggcttgcc aggaaccata tcaacaatgg gcagcatcac    300
cagacttcaa gaatttaagg gccatcttcc agcttttac cagaacggcg atcaatcttt    360
tccttcagct cagcaaactt gcatgcaatg tgagccg                             397

<210> SEQ ID NO 187
<211> LENGTH: 584
<212> TYPE: DNA
<213> ORGANISM: Homo sapiens
<220> FEATURE:
<221> NAME/KEY: misc_feature
<222> LOCATION: 145, 286, 363, 365, 425, 433, 452, 462, 471, 512, 514,
      534, 536, 540, 565, 583
<223> OTHER INFORMATION: n = A,T,C or G

<400> SEQUENCE: 187
tcgagcggcc gcccgggcag gtccagaggg ctgtgctgaa gtttgctgct gccactggag    60
ccactccaat tgctggccgc ttcactcctg gaaccttcac taaccagatc caggcagcct    120
tccgggagcc acggcttctt gtggntactg accccagggc tgaccaccag cctctcacgg    180
aggcatctta tgttaaccta cctaccattg cgctgtgtaa cacagattct cctctgcgct    240
atgtggacat tgccatccca tgcaacaaca agggagctca ctcagngggg tttgatgtgg    300
tggatgctgg ctcgggaagt tctgcgcatg cgtggcacca tttcccgtga acacccatgg    360
gangncatgc ctgatctgga cttctacaga gatcctgaag agattgaaaa agaagaacag    420
gctgnttgct ganaaagcaa gtgaccaagg angaaatttc angggtgaaa nggactgctc    480
ccgctcctga attcactgct actcaacctg angntgcaga ctggtcttga aggngnacan    540
gggccctctg ggcctattta agcancttcg gtcgcgaaca cgnt                    584

<210> SEQ ID NO 188
<211> LENGTH: 579
<212> TYPE: DNA
<213> ORGANISM: Homo sapiens
<220> FEATURE:
<221> NAME/KEY: misc_feature
<222> LOCATION: 7, 136, 486
<223> OTHER INFORMATION: n = A,T,C or G

<400> SEQUENCE: 188
agcgtgngtc gcggccgagg tgctgaatag gcacagaggg cacctgtaca ccttcagacc    60
agtctgcaac ctcaggctga gtagcagtga actcaggagc gggagcagtc cattcaccct    120
gaaattcctc cttggncact gccttctcag cagcagcctg ctcttctttt tcaatctctt    180
caggatctct gtagaagtac agatcaggca tgacctccca tgggtgttca cgggaaatgg    240
tgccacgcat gcgcagaact tcccgagcca gcatccacca catcaaaccc actgagtgag    300
ctcccttgtt gttgcatggg atgggcaatg tccacatagc gcagaggaga atctgtgtta    360
cacagcgcaa tggtaggtag gttaacataa gatgcctccg cgagaagctg gtggtcagcc    420
ctggggtcaa gtaaccacaa gaagccgtgg ctcccggaag gctgcctgga tctggttagt    480
gaaggntcca ggagtgaagc ggccaacaat tggagtggct tcagtggcaa gcagcaaact    540
tcagcacaag ccctctggac ctgcccggcg ccgctcga                           579

<210> SEQ ID NO 189
<211> LENGTH: 374
<212> TYPE: DNA
<213> ORGANISM: Homo sapiens
<220> FEATURE:
```

<221> NAME/KEY: misc_feature
<222> LOCATION: 41, 280, 314, 330, 350, 353
<223> OTHER INFORMATION: n = A,T,C or G

<400> SEQUENCE: 189

| | | | | | |
|---|---|---|---|---|---|
| tcgagcggcc | gcccgggcag | gtccattttc | tccctgacgg | ncccacttct | ctccaatctt | 60 |
| gtagttcaca | ccattgtcat | ggcaccatct | agatgaatca | catctgaaat | gaccacttcc | 120 |
| aaagcctaag | cactggcaca | acagtttaaa | gcctgattca | gacattcgtt | cccactcatc | 180 |
| tccaacggca | taatgggaaa | ctgtgtaggg | gtcaaagcac | gagtcatccg | taggttggtt | 240 |
| caagccttcg | ttgacagagt | tgcccacggt | aacaacctcn | tccccgaacc | ttatgcctct | 300 |
| gctgggcttt | cagngcctcc | actatgatgn | tgtagggggg | cacctctggn | gangacctcg | 360 |
| gccgcgacca | cgct | | | | | 374 |

<210> SEQ ID NO 190
<211> LENGTH: 373
<212> TYPE: DNA
<213> ORGANISM: Homo sapiens
<220> FEATURE:
<221> NAME/KEY: misc_feature
<222> LOCATION: 247, 304, 306, 332, 337
<223> OTHER INFORMATION: n = A,T,C or G

<400> SEQUENCE: 190

| | | | | | |
|---|---|---|---|---|---|
| agcgtggtcg | cggccgaggt | cctcaccaga | ggtgccacct | acaacatcat | agtggaggca | 60 |
| ctgaaagacc | agcagaggca | taaggctcgg | gaagaggttg | ttaccgtggg | caactctgtc | 120 |
| aacgaaggct | tgaaccaacc | tacggatgac | tcgtgctttg | accccctacac | agtttcccat | 180 |
| tatgccgttg | gagatgagtg | ggaacgaatg | tctgaatcag | gctttaaaact | gttgtgccag | 240 |
| tgcttangct | ttggaagtgg | gtcatttcag | atgtgattca | tctagatggt | gccatgacaa | 300 |
| tggngngaac | tacaagattg | gagagaagtg | gnaccgncag | ggagaaaatg | gacctgcccg | 360 |
| ggcggccgct | cga | | | | | 373 |

<210> SEQ ID NO 191
<211> LENGTH: 354
<212> TYPE: DNA
<213> ORGANISM: Homo sapiens
<220> FEATURE:
<221> NAME/KEY: misc_feature
<222> LOCATION: 218, 299, 306, 326, 333, 337, 341
<223> OTHER INFORMATION: n = A,T,C or G

<400> SEQUENCE: 191

| | | | | | |
|---|---|---|---|---|---|
| agcgtggtcg | cggccgaggt | ccacatcggc | agggtcggag | ccctggccgc | catactcgaa | 60 |
| ctggaatcca | tcggtcatgc | tctcgccgaa | ccagacatgc | ctcttgtcct | tggggttctt | 120 |
| gctgatgtac | cagttcttct | gggccacact | gggctgagtg | gggtacacgc | aggtctcacc | 180 |
| agtctccatg | ttgcagaaga | ctttgatggc | atccaggntg | caaccttggt | tggggtcaat | 240 |
| ccagtactct | ccactcttcc | agccagagtg | gcacatcttg | aggtcacggc | aggtgcggnc | 300 |
| gggggntttt | gcggctgccc | tctggncttc | ggntgtnctc | natctgctgg | ctca | 354 |

<210> SEQ ID NO 192
<211> LENGTH: 587
<212> TYPE: DNA
<213> ORGANISM: Homo sapiens
<220> FEATURE:
<221> NAME/KEY: misc_feature
<222> LOCATION: 276
<223> OTHER INFORMATION: n = A,T,C or G

<400> SEQUENCE: 192

```
tcgagcggcc gcccgggcag gtctcgcggt cgcactggtg atgctggtcc tgttggtccc      60
cccggccctc ctggacctcc tggcccccct ggtcctccca gcgctggttt cgacttcagc     120
ttcctgcccc agccacctca agagaaggct cacgatggtg gccgctacta ccgggctgat     180
gatgccaatg tggttcgtga ccgtgacctc gaggtggaca ccaccctcaa gagcctgagc     240
cagcagatcg agaacatccg gagcccagag ggcagncgca agaaccccgc ccgcacctgc     300
cgtgacctca agatgtgcca ctctgactgg aagagtggag agtactggat tgaccccaac     360
caagctgcaa cctggatgcc atcaaagtct tctgcaacat ggagactggt gagacctgcg     420
tgtaccccac tcagcccagt gtggcccaaa gaactggta catcagcaag aaccccaagg      480
acaagaagca tgtctggttc ggcgagaaca tgaccgatgg attccagttc gagtatggcg     540
ggcagggctc cgaccctgcc gatggggacc ttggccgcga acacgct                  587
```

<210> SEQ ID NO 193
<211> LENGTH: 98
<212> TYPE: DNA
<213> ORGANISM: Homo sapiens
<220> FEATURE:
<221> NAME/KEY: misc_feature
<222> LOCATION: 8, 9, 33, 58, 71, 90
<223> OTHER INFORMATION: n = A,T,C or G

<400> SEQUENCE: 193

```
agcgtggnng cggccgaggt ataaatatcc agnccatatc ctccctccac acgctganag      60
atgaagctgt ncaaagatct cagggtggan aaaaccat                              98
```

<210> SEQ ID NO 194
<211> LENGTH: 240
<212> TYPE: DNA
<213> ORGANISM: Homo sapiens

<400> SEQUENCE: 194

```
tcgagcggcc gcccgggcag gtccttcaga cttggactgt gtcacactgc caggcttcca      60
gggctccaac ttgcagacgg cctgttgtgg gacagtctct gtaatcgcga aagcaaccat     120
ggaagacctg ggggaaaaca ccatggtttt atccaccctg agatctttga acaacttcat     180
ctctcagcgt gcggagggag gctctggact ggatatttct acctcggccg cgaccacgct     240
```

<210> SEQ ID NO 195
<211> LENGTH: 400
<212> TYPE: DNA
<213> ORGANISM: Homo sapiens
<220> FEATURE:
<221> NAME/KEY: misc_feature
<222> LOCATION: 22, 37, 39, 105, 268, 276, 302, 323, 331, 335, 347,
      351, 371, 378
<223> OTHER INFORMATION: n = A,T,C or G

<400> SEQUENCE: 195

```
cgagcgggcg accgggcagg tncagactcc aatccanana accatcaagc cagatgtcag      60
aagctacacc atcacaggtt tacaaccagg cactgactac aaganctacc tgcacacctt     120
gaatgacaat gctcggagct cccctgtggt catcgacgcc tccactgcca ttgatgcacc     180
atccaacctg cgtttcctgg ccaccacacc caattccttg ctggtatcat ggcagccgcc     240
acgtgccagg attaccggta catcatcnag tatganaagc ctgggcctcc tcccagagaa     300
gnggtccctc ggccccgccc tgntgtccca naggntacta ttactgngcc ngcaaccggc     360
```

```
aaccgatatc nattttgnca ttggccttca acaataatta                    400
```

<210> SEQ ID NO 196
<211> LENGTH: 494
<212> TYPE: DNA
<213> ORGANISM: Homo sapiens
<220> FEATURE:
<221> NAME/KEY: misc_feature
<222> LOCATION: 19, 83, 168, 252, 271, 292, 430
<223> OTHER INFORMATION: n = A,T,C or G

<400> SEQUENCE: 196

```
agcgtggttc gcggccgang tcctgtcaga gtggcactgg tagaagttcc aggaaccctg    60
aactgtaagg gttcttcatc agngccaaca ggatgacatg aaatgatgta ctcagaagtg   120
tcctggaatg gggcccatga gatggttgtc tgagagagag cttcttgncc tgtcttttc    180
cttccaatca ggggctcgct cttctgatta ttcttcaggg caatgacata aattgtatat   240
tcgggtcccg gntccaggcc agtaatagta ncctctgtga caccagggcg gngccgaggg   300
accacttctc tgggaggaga cccaggcttc tcatacttga tgatgtaacc ggtaatcctg   360
gcacgtggcg gctgccatga taccagcaag gaattggggt gtggtggcca ggaaacgcag   420
gttggatggn gcatcaatgg cagtggaggc cgtcgatgac cacaggggga gctccgacat   480
tgtcattcaa ggtg                                                    494
```

<210> SEQ ID NO 197
<211> LENGTH: 118
<212> TYPE: DNA
<213> ORGANISM: Homo sapiens
<220> FEATURE:
<221> NAME/KEY: misc_feature
<222> LOCATION: 8, 71, 96
<223> OTHER INFORMATION: n = A,T,C or G

<400> SEQUENCE: 197

```
agcgtggncg cggccgaggt gcagcgcggg ctgtgccacc ttctgctctc tgcccaacga    60
taaggagggt ncctgccccc aggagaacat taactntccc cagctcggcc tctgccgg    118
```

<210> SEQ ID NO 198
<211> LENGTH: 403
<212> TYPE: DNA
<213> ORGANISM: Homo sapiens
<220> FEATURE:
<221> NAME/KEY: misc_feature
<222> LOCATION: 41, 53, 98, 195, 350
<223> OTHER INFORMATION: n = A,T,C or G

<400> SEQUENCE: 198

```
tcgagcggcc gcccgggcag gttttttttg ctgaaagtgg ntactttatt ggntgggaaa    60
gggagaagct gtggtcagcc caagagggaa tacagagncc cgaaaaaggg gagggcaggt   120
gggctggaac cagacgcagg gccaggcaga aactttctct cctcactgct cagcctggtg   180
gtggctggag ctcanaaatt gggagtgaca caggacacct tcccacagcc attgcggcgg   240
catttcatct ggccaggaca ctggctgtcc acctggcact ggtcccgaca gaagcccgag   300
ctggggaaag ttaatgttca cctgggggca ggaaccctcc ttatcattgn gcagagagca   360
gaaggtggca cagcccgcgc tgcacctcgg ccgcgaccac gct                    403
```

<210> SEQ ID NO 199
<211> LENGTH: 167
<212> TYPE: DNA

```
<213> ORGANISM: Homo sapiens
<220> FEATURE:
<221> NAME/KEY: misc_feature
<222> LOCATION: 92, 107
<223> OTHER INFORMATION: n = A,T,C or G

<400> SEQUENCE: 199
tcgagcggcc gcccgggcag gtccaccata agtcctgata caaccacgga tgagctgtca      60
ggagcaaggt tgatttcttt cattggtccg gncttctcct tggggncac ccgcactcga     120 tatccagtga gctgaacatt gggtggcgtc cactgggcgc tcaggct                  167

<210> SEQ ID NO 200
<211> LENGTH: 252
<212> TYPE: DNA
<213> ORGANISM: Homo sapiens
<220> FEATURE:
<221> NAME/KEY: misc_feature
<222> LOCATION: 210, 226, 227, 230, 236
<223> OTHER INFORMATION: n = A,T,C or G

<400> SEQUENCE: 200
tcgagcggtt cgcccgggca ggtccaccac acccaattcc ttgctggtat catggcagcc      60
gccacgtgcc aggattaccg gctacatcat caagtatgag aagcctgggt ctcctcccag    120
agaagcggtc cctcggcccc gccctggtgt cacagaggct actattactg gcctggaacc    180
gggaaccgaa tatacaattt atgtcattgn cctgaagaat aatcannaan agcganccc    240 tgattggaag ga                                                        252

<210> SEQ ID NO 201
<211> LENGTH: 91
<212> TYPE: DNA
<213> ORGANISM: Homo sapiens

<400> SEQUENCE: 201
agcgtggtcg cggccgaggt tgtacaagct tttttttttt tttttttttt tttttttttt      60
tttttttttt tttttttttt tttttttttt t                                    91

<210> SEQ ID NO 202
<211> LENGTH: 368
<212> TYPE: DNA
<213> ORGANISM: Homo sapiens
<220> FEATURE:
<221> NAME/KEY: misc_feature
<222> LOCATION: 9, 354
<223> OTHER INFORMATION: n = A,T,C or G

<400> SEQUENCE: 202
tcgagcggnc gcccgggcag gtctgccaac accaagattg gccccgccg catccacaca      60 gtccgtgtgc gggaggtaa caagaaatac cgtgccctga ggttggacgt ggggaatttc    120
tcctggggct cagagtgttg tactcgtaaa acaaggatca tcgatgttgt ctacaatgca    180
tctaataacg agctggttcg taccaagacc ctggtgaaga attgcatcgt gctcatcgac    240
agcacaccgt accgacagtg gtacgagtcc cactatgcgc tgcccctggg ccgcaagaag    300
ggagccaagc tgactcctga ggaagaagag attttaaaca aaaacgatc taanaaaaaa    360 aaaacaat                                                             368

<210> SEQ ID NO 203
<211> LENGTH: 340
<212> TYPE: DNA
<213> ORGANISM: Homo sapiens
```

<400> SEQUENCE: 203

```
agcgtggtcg cggccgaggt gaaatggtat tcagcttcct ggcacttctg gtcagcaacc    60
cagtgttggg caacaaatga tctttgagga acatggtttt aggcggacca caccgcccac   120
aacggccacc cccataaggc ataggccaag accatacccg ccgaatgtag gacaagaagc   180
tctctctcag acaaccatct catgggcccc attccaggac acttctgagt acatcatttc   240
atgtcatcct gttggcactg atgaagaacc cttacagttc agggttcctg gaacttctac   300
cagtgccact ctgacaggac ctgcccgggc ggccgctcga                         340
```

<210> SEQ ID NO 204
<211> LENGTH: 341
<212> TYPE: DNA
<213> ORGANISM: Homo sapiens

<400> SEQUENCE: 204

```
tcgagcggcc gcccgggcag gtcctgtcag agtggcactg gtagaagttc caggaaccct    60
gaactgtaag ggttcttcat cagtgccaac aggatgacat gaaatgatgt actcagaagt   120
gtcctggaat ggggcccatg agatggttgt ctgagagaga gcttcttgtc ctacattcgg   180
cgggtatggt cttggcctat gccttatggg ggtggccgtt gtgggcggtg tggtccgcct   240
aaaaccatgt tcctcaaaga tcatttgttg cccaacactg ggttgctgac cagaagtgcc   300
aggaagctga ataccatttc acctcggccg cgaccacgct a                      341
```

<210> SEQ ID NO 205
<211> LENGTH: 770
<212> TYPE: DNA
<213> ORGANISM: Homo sapiens
<220> FEATURE:
<221> NAME/KEY: misc_feature
<222> LOCATION: 529, 591, 623, 626, 629, 630, 656, 702, 709, 712, 717,
      743, 746, 749, 759, 762, 766
<223> OTHER INFORMATION: n = A,T,C or G

<400> SEQUENCE: 205

```
tcgagcggcc gcccgggcag gtctcccttc ttgcggccca ggggcagcgc atagtgggac    60
tcgtaccact gtcggtacgg tgtgctgtcg atgagcacga tgcaattctt caccagggtc   120
ttggtacgaa ccagctcgtt attagatgca ttgtagacaa catcgatgat ccttgtttta   180
cgagtacaac actctgagcc ccaggagaaa ttccccacgt ccaacctcag ggcacggtat   240
ttcttgttac ctccccgcac acggactgtg tggatgcggc ggggccaag ctgactcctg    300
aggaagaaga gattttaaac aaaaaacgat ctaaaaaaat tcagaagaaa tatgatgaaa   360
ggaaaaagaa tgccaaaatc agcagtctcc tggaggagca gttccagcag gcaagcttc    420
ttgcgtgcat cgcttcaagg ccgggacagt gtgaccgagc agatggctat gtgctagagg   480
gcaaagaagt ggagttctat cttaagaaaa tcagggccca gaatggtgng tcttcaacta   540
atccaaaggg gagtttcaga ccagtgcaat cagcaaaaac attgatactg ntggccaaat   600
ttattggtgc agggcttgca cantangann ggctgggtct tggggcttgg attggnacaa   660
gctttggcag ccttttcttt ggttttgcca aaaaccttt gntgaagang anacctnggg    720
cggaccccct aaccgattcc acnccnggng gcgttctang gncccncttg              770
```

<210> SEQ ID NO 206
<211> LENGTH: 810
<212> TYPE: DNA
<213> ORGANISM: Homo sapiens

```
<220> FEATURE:
<221> NAME/KEY: misc_feature
<222> LOCATION: 574, 621, 625, 636, 668, 673, 704, 728, 743, 767, 772,
      786, 789, 807, 809, 810
<223> OTHER INFORMATION: n = A,T,C or G

<400> SEQUENCE: 206
agcgtggtcg cggccgaggt ctgctgcttc agcgaagggt ttctggcata accaatgata    60
aggctgccaa agactgttcc aataccagca ccagaaccag ccactcctac tgttgcagca   120
cctgcaccaa taaatttggc agcagtatca atgtctctgc tgattgcact ggtctgaaac   180 tcccttttgga ttagctgaga cacaccattc tgggccctga ttttcctaag atagaactcc   240
aactctttgc cctctagcac atagccatct gctcggtcac actgtcccgg ccttgaagcg   300
atgcacgcaa gaagcttgcc ctgctggaac tgctcctcca ggagactgct gattttggca   360 ttcttttttcc tttcatcata tttcttctga atttttttag atcgtttttt gtttaaaatc   420
tcttcttcct caggagtcag cttggcccccc gccgcatcca cacagtccgt gtgcggggag   480
gtaacaagaa ataccgtgcc ctgaggttgg acgtggggaa tttctcctgg ggctcagagt   540
ggtgtactcg taaaacaagg atcatcgatg gtgnctacaa tgcatctaat aacgagctgg   600
gtcggaccca agaacctggg ngaanaaatg gatcgnctca tcgacaggac accgtacccg   660
acaggggnac gantcccact atgcgcttgc cctgggccg caanaaagga aaactgcccg   720
ggcggccntc gaaagcccaa ttntggaaaa aatccatcac actgggnggc cngtcgagca   780
tgcatntana ggggcccatt cccctnann                                      810

<210> SEQ ID NO 207
<211> LENGTH: 257
<212> TYPE: DNA
<213> ORGANISM: Homo sapiens

<400> SEQUENCE: 207
tcgagcggcc gcccgggcag gtccccaacc aaggctgcaa cctggatgcc atcaaagtct    60
tctgcaacat ggagactggt gagacctgcg tgtaccccac tcagcccagt gtggcccaga   120
agaactggta catcagcaag aaccccaagg acaagaggca tgtctggttc ggcgagagca   180
tgaccgatgg attccagttc gagtatggcg gccagggctc cgaccctgcc gatgtggacc   240
tcggccgcga ccacgct                                                   257

<210> SEQ ID NO 208
<211> LENGTH: 257
<212> TYPE: DNA
<213> ORGANISM: Homo sapiens

<400> SEQUENCE: 208
agcgtggtcg cggccgaggt ccacatcggc agggtcggag ccctggccgc catactcgaa    60
ctggaatcca tcggtcatgc tctcgccgaa ccagacatgc ctcttgtcct tggggttctt   120
gctgatgtac cagttcttct gggccacact gggctgagtg gggtacacgc aggtctcacc   180
agtctccatg ttgcagaaga ctttgatggc atccaggttg cagccttggt tggggacctg   240
cccgggcggc cgctcga                                                   257

<210> SEQ ID NO 209
<211> LENGTH: 747
<212> TYPE: DNA
<213> ORGANISM: Homo sapiens
<220> FEATURE:
<221> NAME/KEY: misc_feature
```

```
<222> LOCATION: 453, 538, 540, 542, 546, 554, 556, 598, 659, 670, 679,
      689, 693, 711, 723, 724, 731, 747
<223> OTHER INFORMATION: n = A,T,C or G

<400> SEQUENCE: 209
tcgagcggcc gcccgggcag gtccaccaca cccaattcct tgctggtatc atggcagccg    60
ccacgtgcca ggattaccgg ctacatcatc aagtatgaga agcctgggtc tcctcccaga   120
gaagtggtcc ctcggccccg ccctggtgtc acagaggcta ctattactgg cctggaaccg   180
ggaaccgaat atacaattta tgtcattgcc ctgaagaata tcagaagag cgagcccctg    240 attggaagga aaagacaga cgagcttccc caactggtaa cccttccaca ccccaatctt    300
catggaccag agatcttgga tgttccttcc acagttcaaa agaccccttt cgtcacccac   360
cctgggtatg acactggaaa tggtattcag cttcctggca cttctggtca gcaacccagt   420
gttgggcaac aaatgatctt tgaggaacat ggntttaggc ggaccacacc gcccacaacg   480
gccaccccca taaggcatag gccaagacca tacccgccga atgtaggaca agaagctntn   540
tntcanacac catntnatgg gccccattcc aggacacttc tgagtacatc atttatgnca   600
tctgtggcac ttgatgaaaa cccttacagt tcagggttct ggaactttta ccaggcctnt   660
tacaggactn ggccggacnc cttaagccna ttncaccctg gggcgttcta nggtcccact   720
cgnncactgg ngaaaatggc tactgtn                                       747

<210> SEQ ID NO 210
<211> LENGTH: 872
<212> TYPE: DNA
<213> ORGANISM: Homo sapiens
<220> FEATURE:
<221> NAME/KEY: misc_feature
<222> LOCATION: 165, 174, 181, 256, 260, 269, 271, 277, 286, 289, 294,
      298, 300, 301, 303, 308, 311, 321, 325, 328, 329, 333, 338, 342,
      346, 349, 351, 357, 359, 364, 366, 379, 385, 395, 396, 397,
      407, 408, 410, 414, 415, 429, 431, 434, 435, 440, 443
<223> OTHER INFORMATION: n = A,T,C or G
<220> FEATURE:
<221> NAME/KEY: misc_feature
<222> LOCATION: 444, 446, 447, 448, 449, 450, 451, 464, 470, 472, 475,
      479, 483, 484, 485, 488, 494, 496, 497, 504, 508, 509, 511, 513,
      517, 522, 524, 526, 532, 533, 542, 543, 553, 559, 566, 567,
      571, 572, 578, 582, 588, 591, 594, 595, 596, 600, 606
<223> OTHER INFORMATION: n = A,T,C or G
<220> FEATURE:
<221> NAME/KEY: misc_feature
<222> LOCATION: 612, 614, 617, 618, 629, 630, 631, 652, 654, 655, 661,
      663, 664, 666, 671, 673, 678, 679, 681, 688, 690, 691, 698, 706,
      707, 708, 714, 719, 721, 723, 726, 741, 751, 761, 762, 769,
      770, 778, 779, 781, 782, 785, 791, 802, 807, 808, 812
<223> OTHER INFORMATION: n = A,T,C or G
<220> FEATURE:
<221> NAME/KEY: misc_feature
<222> LOCATION: 815, 820, 827, 828, 838, 841, 844, 851, 857, 864, 866,
      869, 872
<223> OTHER INFORMATION: n = A,T,C or G

<400> SEQUENCE: 210
agcgtggtcg cggccgaggt ccactagagg tctgtgtgcc attgcccagg cagagtctct    60
gcgttacaaa ctcctaggag ggcttgctgt gcggagggcc tgctatggtg tgctgcggtt   120
catcatggag agtggggcca aaggctgcga ggttgtggtg tctgngaaac tccnaggaca   180
ngagggctaa attccatgaa gtttgtggat ggcctgatga tccacaatcg gagaccctgt   240
taactactac cgtctnaccn cctgctgtnc nccccnttt ctgctnaana catgggntn    300 ntncttgncc ntccttgggt ngaanatnna atngcctncc cnttcntanc nctactngnt   360
ccananttgg cctttaaana atccncccttg ccttnnncac tgttcanntn tttnntcgta   420
```

```
aaccctatna nttnnattan atnntnnnnn nctcacccc ctcntcattn anccnatang      480
ctnnnaantc cttnanncct cccnccennt ncnctcntac tnantncttc tnncccatta    540
cnnagctctt tcntttaana taatgnngcc nngctctnca tntctacnat ntgnnnaatn    600 cccccnccce cnancgnntt tttgacctnn naacctcctt tcctcttccc tncnnaaatt    660
ncnnanttcc ncnttccnnc ntttcggntn ntcccatnct ttccannnct tcantctanc    720
ncnctncaac ttattttcct ntcatccctt nttctttaca nnccccctnn tctactcnnc    780
nnttncatta natttgaaac tnccacnnct anttncctcn ctctacnntt ttattttncg    840
ntcnctctac ntaatantt aatnanttnt cn                                   872

<210> SEQ ID NO 211
<211> LENGTH: 517
<212> TYPE: DNA
<213> ORGANISM: Homo sapiens
<220> FEATURE:
<221> NAME/KEY: misc_feature
<222> LOCATION: 462, 464, 506
<223> OTHER INFORMATION: n = A,T,C or G

<400> SEQUENCE: 211
tcgagcggcc gcccgggcag gtctgccaag gagaccctgt tatgctgtgg ggactggctg     60
gggcatggca ggcggctctg gcttcccacc cttctgttct gagatggggg tggtgggcag   120
tatctcatct ttgggttcca caatgctcac gtggtcaggc aggggcttct tagggccaat   180
cttaccagtt gggtcccagg gcagcatgat cttcaccttg atgcccagca caccctgtct   240
gagcaacacg tggcgcacaa gcagtgtcaa cgtagtaagt taacagggtc tccgctgtgg   300
atcatcaggc catccacaaa cttcatggat ttagccctct gtcctcggag tttcccagac   360
accacaacct cgcagccttt ggccccactc tccatgatga accgcagcac accatagcag   420
gccctccgca caagcaagcc ctcctaagaa tttgtaacgc ananactctg ctggcaatgg   480
cacacaaacc tctagtggac ctcggncgcg accacgc                             517

<210> SEQ ID NO 212
<211> LENGTH: 695
<212> TYPE: DNA
<213> ORGANISM: Homo sapiens
<220> FEATURE:
<221> NAME/KEY: misc_feature
<222> LOCATION: 432, 476, 522, 547, 621, 624, 647, 679
<223> OTHER INFORMATION: n = A,T,C or G

<400> SEQUENCE: 212
tcgagcggcc gcccgggcag gtctggtcca ggatagcctg cgagtcctcc tactgctact     60
ccagacttga catcatatga atcatactgg ggagaatagt tctgaggacc agtagggcat   120
gattcacaga ttccaggggg gccaggagaa ccaggggacc ctggttgtcc tggaatacca   180
gggtcaccat ttctcccagg aataccagga gggcctggat ctcccttggg gccttgaggt   240
ccttgaccat taggagggcg agtaggagca gttggaggct gtgggcaaac tgcacaacat   300
tctccaaatg gaatttctgg gttggggcag tctaattctt gatccgtcac atattatgtc   360
atcgcagaga acggatcctg agtcacagac acatatttgg catggttctg gcttccagac   420
atctctatcc gncataggac tgaccaagat gggaacatcc tccttcaaca agcttnctgt   480
tgtgccaaaa ataatagtgg gatgaagcag accgagaagt anccagctcc ccttttttgca   540 caaagcntca tcatgtctaa atatcagaca tgagacttct ttgggcaaaa aaggagaaaa   600
```

| | | |
|---|---|---|
| agaaaaagca gttcaaagta nccnccatca agttggttcc ttgcccnttc agcacccggg | 660 |
| ccccgttata aaacacctng ggccggaccc ccctt | 695 |

<210> SEQ ID NO 213
<211> LENGTH: 804
<212> TYPE: DNA
<213> ORGANISM: Homo sapiens
<220> FEATURE:
<221> NAME/KEY: misc_feature
<222> LOCATION: 552, 555, 592, 624, 629, 633, 658, 695, 697, 698, 700, 702, 745, 753, 755, 762, 773, 786, 788, 793, 795
<223> OTHER INFORMATION: n = A,T,C or G

<400> SEQUENCE: 213

| | |
|---|---|
| agcgtggtcg cggccgaggt gttttatgac gggcccggtg ctgaagggca gggaacaact | 60 |
| tgatggtgct actttgaact gcttttcttt tctccttttt gcacaaagag tctcatgtct | 120 |
| gatatttaga catgatgagc tttgtgcaaa aggggagctg ctacttctc gctctgcttc | 180 |
| atcccactat tattttggca acacaggaag ctgttgaagg aggatgttcc catcttggtc | 240 |
| agtcctatgc ggatagagat gtctggaagc cagaaccatg ccaaatatgt gtctgtgact | 300 |
| caggatccgt tctctgcgat gacataatat gtgacgatca agaattagac tgccccaacc | 360 |
| cagaaattcc atttggagaa tgttgtgcag tttgcccaca gcctccaact gctcctactc | 420 |
| gccctcctaa tggtcaagga cctcaaggcc caagggaga tccaggccct cctggtattc | 480 |
| ctgggagaaa tggtgaccct ggtattccag acaaccagg gtccctggt tctcctggcc | 540 |
| cccctggaat cnggngaatc atgccctact ggtcctcaaa ctattctccc anatgattca | 600 |
| tatgatgtca agtctgggat agcnagtang ganggactcg caggctattc tggaccanac | 660 |
| ctgccggggg ggcgttcgaa agcccgaatc tgcananntn cnttcacact ggcggccgtc | 720 |
| gagctgcttt aaaagggcca ttccnccttt agngnggggg antacaatta ctnggcggcg | 780 |
| ttttanancg cgngnctggg aaat | 804 |

<210> SEQ ID NO 214
<211> LENGTH: 594
<212> TYPE: DNA
<213> ORGANISM: Homo sapiens
<220> FEATURE:
<221> NAME/KEY: misc_feature
<222> LOCATION: 452, 509, 585
<223> OTHER INFORMATION: n = A,T,C or G

<400> SEQUENCE: 214

| | |
|---|---|
| agcgtggtcg cggccgaggt ccacatcggc agggtcggag ccctggccgc catactcgaa | 60 |
| ctggaatcca tcggtcatgc tctcgccgaa ccagacatgc ctcttgtcct tggggttctt | 120 |
| gctgatgtac cagttcttct gggccacact gggctgagtg gggtacacgc aggtctcacc | 180 |
| agtctccatg ttgcagaaga ctttgatggc atccaggttg cagccttggt tggggtcaat | 240 |
| ccagtactct ccactcttcc agtcagagtg gcacatcttg aggtcacggc aggtgcgggc | 300 |
| ggggttcttg cggctgccct ctgggctccg gatgttctcg atctgctggc tcaggctctt | 360 |
| gagggtggtg tccacctcga ggtcacggtc acgaaccaca ttggcatcat cagcccggta | 420 |
| gtagcggcca ccatcgtgag ccttctcttg angtggctgg ggcaggaact gaagtcgaaa | 480 |
| ccagcgctgg gaggaccagg gggaccaana ggtccaggaa gggcccgggg gggaccaaca | 540 |
| ggaccagcat caccaagtgc gacccgcgag aacctgcccg gccgnccgct cgaa | 594 |

<210> SEQ ID NO 215

```
<211> LENGTH: 590
<212> TYPE: DNA
<213> ORGANISM: Homo sapiens
<220> FEATURE:
<221> NAME/KEY: misc_feature
<222> LOCATION: 8, 9
<223> OTHER INFORMATION: n = A,T,C or G

<400> SEQUENCE: 215
tcgagcgnnc gcccgggcag gtctcgcggt cgcactggtg atgctggtcc tgttggtccc      60
cccggccctc ctggacctcc tggtcccccct ggtcctccca gcgctggttt cgacttcagc    120
ttcctgcccc agccacctca agagaaggct cacgatggtg gccgctacta ccgggctgat    180
gatgccaatg tggttcgtga ccgtgacctc gaggtggaca ccaccctcaa gagcctgagc    240
cagcagatcg agaacatccg gagcccagag ggcagccgca agaaccccgc cgcacctgc    300 cgtgacctca agatgtgcca ctctgactgg aagagtggag agtactggat tgaccccaac    360
caaggctgca acctggatgc catcaaagtc ttctgcaaca tggagactgg tgagacctgc    420
gtgtacccca ctcagcccag tgtggcccag aagaactggt acatcagcaa gaaccccaag    480
gacaagaggc atgtctggtt cggcgagagc atgaccgatg gattccagtt cgagtatggc    540
ggccagggct cccacccctgc cgatgtggac ctccggccgc gaccaccctt                590

<210> SEQ ID NO 216
<211> LENGTH: 801
<212> TYPE: DNA
<213> ORGANISM: Homo sapiens
<220> FEATURE:
<221> NAME/KEY: misc_feature
<222> LOCATION: 2, 22, 25, 26, 328, 373, 385, 440, 473, 534, 571, 572,
      573, 582, 587, 589, 593, 600, 605, 617, 633, 642, 653, 672, 681,
      685, 696, 699, 709, 715, 717, 726, 731, 739, 742, 745, 758,
      769, 772, 778, 780, 788, 789, 791, 793, 796
<223> OTHER INFORMATION: n = A,T,C or G

<400> SEQUENCE: 216
tngagcggcc gcccggggcag gntgnnaacg ctggtcctgc tggtcctcct ggcaaggctg      60
gtgaagatgg tcaccctgga aaacccggac gacctggtga gagaggagtt gttggaccac    120
agggtgctcg tggttttccct ggaactcctg gacttcctgg cttcaaaggc attaggggac    180
acaatggtct ggatggattg aagggacagc ccggtgctcc tggtgtgaag ggtgaacctg    240
gtgcccctgg tgaaaatgga actccaggtc aaacaggagc ccgtgggctt cctggtgaga    300
gaggaccgtg ttggtgcccc tggcccanac ctcggccgcg accacgctaa gcccgaattt    360
ccagcacact ggnggccgtt actantggat ccgagctcgg taccaagctt ggcgtaatca    420
tggtcatagc tgtttcctgn gtgaaattgt tatccgctca caatttcaca cancatacga    480
agccggaaag cataaagtgt aaagccttgg ggtgctaatg agtgagctaa ctcncattaa    540
attgcgttgc gctcactgcc cgcttttcca nnngggaaac cntggcntng ccngcttgcn    600
ttaantgaaa tccgccnacc cccggggaaa agncggtttg cngtattggg gncttttttc    660
cctttcctcg gnttacttga nttantgggc tttggncgnt tcgggttgng gcganncggt    720
tcaacntcac nccaaaggng gnaanacggt tttcccanaa tccgggggnt ancccaangn    780
aaaacatnng ncnaangggc t                                              801

<210> SEQ ID NO 217
<211> LENGTH: 349
<212> TYPE: DNA
<213> ORGANISM: Homo sapiens
<220> FEATURE:
```

```
<221> NAME/KEY: misc_feature
<222> LOCATION: 10, 157, 170
<223> OTHER INFORMATION: n = A,T,C or G

<400> SEQUENCE: 217
agcgtggttn gcggccgagg tctgggccag gggcaccaac acgtcctctc tcaccaggaa     60
gcccacgggc tcctgtttga cctggagttc cattttcacc aggggcacca ggttcaccct    120
tcacaccagg agcaccggge tgtcccttca atccatncag accattgtgn ccctaatgc    180
ctttgaagcc aggaagtcca ggagttccag ggaaaccacc gagcaccctg tggtccaaca    240
actcctctct caccaggtcg tccggttttt ccagggtgac catcttcacc agccttgcca    300
ggaggaccag caggaccagc gttaccaacc tgcccgggcg gccgctcga              349

<210> SEQ ID NO 218
<211> LENGTH: 372
<212> TYPE: DNA
<213> ORGANISM: Homo sapiens

<400> SEQUENCE: 218
tcgagcggcc gcccgggcag gtccattttc tccctgacgg tcccacttct ctccaatctt     60
gtagttcaca ccattgtcat ggcaccatct agatgaatca catctgaaat gaccacttcc    120
aaagcctaag cactggcaca acagtttaaa gcctgattca gacattcgtt cccactcatc    180
tccaacggca taatgggaaa ctgtgtaggg gtcaaagcac gagtcatccg taggttggtt    240
caagccttcg ttgacagagt tgcccacggt aacaacctct cccgaacct tatgcctctg    300
ctggtctttc agtgcctcca ctatgatgtt gtaggtggca cctctggtga ggacctcggc    360
cgcgaccacg ct                                                         372

<210> SEQ ID NO 219
<211> LENGTH: 374
<212> TYPE: DNA
<213> ORGANISM: Homo sapiens

<400> SEQUENCE: 219
agcgtggtcg cggccgaggt cctcaccaga ggtgccacct acaacatcat agtggaggca     60
ctgaaagacc agcagaggca taaggttcgg gaagaggttg ttaccgtggg caactctgtc    120
aacgaaggct tgaaccaacc tacgatgac tcgtgctttg acccctacac agtttcccat    180
tatgccgttg gagatgagtg ggaacgaatg tctgaatcag ctttaaaact gttgtgccag    240
tgcttaggct ttggaagtgg tcatttcaag atgtgattca tctagatggt gccatgacaa    300
tggtgtgaac tacaagattg gagagaagtg ggaccgtcag ggagaaaatg gacctgcccg    360
ggccggccgc tcga                                                        374

<210> SEQ ID NO 220
<211> LENGTH: 828
<212> TYPE: DNA
<213> ORGANISM: Homo sapiens
<220> FEATURE:
<221> NAME/KEY: misc_feature
<222> LOCATION: 8, 9, 557, 571, 587, 588, 601, 642, 643, 647, 654, 664,
      681, 688, 698, 719, 720, 725, 734, 738, 743, 744, 757, 765, 773,
      778, 780, 782, 783, 793, 798, 805, 809, 822, 827
<223> OTHER INFORMATION: n = A,T,C or G

<400> SEQUENCE: 220
tcgagcgnnc gcccgggcag gtccagtagt gccttcggga ctgggttcac ccccaggtct     60
gcggcagttg tcacagcgcc agccccgctg gcctccaaag catgtgcagg agcaaatggc    120
```

```
accgagatat tccttctgcc actgttctcc tacgtggtat gtcttcccat catcgtaaca      180
cgttgcctca tgagggtcac acttgaattc tccttttccg ttcccaagac atgtgcagct      240
catttggctg gctctatagt ttggggaaag tttgttgaaa ctgtgccact gacctttact      300
tcctccttct ctactggagc tttcgtacct tccacttctg ctgttggtaa aatggtggat      360
cttctatcaa tttcattgac agtacccact tctcccaaac atccagggaa atagtgattt      420
cagagcgatt aggagaacca aattatgggg cagaaataag gggcttttcc acaggttttc      480
ctttggagga agatttcagt ggtgacttta aagaatact  caacagtgtc ttcatcccca      540
tagcaaaaga agaaacngta aatgatggaa ngcttctgga gatgccnnca tttaagggac      600
ncccagaact tcaccatcta caggacctac ttcagtttac annaagncac atantctgac      660
tcanaaagga cccaagtagc nccatggnca gcactttnag cctttcccct ggggaaaann      720
ttacnttctt aaancctngg ccnngacccc cttaagncca aattntggaa aanttccntn      780
cnnctggggg gcngttcnac atgcntttna agggcccaat tncccncnt               828

<210> SEQ ID NO 221
<211> LENGTH: 476
<212> TYPE: DNA
<213> ORGANISM: Homo sapiens

<400> SEQUENCE: 221
tcgagcggcc gcccgggcag gtgtcggagt ccagcacggg aggcgtggtc ttgtagttgt       60
tctccggctg cccattgctc tcccactcca cggcgatgtc gctgggatag aagcctttga      120 ccagcaggt caggctgacc tggttcttgg tcatctcctc ccgggatggg ggcagggtgt      180
acacctgtgg ttctcggggc tgcccttttgg ctttggagat ggttttctcg atgggggctg      240
ggagggcttt gttggagacc ttgcacttgt actccttgcc attcagccag tcctggtgca      300
ggacggtgag gacgctgacc acacggtacg tgctgttgta ctgctcctcc cgcggctttg      360
tcttggcatt atgcacctcc acgccgtcca cgtaccagtt gaacttgacc tcagggtctt      420
cgtggctcac gtccaccacc acgcatgtaa cctcagacct cggccgcgac cacgct         476

<210> SEQ ID NO 222
<211> LENGTH: 477
<212> TYPE: DNA
<213> ORGANISM: Homo sapiens

<400> SEQUENCE: 222
agcgtggtcg cggccgaggt ctgaggttac atgcgtggtg gtggacgtga gccacgaaga       60
ccctgaggtc aagttcaact ggtacgtgga cggcgtggag gtgcataatg ccaagacaaa      120
gccgcgggag gagcagtaca acagcacgta ccgtgtggtc agcgtcctca ccgtcctgca      180
ccaggactgg ctgaatggca aggagtacaa gtgcaaggtc tccaacaaag ccctcccagc      240
ccccatcgag aaaaccatct ccaaagccaa agggcaagcc cgagaaccac aggtgtaca      300 ccctgccccc atcccgggag gagatgacca gaaccaggt cagcctgacc tgcctggtca      360
aaggcttcta tcccagcgac atcgccgtgg agtgggagag caatgggcag ccggagaaca      420
actacaagac cacgcctccc gtgctggact ccgacacctg cccgggcggc cgctcga        477

<210> SEQ ID NO 223
<211> LENGTH: 361
<212> TYPE: DNA
<213> ORGANISM: Homo sapiens
```

<400> SEQUENCE: 223

```
tcgagcggcc gcccgggcag gttgaatggc tcctcgctga ccaccccggt gctggtggtg      60
ggtacagagc tccgatgggt gaaaccattg acatagagac tgtccctgtc cagggtgtag     120
gggcccagct cagtgatgcc gtgggtcagc tggctcagct tccagtacag ccgctctctg     180
tccagtccag ggcttttggg gtcaggacga tgggtgcaga cagcatccac tctggtggct     240
gccccatcct tctcaggcct gagcaaggtc agtctgcaac cagagtacag agagctgaca     300
ctggtgttct tgaacaaggg cataagcaga ccctgaagga cacctcggcc gcgaccacgc     360
t                                                                    361
```

<210> SEQ ID NO 224
<211> LENGTH: 361
<212> TYPE: DNA
<213> ORGANISM: Homo sapiens

<400> SEQUENCE: 224

```
agcgtggtcg cggccgaggt gtccttcagg gtctgcttat gcccttgttc aagaacacca      60
gtgtcagctc tctgtactct ggttgcagac tgaccttgct caggcctgag aaggatgggg     120
cagccaccag agtggatgct gtctgcaccc atcgtcctga ccccaaaagc cctggactgg     180
acagagagcg gctgtactgg aagctgagcc agctgaccca cggcatcact gagctgggcc     240
cctacaccct ggacagggac agtctctatg tcaatggttt cacccatcgg agctctgtac     300
ccaccaccag caccggggtg gtcagcgagg agccattcaa cctgcccggg cggccgctcg     360
a                                                                    361
```

<210> SEQ ID NO 225
<211> LENGTH: 766
<212> TYPE: DNA
<213> ORGANISM: Homo sapiens
<220> FEATURE:
<221> NAME/KEY: misc_feature
<222> LOCATION: 574, 610, 631, 643, 657, 660, 666, 688, 712, 735, 747
<223> OTHER INFORMATION: n = A,T,C or G

<400> SEQUENCE: 225

```
agcgtggtcg cggccgaggt cctgtcagag tggcactggt agaagttcca ggaaccctga      60
actgtaaggg ttcttcatca gtgccaacag gatgacatga aatgatgtac tcagaagtgt     120
cctggaatgg ggcccatgag atggttgtct gagagagagc ttcttgtcct acattcggcg     180
ggtatggtct tggcctatgc cttatggggg tggccgttgt gggcggtgtg gtccgcctaa     240
aaccatgttc ctcaaagatc atttgttgcc caacactggg ttgctgacca gaagtgccag     300
gaagctgaat accatttcca gtgtcatacc cagggtgggg gacgaaaggg gtcttttgaa     360
ctgtggaagg aacatccaag atctctggtc catgaagatt ggggtgtgga agggttacca     420
gttgggaag ctcgtctgtc tttttccttc caatcagggg ctcgctcttc tgattattct     480
tcagggcaat gacataaatt gtatattcgg tcccggttcc aggccagtaa tagtagcctc     540
tgtgacacca gggcggggcc gagggaccct tctnttggaa gagaccagct tctcatactt     600
gatgatgagn ccggtaatcc tggcacgtgg nggttgcatg atnccaccaa ggaaatnggn     660
gggggnggac ctgcccggcg gccgttcnaa agcccaattc cacacacttg gnggccgtac     720
tatggatccc actcngtcca acttggngga atatggcata actttt                   766
```

<210> SEQ ID NO 226
<211> LENGTH: 364

```
<212> TYPE: DNA
<213> ORGANISM: Homo sapiens

<400> SEQUENCE: 226
tcgagcggcc gcccgggcag gtccttgacc ttttcagcaa gtgggaaggt gtaatccgtc      60
tccacagaca aggccaggac tcgtttgtac ccgttgatga tagaatgggg tactgatgca     120
acagttgggt agccaatctg cagacagaca ctggcaacat tgcggacacc ctccaggaag    180
cgagaatgca gagtttcctc tgtgatatca agcacttcag ggttgtagat gctgccattg    240
tcgaacacct gctggatgac cagcccaaag gagaagggg agatgttgag catgttcagc    300
agcgtggctt cgctggctcc cactttgtct ccagtcttga tcagacctcg gccgcgacca    360
cgct                                                                  364

<210> SEQ ID NO 227
<211> LENGTH: 275
<212> TYPE: DNA
<213> ORGANISM: Homo sapiens

<400> SEQUENCE: 227
agcgtggtcg cggccgaggt ctgtcctaca gtcctcagga ctctactccc tcagcagcgt      60
ggtgaccgtg ccctccagca acttcggcac ccagacctac acctgcaacg tagatcacaa    120
gcccagcaac accaaggtgg acaagagagt tgagcccaaa tcttgtgaca aaactcacac    180
atgcccaccg tgcccagcac ctgaactcct gggggaccg tcagtcttcc tcttccccg    240 catccccctt ccaaacctgc ccgggcggcc gctcg                                275

<210> SEQ ID NO 228
<211> LENGTH: 275
<212> TYPE: DNA
<213> ORGANISM: Homo sapiens

<400> SEQUENCE: 228
cgagcggccg cccgggcagg tttggaaggg ggatgcgggg gaagaggaag actgacggtc      60
cccccaggag ttcaggtgct gggcacggtg ggcatgtgtg agttttgtca caagatttgg    120
gctcaactct cttgtccacc ttggtgttgc tgggcttgtg atctacgttg caggtgtagg    180
tctgggtgcc gaagttgctg gagggcacgg tcaccacgct gctgagggag tagagtcctg    240
aggactgtag gacagacctc ggccgcgacc acgct                                275

<210> SEQ ID NO 229
<211> LENGTH: 40
<212> TYPE: DNA
<213> ORGANISM: Homo sapiens
<220> FEATURE:
<221> NAME/KEY: misc_feature
<222> LOCATION: 1, 4, 5, 13, 15, 17, 29
<223> OTHER INFORMATION: n = A,T,C or G

<400> SEQUENCE: 229
nggnnggtcc ggncngncag gaccactcnt cttcgaaata                            40

<210> SEQ ID NO 230
<211> LENGTH: 208
<212> TYPE: DNA
<213> ORGANISM: Homo sapiens

<400> SEQUENCE: 230
agcgtggtcg cggccgaggt cctcacttgc ctcctgcaaa gcaccgatag ctgcgctctg      60
```

| | |
|---|---|
| gaagcgcaga tctgttttaa agtcctgagc aatttctcgc accagacgct ggaagggaag | 120 |
| tttgcgaatc agaagttcag tggacttctg ataacgtcta atttcacgga gcgccacagt | 180 |
| accaggacct gcccgggcgg ccgctcga | 208 |

<210> SEQ ID NO 231
<211> LENGTH: 208
<212> TYPE: DNA
<213> ORGANISM: Homo sapiens
<220> FEATURE:
<221> NAME/KEY: misc_feature
<222> LOCATION: 33
<223> OTHER INFORMATION: n = A,T,C or G

<400> SEQUENCE: 231

| | |
|---|---|
| tcgagcggcc gcccgggcag gtcctggtac tgnggcgctc cgtgaaatta gacgttatca | 60 |
| gaagtccact gaacttctga ttcgcaaact tcccttccag cgtctggtgc gagaaattgc | 120 |
| tcaggacttt aaaacagatc tgcgcttcca gagcgcagct atcggtgctt tgcaggaggc | 180 |
| aagtgaggac ctcggccgcg accacgct | 208 |

<210> SEQ ID NO 232
<211> LENGTH: 332
<212> TYPE: DNA
<213> ORGANISM: Homo sapiens

<400> SEQUENCE: 232

| | |
|---|---|
| tcgagcggcc gcccgggcag gtccacatcg gcagggtcgg agccctggcc gccatactcg | 60 |
| aactggaatc catcggtcat gctctcgccg aaccagacat gcctcttgtc cttggggttc | 120 |
| ttgctgatgt accagttctt ctgggccaca ctgggctgag tggggtacac gcaggtctca | 180 |
| ccagtctcca tgttgcagaa gactttgatg gcatccaggt tgcagccttg gttggggtca | 240 |
| atccagtact ctccactctt ccagtcgagag tggcacatct tgaggtcacg gcaggtgcgg | 300 |
| gcggggttct tgacctcggc cgcgaccacg ct | 332 |

<210> SEQ ID NO 233
<211> LENGTH: 415
<212> TYPE: DNA
<213> ORGANISM: Homo sapiens
<220> FEATURE:
<221> NAME/KEY: misc_feature
<222> LOCATION: 6, 15, 19, 21
<223> OTHER INFORMATION: n = A,T,C or G

<400> SEQUENCE: 233

| | |
|---|---|
| gtgggnttga acccntttna nctccgcttg gtaccgagct cggatccact agtaacggcc | 60 |
| gccagtgtgc tggaattcgg cttagcgtgg tcgcggccga ggtcaagaac cccgcccgca | 120 |
| cctgccgtga cctcaagatg tgccactctg actggaagag tggagagtac tggattgacc | 180 |
| ccaaccaagg ctgcaacctg gatgccatca agtcttctg caacatggag actggtgaga | 240 |
| cctgcgtgta ccccactcag cccagtgtgg cccagaagaa ctggtacatc agcaagaacc | 300 |
| ccaaggacaa gaggcatgtc tggttcgcg agagcatgac cgatggattc cagttcgagt | 360 |
| atggcggcca gggctccgac cctgccgatg tggacctgcc cggcggccg ctcga | 415 |

<210> SEQ ID NO 234
<211> LENGTH: 776
<212> TYPE: DNA
<213> ORGANISM: Homo sapiens
<220> FEATURE:
<221> NAME/KEY: misc_feature
<222> LOCATION: 505, 550, 574, 601, 604, 608, 612, 649, 656, 657, 680,
      711, 750, 776
<223> OTHER INFORMATION: n = A,T,C or G

<400> SEQUENCE: 234
agcgtggtcg cggccgaggt ctgggatgct cctgctgtca cagtgagata ttacaggatc       60
acttacggag aaacaggagg aaatagccct gtccaggagt tcactgtgcc tgggagcaag      120
tctacagcta ccatcagcgg ccttaaacct ggagttgatt ataccatcac tgtgtatgct      180
gtcactggcc gtggagacag ccccgcaagc agcaagccaa tttccattaa ttaccgaaca      240
gaaattgaca aaccatccca gatgcaagtg accgatgttc aggacaacag cattagtgtc      300
aagtggctgc cttcaagttc ccctgttact ggttacagag taaccaccac tcccaaaaat      360
ggaccaggac caacaaaaac taaaactgca ggtccagatc aaacagaaat gactattgaa      420
ggcttgcagc ccacagtgga gtatgtggtt aagtgtctat gctcagaatc caagcggaga      480
gaagtcagcc tctggttcag actgnaagta accaacattg atcgcctaaa ggactggcat      540
tcactgatgn ggatgccgat tccatcaaaa ttgnttggga aacccacag gggcaagttt      600 ncangtcnag gnggacctac tcgagccctg aggatgnaat cctgactnt tccttnncct      660 gatgggaaa aaaaaccttn aaaacttgaa ggacctgccc gggcggccgt ncaaaccca       720 attccacccc cttgggggcg ttctatgggn cccactcgga ccaaacttgg ggtaan         776

<210> SEQ ID NO 235
<211> LENGTH: 805
<212> TYPE: DNA
<213> ORGANISM: Homo sapiens
<220> FEATURE:
<221> NAME/KEY: misc_feature
<222> LOCATION: 637, 684, 705, 724, 733, 756, 778, 793, 796, 804
<223> OTHER INFORMATION: n = A,T,C or G

<400> SEQUENCE: 235
tcgagcggcc gcccgggcag gtccttgcag ctctgcagtg tcttcttcac catcaggtgc       60
agggaatagc tcatggattc catcctcagg gctcgagtag gtcaccctgt acctggaaac      120
ttgcccctgt gggctttccc aagcaatttt gatggaatcg gcatccacat cagtgaatgc      180
cagtccttta gggcgatcaa tgttggttac tgcagtctga accagaggct gactctctcc      240
gcttggattc tgagcataga cactaaccac atactccact gtgggctgca agccttcaat      300
agtcatttct gtttgatctg gacctgcagt tttagttttt gttggtcctg gtccattttt      360
gggagtggtg ttactctgt aaccagtaac aggggaactt gaaggcagcc acttgacact      420
aatgctgttg tcctgaacat cggtcacttg catctgggat ggtttgtcaa tttctgttcg      480
gtaattaatg gaaattggct tgctgcttgc ggggcttgtc tccacggcca gtgacagcat      540
acacagtgat ggtataatca actccaggtt taagccgctg atggtagctg aaactttgct      600
ccaggcacaa gtgaactcct gacagggcta tttcctnctg ttctccgtaa gtgatcctgt      660
aatatctcac tgggacagca ggangcattc caaaacttcg ggcgngaccc cctaagccga      720
attntgcaat atcatcaca ctggcgggcg ctcgancatt cattaaaagg cccaatcncc       780
cctataggga gtntantaca attng                                            805

<210> SEQ ID NO 236
<211> LENGTH: 262
<212> TYPE: DNA
<213> ORGANISM: Homo sapiens

<400> SEQUENCE: 236

```
tcgagcggcc gcccgggcag gtcacttttg gtttttggtc atgttcggtt ggtcaaagat    60
aaaaactaag tttgagagat gaatgcaaag gaaaaaaata ttttccaaag tccatgtgaa   120
attgtctccc attttttttgg cttttgaggg ggttcagttt gggttgcttg tctgtttccg   180 ggttggggggg aaagttggtt gggtgggagg gagccaggtt gggatggagg gagtttacag   240
gaagcagaca gggccaacgt cg                                             262

<210> SEQ ID NO 237
<211> LENGTH: 372
<212> TYPE: DNA
<213> ORGANISM: Homo sapiens

<400> SEQUENCE: 237
agcgtggtcg cggccgaggt cctcaccaga ggtgccacct acaacatcat agtggaggca    60
ctgaaagacc agcagaggca taaggttcgg aagaggttg ttaccgtggg caactctgtc   120
aacgaaggct tgaaccaacc tacggatgac tcgtgcttttg accectacac agtttcccat   180 tatgccgttg gagatgagtg ggaacgaatg tctgaatcag gctttaaact gttgtgccag   240
tgcttaggct ttggaagtgg tcatttcaga tgtgattcat ctagatggtg ccatgacaat   300
ggtgtgaact acaagattgg agagaagtgg gaccgtcagg gagaaaatgg acctgcccgg   360
gcggccgctc ga                                                       372

<210> SEQ ID NO 238
<211> LENGTH: 372
<212> TYPE: DNA
<213> ORGANISM: Homo sapiens

<400> SEQUENCE: 238
tcgagcggcc gcccgggcag gtccattttc tccctgacgg tcccacttct ctccaatctt    60
gtagttcaca ccattgtcat ggcaccatct agatgaatca catctgaaat gaccacttcc   120
aaagcctaag cactggcaca acagtttaaa gcctgattca gacattcgtt cccactcatc   180
tccaacggca taatgggaaa ctgtgtaggg gtcaaagcac gagtcatccg taggttggtt   240
caagccttcg ttgacagagt tgcccacggt aacaacctct tcccgaacct tatgcctctg   300
ctggtctttc agtgcctcca ctatgatgtt gtaggtggca cctctggtga ggacctcggc   360
cgcgaccacg ct                                                       372

<210> SEQ ID NO 239
<211> LENGTH: 720
<212> TYPE: DNA
<213> ORGANISM: Homo sapiens
<220> FEATURE:
<221> NAME/KEY: misc_feature
<222> LOCATION: 478, 557, 563, 566, 620, 660, 663, 672, 673, 684, 693,
      695
<223> OTHER INFORMATION: n = A,T,C or G

<400> SEQUENCE: 239
tcgagcggcc gcccgggcag gtccaccata agtcctgata caaccacgga tgagctgtca    60
ggagcaaggt tgatttcttt cattggtccg gtcttctcct tgggggtcac ccgcactcga   120
tatccagtga gctgaacatt gggtggtgtc cactgggcgc tcaggcttgt gggtgtgacc   180
tgagtgaact tcaggtcagt tggtgcagga atagtggtta ctgcagtctg aaccagaggc   240
tgactctctc cgcttggatt ctgagcatag acactaacca catactccac tgtgggctgc   300
aagccttcaa tagtcatttc tgtttgatct ggacctgcag ttttagtttt tgttggtcct   360
```

```
ggtccatttt tgggagtggt ggttactctg taaccagtaa caggggaact tgaaggcagc    420
cacttgacac taatgctgtt gtcctgaaca tcggtcactt gcatctggga tggtttgnca    480
atttctgttc ggtaattaat ggaaattggc ttgctgcttg cggggctgtc tccacggcca    540
gtgacagcat acacagngat ggnatnatca actccaagtt taaggccctg atggtaactt    600
taaacttgct cccagccagn gaacttccgg acagggtatt tcttctggtt ttccgaaagn    660
gancctggaa tnntctcctt ggancagaag gancntccaa aacttgggcc ggaacccctt    720
```

<210> SEQ ID NO 240
<211> LENGTH: 691
<212> TYPE: DNA
<213> ORGANISM: Homo sapiens
<220> FEATURE:
<221> NAME/KEY: misc_feature
<222> LOCATION: 564, 582, 640, 651, 666, 669, 690
<223> OTHER INFORMATION: n = A,T,C or G

<400> SEQUENCE: 240

```
agcgtggtcg cggccgaggt cctgtcagag tggcactggt agaagttcca ggaaccctga     60
actgtaaggg ttcttcatca gtgccaacag gatgacatga aatgatgtac tcagaagtgt    120
cctggaatgg ggcccatgag atggttgtct gagagagagc ttcttgtcct acattcggcg    180
ggtatggtct tggcctatgc cttatggggg tggccgttgt gggcggtgtg gtccgcctaa    240
aaccatgttc ctcaaagatc atttgttgcc caacactggg ttgctgacca gaagtgccag    300
gaagctgaat accatttcca gtgtcatacc cagggtgggg gacgaaaggg gtcttttgaa    360
ctgtggaagg aacatccaag atctctggtc catgaagatt ggggtgtgga agggttacca    420
gttggggaag ctcgtctgtc ttttccttc caatcagggg ctcgctcttc tgattattct    480
tcagggcaat gacataaatt gtatattcgg ttcccggttc caggccagta atagtagcct    540
cttgtgacac caggcggggc ccanggacca cttctctggg angagaccca gcttctcata    600
cttgatgatg taacccggta atcctgcacg tggcggctgn catgatacca ncaaggaatt    660
gggtgnggng gacctgcccg gcggccctcn a                                    691
```

<210> SEQ ID NO 241
<211> LENGTH: 808
<212> TYPE: DNA
<213> ORGANISM: Homo sapiens
<220> FEATURE:
<221> NAME/KEY: misc_feature
<222> LOCATION: 680, 715, 721, 728, 735, 749, 757, 762, 772, 776, 779,
      781, 792, 796, 800, 808
<223> OTHER INFORMATION: n = A,T,C or G

<400> SEQUENCE: 241

```
agcgtggtcg cggccgaggt ctgggatgct cctgctgtca cagtgagata ttacaggatc     60
acttacggag aaacaggagg aaatagccct gtccaggagt tcactgtgcc tgggagcaag    120
tctacagcta ccatcagcgg ccttaaacct ggagttgatt ataccatcac tgtgtatgct    180
gtcactggcc gtggagacag ccccgcaagc agcaagccaa tttccattaa ttaccgaaca    240
gaaattgaca aaccatccca gatgcaagtg accgatgttc aggacaacag cattagtgtc    300
aagtggctgc cttcaagttc ccctgttact ggttacagag taaccaccac tcccaaaaat    360
ggaccaggac aacaaaaaac taaaactgca ggtccagatc aaacagaaat gactattgaa    420
ggcttgcagc ccacagtgga gtatgtggtt agtgtctatg ctcagaatcc aagcggagag    480
agtcagcctc tggttcagac tgcagtaacc actattcctg caccaactga cctgaagttc    540
```

```
actcaggtca cacccacaag cctgagccgc cagtggacac cacccaatgt tcactcactg      600
gatatcgagt gcgggtgacc cccaaggaga agacccggac ccatgaaaga aatcaacctt      660
gctcctgaca gctcatccgn gggtgtatca ggacttatgg gggactgccc cggcnggccg      720
ntcgaaancg aattntgaaa tttccttcnc actgggnggc gnttcgagct tncttntana      780
nggcccaatt cncctntagn gggtcgtn                                         808
```

```
<210> SEQ ID NO 242
<211> LENGTH: 26
<212> TYPE: DNA
<213> ORGANISM: Homo sapiens
<220> FEATURE:
<221> NAME/KEY: misc_feature
<222> LOCATION: 22
<223> OTHER INFORMATION: n = A,T,C or G

<400> SEQUENCE: 242
```

```
agcgtggtcg cggccgaggt cnagga                                            26
```

```
<210> SEQ ID NO 243
<211> LENGTH: 697
<212> TYPE: DNA
<213> ORGANISM: Homo sapiens
<220> FEATURE:
<221> NAME/KEY: misc_feature
<222> LOCATION: 496, 541, 624, 662, 679, 688
<223> OTHER INFORMATION: n = A,T,C or G

<400> SEQUENCE: 243
```

```
tcgagcggcc gcccgggcag gtccaccaca cccaattcct tgctggtatc atggcagccg       60
ccacgtgcca ggattaccgg ctacatcatc aagtatgaga agcctgggtc tcctcccaga      120
gaagtggtcc ctcggccccg ccctggtgtc acagaggcta ctattactgg cctggaaccg      180
ggaaccgaat atacaattta tgtcattgcc ctgaagaata atcagaagag cgagcccctg      240
attggaagga aaaagacaga cgagcttccc caactggtaa cccttccaca ccccaatctt      300 catgaccag agatcttgga tgttccttcc acagttcaaa agacccecttt cgtcacccac      360 cctgggtatg acactggaaa tggtattcag cttcctggca cttctggtca gcaacccagt      420
gttgggcaac aaatgatctt tgaggaacat ggttttaggc ggaccacacc gcccacaacg      480
ggcaccccca taaggnatag gccaagacca taccccgccg aatgtaggac aagaagctct      540
ntctcaacaa ccatctcatg ggccccattc caggacactt ctgagtacat catttcatgt      600
catcctggtg ggcacttgat gaanaaccct tacagttcag ggttcctgga acttctacca      660
gngccacttc tgacagganc ttgggcgnga ccaccct                                697
```

```
<210> SEQ ID NO 244
<211> LENGTH: 373
<212> TYPE: DNA
<213> ORGANISM: Homo sapiens

<400> SEQUENCE: 244
```

```
agcgtggtcg cggccgaggt ccattttctc cctgacggtc ccacttctct ccaatcttgt       60
agttcacacc attgtcatgg caccatctag atgaatcaca tctgaaatga ccacttccaa      120
agcctaagca ctggcacaac agtttaaagc ctgattcaga cattcgttcc cactcatctc      180
caacggcata atgggaaact gtgtaggggt caaagcacga gtcatccgta ggttggttca      240
agccttcgtt gacagagttg cccacggtaa caacctcttc ccgaacctta tgcctctgct      300
```

```
ggtctttcag tgcctccact atgatgttgt aggtggcacc tctggtgagg acctgcccgg    360
gcggcccgct cga                                                       373

<210> SEQ ID NO 245
<211> LENGTH: 307
<212> TYPE: DNA
<213> ORGANISM: Homo sapiens

<400> SEQUENCE: 245
agcgtggtcg cggccgaggt gtgccccaga ccaggaattc ggcttcgacg ttggccctgt     60
ctgcttcctg taaactccct ccatcccaac ctggctccct cccacccaac caactttccc    120
cccaacccgg aaacagacaa gcaacccaaa ctgaaccccc tcaaaagcca aaaaaatggg    180
agacaatttc acatggactt tggaaaatat ttttttcctt tgcattcatc tctcaaactt    240
agtttttatc tttgaccaac cgaacatgac caaaaaccaa aagtgacctg cccgggcggc    300
cgctcga                                                              307

<210> SEQ ID NO 246
<211> LENGTH: 372
<212> TYPE: DNA
<213> ORGANISM: Homo sapiens

<400> SEQUENCE: 246
tcgagcggcc gcccgggcag gtcctcacca gaggtgccac ctacaacatc atagtggagg     60
cactgaaaga ccagcagagg cataaggttc gggaagaggt tgttaccgtg gcaactctg    120 tcaacgaagg cttgaaccaa cctacggatg actcgtgctt tgacccctac acagtttccc    180
attatgccgt tggagatgag tgggaacgaa tgtctgaatc aggctttaaa ctgttgtgcc    240
agtgcttagg ctttggaagt ggtcatttca gatgtgattc atctagatgg tgccatgaca    300
atggtgtgaa ctacaagatt ggagagaagt gggaccgtca gggagaaaat ggacctcggc    360
cgcgaccacg ct                                                        372

<210> SEQ ID NO 247
<211> LENGTH: 348
<212> TYPE: DNA
<213> ORGANISM: Homo sapiens
<220> FEATURE:
<221> NAME/KEY: misc_feature
<222> LOCATION: 284, 297, 299, 322, 325, 338, 342, 345
<223> OTHER INFORMATION: n = A,T,C or G

<400> SEQUENCE: 247
tcgagcggcc gcccgggcag gtaccggggt ggtcagcgag gagccattca cactgaactt     60
caccatcaac aacctgcggt atgaggagaa catgcagcac cctggctcca ggaagttcaa    120
caccacggag agggtccttc agggcctgct caggtccctg ttcaagagca ccagtgttgg    180
ccctctgtac tctggctgca gactgacttt gctcagacct gagaaacatg gggcagccac    240
tggagtggac gccatctgca ccctccgcct tgatcccact ggtnctggac tggacanana    300
gcggctatac ttgggagctg anccnaacct ttggcggnga cnccncctt                348

<210> SEQ ID NO 248
<211> LENGTH: 304
<212> TYPE: DNA
<213> ORGANISM: Homo sapiens
<220> FEATURE:
<221> NAME/KEY: misc_feature
<222> LOCATION: 125
<223> OTHER INFORMATION: n = A,T,C or G
```

<400> SEQUENCE: 248

```
gaggactggc tcagctccca gtatagccgc tctctgtcca gtccaggacc agtgggatca      60
aggcggaggg tgcagatggc gtccactcca gtggctgccc catgtttctc aagtctgagc     120
aaagncagtc tgcagccaga gtacagaggg ccaacactgg tgctcttgaa cagggacctg     180
agcaggccct gaaggaccct ctccgtggtg ttgaacttcc tggagccagg gtgctgcatg     240
ttctcctcat accgcaggtt gttgatggtg aagttcagtg tgaatggctc ctcgctgacc     300
accc                                                                   304
```

<210> SEQ ID NO 249
<211> LENGTH: 400
<212> TYPE: DNA
<213> ORGANISM: Homo sapiens
<220> FEATURE:
<221> NAME/KEY: misc_feature
<222> LOCATION: 308, 310, 312, 320, 331, 336, 383, 392, 396
<223> OTHER INFORMATION: n = A,T,C or G

<400> SEQUENCE: 249

```
agcgtggtcg cggccgaggt ccaccacacc caattccttg ctggtatcat ggcagccgcc      60
acgtgccagg attaccggct acatcatcaa gtatgagaag cctgggtctc ctcccagaga     120
agtggtccct cggccccgcc ctggtgtcac agaggctact attactggcc tggaaccggg     180
aaccgaatat acaatttatg tcattgccct gaagaataat cagaagagcg agccctgat     240
tggaaggaaa aagacagacg agcttcccca actggtaacc cttccacacc ccaatcttca     300
tggaccanan ancttggatn gtcctttcac nggttnaaaa aacccttttc gccccccac     360
cttggggatt aaccttggga aangggatt tnaccnttcc                             400
```

<210> SEQ ID NO 250
<211> LENGTH: 400
<212> TYPE: DNA
<213> ORGANISM: Homo sapiens
<220> FEATURE:
<221> NAME/KEY: misc_feature
<222> LOCATION: 338, 357, 361, 369, 388, 394
<223> OTHER INFORMATION: n = A,T,C or G

<400> SEQUENCE: 250

```
tcgagcggcc gcccgggcag gtcctgtcag agtggcactg gtagaagttc caggaaccct      60
gaactgtaag ggttcttcat cagtgccaac aggatgacat gaaatgatgt actcagaagt     120
gtcctggaat ggggcccatg agatggttgt ctgagagaga gcttcttgtc ctacattcgg     180
cgggtatggt cttggcctat gccttatggg ggtggccgtt gtgggcggtg tggtccgcct     240
aaaaccatgt tcctcaaaga tcatttgttg cccaacactg ggttgctgac cagaagtgcc     300
aggaagctga ataccatttc cagtgtcata cccaggngg gtgaccaaag ggggtcnttt     360
ngacctgggng aaaggaacca tccaaaanct ctgncccatg                           400
```

<210> SEQ ID NO 251
<211> LENGTH: 514
<212> TYPE: DNA
<213> ORGANISM: Homo sapiens
<220> FEATURE:
<221> NAME/KEY: misc_feature
<222> LOCATION: 8, 107, 312, 338, 351, 352, 357, 363, 366, 373, 380,
       405, 421, 444, 508
<223> OTHER INFORMATION: n = A,T,C or G

<400> SEQUENCE: 251

```
agcgtggncg cggccgaggt ctgaggatgt aaactcttcc caggggaagg ctgaagtgct    60
gaccatggtg ctactgggtc cttctgagtc agatatgtga ctgatgngaa ctgaagtagg   120
tactgtagat ggtgaagtct gggtgtccct aaatgctgca tctccagagc cttccatcat   180
taccgtttct tcttttgcta tgggatgaga cactgttgag tattctctaa agtcaccact   240
gaaatcttcc tccaaaggaa aacctgtgga aaagccccct tatttctgcc cataatttgg   300
ttctcctaat cnctctgaaa tcactatttc cctggaangt ttgggaaaaa nngggcnacc   360
tgncantgga aantggatan aaagatccca ccattttacc caacnagcag aaagtgggaa   420
nggtaccgaa aagctccaag taanaaaaag gagggaagta aaggtcaagt gggcaccagt   480
ttcaaacaaa actttcccca aactatanaa ccca                               514
```

<210> SEQ ID NO 252
<211> LENGTH: 501
<212> TYPE: DNA
<213> ORGANISM: Homo sapiens
<220> FEATURE:
<221> NAME/KEY: misc_feature
<222> LOCATION: 20, 21, 25, 44, 343, 347, 356, 362, 387, 391, 398, 409,
      428, 430, 453, 494
<223> OTHER INFORMATION: n = A,T,C or G

<400> SEQUENCE: 252

```
aagcggccgc ccgggcaggn ncagnagtgc cttcgggact gggntcaccc ccaggtctgc    60
ggcagttgtc acagcgccag ccccgctggc ctccaaagca tgtgcaggag caaatggcac   120
cgagatattc cttctgccac tgttctccta cgtggtatgt cttcccatca tcgtaacacg   180
ttgcctcatg agggtcacac ttgaattctc cttttccgtt cccaagacat gtgcagctca   240
tttggctggc tctatagttt ggggaaagtt tgttgaaact gtgccactga cctttacttc   300
ctccttctct actggagctt ccgtaccttc ccacttctgc tgntggnaaa aagggnggaa   360
cntcttatca atttcattgg acagtanccc ncttcttnc caaaacatnc aagggaaaat   420
attgattncn agagcggatt aaggaacaac ccnaattatg ggggccagaa ataaagggg    480 cttttccaca ggtnttttcc t                                             501
```

<210> SEQ ID NO 253
<211> LENGTH: 226
<212> TYPE: DNA
<213> ORGANISM: Homo sapiens

<400> SEQUENCE: 253

```
tcgagcggcc gcccgggcag gtctgcaggc tattgtaagt gttctgagca catatgagat    60
aacctgggcc aagctatgat gttcgatacg ttaggtgtat taaatgcact tttgactgcc   120
atctcagtgg atgacagcct tctcactgac agcagagatc ttcctcactg tgccagtggg   180
caggagaaag agcatgctgc gactggacct cggccgcgac cacgct                  226
```

<210> SEQ ID NO 254
<211> LENGTH: 226
<212> TYPE: DNA
<213> ORGANISM: Homo sapiens

<400> SEQUENCE: 254

```
agcgtggtcg cggccgaggt ccagtcgcag catgctcttt ctcctgccca ctggcacagt    60
gaggaagatc tctgctgtca gtgagaaggc tgtcatccac tgagatggca gtcaaaagtg   120
catttaatac acctaacgta tcgaacatca tagcttggcc caggttatct catatgtgct   180
```
cagaacactt acaatagcct gcagacctgc ccgggcggcc gctcga 226

<210> SEQ ID NO 255
<211> LENGTH: 427
<212> TYPE: DNA
<213> ORGANISM: Homo sapiens
<220> FEATURE:
<221> NAME/KEY: misc_feature
<222> LOCATION: 327, 403
<223> OTHER INFORMATION: n = A,T,C or G

<400> SEQUENCE: 255
cgagcggccg cccgggcagg tccagactcc aatccagaga accaccaagc cagatgtcag 60
aagctacacc atcacaggtt tacaaccagg cactgactac aagatctacc tgtacacctt 120
gaatgacaat gctcggagct cccctgtggt catcgacgcc tccactgcca ttgatgcacc 180
atccaacctg cgtttcctgg ccaccacacc caattccttg ctggtatcat ggcagccgcc 240
acgtgccagg attaccggct acatcatcaa gtatgagaag cctgggtctc ctcccagaga 300
agtggtccct cggcccccgcc ctggtgncac agaagctact attactgcc tggaaccggg 360 aaccgaatat acaatttatg tcattgccct gaagaataat canaagagcg agcccctgat 420
tggaagg 427

<210> SEQ ID NO 256
<211> LENGTH: 535
<212> TYPE: DNA
<213> ORGANISM: Homo sapiens
<220> FEATURE:
<221> NAME/KEY: misc_feature
<222> LOCATION: 347, 456, 475
<223> OTHER INFORMATION: n = A,T,C or G

<400> SEQUENCE: 256
agcgtggtcg cggccgaggt cctgtcagag tggcactggt agaagttcca ggaaccctga 60
actgtaaggg ttcttcatca gtgccaacag gatgacatga aatgatgtac tcagaagtgt 120
cctggaatgg ggcccatgag atggttgtct gagagagagc ttcttgtcct gtcttttttcc 180 ttccaatcag gggctcgctc ttctgattat tcttcagggc aatgacataa attgtatatt 240 cggttccgg ttcaggcca gtaatagtag cctctgtgac accagggcgg ggccgaggga 300
ccacttctct gggaggagac ccaggcttct catacttgat gatgtanccg gtaatcctgg 360
caccgtggcg gctgccatga taccagcaag gaattgggtg tggtggccaa gaaacgcagg 420
ttggatggtg catcaatggc agtggaggcg tcgatnacca caggggagct ccgancattg 480
tcattcaagg tggacaggta gaatcttgta atcaggtgcc tggtttgtaa acctg 535

<210> SEQ ID NO 257
<211> LENGTH: 544
<212> TYPE: DNA
<213> ORGANISM: Homo sapiens
<220> FEATURE:
<221> NAME/KEY: misc_feature
<222> LOCATION: 495, 511
<223> OTHER INFORMATION: n = A,T,C or G

<400> SEQUENCE: 257
tcgagcggcc gcccgggcag gtttcgtgac cgtgacctcg aggtggacac caccctcaag 60
agcctgagcc agcagatcga gaacatccgg agcccagagg gcagccgcaa gaaccccgcc 120
cgcacctgcc gtgacctcaa gatgtgccac tctgactgga gagtggagag gtactggatt 180

```
gaccccaacc aaggctgcaa cctggatgcc atcaaagtct tctgcaacat ggagactggt    240
gagacctgcg tgtaccccac tcagcccagt gtggcccaga gaactggta catcagcaag    300 aaccccaagg acaagaagca tgtctggttc ggcgaaagca tgaccgatgg attccagttc    360
gagtatggcg ccagggctc cgaccctgcc gatgtggacc tcggccgcga ccacgctaag    420
cccgaattcc agcacactgg cggccgttac tagtgggatc cgagcttcgg taccaagctt    480
ggcgtaatca tgggncatag ctgtttcctg ngtgaaaatg gtattccgct tcacaatttc    540
ccac                                                                 544

<210> SEQ ID NO 258
<211> LENGTH: 418
<212> TYPE: DNA
<213> ORGANISM: Homo sapiens

<400> SEQUENCE: 258
agcgtggtcg cggccgaggt ccacatcggc agggtcggag ccctggccgc catactcgaa    60
ctggaatcca tcggtcatgc tctcgccgaa ccagacatgc tcttgtcct tggggttctt    120 gctgatgtac cagttcttct gggccacact gggctgagtg gggtacacgc aggtctcacc    180
agtctccatg ttgcagaaga cttt gatggc atccaggttg cagccttggt tggggtcaat    240
ccagtactct ccactcttcc agtcagagtg gcacatcttg aggtcacggc aggtgcgggc    300
ggggttcttg cggctgccct ctgggctccg gatgttctcg atctgctggc tcaagctctt    360
gaagggtggt gtccacctcg aggtcacggt cacgaaacct gcccgggcgg ccgctcga     418

<210> SEQ ID NO 259
<211> LENGTH: 377
<212> TYPE: DNA
<213> ORGANISM: Homo sapiens
<220> FEATURE:
<221> NAME/KEY: misc_feature
<222> LOCATION: 320, 326, 342, 352
<223> OTHER INFORMATION: n = A,T,C or G

<400> SEQUENCE: 259
agcgtggtcg cggccgaggt caagaacccc gcccgcacct gccgtgacct caagatgtgc    60
cactctgact ggaagagtgg agagtactgg attgacccca accaaggctg caacctggat    120
gccatcaaag tcttctgcaa catggagact ggtgagacct gcgtgtaccc cactcagccc    180
agtgtggccc agaagaactg gtacatcagc aagaacccca aggacaagag gcatgtctgg    240
ttcggcgaga gcatgaccga tggattccag ttcgagtatg gcggcagggg ctccgaccct    300
gccgatgtgg acctgcccgn gccggnccgc tcgaaaagcc cnaatttcca gncacacttg    360
gccggccgtt actactg                                                   377

<210> SEQ ID NO 260
<211> LENGTH: 332
<212> TYPE: DNA
<213> ORGANISM: Homo sapiens

<400> SEQUENCE: 260
tcgagcggcc gcccgggcag gtccacatcg gcagggtcgg agccctggcc gccatactcg    60
aactggaatc catcggtcat gctctcgccg aaccagacat gcctcttgtc cttgggttc    120 ttgctgatgt accagttctt ctgggccaca ctgggctgag tggggtacac gcaggtctca    180
ccagtctcca tgttgcagaa gactttgatg gcatccaggt tgcagccttg gttgggtca    240 atccagtact ctccactctt ccagtcagag tggcacatct tgaggtcacg gcaggtgcgg    300
```
gcggggttct tgacctcggc cgcgaccacg ct 332

<210> SEQ ID NO 261
<211> LENGTH: 94
<212> TYPE: DNA
<213> ORGANISM: Homo sapiens

<400> SEQUENCE: 261
cgagcggccg cccgggcagg tccccccct tttttttttt tttttttttt tttttttttt 60
tttttttttt tttttttttt tttttttttt tttt 94

<210> SEQ ID NO 262
<211> LENGTH: 650
<212> TYPE: DNA
<213> ORGANISM: Homo sapiens
<220> FEATURE:
<221> NAME/KEY: misc_feature
<222> LOCATION: 412, 582, 612, 641, 646
<223> OTHER INFORMATION: n = A,T,C or G

<400> SEQUENCE: 262
agcgtggtcg cggccgaggt ctggcattcc ttcgacttct ctccagccga gcttcccaga 60
acatcacata tcactgcaaa aatagcattg catacatgga tcaggccagt ggaaatgtaa 120
agaaggccct gaagctgatg gggtcaaatg aaggtgaatt caaggctgaa ggaaatagca 180
aattcaccta cacagttctg gaggatggtt gcacgaaaca cactggggaa tggagcaaaa 240
cagtctttga atatcgaaca cgcaaggctg tgagactacc tattgtagat attgcaccct 300
atgacattgg tggtcctgat caagaatttg gtgtggacgt tggccctgtt tgcttttat 360 aaaccaaact ctatctgaaa tcccaacaaa aaaaatttaa ctccatatgt gntcctcttg 420
ttctaatctt ggcaaccagt gcaagtgacc gacaaaattc cagttattta tttccaaaat 480
gtttggaaac agtataattt gacaaagaaa aaaggatact tctctttttt tggctggtcc 540
accaaataca attcaaaagg cttttttggtt ttattttttt anccaattcc aatttcaaaa 600
tgtctcaatg gngcttataa taaaataaac tttcacccct nttttntgat 650

<210> SEQ ID NO 263
<211> LENGTH: 573
<212> TYPE: DNA
<213> ORGANISM: Homo sapiens
<220> FEATURE:
<221> NAME/KEY: misc_feature
<222> LOCATION: 453, 458, 544
<223> OTHER INFORMATION: n = A,T,C or G

<400> SEQUENCE: 263
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagaa gtaaccacca ctcccaaaaa 360
tggaccagga ccaacaaaaa ctaaaactgc aggtccagat caaacagaaa atggactatt 420
gaaggcttgc agcccacagt ggaagtatgt ggntaggngt ctatgctcag aatcccaagc 480
cggagaaagt cagccttctg gtttagactg cagtaaccaa cattgatcgc cctaaaggac 540

<210> SEQ ID NO 264
<211> LENGTH: 550
<212> TYPE: DNA
<213> ORGANISM: Homo sapiens
<220> FEATURE:
<221> NAME/KEY: misc_feature
<222> LOCATION: 39, 174, 352, 526
<223> OTHER INFORMATION: n = A,T,C or G

<400> SEQUENCE: 264

```
tcgagcggcc gcccgggcag gtccttgcag ctctgcagng tcttcttcac catcaggtgc      60
agggaatagc tcatggattc catcctcagg gctcgagtag gtcaccctgt acctggaaac     120
ttgcccctgt gggctttccc aagcaatttt gatggaatcg acatccacat cagngaatgc     180
cagtccttta gggcgatcaa tgttggttac tgcagtctga accagaggct gactctctcc     240
gcttggattc tgagcataga cactaaccac atactccact gtgggctgca agccttcaat     300
agtcatttct gtttgatctg gacctgcagt tttaagtttt tggtggtcct gncccatttt     360
tgggaagtgg ggggttactc tgtaaccagt aacaggggaa cttgaaggca gccacttgac     420
actaatgctg ttgtcctgaa catcggtcac ttgcatctgg ggatggtttt gacaatttct     480
ggttcggcaa attaatggaa attggcttgc tgcttggcgg ggctgnctcc acgggccagt     540
gacagcatac                                                           550
```

<210> SEQ ID NO 265
<211> LENGTH: 596
<212> TYPE: DNA
<213> ORGANISM: Homo sapiens
<220> FEATURE:
<221> NAME/KEY: misc_feature
<222> LOCATION: 347, 352, 353, 534, 555, 587
<223> OTHER INFORMATION: n = A,T,C or G

<400> SEQUENCE: 265

```
tcgagcggcc gcccgggcag gtccttgcag ctctgcagtg tcttcttcac catcaggtgc      60
agggaatagc tcatggattc catcctcagg gctcgagtag gtcaccctgt acctggaaac     120
ttgcccctgt gggctttccc aagcaatttt gatggaatcg acatccacat cagtgaatgc     180
cagtccttta gggcgatcaa tgttggttac tgcagtctga accagaggct gactctctcc     240
gcttggattc tgagcataga cactaaccac atactccact gtgggctgca agccttcaat     300
agtcatttct gtttgatctg gacctgcagt tttaagtttt tgttggncct gnnccatttt     360
tggggaaggg gtggttactc ttgtaaccag taacagggga acttgaagca gccacttgac     420
actaatgctg gtggcctgaa catcggtcac ttgcatctgg gatggtttgg tcaatttctg     480
ttcggtaatt aatgggaaat tggcttactg gcttgcgggg gctgtctcca cggncagtga     540
caagcataca caggngatgg gtataatcaa ctccaggttt aaggccnctg atggta        596
```

<210> SEQ ID NO 266
<211> LENGTH: 506
<212> TYPE: DNA
<213> ORGANISM: Homo sapiens
<220> FEATURE:
<221> NAME/KEY: misc_feature
<222> LOCATION: 393, 473
<223> OTHER INFORMATION: n = A,T,C or G

<400> SEQUENCE: 266

```
agcgtggtcg cggccgaggt ctgggatgct cctgctgtca cagtgagata ttacaggatc      60
```

```
acttacggag aaacaggagg aaatagccct gtccaggagt tcactgtgcc tgggagcaag    120
tctacagcta ccatcagcgg ccttaaacct ggagttgatt ataccatcac tgtgtatgct    180
gtcactggcc gtggagacag ccccgcaagc agtaagccaa tttccattaa ttaccgaaca    240
gaaattgaca aaccatccca gatgcaagtg accgatgttc aggacaacag cattagtgtc    300
aagtggctgc cttcaagttc ccctgttact ggttacagag taaccaccac tcccaaaaat    360
gggaccagga ccaacaaaaa actaaaactg canggtccag atcaaacaga aatgactatt    420
gaaggcttgc agcccacagt ggagtatgtg ggttagtgtc tatgctcaga atnccaagcg    480
gagagagtca gcctctggtt cagact                                         506

<210> SEQ ID NO 267
<211> LENGTH: 548
<212> TYPE: DNA
<213> ORGANISM: Homo sapiens
<220> FEATURE:
<221> NAME/KEY: misc_feature
<222> LOCATION: 346, 358, 432, 510, 512
<223> OTHER INFORMATION: n = A,T,C or G

<400> SEQUENCE: 267
tcgagcggcc gcccgggcag gtcagcgctc tcaggacgtc accaccatgg cctgggctct     60
gctcctcctc accctcctca ctcagggcac agggtcctgg gcccagtctg ccctgactca    120
gcctccctcc gcgtccgggt ctcctggaca gtcagtcacc atctcctgca ctggaaccag    180
cagtgacgtt ggtgcttatg aatttgtctc ctggtaccaa caacacccag gcaaggcccc    240
caaactcatg atttctgagg tcactaagcg gccctcaggg gtccctgatc gcttctctgg    300
ctccaagtct ggcaacacgg cctccctgac cgtctctggg ctccangctg aggatgangc    360
tgattattac tggaagctca tatgcaggca acaacaattg ggtgttcggc ggaagggacc    420
aagctgaccg tnctaaggtc aagcccaagg cttgccccc tcggtcactc tgttcccacc    480
ctcctctgaa gaagctttca agccaacaan gncacactgg gtgtgtctca taagtggact    540
ttctaccc                                                             548

<210> SEQ ID NO 268
<211> LENGTH: 584
<212> TYPE: DNA
<213> ORGANISM: Homo sapiens
<220> FEATURE:
<221> NAME/KEY: misc_feature
<222> LOCATION: 98, 380, 421, 454, 495, 506, 512, 561, 565, 579
<223> OTHER INFORMATION: n = A,T,C or G

<400> SEQUENCE: 268
agcgtggtcg cggccgaggt ctgtagcttc tgtgggactt ccactgctca ggcgtcaggc     60
tcaggtagct gctggccgcg tacttgttgt tgctttgntt ggagggtgtg gtggtctcca    120
ctcccgcctt gacggggctg ctatctgcct tccaggccac tgtcacggct cccgggtaga    180
agtcacttat gagacacacc agtgtggcct tgttggcttg aagctcctca gaggagggtg    240
ggaacagagt gaccgagggg gcagccttgg gctgacctag gacggtcagc ttggtccctc    300
cgccgaacac ccaattgttg ttgcctgcat atgagctgca gtaataatca gcctcatcct    360
cagcctggag cccagagacn gtcaagggag gccgtgtttt gccaagactt ggaagccaga    420
naagcgatca gggaccctg agggccgctt tacngacctc aaaaaatcat gaatttgggg    480
ggcctttgcc tgggngttgg ttggtnacca gnaaacaaa atttcataaa gcaccaacgt    540
```

| cactgctggt ttccagtgca ngaanatggt gaactgaant gtcc | 584 |

<210> SEQ ID NO 269
<211> LENGTH: 368
<212> TYPE: DNA
<213> ORGANISM: Homo sapiens
<220> FEATURE:
<221> NAME/KEY: misc_feature
<222> LOCATION: 265, 329
<223> OTHER INFORMATION: n = A,T,C or G

<400> SEQUENCE: 269

| agcgtggtcg cggccgaggt ccagcatcag gagccccgcc ttgccggctc tggtcatcgc | 60 |
| ctttcttttt gtggcctgaa acgatgtcat caattcgcag tagcagaact gccgtctcca | 120 |
| ctgctgtctt ataagtctgc agcttcacag ccaatggctc ccatatgccc agttccttca | 180 |
| tgtccaccaa agtaccgtc tcaccattta cccccaggt ctcacagttc tcctgggtgt | 240 |
| gcttggcccg aagggaggta agtanacgga tggtgctggt cccacagttc tggatcaggg | 300 |
| tacgaggaat gacctctagg gcctgggcna caagccctgt atggacctgc ccgggcgggc | 360 |
| ccgctcga | 368 |

<210> SEQ ID NO 270
<211> LENGTH: 368
<212> TYPE: DNA
<213> ORGANISM: Homo sapiens
<220> FEATURE:
<221> NAME/KEY: misc_feature
<222> LOCATION: 54, 163, 219, 229, 316
<223> OTHER INFORMATION: n = A,T,C or G

<400> SEQUENCE: 270

| tcgagcggcc gcccgggcag gtccatacag ggctgttgcc caggccctag aggncattcc | 60 |
| ttgtaccctg atccagaact gtgggaccag caccatccgt ctacttacct cccttcgggc | 120 |
| caagcacacc caggagaact gtgagacctg gggtgtaaat ggngagacgg gtactttggt | 180 |
| ggacatgaag gaactgggca tatgggagcc attggctgng aagctgcana cttataagac | 240 |
| agcagtggag acggcagttc tgctactgcg aattgatgac atcgtttcag gccacaaaaa | 300 |
| gaaaggcgat gaccanagcc ggcaaggcgg ggcttcctga tgctggacct cggccgccga | 360 |
| ccacgctt | 368 |

<210> SEQ ID NO 271
<211> LENGTH: 424
<212> TYPE: DNA
<213> ORGANISM: Homo sapiens
<220> FEATURE:
<221> NAME/KEY: misc_feature
<222> LOCATION: 279, 329, 362, 384, 400
<223> OTHER INFORMATION: n = A,T,C or G

<400> SEQUENCE: 271

| agcgtggtcg cggccgaggt ccactagagg tctgtgtgcc attgcccagg cagagtctct | 60 |
| gcgttacaaa ctcctaggag ggcttgctgt gcggagggcc tgctatggtg tgctgcggtt | 120 |
| catcatggag agtggggcca aaggctgcga ggttgtggtg tctgggaaac tccgaggaca | 180 |
| gagggctaaa tccatgaagt ttgtggatgg cctgatgatc cacagcggag accctgttaa | 240 |
| ctactacgtt gacactgctg tgcgccacgt gttgctcana cagggtgtgc tgggcatcaa | 300 |
| ggtgaagatc atgctgccct gggacccanc tggcaaaaat ggcccttaaa aaccccttgc | 360 |
| cntgaccacg tgaaccattt gtgngaaccc caagatgaan atacttgccc accaccccc | 420 | attc                                                                      424

<210> SEQ ID NO 272
<211> LENGTH: 541
<212> TYPE: DNA
<213> ORGANISM: Homo sapiens
<220> FEATURE:
<221> NAME/KEY: misc_feature
<222> LOCATION: 422, 442, 510, 513, 515, 525
<223> OTHER INFORMATION: n = A,T,C or G

<400> SEQUENCE: 272
tcgagcggcc gcccgggcag gtctgccaag gagaccctgt tatgctgtgg ggactggctg     60
gggcatggca ggcggctctg gcttcccacc cttctgttct gagatggggg tggtgggcag    120
tatctcatct ttgggttcca caatgctcac gtggtcaggc aggggcttct tagggccaat    180
cttaccagtt gggtcccagg gcagcatgat cttcaccttg atgcccagca caccctgtct    240
gagcaacacg tggcgcacag cagtgtcaac gtagtagtta acagggtctc cgctgtggat    300
catcaggcca tccacaaact tcatggattt agccctctgt cctcggagtt tcccaaaaca    360
ccacaacctc gccagccttt gggccccact tcttcatgaa tgaaaccgca gcacaccatt    420
ancaaggccc ttccgcacag gnaagcccct cctaaggagt tttgtaaacg caaaaaactc    480
ttgcctgggg caaatgggca cacagaccctn tantnggacc ttggnccgcg aaccaccgct    540
t                                                                     541

<210> SEQ ID NO 273
<211> LENGTH: 579
<212> TYPE: DNA
<213> ORGANISM: Homo sapiens
<220> FEATURE:
<221> NAME/KEY: misc_feature
<222> LOCATION: 223, 265, 277, 308, 329, 346, 360, 366, 429, 448, 517,
      524, 531, 578
<223> OTHER INFORMATION: n = A,T,C or G

<400> SEQUENCE: 273
agcgtggtcg cggccgaggt ctggccctcc tggcaaggct ggtgaagatg gtcaccctgg     60
aaaacccgga cgacctggtg agagaggagt tgttggacca cagggtgctc gtggtttccc    120
tggaactcct ggacttcctg gcttcaaagg cattagggga cacaatggtc tggatggatt    180
gaagggacag cccggtgctc ctggtgtgaa gggtgaacct ggngcccctg gtgaaaatgg    240
aactccaggt caaacaggag cccgngggct tcctggngag agaggacgtg ttggtgcccc    300
tggcccanac ctgccggggc ggccgctcna aaagccgaaa tccagnacac tggcggccgn    360
tactantgga atccgaactt cggtaccaaa gcttggccgt aatcatggcc atagcttgtt    420
ccctgggng gaaattggta ttccgctncc aattccacac aacataccga acccggaaag    480
cattaaagtg taaaagccct gggggggcct aaatgangtg agcntaactc ncatttaatt    540
ggcgttgcgc ttcactgccc cgcttttcca gtccgggna                            579

<210> SEQ ID NO 274
<211> LENGTH: 330
<212> TYPE: DNA
<213> ORGANISM: Homo sapiens
<220> FEATURE:
<221> NAME/KEY: misc_feature
<222> LOCATION: 171
<223> OTHER INFORMATION: n = A,T,C or G

<400> SEQUENCE: 274

```
tcgagcggcc gcccgggcag gtctgggcca ggggcaccaa cacgtcctct ctcaccagga      60
agcccacggg ctcctgtttg acctggagtt ccattttcac caggggcacc aggttcaccc     120
ttcacaccag gagcaccggg ctgtcccttc aatccatcca gaccattgtg nccctaatg     180 cctttgaagc caggaagtcc aggagttcca gggaaaccac gagcaccctg tggtccaaca     240
actcctctct caccaggtcg tccgggtttt ccagggtgac catcttcacc agccttgcca     300
ggagggccag acctcggccg cgaccacgct                                     330

<210> SEQ ID NO 275
<211> LENGTH: 97
<212> TYPE: DNA
<213> ORGANISM: Homo sapiens
<220> FEATURE:
<221> NAME/KEY: misc_feature
<222> LOCATION: 2, 35, 72
<223> OTHER INFORMATION: n = A,T,C or G

<400> SEQUENCE: 275
ancgtggtcg cggccgaggt cctcaccaga ggtgncacct acaacatcat agtggaggca      60
ctgaaagacc ancagaggca taaggttcgg gaagagg                              97

<210> SEQ ID NO 276
<211> LENGTH: 610
<212> TYPE: DNA
<213> ORGANISM: Homo sapiens
<220> FEATURE:
<221> NAME/KEY: misc_feature
<222> LOCATION: 358, 360, 363, 382, 424, 433, 464, 468, 477, 491, 499,
     511, 558, 584, 588, 590
<223> OTHER INFORMATION: n = A,T,C or G

<400> SEQUENCE: 276
tcgagcggcc gcccgggcag gtccattttc tccctgacgg tcccacttct ctccaatctt      60
gtagttcaca ccattgtcat ggcaccatct agatgaatca catctgaaat gaccacttcc     120
aaagcctaag cactggcaca acagtttaaa gcctgattca gacattcgtt cccactcatc     180
tccaacggca taatgggaaa ctgtgtaggg gtcaaagcac gagtcatccg taggttggtt     240
caagccttcg ttgacagagt tgtccacggt aacaacctct tcccgaacct tatgcctctg     300
ctggtctttc agtgcctcca ctatgatgtt gtaggtggca cctctggtga ggacctcngn     360
ccngaacaac gcttaagccc gnattctgca gaataatccc atcacacttg gcggccgctt     420
cgancatgca tcntaaaagg ggccccaatt tccccttat aagngaancc gtatttncca     480
atttcactgg ncccgccgnt tttacaaacg ncggtgaact ggggaaaaac cctggcggtt     540
acccaacttt aatcgccntt ggcagcacaa tcccccttt tcgnccancn tgggcgtaaa     600
taaccgaaaa                                                           610

<210> SEQ ID NO 277
<211> LENGTH: 38
<212> TYPE: DNA
<213> ORGANISM: Homo sapiens
<220> FEATURE:
<221> NAME/KEY: misc_feature
<222> LOCATION: 2, 5, 18, 21, 31
<223> OTHER INFORMATION: n = A,T,C or G

<400> SEQUENCE: 277
ancgnggtcg cggccgangt nttttttctt ntttttt                              38
```

<210> SEQ ID NO 278
<211> LENGTH: 443
<212> TYPE: DNA
<213> ORGANISM: Homo sapiens
<220> FEATURE:
<221> NAME/KEY: misc_feature
<222> LOCATION: 156, 212, 233, 245, 327, 331, 336, 361, 364, 381, 391,
      397, 419, 437
<223> OTHER INFORMATION: n = A,T,C or G

<400> SEQUENCE: 278
agcgtggtcg cggccgaggt ctgaggttac atgcgtggtg gtggacgtga gccacgaaga    60
ccctgaggtc aagttcaact ggtacgtgga cggcgtggag gtgcataatg ccaagacaaa   120
gccgcgggag gagcagtaca acagcacgta ccgggnggtc agcgtcctca ccgtcctgca   180
ccagaattgg ttgaatggca aggagtacaa gngcaaggtt tccaacaaag ccntcccagc   240
ccccntcgaa aaaccatttt ccaaagccaa agggcagccc cgagaaccac aggtgtacac   300
cctgccccca tcccgggagg aaaagancaa naaccnggtt cagccttaac ttgcttggtc   360
naangctttt tatcccaacg nacttccccc ntggaantgg gaaaaaccaa tgggccaanc   420
cgaaaaacaa ttacaanaac ccc                                          443

<210> SEQ ID NO 279
<211> LENGTH: 348
<212> TYPE: DNA
<213> ORGANISM: Homo sapiens
<220> FEATURE:
<221> NAME/KEY: misc_feature
<222> LOCATION: 219, 256, 291, 297, 307, 314, 317
<223> OTHER INFORMATION: n = A,T,C or G

<400> SEQUENCE: 279
tcgagcggcc gcccgggcag gtgtcggagt ccagcacggg aggcgtggtc ttgtagttgt    60
tctccggctg cccattgctc tcccactcca cggcgatgtc gctgggatag aagcctttga   120
ccaggcaggt caggctgacc tggttcttgg tcatctcctc ccgggatggg ggcagggtga   180
acacctgggg ttctcggggc ttgccctttg gttttgaana tggttttctc gatggggct    240 ggaagggctt tgttgnaaac cttgcacttg actccttgcc attcacccag ncctggngca   300
ggacggngag gacnctnacc acacggaacc gggctggtgg actgctcc                348

<210> SEQ ID NO 280
<211> LENGTH: 149
<212> TYPE: DNA
<213> ORGANISM: Homo sapiens
<220> FEATURE:
<221> NAME/KEY: misc_feature
<222> LOCATION: 18, 34, 51, 118, 120, 140
<223> OTHER INFORMATION: n = A,T,C or G

<400> SEQUENCE: 280
agcgtggtcg cggacgangt cctgtcagag tggnactggt agaagttcca ngaaccctga    60
actgtaaggg ttcttcatca gtgccaacag gatgacatga aatgatgtac tcagaagngn   120
cctggaatgg ggcccatgan atggttgcc                                    149

<210> SEQ ID NO 281
<211> LENGTH: 404
<212> TYPE: DNA
<213> ORGANISM: Homo sapiens
<220> FEATURE:
<221> NAME/KEY: misc_feature
<222> LOCATION: 383, 386, 388, 393
<223> OTHER INFORMATION: n = A,T,C or G

<400> SEQUENCE: 281

```
tcgagcggcc gcccgggcag gtccaccaca cccaattcct tgctggtatc atggcagccg        60
ccacgtgcca ggattaccgg ctacatcatc aagtatgaga agcctgggtc tcctcccaga      120
gaagtggtcc ctcggccccg ccctggtgtc acagaggcta ctattactgg cctggaaccg      180
ggaaccgaat atacaattta tgtcattgcc ctgaagaata atcagaagag cgagcccctg      240
attggaagga aaagacaga cgagcttccc caactggtaa cccttccaca ccccaatctt       300
catggaccag atcttggga tgttccttcc acagttcaaa agaccccttt cggcaccccc       360
cctgggtatg aacctgggaa aanggnantt aanctttcct ggca                       404
```

<210> SEQ ID NO 282
<211> LENGTH: 507
<212> TYPE: DNA
<213> ORGANISM: Homo sapiens
<220> FEATURE:
<221> NAME/KEY: misc_feature
<222> LOCATION: 320, 341, 424, 450, 459, 487, 498
<223> OTHER INFORMATION: n = A,T,C or G

<400> SEQUENCE: 282

```
agcgtggtcg cggccgaggt ctgggatgct cctgctgtca cagtgagata ttacaggatc        60
acttacggag aaacaggagg aaatagccct gtccaggagt tcactgtgcc tgggagcaag      120
tctacagcta ccatcagcgg ccttaaacct ggagttgatt ataccatcac tgtgtatgct      180
gtcactggcc gtggagacag ccccgcaagc agcaagccaa tttccattaa ttaccgaaca      240
gaaattgaca aaccatccca gatgcaagtg accgatgttc aggacaacag cattagtgtc      300
aagtggctgc cttcaaggtn ccctggtact gggttacaga ntaaccacca ctcccaaaaa      360
tggaccagga accacaaaaa cttaaactgc agggtccaga tcaaaacaga aatgactatt      420
gaangcttgc agcccacagt gggagtatgn gggtagtgnc tatgcttcag aatccaagcg      480
gaaaaangtc aagccttntg ggttcaa                                          507
```

<210> SEQ ID NO 283
<211> LENGTH: 325
<212> TYPE: DNA
<213> ORGANISM: Homo sapiens
<220> FEATURE:
<221> NAME/KEY: misc_feature
<222> LOCATION: 216, 292, 303, 304
<223> OTHER INFORMATION: n = A,T,C or G

<400> SEQUENCE: 283

```
tcgagcggcc gcccgggcag gtccttgcag ctctgcagtg tcttcttcac catcaggtgc        60
agggaatagc tcatggattc catcctcagg gctcgagtag gtcaccctgt acctggaaac      120
ttgcccctgt gggctttccc aagcaatttt gatggaatcg acatccacat cagtgaatgc      180
cagtccttta gggcgatcaa tgttggttac tgcagnctga accagaggct gactctctcc      240
gcttggattc tgagcataga cactaaccac atactccact gtgggctgca anccttcaat      300
aanncatttc tgtttgatct ggacc                                            325
```

<210> SEQ ID NO 284
<211> LENGTH: 331
<212> TYPE: DNA
<213> ORGANISM: Homo sapiens
<220> FEATURE:
<221> NAME/KEY: misc_feature
<222> LOCATION: 54, 59, 63, 121, 312, 327

<223> OTHER INFORMATION: n = A,T,C or G

<400> SEQUENCE: 284

```
tcgagcggcc gcccgggcag gtctggtggg gtcctggcac acgcacatgg gggngttgnt    60
ctnatccagc tgcccagccc ccattggcga gtttgagaag gtgtgcagca atgacaacaa   120
naccttcgac tcttcctgcc acttctttgc cacaaagtgc accctggagg caccaagaa    180
gggccacaag ctccacctgg actacatcgg gccttgcaaa tacatccccc cttgcctgga   240
ctctgagctg accgaattcc cccttgcgca tgcgggactg gctcaagaac cgtcctggca   300
cccttgtatg anaggaatga agacacnacc c                                  331
```

<210> SEQ ID NO 285
<211> LENGTH: 509
<212> TYPE: DNA
<213> ORGANISM: Homo sapiens
<220> FEATURE:
<221> NAME/KEY: misc_feature
<222> LOCATION: 316, 319, 327, 329, 339, 344, 357, 384, 398, 427, 443, 450, 478
<223> OTHER INFORMATION: n = A,T,C or G

<400> SEQUENCE: 285

```
agcgtggtcg cggccgaggt ctgtcctaca gtcctcagga ctctactccc tcagcagcgt    60
ggtgaccgtg ccctccagca acttcggcac ccagacctac acctgcaacg tagatcacaa   120
gcccagcaac accaaggtgg acaagagagt tgagcccaaa tcttgtgaca aaactcacac   180
atgcccaccg tgcccagcac ctgaactcct gggggaccg tcagtcttcc tcttccccg     240
catccccctt ccaaacctgc ccgggcggcc gctcgaaagc cgaattccag cacactggcg   300
gccggtacta gtggancena acttggnanc caacctggng gaantaatgg cataanctg    360
tttctgggg gaaattggta tccngtttac aattcccnca caacatacga gccggaagca   420
taaaagngta aaagcctggg ggnggcctan tgaagtgaag ctaaactcac attaattngc   480
gttgccgctc actggcccgc ttttccagc                                    509
```

<210> SEQ ID NO 286
<211> LENGTH: 336
<212> TYPE: DNA
<213> ORGANISM: Homo sapiens
<220> FEATURE:
<221> NAME/KEY: misc_feature
<222> LOCATION: 188, 251, 267
<223> OTHER INFORMATION: n = A,T,C or G

<400> SEQUENCE: 286

```
tcgagcggcc gcccgggcag gtttggaagg gggatgcggg ggaagaggaa gactgacggt    60
ccccccagga gttcaggtgc tgggcacggt gggcatgtgt gagttttgtc acaagatttg   120
ggctcaactc tcttgtccac cttggtgttg ctgggcttgt gatctacgtt gcaggtgtag   180
gtctgggngc cgaagttgct ggagggcacg gtcaccacgc tgctgaggga gtagagtcct   240
gaggactgta ngacagacct cggccgngac cacgctaagc cgaattctgc agatatccat   300
cacactggcg gccgctccga gcatgcattt tagagg                            336
```

<210> SEQ ID NO 287
<211> LENGTH: 30
<212> TYPE: DNA
<213> ORGANISM: Homo sapiens
<220> FEATURE:
<221> NAME/KEY: misc_feature
<222> LOCATION: 8, 18

<223> OTHER INFORMATION: n = A,T,C or G

<400> SEQUENCE: 287
agcgtggncg cggacganga caacaacccc                              30

<210> SEQ ID NO 288
<211> LENGTH: 316
<212> TYPE: DNA
<213> ORGANISM: Homo sapiens
<220> FEATURE:
<221> NAME/KEY: misc_feature
<222> LOCATION: 22, 130
<223> OTHER INFORMATION: n = A,T,C or G

<400> SEQUENCE: 288
tcgagcggcc gcccgggcag gnccacatcg gcagggtcgg agccctggcc gccatactcg     60
aactggaatc catcggtcat gctcttgccg aaccagacat gcctcttgtc cttggggttc   120
ttgctgatgn accagttctt ctgggccaca ctgggctgag tggggtacac gcaggtctca   180
ccagtctcca tgttgcagaa gactttgatg gcatccaggt tgcagccttg gttggggtca   240
atccagtact ctccactctt ccagtcagag tggcacatct tgaggtcacg gcaggtgcgg   300
gcggggttct tgacct                                                  316

<210> SEQ ID NO 289
<211> LENGTH: 308
<212> TYPE: DNA
<213> ORGANISM: Homo sapiens
<220> FEATURE:
<221> NAME/KEY: misc_feature
<222> LOCATION: 36, 165, 191, 195, 218, 235
<223> OTHER INFORMATION: n = A,T,C or G

<400> SEQUENCE: 289
agcgtggtcg cggccgaggt ccagcctgga gataanggtg aaggtggtgc ccccggactt     60
ccaggtatag ctggacctcg tggtagccct ggtgagagag gtgaaactgg ccctccagga   120
cctgctggtt tccctggtgc tcctggacag aatggtgaac ctggnggtaa aggagaaaga   180
ggggctccgg ntganaaagg tgaaggaggc cctcctgnat tggcaggggc cccangactt   240
agaggtggag ctggcccccc tggccccgaa ggaggaaagg gtgctgctgg tcctcctggg   300
ccacctgg                                                           308

<210> SEQ ID NO 290
<211> LENGTH: 324
<212> TYPE: DNA
<213> ORGANISM: Homo sapiens
<220> FEATURE:
<221> NAME/KEY: misc_feature
<222> LOCATION: 184
<223> OTHER INFORMATION: n = A,T,C or G

<400> SEQUENCE: 290
tcgagcggcc gcccgggcag gtctgggcca ggaggaccaa taggaccagt aggacccctt     60
gggccatctt tccctgggac accatcagca cctggaccgc ctggttcacc cttgtcaccc   120
tttggaccag gacttccaag acctcctctt tctccaggca ttccttgcag accaggagta   180
ccancagcac caggtggccc aggaggacca gcagcaccct ttcctccttc gggaccaggg   240
ggaccagctc cacctctaag tcctggggcc cctgccaatc caggagggcc tccttcacct   300
ttctcacccg gagcccctct ttct                                         324

```
<210> SEQ ID NO 291
<211> LENGTH: 278
<212> TYPE: DNA
<213> ORGANISM: Homo sapiens
<220> FEATURE:
<221> NAME/KEY: misc_feature
<222> LOCATION: 249, 267
<223> OTHER INFORMATION: n = A,T,C or G

<400> SEQUENCE: 291
tcgagcggcc gcccgggcag gtccaccggg atattcgggg gtctggcagg aatgggaggc    60
atccagaacg agaaggagac catgcaaagc ctgaacgacc gcctggcctc ttacctggac   120
agagtgagga gcctggagac cgacaaccgg aggctggaga gcaaaatccg ggagcacttg   180
gagaagaagg gaccccaggt cagagactgg agccattact tcaagatcat cgaggacctg   240
agggctcana tcttcgcaaa tactgcngac aatgcccg                           278

<210> SEQ ID NO 292
<211> LENGTH: 299
<212> TYPE: DNA
<213> ORGANISM: Homo sapiens
<220> FEATURE:
<221> NAME/KEY: misc_feature
<222> LOCATION: 6, 19, 25, 51, 53, 61, 63, 70, 109, 136, 157, 241, 276
<223> OTHER INFORMATION: n = A,T,C or G

<400> SEQUENCE: 292
atgcgnggtc gcggccgang accanctctg gctcatactt gactctaaag ncntcaccag    60
nanttacggn cattgccaat ctgcagaacg atgcgggcat tgtccgcant atttgcgaag   120
atctgagccc tcaggncctc gatgatcttg aagtaanggc tccagtctct gacctggggt   180
cccttcttct ccaagtgctc ccggattttg ctctccagcc tccggttctc ggtctccaag   240
ncttctcact ctgtccagga aaagaggcca ggcggncgat cagggctttt gcatggact    299

<210> SEQ ID NO 293
<211> LENGTH: 101
<212> TYPE: DNA
<213> ORGANISM: Homo sapiens

<400> SEQUENCE: 293
agcgtggtcg cggccgaggt tgtacaagct tttttttttt tttttttttt tttttttttt    60
tttttttttt tttttttttt tttttttttt tttttttttt t                      101

<210> SEQ ID NO 294
<211> LENGTH: 285
<212> TYPE: DNA
<213> ORGANISM: Homo sapiens
<220> FEATURE:
<221> NAME/KEY: misc_feature
<222> LOCATION: 64, 103, 110, 237, 282
<223> OTHER INFORMATION: n = A,T,C or G

<400> SEQUENCE: 294
tcgagcggcc gcccgggcag gtctgccaac accaagattg gccccgccg catccacaca    60 gttngtgtgc ggggaggtaa caagaaatac cgtgccctga ggntggacgn ggggaatttc   120
tcctggggct cagagtgttg tactcgtaaa acaaggatca tcgatgttgt ctacaatgca   180
tctaataacg agctggttcg taccaagacc ctggtgaaga attgcatcgt gctcatngac   240
agcacaccgt accgacagtg ggtaccgaag tcccactatg cncct                   285

<210> SEQ ID NO 295
```

<211> LENGTH: 216
<212> TYPE: DNA
<213> ORGANISM: Homo sapiens

<400> SEQUENCE: 295

```
tcgagcggcc gcccgggcag gtccaccaca cccaattcct tgctggtatc atggcagccg      60
ccacgtgcca ggattaccgg ctacatcatc aagtatgaga agcctgggtc tcctcccaga     120
gaagtggtcc ctcggccccg ccctggtgtc acagaggcta ctattactgg cctggaaccg     180
ggaaccgaat atacaattta tgtcattgcc ctgaag                                216
```

<210> SEQ ID NO 296
<211> LENGTH: 414
<212> TYPE: DNA
<213> ORGANISM: Homo sapiens
<220> FEATURE:
<221> NAME/KEY: misc_feature
<222> LOCATION: 7, 10, 33, 61, 62, 63, 88, 109, 122, 255, 298, 307, 340,
      355, 386, 393
<223> OTHER INFORMATION: n = A,T,C or G

<400> SEQUENCE: 296

```
agcgtgntcn cggccgagga tggggaagct cgnctgtctt tttccttcca atcaggggct      60
nnntcttctg attattcttc agggcaanga cataaattgt atattcggnt cccggttcca     120
gnccagtaat agtagcctct gtgacaccag ggcggggccg agggaccact tctctgggag     180
gagacccagg cttctcatac ttgatgatga agccggtaat cctggcacgt gggcggctgc     240
catgatacca ccaangaatt gggtgtggtg gacctgcccg ggcgggccgc tcgaaaancc     300
gaattcntgc aagaatatcc atcacacttg ggcgggccgn tcgaaccatg catcntaaaa     360
gggcccaat tccccccta ttaggngaag ccncatttaa caaattccac ttgg            414
```

<210> SEQ ID NO 297
<211> LENGTH: 376
<212> TYPE: DNA
<213> ORGANISM: Homo sapiens
<220> FEATURE:
<221> NAME/KEY: misc_feature
<222> LOCATION: 312, 326, 335, 361
<223> OTHER INFORMATION: n = A,T,C or G

<400> SEQUENCE: 297

```
tcgagcggcc gcccgggcag gtctcgcggt cgcactggtg atgctggtcc tgttggtccc      60
cccggccctc ctggacctcc tggtcccccct ggtcctccca gcgctggttt cgacttcagc    120
ttcctgcccc agccacctca agagaaggct cacgatggtg gccgctacta ccgggctgat    180
gatgccaatg tggttcgtga ccgtgacctc gaggtggaca ccaccctcaa gagccttgag    240
ccagcagaat cgaaaacatt cggaacccaa gaagggcaag cccgcaaaga aaccccgccc    300
gcacctggcc gngaacctcc aagaangtgc ccacntcttg actggaaaaa aagggaaaa     360
ntacttggaa ttggac                                                    376
```

<210> SEQ ID NO 298
<211> LENGTH: 357
<212> TYPE: DNA
<213> ORGANISM: Homo sapiens
<220> FEATURE:
<221> NAME/KEY: misc_feature
<222> LOCATION: 345, 346
<223> OTHER INFORMATION: n = A,T,C or G

<400> SEQUENCE: 298

```
agcgtggtcg cggccgaggt ccacatcggc agggtcggag ccctggccgc catactcgaa      60
ctggaatcca tcggtcatgc tctcgccgaa ccagacatgc ctcttgtcct tggggttctt     120
gctgatgtac cagttcttct gggccacact gggctgagtg gggtacacgc aggtctcacc     180
agtctccatg ttgcagaaga ctttgatggc atccaggttg cagccttggt tggggtcaat     240
ccagtactct ccactcttcc agtcagaagt ggcacatctt gaggtcacgg cagggtgcgg     300
gcggggttct tgcgggctgc ccttctgggc tcccggaatg ttctnngaac ttgctgg       357

<210> SEQ ID NO 299
<211> LENGTH: 307
<212> TYPE: DNA
<213> ORGANISM: Homo sapiens
<220> FEATURE:
<221> NAME/KEY: misc_feature
<222> LOCATION: 281, 285, 306
<223> OTHER INFORMATION: n = A,T,C or G

<400> SEQUENCE: 299
agcgtggtcg cggccgaggt ccactagagg tctgtgtgcc attgcccagg cagagtctct      60
gcgttacaaa ctcctaggag ggcttgctgt gcggagggcc tgctatggtg tgctgcggtt     120
catcatggag agtggggcca aaggctgcga ggttgtggtg tctgggaaac tccgaggaca     180
gagggctaaa tccatgaagt ttgtggatgg cctgatgatc cacagcggag accctgttaa     240
ctactacgtt gacacttgct tgtgcgccac gtgttgctca nacangggtg ggctgggcat     300 caaggng                                                                307

<210> SEQ ID NO 300
<211> LENGTH: 351
<212> TYPE: DNA
<213> ORGANISM: Homo sapiens

<400> SEQUENCE: 300
tcgagcggcc gcccgggcag gtctgccaag gagaccctgt tatgctgtgg ggactggctg      60
gggcatggca gcggctctg gcttcccacc cttctgttct gagatggggg tggtgggcag     120
tatctcatct ttgggttcca caatgctcac gtggtcaggc aggggcttct tagggccaat     180
cttaccagtt gggtcccagg gcagcatgat cttcaccttg atgcccagca cccctgtct     240 gagcaacacg tggcgcacag caagtgtcaa cgtaagtaag ttaacagggt ctccgctgtg     300
gatcatcagg ccatccacaa acttcatgga tttaaccctc tgtcctcgga g            351

<210> SEQ ID NO 301
<211> LENGTH: 330
<212> TYPE: DNA
<213> ORGANISM: Homo sapiens

<400> SEQUENCE: 301
tcgagcggcc gcccgggcag gtgtttcaga ggttccaagg tccactgtgg aggtcccagg      60
agtgctggtg gtgggcacag aggtccgatg ggtgaaacca ttgacataga gactgttcct     120
gtccagggtg taggggccca gctctttgat gccattggcc agttggctca gctcccagta     180
cagccgctct ctgttgagtc cagggctttt ggggtcaaga tgatggatgc agatggcatc     240
cactccagtg gctgctccat ccttctcgga cctgagagag gtcagtctgc agccagagta     300
cagagggcca acactggtgt tctttgaata                                       330

<210> SEQ ID NO 302
<211> LENGTH: 317
```

```
<212> TYPE: DNA
<213> ORGANISM: Homo sapiens
<220> FEATURE:
<221> NAME/KEY: misc_feature
<222> LOCATION: 129, 295
<223> OTHER INFORMATION: n = A,T,C or G

<400> SEQUENCE: 302
agcgtggtcg cggccgaggt ctgtactggg agctaagcaa actgaccaat gacattgaag      60
agctgggccc ctacaccctg acaggaaca gtctctatgt caatggtttc acccatcaga     120
gctctgtgnc caccaccagc actcctggga cctccacagt ggatttcaga acctcaggga    180
ctccatcctc cctctccagc cccacaatta tggctgctgg ccctctcctg gtaccattca    240
ccctcaactt caccatcacc aacctgcagt atggggagga catgggtcac cctgnctcca    300
ggaagttcaa caccaca                                                    317

<210> SEQ ID NO 303
<211> LENGTH: 283
<212> TYPE: DNA
<213> ORGANISM: Homo sapiens
<220> FEATURE:
<221> NAME/KEY: misc_feature
<222> LOCATION: 139, 146, 195
<223> OTHER INFORMATION: n = A,T,C or G

<400> SEQUENCE: 303
tcgagcggcc gcccggacag gtctgggcgg atagcaccgg gcatattttg gaatggatga     60
ggtctggcac cctgagcagt ccagcgagga cttggtctta gttgagcaat ttggctagga    120
ggatagtatg cagcacggnt ctgagnctgt gggatagctg ccatgaagta acctgaagga    180
ggtgctggct ggtangggtt gattacaggg ttggaacag ctcgtacact tgccattctc     240
tgcatatact ggttagtgag gtgagcctgg ccctcttctt ttg                      283

<210> SEQ ID NO 304
<211> LENGTH: 72
<212> TYPE: DNA
<213> ORGANISM: Homo sapiens
<220> FEATURE:
<221> NAME/KEY: misc_feature
<222> LOCATION: 59
<223> OTHER INFORMATION: n = A,T,C or G

<400> SEQUENCE: 304
agcgtggtcg cggccgaggt gagccacagg tgaccggggc tgaagctggg gctgctggnc     60
ctgctggtcc tg                                                         72

<210> SEQ ID NO 305
<211> LENGTH: 245
<212> TYPE: DNA
<213> ORGANISM: Homo sapiens
<220> FEATURE:
<221> NAME/KEY: misc_feature
<222> LOCATION: 5, 11, 22, 98, 102
<223> OTHER INFORMATION: n = A,T,C or G

<400> SEQUENCE: 305
cagcngctcc nacggggcct gngggaccaa caacaccgtt ttcaccctta ggcccttggg      60
ctcctctttc tccttagca ccaggttgac cagcagcncc ancaggacca gcaaatccat     120
tggggccagc aggaccgacc tcaccacgtt caccagggct tccccgagga ccagcaggac    180
cagcaggacc agcagcccca gcttcgcccc ggtcacctgt ggctcacctc ggccgcgacc    240
``` acgct                                                                245

<210> SEQ ID NO 306
<211> LENGTH: 246
<212> TYPE: DNA
<213> ORGANISM: Homo sapiens
<220> FEATURE:
<221> NAME/KEY: misc_feature
<222> LOCATION: 144, 159
<223> OTHER INFORMATION: n = A,T,C or G

<400> SEQUENCE: 306
tcgagcggtc gcccgggcag gtccaccggg atagccgggg gtctggcagg aatgggaggc     60
atccagaacg agaaggagac catgcaaagc ctgaacgacc gcctggcctc ttacctggac    120
agagtgagga gcctggagac cganaaccgg aggctggana gcaaaatccg ggagcacttg    180
gagaagaagg acccccaggt caagagactg gagccattac ttcaagatca tcgagggacc    240
tggagg                                                               246

<210> SEQ ID NO 307
<211> LENGTH: 333
<212> TYPE: DNA
<213> ORGANISM: Homo sapiens
<220> FEATURE:
<221> NAME/KEY: misc_feature
<222> LOCATION: 5
<223> OTHER INFORMATION: n = A,T,C or G

<400> SEQUENCE: 307
agcgnggtcg cggccgaggt ccagctctgt ctcatacttg actctaaagt catcagcagc     60
aagacgggca ttgtcaatct gcagaacgat gcgggcattg tccgcagtat ttgcgaagat    120
ctgagccctc aggtcctcga tgatcttgaa gtaatggctc cagtctctga cctggggtcc    180
cttcttctcc aagtgctccc ggattttgct ctccagcctc cggttctcgg tctccaggct    240
cctcactctg tccaggtaag aaggcccagg cggtcgttca ggctttgcat ggtctccttc    300
tcgttctgga tgcctcccat tcctgccaga ccc                                 333

<210> SEQ ID NO 308
<211> LENGTH: 310
<212> TYPE: DNA
<213> ORGANISM: Homo sapiens

<400> SEQUENCE: 308
tcgagcggcc gcccgggcag gtcaggaagc acattggtct tagagccact gcctcctgga     60
ttccacctgt gctgcggaca tctccaggga gtgcagaagg gaagcaggtc aaactgctca    120
gatcagtcag actggctgtt ctcagttctc acctgagcaa ggtcagtctg cagccagagt    180
acagagggcc aacactggtg ttcttgaaca agggcttgag cagaccctgc agaaccctct    240
tccgtggtgt tgaacttcct ggaaaccagg gtgttgcatg ttttcctca taatgcaagg    300 ttggtgatgg                                                           310

<210> SEQ ID NO 309
<211> LENGTH: 429
<212> TYPE: DNA
<213> ORGANISM: Homo sapiens

<400> SEQUENCE: 309
agcgtggtcg cggccgaggt ccacatcggc agggtcggag ccctggccgc catactcgaa     60
ctggaatcca tcggtcatgc tctcgccgaa ccagacatgc ctcttgtcct tggggttctt    120

```
gctgatgtac cagttcttct gggccacact gggctgagtg gggtacaccg caggtctcac    180
cagtctccat gttgcagaag actttgatgg catccaggtt gcagccttgg ttggggtcaa    240
tccagtactc tccactcttc cagtcagaag tgggcacatc ttgaggtcac cggcaggtgc    300
cgggccgggg gttcttgcgg cttgccctct gggctccgga tgttctcgat ctgcttggct    360
caggctcttg agggtgggtg tccacctcga ggtcacggtc accgaaacct gcccgggcgg    420
cccgctcga                                                            429

<210> SEQ ID NO 310
<211> LENGTH: 430
<212> TYPE: DNA
<213> ORGANISM: Homo sapiens
<220> FEATURE:
<221> NAME/KEY: misc_feature
<222> LOCATION: 342
<223> OTHER INFORMATION: n = A,T,C or G

<400> SEQUENCE: 310
tcgagcggtc gcccgggcag gtttcgtgac cgtgacctcg aggtggacac caccctcaag    60
agcctgagcc agcagatcga gaacatccgg agcccagagg gcagccgcaa gaaccccgcc    120
cgcacctgcc gtgacctcaa gatgtgccac tctgactgga gagtggaga gtactggatt    180 gaccccaacc aaggctgcaa cctggatgcc atcaaagtct tctgcaacat ggagactggt    240
gagacctgcg tgtaccccac tcagcccagt gtgggcccag aagaaactgg tacatcagca    300 aggaaccccca aggacaagag gcattgtctt ggttcggcga gnagcatgac ccgatggatt    360
ccagtttcga gtattggcgg ccagggcttc ccgacccttg ccgatgtgga cctcggccgc    420
gaccaccgct                                                           430

<210> SEQ ID NO 311
<211> LENGTH: 2996
<212> TYPE: DNA
<213> ORGANISM: Homo sapiens

<400> SEQUENCE: 311
cagccaccgg agtggatgcc atctgcaccc accgccctga ccccacaggc cctgggctgg    60
acagagagca gctgtatttg gagctgagcc agctgaccca cagcatcact gagctgggcc    120
cctacaccct ggacagggac agtctctatg tcaatggttt cacacagcgg agctctgtgc    180
ccaccactag cattcctggg accccacag tggacctggg aacatctggg actccagttt    240
ctaaacctgg tccctcggct gccagccctc tcctggtgct attcactctc aacttcacca    300
tcaccaacct gcggtatgag gagaacatgc agcaccctgg ctccaggaag ttcaacacca    360
cggagagggt ccttcagggc ctggtccctg ttcaagagca ccagtgttgg ccctctgtac    420
tctggctgca gactgacttt gctcaggcct gaaaaggatg ggacagccac tggagtggat    480
gccatctgca cccaccaccc tgaccccaaa agccctaggc tggacagaga gcagctgtat    540
tgggagctga gccagctgac ccacaatatc actgagctgg gccccctatgc cctggacaac    600 gacagcctct ttgtcaatgg tttcactcat cggagctctg tgtccaccac cagcactcct    660 gggacccccca cagtgtatct gggagcatct aagactccag cctcgatatt tggcccttca    720
gctgccagcc atctcctgat actattcacc ctcaacttca ccatcactaa cctgcggtat    780
gaggagaaca tgtggcctgg ctccaggaag ttcaacacta cagagagggt ccttcagggc    840
ctgctaaggc ccttgttcaa gaacaccagt gttggccctc tgtactctgg ctgcaggctg    900
```

-continued

```
accttgctca ggccagagaa agatggggaa gccaccggag tggatgccat ctgcacccac    960
cgccctgacc ccacaggccc tgggctggac agagagcagc tgtatttgga gctgagccag   1020
ctgacccaca gcatcactga gctgggcccc tacacactgg acagggacag tctctatgtc   1080
aatggtttca cccatcggag ctctgtaccc accaccagca ccggggtggt cagcgaggag   1140
ccattcacac tgaacttcac catcaacaac ctgcgctaca tggcggacat gggccaaccc   1200
ggctccctca agttcaacat cacagacaac gtcatgaagc acctgctcag tcctttgttc   1260
cagaggagca gcctgggtgc acggtacaca ggctgcaggg tcatcgcact aaggtctgtg   1320
aagaacggtg ctgagacacg ggtggacctc ctctgcacct acctgcagcc ctcagcggc    1380
ccaggtctgc ctatcaagca ggtgttccat gagctgagcc agcagaccca tggcatcacc   1440
cggctgggcc cctactctct ggacaaagac agcctctacc ttaacggtta caatgaacct   1500
ggtccagatg agcctcctac aactcccaag ccagccacca cattcctgcc tcctctgtca   1560
gaagccacaa cagccatggg gtaccacctg aagaccctca cactcaactt caccatctcc   1620
aatctccagt attcaccaga tatgggcaag ggctcagcta cattcaactc caccgagggg   1680
gtccttcagc acctgctcag acccttgttc cagaagagca gcatgggccc cttctacttg   1740
ggttgccaac tgatctccct caggcctgag aaggatgggg cagccactgg tgtggacacc   1800
acctgcacct accaccctga ccctgtgggc ccgggctgg acatacagca gctttactgg    1860
gagctgagtc agctgaccca tggtgtcacc caactgggct tctatgtcct ggacagggat   1920
agcctcttca tcaatggcta tgcaccccag aatttatcaa tccggggcga gtaccagata   1980
aatttccaca ttgtcaactg gaacctcagt aatccagacc ccacatcctc agagtacatc   2040
accctgctga gggacatcca ggacaaggtc accacactct acaaaggcag tcaactacat   2100
gacacattcc gcttctgcct ggtcaccaac ttgacgatgg actccgtgtt ggtcactgtc   2160
aaggcattgt tctcctccaa tttggacccc agcctggtgg agcaagtctt tctagataag   2220
accctgaatg cctcattcca ttggctgggc tccacctacc agttggtgga catccatgtg   2280
acagaaatgg agtcatcagt ttatcaacca caagcagct ccagcaccca gcacttctac    2340
ctgaatttca ccatcaccaa cctaccatat tcccaggaca aagcccagcc aggcaccacc   2400
aattaccaga ggaacaaaag gaatattgag gatgcgctca ccaactcttc cgaaacagc    2460
agcatcaaga gttattttc tgactgtcaa gtttcaacat tcaggtctgt ccccaacagg   2520
caccacaccg gggtggactc cctgtgtaac ttctcgccac tggctcggag agtagacaga   2580
gttgccatct atgaggaatt tctgcggatg acccggaatg gtacccagct gcagaacttc   2640
accctggaca ggagcagtgt ccttgtggat gggtattttc ccaacagaaa tgagccctta   2700
actgggaatt ctgaccttcc cttctgggct gtcatcctca tcggcttggc aggactcctg   2760
ggactcatca catgcctgat ctgcggtgtc ctggtgacca cccgccggcg gaagaaggaa   2820
ggagaataca acgtccagca acagtgccca ggctactacc agtcacacct agacctggag   2880
gatctgcaat gactggaact tgccggtgcc tggggtgcct tcccccagc cagggtccaa    2940
agaagcttgg ctggggcaga aataaaccat attggtcgga cacaaaaaaa aaaaaa       2996
```

<210> SEQ ID NO 312
<211> LENGTH: 914
<212> TYPE: PRT
<213> ORGANISM: Homo sapiens

<400> SEQUENCE: 312

Met Ser Met Val Ser His Ser Gly Ala Leu Cys Pro Pro Leu Ala Phe

-continued

```
  1               5                   10                  15
Leu Gly Pro Pro Gln Trp Thr Trp Glu His Leu Gly Leu Gln Phe Leu
                 20                  25                  30

Asn Leu Val Pro Arg Leu Pro Ala Leu Ser Trp Cys Tyr Ser Leu Ser
             35                  40                  45

Thr Ser Pro Ser Pro Thr Cys Gly Met Arg Arg Thr Cys Ser Thr Leu
         50                  55                  60

Ala Pro Gly Ser Ser Thr Pro Arg Arg Gly Ser Phe Arg Ala Trp Ser
 65                  70                  75                  80

Leu Phe Lys Ser Thr Ser Val Gly Pro Leu Tyr Ser Gly Cys Arg Leu
                 85                  90                  95

Thr Leu Leu Arg Pro Glu Lys Asp Gly Thr Ala Thr Gly Val Asp Ala
                100                 105                 110

Ile Cys Thr His His Pro Asp Pro Lys Ser Pro Arg Leu Asp Arg Glu
             115                 120                 125

Gln Leu Tyr Trp Glu Leu Ser Gln Leu Thr His Asn Ile Thr Glu Leu
         130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
                180                 185                 190

Ala Ser His Leu Leu Ile Leu Phe Thr Leu Asn Phe Thr Ile Thr Asn
             195                 200                 205

Leu Arg Tyr Glu Glu Asn Met Trp Pro Gly Ser Arg Lys Phe Asn Thr
         210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
                260                 265                 270

Pro Asp Pro Thr Gly Pro Gly Leu Asp Arg Glu Gln Leu Tyr Leu Glu
             275                 280                 285

Leu Ser Gln Leu Thr His Ser Ile Thr Glu Leu Gly Pro Tyr Thr Leu
         290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
             340                 345                 350

Ser Leu Lys Phe Asn Ile Thr Asp Asn Val Met Lys His Leu Leu Ser
         355                 360                 365

Pro Leu Phe Gln Arg Ser Ser Leu Gly Ala Arg Tyr Thr Gly Cys Arg
     370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
                420                 425                 430
```

-continued

```
Leu Gly Pro Tyr Ser Leu Asp Lys Asp Ser Leu Tyr Leu Asn Gly Tyr
            435                 440                 445

Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525

Phe Tyr Leu Gly Cys Gln Leu Ile Ser Leu Arg Pro Glu Lys Asp Gly
        530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
        595                 600                 605

Tyr Gln Ile Asn Phe His Ile Val Asn Trp Asn Leu Ser Asn Pro Asp
        610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
                645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
        675                 680                 685

Leu Asp Lys Thr Leu Asn Ala Ser Phe His Trp Leu Gly Ser Thr Tyr
        690                 695                 700

Gln Leu Val Asp Ile His Val Thr Glu Met Glu Ser Ser Val Tyr Gln
705                 710                 715                 720

Pro Thr Ser Ser Ser Thr Gln His Phe Tyr Leu Asn Phe Thr Ile
                725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Leu Asn Gln Leu Phe
        755                 760                 765

Arg Asn Ser Ser Ile Lys Ser Tyr Phe Ser Asp Cys Gln Val Ser Thr
        770                 775                 780

Phe Arg Ser Val Pro Asn Arg His His Thr Gly Val Asp Ser Leu Cys
785                 790                 795                 800

Asn Phe Ser Pro Leu Ala Arg Arg Val Asp Arg Val Ala Ile Tyr Glu
                805                 810                 815

Glu Phe Leu Arg Met Thr Arg Asn Gly Thr Gln Leu Gln Asn Phe Thr
            820                 825                 830

Leu Asp Arg Ser Ser Val Leu Val Asp Gly Tyr Phe Pro Asn Arg Asn
        835                 840                 845
```

```
Glu Pro Leu Thr Gly Asn Ser Asp Leu Pro Phe Trp Ala Val Ile Leu
    850                 855                 860

Ile Gly Leu Ala Gly Leu Leu Gly Leu Ile Thr Cys Leu Ile Cys Gly
865                 870                 875                 880

Val Leu Val Thr Thr Arg Arg Arg Lys Lys Glu Gly Glu Tyr Asn Val
                885                 890                 895

Gln Gln Gln Cys Pro Gly Tyr Tyr Gln Ser His Leu Asp Leu Glu Asp
            900                 905                 910

Leu Gln

<210> SEQ ID NO 313
<211> LENGTH: 656
<212> TYPE: DNA
<213> ORGANISM: Homo sapiens

<400> SEQUENCE: 313
acagccagtc ggagctgcaa gtgttctggg tggatcgcgy atatgcactc aaaatgctct      60
ttgtaaagga aagccacaac atgtccaagg gacctgaggc gacttggagg ctgagcaaag     120
tgcagtttgt ctacgactcc tcggagaaaa cccacttcaa agacgcagtc agtgctggga     180
agcacacagc caactcgcac cacctctctg ccttggtcac ccccgctggg aagtcctatg     240
agtgtcaagt caacaaacc atttcactgg cctctagtga tccgcagaag acggtcacca     300
tgatcctgtc tgcggtccac atccaacctt ttgacattat ctcagatttt gtcttcagtg     360
aagagcataa atgcccagtg gatgagcggg agcaactgga agaaaccttg cccctgattt     420
tggggctcat cttgggcctc gtcatcatgg taacactcgc gatttaccac gtccaccaca     480
aaatgactgc caaccaggtg cagatccctc gggacagatc ccagtataag cacatgggct     540
agaggccgtt aggcaggcac cccctattcc tgctccccca actggatcag gtagaacaac     600
aaaagcactt ttccatcttg tacacgagat acaccaacat agctacaatc aaacag         656

<210> SEQ ID NO 314
<211> LENGTH: 519
<212> TYPE: DNA
<213> ORGANISM: Homo sapiens

<400> SEQUENCE: 314
tgtgcgtgga ccagtcagct tccgggtgtg actggagcag ggcttgtcgt cttcttcaga      60
gtcactttgc aggggttggt gaagctgctc ccatccatgt acagctccca gtctactgat     120
gtttaaggat ggtctcggtg gttaggccca ctagaataaa ctgagtccaa tacctctaca     180
cagttatgtt taactgggct ctctgacacc gggaggaagg tggcggggtt taggtgttgc     240
aaacttcaat ggttatgcgg ggatgttcac agagcaagct ttggtatcta gctagtctag     300
cattcattag ctaatggtgt cctttggtat ttattaaaat caccacagca tagggggact     360
ttatgtttag gttttgtcta agagttagct tatctgcttc ttgtgctaac agggctattg     420
ctaccaggga ctttggacat gggggccagc gtttggaaac ctcatctagt ttttttgaga     480
gataggccac tggccttgga cctcggccgc gaccacgct                            519

<210> SEQ ID NO 315
<211> LENGTH: 441
<212> TYPE: DNA
<213> ORGANISM: Homo sapiens

<400> SEQUENCE: 315
cacagagcgt ttattgacac caccactcct gaaaattggg atttcttatt aggttcccct      60
```

```
aaaagttccc atgttgatta catgtaaata gtcacatata tacaatgaag gcagtttctt      120
cagaggcaac cagggtttat agtgctaggt aaatgtcatc tcttttgtgc tactgactca      180
ttgtcaaacg tctctgcact gttttcagcc tctccacgtt gcctctgtcc tgcttcttag      240
ttccttcttt gtgacaaacc aaaagaataa gaggatttag aacaggactg cttttcccct      300
atgatttaaa aattccaatg actttcgccc ttgggagaaa tttccaagga aatctctctc      360
gctcgctctc tccgttttcc tttgtgagct tctgggggag ggttagtggt gacttttga      420 tacgaaaaaa tgcattttgt g                                               441

<210> SEQ ID NO 316
<211> LENGTH: 247
<212> TYPE: DNA
<213> ORGANISM: Homo sapiens

<400> SEQUENCE: 316
tggcgcggct gctggatttc accttcttgc acctgccggt gagcgcctgg ggtctaaagg       60
ggcgggatac tccattatgg cccctcgccc tgtagggctg gaatagttag aaaaggcaac      120
ccagtctagc ttggtaagaa gagagacatg cccccaacct cggcgccctt tttcctcacg      180
atctgctgtc cttacttcag cgactgcagg agcttcacct gcaagaaaac agcattgagc      240
tgctgac                                                               247

<210> SEQ ID NO 317
<211> LENGTH: 409
<212> TYPE: DNA
<213> ORGANISM: Homo sapiens

<400> SEQUENCE: 317
tgacagggct cctggagttg ttaagtcacc aagtagctgc aggggatgga cactgcccca       60
cacgatgtgg gatgaacagc agccttggtt tgtagcccag ggtgtccatg gatttgaccc      120
gaatgctccc tggaggccct gtggcgagga caggcactgg atggtccaga ccctctggct      180
ggaggagtgg tggagccagg actgggcctt cagccatgag ggctagaata acctgacctc      240
ttgcattcta acactgggtc attaatgaca cctttccagt ggatgttgca aaaaccaaca      300
ctgtcaggaa cctggccctg ggagggctca ggtgagctca caaggagagg tcaagccaag      360
ccaaagggta ggkaacacac aacaccaggg gaaaccagcc cccaaacca                 409

<210> SEQ ID NO 318
<211> LENGTH: 320
<212> TYPE: DNA
<213> ORGANISM: Homo sapiens
<220> FEATURE:
<221> NAME/KEY: misc_feature
<222> LOCATION: 6, 17, 24, 271
<223> OTHER INFORMATION: n = A,T,C or G

<400> SEQUENCE: 318
caaggnagat cttaagnggg gtcntatgta agtgtgctcc tggctccagg gttcctggag       60
cctcacgagg tcaggggaac ccttgtagaa ctccaccagc agcatcatct cgtgaaggat      120
gtcattggtc aggaagctgt cctggacgta ggccatctcc acatccatgg ggatgccata      180
gtcactgggc ctttgctcgg gaggaggcat cacccagaaa ggcgagatct tggactcggg      240
gcctgggttg ccagaatagt aaggggagca nagcagggcg aggcagggct ggaagccatt      300
gctggagccc tgcagccgca                                                 320
```

<210> SEQ ID NO 319
<211> LENGTH: 212
<212> TYPE: DNA
<213> ORGANISM: Homo sapiens
<220> FEATURE:
<221> NAME/KEY: misc_feature
<222> LOCATION: 172
<223> OTHER INFORMATION: n = A,T,C or G

<400> SEQUENCE: 319

```
tgaagcaata gcgcccccat tttacaggcg gagcatggaa gccagagagg tgggtggggg      60
agggggtcct tccctggctc aggcagatgg gaagatgagg aagccgctga agacgctgtc     120
ggcctcagag ccctggtaaa tgtgacccct tttggggtct ttttcaaccc anacctggtc     180
accctgctgc agacctcggc cgcgaccacg ct                                   212
```

<210> SEQ ID NO 320
<211> LENGTH: 769
<212> TYPE: DNA
<213> ORGANISM: Homo sapiens

<400> SEQUENCE: 320

```
tggaggtgta gcagtgagag gagatytcag gcaagagtgt cacagcagag ccctaaaascc    60 tccaactcac cagtgagaga tgagactgcc cagtactcag ccttcatctc ctgggccacc    120
tggagggcgt ctttctccat cagcgcatac tgagcagggg tactcagatc cttcttggaa    180
cctacaagga agagaagcac actggaaggg tcattctcct tcagggcatc ggccagccac    240
tgcctgccat gggaggtgga aagtaaggga tgagtgagtc tgcagggccc ctcccactga    300
cattcatagg cccaattacc ccctctctgg tcctacatgc attcttcttc ttcctgacca    360
cccctctgtt ctgaaccctc tcttcccgga gcctcccatt atattgcagg atgctcactt    420
acttggtatg ttccagagat gccacatcat tcaggttgaa gacaatgatg atggcttgga    480
agagtggcag aaacagcccc aggttgacag ggaagacact actgctcatt tccccaatcc    540
ttccagctcc atatgagaaa gccatgtgca ctctgagacc cacctacccc acttcaccca    600
gccccttacc ttgagctcct ctatagtagg ttgatgcaat gcatttgaac ctctcctgcc    660
cagcggtatc ccaactggaa ggaaggaaga gtgaagcaca ggtatgtatc ttgggggtg    720 tgggtgctgg ggagaaggga tagctggaag gggtgtggaa gcactcaca               769
```

<210> SEQ ID NO 321
<211> LENGTH: 690
<212> TYPE: DNA
<213> ORGANISM: Homo sapiens
<220> FEATURE:
<221> NAME/KEY: misc_feature
<222> LOCATION: 633, 666
<223> OTHER INFORMATION: n = A,T,C or G

<400> SEQUENCE: 321

```
tgggctgtgg gcggcacctg tgctctgcag gccagacagc gatagaagcc tttgtctgtg     60
cctactcccc cggaggcaac tgggaggtca acgggaagac aatcatcccc tataagaagg    120
gtgcctggtg ttcgctctgc acagccagtg tctcaggctg cttcaaagcc tgggaccatg    180
caggggggct ctgtgaggtc cccaggaatc cttgtcgcat gagctgccag aaccatggac    240
gtctcaacat cagcacctgc cactgccact gtcccctgg ctacacgggc agatactgcc     300
aagtgaggtg cagcctgcag tgtgtgcacg gccggttccg ggaggaggag tgctcgtgcg    360
tctgtgacat cggctacggg ggagcccagt gtgccaccaa ggtgcatttt cccttccaca    420
```

```
cctgtgacct gaggatcgac ggagactgct tcatggtgtc ttcagaggca gacacctatt    480
acagaagcca ggatgaaatg tcagaggaat ggcggggtgc tggcccagat caagagccag    540
aaagtgcagg acatcctcgc cttctatctg ggccgcctgg agaccaccaa cgaggtgact    600
gacagtgact ttgagaccag gaacttctgg atngggctca cctacaagac cgccaaggac    660
tccttncgct gggccacagg ggagcaccag                                      690

<210> SEQ ID NO 322
<211> LENGTH: 104
<212> TYPE: DNA
<213> ORGANISM: Homo sapiens

<400> SEQUENCE: 322
gtcgcaagcc ggagcaccac catgtagcct ttcccgaagt accggacctt ctcctcctcc     60
acgctcacat cacggacatc atggagcagg accaccacct ggtc                     104

<210> SEQ ID NO 323
<211> LENGTH: 118
<212> TYPE: DNA
<213> ORGANISM: Homo sapiens

<400> SEQUENCE: 323
gggccctggg cgcttccaaa tgacccagga ggtggtctgc gacgaatgcc ctaatgtcaa     60
actagtgaat gaagaacgaa cactggaagt agaaatagag cctggggtga gagacgga    118

<210> SEQ ID NO 324
<211> LENGTH: 354
<212> TYPE: DNA
<213> ORGANISM: Homo sapiens

<400> SEQUENCE: 324
tgctctccgg gagcttgaag aagaaactgg ctacaaaggg gacattgccg aatgttctcc     60
agcggtctgt atggacccag gcttgtcaaa ctgtactata cacatcgtga cagtcaccat    120
taacggagat gatgccgaaa acgcaaggcc gaagccaaag ccaggggatg gagagtttgt    180
ggaagtcatt tctttaccca agaatgacct gctgcagaga cttgatgctc tggtagctga    240
agaacatctc acagtggacg ccagggtcta ttcctacgct ctagcgctga acatgcaaa    300 tgcaaagcca tttgaagtgc ccttcttgaa atttttaagcc caaatatgac actg          354

<210> SEQ ID NO 325
<211> LENGTH: 642
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 325
ncatgcttga atgggctcct ggtgagagat tgccccctgg tggtgaaaca atcgtgtgtg     60
cccactgata ccaagaccaa tgaaagagac acagttaagc agcaatccat ctcatttcca    120
ggcacttcaa taggtcgctg attggtcctt gcaccagcag tggtagtcgt acctatttca    180
gagaggtctg aaattcaggt tcttagtttg ccagggcagg gccctacctt atatttttt    240 ccatcttcat catccacttc tgcttacagt ttgctgctta caataactta atgatggatt    300
gagttatctg ggtggtctct agccatctgg gcagtgtggt tctgtctaac caaagggcat    360
```

```
tggcctcaaa ccctgcattt ggtttagggg ctaacagagc tcctcagata atcttcacac    420
acatgtaact gctggagatc ttattctatt atgaataaga aacgagaagt ttttccaaag    480
tgttagtcag gatctgaagg ctgtcattca gataacccag cttttccttt tggcttttag    540
cccattcaga ctttgccaga gtcaagccaa ggattgcttt tttgctacag ttttctgcca    600
aatggcctag ttcctgagta cctggaaacc agagagaaag ag                      642

<210> SEQ ID NO 326
<211> LENGTH: 455
<212> TYPE: DNA
<213> ORGANISM: Homo sapiens

<400> SEQUENCE: 326
tccgtgagga tgagcttcga gtccttcacc aggcactgca ggggcacagt cacgtcaatc     60
accttcacct tctcgctctt cctgctcttg tcattgacaa acttcccgta ccaggcattg    120
acgatgatga ggcccattct ggactcttct gcctcaatta ccttcggac agattcctgc    180 atcagccgga cagcggactc cgcctcttgc ttcttctgca gcacatcggt ggcggcgctt    240
tccctctgct tctccaattc cttctctttc tgagccctga ggtatggttt gatgatcaga    300
cggtgcatgg caaagtagac cactagaggc cccacggtgg catagaacat ggcgctgggc    360
agaagctggt ccgtcaagtg aatagggaag aagtatgtct gactggccct gttgagcttg    420
actttgagag aaacgccctg tggaactcca acgct                              455

<210> SEQ ID NO 327
<211> LENGTH: 321
<212> TYPE: DNA
<213> ORGANISM: Homo sapiens

<400> SEQUENCE: 327
ttcactgtga actcgcagtc ctcgatgaac tcgcacagat gtgacagccc tgtctccttg     60
ctctctgagt tctcttcaat gatgctgatg atgcagtcca cgatagcgcg cttatactca    120
aagccaccct cttcccgcag catggtgaac aggaagttca taggacggc gtgtttgcga    180 ggatatttct gacacagggc actgatggcc tggacaacca ccaccttgaa ttcatccgag    240
atttctgaca tgaaggagga gatctgcttc atgaggcggt cgatgctgct ctcgctgccc    300
gtcttaagga gggtggtgat g                                             321

<210> SEQ ID NO 328
<211> LENGTH: 476
<212> TYPE: DNA
<213> ORGANISM: Homo sapiens
<220> FEATURE:
<221> NAME/KEY: misc_feature
<222> LOCATION: 302, 311
<223> OTHER INFORMATION: n = A,T,C or G

<400> SEQUENCE: 328
tgcaggaggg gccatggggg ctgtgaatgg gatgcagccc catggtgtcc ctgataaatc     60
cagtgtgcag tctgatgaag tctgggtggg tgtggtctac gggctggcag ctaccatgat    120
ccaagaggta atgcactcct tttcccatct ctccaccatc tgtatcctgg ccmagaaaaa    180
cttcccttca aaccaaccaa aatttccttt caaaggcata acccaaatgc catccttggt    240
ccggtctaat aaagcctccc ccattttttcc cctggtatgc attcccaggc tccctggcct    300 tncaggggctt nctgtctgtg ggtcatagtt tatctcctcc cacttgctgg gagctccttg    360
aaggcaaaga ctctactgcc tccatctatc cagtggaagt ggctcttcag agggtgccaa    420
```

```
gttagtatgt atgactgtca tctctcccaa cagggcctga cttggsaggg cttcca        476

<210> SEQ ID NO 329
<211> LENGTH: 340
<212> TYPE: DNA
<213> ORGANISM: Homo sapiens

<400> SEQUENCE: 329
cgagggagat tgccagcacc ctgatggaga gtgagatgat ggagatcttg tcagtgctag     60
ctaaggtgga ccacagccct gtcacaaggg ctgctgcagc ctgcctggac aaagcagtgg    120
aatatgggct tatccaaccc aaccaagatg agagtgagg gggttgtccc tgggcccaag     180
gctcatgcac acgctaccta ttgtggcacg gagagtaagg acggaagcag ctttggctgg    240
tggtggctgg catgcccaat actcttgccc atcctcgctt gctgccctag gatgtcctct    300
gttctgagtc agcggccacg ttcagtcaca cagccctgct                          340

<210> SEQ ID NO 330
<211> LENGTH: 277
<212> TYPE: DNA
<213> ORGANISM: Homo sapiens

<400> SEQUENCE: 330
tgtcaccatc acattggtgc caaatacccca gaagacatcg tagatgaaga gtccgcccag    60
caggatgcag ccagtgctga cattgttgag gtgcaggagc tctactccat taagggagaa   120
ggccaggcca aaaaggttgt tggcaatcca gtgcttcctc agcaggtacc agacgccaac   180
gatgctgctc aggcccaggc acaccaggtc cttggtgtca aattcataat tgatgatctc   240
ctccttgttt tcccagaacc ctgtgtgaag agcagac                            277

<210> SEQ ID NO 331
<211> LENGTH: 136
<212> TYPE: DNA
<213> ORGANISM: Homo sapiens

<400> SEQUENCE: 331
ttgcttccca cctcctttct ctgtcctctc ctgaggttct gccttacaat ggggacactg     60
atacaaacca cacacacaat gaggatgaaa acagataaca ggtaaaatga cctcacctgc   120
ccgggcggcc gctcga                                                   136

<210> SEQ ID NO 332
<211> LENGTH: 184
<212> TYPE: DNA
<213> ORGANISM: Homo sapiens

<400> SEQUENCE: 332
ttgtgagata aacgcagata ctgcaatgca ttaaaacgct tgaaatactc atcagggatg     60
ttgctgatct tattgttgtc taagtagaga gttagaagag agacagggag accagaaggc   120
agtctggcta tctgattgaa gctcaagtca aggtattcga gtgatttaag accttttaaaa   180 gcag                                                                184

<210> SEQ ID NO 333
<211> LENGTH: 384
<212> TYPE: DNA
<213> ORGANISM: Homo sapiens

<400> SEQUENCE: 333
```

| | |
|---|---|
| cggaaaactt cgaggaattg ctcaaagtgc tggggtgaa tgtgatgctg aggaagattg | 60 |
| ctgtggctgc agcgtccaag ccagcagtgg agatcaaaca ggagggagac actttctaca | 120 |
| tcaaaacctc caccaccgtg cgcaccacag agattaactt caaggttggg gaggagtttg | 180 |
| aggagcagac tgtggatggg aggccctgta agagcctggt gaaatgggag agtgagaata | 240 |
| aaatggtctg tgagcagaag ctcctgaagg gagagggccc caagacctcg tggaccagag | 300 |
| aactgaccaa cgatggggaa ctgatcctga ccatgacggc ggatgacgtt gtgtgcacca | 360 |
| gggtctacgt ccgagagtga gcgg | 384 |

<210> SEQ ID NO 334
<211> LENGTH: 169
<212> TYPE: DNA
<213> ORGANISM: Homo sapiens
<220> FEATURE:
<221> NAME/KEY: misc_feature
<222> LOCATION: 2, 165
<223> OTHER INFORMATION: n = A,T,C or G

<400> SEQUENCE: 334

| | |
|---|---|
| cnacaaacag agcagacacc ctggatccgg tcctgctact ggccaggacg gctggaccgt | 60 |
| aaaattgaat ttccacttcc tgaccgccgc cagaagagat tgattttctc cactatcact | 120 |
| agcaagatga acctctctga ggaggttgac ttggaagact atgtngccc | 169 |

<210> SEQ ID NO 335
<211> LENGTH: 185
<212> TYPE: DNA
<213> ORGANISM: Homo sapiens

<400> SEQUENCE: 335

| | |
|---|---|
| ccaggtttgc agcccaggct gcacatcagg ggactgcctc gcaatacttc atgctgttgc | 60 |
| tgctgactga tggtgctgtg acggatgtgg aagccacacg tgaggctgtg gtgcgtgcct | 120 |
| cgaacctgcc catgtcagtg atcattgtgg gtgtgggtgg tgctgacttt gaggccatgg | 180 |
| agcag | 185 |

<210> SEQ ID NO 336
<211> LENGTH: 358
<212> TYPE: DNA
<213> ORGANISM: Homo sapiens
<220> FEATURE:
<221> NAME/KEY: misc_feature
<222> LOCATION: 26
<223> OTHER INFORMATION: n = A,T,C or G

<400> SEQUENCE: 336

| | |
|---|---|
| ctgcccctgc cttacggcgg ccaganacac acccaggatg gcattggccc caaacttgga | 60 |
| tttgttctca gtcccatcca actccagcat caggttgtcc agtttctctt gctccaccac | 120 |
| agagagacct gagctgatga gggctggcgc gatggtggag ttgatgtggt ccactgcctt | 180 |
| caggacacct ttgcctaagt aacgctgttt gtctccatcc ctcagctcca gggcctcata | 240 |
| gatgcccgta gaggctccac tgggcactgc agcccggaaa agacctttgg cagtatagag | 300 |
| atccacctcc actgtggggt tcccgcggga gtccaggatc tcccgggccc agatcttc | 358 |

<210> SEQ ID NO 337
<211> LENGTH: 271
<212> TYPE: DNA
<213> ORGANISM: Homo sapiens
<220> FEATURE:
<221> NAME/KEY: misc_feature

```
<222> LOCATION: 17
<223> OTHER INFORMATION: n = A,T,C or G

<400> SEQUENCE: 337
cacaaagcca ccagccnggg aaatcagaat ttacttgatg caactgactt gtaatagcca      60
gaaatcctgc ccagcatggg attcagaacc tggtctgcaa ccaaatccac cgtcaaagtt     120
catacaggat aaacaaatt caattgcctt ttccacatta atagcatcaa gcttccccaa      180
caaagccaaa gttgccaccg cacaaaaaga gaatcttgtg tcaatttctc cctactttat     240
aaaagtagat ttttcacatc ccatgaagca g                                    271

<210> SEQ ID NO 338
<211> LENGTH: 326
<212> TYPE: DNA
<213> ORGANISM: Homo sapiens
<220> FEATURE:
<221> NAME/KEY: misc_feature
<222> LOCATION: 15, 17, 18
<223> OTHER INFORMATION: n = A,T,C or G

<400> SEQUENCE: 338
ctgtgctccc gactngnnca tctcaggtac caccgactgc actgggcggg gccctctggg      60
gggaaaggct ccacggggca gggatacatc tcgaggccag tcatcctctg gaggcagccc     120
aatcaggtca aagattttgc ccaactggtc ggcttcagag tttccacaga agagaggctt     180
tcgacgaaac atctctgcaa agatacagcc aacactccac atgtccacag gtgttgcata     240
tgtggactgc agaagaactt cgggagctcg gtaccagagt gtaacaacca cgggtgtaag     300
tgccatctgg tagctgtaga ttctgg                                          326

<210> SEQ ID NO 339
<211> LENGTH: 260
<212> TYPE: DNA
<213> ORGANISM: Homo sapiens
<220> FEATURE:
<221> NAME/KEY: misc_feature
<222> LOCATION: 47, 54, 60, 69, 90, 91, 96, 113, 117, 119, 195
<223> OTHER INFORMATION: n = A,T,C or G

<400> SEQUENCE: 339
ttcacctgag gactcatttc gtgcccttg ttgacttcaa gcaaagncct tcanggtctn       60
caaggacgnc acatttccac ttgcgaatgn nctcanggct catcttgaag aanaagnanc     120
ccaagtgctg gatcccagac tcgggggtaa ccttgtgggt aagagctcat ccagtttatg     180
ctttaggacg tccanctact cggggagct ggaagcctgc gtggatgcgg ccctgctgga      240
cctcggccgc gaccacgcta                                                 260

<210> SEQ ID NO 340
<211> LENGTH: 220
<212> TYPE: DNA
<213> ORGANISM: Homo sapiens
<220> FEATURE:
<221> NAME/KEY: misc_feature
<222> LOCATION: 15, 18
<223> OTHER INFORMATION: n = A,T,C or G

<400> SEQUENCE: 340
ctggaagccc ggctnggnct ggcagcggaa ggagccaggc aggttcacgc agcggtgctg      60
gcagtagcgg tagcggcact cgtctatgtc cacacactcg ggcccgatct tgcggtaacc     120
atcagggcag gtgcactgat aggagccagg caagttatgg cagtcctggc tggggcgaca     180
```

| gtcgtgcagg gcctgggcac actcgtccac atccacacag | 220 |

<210> SEQ ID NO 341
<211> LENGTH: 384
<212> TYPE: DNA
<213> ORGANISM: Homo sapiens

<400> SEQUENCE: 341

| ctgctaccag gggagcgaga gctgactatc ccagcctcgg ctaatgtatt ctacgccatg | 60 |
| gatggagctt cacacgattt cctcctgcgg cagcggcgaa ggtcctctac tgctacaccg | 120 |
| ggcgtcacca gtggcccgtc tgcctcagga actcctccga gtgagggagg aggggggctcc | 180 |
| tttcccagga tcaaggccac agggaggaag attgcacggg cactgttctg aggaggaagc | 240 |
| cccgttggct tacagaagtc atggtgttca taccagatgt gggtagccat cctgaatggt | 300 |
| ggcaattata tcacattgag acagaaattc agaaagggag ccagccaccc tggggcagtg | 360 |
| aagtgccact ggtttaccag acag | 384 |

<210> SEQ ID NO 342
<211> LENGTH: 245
<212> TYPE: DNA
<213> ORGANISM: Homo sapiens

<400> SEQUENCE: 342

| ctggctaagc tcatcattgt tactggtggg caccatgtcc ttgaagcttc aggcaagcaa | 60 |
| tgtaaccaac aagaatgacc ccaagtccat caactctcga gtcttcattg gaaacctcaa | 120 |
| cacagctctg gtgaagaaat cagatgtgga gaccatcttc tctaagtatg ccgtgtggc | 180 |
| cggctgttct gtgcacaagg gctatgcctt tgttcagtac tccaatgagc gccatgcccg | 240 |
| ggcag | 245 |

<210> SEQ ID NO 343
<211> LENGTH: 611
<212> TYPE: DNA
<213> ORGANISM: Homo sapiens

<400> SEQUENCE: 343

| ccaaaaaaat caagatttaa ttttttttatt tgcactgaaa aactaatcat aactgttaat | 60 |
| tctcagccat ctttgaagct tgaaagaaga gtctttggta ttttgtaaac gttagcagac | 120 |
| tttcctgcca gtgtcagaaa atcctattta tgaatcctgt cggtattcct tggtatctga | 180 |
| aaaaaatacc aaatagtacc atacatgagt tatttctaag tttgaaaaat aaaaagaaat | 240 |
| tgcatcacac taattacaaa atacaagttc tggaaaaaat attttttcttc attttaaaac | 300 |
| ttttttttaac taataatggc tttgaaagaa gaggcttaat ttggggggtgg taactaaaat | 360 |
| caaaagaaat gattgacttg agggtctctg tttggtaaga atacatcatt agcttaaata | 420 |
| agcagcagaa ggttagtttt aattatgtag cttctgttaa tattaagtgt ttttttgtctg | 480 |
| ttttacctca atttgaacag ataagtttgc ctgcatgctg gacatgcctc agaaccatga | 540 |
| atagcccgta ctagatcttg ggaacatgga tcttagagtc ctttggaata agttcttata | 600 |
| taaatacccc c | 611 |

<210> SEQ ID NO 344
<211> LENGTH: 311
<212> TYPE: DNA
<213> ORGANISM: Homo sapiens
<220> FEATURE:
<221> NAME/KEY: misc_feature

```
<222> LOCATION: 1, 275, 284, 296, 297, 300
<223> OTHER INFORMATION: n = A,T,C or G

<400> SEQUENCE: 344
nctcgaaaaa gcccaagaca gcagaagcag acacctccag tgaactagca aagaaaagca      60
aagaagtatt cagaaaagag atgtcccagt tcatcgtcca gtgcctgaac ccttaccgga     120
aacctgactg caaagtggga agaattacca caactgaaga ctttaaacat ctggctcgca     180
agctgactca cggtgttatg aataaggagc tgaagtactg taagaatcct gaggacctgg     240
agtgcaatga gaatgtgaaa cacaaaacca aggantacat taanaagtac atgcannaan     300
tttggggctt g                                                          311

<210> SEQ ID NO 345
<211> LENGTH: 201
<212> TYPE: DNA
<213> ORGANISM: Homo sapiens

<400> SEQUENCE: 345
cacacggtca tcccgactgc caacctggag gcccaggccc tgtggaagga gccgggcagc      60
aatgtcacca tgagtgtgga tgctgagtgt gtgcccatgg tcaggaccct tctcaggtac     120
ttctactccc gaaggattga catcaccctg tcgtcagtca agtgcttcca caagctggcc     180
tctgcctatg gggccaggca g                                               201

<210> SEQ ID NO 346
<211> LENGTH: 370
<212> TYPE: DNA
<213> ORGANISM: Homo sapiens

<400> SEQUENCE: 346
ctgctccagg gcgtggtgtg ccttcgtggc ctctgcctcc tccgaggagc caggctgtgt      60
tctcttcaga atgttctgga gcagcagttt gaggcgggtg atgcgttgga agggcagaat     120
cagaaaggac ttgagggaaa ggcgctggca gacggggtcg ctctccagct tctccaagac     180
ctcccggaaa ttgctgttgc tattcatcag gctctggaag gtgcgttcct gataggtctg     240
gttggtgaca taaggcaggt agacccggcg gaagtctggg gcgtggttca ggactacgtc     300
acatacttgg aaggagaaga tattgttctc aaagttctct tccaggtctg aaaggaacgt     360
ggcgctgacg                                                            370

<210> SEQ ID NO 347
<211> LENGTH: 416
<212> TYPE: DNA
<213> ORGANISM: Homo sapiens
<220> FEATURE:
<221> NAME/KEY: misc_feature
<222> LOCATION: 416
<223> OTHER INFORMATION: n = A,T,C or G

<400> SEQUENCE: 347
ctgttgtgct gtgtatggac gtgggcttta ccatgagtaa ctccattcct ggtatagaat      60
ccccatttga acaagcaaag aaggtgataa ccatgtttgt acagcgacag gtgtttgctg     120
agaacaagga tgagattgct ttagtcctgt ttggtacaga tggcactgac aatcccttt      180 ctggtgggga tcagtatcag aacatcacag tgcacagaca tctgatgcta ccagattttg     240
atttgctgga ggacattgaa agcaaaatcc aaccaggttc tcaacaggct gacttcctgg     300
atgcactaat cgtgagcatg gatgtgattc aacatgaaac aataggaaag aagtttggag     360
```

```
aagaggcata ttgaaatatt cactgacctc aagcagcccg attcagcaaa agtcan         416
```

<210> SEQ ID NO 348
<211> LENGTH: 351
<212> TYPE: DNA
<213> ORGANISM: Homo sapiens

<400> SEQUENCE: 348

```
gtacaggaga ggatggcagg tgcagagcgg gcactgagct ctgcaggtga aagggctcgg      60
cagttggatg ctctcctgga ggctctgaaa ttgaaacggg caggaaatag tctggcagcc    120
tctacagcag aagaaacggc aggcagtgcc cagggacgag caggagacag atgccttcct    180
cttgtctcaa ctgcaaagag gcgttccttc ctctttcact aatcctcctc agcacagacc    240
ctttacgggt gtcaggctgg gggacagtaa ggtctttccc ttcccacaag gccatatctc    300
aggctgtctc agtgggggga aaccttggac aatacccggg ctttcttggg c             351
```

<210> SEQ ID NO 349
<211> LENGTH: 207
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 349

```
nccgggacat ctccaccctc aacagtggca agaagagcct ggagactgaa cacaaggcct      60
tgaccagtga gattgcactg ctgcagtcca ggctgaagac agaggctct gatctgtgcg     120 acagagtgag cgaaatgcag aagctggatg cacaggtcaa ggagctggtg ctgaagtcgg    180
cggtggaggc tgagcgcctg gtggctg                                         207
```

<210> SEQ ID NO 350
<211> LENGTH: 323
<212> TYPE: DNA
<213> ORGANISM: Homo sapiens

<400> SEQUENCE: 350

```
ccatacaggg ctgttgccca ggccctagag gtcattcctc gtaccctgat ccagaactgt      60
ggggccagca ccatccgtct acttacctcc cttcgggcca agcacaccca ggagaactgt    120
gagacctggg gtgtaaatgg tgagacgggt actttggtgg acatgaagga actgggcata    180
tgggagccat tggctgtgaa gctgcagact tataagacag cagtggagac ggcagttctg    240
ctactgcgaa ttgatgacat cgtttcaggc cacgaaaaga aggcgatga ccagagccgg     300 caaggcgggg ctcctgatgc tgg                                            323
```

<210> SEQ ID NO 351
<211> LENGTH: 353
<212> TYPE: DNA
<213> ORGANISM: Homo sapiens
<220> FEATURE:
<221> NAME/KEY: misc_feature
<222> LOCATION: 12, 25, 39, 42
<223> OTHER INFORMATION: n = A,T,C or G

<400> SEQUENCE: 351

```
cgccgcatcc cntggtccct tccantccct tttcctttnt cngggaacgt gtatgcggtt      60 tgttttgtt ttgtagggtt ttttccttc tccacctctc cctgtctctt ttgctccatg      120
ttgtccgttt ctgtggggtt aggtttatgt ttttaatcat ctgaggtcac gtctatttcc    180
```

```
tccggactcg cctgcttggt ggcgattctc caccggttaa tatggtgcgt ccctttttc    240 ttttgttgcg aatctgagcc ttcttcctcc agcttctgcc ttttgaactt tgttcttcgg   300
ttctgaaacc atactttac ctgagtttcc gtgaggctga ggctgtgtgc caa           353
```

<210> SEQ ID NO 352
<211> LENGTH: 467
<212> TYPE: DNA
<213> ORGANISM: Homo sapiens

<400> SEQUENCE: 352

```
ctgcccacac tgatcacttg cgagatgtcc ttagggtaca agaacaggaa ttgaagtctg    60
aatttgagca gaacctgtct gagaaactct ctgaacaaga attacaattt cgtcgtctca   120
gtcaagagca agttgacaac tttactctgg atataaatac tgcctatgcc agactcagag   180
gaatcgaaca ggctgttcag agccatgcag ttgctgaaga ggaagccaga aaagcccacc   240
aactctggct ttcagtggag gcattaaagt acagcatgaa gacctcatct gcagaaacac   300
ctactatccc gctgggtagt gcagttgagg ccatcaaagc caactgttct gataatgaat   360
tcacccaagc tttaaccgca gctatccctc cagagtccct gacccgtggg gtgtacagtg   420
aagagaccct tagagcccgt ttctatgctg ttcaaaaact ggcccga                 467
```

<210> SEQ ID NO 353
<211> LENGTH: 350
<212> TYPE: DNA
<213> ORGANISM: Homo sapiens

<400> SEQUENCE: 353

```
ctgctgcagc cacagtagtt cctcccatgg tgggtggccc tcctggtcct gctggcccag    60
gaaatctgtc cccaccagga acagcccctg gaaaacggcc ccgtcctcta ccaccttgtg   120
gaaatgctgc acgggaactg cctcctggag accagctttt accttcccca gacatttgtc   180
ctgattgtgt agttttcctg gactgcattt caaattgact caggaactgt ttattgcatg   240
gagttacaac aggattctga ccatgaagtt ctcttttagg taacagatcc attaactttt   300
ttgaagatgc ttcagatcca acaccaacaa gggcaaaccc ctttgactgg                350
```

<210> SEQ ID NO 354
<211> LENGTH: 351
<212> TYPE: DNA
<213> ORGANISM: Homo sapiens

<400> SEQUENCE: 354

```
atttagatga gatctgaggc atggagacat ggagacagta tacagactcc tagatttaag    60
ttttaggttt tttgcttttc taatcaccaa ttcttatata caatgtatat tttagactcg   120
agcagatgat catcttcatc ttaagtcatt ccttttgact gagtatggca ggattagagg   180
gaatggcagt atagatcaat gtcttttct gtaaagtata ggaaaaacca gagaggaaaa   240
aaagagctga caattggaag gtagtagaaa attgacgata atttcttctt aacaaataat   300
agttgtatat acaaggaggc tagtcaacca gattttattt gttgagggcg a            351
```

<210> SEQ ID NO 355
<211> LENGTH: 308
<212> TYPE: DNA
<213> ORGANISM: Homo sapiens

<400> SEQUENCE: 355

```
ttttggcgca agttttacag attttattaa agtcgaagct attggtcttg gaagatgaaa    60
atgcaaatgt tgatgaggtg gaattgaagc cagatacctt aataaaatta tatcttggtt   120
ataaaaataa gaattaagg gttaacatca atgtgccaat gaaaaccgaa cagaagcagg    180
aacaagaaac cacacacaaa aacatcgagg aagaccgcaa actactgatt caggcggcca   240
tcgtgagaat catgaagatg aggaaggttc tgaaacacca gcagttactt ggcgaggtcc   300
tcactcag                                                            308

<210> SEQ ID NO 356
<211> LENGTH: 207
<212> TYPE: DNA
<213> ORGANISM: Homo sapiens

<400> SEQUENCE: 356
ctgtcccaag tgctcccaga aggcaggatt ctgaagacca ctccagcgat atgttcaact    60
atgaagaata ctgcaccgcc aacgcagtca ctgggccttg ccgtgcatcc ttcccacgct   120
ggtactttga cgtggagagg aactcctgca ataacttcat ctatggaggc tgccggggca   180
ataagaacag ctaccgctct gaggagg                                       207

<210> SEQ ID NO 357
<211> LENGTH: 188
<212> TYPE: DNA
<213> ORGANISM: Homo sapiens
<220> FEATURE:
<221> NAME/KEY: misc_feature
<222> LOCATION: 25, 29
<223> OTHER INFORMATION: n = A,T,C or G

<400> SEQUENCE: 357
tcgaccacgc cctcgtagcg catgngctnc aggacgatgc tcagagtgat gaacaccccg    60
gtgcggccca cgccagcact gcagtgcacc gtgataggcc catcctgtcc aaactgctcc   120
ttggtcttat gcacctgccc gatgaagtca atgaatccct cgcctgtctt gggcacgccc   180
tgctctgg                                                            188

<210> SEQ ID NO 358
<211> LENGTH: 291
<212> TYPE: DNA
<213> ORGANISM: Homo sapiens

<400> SEQUENCE: 358
ctgggagcat cggcaagcta ctgccttaaa atccgatctc cccgagtgca caatttctgt    60 ccctttttaag ggttcacaac actaaagatt tcacatgaaa gggttgtgat tgatttgagc  120
aggcaggcgg tacgtgacag gggctgcatg caccggtggt cagagagaaa cagaacaggg   180
cagggaattt cacaatgttc ttctatacaa tggctggaat ctatgaataa catcagtttc   240
taagttatgg gttgattttt aactactggg tttaggccag gcaggcccag g            291

<210> SEQ ID NO 359
<211> LENGTH: 117
<212> TYPE: DNA
<213> ORGANISM: Homo sapiens
<220> FEATURE:
<221> NAME/KEY: misc_feature
<222> LOCATION: 79, 98, 100
<223> OTHER INFORMATION: n = A,T,C or G

<400> SEQUENCE: 359
gccaccacac tccagcctgg gcaatacagc aagactgtct caaaaaaaaa aaaaaaaaa     60
```
cccaaaaaaa ctcaaaaang taatgaatga tacccaangn gccttttcta gaaaaag    117

<210> SEQ ID NO 360
<211> LENGTH: 394
<212> TYPE: DNA
<213> ORGANISM: Homo sapiens

<400> SEQUENCE: 360
ctgttcctct ggggtggtcc agttctagag tgggagaaag ggagtcaggc gcattgggaa    60
tcgtggttcc agtctggttg cagaatctgc acatttgcca agaaattttc cctgtttgga   120
aagtttgccc cagctttccc gggcacacca ccttttgtcc caagtgtctg ccggtcgacc   180
aatctgcctg ccacacattg accaagccag acccggttca cccagctcga ggatcccagg   240
ttgaagagtg gccccttgag gccctggaaa gaccaatcac tggacttctt cccttgagag   300
tcagaggtca cccgtgattc tgcctgcacc ttatcattga tctgcagtga tttctgcaaa   360
tcaagagaaa ctctgcaggg cactcccctg tttc                               394

<210> SEQ ID NO 361
<211> LENGTH: 394
<212> TYPE: DNA
<213> ORGANISM: Homo sapiens
<220> FEATURE:
<221> NAME/KEY: misc_feature
<222> LOCATION: 28, 31
<223> OTHER INFORMATION: n = A,T,C or G

<400> SEQUENCE: 361
ctgggcggat agcaccgggc atattttntt natggatgag gtctggcacc ctgagcagtc    60
cagcgaggac ttggtcttag ttgagcaatt tggctaggag gatagtatgc agcacggttc   120
tgagtctgtg ggatagctgc catgaagtaa cctgaaggag gtgctggctg gtagggttg    180 attacagggt tgggaacagc tcgtacactt gccattctct gcatatactg gttagtgagg   240
tgagcctggc gctcttcttt gcgctgagct aaagctacat acaatggctt tgtggacctc   300
ggccgcgacc acgctaagcc gaattccagc acactggcgg ccgttactag tggatccgag   360
ctcggtacca agcttggcgt aatcatggtc atag                               394

<210> SEQ ID NO 362
<211> LENGTH: 268
<212> TYPE: DNA
<213> ORGANISM: Homo sapiens

<400> SEQUENCE: 362
ctgcgcgtgg accagtcagc ttccgggtgt gactggagca gggcttgtcg tcttcttcag    60
agtcactttg caggggttgg tgaagctgct cccatccatg tacagctccc agtctactga   120
tgtttaagga tggtctcggt ggttaggccc actagaataa actgagtcca atacctctac   180
acagttatgt ttaactgggc tctctgacac cgggaggaag gtggcggggt ttaggtgttg   240
caaacttcaa tggttatgcg gggatgtt                                      268

<210> SEQ ID NO 363
<211> LENGTH: 323
<212> TYPE: DNA
<213> ORGANISM: Homo sapiens

<400> SEQUENCE: 363
ccttgacctt ttcagcaagt gggaaggtgt aatccgtctc cacagacaag gccaggactc    60

| | |
|---|---|
| gtttgtaccc gttgatgata gaatggggta ctgatgcaac agttgggtag ccaatctgca | 120 |
| gacagacact ggcaacattg cggacaccct ccaggaagcg agaatgcaga gtttcctctg | 180 |
| tgatatcaag cacttcaggg ttgtagatgc tgccattgtc gaacacctgc tggatgacca | 240 |
| gcccaaagga gaaggggag atgttgagca tgttcagcag cgtggcttcg ctggctccca | 300 |
| ctttgtctcc agtcttgatc aga | 323 |

<210> SEQ ID NO 364
<211> LENGTH: 393
<212> TYPE: DNA
<213> ORGANISM: Homo sapiens
<220> FEATURE:
<221> NAME/KEY: misc_feature
<222> LOCATION: 29
<223> OTHER INFORMATION: n = A,T,C or G

<400> SEQUENCE: 364

| | |
|---|---|
| ccaagctctc catcgtcccc gtgcgcagng gctactgggg gaacaagatc ggcaagcccc | 60 |
| acactgtccc ttgcaaggtg acaggccgct gcggctctgt gctggtacgc ctcatcactg | 120 |
| cacccagggg cactggcatc gtctccgcac ctgtgcctaa gaagctgctc atgatggctg | 180 |
| gcatcgatga ctgctacacc tcagcccggg gctgcactgc caccctgggc aacttcgcca | 240 |
| aggccacctt tgatgccatt tctaagacct acagctacct gaccccgac tctggaagg | 300 |
| agactgtatt caccaagtct ccctatcagg agttcactga ccacctcgtc aagacccaca | 360 |
| ccagagtctc cgtgcagcgg actcaggctc cag | 393 |

<210> SEQ ID NO 365
<211> LENGTH: 371
<212> TYPE: DNA
<213> ORGANISM: Homo sapiens

<400> SEQUENCE: 365

| | |
|---|---|
| cctcctcaga gcggtagctg ttcttattgc cccggcagcc tccatagatg aagttattgc | 60 |
| aggagttcct ctccacgtca agtaccagc gtgggaagga tgcacggcaa ggcccagtga | 120 |
| ctgcgttggc ggtgcagtat tcttcatagt tgaacatatc gctggagtgg tcttcagaat | 180 |
| cctgccttct gggagcactt gggacagagg aatccgctgc attcctgctg gtggacctcg | 240 |
| gccgcgacca cgctaagccg aattccagca cactggcggc cgttactagt ggatccgagc | 300 |
| tcggtaccaa gcttggcgta atcatggtca tagctgtttc ctgtgtgaaa ttgttatccg | 360 |
| ctcacaattc c | 371 |

<210> SEQ ID NO 366
<211> LENGTH: 393
<212> TYPE: DNA
<213> ORGANISM: Homo sapiens

<400> SEQUENCE: 366

| | |
|---|---|
| atttcttgcc agatgggagc tctttggtga agactccttt cgggaaaagt tttttggctt | 60 |
| cttcttcagg gatggttgga aggaccatca cactatcccc atccttccaa tcaactgggg | 120 |
| tggcaaccct ttttctgct gtcagctgga gagagatgac taccctgaga atctcatcaa | 180 |
| agttcctgcc agtggtagct gggtagagga tagacagctt cagcttctta tcaggaccaa | 240 |
| aaacaaacac cacacgagct gccacaggca tgccttttc atccttctct gctggatcca | 300 |
| gcatgcccaa caggatggca agctcccgat tcctatcatc gatgatggga aaggtaact | 360 |
| tttctgtggg ctcttcacaa ttgtaagcat tga | 393 |

<210> SEQ ID NO 367
<211> LENGTH: 327
<212> TYPE: DNA
<213> ORGANISM: Homo sapiens
<220> FEATURE:
<221> NAME/KEY: misc_feature
<222> LOCATION: 34, 54, 55
<223> OTHER INFORMATION: n = A,T,C or G

<400> SEQUENCE: 367
ccagctctgt ctcatacttg actctaaagt cttnagcagc aagacgggca ttgnnaatct      60
gcagaacgat gcgggcattg tccacagtat ttgcgaagat ctgagccctc aggtcctcga     120
tgatcttgaa gtaatggctc cagtctctga cctggggtcc cttcttctcc aagtgctccc     180
ggattttgct ctccagcctc cggttctcgg tctccaggct cctcactctg tccaggtaag     240
aggccaggcg gtcgttcagg ctttgcatgg tctccttctc gttctggatg cctcccattc     300
ctgccagacc cccggctatc ccggtgg                                         327

<210> SEQ ID NO 368
<211> LENGTH: 306
<212> TYPE: DNA
<213> ORGANISM: Homo sapiens
<220> FEATURE:
<221> NAME/KEY: misc_feature
<222> LOCATION: 24
<223> OTHER INFORMATION: n = A,T,C or G

<400> SEQUENCE: 368
ctggagaagg acttcagcag tttnaagaag tactgccaag tcatccgtgt cattgcccac      60
acccagatgc gcctgcttcc tctgcgccag aagaaggccc acctgatgga gatccaggtg     120
aacggaggca ctgtggccga gaagctggac tgggcccgcg agaggcttga gcagcaggta     180
cctgtgaacc aagtgtttgg gcaggatgag atgatcgacg tcatcggggt gaccaagggc     240
aaaggctaca aggggtcac cagtcgttgg cacaccaaga agctgccccg caagacccac     300
cgagga                                                                306

<210> SEQ ID NO 369
<211> LENGTH: 394
<212> TYPE: DNA
<213> ORGANISM: Homo sapiens

<400> SEQUENCE: 369
tcgacccaca ccggaacacg gagagctggg ccagcattgg cacttgatag gatttcccgt      60
cggctgccac gaaagtgcgt ttctttgtgt tctcgggttg gaaccgtgat ttccacagac     120
ccttgaaata cactgcgttg acgaggacca gtctggtgag cacaccatca ataagatctg     180
gggacagcag attgtcaatc atatccctgg tttcattttt aacccatgca ttgatggaat     240
cacaggcaga ggctggatcc tcaaagttca cattccggac ctcacactgg aacacatctt     300
tgttccttgt aacaaaaggc acttcaattt cagaggcatt cttaacaaac acggcgttag     360
ccactgtcac aatgtcttta ttcttcttgg agac                                 394

<210> SEQ ID NO 370
<211> LENGTH: 653
<212> TYPE: DNA
<213> ORGANISM: Homo sapiens

<400> SEQUENCE: 370

```
ccaccacacc caattccttg ctggtatcat ggcagccgcc acgtgccagg attaccggct      60
acatcatcaa gtatgagaag cctgggtctc ctcccagaga agtggtccct cggccccgcc     120
ctggtgtcac agaggctact attactggcc tggaaccggg aaccgaatat acaatttatg     180
tcattgccct gaagaataat cagaagagcg agccctgat tggaaggaaa aagacagacg      240
agcttcccca actggtaacc cttccacacc ccaatcttca tggaccagag atcttggatg     300
ttccttccac agttcaaaag accccttcg tcacccaccc tgggtatgac actggaaatg     360
gtattcagct tcctggcact tctggtcagc aacccagtgt tgggcaacaa atgatctttg     420
aggaacatgg ttttaggcgg accacaccgc ccacaacggc cacccccata aggcataggc     480
caagaccata cccgccgaat gtaggacaag aagctctctc tcagacaacc atctcatggg     540
ccccattcca ggacacttct gagtacatca tttcatgtca tcctgttggc actgatgaag     600
aacccttaca gttcagggtt cctggaactt ctaccagtgc cactctgaca gga            653

<210> SEQ ID NO 371
<211> LENGTH: 268
<212> TYPE: DNA
<213> ORGANISM: Homo sapiens

<400> SEQUENCE: 371
ctgcccagcc cccattggcg agtttgagaa ggtgtgcagc aatgacaaca agaccttcga      60
ctcttcctgc cacttctttg ccacaaagtg caccctggag ggcaccaaga agggccacaa     120
gctccacctg gactacatcg ggccttgcaa atacatcccc ccttgcctgg actctgagct     180
gaccgaattc cccctgcgca tgcgggactg gctcaagaac gtcctggtca ccctgtatga     240
gagggatgag gacaacaacc ttctgact                                        268

<210> SEQ ID NO 372
<211> LENGTH: 392
<212> TYPE: DNA
<213> ORGANISM: Homo sapiens

<400> SEQUENCE: 372
gctggtgccc ctggtgaacg tggacctcct ggattggcag gggccccagg acttagaggt      60
ggaactggtc cccctggtcc cgaaggagga aagggtgctg ctggtcctcc tgggccacct     120
ggtgctgctg gtactcctgg tctgcaagga atgcctggag aaagaggagg tcttggaagt     180
cctggtccaa agggtgacaa gggtgaacca ggcggtccag gtgctgatgg tgtcccaggg     240
aaagatggcc caagggggtcc tactggtcct attggtcctc ctggcccagc tggccagcct     300
ggagataagg gtgaaggtgg tgccccggga cttccaggta tagctggacc tcgtggtagc     360
cctggtgaga gaggtgaaac ctcggccgcg ac                                   392

<210> SEQ ID NO 373
<211> LENGTH: 388
<212> TYPE: DNA
<213> ORGANISM: Homo sapiens
<220> FEATURE:
<221> NAME/KEY: misc_feature
<222> LOCATION: 30
<223> OTHER INFORMATION: n = A,T,C or G

<400> SEQUENCE: 373
ccaagcgctc agatcggcaa ggggcaccan ttttgatctg cccagtgcac agccccacaa      60
ccaggtcagc gatgaaggta tcttcagtct ccccgaacg atgagacacc atgacgcccc     120
aaccattggc ctgggccagc ttgcacgcct gaagagactc ggtcacggag ccaatctggt     180
```

```
tgactttgag caggaggcag ttgcaggact tctcgttcac ggccttggcg atcctctttg    240
ggttggtcac tgtgagatca tcccccacta cctggattcc tgcactggct gtgaacttct    300
gccaagctcc ccagtcatcc tggtcaaagg gatcttcgat agacaccact gggtagtcct    360
tgatgaagga cttgtacagg tcagccag                                       388

<210> SEQ ID NO 374
<211> LENGTH: 393
<212> TYPE: DNA
<213> ORGANISM: Homo sapiens

<400> SEQUENCE: 374
ctgacgaccg cgtgaacccc tgcattgggg gtgtcatcct cttccatgag acactctacc     60
agaaggcgga tgatgggcgt cccttccccc aagttatcaa atccaagggc ggtgttgtgg    120
gcatcaaggt agacaagggc gtggtccccc tggcagggac aaatggcgag actaccaccc    180
aagggttgga tgggctgtct gagcgctgtg cccagtacaa gaaggacgga gctgacttcg    240
ccaagtggcg ttgtgtgctg aagattgggg aacacacccc ctcagccctc gccatcatgg    300
aaaatgccaa tgttctggcc cgttatgcca gtatctgcca gcagaatggc attgtgccca    360
tcgtggagcc tgagatcctc cctgatgggg acc                                 393

<210> SEQ ID NO 375
<211> LENGTH: 394
<212> TYPE: DNA
<213> ORGANISM: Homo sapiens
<220> FEATURE:
<221> NAME/KEY: misc_feature
<222> LOCATION: 30, 33
<223> OTHER INFORMATION: n = A,T,C or G

<400> SEQUENCE: 375
ccacaaatgg cgtggtccat gtcatcaccn ttnttctgca gcctccagcc aacagacctc     60
aggaaagagg ggatgaactt gcagactctg cgcttgagat cttcaaacaa gcatcagcgt    120
tttccagggc ttcccagagg tctgtgcgac tagcccctgt ctatcaaaag ttattagaga    180
ggatgaagca ttagcttgaa gcactacagg aggaatgcac cacggcagct ctccgccaat    240
ttctctcaga tttccacaga gactgtttga atgttttcaa aaccaagtat cacactttaa    300
tgtacatggg ccgcaccata atgagatgtg agccttgtgc atgtggggga ggagggagag    360
agatgtactt tttaaatcat gttcccccta aaca                                394

<210> SEQ ID NO 376
<211> LENGTH: 392
<212> TYPE: DNA
<213> ORGANISM: Homo sapiens
<220> FEATURE:
<221> NAME/KEY: misc_feature
<222> LOCATION: 30
<223> OTHER INFORMATION: n = A,T,C or G

<400> SEQUENCE: 376
ctgcccagcc cccattggcg agtttgattn ggtgtgcagc aatgacaaca agaccttcga     60
ctcttcctgc cacttctttg ccacaaagtg caccctggag ggcaccaaga agggccacaa    120
gctccacctg gactacatcg ggccttgcaa atacatcccc ccttgcctgg actctgagct    180
gaccgaattc cccctgcgca tgcgggactg gctcaagaac gtcctggtca ccctgtatga    240
gagggatgag gacaacaacc ttctgactga gaagcagaag ctgcgggtga agaagatcca    300
```

```
tgagaatgag aagcgcctgg aggcaggaga ccaccccgtg gagctgctgg cccgggactt    360
cgagaagaac tataacatgt acatcttccc tg                                  392
```

<210> SEQ ID NO 377
<211> LENGTH: 292
<212> TYPE: DNA
<213> ORGANISM: Homo sapiens

<400> SEQUENCE: 377

```
caatgtttga tgcttaaccc ccccaatttc tgtgagatgg atggccagtg caagcgtgac    60
ttgaagtgtt gcatgggcat gtgtgggaaa tcctgcgttt ccctgtgaa agcttgattc    120 ctgccatatg gaggaggctc tggagtcctg ctctgtgtgg tccaggtcct ttccaccctg   180
agacttggct ccaccactga tatcctcctt tggggaaagg cttggcacac agcaggcttt    240
caagaagtgc cagttgatca atgaataaat aaacgagcct atttctcttt gc            292
```

<210> SEQ ID NO 378
<211> LENGTH: 395
<212> TYPE: DNA
<213> ORGANISM: Homo sapiens

<400> SEQUENCE: 378

```
ctgctgcttc agcgaagggt ttctggcata tccaatgata aggctgccaa agactgttcc    60
aataccagca ccagaaccag ccactcctac tgttgcagca cctgcaccaa taaatttggc   120
agcagtatca atgtctctgc tgattgcact ggtctgaaac tccctttgga ttagctgaga   180
cacaccattc tgggccctga ttttcctaag atagaactcc aactctttgc cctctagcac    240
atagccatct gctcggccac actgtcccgg ccttgaagcg atgcacgcaa gaagcttgcc    300
ctgctggaac tgctcctcca ggagactgct gattttggca ttcttttttcc tttcatcata    360 tttcttctga attttttaga tcgttttttg tttaa                              395
```

<210> SEQ ID NO 379
<211> LENGTH: 223
<212> TYPE: DNA
<213> ORGANISM: Homo sapiens

<400> SEQUENCE: 379

```
ccagatgaaa tgctgccgca atggctgtgg aaggtgtcc tgtgtcactc ccaatttctg    60
agctccagcc accaccaggc tgagcagtga ggagagaaag tttctgcctg ccctgcatc   120 tggttccagc ccacctgccc tcccctttt cgggactctg tattccctct tgggctgacc    180
acagcttctc cctttcccaa ccaataaagt aaccactttc agc                     223
```

<210> SEQ ID NO 380
<211> LENGTH: 317
<212> TYPE: DNA
<213> ORGANISM: Homo sapiens
<220> FEATURE:
<221> NAME/KEY: misc_feature
<222> LOCATION: 30, 32
<223> OTHER INFORMATION: n = A,T,C or G

<400> SEQUENCE: 380

```
tcgaccacag tattccaacc ctcctgtgcn tngagaagtg atggagggtg ctgacaacca    60
gggtgcagga gaacaaggta gaccagtgag gcagaatatg tatcggggat atagaccacg   120
attccgcagg ggccctcctc gccaaagaca gcctagagag gacggcaatg aagaagataa   180
agaaaatcaa ggagatgaga cccaaggtca gcagccacct caacgtcggt accgccgcaa   240
```

```
cttcaattac cgacgcagac gcccagaaaa ccctaaacca caagatggca aagagacaaa    300
agcagccgat ccaccag                                                   317
```

<210> SEQ ID NO 381
<211> LENGTH: 392
<212> TYPE: DNA
<213> ORGANISM: Homo sapiens
<220> FEATURE:
<221> NAME/KEY: misc_feature
<222> LOCATION: 29, 30, 31
<223> OTHER INFORMATION: n = A,T,C or G
<400> SEQUENCE: 381

```
cctgaaggaa gagctggcct acctgaatnn naaccatgag gaggaaatca gtacgctgag     60
gggccaagtg ggaggccagg tcagtgtgga ggtggattcc gctccgggca ccgatctcgc    120
caagatcctg agtgacatgc gaagccaata tgaggtcatg gccgagcaga accggaagga    180
tgctgaagcc tggttcacca gccggactga agaattgaac cgggaggtcg ctggccacac    240
ggagcagctc cagatgagca ggtccgaggt tactgacctg cggcgcaccc ttcagggtct    300
tgagattgag ctgcagtcac agacctcggc cgcgaccacg ctaagccgaa ttccagcaca    360
ctggcggccg ttactagtgg atccgagctc gg                                  392
```

<210> SEQ ID NO 382
<211> LENGTH: 234
<212> TYPE: DNA
<213> ORGANISM: Homo sapiens
<400> SEQUENCE: 382

```
cctcgatgtc taaatgagcg tggtaaagga tggtgcctgc tggggtctcg tagatacctc     60
gggacttcat tccaatgaag cggttctcca cgatgtcaat acggcccacg ccatgcttgc    120
ccgcgacttc gttcaggtac atgaagagct ccaaggaggt ctggtgggtg gtgccatcct    180
tgacgttggt caccttcaca gggaccccctt ttttgaactc catctccaga atgt          234
```

<210> SEQ ID NO 383
<211> LENGTH: 396
<212> TYPE: DNA
<213> ORGANISM: Homo sapiens
<220> FEATURE:
<221> NAME/KEY: misc_feature
<222> LOCATION: 66
<223> OTHER INFORMATION: n = A,T,C or G
<400> SEQUENCE: 383

```
ccttgacctt ttcagcaagt gggaaggtgt tttccgtctc cacagacaag gccaggactc     60
gtttgnaccc gttgatgata gaatgggggta ctgatgcaac agttgggtag ccaatctgca   120
gacagacact ggcaacattg cggacaccca ggatttcaat ggtgcccctg gagattttag    180
tggtgatacc taaagcctgg aaaaggagg tcttctcggg cccgagacca gtgttctggg    240
ctggcacagt gacttcacat ggggcaatgg caccagcacg ggcagcagac ctgcccgggc    300
ggccgctcga aagccgaatt ccagcacact ggcggccgtt actagtggat ccgagctcgg    360
taccaagctt ggcgtaatca tggtcatagc tgtttc                              396
```

<210> SEQ ID NO 384
<211> LENGTH: 396
<212> TYPE: DNA
<213> ORGANISM: Homo sapiens

<400> SEQUENCE: 384

```
gctgaatagg cacagagggc acctgtacac cttcagacca gtctgcaacc tcaggctgag      60
tagcagtgaa ctcaggagcg ggagcagtcc attcaccctg aaattcctcc ttggtcactg     120
ccttctcagc agcagcctgc tcttcttttt caatctcttc aggatctctg tagaagtaca     180
gatcaggcat gacctcccat gggtgttcac gggaaatggt gccacgcatg cgcagaactt     240
cccgagccag catccaccac atcaaaccca ctgagtgagc tcccttgttg ttgcatggga     300
tggcaatgtc cacatagcgc agaggagaat ctgtgttaca cagcgcaatg gtaggtaggt     360
taacataaga tgcctccgtg agaggctggt ggtcag                               396
```

<210> SEQ ID NO 385
<211> LENGTH: 2943
<212> TYPE: DNA
<213> ORGANISM: Homo sapiens

<400> SEQUENCE: 385

```
cagccaccgg agtggatgcc atctgcaccc accgccctga ccccacaggc cctgggctgg      60
acagagagca gctgtatttg gagctgagcc agctgaccca cagcatcact gagctgggcc     120
cctacaccct ggacagggac agtctctatg tcaatggttt cacacagcgg agctctgtgc     180
ccaccactag cattcctggg acccccacag tggacctggg aacatctggg actccagttt     240
ctaaacctgg tccctcggct gccagccctc tcctggtgct attcactctc aacttcacca     300
tcaccaacct gcggtatgag gagaacatgc agcaccctgg ctccaggaag ttcaacacca     360
cggagagggt ccttcagggc ctggtccctg ttcaagagca ccagtgttgg ccctctgtac     420
tctggctgca gactgacttt gctcaggcct gaaaaggatg ggacagccac tggagtggat     480
gccatctgca cccaccaccc tgaccccaaa agccctaggc tggacagaga gcagctgtat     540
tgggagctga ccagctgac ccacaatatc actgagctgg ccctatgcc ctggacaac      600
gacagcctct ttgtcaatgg tttcactcat cggagctctg tgtccaccac cagcactcct     660
gggacccca cagtgtatct gggagcatct aagactccag cctcgatatt tggcccttca     720
gctgccagcc atctcctgat actattcacc ctcaacttca ccatcactaa cctgcggtat     780
gaggagaaca tgtggcctgg ctccaggaag ttcaacacta cagagagggt ccttcagggc     840
ctgctaaggc ccttgttcaa gaacaccagt gttggccctc tgtactctgg ctgcaggctg     900
accttgctca ggccagagaa agatggggaa gccaccggag tggatgccat ctgcacccac     960
cgccctgacc ccacaggccc tgggctggac agagagcagc tgtatttgga gctgagccag    1020
ctgacccaca gcatcactga gctgggcccc tacacactgg acaggacag tctctatgtc    1080
aatggttta cccatcggag ctctgtaccc accaccagca ccggggtggt cagcgaggag    1140
ccattcacac tgaacttcac catcaacaac ctgcgctaca tggcggacat gggccaaccc    1200
ggctccctca gttcaacat cacagacaac gtcatgaagc acctgctcag tcctttgttc    1260
cagaggagca gctgggtgc acggtacaca ggctgcaggg tcatcgcact aaggtctgtg    1320
aagaacggtg ctgagacacg ggtggacctc tctgcacct acctgcagcc cctcagcggc    1380
ccaggtctgc ctatcaagca ggtgttccat gagctgagcc agcagaccca tggcatcacc    1440
cggctgggcc cctactctct ggacaaagac agcctctacc ttaacggtta caatgaacct    1500
ggtccagatg agcctcctac aactcccaag ccagccacca cattcctgcc tcctctgtca    1560
gaagccacaa cagccatggg gtaccacctg aagaccctca cactcaactt caccatctcc    1620
aatctccagt attcaccaga tatgggcaag ggctcagcta cattcaactc caccgagggg    1680
```

```
gtccttcagc acctgctcag acccttgttc cagaagagca gcatgggccc cttctacttg    1740
ggttgccaac tgatctccct caggcctgag aaggatgggg cagccactgg tgtggacacc    1800
acctgcacct accaccctga ccctgtgggc cccgggctgg acatacagca gctttactgg    1860
gagctgagtc agctgaccca tggtgtcacc caactgggct tctatgtcct ggacagggat    1920
agcctcttca tcaatggcta tgcacccag aatttatcaa tccggggcga gtaccagata    1980
aatttccaca ttgtcaactg gaacctcagt aatccagacc ccacatcctc agagtacatc    2040
accctgctga gggacatcca ggacaaggtc accacactct acaaaggcag tcaactacat    2100
gacacattcc gcttctgcct ggtcaccaac ttgacgatgg actccgtgtt ggtcactgtc    2160
aaggcattgt tctcctccaa tttggacccc agcctggtgg agcaagtctt tctagataag    2220
accctgaatg cctcattcca ttggctgggc tccacctacc agttggtgga catccatgtg    2280
acagaaatgg agtcatcagt ttatcaacca caagcagct ccagcaccca gcacttctac    2340
ctgaatttca ccatcaccaa cctaccatat tcccaggaca aagcccagcc aggcaccacc    2400
aattaccaga ggaacaaaag gaatattgag gatgcggcac cacccgggg tggactccct    2460 gtgtaacttc tcgccactgg ctcggagagt agacagagtt gccatctatg aggaatttct    2520
gcggatgacc cggaatggta cccagctgca gaacttcacc ctggacagga gcagtgtcct    2580
tgtggatggg tattttccca acagaaatga gcccttaact gggaattctg accttccctt    2640
ctgggctgtc atcctcatcg gcttggcagg actcctggga ctcatcacat gcctgatctg    2700
cggtgtcctg gtgaccaccc gccggcgaa gaaggaagga gaatacaacg tccagcaaca    2760
gtgcccaggc tactaccagt cacacctaga cctggaggat ctgcaatgac tggaacttgc    2820
cggtgcctgg ggtgccttc ccccagccag ggtccaaaga agcttggctg gggcagaaat    2880
aaaccatatt ggtcggaaaa aaaaaaaaaa aaaaaaaaaa aaaaaaaaa aaaaaaaaa       2940 aaa                                                                  2943
```

<210> SEQ ID NO 386
<211> LENGTH: 2608
<212> TYPE: DNA
<213> ORGANISM: Homo sapiens

<400> SEQUENCE: 386

```
gttcaagagc accagtgttg gccctctgta ctctggctgc agactgactt tgctcaggcc      60
tgaaaaggat gggacagcca ctggagtgga tgccatctgc acccaccacc ctgaccccaa     120
aagccctagg ctggacagag agcagctgta ttgggagctg agccagctga cccacaatat     180
cactgagctg ggcccctatg ccctggacaa cgacagcctc tttgtcaatg gtttcactca     240
tcggagctct gtgtccacca ccagcactcc tgggaccccc acagtgtatc tgggagcatc     300
taagactcca gcctcgatat ttggcccttc agctgccagc catctcctga tactattcac     360
cctcaacttc accatcacta acctgcggta tgaggagaac atgtggcctg ctccaggaa     420 gttcaacact acagagaggg tccttcaggg cctgctaagg cccttgttca gaacaccag     480 tgttggccct ctgtactctg gctgcaggct gaccttgctc aggccagaga agatgggga     540 agccaccgga gtggatgcca tctgcaccca ccgccctgac ccacaggcc tgggctgga     600 cagagagcag ctgtatttgg agctgagcca gctgacccac agcatcactg agctgggccc     660
ctacacactg acagggaca gtctctatgt caatggtttc acccatcgga gctctgtacc     720
caccaccagc accggggtgg tcagcgagga gccattcaca ctgaacttca ccatcaacaa     780
```

| | |
|---|---|
| cctgcgctac atggcggaca tgggccaacc cggctccctc aagttcaaca tcacagacaa | 840 |
| cgtcatgaag cacctgctca gtcctttgtt ccagaggagc agcctgggtg cacggtacac | 900 |
| aggctgcagg gtcatcgcac taaggtctgt gaagaacggt gctgagacac gggtggacct | 960 |
| cctctgcacc tacctgcagc ccctcagcgg cccaggtctg cctatcaagc aggtgttcca | 1020 |
| tgagctgagc cagcagaccc atggcatcac ccggctgggc ccctactctc tggacaaaga | 1080 |
| cagcctctac cttaacggtt acaatgaacc tggtccagat gagcctccta caactcccaa | 1140 |
| gccagccacc acattcctgc ctcctctgtc agaagccaca acagccatgg ggtaccacct | 1200 |
| gaagaccctc acactcaact tcaccatctc caatctccag tattcaccag atatgggcaa | 1260 |
| gggctcagct acattcaact ccaccgaggg ggtccttcag cacctgctca gacccttgtt | 1320 |
| ccagaagagc agcatgggcc ccttctactt gggttgccaa ctgatctccc tcaggcctga | 1380 |
| gaaggatggg gcagccactg gtgtggacac cacctgcacc taccaccctg accctgtggg | 1440 |
| cccccgggctg gacatacagc agctttactg ggagctgagt cagctgaccc atggtgtcac | 1500 |
| ccaactgggc ttctatgtcc tggacaggga tagcctcttc atcaatggct atgcacccca | 1560 |
| gaatttatca atccggggcg agtaccagat aaatttccac attgtcaact ggaacctcag | 1620 |
| taatccagac cccacatcct cagagtacat caccctgctg agggacatcc aggacaaggt | 1680 |
| caccacactc tacaaaggca gtcaactaca tgacacattc cgcttctgcc tggtcaccaa | 1740 |
| cttgacgatg gactccgtgt tggtcactgt caaggcattg ttctcctcca atttggaccc | 1800 |
| cagcctggtg gagcaagtct ttctagataa gaccctgaat gcctcattcc attggctggg | 1860 |
| ctccacctac cagttggtgg acatccatgt gacagaaatg gagtcatcag tttatcaacc | 1920 |
| aacaagcagc tccagcaccc agcacttcta cctgaatttc accatcacca acctaccata | 1980 |
| ttcccaggac aaagcccagc caggcaccac caattaccag aggaacaaaa ggaatattga | 2040 |
| ggatgcgctc aaccaactct tccgaaacag cagcatcaag agttattttt ctgactgtca | 2100 |
| agtttcaaca ttcaggtctg tccccaacag gcaccacacc ggggtggact ccctgtgtaa | 2160 |
| cttctcgcca ctggctcgga gagtagacag agttgccatc tatgaggaat ttctgcggat | 2220 |
| gacccggaat ggtacccagc tgcagaactt caccctggac aggagcagtg tccttgtgga | 2280 |
| tgggtatttt cccaacagaa atgagcccctt aactgggaat tctgaccttc ccttctgggc | 2340 |
| tgtcatcctc atcggcttgg caggactcct gggactcatc acatgcctga tctgcggtgt | 2400 |
| cctggtgacc acccgccggc ggaagaagga aggagaatac aacgtccagc aacagtgccc | 2460 |
| aggctactac cagtcacacc tagacctgga ggatctgcaa tgactggaac ttgccggtgc | 2520 |
| ctggggtgcc tttcccccag ccagggtcca aagaagcttg gctggggcag aaataaacca | 2580 |
| tattggtcgg acacaaaaaa aaaaaaaa | 2608 |

<210> SEQ ID NO 387
<211> LENGTH: 1761
<212> TYPE: DNA
<213> ORGANISM: Homo sapiens

<400> SEQUENCE: 387

| | |
|---|---|
| ctgaacttca ccatcaacaa cctgcgctac atggcggaca tgggccaacc cggctccctc | 60 |
| aagttcaaca tcacagacaa cgtcatgaag cacctgctca gtcctttgtt ccagaggagc | 120 |
| agcctgggtg cacggtacac aggctgcagg gtcatcgcac taaggtctgt gaagaacggt | 180 |
| gctgagacac gggtggacct cctctgcagg taggtcagag ggaggtccac ggcatcaccc | 240 |
| ggctgggccc ctactctctg gacaaagaca gcctctacct taacgctccc aagccagcca | 300 |

```
ccacattcct gcctcctctg tcagaagcca caacagccat ggggtaccac ctgaagaccc      360
tcacactcaa cttcaccatc tccaatctcc agtattcacc agatatgggc aagggctcag      420
ctacattcaa ctccaccgag ggggtccttc agcacctgct cagacccttg ttccagaaga      480
gcagcatggg ccccttctac ttgggttgcc aactgatctc cctcaggcct gagaaggatg      540
gggcagccac tggtgtggac accacctgca cctaccaccc tgaccctgtg ggccccgggc      600
tggacataca gcagctttac tgggagctga gtcagctgac ccatggtgtc acccaactgg      660
gcttctatgt cctggacagg gatagcctct catcaatggc ctatgcaccc cagaatttat      720
caatccgggg cgagtaccag ataaatttcc acattgtcaa ctggaacctc agtaatccag      780
accccacatc ctcagagtac atcaccctgc tgagggacat ccaggacaag gtcaccacac      840
tctacaaagg cagtcaacta catgacacat tccgcttctg cctggtcacc aacttgacga      900
tggactccgt gttggtcact gtcaaggcat tgttctcctc caatttggac ccagcctgg       960 tggagcaagt ctttctagat aagaccctga atgcctcatt ccattggctg ggctccacct     1020
accagttggt ggacatccat gtgacagaaa tggagtcatc agtttatcaa ccaacaagca     1080
gctccagcac ccagcacttc tacctgaatt tcaccatcac caacctacca tattcccagg     1140
acaaagccca gccaggcacc accaattacc agaggaacaa aaggaatatt gaggatgcgc     1200
tcaaccaact cttccgaaac agcagcatca agagttattt ttctgactgt caagtttcaa     1260
cattcaggtc tgtccccaac aggcaccaca ccggggtgga ctccctgtgt aacttctcgc     1320
cactggctcg gagagtagac agagttgcca tctatgagga atttctgcgg atgacccgga     1380
atggtaccca gctgcagaac ttcaccctgg acaggagcag tgtccttgtg gatgggtatt     1440
ttcccaacag aaatgagccc ttaactggga attctgacct tccttctgg gctgtcatcc       1500 tcatcggctt ggcaggactc ctgggactca tcacatgcct gatctgcggt gtcctggtga     1560
ccaccccgcc gcggaagaag gaaggagaat acaacgtcca gcaacagtgc ccaggctact     1620
accagtcaca cctagacctg gaggatctgc aatgactgga acttgccggt gcctggggtg     1680
cctttccccc agccagggtc caaagaagct tggctggggc agaaataaac catattggtc     1740
ggacacaaaa aaaaaaaaaa a                                                 1761
```

<210> SEQ ID NO 388
<211> LENGTH: 772
<212> TYPE: PRT
<213> ORGANISM: Homo sapiens

<400> SEQUENCE: 388

```
Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110
```

```
Ile Cys Thr His His Pro Asp Pro Lys Ser Pro Arg Leu Asp Arg Glu
            115                 120                 125

Gln Leu Tyr Trp Glu Leu Ser Gln Leu Thr His Asn Ile Thr Glu Leu
        130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365

Pro Leu Phe Gln Arg Ser Ser Leu Gly Ala Arg Tyr Thr Gly Cys Arg
    370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
        435                 440                 445

Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525
```

```
Phe Tyr Leu Gly Cys Gln Leu Ile Ser Leu Arg Pro Glu Lys Asp Gly
    530                 535                 540
Ala Ala Thr Gly Val Asp Thr Thr Cys Thr Tyr His Pro Asp Pro Val
545                 550                 555                 560
Gly Pro Gly Leu Asp Ile Gln Gln Leu Tyr Trp Glu Leu Ser Gln Leu
                565                 570                 575
Thr His Gly Val Thr Gln Leu Gly Phe Tyr Val Leu Asp Arg Asp Ser
            580                 585                 590
Leu Phe Ile Asn Gly Tyr Ala Pro Gln Asn Leu Ser Ile Arg Gly Glu
        595                 600                 605
Tyr Gln Ile Asn Phe His Ile Val Asn Trp Asn Leu Ser Asn Pro Asp
    610                 615                 620
Pro Thr Ser Ser Glu Tyr Ile Thr Leu Leu Arg Asp Ile Gln Asp Lys
625                 630                 635                 640
Val Thr Thr Leu Tyr Lys Gly Ser Gln Leu His Asp Thr Phe Arg Phe
                645                 650                 655
Cys Leu Val Thr Asn Leu Thr Met Asp Ser Val Leu Val Thr Val Lys
            660                 665                 670
Ala Leu Phe Ser Ser Asn Leu Asp Pro Ser Leu Val Glu Gln Val Phe
        675                 680                 685
Leu Asp Lys Thr Leu Asn Ala Ser Phe His Trp Leu Gly Ser Thr Tyr
    690                 695                 700
Gln Leu Val Asp Ile His Val Thr Glu Met Glu Ser Ser Val Tyr Gln
705                 710                 715                 720
Pro Thr Ser Ser Ser Thr Gln His Phe Tyr Leu Asn Phe Thr Ile
                725                 730                 735
Thr Asn Leu Pro Tyr Ser Gln Asp Lys Ala Gln Pro Gly Thr Thr Asn
            740                 745                 750
Tyr Gln Arg Asn Lys Arg Asn Ile Glu Asp Ala Ala Pro His Arg Gly
        755                 760                 765
Gly Leu Pro Val
    770

<210> SEQ ID NO 389
<211> LENGTH: 833
<212> TYPE: PRT
<213> ORGANISM: Homo sapiens

<400> SEQUENCE: 389

Phe Lys Ser Thr Ser Val Gly Pro Leu Tyr Ser Gly Cys Arg Leu Thr
1               5                   10                  15
Leu Leu Arg Pro Glu Lys Asp Gly Thr Ala Thr Gly Val Asp Ala Ile
            20                  25                  30
Cys Thr His His Pro Asp Pro Lys Ser Pro Arg Leu Asp Arg Glu Gln
        35                  40                  45
Leu Tyr Trp Glu Leu Ser Gln Leu Thr His Asn Ile Thr Glu Leu Gly
    50                  55                  60
Pro Tyr Ala Leu Asp Asn Asp Ser Leu Phe Val Asn Gly Phe Thr His
65                  70                  75                  80
Arg Ser Ser Val Ser Thr Thr Ser Thr Pro Gly Thr Pro Thr Val Tyr
                85                  90                  95
Leu Gly Ala Ser Lys Thr Pro Ala Ser Ile Phe Gly Pro Ser Ala Ala
            100                 105                 110
Ser His Leu Leu Ile Leu Phe Thr Leu Asn Phe Thr Ile Thr Asn Leu
        115                 120                 125
```

-continued

```
Arg Tyr Glu Glu Asn Met Trp Pro Gly Ser Arg Lys Phe Asn Thr Thr
    130                 135                 140

Glu Arg Val Leu Gln Gly Leu Leu Arg Pro Leu Phe Lys Asn Thr Ser
145                 150                 155                 160

Val Gly Pro Leu Tyr Ser Gly Cys Arg Leu Thr Leu Leu Arg Pro Glu
                165                 170                 175

Lys Asp Gly Glu Ala Thr Gly Val Asp Ala Ile Cys Thr His Arg Pro
            180                 185                 190

Asp Pro Thr Gly Pro Gly Leu Asp Arg Glu Gln Leu Tyr Leu Glu Leu
        195                 200                 205

Ser Gln Leu Thr His Ser Ile Thr Glu Leu Gly Pro Tyr Thr Leu Asp
    210                 215                 220

Arg Asp Ser Leu Tyr Val Asn Gly Phe Thr His Arg Ser Ser Val Pro
225                 230                 235                 240

Thr Thr Ser Thr Gly Val Val Ser Glu Glu Pro Phe Thr Leu Asn Phe
                245                 250                 255

Thr Ile Asn Asn Leu Arg Tyr Met Ala Asp Met Gly Gln Pro Gly Ser
            260                 265                 270

Leu Lys Phe Asn Ile Thr Asp Asn Val Met Lys His Leu Leu Ser Pro
        275                 280                 285

Leu Phe Gln Arg Ser Ser Leu Gly Ala Arg Tyr Thr Gly Cys Arg Val
    290                 295                 300

Ile Ala Leu Arg Ser Val Lys Asn Gly Ala Glu Thr Arg Val Asp Leu
305                 310                 315                 320

Leu Cys Thr Tyr Leu Gln Pro Leu Ser Gly Pro Gly Leu Pro Ile Lys
                325                 330                 335

Gln Val Phe His Glu Leu Ser Gln Gln Thr His Gly Ile Thr Arg Leu
            340                 345                 350

Gly Pro Tyr Ser Leu Asp Lys Asp Ser Leu Tyr Leu Asn Gly Tyr Asn
        355                 360                 365

Glu Pro Gly Pro Asp Glu Pro Pro Thr Thr Pro Lys Pro Ala Thr Thr
    370                 375                 380

Phe Leu Pro Pro Leu Ser Glu Ala Thr Thr Ala Met Gly Tyr His Leu
385                 390                 395                 400

Lys Thr Leu Thr Leu Asn Phe Thr Ile Ser Asn Leu Gln Tyr Ser Pro
                405                 410                 415

Asp Met Gly Lys Gly Ser Ala Thr Phe Asn Ser Thr Glu Gly Val Leu
            420                 425                 430

Gln His Leu Leu Arg Pro Leu Phe Gln Lys Ser Ser Met Gly Pro Phe
        435                 440                 445

Tyr Leu Gly Cys Gln Leu Ile Ser Leu Arg Pro Glu Lys Asp Gly Ala
    450                 455                 460

Ala Thr Gly Val Asp Thr Thr Cys Thr Tyr His Pro Asp Pro Val Gly
465                 470                 475                 480

Pro Gly Leu Asp Ile Gln Gln Leu Tyr Trp Glu Leu Ser Gln Leu Thr
                485                 490                 495

His Gly Val Thr Gln Leu Gly Phe Tyr Val Leu Asp Arg Asp Ser Leu
            500                 505                 510

Phe Ile Asn Gly Tyr Ala Pro Gln Asn Leu Ser Ile Arg Gly Glu Tyr
        515                 520                 525

Gln Ile Asn Phe His Ile Val Asn Trp Asn Leu Ser Asn Pro Asp Pro
    530                 535                 540
```

```
Thr Ser Ser Glu Tyr Ile Thr Leu Leu Arg Asp Ile Gln Asp Lys Val
545                 550                 555                 560

Thr Thr Leu Tyr Lys Gly Ser Gln Leu His Asp Thr Phe Arg Phe Cys
                565                 570                 575

Leu Val Thr Asn Leu Thr Met Asp Ser Val Leu Val Thr Val Lys Ala
            580                 585                 590

Leu Phe Ser Ser Asn Leu Asp Pro Ser Leu Val Glu Gln Val Phe Leu
        595                 600                 605

Asp Lys Thr Leu Asn Ala Ser Phe His Trp Leu Gly Ser Thr Tyr Gln
    610                 615                 620

Leu Val Asp Ile His Val Thr Glu Met Glu Ser Ser Val Tyr Gln Pro
625                 630                 635                 640

Thr Ser Ser Ser Thr Gln His Phe Tyr Leu Asn Phe Thr Ile Thr
                645                 650                 655

Asn Leu Pro Tyr Ser Gln Asp Lys Ala Gln Pro Gly Thr Thr Asn Tyr
                660                 665                 670

Gln Arg Asn Lys Arg Asn Ile Glu Asp Ala Leu Asn Gln Leu Phe Arg
            675                 680                 685

Asn Ser Ser Ile Lys Ser Tyr Phe Ser Asp Cys Gln Val Ser Thr Phe
690                 695                 700

Arg Ser Val Pro Asn Arg His His Thr Gly Val Asp Ser Leu Cys Asn
705                 710                 715                 720

Phe Ser Pro Leu Ala Arg Arg Val Asp Arg Val Ala Ile Tyr Glu Glu
                725                 730                 735

Phe Leu Arg Met Thr Arg Asn Gly Thr Gln Leu Gln Asn Phe Thr Leu
            740                 745                 750

Asp Arg Ser Ser Val Leu Val Asp Gly Tyr Phe Pro Asn Arg Asn Glu
        755                 760                 765

Pro Leu Thr Gly Asn Ser Asp Leu Pro Phe Trp Ala Val Ile Leu Ile
    770                 775                 780

Gly Leu Ala Gly Leu Leu Gly Leu Ile Thr Cys Leu Ile Cys Gly Val
785                 790                 795                 800

Leu Val Thr Thr Arg Arg Arg Lys Lys Glu Gly Glu Tyr Asn Val Gln
                805                 810                 815

Gln Gln Cys Pro Gly Tyr Tyr Gln Ser His Leu Asp Leu Glu Asp Leu
            820                 825                 830

Gln

<210> SEQ ID NO 390
<211> LENGTH: 438
<212> TYPE: PRT
<213> ORGANISM: Homo sapiens

<400> SEQUENCE: 390

Met Gly Tyr His Leu Lys Thr Leu Thr Leu Asn Phe Thr Ile Ser Asn
 1               5                  10                  15

Leu Gln Tyr Ser Pro Asp Met Gly Lys Gly Ser Ala Thr Phe Asn Ser
                20                  25                  30

Thr Glu Gly Val Leu Gln His Leu Leu Arg Pro Leu Phe Gln Lys Ser
            35                  40                  45

Ser Met Gly Pro Phe Tyr Leu Gly Cys Gln Leu Ile Ser Leu Arg Pro
        50                  55                  60

Glu Lys Asp Gly Ala Ala Thr Gly Val Asp Thr Thr Cys Thr Tyr His
65                  70                  75                  80
```

```
Pro Asp Pro Val Gly Pro Gly Leu Asp Ile Gln Gln Leu Tyr Trp Glu
                85                  90                  95
Leu Ser Gln Leu Thr His Gly Val Thr Gln Leu Gly Phe Tyr Val Leu
            100                 105                 110
Asp Arg Asp Ser Leu Phe Ile Asn Gly Tyr Ala Pro Gln Asn Leu Ser
        115                 120                 125
Ile Arg Gly Glu Tyr Gln Ile Asn Phe His Ile Val Asn Trp Asn Leu
    130                 135                 140
Ser Asn Pro Asp Pro Thr Ser Ser Glu Tyr Ile Thr Leu Leu Arg Asp
145                 150                 155                 160
Ile Gln Asp Lys Val Thr Thr Leu Tyr Lys Gly Ser Gln Leu His Asp
                165                 170                 175
Thr Phe Arg Phe Cys Leu Val Thr Asn Leu Thr Met Asp Ser Val Leu
            180                 185                 190
Val Thr Val Lys Ala Leu Phe Ser Ser Asn Leu Asp Pro Ser Leu Val
        195                 200                 205
Glu Gln Val Phe Leu Asp Lys Thr Leu Asn Ala Ser Phe His Trp Leu
    210                 215                 220
Gly Ser Thr Tyr Gln Leu Val Asp Ile His Val Thr Glu Met Glu Ser
225                 230                 235                 240
Ser Val Tyr Gln Pro Thr Ser Ser Ser Thr Gln His Phe Tyr Leu
                245                 250                 255
Asn Phe Thr Ile Thr Asn Leu Pro Tyr Ser Gln Asp Lys Ala Gln Pro
            260                 265                 270
Gly Thr Thr Asn Tyr Gln Arg Asn Lys Arg Asn Ile Glu Asp Ala Leu
        275                 280                 285
Asn Gln Leu Phe Arg Asn Ser Ser Ile Lys Ser Tyr Phe Ser Asp Cys
    290                 295                 300
Gln Val Ser Thr Phe Arg Ser Val Pro Asn Arg His His Thr Gly Val
305                 310                 315                 320
Asp Ser Leu Cys Asn Phe Ser Pro Leu Ala Arg Arg Val Asp Arg Val
                325                 330                 335
Ala Ile Tyr Glu Glu Phe Leu Arg Met Thr Arg Asn Gly Thr Gln Leu
            340                 345                 350
Gln Asn Phe Thr Leu Asp Arg Ser Ser Val Leu Val Asp Gly Tyr Phe
        355                 360                 365
Pro Asn Arg Asn Glu Pro Leu Thr Gly Asn Ser Asp Leu Pro Phe Trp
    370                 375                 380
Ala Val Ile Leu Ile Gly Leu Ala Gly Leu Leu Gly Leu Ile Thr Cys
385                 390                 395                 400
Leu Ile Cys Gly Val Leu Val Thr Thr Arg Arg Arg Lys Lys Glu Gly
                405                 410                 415
Glu Tyr Asn Val Gln Gln Gln Cys Pro Gly Tyr Tyr Gln Ser His Leu
            420                 425                 430
Asp Leu Glu Asp Leu Gln
        435

<210> SEQ ID NO 391
<211> LENGTH: 2627
<212> TYPE: DNA
<213> ORGANISM: Homo sapiens

<400> SEQUENCE: 391
ccacgcgtcc gcccacgcgt ccggaaggca gcggcagctc cactcagcca gtacccagat      60
```

-continued

```
acgctgggaa ccttccccag ccatggcttc cctggggcag atcctcttct ggagcataat      120
tagcatcatc attattctgg ctggagcaat tgcactcatc attggctttg gtatttcagg      180
gagacactcc atcacagtca ctactgtcgc ctcagctggg aacattgggg aggatggaat      240
cctgagctgc acttttgaac ctgacatcaa actttctgat atcgtgatac aatggctgaa      300
ggaaggtgtt ttaggcttgg tccatgagtt caaagaaggc aaagatgagc tgtcggagca      360
ggatgaaatg ttcagaggcc ggacagcagt gtttgctgat caagtgatag ttggcaatgc      420
ctctttgcgg ctgaaaaacg tgcaactcac agatgctggc acctacaaat gttatatcat      480
cacttctaaa ggcaagggga atgctaacct tgagtataaa actggagcct tcagcatgcc      540
ggaagtgaat gtggactata atgccagctc agagaccttg cggtgtgagg ctccccgatg      600
gttcccccag cccacagtgg tctgggcatc ccaagttgac cagggagcca acttctcgga      660
agtctccaat accagctttg agctgaactc tgagaatgtg accatgaagg ttgtgtctgt      720
gctctacaat gttacgatca acaacacata ctcctgtatg attgaaaatg acattgccaa      780
agcaacaggg gatatcaaag tgacagaatc ggagatcaaa aggcggagtc acctacagct      840
gctaaactca aaggcttctc tgtgtgtctc ttctttcttt gccatcagct gggcacttct      900
gcctctcagc ccttacctga tgctaaaata atgtgccttg ccacaaaaa agcatgcaaa      960 gtcattgtta caacagggat ctacagaact atttcaccac cagatatgac ctagttttat     1020
atttctggga ggaaatgaat tcatatctag aagtctggag tgagcaaaca agagcaagaa     1080
acaaaaagaa gccaaaagca gaaggctcca atatgaacaa gataaatcta tcttcaaaga     1140
catattagaa gttgggaaaa taattcatgt gaactagaca agtgtgttaa gagtgataag     1200
taaaatgcac gtggagacaa gtgcatcccc agatctcagg gacctccccc tgcctgtcac     1260
ctggggagtg agaggacagg atagtgcatg ttctttgtct ctgaattttt agttatatgt     1320
gctgtaatgt tgctctgagg aagccccctgg aaagtctatc ccaacatatc cacatcttat     1380
attccacaaa ttaagctgta gtatgtaccc taagacgctg ctaattgact gccacttcgc     1440
aactcagggg cggctgcatt ttagtaatgg gtcaaatgat tcacttttta tgatgcttcc     1500
aaaggtgcct tggcttctct tcccaactga caaatgccaa agttgagaaa aatgatcata     1560
attttagcat aaacagagca gtcggcgaca ccgattttat aaataaactg agcaccttct     1620
ttttaaacaa acaaatgcgg gtttatttct cagatgatgt tcatccgtga atggtccagg     1680
gaaggacctt tcaccttgac tatatggcat tatgtcatca caagctctga ggcttctcct     1740
ttccatcctg cgtggacagc taagacctca gttttcaata gcatctagag cagtgggact     1800
cagctggggt gatttcgccc ccatctccg ggggaatgtc tgaagacaat tttggttacc     1860
tcaatgaggg agtggaggag gatacagtgc tactaccaac tagtggataa aggccaggga     1920
tgctgctcaa cctcctacca tgtacaggac gtctccccat tacaactacc caatccgaag     1980
tgtcaactgt gtcaggacta agaaaccctg gttttgagta gaaagggcc tggaagagg     2040 ggagccaaca aatctgtctg cttcctcaca ttagtcattg gcaaataagc attctgtctc     2100
tttggctgct gcctcagcac agagagccag aactctatcg gcaccagga taacatctct     2160 cagtgaacag agttgacaag gcctatggga aatgcctgat gggattatct tcagcttgtt     2220
gagcttctaa gttctttcc cttcattcta ccctgcaagc caagttctgt aagagaaatg     2280
cctgagttct agctcaggtt ttcttactct gaatttagat ctccagaccc ttcctggcca     2340
caattcaaat taaggcaaca aacatatacc ttccatgaag cacacacaga cttttgaaag     2400
caaggacaat gactgcttga attgaggcct tgaggaatga agctttgaag gaaaagaata     2460
```

```
ctttgtttcc agcccccttc ccacactctt catgtgttaa ccactgcctt cctggacctt    2520
ggagccacgg tgactgtatt acatgttgtt atagaaaact gattttagag ttctgatcgt    2580
tcaagagaat gattaaatat acatttccta caccaaaaaa aaaaaaa                  2627
```

<210> SEQ ID NO 392
<211> LENGTH: 309
<212> TYPE: PRT
<213> ORGANISM: Homo sapiens

<400> SEQUENCE: 392

```
His Ala Ser Ala His Ala Ser Gly Arg Gln Arg Gln Leu His Ser Ala
 1               5                  10                  15

Ser Thr Gln Ile Arg Trp Glu Pro Ser Pro Ala Met Ala Ser Leu Gly
            20                  25                  30

Gln Ile Leu Phe Trp Ser Ile Ile Ser Ile Ile Ile Leu Ala Gly
        35                  40                  45

Ala Ile Ala Leu Ile Ile Gly Phe Gly Ile Ser Gly Arg His Ser Ile
    50                  55                  60

Thr Val Thr Thr Val Ala Ser Ala Gly Asn Ile Gly Glu Asp Gly Ile
65                  70                  75                  80

Leu Ser Cys Thr Phe Glu Pro Asp Ile Lys Leu Ser Asp Ile Val Ile
                85                  90                  95

Gln Trp Leu Lys Glu Gly Val Leu Gly Leu Val His Glu Phe Lys Glu
            100                 105                 110

Gly Lys Asp Glu Leu Ser Glu Gln Asp Glu Met Phe Arg Gly Arg Thr
        115                 120                 125

Ala Val Phe Ala Asp Gln Val Ile Val Gly Asn Ala Ser Leu Arg Leu
    130                 135                 140

Lys Asn Val Gln Leu Thr Asp Ala Gly Thr Tyr Lys Cys Tyr Ile Ile
145                 150                 155                 160

Thr Ser Lys Gly Lys Gly Asn Ala Asn Leu Glu Tyr Lys Thr Gly Ala
                165                 170                 175

Phe Ser Met Pro Glu Val Asn Val Asp Tyr Asn Ala Ser Ser Glu Thr
            180                 185                 190

Leu Arg Cys Glu Ala Pro Arg Trp Phe Pro Gln Pro Thr Val Val Trp
        195                 200                 205

Ala Ser Gln Val Asp Gln Gly Ala Asn Phe Ser Glu Val Ser Asn Thr
    210                 215                 220

Ser Phe Glu Leu Asn Ser Glu Asn Val Thr Met Lys Val Val Ser Val
225                 230                 235                 240

Leu Tyr Asn Val Thr Ile Asn Asn Thr Tyr Ser Cys Met Ile Glu Asn
                245                 250                 255

Asp Ile Ala Lys Ala Thr Gly Asp Ile Lys Val Thr Glu Ser Glu Ile
            260                 265                 270

Lys Arg Arg Ser His Leu Gln Leu Leu Asn Ser Lys Ala Ser Leu Cys
        275                 280                 285

Val Ser Ser Phe Phe Ala Ile Ser Trp Ala Leu Leu Pro Leu Ser Pro
    290                 295                 300

Tyr Leu Met Leu Lys
305
```

<210> SEQ ID NO 393
<211> LENGTH: 282
<212> TYPE: PRT

<213> ORGANISM: Homo sapiens

<400> SEQUENCE: 393

Met Ala Ser Leu Gly Gln Ile Leu Phe Trp Ser Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
            165                 170                 175

Pro Thr Val Val Trp Ala Ser Gln Val Asp Gln Gly Ala Asn Phe Ser
        180                 185                 190

Glu Val Ser Asn Thr Ser Phe Glu Leu Asn Ser Glu Asn Val Thr Met
    195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
            245                 250                 255

Lys Ala Ser Leu Cys Val Ser Ser Phe Phe Ala Ile Ser Trp Ala Leu
        260                 265                 270

Leu Pro Leu Ser Pro Tyr Leu Met Leu Lys
    275                 280

<210> SEQ ID NO 394
<211> LENGTH: 20
<212> TYPE: PRT
<213> ORGANISM: Homo sapiens

<400> SEQUENCE: 394

Met Ala Ser Leu Gly Gln Ile Leu Phe Trp Ser Ile Ser Ile Ile
1               5                   10                  15

Ile Ile Leu Ala
            20

<210> SEQ ID NO 395
<211> LENGTH: 20
<212> TYPE: PRT
<213> ORGANISM: Homo sapiens

<400> SEQUENCE: 395

```
Ile Ile Ile Leu Ala Gly Ala Ile Ala Leu Ile Ile Gly Phe Gly Ile
1               5                   10                  15

Ser Gly Arg His
            20
```

<210> SEQ ID NO 396
<211> LENGTH: 20
<212> TYPE: PRT
<213> ORGANISM: Homo sapiens

<400> SEQUENCE: 396

```
Ile Ser Gly Arg His Ser Ile Thr Val Thr Thr Val Ala Ser Ala Gly
1               5                   10                  15

Asn Ile Gly Glu
            20
```

<210> SEQ ID NO 397
<211> LENGTH: 20
<212> TYPE: PRT
<213> ORGANISM: Homo sapiens

<400> SEQUENCE: 397

```
Gly Asn Ile Gly Glu Asp Gly Ile Leu Ser Cys Thr Phe Glu Pro Asp
1               5                   10                  15

Ile Lys Leu Ser
            20
```

<210> SEQ ID NO 398
<211> LENGTH: 20
<212> TYPE: PRT
<213> ORGANISM: Homo sapiens

<400> SEQUENCE: 398

```
Asp Ile Lys Leu Ser Asp Ile Val Ile Gln Trp Leu Lys Glu Gly Val
1               5                   10                  15

Leu Gly Leu Val
            20
```

<210> SEQ ID NO 399
<211> LENGTH: 20
<212> TYPE: PRT
<213> ORGANISM: Homo sapiens

<400> SEQUENCE: 399

```
Val Leu Gly Leu Val His Glu Phe Lys Glu Gly Lys Asp Glu Leu Ser
1               5                   10                  15

Glu Gln Asp Glu
            20
```

<210> SEQ ID NO 400
<211> LENGTH: 20
<212> TYPE: PRT
<213> ORGANISM: Homo sapiens

<400> SEQUENCE: 400

```
Ser Glu Gln Asp Glu Met Phe Arg Gly Arg Thr Ala Val Phe Ala Asp
1               5                   10                  15

Gln Val Ile Val
            20
```

<210> SEQ ID NO 401

-continued

```
<211> LENGTH: 20
<212> TYPE: PRT
<213> ORGANISM: Homo sapiens

<400> SEQUENCE: 401

Asp Gln Val Ile Val Gly Asn Ala Ser Leu Arg Leu Lys Asn Val Gln
1               5                   10                  15

Leu Thr Asp Ala
            20

<210> SEQ ID NO 402
<211> LENGTH: 21
<212> TYPE: PRT
<213> ORGANISM: Homo sapiens

<400> SEQUENCE: 402

Val Gln Leu Thr Asp Ala Gly Thr Tyr Lys Cys Tyr Ile Ile Thr Ser
1               5                   10                  15

Lys Gly Lys Gly Asn
            20

<210> SEQ ID NO 403
<211> LENGTH: 20
<212> TYPE: PRT
<213> ORGANISM: Homo sapiens

<400> SEQUENCE: 403

Lys Gly Lys Gly Asn Ala Asn Leu Glu Tyr Lys Thr Gly Ala Phe Ser
1               5                   10                  15

Met Pro Glu Val
            20

<210> SEQ ID NO 404
<211> LENGTH: 20
<212> TYPE: PRT
<213> ORGANISM: Homo sapiens

<400> SEQUENCE: 404

Ser Met Pro Glu Val Asn Val Asp Tyr Asn Ala Ser Ser Glu Thr Leu
1               5                   10                  15

Arg Cys Glu Ala
            20

<210> SEQ ID NO 405
<211> LENGTH: 20
<212> TYPE: PRT
<213> ORGANISM: Homo sapiens

<400> SEQUENCE: 405

Leu Arg Cys Glu Ala Pro Arg Trp Phe Pro Gln Pro Thr Val Val Trp
1               5                   10                  15

Ala Ser Gln Val
            20

<210> SEQ ID NO 406
<211> LENGTH: 20
<212> TYPE: PRT
<213> ORGANISM: Homo sapiens

<400> SEQUENCE: 406

Trp Ala Ser Gln Val Asp Gln Gly Ala Asn Phe Ser Glu Val Ser Asn
1               5                   10                  15
```

-continued

Thr Ser Phe Glu
            20

<210> SEQ ID NO 407
<211> LENGTH: 20
<212> TYPE: PRT
<213> ORGANISM: Homo sapiens

<400> SEQUENCE: 407

Asn Thr Ser Phe Glu Leu Asn Ser Glu Asn Val Thr Met Lys Val Val
1               5                   10                  15

Ser Val Leu Tyr
            20

<210> SEQ ID NO 408
<211> LENGTH: 20
<212> TYPE: PRT
<213> ORGANISM: Homo sapiens

<400> SEQUENCE: 408

Val Ser Val Leu Tyr Asn Val Thr Ile Asn Asn Thr Tyr Ser Cys Met
1               5                   10                  15

Ile Glu Asn Asp
            20

<210> SEQ ID NO 409
<211> LENGTH: 20
<212> TYPE: PRT
<213> ORGANISM: Homo sapiens

<400> SEQUENCE: 409

Met Ile Glu Asn Asp Ile Ala Lys Ala Thr Gly Asp Ile Lys Val Thr
1               5                   10                  15

Glu Ser Glu Ile
            20

<210> SEQ ID NO 410
<211> LENGTH: 20
<212> TYPE: PRT
<213> ORGANISM: Homo sapiens

<400> SEQUENCE: 410

Thr Glu Ser Glu Ile Lys Arg Arg Ser His Leu Gln Leu Leu Asn Ser
1               5                   10                  15

Lys Ala Ser Leu
            20

<210> SEQ ID NO 411
<211> LENGTH: 20
<212> TYPE: PRT
<213> ORGANISM: Homo sapiens

<400> SEQUENCE: 411

Ser Lys Ala Ser Leu Cys Val Ser Ser Phe Phe Ala Ile Ser Trp Ala
1               5                   10                  15

Leu Leu Pro Leu
            20

<210> SEQ ID NO 412
<211> LENGTH: 20
<212> TYPE: PRT
<213> ORGANISM: Homo sapiens

```
<400> SEQUENCE: 412

Ser Ser Phe Phe Ala Ile Ser Trp Ala Leu Leu Pro Leu Ser Pro Tyr
1               5                   10                  15

Leu Met Leu Lys
            20

<210> SEQ ID NO 413
<211> LENGTH: 35
<212> TYPE: PRT
<213> ORGANISM: Homo sapiens

<400> SEQUENCE: 413

Ile Ser Gly Arg His Ser Ile Thr Val Thr Val Ala Ser Ala Gly
1               5                   10                  15

Asn Ile Gly Glu Asp Gly Ile Leu Ser Cys Thr Phe Gly Pro Asp Ile
                20                  25                  30

Lys Leu Ser
        35

<210> SEQ ID NO 414
<211> LENGTH: 35
<212> TYPE: PRT
<213> ORGANISM: Homo sapiens

<400> SEQUENCE: 414

Val Leu Gly Leu Val His Glu Phe Lys Glu Gly Lys Asp Glu Leu Ser
1               5                   10                  15

Glu Gln Asp Glu Met Phe Arg Gly Arg Thr Ala Val Phe Ala Asp Gln
                20                  25                  30

Val Ile Val
        35

<210> SEQ ID NO 415
<211> LENGTH: 65
<212> TYPE: PRT
<213> ORGANISM: Homo sapiens

<400> SEQUENCE: 415

Lys Gly Lys Gly Asn Ala Asn Leu Glu Tyr Lys Thr Gly Ala Phe Ser
1               5                   10                  15

Met Pro Glu Val Asn Val Asp Tyr Asn Ala Ser Ser Glu Thr Leu Arg
                20                  25                  30

Cys Glu Ala Pro Arg Trp Phe Pro Gln Pro Thr Val Val Trp Ala Ser
            35                  40                  45

Gln Val Asp Gln Gly Ala Asn Phe Ser Glu Val Ser Asn Thr Ser Phe
        50                  55                  60

Glu
65

<210> SEQ ID NO 416
<211> LENGTH: 10
<212> TYPE: PRT
<213> ORGANISM: Homo sapiens

<400> SEQUENCE: 416

Lys Leu Ser Asp Ile Val Ile Gln Trp Leu
1               5                   10

<210> SEQ ID NO 417
<211> LENGTH: 10
```

<212> TYPE: PRT
<213> ORGANISM: Homo sapiens

<400> SEQUENCE: 417

Ser Leu Gly Gln Ile Leu Phe Trp Ser Ile
1               5                   10

<210> SEQ ID NO 418
<211> LENGTH: 10
<212> TYPE: PRT
<213> ORGANISM: Homo sapiens

<400> SEQUENCE: 418

Leu Leu Asn Ser Lys Ala Ser Leu Cys Val
1               5                   10

<210> SEQ ID NO 419
<211> LENGTH: 10
<212> TYPE: PRT
<213> ORGANISM: Homo sapiens

<400> SEQUENCE: 419

Ser Leu Cys Val Ser Ser Phe Phe Ala Ile
1               5                   10

<210> SEQ ID NO 420
<211> LENGTH: 10
<212> TYPE: PRT
<213> ORGANISM: Homo sapiens

<400> SEQUENCE: 420

Val Leu Tyr Asn Val Thr Ile Asn Asn Thr
1               5                   10

<210> SEQ ID NO 421
<211> LENGTH: 10
<212> TYPE: PRT
<213> ORGANISM: Homo sapiens

<400> SEQUENCE: 421

Ile Leu Phe Trp Ser Ile Ile Ser Ile Ile
1               5                   10

<210> SEQ ID NO 422
<211> LENGTH: 10
<212> TYPE: PRT
<213> ORGANISM: Homo sapiens

<400> SEQUENCE: 422

Leu Leu Pro Leu Ser Pro Tyr Leu Met Leu
1               5                   10

<210> SEQ ID NO 423
<211> LENGTH: 10
<212> TYPE: PRT
<213> ORGANISM: Homo sapiens

<400> SEQUENCE: 423

Cys Met Ile Glu Asn Asp Ile Ala Lys Ala
1               5                   10

<210> SEQ ID NO 424
<211> LENGTH: 10
<212> TYPE: PRT
<213> ORGANISM: Homo sapiens

<400> SEQUENCE: 424

Lys Thr Gly Ala Phe Ser Met Pro Glu Val
1               5                   10

<210> SEQ ID NO 425
<211> LENGTH: 10
<212> TYPE: PRT
<213> ORGANISM: Homo sapiens

<400> SEQUENCE: 425

Trp Ala Leu Leu Pro Leu Ser Pro Tyr Leu
1               5                   10

<210> SEQ ID NO 426
<211> LENGTH: 10
<212> TYPE: PRT
<213> ORGANISM: Homo sapiens

<400> SEQUENCE: 426

Ile Ile Leu Ala Gly Ala Ile Ala Leu Ile
1               5                   10

<210> SEQ ID NO 427
<211> LENGTH: 10
<212> TYPE: PRT
<213> ORGANISM: Homo sapiens

<400> SEQUENCE: 427

Gln Leu Thr Asp Ala Gly Thr Tyr Lys Cys
1               5                   10

<210> SEQ ID NO 428
<211> LENGTH: 10
<212> TYPE: PRT
<213> ORGANISM: Homo sapiens

<400> SEQUENCE: 428

Ala Leu Leu Pro Leu Ser Pro Tyr Leu Met
1               5                   10

<210> SEQ ID NO 429
<211> LENGTH: 10
<212> TYPE: PRT
<213> ORGANISM: Homo sapiens

<400> SEQUENCE: 429

Gln Leu Leu Asn Ser Lys Ala Ser Leu Cys
1               5                   10

<210> SEQ ID NO 430
<211> LENGTH: 10
<212> TYPE: PRT
<213> ORGANISM: Homo sapiens

<400> SEQUENCE: 430

Ile Leu Ser Cys Thr Phe Glu Pro Asp Ile
1               5                   10

<210> SEQ ID NO 431
<211> LENGTH: 10
<212> TYPE: PRT
<213> ORGANISM: Homo sapiens

<400> SEQUENCE: 431

```
Trp Leu Lys Glu Gly Val Leu Gly Leu Val
 1               5                   10
```

<210> SEQ ID NO 432
<211> LENGTH: 10
<212> TYPE: PRT
<213> ORGANISM: Homo sapiens

<400> SEQUENCE: 432

```
Leu Gln Leu Leu Asn Ser Lys Ala Ser Leu
 1               5                   10
```

<210> SEQ ID NO 433
<211> LENGTH: 10
<212> TYPE: PRT
<213> ORGANISM: Homo sapiens

<400> SEQUENCE: 433

```
Gln Ile Leu Phe Trp Ser Ile Ile Ser Ile
 1               5                   10
```

<210> SEQ ID NO 434
<211> LENGTH: 10
<212> TYPE: PRT
<213> ORGANISM: Homo sapiens

<400> SEQUENCE: 434

```
Gly Ile Ser Gly Arg His Ser Ile Thr Val
 1               5                   10
```

<210> SEQ ID NO 435
<211> LENGTH: 10
<212> TYPE: PRT
<213> ORGANISM: Homo sapiens

<400> SEQUENCE: 435

```
Phe Glu Pro Asp Ile Lys Leu Ser Asp Ile
 1               5                   10
```

<210> SEQ ID NO 436
<211> LENGTH: 9
<212> TYPE: PRT
<213> ORGANISM: Homo sapiens

<400> SEQUENCE: 436

```
Ala Leu Leu Pro Leu Ser Pro Tyr Leu
 1               5
```

<210> SEQ ID NO 437
<211> LENGTH: 9
<212> TYPE: PRT
<213> ORGANISM: Homo sapiens

<400> SEQUENCE: 437

```
Ser Leu Cys Val Ser Ser Phe Phe Ala
 1               5
```

<210> SEQ ID NO 438
<211> LENGTH: 9
<212> TYPE: PRT
<213> ORGANISM: Homo sapiens

<400> SEQUENCE: 438

```
Ile Leu Phe Trp Ser Ile Ile Ser Ile
```

<210> SEQ ID NO 439
<211> LENGTH: 9
<212> TYPE: PRT
<213> ORGANISM: Homo sapiens

<400> SEQUENCE: 439

Gln Leu Leu Asn Ser Lys Ala Ser Leu
1               5

<210> SEQ ID NO 440
<211> LENGTH: 9
<212> TYPE: PRT
<213> ORGANISM: Homo sapiens

<400> SEQUENCE: 440

Lys Val Val Ser Val Leu Tyr Asn Val
1               5

<210> SEQ ID NO 441
<211> LENGTH: 9
<212> TYPE: PRT
<213> ORGANISM: Homo sapiens

<400> SEQUENCE: 441

Ile Leu Ala Gly Ala Ile Ala Leu Ile
1               5

<210> SEQ ID NO 442
<211> LENGTH: 9
<212> TYPE: PRT
<213> ORGANISM: Homo sapiens

<400> SEQUENCE: 442

Trp Leu Lys Glu Gly Val Leu Gly Leu
1               5

<210> SEQ ID NO 443
<211> LENGTH: 9
<212> TYPE: PRT
<213> ORGANISM: Homo sapiens

<400> SEQUENCE: 443

Ile Ile Leu Ala Gly Ala Ile Ala Leu
1               5

<210> SEQ ID NO 444
<211> LENGTH: 9
<212> TYPE: PRT
<213> ORGANISM: Homo sapiens

<400> SEQUENCE: 444

Asn Val Thr Met Lys Val Val Ser Val
1               5

<210> SEQ ID NO 445
<211> LENGTH: 9
<212> TYPE: PRT
<213> ORGANISM: Homo sapiens

<400> SEQUENCE: 445

Glu Met Phe Arg Gly Arg Thr Ala Val
1               5

```
<210> SEQ ID NO 446
<211> LENGTH: 9
<212> TYPE: PRT
<213> ORGANISM: Homo sapiens

<400> SEQUENCE: 446

Ala Val Phe Ala Asp Gln Val Ile Val
1               5

<210> SEQ ID NO 447
<211> LENGTH: 9
<212> TYPE: PRT
<213> ORGANISM: Homo sapiens

<400> SEQUENCE: 447

Leu Leu Pro Leu Ser Pro Tyr Leu Met
1               5

<210> SEQ ID NO 448
<211> LENGTH: 9
<212> TYPE: PRT
<213> ORGANISM: Homo sapiens

<400> SEQUENCE: 448

Leu Leu Asn Ser Lys Ala Ser Leu Cys
1               5

<210> SEQ ID NO 449
<211> LENGTH: 9
<212> TYPE: PRT
<213> ORGANISM: Homo sapiens

<400> SEQUENCE: 449

Val Ile Gln Trp Leu Lys Glu Gly Val
1               5

<210> SEQ ID NO 450
<211> LENGTH: 9
<212> TYPE: PRT
<213> ORGANISM: Homo sapiens

<400> SEQUENCE: 450

Ala Ile Ser Trp Ala Leu Leu Pro Leu
1               5

<210> SEQ ID NO 451
<211> LENGTH: 9
<212> TYPE: PRT
<213> ORGANISM: Homo sapiens

<400> SEQUENCE: 451

Ser Leu Gly Gln Ile Leu Phe Trp Ser
1               5

<210> SEQ ID NO 452
<211> LENGTH: 9
<212> TYPE: PRT
<213> ORGANISM: Homo sapiens

<400> SEQUENCE: 452

Ile Ala Leu Ile Ile Gly Phe Gly Ile
1               5

<210> SEQ ID NO 453
```

```
<211> LENGTH: 9
<212> TYPE: PRT
<213> ORGANISM: Homo sapiens

<400> SEQUENCE: 453

Cys Thr Phe Glu Pro Asp Ile Lys Leu
  1               5

<210> SEQ ID NO 454
<211> LENGTH: 9
<212> TYPE: PRT
<213> ORGANISM: Homo sapiens

<400> SEQUENCE: 454

Ile Val Gly Asn Ala Ser Leu Arg Leu
  1               5

<210> SEQ ID NO 455
<211> LENGTH: 9
<212> TYPE: PRT
<213> ORGANISM: Homo sapiens

<400> SEQUENCE: 455

Gly Gln Ile Leu Phe Trp Ser Ile Ile
  1               5

<210> SEQ ID NO 456
<211> LENGTH: 3447
<212> TYPE: DNA
<213> ORGANISM: Homo sapiens

<400> SEQUENCE: 456
```

| | | | | | |
|---|---|---|---|---|---|
| atgcccttgt | tcaagaacac | cagtgtcagc | tctctgtact | ctggttgcag | actgaccttg      60 |
| ctcaggcctg | agaaggatgg | ggcagccacc | agagtggatg | ctgtctgcac | ccatcgtcct     120 |
| gaccccaaaa | gccctggact | ggacagagag | cggctgtact | ggaagctgag | ccagctgacc     180 |
| cacggcatca | ctgagctggg | ccctacaccc | tggacaggc  | acagtctcta | tgtcaatggt     240 |
| ttcacccatc | agagctctat | gacgaccacc | agaactcctg | atacctccac | aatgcacctg     300 |
| gcaacctcga | gaactccagc | ctccctgtct | ggacctacga | ccgccagccc | tctcctggtg     360 |
| ctattcacaa | ttaacttcac | catcactaac | ctgcggtatg | aggagaacat | gcatcaccct     420 |
| ggctctagaa | agtttaacac | cacggagaga | gtccttcagg | gtctgctcag | gcctgtgttc     480 |
| aagaacacca | gtgttggccc | tctgtactct | ggctgcagac | tgaccttgct | caggcccaag     540 |
| aaggatgggg | cagccaccaa | agtggatgcc | atctgcacct | accgccctga | tcccaaaagc     600 |
| cctggactgg | acagagagca | gctatactgg | gagctgagcc | agctaaccca | cagcatcact     660 |
| gagctgggcc | cctacaccct | ggacagggac | agtctctatg | tcaatggttt | cacacagcgg     720 |
| agctctgtgc | ccaccactag | cattcctggg | accccacag  | tggacctggg | aacatctggg     780 |
| actccagttt | ctaaacctgg | tccctcggct | gccagccctc | tcctggtgct | attcactctc     840 |
| aacttcacca | tcaccaacct | gcggtatgag | gagaacatgc | agcaccctgg | ctccaggaag     900 |
| ttcaacacca | cggagagggt | ccttcagggc | ctgctcaggt | ccctgttcaa | gagcaccagt     960 |
| gttggccctc | tgtactctgg | ctgcagactg | actttgctca | ggcctgaaaa | ggatgggaca    1020 |
| gccactggag | tggatgccat | ctgcacccac | caccctgacc | ccaaaagccc | taggctggac    1080 |
| agagagcagc | tgtattggga | gctgagccag | ctgaccacc  | atatcactga | gctgggccac    1140 |
| tatgccctgg | acaacgacag | cctctttgtc | aatggtttca | ctcatcggag | ctctgtgtcc    1200 |

-continued

```
accaccagca ctcctgggac ccccacagtg tatctgggag catctaagac tccagcctcg    1260
atatttggcc cttcagctgc cagccatctc ctgatactat tcaccctcaa cttcaccatc    1320
actaacctgc ggtatgagga gaacatgtgg cctggctcca ggaagttcaa cactacagag    1380
agggtccttc agggcctgct aaggcccttg ttcaagaaca ccagtgttgg ccctctgtac    1440
tctggctcca ggctgacctt gctcaggcca gagaaagatg gggaagccac cggagtggat    1500
gccatctgca cccaccgccc tgaccccaca ggccctgggc tggacagaga gcagctgtat    1560
ttggagctga ccagctgac ccacagcatc actgagctgg cccctacac actggacagg    1620 gacagtctct atgtcaatgg tttcacccat cggagctctg tacccaccac cagcaccggg    1680
gtggtcagcg aggagccatt cacactgaac ttcaccatca acaacctgcg ctacatggcg    1740
gacatgggcc aacccggctc cctcaagttc aacatcacag acaacgtcat gaagcacctg    1800
ctcagtcctt tgttccagag gagcagcctg ggtgcacggt acacaggctg cagggtcatc    1860
gcactaaggt ctgtgaagaa cggtgctgag acacgggtgg acctcctctg cacctacctg    1920
cagcccctca gcggcccagg tctgcctatc aagcaggtgt ccatgagct gagccagcag    1980 acccatggca tcacccggct gggccccac tctctggaca agacagcct ctaccttaac    2040 ggttacaatg aacctggtct agatgagcct cctacaactc ccaagccagc caccacattc    2100
ctgcctcctc tgtcagaagc cacaacagcc atggggtacc acctgaagac cctcacactc    2160
aacttcacca tctccaatct ccagtattca ccagatatgg caagggctc agctacattc    2220 aactccaccg aggggtcct tcagcacctg ctcagaccct tgttccagaa gagcagcatg    2280
ggccccttct acttgggttg ccaactgatc tccctcaggc ctgagaagga tggggcagcc    2340
actggtgtgg acaccacctg cacctaccac cctgaccctg tgggcccgg gctggacata    2400 cagcagcttt actgggagct gagtcagctg acccatggtg tcacccaact gggcttctat    2460
gtcctggaca gggatagcct cttcatcaat ggctatgcac cccagaattt atcaatccgg    2520
ggcgagtacc agataaattt ccacattgtc aactggaacc tcagtaatcc agaccccaca    2580
tcctcagagt catcacccct gctgagggac atccaggaca aggtcaccac actctacaaa    2640
ggcagtcaac tacatgacac attccgcttc tgcctggtca ccaacttgac gatggactcc    2700
gtgttggtca ctgtcaaggc attgttctcc tccaatttgg accccagcct ggtggagcaa    2760
gtctttctag ataagaccct gaatgcctca ttccattggc tgggctccac ctaccagttg    2820
gtggacatcc atgtgacaga aatggagtca tcagtttatc aaccaacaag cagctccagc    2880
acccagcact tctacccgaa tttcaccatc accaacctac catattccca ggacaaagcc    2940
cagccaggca ccaccaatta ccagaggaac aaaaggaata ttgaggatgc gctcaaccaa    3000
ctcttccgaa acagcagcat caagagttat ttttctgact gtcaagtttc aacattcagg    3060
tctgtcccca acaggcacca caccggggtg gactccctgt gtaacttctc gccactggct    3120
cggagagtag acagagttgc catctatgag gaatttctgc ggatgacccg gaatggtacc    3180
cagctgcaga acttcaccct ggacaggagc agtgtccttg tggatgggta ttctcccaac    3240
agaaatgagc ccttaactgg gaattctgac cttcccttct gggctgtcat cttcatcggc    3300
ttggcaggac tcctgggact catcacatgc ctgatctgcg gtgtcctggt gaccacccgc    3360
cggcggaaga aggaaggaga atacaacgtc agcaacagt gcccaggcta ctaccagtca    3420
cacctagacc tggaggatct gcaatga                                       3447
```

<210> SEQ ID NO 457
<211> LENGTH: 3557

<212> TYPE: DNA
<213> ORGANISM: Homo sapiens

<400> SEQUENCE: 457

```
gagagggtcc ttcagggtct gcttatgccc ttgttcaaga acaccagtgt cagctctctg      60
tactctggtt gcagactgac cttgctcagg cctgagaagg atggggcagc caccagagtg     120
gatgctgtct gcacccatcg tcctgacccc aaaagccctg gactggacag agagcggctg     180
tactggaagc tgagccagct gacccacggc atcactgagc tgggccccta caccctggac     240
aggcacagtc tctatgtcaa tggtttcacc catcagagct ctatgacgac caccagaact     300
cctgatacct ccacaatgca cctggcaacc tcgagaactc cagcctccct gtctggacct     360
acgaccgcca gccctctcct ggtgctattc acaattaact tcaccatcac taacctgcgg     420
tatgaggaga acatgcatca ccctggctct agaaagttta acaccacgga gagtccctt     480
cagggtctgc tcaggcctgt gttcaagaac accagtgttg ccctctgta ctctggctgc      540
agactgacct tgctcaggcc caagaaggat ggggcagcca ccaaagtgga tgccatctgc     600
acctaccgcc ctgatcccaa aagccctgga ctggacagag agcagctata ctgggagctg     660
agccagctaa cccacagcat cactgagctg ggcccctaca ccctggacag ggacagtctc     720
tatgtcaatg gtttcacaca gcggagctct gtgccacca ctagcattcc tgggaccccc      780
acagtggacc tgggaacatc tgggactcca gtttctaaac ctggtccctc ggctgccagc     840
cctctcctgg tgctattcac tctcaacttc accatcacca acctgcggta tgaggagaac     900
atgcagcacc ctggctccag gaagttcaac accacggaga gggtccttca gggcctgctc     960
aggtccctgt tcaagagcac cagtgttggc cctctgtact ctggctgcag actgactttg    1020
ctcaggcctg aaaaggatgg gacagccact ggagtggatg ccatctgcac ccaccaccct    1080
gaccccaaaa gcctaggct ggacagagag cagctgtatt gggagctgag ccagctgacc      1140
cacaatatca ctgagctggg ccactatgcc ctggacaacg acagcctctt tgtcaatggt    1200
ttcactcatc ggagctctgt gtccaccacc agcactcctg gaccccacac agtgtatctg    1260
ggagcatcta agactccagc ctcgatattt ggcccttcag ctgccagcca tctcctgata    1320
ctattcaccc tcaacttcac catcactaac ctgcggtatg aggagaacat gtggcctggc    1380
tccaggaagt tcaacactac agagagggtc cttcagggcc tgctaaggcc cttgttcaag    1440
aacaccagtg ttggccctct gtactctggc tccaggctga ccttgctcag gccagagaaa    1500
gatggggaag ccaccggagt ggatgccatc tgcacccacc gccctgaccc cacaggccct    1560
gggctggaca gagagcagct gtatttggag ctgagccagc tgacccacag catcactgag    1620
ctgggccct acacactgga cagggacagt ctctatgtca atggtttcac ccatcggagc     1680
tctgtaccca ccaccagcac cggggtggtc agcgaggagc cattcacact gaacttcacc    1740
atcaacaacc tgcgctacat ggcggacatg gccaacccg ctccctcaa gttcaacatc      1800
acagacaacg tcatgaagca cctgctcagt ccttttgttcc agaggagcag cctgggtgca    1860
cggtacacag gctgcagggt catcgcacta aggtctgtga agaacggtgc tgagacacgg    1920
gtggacctcc tctgcaccta cctgcagccc ctcagcggcc caggtctgcc tatcaagcag    1980
gtgttccatg agctgagcca gcagacccat ggcatcaccc ggctgggccc ctactctctg    2040
gacaaagaca gcctctacct taacggttac aatgaacctg gtctagatga gcctcctaca    2100
actcccaagc cagccaccac attcctgcct cctctgtcag aagccacaac agccatgggg    2160
taccacctga agaccctcac actcaacttc accatctcca atctccagta ttcaccagat    2220
```

```
atgggcaagg gctcagctac attcaactcc accgaggggg tccttcagca cctgctcaga      2280
cccttgttcc agaagagcag catgggcccc ttctacttgg gttgccaact gatctccctc      2340
aggcctgaga aggatggggc agccactggt gtggacacca cctgcaccta ccacccctgac     2400
cctgtgggcc ccgggctgga catacagcag ctttactggg agctgagtca gctgacccat      2460
ggtgtcaccc aactgggctt ctatgtcctg gacagggata gcctcttcat caatggctat      2520
gcaccccaga atttatcaat ccggggcgag taccagataa atttccacat tgtcaactgg      2580
aacctcagta atccagaccc cacatcctca gagtacatca ccctgctgag ggacatccag      2640
gacaaggtca ccacactcta caaggcagt caactacatg acacattccg cttctgcctg      2700
gtcaccaact tgacgatgga ctccgtgttg gtcactgtca aggcattgtt ctcctccaat      2760
ttggacccca gctggtgga gcaagtcttt ctagataaga ccctgaatgc ctcattccat      2820
tggctgggct ccacctacca gttggtggac atccatgtga cagaaatgga gtcatcagtt      2880
tatcaaccaa caagcagctc cagcacccag cacttctacc cgaatttcac catcaccaac      2940
ctaccatatt cccaggacaa agcccagcca ggcaccacca attaccagag gaacaaaagg      3000
aatattgagg atgcgctcaa ccaactcttc gaaacagca gcatcaagag ttattttcct      3060
gactgtcaag tttcaacatt caggtctgtc cccaacaggc accacccgg ggtggactcc      3120
ctgtgtaact tctcgccact ggctcggaga gtagacagag ttgccatcta tgaggaattt      3180
ctgcggatga cccggaatgg taccagctg cagaacttca ccctggacag gagcagtgtc      3240
cttgtggatg ggtattctcc caacagaaat gagcccttaa ctgggaattc tgaccttccc      3300
ttctgggctg tcatcttcat cggcttggca ggactcctgg gactcatcac atgcctgatc      3360
tgcggtgtcc tggtgaccac ccgccggcgg aagaaggaag gagaatacaa cgtccagcaa      3420
cagtgcccag gctactacca gtcacaccta gacctggagg atctgcaatg actggaactt      3480
gccggtgcct ggggtgcctt tcccccagcc agggtccaaa gaagcttggc tggggcagaa      3540
ataaaccata ttggtcg                                                    3557
```

<210> SEQ ID NO 458
<211> LENGTH: 1148
<212> TYPE: PRT
<213> ORGANISM: Homo sapiens

<400> SEQUENCE: 458

```
Met Pro Leu Phe Lys Asn Thr Ser Val Ser Ser Leu Tyr Ser Gly Cys
  1               5                  10                  15
Arg Leu Thr Leu Leu Arg Pro Glu Lys Asp Gly Ala Ala Thr Arg Val
             20                  25                  30
Asp Ala Val Cys Thr His Arg Pro Asp Pro Lys Ser Pro Gly Leu Asp
         35                  40                  45
Arg Glu Arg Leu Tyr Trp Lys Leu Ser Gln Leu Thr His Gly Ile Thr
     50                  55                  60
Glu Leu Gly Pro Tyr Thr Leu Asp Arg His Ser Leu Tyr Val Asn Gly
 65                  70                  75                  80
Phe Thr His Gln Ser Ser Met Thr Thr Thr Arg Thr Pro Asp Thr Ser
                 85                  90                  95
Thr Met His Leu Ala Thr Ser Arg Thr Pro Ala Ser Leu Ser Gly Pro
            100                 105                 110
Thr Thr Ala Ser Pro Leu Leu Val Leu Phe Thr Ile Asn Phe Thr Ile
        115                 120                 125
Thr Asn Leu Arg Tyr Glu Glu Asn Met His His Pro Gly Ser Arg Lys
```

-continued

```
            130                 135                 140
Phe Asn Thr Thr Glu Arg Val Leu Gln Gly Leu Leu Arg Pro Val Phe
145                 150                 155                 160

Lys Asn Thr Ser Val Gly Pro Leu Tyr Ser Gly Cys Arg Leu Thr Leu
                165                 170                 175

Leu Arg Pro Lys Lys Asp Gly Ala Ala Thr Lys Val Asp Ala Ile Cys
                180                 185                 190

Thr Tyr Arg Pro Asp Pro Lys Ser Pro Gly Leu Asp Arg Glu Gln Leu
                195                 200                 205

Tyr Trp Glu Leu Ser Gln Leu Thr His Ser Ile Thr Glu Leu Gly Pro
210                 215                 220

Tyr Thr Leu Asp Arg Asp Ser Leu Tyr Val Asn Gly Phe Thr Gln Arg
225                 230                 235                 240

Ser Ser Val Pro Thr Thr Ser Ile Pro Gly Thr Pro Thr Val Asp Leu
                245                 250                 255

Gly Thr Ser Gly Thr Pro Val Ser Lys Pro Gly Pro Ser Ala Ala Ser
                260                 265                 270

Pro Leu Leu Val Leu Phe Thr Leu Asn Phe Thr Ile Thr Asn Leu Arg
                275                 280                 285

Tyr Glu Glu Asn Met Gln His Pro Gly Ser Arg Lys Phe Asn Thr Thr
290                 295                 300

Glu Arg Val Leu Gln Gly Leu Leu Arg Ser Leu Phe Lys Ser Thr Ser
305                 310                 315                 320

Val Gly Pro Leu Tyr Ser Gly Cys Arg Leu Thr Leu Leu Arg Pro Glu
                325                 330                 335

Lys Asp Gly Thr Ala Thr Gly Val Asp Ala Ile Cys Thr His His Pro
                340                 345                 350

Asp Pro Lys Ser Pro Arg Leu Asp Arg Glu Gln Leu Tyr Trp Glu Leu
                355                 360                 365

Ser Gln Leu Thr His Asn Ile Thr Glu Leu Gly His Tyr Ala Leu Asp
                370                 375                 380

Asn Asp Ser Leu Phe Val Asn Gly Phe Thr His Arg Ser Ser Val Ser
385                 390                 395                 400

Thr Thr Ser Thr Pro Gly Thr Pro Thr Val Tyr Leu Gly Ala Ser Lys
                405                 410                 415

Thr Pro Ala Ser Ile Phe Gly Pro Ser Ala Ala Ser His Leu Leu Ile
                420                 425                 430

Leu Phe Thr Leu Asn Phe Thr Ile Thr Asn Leu Arg Tyr Glu Glu Asn
                435                 440                 445

Met Trp Pro Gly Ser Arg Lys Phe Asn Thr Thr Glu Arg Val Leu Gln
450                 455                 460

Gly Leu Leu Arg Pro Leu Phe Lys Asn Thr Ser Val Gly Pro Leu Tyr
465                 470                 475                 480

Ser Gly Ser Arg Leu Thr Leu Leu Arg Pro Glu Lys Asp Gly Glu Ala
                485                 490                 495

Thr Gly Val Asp Ala Ile Cys Thr His Arg Pro Asp Pro Thr Gly Pro
                500                 505                 510

Gly Leu Asp Arg Glu Gln Leu Tyr Leu Glu Leu Ser Gln Leu Thr His
                515                 520                 525

Ser Ile Thr Glu Leu Gly Pro Tyr Thr Leu Asp Arg Asp Ser Leu Tyr
                530                 535                 540

Val Asn Gly Phe Thr His Arg Ser Ser Val Pro Thr Thr Ser Thr Gly
545                 550                 555                 560
```

-continued

```
Val Val Ser Glu Glu Pro Phe Thr Leu Asn Phe Thr Ile Asn Asn Leu
            565             570             575
Arg Tyr Met Ala Asp Met Gly Gln Pro Gly Ser Leu Lys Phe Asn Ile
            580             585             590
Thr Asp Asn Val Met Lys His Leu Leu Ser Pro Leu Phe Gln Arg Ser
            595             600             605
Ser Leu Gly Ala Arg Tyr Thr Gly Cys Arg Val Ile Ala Leu Arg Ser
            610             615             620
Val Lys Asn Gly Ala Glu Thr Arg Val Asp Leu Leu Cys Thr Tyr Leu
625             630             635             640
Gln Pro Leu Ser Gly Pro Gly Leu Pro Ile Lys Gln Val Phe His Glu
            645             650             655
Leu Ser Gln Gln Thr His Gly Ile Thr Arg Leu Gly Pro Tyr Ser Leu
            660             665             670
Asp Lys Asp Ser Leu Tyr Leu Asn Gly Tyr Asn Glu Pro Gly Leu Asp
            675             680             685
Glu Pro Pro Thr Thr Pro Lys Pro Ala Thr Thr Phe Leu Pro Pro Leu
            690             695             700
Ser Glu Ala Thr Thr Ala Met Gly Tyr His Leu Lys Thr Leu Thr Leu
705             710             715             720
Asn Phe Thr Ile Ser Asn Leu Gln Tyr Ser Pro Asp Met Gly Lys Gly
            725             730             735
Ser Ala Thr Phe Asn Ser Thr Glu Gly Val Leu Gln His Leu Leu Arg
            740             745             750
Pro Leu Phe Gln Lys Ser Ser Met Gly Pro Phe Tyr Leu Gly Cys Gln
            755             760             765
Leu Ile Ser Leu Arg Pro Glu Lys Asp Gly Ala Ala Thr Gly Val Asp
            770             775             780
Thr Thr Cys Thr Tyr His Pro Asp Pro Val Gly Pro Gly Leu Asp Ile
785             790             795             800
Gln Gln Leu Tyr Trp Glu Leu Ser Gln Leu Thr His Gly Val Thr Gln
            805             810             815
Leu Gly Phe Tyr Val Leu Asp Arg Asp Ser Leu Phe Ile Asn Gly Tyr
            820             825             830
Ala Pro Gln Asn Leu Ser Ile Arg Gly Glu Tyr Gln Ile Asn Phe His
            835             840             845
Ile Val Asn Trp Asn Leu Ser Asn Pro Asp Pro Thr Ser Ser Glu Tyr
            850             855             860
Ile Thr Leu Leu Arg Asp Ile Gln Asp Lys Val Thr Thr Leu Tyr Lys
865             870             875             880
Gly Ser Gln Leu His Asp Thr Phe Arg Phe Cys Leu Val Thr Asn Leu
            885             890             895
Thr Met Asp Ser Val Leu Val Thr Val Lys Ala Leu Phe Ser Ser Asn
            900             905             910
Leu Asp Pro Ser Leu Val Glu Gln Val Phe Leu Asp Lys Thr Leu Asn
            915             920             925
Ala Ser Phe His Trp Leu Gly Ser Thr Tyr Gln Leu Val Asp Ile His
            930             935             940
Val Thr Glu Met Glu Ser Ser Val Tyr Gln Pro Thr Ser Ser Ser Ser
945             950             955             960
Thr Gln His Phe Tyr Pro Asn Phe Thr Ile Thr Asn Leu Pro Tyr Ser
            965             970             975
```

```
Gln Asp Lys Ala Gln Pro Gly Thr Thr Asn Tyr Gln Arg Asn Lys Arg
            980                 985                 990

Asn Ile Glu Asp Ala Leu Asn Gln Leu Phe Arg Asn Ser Ser Ile Lys
        995                1000                1005

Ser Tyr Phe Ser Asp Cys Gln Val Ser Thr Phe Arg Ser Val Pro Asn
    1010                1015                1020

Arg His His Thr Gly Val Asp Ser Leu Cys Asn Phe Ser Pro Leu Ala
1025                1030                1035                1040

Arg Arg Val Asp Arg Val Ala Ile Tyr Glu Glu Phe Leu Arg Met Thr
                1045                1050                1055

Arg Asn Gly Thr Gln Leu Gln Asn Phe Thr Leu Asp Arg Ser Ser Val
            1060                1065                1070

Leu Val Asp Gly Tyr Ser Pro Asn Arg Asn Glu Pro Leu Thr Gly Asn
        1075                1080                1085

Ser Asp Leu Pro Phe Trp Ala Val Ile Phe Ile Gly Leu Ala Gly Leu
1090                1095                1100

Leu Gly Leu Ile Thr Cys Leu Ile Cys Gly Val Leu Val Thr Thr Arg
1105                1110                1115                1120

Arg Arg Lys Lys Glu Gly Glu Tyr Asn Val Gln Gln Gln Cys Pro Gly
                1125                1130                1135

Tyr Tyr Gln Ser His Leu Asp Leu Glu Asp Leu Gln
            1140                1145

<210> SEQ ID NO 459
<211> LENGTH: 1156
<212> TYPE: PRT
<213> ORGANISM: Homo sapiens

<400> SEQUENCE: 459

Glu Arg Val Leu Gln Gly Leu Leu Met Pro Leu Phe Lys Asn Thr Ser
1               5                  10                  15

Val Ser Ser Leu Tyr Ser Gly Cys Arg Leu Thr Leu Leu Arg Pro Glu
            20                  25                  30

Lys Asp Gly Ala Ala Thr Arg Val Asp Ala Val Cys Thr His Arg Pro
        35                  40                  45

Asp Pro Lys Ser Pro Gly Leu Asp Arg Glu Arg Leu Tyr Trp Lys Leu
    50                  55                  60

Ser Gln Leu Thr His Gly Ile Thr Glu Leu Gly Pro Tyr Thr Leu Asp
65                  70                  75                  80

Arg His Ser Leu Tyr Val Asn Gly Phe Thr His Gln Ser Ser Met Thr
                85                  90                  95

Thr Thr Arg Thr Pro Asp Thr Ser Thr Met His Leu Ala Thr Ser Arg
            100                 105                 110

Thr Pro Ala Ser Leu Ser Gly Pro Thr Thr Ala Ser Pro Leu Leu Val
        115                 120                 125

Leu Phe Thr Ile Asn Phe Thr Ile Thr Asn Leu Arg Tyr Glu Glu Asn
    130                 135                 140

Met His His Pro Gly Ser Arg Lys Phe Asn Thr Thr Glu Arg Val Leu
145                 150                 155                 160

Gln Gly Leu Leu Arg Pro Val Phe Lys Asn Thr Ser Val Gly Pro Leu
                165                 170                 175

Tyr Ser Gly Cys Arg Leu Thr Leu Leu Arg Pro Lys Lys Asp Gly Ala
            180                 185                 190

Ala Thr Lys Val Asp Ala Ile Cys Thr Tyr Arg Pro Asp Pro Lys Ser
        195                 200                 205
```

```
Pro Gly Leu Asp Arg Glu Gln Leu Tyr Trp Glu Leu Ser Gln Leu Thr
    210                 215                 220

His Ser Ile Thr Glu Leu Gly Pro Tyr Thr Leu Asp Arg Asp Ser Leu
225                 230                 235                 240

Tyr Val Asn Gly Phe Thr Gln Arg Ser Ser Val Pro Thr Thr Ser Ile
                    245                 250                 255

Pro Gly Thr Pro Thr Val Asp Leu Gly Thr Ser Gly Thr Pro Val Ser
                260                 265                 270

Lys Pro Gly Pro Ser Ala Ala Ser Pro Leu Leu Val Leu Phe Thr Leu
                275                 280                 285

Asn Phe Thr Ile Thr Asn Leu Arg Tyr Glu Glu Asn Met Gln His Pro
290                 295                 300

Gly Ser Arg Lys Phe Asn Thr Thr Glu Arg Val Leu Gln Gly Leu Leu
305                 310                 315                 320

Arg Ser Leu Phe Lys Ser Thr Ser Val Gly Pro Leu Tyr Ser Gly Cys
                325                 330                 335

Arg Leu Thr Leu Leu Arg Pro Glu Lys Asp Gly Thr Ala Thr Gly Val
                340                 345                 350

Asp Ala Ile Cys Thr His His Pro Asp Pro Lys Ser Pro Arg Leu Asp
                355                 360                 365

Arg Glu Gln Leu Tyr Trp Glu Leu Ser Gln Leu Thr His Asn Ile Thr
370                 375                 380

Glu Leu Gly His Tyr Ala Leu Asp Asn Asp Ser Leu Phe Val Asn Gly
385                 390                 395                 400

Phe Thr His Arg Ser Ser Val Ser Thr Thr Ser Thr Pro Gly Thr Pro
                405                 410                 415

Thr Val Tyr Leu Gly Ala Ser Lys Thr Pro Ala Ser Ile Phe Gly Pro
                420                 425                 430

Ser Ala Ala Ser His Leu Leu Ile Leu Phe Thr Leu Asn Phe Thr Ile
                435                 440                 445

Thr Asn Leu Arg Tyr Glu Glu Asn Met Trp Pro Gly Ser Arg Lys Phe
450                 455                 460

Asn Thr Thr Glu Arg Val Leu Gln Gly Leu Leu Arg Pro Leu Phe Lys
465                 470                 475                 480

Asn Thr Ser Val Gly Pro Leu Tyr Ser Gly Ser Arg Leu Thr Leu Leu
                485                 490                 495

Arg Pro Glu Lys Asp Gly Glu Ala Thr Gly Val Asp Ala Ile Cys Thr
                500                 505                 510

His Arg Pro Asp Pro Thr Gly Pro Gly Leu Asp Arg Glu Gln Leu Tyr
                515                 520                 525

Leu Glu Leu Ser Gln Leu Thr His Ser Ile Thr Glu Leu Gly Pro Tyr
530                 535                 540

Thr Leu Asp Arg Asp Ser Leu Tyr Val Asn Gly Phe Thr His Arg Ser
545                 550                 555                 560

Ser Val Pro Thr Thr Ser Thr Gly Val Val Ser Glu Glu Pro Phe Thr
                565                 570                 575

Leu Asn Phe Thr Ile Asn Asn Leu Arg Tyr Met Ala Asp Met Gly Gln
                580                 585                 590

Pro Gly Ser Leu Lys Phe Asn Ile Thr Asp Asn Val Met Lys His Leu
                595                 600                 605

Leu Ser Pro Leu Phe Gln Arg Ser Ser Leu Gly Ala Arg Tyr Thr Gly
610                 615                 620
```

-continued

```
Cys Arg Val Ile Ala Leu Arg Ser Val Lys Asn Gly Ala Glu Thr Arg
625                 630                 635                 640

Val Asp Leu Leu Cys Thr Tyr Leu Gln Pro Leu Ser Gly Pro Gly Leu
                645                 650                 655

Pro Ile Lys Gln Val Phe His Glu Leu Ser Gln Gln Thr His Gly Ile
            660                 665                 670

Thr Arg Leu Gly Pro Tyr Ser Leu Asp Lys Asp Ser Leu Tyr Leu Asn
        675                 680                 685

Gly Tyr Asn Glu Pro Gly Leu Asp Glu Pro Thr Thr Pro Lys Pro
690                 695                 700

Ala Thr Thr Phe Leu Pro Pro Leu Ser Glu Ala Thr Thr Ala Met Gly
705                 710                 715                 720

Tyr His Leu Lys Thr Leu Thr Leu Asn Phe Thr Ile Ser Asn Leu Gln
                725                 730                 735

Tyr Ser Pro Asp Met Gly Lys Gly Ser Ala Thr Phe Asn Ser Thr Glu
                740                 745                 750

Gly Val Leu Gln His Leu Leu Arg Pro Leu Phe Gln Lys Ser Ser Met
            755                 760                 765

Gly Pro Phe Tyr Leu Gly Cys Gln Leu Ile Ser Leu Arg Pro Glu Lys
770                 775                 780

Asp Gly Ala Ala Thr Gly Val Asp Thr Thr Cys Thr Tyr His Pro Asp
785                 790                 795                 800

Pro Val Gly Pro Gly Leu Asp Ile Gln Gln Leu Tyr Trp Glu Leu Ser
                805                 810                 815

Gln Leu Thr His Gly Val Thr Gln Leu Gly Phe Tyr Val Leu Asp Arg
                820                 825                 830

Asp Ser Leu Phe Ile Asn Gly Tyr Ala Pro Gln Asn Leu Ser Ile Arg
            835                 840                 845

Gly Glu Tyr Gln Ile Asn Phe His Ile Val Asn Trp Asn Leu Ser Asn
850                 855                 860

Pro Asp Pro Thr Ser Ser Glu Tyr Ile Thr Leu Leu Arg Asp Ile Gln
865                 870                 875                 880

Asp Lys Val Thr Thr Leu Tyr Lys Gly Ser Gln Leu His Asp Thr Phe
                885                 890                 895

Arg Phe Cys Leu Val Thr Asn Leu Thr Met Asp Ser Val Leu Val Thr
                900                 905                 910

Val Lys Ala Leu Phe Ser Ser Asn Leu Asp Pro Ser Leu Val Glu Gln
            915                 920                 925

Val Phe Leu Asp Lys Thr Leu Asn Ala Ser Phe His Trp Leu Gly Ser
930                 935                 940

Thr Tyr Gln Leu Val Asp Ile His Val Thr Glu Met Glu Ser Ser Val
945                 950                 955                 960

Tyr Gln Pro Thr Ser Ser Ser Thr Gln His Phe Tyr Pro Asn Phe
                965                 970                 975

Thr Ile Thr Asn Leu Pro Tyr Ser Gln Asp Lys Ala Gln Pro Gly Thr
            980                 985                 990

Thr Asn Tyr Gln Arg Asn Lys Arg Asn Ile Glu Asp Ala Leu Asn Gln
        995                 1000                1005

Leu Phe Arg Asn Ser Ser Ile Lys Ser Tyr Phe Ser Asp Cys Gln Val
        1010                1015                1020

Ser Thr Phe Arg Ser Val Pro Asn Arg His His Thr Gly Val Asp Ser
1025                1030                1035                1040

Leu Cys Asn Phe Ser Pro Leu Ala Arg Arg Val Asp Arg Val Ala Ile
```

```
                   1045                1050                1055
Tyr Glu Glu Phe Leu Arg Met Thr Arg Asn Gly Thr Gln Leu Gln Asn
                1060                1065                1070

Phe Thr Leu Asp Arg Ser Ser Val Leu Val Asp Gly Tyr Ser Pro Asn
            1075                1080                1085

Arg Asn Glu Pro Leu Thr Gly Asn Ser Asp Leu Pro Phe Trp Ala Val
        1090                1095                1100

Ile Phe Ile Gly Leu Ala Gly Leu Leu Gly Leu Ile Thr Cys Leu Ile
1105                1110                1115                1120

Cys Gly Val Leu Val Thr Thr Arg Arg Lys Lys Glu Gly Glu Tyr
                1125                1130                1135

Asn Val Gln Gln Gln Cys Pro Gly Tyr Tyr Gln Ser His Leu Asp Leu
            1140                1145                1150

Glu Asp Leu Gln
        1155

<210> SEQ ID NO 460
<211> LENGTH: 79
<212> TYPE: PRT
<213> ORGANISM: Homo sapiens

<400> SEQUENCE: 460

Met Ser Met Val Ser His Ser Gly Ala Leu Cys Pro Pro Leu Ala Phe
1               5                   10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp
65                  70                  75

<210> SEQ ID NO 461
<211> LENGTH: 313
<212> TYPE: PRT
<213> ORGANISM: Homo sapiens

<400> SEQUENCE: 461

Met Pro Leu Phe Lys Asn Thr Ser Val Ser Ser Leu Tyr Ser Gly Cys
1               5                   10                  15

Arg Leu Thr Leu Leu Arg Pro Glu Lys Asp Gly Ala Ala Thr Arg Val
            20                  25                  30

Asp Ala Val Cys Thr His Arg Pro Asp Pro Lys Ser Pro Gly Leu Asp
        35                  40                  45

Arg Glu Arg Leu Tyr Trp Lys Leu Ser Gln Leu Thr His Gly Ile Thr
    50                  55                  60

Glu Leu Gly Pro Tyr Thr Leu Asp Arg His Ser Leu Tyr Val Asn Gly
65                  70                  75                  80

Phe Thr His Gln Ser Ser Met Thr Thr Thr Arg Thr Pro Asp Thr Ser
                85                  90                  95

Thr Met His Leu Ala Thr Ser Arg Thr Pro Ala Ser Leu Ser Gly Pro
            100                 105                 110

Thr Thr Ala Ser Pro Leu Leu Val Leu Phe Thr Ile Asn Phe Thr Ile
        115                 120                 125

Thr Asn Leu Arg Tyr Glu Glu Asn Met His His Pro Gly Ser Arg Lys
```

-continued

```
                  130                 135                 140
Phe Asn Thr Thr Glu Arg Val Leu Gln Gly Leu Leu Arg Pro Val Phe
145                 150                 155                 160

Lys Asn Thr Ser Val Gly Pro Leu Tyr Ser Gly Cys Arg Leu Thr Leu
                165                 170                 175

Leu Arg Pro Lys Lys Asp Gly Ala Ala Thr Lys Val Asp Ala Ile Cys
            180                 185                 190

Thr Tyr Arg Pro Asp Pro Lys Ser Pro Gly Leu Asp Arg Glu Gln Leu
        195                 200                 205

Tyr Trp Glu Leu Ser Gln Leu Thr His Ser Ile Thr Glu Leu Gly Pro
210                 215                 220

Tyr Thr Leu Asp Arg Asp Ser Leu Tyr Val Asn Gly Phe Thr Gln Arg
225                 230                 235                 240

Ser Ser Val Pro Thr Thr Ser Ile Pro Gly Thr Pro Thr Val Asp Leu
                245                 250                 255

Gly Thr Ser Gly Thr Pro Val Ser Lys Pro Gly Pro Ser Ala Ala Ser
            260                 265                 270

Pro Leu Leu Val Leu Phe Thr Leu Asn Phe Thr Ile Thr Asn Leu Arg
        275                 280                 285

Tyr Glu Glu Asn Met Gln His Pro Gly Ser Arg Lys Phe Asn Thr Thr
    290                 295                 300

Glu Arg Val Leu Gln Gly Leu Leu Arg
305                 310

<210> SEQ ID NO 462
<211> LENGTH: 2996
<212> TYPE: DNA
<213> ORGANISM: Homo sapiens

<400> SEQUENCE: 462
cagccaccgg agtggatgcc atctgcaccc accgccctga ccccacaggc cctgggctgg      60
acagagagca gctgtatttg agctgagcc agctgaccca cagcatcact gagctgggcc     120
cctacaccct ggacagggac agtctctatg tcaatggttt cacacagcgg agctctgtgc     180
ccaccactag cattcctggg accccacag tggacctggg aacatctggg actccagttt     240
ctaaacctgg tccctcggct gccagccctc tcctggtgct attcactctc aacttcacca     300
tcaccaacct gcggtatgag gagaacatgc agcaccctgg ctccaggaag ttcaacacca     360
cggagagggt ccttcagggc ctggtccctg ttcaagagca ccagtgttgg ccctctgtac     420
tctggctgca gactgacttt gctcaggcct gaaaaggatg ggacagccac tggagtggat     480
gccatctgca cccaccaccc tgaccccaaa agccctaggc tggacagaga gcagctgtat     540
tgggagctga gccagctgac ccacaatatc actgagctgg ccctatgc cctggacaac     600 gacagcctct tgtcaatgg tttcactcat cggagctctg tgtccaccac cagcactcct     660 gggacccca cagtgtatct gggagcatct aagactccag cctcgatat tggcccttca     720 gctgccagcc atctcctgat actattcacc ctcaacttca ccatcactaa cctgcggtat     780
gaggagaaca tgtggcctgg ctccaggaag ttcaacacta cagagagggt ccttcagggc     840
ctgctaaggc ccttgttcaa gaacaccagt gttggccctc tgtactctgg ctgcaggctg     900
accttgctca ggcagagaa agatggggaa gccaccggag tggatgccat ctgcacccac     960
cgccctgacc ccacaggccc tgggctggac agagagcagc tgtatttgga gctgagccag    1020
ctgacccaca gcatcactga gctgggcccc tacacactgg acaggacag tctctatgtc    1080
```

-continued

```
aatggtttca cccatcggag ctctgtaccc accaccagca ccggggtggt cagcgaggag    1140
ccattcacac tgaacttcac catcaacaac ctgcgctaca tggcggacat gggccaaccc    1200
ggctccctca agttcaacat cacagacaac gtcatgaagc acctgctcag tcctttgttc    1260
cagaggagca gcctgggtgc acggtacaca ggctgcaggg tcatcgcact aaggtctgtg    1320
aagaacggtg ctgagacacg ggtggacctc tctgcacct acctgcagcc cctcagcggc     1380
ccaggtctgc ctatcaagca ggtgttccat gagctgagcc agcagaccca tggcatcacc    1440
cggctgggcc cctactctct ggacaaagac agcctctacc ttaacggtta caatgaacct    1500
ggtccagatg agcctcctac aactcccaag ccagccacca cattcctgcc tcctctgtca    1560
gaagccacaa cagccatggg gtaccacctg aagaccctca cactcaactt caccatctcc    1620
aatctccagt attcaccaga tatgggcaag ggctcagcta cattcaactc caccgagggg    1680
gtccttcagc acctgctcag acccttgttc cagaagagca gcatgggccc cttctacttg    1740
ggttgccaac tgatctccct caggcctgag aaggatgggg cagccactgg tgtggacacc    1800
acctgcacct accaccctga ccctgtgggc cccgggctgg acatacagca gctttactgg    1860
gagctgagtc agctgaccca tggtgtcacc caactgggct tctatgtcct ggacaggggat   1920 agcctcttca tcaatggcta tgcaccccag aatttatcaa tccggggcga gtaccagata    1980
aatttccaca ttgtcaactg gaacctcagt aatccagacc ccacatcctc agagtacatc    2040
accctgctga gggacatcca ggacaaggtc accacactct acaaaggcag tcaactacat    2100
gacacattcc gcttctgcct ggtcaccaac ttgacgatgg actccgtgtt ggtcactgtc    2160
aaggcattgt tctcctccaa tttggacccc agcctggtgg agcaagtctt tctagataag    2220
accctgaatg cctcattcca ttggctgggc tccacctacc agttggtgga catccatgtg    2280
acagaaatgg agtcatcagt ttatcaacca caagcagct ccagcaccca gcacttctac      2340
ctgaatttca ccatcaccaa cctaccatat tcccaggaca aagcccagcc aggcaccacc    2400
aattaccaga ggaacaaaag gaatattgag gatgcgctca accaactctt ccgaaacagc    2460
agcatcaaga gttattttc tgactgtcaa gtttcaacat tcaggtctgt ccccaacagg    2520
caccacaccg gggtggactc cctgtgtaac ttctcgccac tggctcggag agtagacaga    2580
gttgccatct atgaggaatt tctgcggatg acccggaatg gtaccagct gcagaacttc     2640 accctggaca ggagcagtgt ccttgtggat gggtatttc ccaacagaaa tgagcccta     2700 actgggaatt ctgaccttcc cttctgggct gtcatcctca tcggcttggc aggactcctg   2760
ggactcatca catgcctgat ctgcggtgtc ctggtgacca cccgccggcg gaagaaggaa   2820
ggagaataca acgtccagca acagtgccca ggctactacc agtcacacct agacctggag    2880
gatctgcaat gactggaact tgccggtgcc tggggtgcct ttcccccagc cagggtccaa    2940
agaagcttgg ctggggcaga aataaaccat attggtcgga cacaaaaaaa aaaaaa        2996
```

```
<210> SEQ ID NO 463
<211> LENGTH: 3557
<212> TYPE: DNA
<213> ORGANISM: Homo sapiens

<400> SEQUENCE: 463
```

```
gagagggtcc ttcagggtct gcttatgccc ttgttcaaga acaccagtgt cagctctctg      60
tactctggtt gcagactgac cttgctcagg cctgagaagg atggggcagc caccagagtg    120
gatgctgtct gcacccatcg tcctgacccc aaaagccctg gactgacag agagcggctg     180 tactggaagc tgagccagct gacccacggc atcactgagc tgggcccta caccctggac    240
```

```
aggcacagtc tctatgtcaa tggtttcacc catcagagct ctatgacgac caccagaact    300
cctgataacct ccacaatgca cctggcaacc tcgagaactc cagcctccct gtctggacct    360
acgaccgcca gccctctcct ggtgctattc acaattaact tcaccatcac taacctgcgg    420
tatgaggaga acatgcatca ccctggctct agaaagttta acaccacgga gagagtcctt    480
cagggtctgc tcaggcctgt gttcaagaac accagtgttg ccctctgta ctctggctgc    540
agactgacct tgctcaggcc caagaaggat ggggcagcca ccaaagtgga tgccatctgc    600
acctaccgcc ctgatcccaa aagccctgga ctggacagag agcagctata ctgggagctg    660
agccagctaa cccacagcat cactgagctg ggcccctaca ccctggacag ggacagtctc    720
tatgtcaatg gtttcacaca gcggagctct gtgcccacca ctagcattcc tgggaccccc    780
acagtggacc tgggaacatc tgggactcca gtttctaaac ctggtccctc ggctgccagc    840
cctctcctgg tgctattcac tctcaacttc accatcacca acctgcggta tgaggagaac    900
atgcagcacc ctggctccag gaagttcaac accacggaga gggtccttca gggcctgctc    960
aggtccctgt tcaagagcac cagtgttggc cctctgtact ctggctgcag actgactttg   1020
ctcaggcctg aaaaggatgg gacagccact ggagtggatg ccatctgcac ccaccaccct   1080
gaccccaaaa gccctaggct ggacagagag cagctgtatt gggagctgag ccagctgacc   1140
cacaatatca ctgagctggg ccactatgcc ctggacaacg acagcctctt tgtcaatggt   1200
ttcactcatc ggagctctgt gtccaccacc agcactcctg gaccccccac agtgtatctg   1260
ggagcatcta agactccagc ctcgatattt ggccctttcag ctgccagcca tctcctgata   1320
ctattcaccc tcaacttcac catcactaac ctgcggtatg aggagaacat gtggcctggc   1380
tccaggaagt tcaacactac agagagggtc cttcagggcc tgctaaggcc cttgttcaag   1440
aacaccagtg ttggccctct gtactctggc tccaggctga ccttgctcag gccagagaaa   1500
gatggggaag ccaccggagt ggatgccatc tgcacccacc gccctgaccc cacaggccct   1560
gggctggaca gagagcagct gtatttggag ctgagccagc tgacccacag catcactgag   1620
ctgggccccct acacactgga cagggacagt ctctatgtca atggtttcac ccatcggagc   1680
tctgtacccca ccaccagcac cggggtggtc agcgaggagc cattcacact gaacttcacc   1740
atcaacaacc tgcgctacat ggcggacatg ggccaacccg ctccctcaa gttcaacatc   1800
acagacaacg tcatgaagca cctgctcagt cctttgttcc agaggagcag cctgggtgca   1860
cggtacacag gctgcagggt catcgcacta aggtctgtga agaacggtgc tgagacacgg   1920
gtggacctcc tctgcaccta cctgcagccc ctcagcggcc caggtctgcc tatcaagcag   1980
gtgttccatg agctgagcca gcagacccat ggcatcaccc ggctgggccc ctactctctg   2040
gacaaagaca gcctctacct taacggttac aatgaacctg gtctagatga gcctcctaca   2100
actcccaagc cagccaccac attcctgcct cctctgtcag aagccacaac agccatgggg   2160
taccacctga agaccctcac actcaacttc accatctcca atcccagta ttcaccagat   2220
atgggcaagg gctcagctac attcaactcc accgaggggg tccttcagca cctgctcaga   2280
cccttgttcc agaagagcag catgggcccc ttctacttgg gttgccaact gatctccctc   2340
aggcctgaga aggatggggc agccactggt gtggacacca cctgcaccta ccaccctgac   2400
cctgtgggcc ccgggctgga catacagcag ctttactggg agctgagtca gctgacccat   2460
ggtgtcaccc aactgggctt ctatgtcctg gacagggata gcctcttcat caatggctat   2520
gcaccccaga atttatcaat ccggggcgag taccagataa atttccacat tgtcaactgg   2580
```

| | |
|---|---:|
| aacctcagta atccagaccc cacatcctca gagtacatca ccctgctgag ggacatccag | 2640 |
| gacaaggtca ccacactcta caaaggcagt caactacatg acacattccg cttctgcctg | 2700 |
| gtcaccaact tgacgatgga ctccgtgttg gtcactgtca aggcattgtt ctcctccaat | 2760 |
| ttggacccca gcctggtgga gcaagtcttt ctagataaga ccctgaatgc ctcattccat | 2820 |
| tggctgggct ccacctacca gttggtggac atccatgtga cagaaatgga gtcatcagtt | 2880 |
| tatcaaccaa caagcagctc cagcacccag cacttctacc cgaatttcac catcaccaac | 2940 |
| ctaccatatt cccaggacaa agcccagcca ggcaccacca attaccagag gaacaaaagg | 3000 |
| aatattgagg atgcgctcaa ccaactcttc gaaacagca gcatcaagag ttatttttct | 3060 |
| gactgtcaag tttcaacatt caggtctgtc cccaacaggc accacaccgg ggtggactcc | 3120 |
| ctgtgtaact tctcgccact ggctcggaga gtagacagag ttgccatcta tgaggaattt | 3180 |
| ctgcggatga cccggaatgg tacccagctg cagaacttca ccctggacag gagcagtgtc | 3240 |
| cttgtggatg ggtattctcc caacagaaat gagcccttaa ctgggaattc tgaccttccc | 3300 |
| ttctgggctg tcatcttcat cggcttggca ggactcctgg gactcatcac atgcctgatc | 3360 |
| tgcggtgtcc tggtgaccac ccgccggcgg aagaaggaag gagaatacaa cgtccagcaa | 3420 |
| cagtgcccag gctactacca gtcacaccta gacctggagg atctgcaatg actggaactt | 3480 |
| gccggtgcct ggggtgcctt ccccccagcc agggtccaaa gaagcttggc tggggcagaa | 3540 |
| ataaaccata ttggtcg | 3557 |

<210> SEQ ID NO 464
<211> LENGTH: 2712
<212> TYPE: DNA
<213> ORGANISM: Homo sapiens

<400> SEQUENCE: 464

| | |
|---|---:|
| aggacatgcg tcaccctggc tccaggaagt tcaacaccac agagagggtc ctgcagggtc | 60 |
| tgcttggtcc cttgttcaag aactccagtg tcggccctct gtactctggc tgcagactga | 120 |
| tctctctcag gtctgagaag gatggggcag ccactggagt ggatgccatc tgcacccacc | 180 |
| accttaaccc tcaaagcctg gactggacag ggagcagctg tactggcagc tgagccagat | 240 |
| gaccaatggc atcaaagagc tgggccccta caccctggac cggaacagtc tctacgtcaa | 300 |
| tggtttcacc catcggagct ctgggctcac caccagcact ccttggactt ccacagttga | 360 |
| ccttggaacc tcagggactc catccccgt ccccagcccc acaactgctg gccctctcct | 420 |
| ggtgccattc accctaaact tcaccatcac caacctgcag tatgaggagg acatgcatcg | 480 |
| ccctggatct aggaagttca cgccacaga gagggtcctg cagggtctgc ttagtcccat | 540 |
| attcaagaac tccagtgttg gccctctgta ctctggctgc agactgacct ctctcaggcc | 600 |
| cgagaaggat ggggcagcaa ctggaatgga tgctgtctgc ctctaccacc ctaatcccaa | 660 |
| aagacctggg ctggacagag agcagctgta ctggagctga agccagctga cccacaacat | 720 |
| cactgagctg ggcccctaca gcctggacag ggacagtctc tatgtcaatg gtttcaccca | 780 |
| tcagaactct gtgccaccca ccagtactcc tgggacctcc acagtgtact gggcaaccac | 840 |
| tgggactcca tcctccttcc ccggccacac agagcctggc cctctcctga taccattcac | 900 |
| attcaacttt accatcacca acctgcatta tgaggaaaac atgcaacacc ctggttccag | 960 |
| gaagttcaac gccacagaga gggtcctgca gggtctgctt agtcccatat tcaagaactc | 1020 |
| cagtgttggc cctctgtact ctggctgcag actgacctct ctcaggcccg agaaggatgg | 1080 |
| ggcagcaact ggaatggatg ctgtctgtct ctaccgaccc taatcccatc ggacctgggc | 1140 |

```
tggacagaga gcagctgtac tgggagctga gccagctgac ccacgacatc actgagctgg      1200
gccactacag ccctggacag ggacagtctc tatgtcaatg gtttcaccca tcagaactct      1260
gtgcccacca ccagtactcc tgggacctcc acagtgtact gggcaaccac tgggactcca      1320
tcctccttcc ccggccacac agagcctggc cctctcctga taccattcac tttcaacttt      1380
accatcacca acctgcatta tgaggaaaac atgcaacacc tggttccagg aagttcaaca      1440
ccacggagag ggttctgcag ggtctgctca cgcccttgtt caagaacacc agtgttggcc      1500
ctctgtactc tggctgcaga ctgacccttgc tcagacctga aagcaggag gcagccactg      1560 gagtggacac catctgcact caccgccttg accctctaaa ccctggactg gacagagagc      1620
agctatactg ggagctgagc aaactgaccc gtggcatcat cgagctgggc cctacctcc       1680 tggacagagg cagtctctat gtcaatggtt tcacccatcg gaactttgtg cccatcacca      1740
gcactcctgg gacctccaca gtacacctag gaacctctga aactccatcc tccctaccta      1800
gacccatagt gcctggccct ctcctggtgc cattcaccct caacttcacc atcaccaact      1860
tgcagtatga ggaggccatg cgacaccctg gctccaggaa gttcaatacc acggagaggg      1920
tcctacaggg tctgctcagg ccccttgttca agaataccag tatcggcct ctgtactcca      1980 gctgcagact gaccttgctc aggccagaga aggacaaggc agccaccaga gtggatgcca      2040
tctgtaccca ccaccctgac cctcaaagcc ctggactgaa cagagagcag ctgtactggg      2100
agctgagcca gctgacccac ggcatcactg agctgggccc ctacaccctg acaggcaca       2160 gtctctatgt caatggtttc acccatcaga gccccatacc aaccaccagc actcctgata      2220
cctccacaat gcacctggga acctcgagaa ctccagcctc cctgtctgga cctacgaccg      2280 ccagcccttct cctggtgcta ttcacaatta acttcaccat cactaacctg cggtatgagg      2340
agaacatgca tcaccgctgg ctctagaaag tttaacacca cggagagagt ccttcagggt      2400
ctgctcaggc ctgtgttcaa agaacaccag tgttggccct ctgtactctg gctgcagact      2460
gaccttgctc aggcccgaga aggatggggc agccacgcaa agtggatgcc atctgcacct      2520
accgccctga tcccaaaagc cctggactgg acagagagca gctatactgg gagctgagcc      2580
agggtgatgc atgttctcct catatcgcag gttagtgatg gtgaagttaa ttgtgaatag      2640
caccaggaga gggctggcgg tcatgggtcc agacagggag cctggagttc tcgaggttgc      2700
caggtgcatg tc                                                         2712

<210> SEQ ID NO 465
<211> LENGTH: 1175
<212> TYPE: DNA
<213> ORGANISM: Homo sapiens

<400> SEQUENCE: 465
gaggtatgct aactactact attatttagt aggctttgtt agaaacttct gttgttatag        60
tcaagggacg catggaaact ttttatatta ttctctcttt aaatcctgtt gcatatgttt       120
agaagtaggc cttttggaaa tatataaagt tctccacttt tgaacatgtt gtttctttcc       180
cacctccacg acagctgcca gccctctcct ggtgctattc actctcaact tcaccatcac       240
caacctgcgg tatgaggaga acatgcagca ccctggctcc aggaagttca acactacaga       300
gagggtcctt cagggcctgc taaggccctt gttcaagaac accagtgttg ccctctgta       360 ctctggctgc aggctgacct tgctcaggcc agagaaagat ggggaagcca ccggagtgga       420
tgccatctgc acccaccgcc ctgaccccac aggccctggg ctggacagag agcagctgta       480
```

| | |
|---|---|
| tttggagctg agccagctga cccacagcat cactgagctg ggcccctaca cactggacag | 540 |
| ggacagtctc tatgtcaatg gtttcaccca tcggagctct gtacccacca ccagcaccgg | 600 |
| ggtggtcagc gaggagccat tcacactgaa cttcaccatc aacaacctgc gctacatggc | 660 |
| ggacatgggc caacccggct ccctcaagtt caacatcaca gacaacgtca tgaagcacct | 720 |
| gctcagtcct tgttccaga ggagcagcct gggtgcacgg tacacaggct gcagggtcat | 780 |
| cgcactaagg tctgtgaaga cggtgctga cacgggtg gacctcctct gcacctacct | 840 |
| gcagccctc agcggcccag gtctgcctat caagcaggtg ttccatgagc tgagccagca | 900 |
| gacccatggc atcacccggc tgggccccta ctctctggac aaagacagcc tctaccttaa | 960 |
| cggttacaat gaacctggtc cagatgagcc tcctacaact cccaagccag ccaccacatt | 1020 |
| cctgcctcct ctgtcagaag ccacaacagc catggggtac cacctgaaga ccctcacact | 1080 |
| caattcacat ctccaatctc cagtattcac cagatatggg caagggctca aggtacattc | 1140 |
| aatccaccga gggggtcct tcagcaactg gtcag | 1175 |

<210> SEQ ID NO 466
<211> LENGTH: 1959
<212> TYPE: DNA
<213> ORGANISM: Homo sapiens

<400> SEQUENCE: 466

| | |
|---|---|
| catccccagc tcgaacagca gccacagtcc cattcatggt gccattcacc ctcaacttca | 60 |
| actcatcacc aacctgcagt acgaggagga catgcggcac ctggttccag gaagttcaac | 120 |
| gcgcacagag agagaactgc agggtcgtgc tcaaacccta gatcaggaat agcagtctgg | 180 |
| aatacctcta ttcaggctgc agactagcct cactcaggcc agagaaggat agctcagcca | 240 |
| cggcagtgga tgccatctgc acacatcgcc ctgaccctga gacctcgga ctggacagag | 300 |
| agcgactgta ctgggagctg agcaatctga caaatggcat ccaggagctg ggcccctaca | 360 |
| ccctggaccg gaacagtctc tatgtcaatg gtttcaccca tcgaagctct atgcccacca | 420 |
| ccagcactcc tgggacctcc acagtggatg tgggaacctc agggactcca tcctccagcc | 480 |
| ccagccccac gactgctggc cctctcctga tgccgttcac cctcaacttc accatcacca | 540 |
| acctgcagta cgaggaggac atgcgtcgca ctggctccag gaagttcaac accatggaga | 600 |
| gtgtcctgca gggtctgctc aagcccttgt tcaagaacac cagtgttggc cctctgtact | 660 |
| ctggctgcag attgaccttg ctcaggccca gaaagatgg ggcagccact ggagtggatg | 720 |
| ccatctgcac ccaccgcctt gaccccaaaa gccctggact caacagggag cagctgtact | 780 |
| gggagctaag caaactgacc aatgacattg aagagctggg ccctacacc ctggacagga | 840 |
| acagtctcta tgtcaatggt ttcacccatc agagctctgt gtccaccacc agcactcctg | 900 |
| ggacctccac agtggatctc agaacctcag tggactccat cctccctctc cagccccaca | 960 |
| attatgctg ctggccctct cctggtacca ttccccctca acttcaccat caccaacctg | 1020 |
| cagtatgggg aggacatggg tcaccctggc tccaggaagt tcaacaccac agagagggtc | 1080 |
| ctgcagggtc tgcttggtcc catattcaag aacaccagtt tggcccctct gtactctggc | 1140 |
| tgcagactga cctctctcag gtccaagaag gatggagcag ccactggagt ggatgccatc | 1200 |
| tgcatccatc atcttgaccc caaaagccct ggactcaaca gagagcggct gtactgggag | 1260 |
| ctgagccaac tgaccaatgg catcaaagag ctgggcccct acaccctgga caggaacagt | 1320 |
| ctctatgtca atggtttcac ccatcggacc tctgtgccca ccaccagtac tcctgggacc | 1380 |
| tccacagtgt actgggcaac cactgggact ccatcctccc tccccgccac acagagcctg | 1440 |

```
gccctctcct gataccattc acattcaact ttaccatcac ctacctgcat tatagaggaa    1500
aacatgcaac acccgtggtt ccaggaacga tgtcaacacc acaggagagg gttctgcagg    1560
gtcttcgctc acgccattg ttacaagaac accagtagtt ggccctctgt actctggctg     1620
cagaatgacc ttgctcagac ctgagaagca ggaggcaaca cactggaatg acaccatct     1680 gtatccacca gcgttagatc ccatcaggac ctggactgga cagagagcag gctatactgg    1740
gagctagagc cagctgaccc acagcatcac agagctggga ccctacagcc ctggataggg    1800
acagtctcta tgtcaatggc ttcaacccctt ggagctctgt gccaaccacc agcactcctg   1860
ggacctccac agtgcacctg gcaacctctg ggactccatc ctccctgcct ggccacacag    1920
cccctgtccc tctcttgata ccattcaccc tcaacttac                           1959

<210> SEQ ID NO 467
<211> LENGTH: 1636
<212> TYPE: DNA
<213> ORGANISM: Homo sapiens

<400> SEQUENCE: 467
gacctcctct gcacctacct gcagcccctc agcggcccag gtctgcctat caagcaggtg     60
ttccatgagc tgagccagca gacccatggc atcacccggc tgggccccta ctctctggac    120
aaagacagcc tctaccttaa cggttacaat gaacctggtc cagatgagcc tcctacaact    180
cccaagccag ccaccacatt cctgcctcct ctgtcagaag ccacaacagc catggggtac    240
cacctgaaga ccctcacact caacttcacc atctccaatc tccagtattc accagatatg    300
ggcaagggct cagctacatt caactccacc gaggggtcc ttcagcacct gctcagaccc     360
ttgttccaga gagcagcat gggccccttc tacttgggtt gccaactgat ctccctcagg    420
cctgagaagg atggggcagc cactggtgtg gacaccacct gcacctacca ccctgaccct    480
gtgggccccg ggctggacat acagcagctt tactgggagc tgagtcagct gacccatggt    540
gtcacccaac tgggcttcta tgtcctggac agggatagcc tcttcatcaa tggctatgca    600
ccccagaatt tatcaatccg gggcgagtac cagataaatt ccacattgt caactggaac    660 ctcagtaatc cagaccccac atcctcagag tacatcaccc tgctgaggga catccaggac    720
aaggtcacca cactctacaa aggcagtcaa ctacatgaca cattccgctt ctgcctggtc    780
accaacttga cgatggactc cgtgttggtc actgtcaagg cattgttctc ctccaatttg    840
gaccccagcc tggtgagca agtctttcta gataagaccc tgaatgcctc attccattgg    900
ctgggctcca cctaccagtt ggtggacatc catgtgacag aaatggagtc atcagtttat    960
caaccaacaa gcagctccag cacccagcac ttctacctga tttcaccat caccaaccta    1020 ccatattccc aggacaaagc ccagccaggc accaccaatt accagaggaa caaaaggaat    1080
attgaggatg cgctcaacca actcttccga aacagcagca tcaagagtta tttttctgac    1140
tgtcaagttt caacattcag gtctgtcccc aacaggcacc acaccggggt ggactccctg    1200
tgtaacttct cgccactggc tcggagagta gacagagttg ccatctatga ggaatttctg    1260
cggatgaccc ggaatggtac ccagctgcag aacttcaccc tggacaggag cagtgtcctt    1320
gtggatgggt attctcccaa cagaaatgag cccttaactg ggaattctga ccttcccttc    1380
tgggctgtca tcctcatcgg cttggcagga ctcctgggac tcatcacatg cctgatctgc    1440
ggtgtcctgg tgaccacccg ccggcggaag aaggaaggag aatacaacgt ccagcaacag    1500
tgcccaggct actaccagtc acacctagac ctggaggatc tgcaatgact ggaacttgcc    1560
```

| | |
|---|---|
| ggtgcctggg gtgcctttcc cccagccagg gtccaaagaa gcttggctgg ggcagaaata | 1620 |
| aaccatattg gtcgga | 1636 |

<210> SEQ ID NO 468
<211> LENGTH: 231
<212> TYPE: DNA
<213> ORGANISM: Homo sapiens

<400> SEQUENCE: 468

| | |
|---|---|
| actacatgac acattccgct tctgcctggt caccaacttg acaaatggag tcatcagttt | 60 |
| atcaaccaac aagcagctcc agcacccagc acttctacct gaatttcacc atcaccaacc | 120 |
| taccatattc ccaggacaaa gcccagccag gcaccaccaa ttaccagagg aacaaaagga | 180 |
| atattgagga tgcgctcaac caactcttcc gaaacagcag catcgagagt t | 231 |

<210> SEQ ID NO 469
<211> LENGTH: 607
<212> TYPE: DNA
<213> ORGANISM: Homo sapiens

<400> SEQUENCE: 469

| | |
|---|---|
| atgaagagct atcgctgtcc aggacataga agcccagttg ggtgacacca tgggtcagct | 60 |
| gactcagctc ccagtaaagc tgctgtatgt ccagcccggg gcccacaggg tcagggtggt | 120 |
| aggtgcaggt ggtgtccaca ccagtggctg ccccatcctt ctcaggccag gtgctgaagg | 180 |
| accccctcgg tggagttgaa tgtagctgag cccttgccca tatctggtga atactggaga | 240 |
| ttggagatgg tgaagttgag tgtgagggtc ttcaggtggt accccatggc tgttgtggct | 300 |
| tctgacagag gaggcaggaa tgtggtggct ggcttgggag ttgtaggagg ctcatctgga | 360 |
| ccaggttcat tgtaaccgtt aaggtagagg ctgtctttgt ccagagagta ggggcccagc | 420 |
| cgggtgatgc catgggtctg ctggctcagc tcatggaaca cctgcttgat aggcagacct | 480 |
| gggccgctga ggggctgcag gtaggtgcag aggaggtcca cccgtgtctc agcaccgttc | 540 |
| ttcacagacc ttagtgcgat gaccctgcag cctgtgtacc gtgcacccag gctgctcctc | 600 |
| tggaaca | 607 |

<210> SEQ ID NO 470
<211> LENGTH: 981
<212> TYPE: DNA
<213> ORGANISM: Homo sapiens

<400> SEQUENCE: 470

| | |
|---|---|
| ggtaaccaca gctgacccat ggcatcaaag agctgggccc ctacaccctg gacaggaaca | 60 |
| gtctctatgt caatggtttc acccatcgga gctctgtggc ccccaccagc actcctggga | 120 |
| cctccacagt ggaccttggg acctcaggga ctccatcctc cctccccagc cccacaacag | 180 |
| ctgttcctct cctggtgccg ttcaccctca actttaccat caccaatctg cagtatgggg | 240 |
| aggacatgcg tcaccctggc tccaggaagt tcaacaccac agagagggtc ctgcagggtc | 300 |
| tgcttggtcc cttgttcaag aactccagtg tcggccctct gtactctggc tgcagactga | 360 |
| tctctctcag gtctgagaag gatggggcag ccactggagt ggatgccatc tgcacccacc | 420 |
| accttaaccc tcaaagccct ggactggaca gggagcagct gtactggcag ctgagccaga | 480 |
| gaccacaacc tcatttatca cctattctga gacacacaca agttcagcca ttccaactct | 540 |
| ccctgtctcc ccctggtgca tcaaagatgc tgacctcact ggtcatcagt tctgggacag | 600 |
| acagcactac aactttccca acactgacgg agaccccata tgaaccagag acaacagcca | 660 |

```
tacagctcat tcatcctgca gagaccaaca caatggttcc caggacaact cccaagtttt    720
cccatagtaa gtcagacacc acactcccag tagccatcac cagtcctggg ccagaagcca    780
gttcagctgt ttcaacgaca actatctcac ctgatatgtc agatctggtg acctcactgg    840
tccctagttc tgggacagac accagtacaa ccttcccaac attgagtgag accccatatg    900
aaccagagac tacagccacg tggctcactc atcctgcaga aaccagaaca acggtttctg    960
ggacaattcc caacttttcc c                                              981
```

<210> SEQ ID NO 471
<211> LENGTH: 959
<212> TYPE: DNA
<213> ORGANISM: Homo sapiens

<400> SEQUENCE: 471

```
cagatggcat ccactccggt ggcttcccca tctttctctg gcctgagcaa ggtcagcctg     60
cagccagagt acagagggcc aacactggtg ttcttgaaca agggccttag caggccctga    120
aggaccctct ctgtagtgtt gaacttcctg gagccaggcc acatgttctc ctcataccgc    180
aggttagtga tggtgaagtt gagggtgaat agtatcagga gatggctggc agctgaaggg    240
ccaaatatcg aggctggagt cttagatgct cccagataca ctgtgggggt cccaggagtg    300
ctggtggtgg acacagagct ccgatgagtg aaaccattga caaagaggct gtcgttgtcc    360
agggcatagg ggcccagctc agtgatattg tgggtcagct ggctcagctc ccaatacagc    420
tgctctctgt ccagcctagg gcttttgggg tcagggtggt gggtgcagat ggcatccact    480
ccagtggctg tcccatcctt ttcaggcctg agcaaagtca gtctgcagcc agagtacaga    540
gggccaacac tggtgctctt gaacaggac ctgagcaggc cctgaaggac cctctccgtg    600
gtgttgaact tcctggagcc agggtgctgc atgttctcct cataccgcag gttggtgatg    660
gtgaagttga gagtgaatag caccaggaga gggctggcag ccgagggacc aggtttagaa    720
actggagtcc cagatgttcc caggtccact gtgggggtcc caggaatgct agtggtgggc    780
acagagctcc gctgtgtgaa accattgaca tagagactgt ccctgtccag ggtgtagggg    840
cccagctcag tgatgctgtg ggttagctgg ctcagctccc agtatagctg ctctctgtcc    900
agtccagggc ttttgggatc agggcggtag gtgcagatgg catccacttt ggtggctgc    959
```

<210> SEQ ID NO 472
<211> LENGTH: 1315
<212> TYPE: DNA
<213> ORGANISM: Homo sapiens

<400> SEQUENCE: 472

```
ccaccgtctt gaccccaaaa gccctggagt ggacagggag cagctatact gggagctgag     60
ccagctgacc aatggcatca aagagctggg ccctacacc tggacaggaa cagtctctat    120
gtcaatggtt tcacccatcg gacctctgtg cccaccacca gcactcctgg gacctccaca    180
gtggaccttg gaacctcagg gactccattc tccctcccaa gccccgcaac tgctggccct    240
ctcctggtgc tgttcaccct caacttcacc atcaccaacc tgaagtatga ggaggacatg    300
catcgccctg gctccaggaa gttcaacacc actgagaggg tcctgcagac tctgcttggt    360
cctatgttca agaacaccag tgttggcctt ctgtactctg gctgcagact gaccttgctc    420
aggtccgaga aggatggagc agccactgga gtggatgcca tctgcaccca ccgtcttgac    480
cccaaaagcc ctggagtgga cagggagcag ctatactggg agctgagcca gctgaccaat    540
```

| | |
|---|---:|
| ggcatcaaag agctgggccc ctacaccctg gacaggaaca gtctctatgt caatggtttc | 600 |
| acccattgga tccctgtgcc caccagcagc actcctggga cctccacagt ggaccttggg | 660 |
| tcagggactc catcctccct ccccagcccc acaactgctg ccctctcct ggtgccgttc | 720 |
| accctcaact tcaccatcac caacctgaag tacgaggagg acatgcattg ccctggctcc | 780 |
| aggaagttca acaccacaga gagagtcctg cagagtctgc ttggtcccat gttcaagaac | 840 |
| accagtgttg gccctctgta ctctggctgc agactgacct tgctcaggtc cgagaaggat | 900 |
| ggagcagcca ctggagtgga tgccatctgc acccaccgtc ttgacccaa aagcctggag | 960 |
| tggacaggga gcagctatac tgggagctga gccagctgac caatgccatc aaagagctgg | 1020 |
| gtccctacac cctggacagc aacagtcttc tatgtcaatg gtttcaccca tcagacctct | 1080 |
| gcgcccaaca ccagcactcc tgggacctcc acagtggacc ttgggacctc agggactcca | 1140 |
| tcctccctcc ccagccctac atctgctggc cctctcctgg tgccattcac cctcaacttc | 1200 |
| accatcacca acctgcagta cgaggaggac atgcatcacc caggctccag gaagttcaac | 1260 |
| accacggagc gggtcctgca gggtctgctt ggtcccatgt tcaagaacac tacga | 1315 |

<210> SEQ ID NO 473
<211> LENGTH: 689
<212> TYPE: DNA
<213> ORGANISM: Homo sapiens

<400> SEQUENCE: 473

| | |
|---|---:|
| acggcatcag gagagggcca gcagtcgtgg ggctggggct ggaggatgga gtccctgagg | 60 |
| ttcccacatc cactgtggag gtcccaggag tgctggtggt gggcatagag cttcgatggg | 120 |
| tgaaaccatt gacatagaga ctgttccggt ccagggtgta ggggcccagc tcagtgatgc | 180 |
| cgtgggtcag ctggctcagc tcccagtaca gctgctctct gttcagtcca gggctttgag | 240 |
| ggtcagggtg gtgggtacag atggcatcca ctctggtggc tgccttgtcc ttctctggcc | 300 |
| ttgagcaagg tcagtctgca gcctgagagc taacagaggt ccgataactg gtattcttga | 360 |
| acaagggcct agagcagaac cctgtaggac catcgccgtg gtatatgaac ttcctagagc | 420 |
| caggatttcg cacggccatc actcatactg caacttgctg atggcaaagt tgaggataaa | 480 |
| cggcaccagg agagggccag ccacttatgg gtctaggtag ggaggatgga gtttcagagg | 540 |
| ttctcgagat ccactgtgga ggtcccagga gtgctggtgg tggacacaga gctctgatgg | 600 |
| gtgaaaccat tgacatagag actgttcctg tccagggtgt aggggcccag ctcttcaatg | 660 |
| tcattggtca gtttgcttag ctcccagta | 689 |

<210> SEQ ID NO 474
<211> LENGTH: 495
<212> TYPE: DNA
<213> ORGANISM: Homo sapiens

<400> SEQUENCE: 474

| | |
|---|---:|
| gtggatatga gttgaatact cactgctggt ggtggacaca gagctctgat gggtgaaacc | 60 |
| tgcatagaga aggagggagg agagtgggta agagacaagg agaggtgggg gaccaaatgg | 120 |
| aggtcaatgc taccctggtg caatgaaccg agtttcatgg tacagggaca attgaagatt | 180 |
| ttctatcagc atcctcacat caggaaagaa tgccctgagg gaacacagtc catgatggta | 240 |
| aggaaaccat gaagtccaga ccttagtcat cccatgtaga gcacatgaca gaattttcaa | 300 |
| aggccaggca gggagtgtga cctctagtta gagattagag gctgcccagc aaggggggaag | 360 |
| agatttcaac cacatcacag ccactcacca ttgacataga gactgttcct gtccagggtg | 420 |

```
tagggggccca gctcttcaat gtcattggtc agtttgctta gctcccagta cagctgctcc    480
ctgttgagtc caggg                                                      495

<210> SEQ ID NO 475
<211> LENGTH: 192
<212> TYPE: DNA
<213> ORGANISM: Homo sapiens

<400> SEQUENCE: 475
agtgcccagg ctactaccag tcacacctag acctggagga tctgcaatga ctggaacttg    60
ccggtgcctg gggatagcct cttcatcaat ggctatgcac cccagaattt atcaatccgg   120
ggcgagtacc agataaattt ccacattgtc aactggaacc tcagtaatcc agacccaca    180 tcctcagagt ac                                                        192

<210> SEQ ID NO 476
<211> LENGTH: 500
<212> TYPE: DNA
<213> ORGANISM: Homo sapiens

<400> SEQUENCE: 476
ccggtggctg ccccacgttt ttcaggcctg agcaaggtca gtctgcagcc agagtacaga    60
gggccaacac tggtgctctt gaacaagggc ttgagcagac cctgcaggac tctctccgtg   120
gtgttgaact tcctggaacc agggtgacgc atgtcctcct catactgcag gttggtgata   180
gtgaagttga gggtgaatgg caccaggaga gggccagggc tgtgtggcca gggagggagg   240
ctggagtccc agaggtttcc aggtgcactg cagaggtccc aggaatactg gtggttggca   300
cagagctccg atgggtgaag ccattgacat agagactgtc cctgtccagg tgtaggggcc   360
cagctctgta acgctgttgg tcagctggct cagctcccag tatagccgct ctctgtccag   420
tccaggacca gtgggatcaa ggcggagggt gcagatggcg tccactccag tggctgcccc   480
atgtttctca ggtctgagca                                                500

<210> SEQ ID NO 477
<211> LENGTH: 191
<212> TYPE: DNA
<213> ORGANISM: Homo sapiens

<400> SEQUENCE: 477
gaggtatgct aactactact attatttagt aggctttgtt agaaacttct gttgttatag    60
tcaagggacg catggaaact ttttatatta ttctctcttt aaatcctgtt gcatatgttt   120
agaagtaggc cttttggaaa tatataaagt tctccacttt tgaacatgtt gtttctttcc   180
cacctccacg a                                                         191

<210> SEQ ID NO 478
<211> LENGTH: 914
<212> TYPE: PRT
<213> ORGANISM: Homo sapiens

<400> SEQUENCE: 478

Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
                20                  25                  30

Asn Leu Val Pro Arg Leu Pro Ala Leu Ser Trp Cys Tyr Ser Leu Ser
            35                  40                  45
```

-continued

```
Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365

Pro Leu Phe Gln Arg Ser Ser Leu Gly Ala Arg Tyr Thr Gly Cys Arg
    370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
        435                 440                 445

Asn Glu Pro Gly Pro Asp Glu Pro Pro Thr Thr Pro Lys Pro Ala Thr
    450                 455                 460
```

```
Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
            485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
            515                 520                 525

Phe Tyr Leu Gly Cys Gln Leu Ile Ser Leu Arg Pro Glu Lys Asp Gly
            530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
            565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
            595                 600                 605

Tyr Gln Ile Asn Phe His Ile Val Asn Trp Asn Leu Ser Asn Pro Asp
610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
            645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
            675                 680                 685

Leu Asp Lys Thr Leu Asn Ala Ser Phe His Trp Leu Gly Ser Thr Tyr
690                 695                 700

Gln Leu Val Asp Ile His Val Thr Glu Met Glu Ser Ser Val Tyr Gln
705                 710                 715                 720

Pro Thr Ser Ser Ser Thr Gln His Phe Tyr Leu Asn Phe Thr Ile
            725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Leu Asn Gln Leu Phe
            755                 760                 765

Arg Asn Ser Ser Ile Lys Ser Tyr Phe Ser Asp Cys Gln Val Ser Thr
770                 775                 780

Phe Arg Ser Val Pro Asn Arg His His Thr Gly Val Asp Ser Leu Cys
785                 790                 795                 800

Asn Phe Ser Pro Leu Ala Arg Arg Val Asp Arg Val Ala Ile Tyr Glu
            805                 810                 815

Glu Phe Leu Arg Met Thr Arg Asn Gly Thr Gln Leu Gln Asn Phe Thr
            820                 825                 830

Leu Asp Arg Ser Ser Val Leu Val Asp Gly Tyr Phe Pro Asn Arg Asn
            835                 840                 845

Glu Pro Leu Thr Gly Asn Ser Asp Leu Pro Phe Trp Ala Val Ile Leu
            850                 855                 860

Ile Gly Leu Ala Gly Leu Leu Gly Leu Ile Thr Cys Leu Ile Cys Gly
865                 870                 875                 880

Val Leu Val Thr Thr Arg Arg Arg Lys Lys Glu Gly Glu Tyr Asn Val
```

885                 890                 895
Gln Gln Gln Cys Pro Gly Tyr Tyr Gln Ser His Leu Asp Leu Glu Asp
                900                 905                 910

Leu Gln

<210> SEQ ID NO 479
<211> LENGTH: 1148
<212> TYPE: PRT
<213> ORGANISM: Homo sapiens

<400> SEQUENCE: 479

Met Pro Leu Phe Lys Asn Thr Ser Val Ser Leu Tyr Ser Gly Cys
 1               5                  10                  15

Arg Leu Thr Leu Leu Arg Pro Glu Lys Asp Gly Ala Ala Thr Arg Val
                20                  25                  30

Asp Ala Val Cys Thr His Arg Pro Asp Pro Lys Ser Pro Gly Leu Asp
                35                  40                  45

Arg Glu Arg Leu Tyr Trp Lys Leu Ser Gln Leu Thr His Gly Ile Thr
50                  55                  60

Glu Leu Gly Pro Tyr Thr Leu Asp Arg His Ser Leu Tyr Val Asn Gly
65                  70                  75                  80

Phe Thr His Gln Ser Ser Met Thr Thr Thr Arg Thr Pro Asp Thr Ser
                85                  90                  95

Thr Met His Leu Ala Thr Ser Arg Thr Pro Ala Ser Leu Ser Gly Pro
                100                 105                 110

Thr Thr Ala Ser Pro Leu Leu Val Leu Phe Thr Ile Asn Phe Thr Ile
                115                 120                 125

Thr Asn Leu Arg Tyr Glu Glu Asn Met His His Pro Gly Ser Arg Lys
            130                 135                 140

Phe Asn Thr Thr Glu Arg Val Leu Gln Gly Leu Leu Arg Pro Val Phe
145                 150                 155                 160

Lys Asn Thr Ser Val Gly Pro Leu Tyr Ser Gly Cys Arg Leu Thr Leu
                165                 170                 175

Leu Arg Pro Lys Lys Asp Gly Ala Ala Thr Lys Val Asp Ala Ile Cys
                180                 185                 190

Thr Tyr Arg Pro Asp Pro Lys Ser Pro Gly Leu Asp Arg Glu Gln Leu
                195                 200                 205

Tyr Trp Glu Leu Ser Gln Leu Thr His Ser Ile Thr Glu Leu Gly Pro
            210                 215                 220

Tyr Thr Leu Asp Arg Asp Ser Leu Tyr Val Asn Gly Phe Thr Gln Arg
225                 230                 235                 240

Ser Ser Val Pro Thr Thr Ser Ile Pro Gly Thr Pro Thr Val Asp Leu
                245                 250                 255

Gly Thr Ser Gly Thr Pro Val Ser Lys Pro Gly Pro Ser Ala Ala Ser
                260                 265                 270

Pro Leu Leu Val Leu Phe Thr Leu Asn Phe Thr Ile Thr Asn Leu Arg
                275                 280                 285

Tyr Glu Glu Asn Met Gln His Pro Gly Ser Arg Lys Phe Asn Thr Thr
                290                 295                 300

Glu Arg Val Leu Gln Gly Leu Leu Arg Ser Leu Phe Lys Ser Thr Ser
305                 310                 315                 320

Val Gly Pro Leu Tyr Ser Gly Cys Arg Leu Thr Leu Leu Arg Pro Glu
                325                 330                 335

Lys Asp Gly Thr Ala Thr Gly Val Asp Ala Ile Cys Thr His His Pro

-continued

```
                340                 345                 350
Asp Pro Lys Ser Pro Arg Leu Asp Arg Glu Gln Leu Tyr Trp Glu Leu
            355                 360                 365
Ser Gln Leu Thr His Asn Ile Thr Glu Leu Gly His Tyr Ala Leu Asp
        370                 375                 380
Asn Asp Ser Leu Phe Val Asn Gly Phe Thr His Arg Ser Ser Val Ser
385                 390                 395                 400
Thr Thr Ser Thr Pro Gly Thr Pro Thr Val Tyr Leu Gly Ala Ser Lys
                405                 410                 415
Thr Pro Ala Ser Ile Phe Gly Pro Ser Ala Ser His Leu Leu Ile
            420                 425                 430
Leu Phe Thr Leu Asn Phe Thr Ile Thr Asn Leu Arg Tyr Glu Glu Asn
        435                 440                 445
Met Trp Pro Gly Ser Arg Lys Phe Asn Thr Thr Glu Arg Val Leu Gln
    450                 455                 460
Gly Leu Leu Arg Pro Leu Phe Lys Asn Thr Ser Val Gly Pro Leu Tyr
465                 470                 475                 480
Ser Gly Ser Arg Leu Thr Leu Leu Arg Pro Glu Lys Asp Gly Glu Ala
                485                 490                 495
Thr Gly Val Asp Ala Ile Cys Thr His Arg Pro Asp Pro Thr Gly Pro
            500                 505                 510
Gly Leu Asp Arg Glu Gln Leu Tyr Leu Glu Leu Ser Gln Leu Thr His
        515                 520                 525
Ser Ile Thr Glu Leu Gly Pro Tyr Thr Leu Asp Arg Asp Ser Leu Tyr
    530                 535                 540
Val Asn Gly Phe Thr His Arg Ser Ser Val Pro Thr Thr Ser Thr Gly
545                 550                 555                 560
Val Val Ser Glu Glu Pro Phe Thr Leu Asn Phe Thr Ile Asn Asn Leu
                565                 570                 575
Arg Tyr Met Ala Asp Met Gly Gln Pro Gly Ser Leu Lys Phe Asn Ile
            580                 585                 590
Thr Asp Asn Val Met Lys His Leu Leu Ser Pro Leu Phe Gln Arg Ser
        595                 600                 605
Ser Leu Gly Ala Arg Tyr Thr Gly Cys Arg Val Ile Ala Leu Arg Ser
    610                 615                 620
Val Lys Asn Gly Ala Glu Thr Arg Val Asp Leu Leu Cys Thr Tyr Leu
625                 630                 635                 640
Gln Pro Leu Ser Gly Pro Gly Leu Pro Ile Lys Gln Val Phe His Glu
                645                 650                 655
Leu Ser Gln Gln Thr His Gly Ile Thr Arg Leu Gly Pro Tyr Ser Leu
            660                 665                 670
Asp Lys Asp Ser Leu Tyr Leu Asn Gly Tyr Asn Glu Pro Gly Leu Asp
        675                 680                 685
Glu Pro Pro Thr Thr Pro Lys Pro Ala Thr Thr Phe Leu Pro Pro Leu
    690                 695                 700
Ser Glu Ala Thr Ala Met Gly Tyr His Leu Lys Thr Leu Thr Leu
705                 710                 715                 720
Asn Phe Thr Ile Ser Asn Leu Gln Tyr Ser Pro Asp Met Gly Lys Gly
                725                 730                 735
Ser Ala Thr Phe Asn Ser Thr Glu Gly Val Leu Gln His Leu Leu Arg
            740                 745                 750
Pro Leu Phe Gln Lys Ser Ser Met Gly Pro Phe Tyr Leu Gly Cys Gln
        755                 760                 765
```

-continued

```
Leu Ile Ser Leu Arg Pro Glu Lys Asp Gly Ala Thr Gly Val Asp
        770                 775                 780

Thr Thr Cys Thr Tyr His Pro Asp Pro Val Gly Pro Gly Leu Asp Ile
785                 790                 795                 800

Gln Gln Leu Tyr Trp Glu Leu Ser Gln Leu Thr His Gly Val Thr Gln
                805                 810                 815

Leu Gly Phe Tyr Val Leu Asp Arg Asp Ser Leu Phe Ile Asn Gly Tyr
            820                 825                 830

Ala Pro Gln Asn Leu Ser Ile Arg Gly Glu Tyr Gln Ile Asn Phe His
        835                 840                 845

Ile Val Asn Trp Asn Leu Ser Asn Pro Asp Pro Thr Ser Ser Glu Tyr
850                 855                 860

Ile Thr Leu Leu Arg Asp Ile Gln Asp Lys Val Thr Thr Leu Tyr Lys
865                 870                 875                 880

Gly Ser Gln Leu His Asp Thr Phe Arg Phe Cys Leu Val Thr Asn Leu
                885                 890                 895

Thr Met Asp Ser Val Leu Val Thr Val Lys Ala Leu Phe Ser Ser Asn
            900                 905                 910

Leu Asp Pro Ser Leu Val Glu Gln Val Phe Leu Asp Lys Thr Leu Asn
        915                 920                 925

Ala Ser Phe His Trp Leu Gly Ser Thr Tyr Gln Leu Val Asp Ile His
    930                 935                 940

Val Thr Glu Met Glu Ser Ser Val Tyr Gln Pro Thr Ser Ser Ser Ser
945                 950                 955                 960

Thr Gln His Phe Tyr Pro Asn Phe Thr Ile Thr Asn Leu Pro Tyr Ser
                965                 970                 975

Gln Asp Lys Ala Gln Pro Gly Thr Thr Asn Tyr Gln Arg Asn Lys Arg
            980                 985                 990

Asn Ile Glu Asp Ala Leu Asn Gln Leu Phe Arg Asn Ser Ser Ile Lys
        995                 1000                1005

Ser Tyr Phe Ser Asp Cys Gln Val Ser Thr Phe Arg Ser Val Pro Asn
    1010                1015                1020

Arg His His Thr Gly Val Asp Ser Leu Cys Asn Phe Ser Pro Leu Ala
1025                1030                1035                1040

Arg Arg Val Asp Arg Val Ala Ile Tyr Glu Glu Phe Leu Arg Met Thr
                1045                1050                1055

Arg Asn Gly Thr Gln Leu Gln Asn Phe Thr Leu Asp Arg Ser Ser Val
            1060                1065                1070

Leu Val Asp Gly Tyr Ser Pro Asn Arg Asn Glu Pro Leu Thr Gly Asn
        1075                1080                1085

Ser Asp Leu Pro Phe Trp Ala Val Ile Phe Ile Gly Leu Ala Gly Leu
    1090                1095                1100

Leu Gly Leu Ile Thr Cys Leu Ile Cys Gly Val Leu Val Thr Thr Arg
1105                1110                1115                1120

Arg Arg Lys Lys Glu Gly Glu Tyr Asn Val Gln Gln Gln Cys Pro Gly
                1125                1130                1135

Tyr Tyr Gln Ser His Leu Asp Leu Glu Asp Leu Gln
            1140                1145

<210> SEQ ID NO 480
<211> LENGTH: 230
<212> TYPE: PRT
<213> ORGANISM: Homo sapiens
```

-continued

```
<400> SEQUENCE: 480

Met His Arg Pro Gly Ser Arg Lys Phe Asn Thr Thr Glu Arg Val Leu
1               5                   10                  15

Gln Thr Leu Leu Gly Pro Met Phe Lys Asn Thr Ser Val Gly Leu Leu
            20                  25                  30

Tyr Ser Gly Cys Arg Leu Thr Leu Leu Arg Ser Glu Lys Asp Gly Ala
        35                  40                  45

Ala Thr Gly Val Asp Ala Ile Cys Thr His Arg Leu Asp Pro Lys Ser
    50                  55                  60

Pro Gly Val Asp Arg Glu Gln Leu Tyr Trp Glu Leu Ser Gln Leu Thr
65                  70                  75                  80

Asn Gly Ile Lys Glu Leu Gly Pro Tyr Thr Leu Asp Arg Asn Ser Leu
                85                  90                  95

Tyr Val Asn Gly Phe Thr His Trp Ile Pro Val Pro Thr Ser Ser Thr
            100                 105                 110

Pro Gly Thr Ser Thr Val Asp Leu Gly Ser Gly Thr Pro Ser Ser Leu
        115                 120                 125

Pro Ser Pro Thr Thr Ala Gly Pro Leu Leu Val Pro Phe Thr Leu Asn
130                 135                 140

Phe Thr Ile Thr Asn Leu Lys Tyr Glu Glu Asp Met His Cys Pro Gly
145                 150                 155                 160

Ser Arg Lys Phe Asn Thr Thr Glu Arg Val Leu Gln Ser Leu Leu Gly
                165                 170                 175

Pro Met Phe Lys Asn Thr Ser Val Gly Pro Leu Tyr Ser Gly Cys Arg
            180                 185                 190

Leu Thr Leu Leu Arg Ser Glu Lys Asp Gly Ala Ala Thr Gly Val Asp
        195                 200                 205

Ala Ile Cys Thr His Arg Leu Asp Pro Lys Ser Leu Glu Trp Thr Gly
    210                 215                 220

Ser Ser Tyr Thr Gly Ser
225                 230

<210> SEQ ID NO 481
<211> LENGTH: 210
<212> TYPE: PRT
<213> ORGANISM: Homo sapiens

<400> SEQUENCE: 481

Met Gln His Pro Gly Ser Arg Lys Phe Asn Thr Thr Glu Arg Val Leu
1               5                   10                  15

Gln Gly Leu Leu Arg Ser Leu Phe Lys Ser Thr Ser Val Gly Pro Leu
            20                  25                  30

Tyr Ser Gly Cys Arg Leu Thr Leu Leu Arg Pro Glu Lys Asp Gly Thr
        35                  40                  45

Ala Thr Gly Val Asp Ala Ile Cys Thr His His Pro Asp Pro Lys Ser
    50                  55                  60

Pro Arg Leu Asp Arg Glu Gln Leu Tyr Trp Glu Leu Ser Gln Leu Thr
65                  70                  75                  80

His Asn Ile Thr Glu Leu Gly Pro Tyr Ala Leu Asp Asn Asp Ser Leu
                85                  90                  95

Phe Val Asn Gly Phe Thr His Arg Ser Ser Val Ser Thr Thr Ser Thr
            100                 105                 110

Pro Gly Thr Pro Thr Val Tyr Leu Gly Ala Ser Lys Thr Pro Ala Ser
        115                 120                 125
```

```
Ile Phe Gly Pro Ser Ala Ala Ser His Leu Leu Ile Leu Phe Thr Leu
            130                 135                 140

Asn Phe Thr Ile Thr Asn Leu Arg Tyr Glu Glu Asn Met Trp Pro Gly
145                 150                 155                 160

Ser Arg Lys Phe Asn Thr Thr Glu Arg Val Leu Gln Gly Leu Leu Arg
                165                 170                 175

Pro Leu Phe Lys Asn Thr Ser Val Gly Pro Leu Tyr Ser Gly Cys Arg
                180                 185                 190

Leu Thr Leu Leu Arg Pro Glu Lys Asp Gly Glu Ala Thr Gly Val Asp
            195                 200                 205

Ala Ile
    210

<210> SEQ ID NO 482
<211> LENGTH: 97
<212> TYPE: PRT
<213> ORGANISM: Homo sapiens

<400> SEQUENCE: 482

Met Ser Met Val Ser His Ser Gly Ala Leu Cys Pro Pro Leu Ala Phe
1               5                   10                  15

Leu Gly Pro Pro Gln Trp Thr Trp Glu His Leu Gly Leu Gln Phe Leu
                20                  25                  30

Asn Leu Val Pro Arg Leu Pro Ala Leu Ser Trp Cys Tyr Ser Leu Ser
            35                  40                  45

Thr Ser Pro Ser Pro Thr Cys Gly Met Arg Arg Thr Cys Ser Thr Leu
        50                  55                  60

Ala Pro Gly Ser Ser Thr Pro Arg Arg Gly Ser Phe Arg Ala Cys Ser
65                  70                  75                  80

Gly Pro Cys Ser Arg Ala Pro Val Leu Ala Leu Cys Thr Leu Ala Ala
                85                  90                  95

Asp

<210> SEQ ID NO 483
<211> LENGTH: 438
<212> TYPE: PRT
<213> ORGANISM: Homo sapiens

<400> SEQUENCE: 483

Met Gly Tyr His Leu Lys Thr Leu Thr Leu Asn Phe Thr Ile Ser Asn
1               5                   10                  15

Leu Gln Tyr Ser Pro Asp Met Gly Lys Gly Ser Ala Thr Phe Asn Ser
                20                  25                  30

Thr Glu Gly Val Leu Gln His Leu Leu Arg Pro Leu Phe Gln Lys Ser
            35                  40                  45

Ser Met Gly Pro Phe Tyr Leu Gly Cys Gln Leu Ile Ser Leu Arg Pro
        50                  55                  60

Glu Lys Asp Gly Ala Ala Thr Gly Val Asp Thr Thr Cys Thr Tyr His
65                  70                  75                  80

Pro Asp Pro Val Gly Pro Gly Leu Asp Ile Gln Gln Leu Tyr Trp Glu
                85                  90                  95

Leu Ser Gln Leu Thr His Gly Val Thr Gln Leu Gly Phe Tyr Val Leu
                100                 105                 110

Asp Arg Asp Ser Leu Phe Ile Asn Gly Tyr Ala Pro Gln Asn Leu Ser
            115                 120                 125

Ile Arg Gly Glu Tyr Gln Ile Asn Phe His Ile Val Asn Trp Asn Leu
```

-continued

```
            130                 135                 140
Ser Asn Pro Asp Pro Thr Ser Ser Glu Tyr Ile Thr Leu Leu Arg Asp
145                 150                 155                 160

Ile Gln Asp Lys Val Thr Thr Leu Tyr Lys Gly Ser Gln Leu His Asp
                165                 170                 175

Thr Phe Arg Phe Cys Leu Val Thr Asn Leu Thr Met Asp Ser Val Leu
            180                 185                 190

Val Thr Val Lys Ala Leu Phe Ser Ser Asn Leu Asp Pro Ser Leu Val
        195                 200                 205

Glu Gln Val Phe Leu Asp Lys Thr Leu Asn Ala Ser Phe His Trp Leu
210                 215                 220

Gly Ser Thr Tyr Gln Leu Val Asp Ile His Val Thr Glu Met Glu Ser
225                 230                 235                 240

Ser Val Tyr Gln Pro Thr Ser Ser Ser Thr Gln His Phe Tyr Leu
                245                 250                 255

Asn Phe Thr Ile Thr Asn Leu Pro Tyr Ser Gln Asp Lys Ala Gln Pro
            260                 265                 270

Gly Thr Thr Asn Tyr Gln Arg Asn Lys Arg Asn Ile Glu Asp Ala Leu
        275                 280                 285

Asn Gln Leu Phe Arg Asn Ser Ser Ile Lys Ser Tyr Phe Ser Asp Cys
290                 295                 300

Gln Val Ser Thr Phe Arg Ser Val Pro Asn Arg His His Thr Gly Val
305                 310                 315                 320

Asp Ser Leu Cys Asn Phe Ser Pro Leu Ala Arg Arg Val Asp Arg Val
                325                 330                 335

Ala Ile Tyr Glu Glu Phe Leu Arg Met Thr Arg Asn Gly Thr Gln Leu
            340                 345                 350

Gln Asn Phe Thr Leu Asp Arg Ser Ser Val Leu Val Asp Gly Tyr Ser
        355                 360                 365

Pro Asn Arg Asn Glu Pro Leu Thr Gly Asn Ser Asp Leu Pro Phe Trp
370                 375                 380

Ala Val Ile Leu Ile Gly Leu Ala Gly Leu Leu Gly Leu Ile Thr Cys
385                 390                 395                 400

Leu Ile Cys Gly Val Leu Val Thr Thr Arg Arg Arg Lys Lys Glu Gly
                405                 410                 415

Glu Tyr Asn Val Gln Gln Gln Cys Pro Gly Tyr Tyr Gln Ser His Leu
            420                 425                 430

Asp Leu Glu Asp Leu Gln
        435

<210> SEQ ID NO 484
<211> LENGTH: 216
<212> TYPE: PRT
<213> ORGANISM: Homo sapiens

<400> SEQUENCE: 484

Met Thr Leu Lys Ser Trp Ala Pro Thr Pro Trp Thr Gly Thr Val Ser
1               5                   10                  15

Met Ser Met Val Ser Pro Ile Arg Ala Leu Cys Pro Pro Ala Leu
            20                  25                  30

Leu Gly Pro Pro Gln Trp Ile Ser Glu Pro Gln Trp Thr Pro Ser Ser
        35                  40                  45

Leu Ser Ser Pro Thr Ile Met Ala Ala Gly Pro Leu Leu Val Pro Phe
    50                  55                  60
```

```
Thr Leu Asn Phe Thr Ile Thr Asn Leu Gln Tyr Gly Glu Asp Met Gly
 65                  70                  75                  80

His Pro Gly Ser Arg Lys Phe Asn Thr Thr Glu Arg Val Leu Gln Gly
             85                  90                  95

Leu Leu Gly Pro Ile Phe Lys Asn Thr Ser Val Gly Pro Leu Tyr Ser
            100                 105                 110

Gly Cys Arg Leu Thr Ser Leu Arg Ser Lys Lys Asp Gly Ala Ala Thr
            115                 120                 125

Gly Val Asp Ala Ile Cys Ile His Leu Asp Pro Lys Ser Pro Gly
130                 135                 140

Leu Asn Arg Glu Arg Leu Tyr Trp Glu Leu Ser Gln Leu Thr Asn Gly
145                 150                 155                 160

Ile Lys Glu Leu Gly Pro Tyr Thr Leu Asp Arg Asn Ser Leu Tyr Val
                165                 170                 175

Asn Gly Phe Thr His Arg Thr Ser Val Pro Thr Thr Ser Thr Pro Gly
            180                 185                 190

Thr Ser Thr Val Tyr Trp Ala Thr Gly Thr Pro Ser Ser Leu Pro
            195                 200                 205

Ala Thr Gln Ser Leu Ala Leu Ser
210                 215

<210> SEQ ID NO 485
<211> LENGTH: 268
<212> TYPE: PRT
<213> ORGANISM: Homo sapiens

<400> SEQUENCE: 485

Met Pro Thr Thr Ser Thr Pro Gly Thr Ser Thr Val Asp Val Gly Thr
 1               5                  10                  15

Ser Gly Thr Pro Ser Ser Pro Ser Pro Thr Thr Ala Gly Pro Leu
             20                  25                  30

Leu Met Pro Phe Thr Leu Asn Phe Thr Ile Thr Asn Leu Gln Tyr Glu
            35                  40                  45

Glu Asp Met Arg Arg Thr Gly Ser Arg Lys Phe Asn Thr Met Glu Ser
 50                  55                  60

Val Leu Gln Gly Leu Leu Lys Pro Leu Phe Lys Asn Thr Ser Val Gly
 65                  70                  75                  80

Pro Leu Tyr Ser Gly Cys Arg Leu Thr Leu Arg Pro Lys Lys Asp
                 85                  90                  95

Gly Ala Ala Thr Gly Val Asp Ala Ile Cys Thr His Arg Leu Asp Pro
            100                 105                 110

Lys Ser Pro Gly Leu Asn Arg Glu Gln Leu Tyr Trp Glu Leu Ser Lys
            115                 120                 125

Leu Thr Asn Asp Ile Glu Glu Leu Gly Pro Tyr Thr Leu Asp Arg Asn
130                 135                 140

Ser Leu Tyr Val Asn Gly Phe Thr His Gln Ser Ser Val Ser Thr Thr
145                 150                 155                 160

Ser Thr Pro Gly Thr Ser Thr Val Asp Leu Arg Thr Ser Val Asp Ser
            165                 170                 175

Ile Leu Pro Leu Gln Pro His Asn Tyr Gly Cys Trp Pro Ser Pro Gly
            180                 185                 190

Thr Ile His Pro Gln Leu His His His Gln Pro Ala Val Trp Gly Gly
            195                 200                 205

His Gly Ser Pro Trp Leu Gln Glu Val Gln His Arg Glu Gly Pro
210                 215                 220
```

```
Ala Gly Ser Ala Trp Ser His Ile Gln Glu His Gln Cys Trp Pro Ser
225                 230                 235                 240

Val Leu Trp Leu Gln Thr Asp Leu Ser Gln Val Gln Glu Gly Trp Ser
            245                 250                 255

Ser His Trp Ser Gly Cys His Leu His Pro Ser Ser
        260                 265
```

<210> SEQ ID NO 486
<211> LENGTH: 304
<212> TYPE: PRT
<213> ORGANISM: Homo sapiens

<400> SEQUENCE: 486

```
Met Gln His Pro Gly Ser Arg Lys Phe Asn Thr Thr Glu Arg Val Leu
 1               5                  10                  15

Gln Gly Leu Leu Arg Pro Leu Phe Lys Asn Thr Ser Val Gly Pro Leu
            20                  25                  30

Tyr Ser Gly Cys Arg Leu Thr Leu Leu Arg Pro Glu Lys Asp Gly Glu
        35                  40                  45

Ala Thr Gly Val Asp Ala Ile Cys Thr His Arg Pro Asp Pro Thr Gly
    50                  55                  60

Pro Gly Leu Asp Arg Glu Gln Leu Tyr Leu Glu Leu Ser Gln Leu Thr
65                  70                  75                  80

His Ser Ile Thr Glu Leu Gly Pro Tyr Thr Leu Asp Arg Asp Ser Leu
                85                  90                  95

Tyr Val Asn Gly Phe Thr His Arg Ser Ser Val Pro Thr Thr Ser Thr
            100                 105                 110

Gly Val Val Ser Glu Glu Pro Phe Thr Leu Asn Phe Thr Ile Asn Asn
        115                 120                 125

Leu Arg Tyr Met Ala Asp Met Gly Gln Pro Gly Ser Leu Lys Phe Asn
    130                 135                 140

Ile Thr Asp Asn Val Met Lys His Leu Leu Ser Pro Leu Phe Gln Arg
145                 150                 155                 160

Ser Ser Leu Gly Ala Arg Tyr Thr Gly Cys Arg Val Ile Ala Leu Arg
                165                 170                 175

Ser Val Lys Asn Gly Ala Glu Thr Arg Val Asp Leu Leu Cys Thr Tyr
            180                 185                 190

Leu Gln Pro Leu Ser Gly Pro Gly Leu Pro Ile Lys Gln Val Phe His
    195                 200                 205

Glu Leu Ser Gln Gln Thr His Gly Ile Thr Arg Leu Gly Pro Tyr Ser
210                 215                 220

Leu Asp Lys Asp Ser Leu Tyr Leu Asn Gly Tyr Asn Glu Pro Gly Pro
225                 230                 235                 240

Asp Glu Pro Pro Thr Thr Pro Lys Pro Ala Thr Thr Phe Leu Pro Pro
                245                 250                 255

Leu Ser Glu Ala Thr Thr Ala Met Gly Tyr His Leu Lys Thr Leu Thr
            260                 265                 270

Leu Asn Ser His Leu Gln Ser Pro Val Phe Thr Arg Tyr Gly Gln Gly
    275                 280                 285

Leu Lys Val His Ser Ile His Arg Gly Gly Ser Phe Ser Asn Trp Ser
290                 295                 300
```

<210> SEQ ID NO 487
<211> LENGTH: 294
<212> TYPE: PRT

<213> ORGANISM: Homo sapiens

<400> SEQUENCE: 487

Met Thr Asn Gly Ile Lys Glu Leu Gly Pro Tyr Thr Leu Asp Arg Asn
1               5                   10                  15

Ser Leu Tyr Val Asn Gly Phe Thr His Arg Ser Ser Gly Leu Thr Thr
            20                  25                  30

Ser Thr Pro Trp Thr Ser Val Asp Leu Gly Thr Ser Gly Thr Pro
        35                  40                  45

Ser Pro Val Pro Ser Pro Thr Thr Ala Gly Pro Leu Leu Val Pro Phe
    50                  55                  60

Thr Leu Asn Phe Thr Ile Thr Asn Leu Gln Tyr Glu Glu Asp Met His
65                  70                  75                  80

Arg Pro Gly Ser Arg Lys Phe Asn Ala Thr Glu Arg Val Leu Gln Gly
                85                  90                  95

Leu Leu Ser Pro Ile Phe Lys Asn Ser Ser Val Gly Pro Leu Tyr Ser
            100                 105                 110

Gly Cys Arg Leu Thr Ser Leu Arg Pro Glu Lys Asp Gly Ala Ala Thr
        115                 120                 125

Gly Met Asp Ala Val Cys Leu Tyr His Pro Asn Pro Lys Arg Pro Gly
    130                 135                 140

Leu Asp Arg Glu Gln Leu Tyr Trp Glu Leu Ser Gln Leu Thr His Asn
145                 150                 155                 160

Ile Thr Glu Leu Gly Pro Tyr Ser Leu Asp Arg Asp Ser Leu Tyr Val
                165                 170                 175

Asn Gly Phe Thr His Gln Asn Ser Val Pro Thr Thr Ser Thr Pro Gly
            180                 185                 190

Thr Ser Thr Val Tyr Trp Ala Thr Gly Thr Pro Ser Ser Phe Pro
        195                 200                 205

Gly His Thr Glu Pro Gly Pro Leu Leu Ile Pro Phe Thr Phe Asn Phe
    210                 215                 220

Thr Ile Thr Asn Leu His Tyr Glu Glu Asn Met Gln His Pro Gly Ser
225                 230                 235                 240

Arg Lys Phe Asn Ala Thr Glu Arg Val Leu Gln Gly Leu Leu Ser Pro
                245                 250                 255

Ile Phe Lys Asn Ser Ser Val Gly Pro Leu Tyr Ser Gly Cys Arg Leu
            260                 265                 270

Thr Ser Leu Arg Pro Glu Lys Asp Gly Ala Ala Thr Gly Met Asp Ala
        275                 280                 285

Val Cys Leu Tyr Arg Pro
    290

<210> SEQ ID NO 488
<211> LENGTH: 233
<212> TYPE: PRT
<213> ORGANISM: Homo sapiens

<400> SEQUENCE: 488

Ser Leu Val Glu Gln Val Phe Leu Asp Lys Thr Leu Asn Ala Ser Phe
1               5                   10                  15

His Trp Leu Gly Ser Thr Tyr Gln Leu Val Asp Ile His Val Thr Glu
            20                  25                  30

Met Glu Ser Ser Val Tyr Gln Pro Thr Ser Ser Ser Thr Gln His
        35                  40                  45

Phe Tyr Leu Asn Phe Thr Ile Thr Asn Leu Pro Tyr Ser Gln Asp Lys

```
            50                  55                  60
Ala Gln Pro Gly Thr Thr Asn Tyr Gln Arg Asn Lys Arg Asn Ile Glu
 65                  70                  75                  80

Asp Ala Leu Asn Gln Leu Phe Arg Asn Ser Ser Ile Lys Ser Tyr Phe
                 85                  90                  95

Ser Asp Cys Gln Val Ser Thr Phe Arg Ser Val Pro Asn Arg His His
            100                 105                 110

Thr Gly Val Asp Ser Leu Cys Asn Phe Ser Pro Leu Ala Arg Arg Val
            115                 120                 125

Asp Arg Val Ala Ile Tyr Glu Glu Phe Leu Arg Met Thr Arg Asn Gly
130                 135                 140

Thr Gln Leu Gln Asn Phe Thr Leu Asp Arg Ser Ser Val Leu Val Asp
145                 150                 155                 160

Gly Tyr Phe Pro Asn Arg Asn Glu Pro Leu Thr Gly Asn Ser Asp Leu
                165                 170                 175

Pro Phe Trp Ala Val Ile Leu Ile Gly Leu Ala Gly Leu Leu Gly Leu
            180                 185                 190

Ile Thr Cys Leu Ile Cys Gly Val Leu Val Thr Arg Arg Arg Lys
            195                 200                 205

Lys Glu Gly Glu Tyr Asn Val Gln Gln Gln Cys Pro Gly Tyr Tyr Gln
210                 215                 220

Ser His Leu Asp Leu Glu Asp Leu Gln
225                 230

<210> SEQ ID NO 489
<211> LENGTH: 178
<212> TYPE: PRT
<213> ORGANISM: Homo sapiens

<400> SEQUENCE: 489

Ser Leu Val Glu Gln Val Phe Leu Asp Lys Thr Leu Asn Ala Ser Phe
  1               5                  10                  15

His Trp Leu Gly Ser Thr Tyr Gln Leu Val Asp Ile His Val Thr Glu
             20                  25                  30

Met Glu Ser Ser Val Tyr Gln Pro Thr Ser Ser Ser Thr Gln His
             35                  40                  45

Phe Tyr Leu Asn Phe Thr Ile Thr Asn Leu Pro Tyr Ser Gln Asp Lys
 50                  55                  60

Ala Gln Pro Gly Thr Thr Asn Tyr Gln Arg Asn Lys Arg Asn Ile Glu
 65                  70                  75                  80

Asp Ala Leu Asn Gln Leu Phe Arg Asn Ser Ser Ile Lys Ser Tyr Phe
                 85                  90                  95

Ser Asp Cys Gln Val Ser Thr Phe Arg Ser Val Pro Asn Arg His His
            100                 105                 110

Thr Gly Val Asp Ser Leu Cys Asn Phe Ser Pro Leu Ala Arg Arg Val
            115                 120                 125

Asp Arg Val Ala Ile Tyr Glu Glu Phe Leu Arg Met Thr Arg Asn Gly
130                 135                 140

Thr Gln Leu Gln Asn Phe Thr Leu Asp Arg Ser Ser Val Leu Val Asp
145                 150                 155                 160

Gly Tyr Phe Pro Asn Arg Asn Glu Pro Leu Thr Gly Asn Ser Asp Leu
                165                 170                 175

Pro Phe
```

```
<210> SEQ ID NO 490
<211> LENGTH: 15
<212> TYPE: PRT
<213> ORGANISM: Homo sapiens

<400> SEQUENCE: 490

Thr Cys Gly Met Arg Arg Thr Cys Ser Thr Leu Ala Pro Gly Ser
  1               5                  10                  15

<210> SEQ ID NO 491
<211> LENGTH: 15
<212> TYPE: PRT
<213> ORGANISM: Homo sapiens

<400> SEQUENCE: 491

Cys Arg Leu Thr Leu Leu Arg Pro Glu Lys Asp Gly Thr Ala Thr
  1               5                  10                  15

<210> SEQ ID NO 492
<211> LENGTH: 15
<212> TYPE: PRT
<213> ORGANISM: Homo sapiens

<400> SEQUENCE: 492

Asp Gly Thr Ala Thr Gly Val Asp Ala Ile Cys Thr His His Pro
  1               5                  10                  15

<210> SEQ ID NO 493
<211> LENGTH: 15
<212> TYPE: PRT
<213> ORGANISM: Homo sapiens

<400> SEQUENCE: 493

Cys Thr His His Pro Asp Pro Lys Ser Pro Arg Leu Asp Arg Glu
  1               5                  10                  15

<210> SEQ ID NO 494
<211> LENGTH: 15
<212> TYPE: PRT
<213> ORGANISM: Homo sapiens

<400> SEQUENCE: 494

Arg Leu Asp Arg Glu Gln Leu Tyr Trp Glu Leu Ser Gln Leu Thr
  1               5                  10                  15

<210> SEQ ID NO 495
<211> LENGTH: 15
<212> TYPE: PRT
<213> ORGANISM: Homo sapiens

<400> SEQUENCE: 495

Leu Gly Pro Tyr Ala Leu Asp Asn Asp Ser Leu Phe Val Asn Gly
  1               5                  10                  15

<210> SEQ ID NO 496
<211> LENGTH: 15
<212> TYPE: PRT
<213> ORGANISM: Homo sapiens

<400> SEQUENCE: 496

Ser Val Ser Thr Thr Ser Thr Pro Gly Thr Pro Thr Tyr Val Leu
  1               5                  10                  15

<210> SEQ ID NO 497
<211> LENGTH: 15
```

<210> SEQ ID NO 497 (continued)
<212> TYPE: PRT
<213> ORGANISM: Homo sapiens

<400> SEQUENCE: 497

Leu Arg Pro Glu Lys Asp Gly Glu Ala Thr Gly Val Asp Ala Ile
1               5                   10                  15

<210> SEQ ID NO 498
<211> LENGTH: 15
<212> TYPE: PRT
<213> ORGANISM: Homo sapiens

<400> SEQUENCE: 498

Asp Pro Thr Gly Pro Gly Leu Asp Arg Glu Gln Leu Tyr Leu Glu
1               5                   10                  15

<210> SEQ ID NO 499
<211> LENGTH: 15
<212> TYPE: PRT
<213> ORGANISM: Homo sapiens

<400> SEQUENCE: 499

Leu Asp Arg Asp Ser Leu Tyr Val Asn Gly Phe Thr His Arg Ser
1               5                   10                  15

<210> SEQ ID NO 500
<211> LENGTH: 15
<212> TYPE: PRT
<213> ORGANISM: Homo sapiens

<400> SEQUENCE: 500

Gly Pro Tyr Ser Leu Asp Lys Asp Ser Leu Tyr Leu Asn Gly Tyr
1               5                   10                  15

<210> SEQ ID NO 501
<211> LENGTH: 15
<212> TYPE: PRT
<213> ORGANISM: Homo sapiens

<400> SEQUENCE: 501

Tyr Leu Asn Gly Tyr Asn Glu Pro Gly Pro Asp Glu Pro Pro Thr
1               5                   10                  15

<210> SEQ ID NO 502
<211> LENGTH: 15
<212> TYPE: PRT
<213> ORGANISM: Homo sapiens

<400> SEQUENCE: 502

Ala Thr Phe Asn Ser Thr Glu Gly Val Leu Gln His Leu Leu Arg
1               5                   10                  15

<210> SEQ ID NO 503
<211> LENGTH: 15
<212> TYPE: PRT
<213> ORGANISM: Homo sapiens

<400> SEQUENCE: 503

Gln Leu Ile Ser Leu Arg Pro Glu Lys Asp Gly Ala Ala Thr Gly
1               5                   10                  15

<210> SEQ ID NO 504
<211> LENGTH: 15
<212> TYPE: PRT
<213> ORGANISM: Homo sapiens

```
<400> SEQUENCE: 504

Gly Ala Ala Gly Val Asp Thr Thr Cys Thr Tyr His Pro Asp
1               5                   10                  15

<210> SEQ ID NO 505
<211> LENGTH: 15
<212> TYPE: PRT
<213> ORGANISM: Homo sapiens

<400> SEQUENCE: 505

Thr Tyr His Pro Asp Pro Val Gly Pro Gly Leu Asp Ile Gln Gln
1               5                   10                  15

<210> SEQ ID NO 506
<211> LENGTH: 15
<212> TYPE: PRT
<213> ORGANISM: Homo sapiens

<400> SEQUENCE: 506

Leu Asp Ile Gln Gln Leu Tyr Trp Glu Leu Ser Gln Leu Thr His
1               5                   10                  15

<210> SEQ ID NO 507
<211> LENGTH: 15
<212> TYPE: PRT
<213> ORGANISM: Homo sapiens

<400> SEQUENCE: 507

His Ile Val Asn Trp Asn Leu Ser Asn Pro Asp Pro Thr Ser Ser
1               5                   10                  15

<210> SEQ ID NO 508
<211> LENGTH: 15
<212> TYPE: PRT
<213> ORGANISM: Homo sapiens

<400> SEQUENCE: 508

Asp Pro Thr Ser Ser Glu Tyr Ile Thr Leu Leu Arg Asp Ile Gln
1               5                   10                  15

<210> SEQ ID NO 509
<211> LENGTH: 15
<212> TYPE: PRT
<213> ORGANISM: Homo sapiens

<400> SEQUENCE: 509

Leu Arg Asp Ile Gln Asp Lys Val Thr Thr Leu Tyr Lys Gly Ser
1               5                   10                  15

<210> SEQ ID NO 510
<211> LENGTH: 15
<212> TYPE: PRT
<213> ORGANISM: Homo sapiens

<400> SEQUENCE: 510

Leu Tyr Lys Gly Ser Gln Leu His Asp Thr Phe Arg Phe Cys Leu
1               5                   10                  15

<210> SEQ ID NO 511
<211> LENGTH: 15
<212> TYPE: PRT
<213> ORGANISM: Homo sapiens

<400> SEQUENCE: 511
```

Asp Lys Ala Gln Pro Gly Thr Thr Asn Tyr Gln Arg Asn Lys Arg
 1               5                  10                  15

<210> SEQ ID NO 512
<211> LENGTH: 450
<212> TYPE: DNA
<213> ORGANISM: Homo sapiens

<400> SEQUENCE: 512
gttacaatga acctggtcca gatgagcctc ctacaactcc caagccagcc accacattcc      60
tgcctcctct gtcagaagcc acaacagcca tggggtacca cctgaagacc ctcacactca     120
acttcaccat ctccaatctc cagtattcac cagatatggg caagggctca gctacattca     180
actccaccga gggggtcctt cagcacctgc tcagacccctt gttccagaag agcagcatgg    240
gccccttcta cttgggttgc aactgatct ccctcaggcc tgagaaggat ggggcagcca      300
ctggtgtgga caccacctgc acctaccacc ctgaccctgt gggccccggg ctggacatac     360
agcagcttta ctgggagctg agtcagctga cccatggtgt cacccaactg ggcttctatg    420
tcctggacag ggatagcctc ttcatcaatg                                      450

<210> SEQ ID NO 513
<211> LENGTH: 402
<212> TYPE: DNA
<213> ORGANISM: Homo sapiens

<400> SEQUENCE: 513
gtttcaccca tcggagctct gtacccacca ccagcaccgg ggtggtcagc gaggagccat      60
tcacactgaa cttcaccatc aacaacctgc gctacatggc ggacatgggc caacccggct     120
ccctcaagtt caacatcaca gacaacgtca tgaagcacct gctcagtcct tgttccaga     180 ggagcagcct gggtgcacgg tacacaggct gcagggtcat cgcactaagg tctgtgaaga    240
acggtgctga gacacggtg gacctcctct gcacctacct gcagcccctc agcggcccag     300
gtctgcctat caagcaggtg ttccatgagc tgagccagca gacccatggc atcacccggc    360
tgggccccta ctctctggac aaagacagcc tctaccttaa cg                        402

<210> SEQ ID NO 514
<211> LENGTH: 465
<212> TYPE: DNA
<213> ORGANISM: Homo sapiens

<400> SEQUENCE: 514
gtttcactca tcggagctct gtgtccacca ccagcactcc tgggacccccc acagtgtatc     60 tgggagcatc taagactcca gcctcgatat ttggcccttc agctgccagc catctcctga    120
tactattcac cctcaacttc accatcacta acctgcggta tgaggagaac atgtggcctg    180
gctccaggaa gttcaacact acagagaggg tccttcaggg cctgctaagg cccttgttca   240
agaacaccag tgttggccct ctgtactctg gctgcaggct gaccttgctc aggccagaga    300
aagatgggga agccaccgga gtggatgcca tctgcaccca ccgccctgac ccacaggcc    360 ctgggctgga cagagagcag ctgtatttgg agctgagcca gctgacccac agcatcactg    420
agctgggccc ctacacactg gacagggaca gtctctatgt caatg                    465

<210> SEQ ID NO 515
<211> LENGTH: 463
<212> TYPE: DNA
<213> ORGANISM: Homo sapiens

<400> SEQUENCE: 515

```
gtttcacaca gcggagctct gtgcccacca ctagcattcc tgggaccccc acagtggacc      60
tgggaacatc tgggactcca gtttctaaac ctggtccctc ggctgccagc cctctcctgg     120
tgctattcac tctcaacttc accatcacca acctgcggta tgaggagaac atgcagcacc     180
ctggctccag gaagttcaac accacggaga gggtccttca gggcctggtc cctgttcaag     240
agcaccagtg ttggccctct gtactctggc tgcagactga ctttgctcag gcctgaaaag     300
gatgggacag ccactggagt ggatgccatc tgcacccacc acctgaccc caaaagccct      360
aggctggaca gagagcagct gtattgggag ctgagccagc tgacccacaa tatcactgag     420
ctgggcccct atgccctgga acgacagcc ctctttgtca atg                        463
```

<210> SEQ ID NO 516
<211> LENGTH: 156
<212> TYPE: DNA
<213> ORGANISM: Homo sapiens

<400> SEQUENCE: 516

```
cagccaccgg agtggatgcc atctgcaccc accgccctga ccccacaggc cctgggctgg      60
acagagagca gctgtatttg gagctgagcc agctgaccca cagcatcact gagctgggcc     120
cctacacccct ggacagggac agtctctatg tcaatg                              156
```

<210> SEQ ID NO 517
<211> LENGTH: 450
<212> TYPE: DNA
<213> ORGANISM: Homo sapiens

<400> SEQUENCE: 517

```
gttacaatga acctggtcta gatgagcctc ctacaactcc caagccagcc accacattcc      60
tgcctcctct gtcagaagcc acaacagcca tggggtacca cctgaagacc ctcacactca     120
acttcaccat ctccaatctc cagtattcac cagatatggg caagggctca gctacattca     180
actccaccga gggggtcctt cagcacctgc tcagacccctt gttccagaag agcagcatgg    240
gccccttcta cttgggttgc caactgatct ccctcaggcc tgagaaggat ggggcagcca     300
ctggtgtgga caccacctgc acctaccacc ctgaccctgt gggcccctgg ctggacatac     360
agcagcttta ctgggagctg agtcagctga cccatggtgt cacccaactg ggcttctatg     420
tcctggacag ggatagcctc ttcatcaatg                                      450
```

<210> SEQ ID NO 518
<211> LENGTH: 402
<212> TYPE: DNA
<213> ORGANISM: Homo sapiens

<400> SEQUENCE: 518

```
gtttcaccca tcggagctct gtacccacca ccagcaccgg ggtggtcagc gaggagccat      60
tcacactgaa cttcaccatc aacaacctgc gctacatggc ggacatgggc caacccggct     120
ccctcaagtt caacatcaca gacaacgtca tgaagcacct gctcagtcct tgttccaga     180
ggagcagcct gggtgcacgg tacacaggct gcagggtcat cgcactaagg tctgtgaaga     240
acggtgctga gacacgggtg gacctcctct gcacctacct gcagccctc agcggcccag     300
gtctgcctat caagcaggtg ttccatgagc tgagccagca gacccatggc atcacccggc     360
tgggccccta ctctctggac aaagacagcc tctaccttaa cg                        402
```

<210> SEQ ID NO 519
<211> LENGTH: 465
<212> TYPE: DNA
<213> ORGANISM: Homo sapiens

<400> SEQUENCE: 519

| | | | | | |
|---|---|---|---|---|---|
| gtttcactca | tcggagctct | gtgtccacca | ccagcactcc | tgggacccca | 60 |
| tgggagcatc | taagactcca | gcctcgatat | ttggcccttc | agctgccagc catctcctga | 120 |
| tactattcac | cctcaacttc | accatcacta | acctgcggta | tgaggagaac atgtggcctg | 180 |
| gctccaggaa | gttcaacact | acagagaggg | tccttcaggg | cctgctaagg cccttgttca | 240 |
| agaacaccag | tgttggccct | ctgtactctg | gctccaggct | gaccttgctc aggccagaga | 300 |
| aagatgggga | agccaccgga | gtggatgcca | tctgcaccca | ccgccctgac cccacaggcc | 360 |
| ctgggctgga | cagagagcag | ctgtatttgg | agctgagcca | gctgacccac agcatcactg | 420 |
| agctgggccc | ctacacactg | gacagggaca | gtctctatgt | caatg | 465 |

<210> SEQ ID NO 520
<211> LENGTH: 468
<212> TYPE: DNA
<213> ORGANISM: Homo sapiens

<400> SEQUENCE: 520

| | | | | | |
|---|---|---|---|---|---|
| gtttcacaca | gcggagctct | gtgcccacca | ctagcattcc | tgggacccca | acagtggacc | 60 |
| tgggaacatc | tgggactcca | gtttctaaac | ctggtccctc | ggctgccagc cctctcctgg | 120 |
| tgctattcac | tctcaacttc | accatcacca | acctgcggta | tgaggagaac atgcagcacc | 180 |
| ctggctccag | gaagttcaac | accacggaga | gggtccttca | gggcctgctc aggtccctgt | 240 |
| tcaagagcac | cagtgttggc | cctctgtact | ctggctgcag | actgactttg ctcaggcctg | 300 |
| aaaaggatgg | gacagccact | ggagtggatg | ccatctgcac | ccaccaccct gaccccaaaa | 360 |
| gccctaggct | ggacagagag | cagctgtatt | gggagctgag | ccagctgacc cacaatatca | 420 |
| ctgagctggg | ccactatgcc | ctggacaacg | acagcctctt | tgtcaatg | 468 |

<210> SEQ ID NO 521
<211> LENGTH: 468
<212> TYPE: DNA
<213> ORGANISM: Homo sapiens

<400> SEQUENCE: 521

| | | | | | |
|---|---|---|---|---|---|
| gtttcaccca | tcagagctct | atgacgacca | ccagaactcc | tgatacctcc | acaatgcacc | 60 |
| tggcaacctc | gagaactcca | gcctccctgt | ctggacctac | gaccgccagc cctctcctgg | 120 |
| tgctattcac | aattaacttc | accatcacta | acctgcggta | tgaggagaac atgcatcacc | 180 |
| ctggctctag | aaagtttaac | accacggaga | gagtccttca | gggtctgctc aggcctgtgt | 240 |
| tcaagaacac | cagtgttggc | cctctgtact | ctggctgcag | actgacctt gctcaggccca | 300 |
| agaaggatgg | ggcagccacc | aaagtggatg | ccatctgcac | ctaccgccct gatcccaaaa | 360 |
| gccctggact | ggacagagag | cagctatact | gggagctgag | ccagctaacc cacagcatca | 420 |
| ctgagctggg | cccctacacc | ctggacaggg | acagtctcta | tgtcaatg | 468 |

<210> SEQ ID NO 522
<211> LENGTH: 262
<212> TYPE: DNA
<213> ORGANISM: Homo sapiens

<400> SEQUENCE: 522

```
gagagggtcc ttcagggtct gcttatgccc ttgttcaaga acaccagtgt cagctctctg    60
tactctggtt gcagactgac cttgctcagg cctgagaagg atggggcagc caccagagtg   120
gatgctgtct gcacccatcg tcctgacccc aaaagccctg gactggacag agagcggctg   180
tactggaagc tgagccagct gacccacggc atcactgagc tgggccccta caccctggac   240
aggcacagtc tctatgtcaa tg                                            262

<210> SEQ ID NO 523
<211> LENGTH: 302
<212> TYPE: DNA
<213> ORGANISM: Homo sapiens

<400> SEQUENCE: 523
aggacatgcg tcaccctggc tccaggaagt tcaacaccac agagagggtc ctgcagggtc    60
tgcttggtcc cttgttcaag aactccagtg tcggccctct gtactctggc tgcagactga   120
tctctctcag gtctgagaag gatggggcag ccactggagt ggatgccatc tgcacccacc   180
accttaaccc tcaaagcctg gactggacag ggagcagctg tactggcagc tgagccagat   240
gaccaatggc atcaaagagc tgggccccta caccctggac cggaacagtc tctacgtcaa   300
tg                                                                  302

<210> SEQ ID NO 524
<211> LENGTH: 468
<212> TYPE: DNA
<213> ORGANISM: Homo sapiens

<400> SEQUENCE: 524
gtttcaccca tcggagctct gggctcacca ccagcactcc ttggacttcc acagttgacc    60
ttggaacctc agggactcca tcccccgtcc ccagccccac aactgctggc cctctcctgg   120
tgccattcac cctaaacttc accatcacca acctgcagta tgaggaggac atgcatcgcc   180
ctggatctag gaagttcaac gccacagaga gggtcctgca gggtctgctt agtcccatat   240
tcaagaactc cagtgttggc cctctgtact ctggctgcag actgacctct ctcaggcccg   300
agaaggatgg ggcagcaact ggaatggatg ctgtctgcct ctaccaccct aatcccaaaa   360
gacctgggct ggacagagag cagctgtact gggagctaag ccagctgacc cacaacatca   420
ctgagctggg ccctacagc ctggacaggg acagtctcta tgtcaatg                 468

<210> SEQ ID NO 525
<211> LENGTH: 470
<212> TYPE: DNA
<213> ORGANISM: Homo sapiens

<400> SEQUENCE: 525
gtttcaccca tcagaactct gtgcccacca ccagtactcc tgggacctcc acagtgtact    60
gggcaaccac tgggactcca tcctccttcc ccggccacac agagcctggc cctctcctga   120
taccattcac attcaacttt accatcacca acctgcatta tgaggaaaac atgcaacacc   180
ctggttccag gaagttcaac gccacagaga gggtcctgca gggtctgctt agtcccatat   240
tcaagaactc cagtgttggc cctctgtact ctggctgcag actgacctct ctcaggcccg   300
agaaggatgg ggcagcaact ggaatggatg ctgtctgtct ctaccgaccc taatcccatc   360
ggacctgggc tggacagaga gcagctgtac tgggagctga ccagctgacc cacgacatc   420 actgagctgg gccctacag ccctggacag ggacagtctc tatgtcaatg                470
```

<210> SEQ ID NO 526
<211> LENGTH: 467
<212> TYPE: DNA
<213> ORGANISM: Homo sapiens

<400> SEQUENCE: 526

| | | | | | |
|---|---|---|---|---|---|
| gtttcaccca | tcagaactct | gtgcccacca | ccagtactcc | tgggacctcc | acagtgtact | 60 |
| gggcaaccac | tgggactcca | tcctccttcc | ccggccacac | agagcctggc | cctctcctga | 120 |
| taccattcac | tttcaacttt | accatcacca | acctgcatta | tgaggaaaac | atgcaacacc | 180 |
| tggttccagg | aagttcaaca | ccacggagag | ggttctgcag | gtctgctca | cgccttgtt | 240 |
| caagaacacc | agtgttggcc | ctctgtactc | tggctgcaga | ctgaccttgc | tcagacctga | 300 |
| gaagcaggag | gcagccactg | gagtggacac | catctgcact | caccgccttg | accctctaaa | 360 |
| ccctggactg | gacagagagc | agctatactg | ggagctgagc | aaactgaccc | gtggcatcat | 420 |
| cgagctgggc | ccctacctcc | tggacagagg | cagtctctat | gtcaatg | 467 |

<210> SEQ ID NO 527
<211> LENGTH: 468
<212> TYPE: DNA
<213> ORGANISM: Homo sapiens

<400> SEQUENCE: 527

| | | | | | |
|---|---|---|---|---|---|
| gtttcaccca | tcggaacttt | gtgcccatca | ccagcactcc | tgggacctcc | acagtacacc | 60 |
| taggaacctc | tgaaactcca | tcctccctac | ctagacccat | agtgcctggc | cctctcctgg | 120 |
| tgccattcac | cctcaacttc | accatcacca | acttgcagta | tgaggaggcc | atgcgacacc | 180 |
| ctggctccag | gaagttcaat | accacggaga | gggtcctaca | gggtctgctc | aggcccttgt | 240 |
| tcaagaatac | cagtatcggc | cctctgtact | ccagctgcag | actgaccttg | ctcaggccag | 300 |
| agaaggacaa | ggcagccacc | agagtggatg | ccatctgtac | ccaccaccct | gaccctcaaa | 360 |
| gccctggact | gaacagagag | cagctgtact | gggagctgag | ccagctgacc | cacggcatca | 420 |
| ctgagctggg | ccctacacc | ctggacaggc | acagtctcta | tgtcaatg | 468 |

<210> SEQ ID NO 528
<211> LENGTH: 537
<212> TYPE: DNA
<213> ORGANISM: Homo sapiens

<400> SEQUENCE: 528

| | | | | | |
|---|---|---|---|---|---|
| gtttcaccca | tcagagcccc | ataccaacca | ccagcactcc | tgatacctcc | acaatgcacc | 60 |
| tgggaacctc | gagaactcca | gcctccctgt | ctggacctac | gaccgccagc | cctctcctgg | 120 |
| tgctattcac | aattaacttc | accatcacta | acctgcggta | tgaggagaac | atgcatcacc | 180 |
| gctggctcta | gaaagtttaa | caccacggag | agagtccttc | agggtctgct | caggcctgtg | 240 |
| ttcaaagaac | accagtgttg | gccctctgta | ctctggctgc | agactgacct | tgctcaggcc | 300 |
| cgagaaggat | ggggcagcca | cgcaaagtgg | atgccatctg | cacctaccgc | cctgatccca | 360 |
| aaagccctgg | actggacaga | gagcagctat | actgggagct | gagccagggt | gatgcatgtt | 420 |
| ctcctcatat | cgcaggttag | tgatggtgaa | gttaattgtg | aatagcacca | ggagagggct | 480 |
| ggcggtcatg | ggtccagaca | gggagcctgg | agttctcgag | gttgccaggt | gcatgtc | 537 |

<210> SEQ ID NO 529
<211> LENGTH: 231
<212> TYPE: DNA
<213> ORGANISM: Homo sapiens

```
<400> SEQUENCE: 529
tgttccagag gagcagcctg ggtgcacggt acacaggctg cagggtcatc gcactaaggt    60
ctgtgaagaa cggtgctgag acacgggtgg acctcctctg cacctacctg cagcccctca   120
gcggcccagg tctgcctatc aagcaggtgt tccatgagct gagccagcag acccatggca   180
tcacccggct gggcccctac tctctggaca agacagcct ctaccttaac g             231

<210> SEQ ID NO 530
<211> LENGTH: 376
<212> TYPE: DNA
<213> ORGANISM: Homo sapiens

<400> SEQUENCE: 530
gttacaatga acctggtcca gatgagcctc ctacaactcc caagccagcc accacattcc    60
tgcctcctct gtcagaagcc acaacagcca tggggtacca cctgaagacc ctcacactca   120
acttcaccat ctccaatctc cagtattcac cagatatggg caagggctca gctacattca   180
actccaccga gggggtcctt cagcacctgg cctgagaagg atggggcagc cactggtgtg   240
gacaccacct gcacctacca ccctgaccct gtgggccccg ggctggacat acagcagctt   300
tactgggagc tgagtcagct gacccatggt gtcacccaac tgggcttcta tgtcctggac   360
agcgatagct cttcat                                                   376

<210> SEQ ID NO 531
<211> LENGTH: 75
<212> TYPE: DNA
<213> ORGANISM: Homo sapiens

<400> SEQUENCE: 531
ggtaaccaca gctgacccat ggcatcaaag agctgggccc ctacaccctg acaggaaca    60 gtctctatgt caatg                                                    75

<210> SEQ ID NO 532
<211> LENGTH: 906
<212> TYPE: DNA
<213> ORGANISM: Homo sapiens

<400> SEQUENCE: 532
gtttcaccca tcggagctct gtggcccca ccagcactcc tgggacctcc acagtggacc    60
ttgggacctc agggactcca tcctcctcc ccagccccac aacagctgtt cctctcctgg   120
tgccgttcac cctcaacttt accatcacca atctgcagta tggggaggac atgcgtcacc   180
ctggctccag gaagttcaac accacagaga ggtcctgca gggtctgctt ggtcccttgt   240
tcaagaactc cagtgtcggc cctctgtact ctggctgcag actgatctct ctcaggtctg   300
agaaggatgg ggcagccact ggagtggatg ccatctgcac ccaccacctt aaccctcaaa   360
gccctggact ggacagggag cagctgtact ggcagctgag ccagagacca acctcatt    420 tatcacctat tctgagacac acacaagttc agccattcca actctccctg tctcccctg   480 gtgcatcaaa gatgctgacc tcactggtca tcagttctgg gacagacagc actacaactt   540
tcccaacact gacggagacc ccatatgaac cagagacaac agccatacag ctcattcatc   600
ctgcagagac caacacaatg gttcccagga caactcccaa gttttcccat agtaagtcag   660
acaccacact cccagtagcc atcaccagtc tgggccagag agccagttca gctgtttcaa   720
cgacaactat ctcacctgat atgtcagatc tggtgacctc actggtccct agttctggga   780
```
cagacaccag tacaaccttc ccaacattga gtgagacccc atatgaacca gagactacag    840
ccacgtggct cactcatcct gcagaaacca gaacaacggt ttctgggaca attcccaact    900
tttccc    906

<210> SEQ ID NO 533
<211> LENGTH: 404
<212> TYPE: DNA
<213> ORGANISM: Homo sapiens

<400> SEQUENCE: 533
gtttcaccca tcggagctct gtggcccccca ccagcactcc tgggacctcc acagtggacc    60
ttgggacctc agggactcca tcctccctcc ccagccccac aacagctgtt cctctcctgg    120
tgccgttcac cctcaacttt accatcacca atctgcagta tggggaggac atgcgtcacc    180
ctggctccag gaagttcaac accacagaga gggtcctgca gggtctgctt ggtcccttgt    240
tcaagaactc cagtgtcggc cctctgtact ctggctgcag actgatctct ctcaggtctg    300
agaaggatgg ggcagccact ggagtggatg ccatctgcac ccaccacctt aaccctcaaa    360
gccctggact ggacagggag cagctgtact ggcagctgag ccag    404

<210> SEQ ID NO 534
<211> LENGTH: 157
<212> TYPE: DNA
<213> ORGANISM: Homo sapiens

<400> SEQUENCE: 534
gcagccacca aagtggatgc catctgcacc taccgccctg atcccaaaag ccctggactg    60
gacagagagc agctatactg ggagctgagc cagctaaccc acagcatcac tgagctgggc    120
ccctacaccc tggacaggga cagtctctat gtcaatg    157

<210> SEQ ID NO 535
<211> LENGTH: 468
<212> TYPE: DNA
<213> ORGANISM: Homo sapiens

<400> SEQUENCE: 535
gtttcacaca gcggagctct gtgcccacca ctagcattcc tgggaccccc acagtggacc    60
tgggaacatc tgggactcca gtttctaaac ctggtccctc ggctgccagc cctctcctgg    120
tgctattcac tctcaacttc accatcacca acctgcggta tgaggagaac atgcagcacc    180
ctggctccag gaagttcaac accacggaga gggtccttca gggcctgctc aggtccctgt    240
tcaagagcac cagtgttggc cctctgtact ctggctgcag actgactttg ctcaggcctg    300
aaaaggatgg gacagccact ggagtggatg ccatctgcac ccaccaccct gaccccaaaa    360
gccctaggct ggacagagag cagctgtatt gggagctgag ccagctgacc cacaatatca    420
ctgagctggg ccctatgcc ctggacaacg acagcctctt tgtcaatg    468

<210> SEQ ID NO 536
<211> LENGTH: 334
<212> TYPE: DNA
<213> ORGANISM: Homo sapiens

<400> SEQUENCE: 536
gtttcactca tcggagctct gtgtccacca ccagcactcc tgggacccccc acagtgtatc    60 tgggagcatc taagactcca gcctcgatat ttgcccttc agctgccagc catctcctga    120
tactattcac cctcaacttc accatcacta acctgcggta tgaggagaac atgtggcctg    180

```
gctccaggaa gttcaacact acagagaggg tccttcaggg cctgctaagg cccttgttca      240
agaacaccag tgttggccct ctgtactctg gctgcaggct gaccttgctc aggccagaga      300
aagatgggga agccaccgga gtggatgcca tctg                                  334

<210> SEQ ID NO 537
<211> LENGTH: 127
<212> TYPE: DNA
<213> ORGANISM: Homo sapiens

<400> SEQUENCE: 537
ccaccgtctt gaccccaaaa gccctggagt ggacagggag cagctatact gggagctgag      60
ccagctgacc aatggcatca aagagctggg cccctacacc tggacaggaa cagtctctat      120
gtcaatg                                                                127

<210> SEQ ID NO 538
<211> LENGTH: 468
<212> TYPE: DNA
<213> ORGANISM: Homo sapiens

<400> SEQUENCE: 538
gtttcaccca tcggacctct gtgcccacca ccagcactcc tgggacctcc acagtggacc      60
ttggaacctc agggactcca ttctccctcc caagccccgc aactgctggc cctctcctgg      120
tgctgttcac cctcaacttc accatcacca acctgaagta tgaggaggac atgcatcgcc      180
ctggctccag gaagttcaac accactgaga gggtcctgca gactctgctt ggtcctatgt      240
tcaagaacac cagtgttggc cttctgtact ctggctgcag actgaccttg ctcaggtccg      300
agaaggatgg agcagccact ggagtggatg ccatctgcac ccaccgtctt gaccccaaaa      360
gccctggagt ggacagggag cagctatact gggagctgag ccagctgacc aatggcatca      420
aagagctggg cccctacacc tggacagga acagtctcta tgtcaatg                   468

<210> SEQ ID NO 539
<211> LENGTH: 465
<212> TYPE: DNA
<213> ORGANISM: Homo sapiens

<400> SEQUENCE: 539
gtttcaccca ttggatccct gtgcccacca gcagcactcc tggacctcc acagtggacc       60 ttgggtcagg gactccatcc tccctcccca gccccacaac tgctggccct ctcctggtgc      120
cgttcaccct caacttcacc atcaccaacc tgaagtacga ggaggacatg cattgccctg      180
gctccaggaa gttcaacacc acagagagag tcctgcagag tctgcttggt ccatgttca      240 agaacaccag tgttggccct ctgtactctg gctgcagact gaccttgctc aggtccgaga      300
aggatggagc agccactgga gtggatgcca tctgcaccca ccgtcttgac cccaaaagcc      360
tggagtggac agggagcagc tatactggga gctgagccag ctgaccaatg ccatcaaaga      420
gctgggtccc tacaccctgg acagcaacag tcttctatgt caatg                     465

<210> SEQ ID NO 540
<211> LENGTH: 255
<212> TYPE: DNA
<213> ORGANISM: Homo sapiens

<400> SEQUENCE: 540
gtttcaccca tcagacctct gcgcccaaca ccagcactcc tgggacctcc acagtggacc      60
```

| | |
|---|---|
| ttgggacctc agggactcca tcctccctcc ccagccctac atctgctggc cctctcctgg | 120 |
| tgccattcac cctcaacttc accatcacca acctgcagta cgaggaggac atgcatcacc | 180 |
| caggctccag gaagttcaac accacggagc gggtcctgca gggtctgctt ggtcccatgt | 240 |
| tcaagaacac tacga | 255 |

<210> SEQ ID NO 541
<211> LENGTH: 390
<212> TYPE: DNA
<213> ORGANISM: Homo sapiens

<400> SEQUENCE: 541

| | |
|---|---|
| catccccagc tcgaacagca gccacagtcc cattcatggt gccattcacc ctcaacttca | 60 |
| actcatcacc aacctgcagt acgaggagga catgcgcac ctggttccag gaagttcaac | 120 |
| gcgcacagag agagaactgc agggtcgtgc tcaaaccta gatcaggaat agcagtctgg | 180 |
| aatacctcta ttcaggctgc agactagcct cactcaggcc agagaaggat agctcagcca | 240 |
| cggcagtgga tgccatctgc acacatcgcc ctgaccctga agacctcgga ctggacagag | 300 |
| agcgactgta ctgggagctg agcaatctga caaatggcat ccaggagctg ggcccctaca | 360 |
| ccctggaccg gaacagtctc tatgtcaatg | 390 |

<210> SEQ ID NO 542
<211> LENGTH: 468
<212> TYPE: DNA
<213> ORGANISM: Homo sapiens

<400> SEQUENCE: 542

| | |
|---|---|
| gtttcaccca tcgaagctct atgcccacca ccagcactcc tgggacctcc acagtggatg | 60 |
| tgggaacctc agggactcca tcctccagcc ccagccccac gactgctggc cctctcctga | 120 |
| tgccgttcac cctcaacttc accatcacca acctgcagta cgaggaggac atgcgtcgca | 180 |
| ctggctccag gaagttcaac accatggaga gtgtcctgca gggtctgctc aagcccttgt | 240 |
| tcaagaacac cagtgttggc cctctgtact ctggctgcag attgaccttg ctcaggccca | 300 |
| agaaagatgg ggcagccact ggagtggatg ccatctgcac ccaccgcctt gaccccaaaa | 360 |
| gccctggact caacagggag cagctgtact gggagctaag caaactgacc aatgacattg | 420 |
| aagagctggg cccctacacc ctggacagga acagtctcta tgtcaatg | 468 |

<210> SEQ ID NO 543
<211> LENGTH: 475
<212> TYPE: DNA
<213> ORGANISM: Homo sapiens

<400> SEQUENCE: 543

| | |
|---|---|
| gtttcaccca tcagagctct gtgtccacca ccagcactcc tgggacctcc acagtggatc | 60 |
| tcagaacctc agtggactcc atcctccctc tccagcccca caattatggc tgctggccct | 120 |
| ctcctggtac cattcaccct caacttcacc atcaccaacc tgcagtatgg ggaggacatg | 180 |
| ggtcaccctg ctccaggaa gttcaacacc acagagaggg tcctgcaggg tctgcttggt | 240 |
| cccatattca agaacaccag tgttggccct ctgtactctg gctgcagact gacctctctc | 300 |
| aggtccaaga aggatggagc agccactgga gtggatgcca tctgcatcca tcatcttgac | 360 |
| cccaaaagcc ctggactcaa cagagagcgg ctgtactggg agctgagcca actgaccaat | 420 |
| ggcatcaaag agctgggccc ctacaccctg acaggaaca gtctctatgt caatg | 475 |

<210> SEQ ID NO 544
<211> LENGTH: 485
<212> TYPE: DNA
<213> ORGANISM: Homo sapiens

<400> SEQUENCE: 544

| gtttcaccca tcggacctct gtgcccacca ccagtactcc tgggacctcc acagtgtact | 60 |
| gggcaaccac tgggactcca tcctccctcc ccgccacaca gagcctggcc ctctcctgat | 120 |
| accattcaca ttcaacttta ccatcaccta cctgcattat agaggaaaac atgcaacacc | 180 |
| cgtggttcca ggaacgatgt caacaccaca ggagagggtt ctgcaggtc ttcgctcacg | 240 |
| cccattgtta caagaacacc agtagttggc cctctgtact ctggctgcag aatgaccttg | 300 |
| ctcagacctg agaagcagga ggcaacacac tggaatggac accatctgta tccaccagcg | 360 |
| ttagatccca tcaggacctg gactggacag agagcaggct atactgggag ctagagccag | 420 |
| ctgacccaca gcatcacaga gctgggaccc tacagccctg atagggaca gtctctatgt | 480 |
| caatg | 485 |

<210> SEQ ID NO 545
<211> LENGTH: 141
<212> TYPE: DNA
<213> ORGANISM: Homo sapiens

<400> SEQUENCE: 545

| gcttcaaccc ttggagctct gtgccaacca ccagcactcc tgggacctcc acagtgcacc | 60 |
| tggcaacctc tgggactcca tcctccctgc ctggccacac agcccctgtc cctctcttga | 120 |
| taccattcac cctcaactta c | 141 |

<210> SEQ ID NO 546
<211> LENGTH: 142
<212> TYPE: DNA
<213> ORGANISM: Homo sapiens

<400> SEQUENCE: 546

| gacctcctct gcacctacct gcagcccctc agcggcccag gtctgcctat caagcaggtg | 60 |
| ttccatgagc tgagccagca gacccatggc atcacccggc tgggccccta ctctctggac | 120 |
| aaagacagcc tctaccttaa cg | 142 |

<210> SEQ ID NO 547
<211> LENGTH: 185
<212> TYPE: DNA
<213> ORGANISM: Homo sapiens

<400> SEQUENCE: 547

| gttcttaccc aggccagaga aggatagctc agccacggca gtggatgcca tctgcacaca | 60 |
| tcgccctgac cctgaagacc tcggactgga cagagagcga ctgtactggg agctgagcaa | 120 |
| tctgacaaat ggcatccagg agctgggccc ctacaccctg gaccggaaca gtctctatgt | 180 |
| caatg | 185 |

<210> SEQ ID NO 548
<211> LENGTH: 462
<212> TYPE: DNA
<213> ORGANISM: Homo sapiens

<400> SEQUENCE: 548

| gtttcaccca tcgaagctct atgcccacca ccagcactcc tgggacctcc acagtggatg | 60 |

```
tgggaacctc agggactcca tcctccagcc ccagccccac gactgctggc cctctcctga    120
tgccgttcac cctcaacttc accatcacca acctgcagta cgaggaggac atgcgtcgca    180
ctggctccag gaagttcaac accatggaga gtgtcctgca gggtctgccc ttgttcaaga    240
acaccagtgt tggccctctg tactctggct gcagattgac cttgctcagg cccgagaaag    300
atggggcagc cactggagtg gatgccatct gcacccaccg ccttgacccc aaaagccctg    360
gactcaacag ggagcagctg tactgggagc taagcaaact gaccaatgac attgaagagc    420
tgggccccta cccctggac aggaacagtc tctatgtcaa tg                       462
```

```
<210> SEQ ID NO 549
<211> LENGTH: 400
<212> TYPE: DNA
<213> ORGANISM: Homo sapiens

<400> SEQUENCE: 549
actccatcct ccctctccag ccccacaatt atggctgctg ccctctcct ggtaccattc     60 accctcaact tcaccatcac caacctgcag tatggggagg acatgggtca ccctggctcc    120
aggaagttca acaccacaga gagggtcctg cagggtctgc ttggtcccat attcaagaac    180
accagtgttg ccctctgta ctctggctgc agactgacct ctctcaggtc tgagaaggat    240
ggagcagcca ctggagtgga tgccatctgc atccatcatc ttgaccccaa agccctgga    300 ctcaacagag agcggctgta ctgggagctg agccaactga ccaatggcat caaagagctg    360
ggcccctaca ccctggacag gaacagtctc tatgtcaatg                         400
```

```
<210> SEQ ID NO 550
<211> LENGTH: 468
<212> TYPE: DNA
<213> ORGANISM: Homo sapiens

<400> SEQUENCE: 550
gtttcaccca tcggacctct gtgcccacca gcagcactcc tgggacctcc acagtggacc    60
ttggaacctc agggactcca ttctccctcc caagccccgc aactgctggc cctctcctgg    120
tgctgttcac cctcaacttc accatcacca acctgaagta tgaggaggac atgcatcgcc    180
ctggctccag gaagttcaac accactgaga gggtcctgca gactctgctt ggtcctatgt    240
tcaagaacac cagtgttggc cttctgtact ctggctgcag actgaccttg ctcaggtccg    300
agaaggatgg agcagtcact ggagtggatg ccatctgcac ccaccgtctt gaccccaaaa    360
gccctggagt ggacagggag cagctatact gggagctgag ccagctgacc aatggcatca    420
aagagctggg cccctacacc ctggacaggc acagtctcta tgtcaatg                 468
```

```
<210> SEQ ID NO 551
<211> LENGTH: 366
<212> TYPE: DNA
<213> ORGANISM: Homo sapiens

<400> SEQUENCE: 551
ctgctggccc tctcctggtg ctgttcaccc tcaacttcac catcaccaac ctgaagtatg    60
aggaggacat gcatcgccct ggctccagga agttcaacac cactgagagg gtcctgcaga    120
ctctgcgtgg tcctatgttc aagaacacca gtggtggcct tctgtactct ggctgcagac    180
tgaccttgct caggtccgag aaggatggag cagccactgg agtggatgcc atctgcaccc    240
accgtcttga ccccaaaagc cctggagtgg acagggagca gctatactgg agctgagcc    300 agctgaccaa tggcatcaaa gagctgggcc cctacaccct ggacaggaac agtctctatg    360
``` tcaatg 366

<210> SEQ ID NO 552
<211> LENGTH: 465
<212> TYPE: DNA
<213> ORGANISM: Homo sapiens

<400> SEQUENCE: 552
gtttcaccca ttggatccct gtgcccacca gcagcactcc tgggacctcc acagtggacc    60
ttgggtcagg gactccatcc tccctcccca gccccacaac tgctggccct ctcctggtgc   120
cattcaccct caacttcacc atcaccaacc tgcagtacga ggaggacatg catcacccag   180
gctccaggaa gttcaacacc acggagcggg tcctgcaggg tctgcttggt cccatgttca   240
agaacaccag tgtcggcctt ctgtactctg gctgcagact gaccttgctc aggcctgaga   300
agaatggggc agccactgga atggatgcca tctcagcca ccgtcttgac cccaaaagcc   360
ctggactcaa cagagagcag ctgtactggg agctgagcca gctgacccat ggcatcaaag   420
agctgggccc ctacaccctg acaggcaca gtctctatgt caatg                    465

<210> SEQ ID NO 553
<211> LENGTH: 401
<212> TYPE: DNA
<213> ORGANISM: Homo sapiens

<400> SEQUENCE: 553
aacgattcga ccttctcctg ggacctccac agtggacctt gggtcaggga ctccatcctc    60
cctccccagc cccacaactg ctggccctct cctggtgccg ttcaccctca acttcaccat   120
caccaacctg gagtacgagg aggacatgca ttgccctggc tccaggaagt tcaacaccac   180
agagagagtc ctgcagagtc tgcttggtcc catgttcaag aacaccagtg ttggccctct   240
gtactctggc tgcagactga ccttgctcag gtccgagaag gatggagcag ccactggagt   300
ggatgccatc tgcacccacc gtcttgaccc caaaagccct ggagtggaca gggagcagct   360
atactgggag ctgagccagc tgaccaatgg catcaaagaa a                       401

<210> SEQ ID NO 554
<211> LENGTH: 385
<212> TYPE: DNA
<213> ORGANISM: Homo sapiens

<400> SEQUENCE: 554
tcctgggacc tccacagtgg accttgggtc tcagggact ccatcctccc tccccagccc     60
tacatctgct ggccctctcc tggtgccatt caccctcaac ttcaccatca ccaacctgca   120
gtacgaggag gacatgcatc acccaggctc caggaagttc aacaccacgg agcgggtcct   180
gcagggtctg cttggtccca tgttcaagaa caccagtgtc ggccttctgt actctggctg   240
cagactgacc ttgctcaggc ctgagaagaa tggggcagcc actggaatgg atgccatctg   300
cagccaccgt cttgaccca aaagccctgg actcaacaga gagcagctgt actgggagct   360
gagccagctg acccatggca tcaaa                                          385

<210> SEQ ID NO 555
<211> LENGTH: 173
<212> TYPE: DNA
<213> ORGANISM: Homo sapiens

<400> SEQUENCE: 555

```
gtctgagaag gatggggcag ccactggagt ggatgccatc tgcacccacc accttaaccc    60
tcaaagccct ggactggaca gggagcagct gtactggcag ctgagccaga tgaccaatgg   120
catcaaagag ctgggcccct acaccctgga ccggaacagt ctctacgtca atg          173

<210> SEQ ID NO 556
<211> LENGTH: 468
<212> TYPE: DNA
<213> ORGANISM: Homo sapiens

<400> SEQUENCE: 556
gtttcaccca tcggagctct gggctcacca ccagcactcc ttggacttcc acagttgacc    60
ttggaacctc agggactcca tcccccgtcc ccagccccac aactgctggc cctctcctgg   120
tgccattcac cctaaacttc accatcacca acctgcagta tgaggaggac atgcatcgcc   180
ctggatctag aagttcaac gccacagaga gggtcctgca gggtctgctt agtcccatat    240
tcaagaactc cagtgttggc cctctgtact ctggctgcag actgacctct tcaggcccg    300 agaaggatgg ggcagcaact ggaatggatg ctgtctgcct ctaccaccct aatcccaaaa   360
gacctgggct ggacagagag cagctgtact gggagctaag ccagctgacc cacaacatca   420
ctgagctggg ccctacagc ctggacaggc acagtctcta tgtcaatg                468

<210> SEQ ID NO 557
<211> LENGTH: 468
<212> TYPE: DNA
<213> ORGANISM: Homo sapiens

<400> SEQUENCE: 557
gtttcaccca tcagaactct gtgcccacca ccagtactcc tgggacctcc acagtgtact    60
gggcaaccac tgggactcca tcctccttcc ccggccacac agagcctggc cctctcctga   120
taccattcac tttcaactt accatcacca acctgcatta tgaggaaaac atgcaacacc    180
ctggttccag gaagttcaac accacggaga gggttctgca gggtctgctc acgcccttgt   240
tcaagaacac cagtgttggc cctctgtact ctggctgcag actgaccttg ctcagacctg   300
agaagcagga ggcagccact ggagtggaca ccatctgtac ccaccgcgtt gatcccatcg   360
gacctggact ggacagagag cggctatact gggagctgag ccagctgacc aacagcatca   420
cagagctggg accctacacc ctggataggg acagtctcta tgtcaatg                468

<210> SEQ ID NO 558
<211> LENGTH: 468
<212> TYPE: DNA
<213> ORGANISM: Homo sapiens

<400> SEQUENCE: 558
gcttcaaccc ttggagctct gtgccaacca ccagcactcc tgggacctcc acagtgcacc    60
tggcaacctc tgggactcca tcctccctgc ctggccacac agcccctgtc cctctcttga   120
taccattcac cctcaacttt accatcacca acctgcatta tgaagaaaac atgcaacacc   180
ctggttccag gaagttcaac accacggaga gggttctgca gggtctgctc aagcccttgt   240
tcaagagcac cagcgttggc cctctgtact ctggctgcag actgaccttg ctcagacctg   300
agaaacatgg ggcagccact ggagtggacg ccatctgcac cctccgcctt gatcccactg   360
gtcctggact ggacagagag cggctatact gggagctgag ccagctgacc aacagcgtta   420
cagagctggg cccctacacc ctggacaggg acagtctcta tgtcaatg                468
```

<210> SEQ ID NO 559
<211> LENGTH: 468
<212> TYPE: DNA
<213> ORGANISM: Homo sapiens

<400> SEQUENCE: 559

| | | | | | |
|---|---|---|---|---|---|
| gcttcaccca | tcggagctct | gtgccaacca | ccagtattcc | tgggacctct | gcagtgcacc | 60 |
| tggaaacctc | tgggactcca | gcctccctcc | ctgccacac | agcccctggc | cctctcctgg | 120 |
| tgccattcac | cctcaacttc | actatcacca | acctgcagta | tgaggaggac | atgcgtcacc | 180 |
| ctggttccag | gaagttcaac | accacggaga | gagtcctgca | gggtctgctc | aagcccttgt | 240 |
| tcaagagcac | cagtgttggc | cctctgtact | ctggctgcag | actgaccttg | ctcaggcctg | 300 |
| aaaaacgtgg | ggcagccacc | ggcgtggaca | ccatctgcac | tcaccgcctt | gaccctctaa | 360 |
| accctggact | ggacagagag | cagctatact | gggagctgag | caaactgacc | tgtggcatca | 420 |
| tcgagctggg | ccctaccctc | ctggacagag | gcagtctcta | tgtcaatg | | 468 |

<210> SEQ ID NO 560
<211> LENGTH: 468
<212> TYPE: DNA
<213> ORGANISM: Homo sapiens

<400> SEQUENCE: 560

| | | | | | |
|---|---|---|---|---|---|
| gtttcaccca | tcggaacttt | gtgcccatca | ccagcactcc | tgggacctcc | acagtacacc | 60 |
| taggaacctc | tgaaactcca | tcctccctac | ctagacccat | agtgcctggc | cctctcctgg | 120 |
| tgccattcac | cctcaacttc | accatcacca | acttgcagta | tgaggaggcc | atgcgacacc | 180 |
| ctggctccag | gaagttcaat | accacggaga | gggtcctaca | gggtctgctc | aggcccttgt | 240 |
| tcaagaatac | cagtatcggc | cctctgtact | ccagctgcag | actgaccttg | ctcaggccag | 300 |
| agaaggacaa | ggcagccacc | agagtggatg | ccatctgtac | ccaccaccct | gaccctcaaa | 360 |
| gccctggact | gaacagagag | cagctgtact | gggagctgag | ccagctgacc | cacggcatca | 420 |
| ctgagctggg | ccctacacc | ctggacaggg | acagtctcta | tgtcgatg | | 468 |

<210> SEQ ID NO 561
<211> LENGTH: 468
<212> TYPE: DNA
<213> ORGANISM: Homo sapiens

<400> SEQUENCE: 561

| | | | | | |
|---|---|---|---|---|---|
| gtttcactca | ttggagcccc | ataccaacca | ccagcactcc | tgggacctcc | atagtgaacc | 60 |
| tgggaacctc | tgggatccca | ccttccctcc | ctgaaactac | agccaccggc | cctctcctgg | 120 |
| tgccattcac | actcaacttc | accatcacta | acctacagta | tgaggagaac | atgggtcacc | 180 |
| ctggctccag | gaagttcaac | atcacggaga | gtgttctgca | gggtctgctc | aagcccttgt | 240 |
| tcaagagcac | cagtgttggc | cctctgtatt | ctggctgcag | actgaccttg | ctcaggcctg | 300 |
| agaaggacgg | agtagccacc | agagtggacg | ccatctgcac | ccaccgccct | gaccccaaaa | 360 |
| tccctgggct | agacagacag | cagctatact | gggagctgag | ccagctgacc | cacagcatca | 420 |
| ctgagctggg | accctacacc | ctggataggg | acagtctcta | tgtcaatg | | 468 |

<210> SEQ ID NO 562
<211> LENGTH: 407
<212> TYPE: DNA
<213> ORGANISM: Homo sapiens

<400> SEQUENCE: 562

```
gtttcacccca gcggagctct gtgcccacca ccagcaccac tggccctgtc ctgctgccat      60
tcaccctcaa ttttaccatc attaacctgc agtatgagga ggacatgcat cgccctggct     120
ccaggaagtt caacaccacg agagggtcc  ttcagggtct gcttatgccc ttgttcaaga     180
acaccagtgt cagctctctg tactctggtt gcagactgac cttgctcagg cctgagaagg     240
atggggcagc caccagagtg gatgctgtct gcacccatcg tcctgacccc aaaagccctg     300
gactggacag agagcggctg tactggaagc tgagccagct gacccacggc atcactgagc     360
tgggccccta caccctggac aggcacagtc tctatgtcaa tggtttc                   407
```

<210> SEQ ID NO 563
<211> LENGTH: 468
<212> TYPE: DNA
<213> ORGANISM: Homo sapiens

<400> SEQUENCE: 563

```
gtttcaccca tcagagctct atgacgacca ccagaactcc tgatacctcc acaatgcacc      60
tggcaacctc gagaactcca gcctccctgt ctggacctac gaccgccagc cctctcctgg     120
tgctattcac aattaacttc accatcacta acctgcggta tgaggagaac atgcatcacc     180
ctggctctag aaagtttaac accacggaga gagtccttca gggtctgctc aggcctgtgt     240
tcaagaacac cagtgttggc cctctgtact ctggctgcag actgaccttg ctcaggccca     300
agaaggatgg ggcagccacc aaagtggatg ccatctgcac ctaccgccct gatcccaaaa     360
gccctggact ggacagagag cagctatact gggagctgag ccagctaacc cacagcatca     420
ctgagctggg ccccctacacc ctggacaggg acagtctcta tgtcaatg                 468
```

<210> SEQ ID NO 564
<211> LENGTH: 468
<212> TYPE: DNA
<213> ORGANISM: Homo sapiens

<400> SEQUENCE: 564

```
gtttcacaca gcggagctct gtgcccacca ctagcattcc tgggacccc  acagtggacc      60 tgggaacatc tgggactcca gtttctaaac ctggtccctc ggctgccagc cctctcctgg     120
tgctattcac tctcaacttc accatcacca acctgcggta tgaggagaac atgcagcacc     180
ctggctccag gaagttcaac accacggaga gggtccttca gggcctgctc aggtccctgt     240
tcaagagcac cagtgttggc cctctgtact ctggctgcag actgactttg ctcaggcctg     300
aaaaggatgg gacagccact ggagtggatg ccatctgcac ccaccaccct gaccccaaaa     360
gccctaggct ggacagagag cagctgtatt gggagctgag ccagctgacc cacaatatca     420
ctgagctggg ccactatgcc ctggacaacg acagcctctt tgtcaatg                  468
```

<210> SEQ ID NO 565
<211> LENGTH: 465
<212> TYPE: DNA
<213> ORGANISM: Homo sapiens

<400> SEQUENCE: 565

```
gtttcactca tcggagctct gtgtccacca ccagcactcc tgggacccc  acagtgtatc      60 tgggagcatc taagactcca gcctcgatat ttgcccttc  agctgccagc catctcctga     120
tactattcac cctcaacttc accatcacta acctgcggta tgaggagaac atgtggcctg     180
gctccaggaa gttcaacact acagagaggg tccttcaggg cctgctaagg cccttgttca     240
agaacaccag tgttggccct ctgtactctg gctgcaggct gaccttgctc aggccagaga     300
```

```
aagatgggga agccaccgga gtggatgcca tctgcaccca ccgccctgac cccacaggcc    360
ctgggctgga cagagagcag ctgtatttgg agctgagcca gctgacccac agcatcactg    420
agctgggccc ctacacactg gacagggaca gtctctatgt caatg                    465

<210> SEQ ID NO 566
<211> LENGTH: 402
<212> TYPE: DNA
<213> ORGANISM: Homo sapiens

<400> SEQUENCE: 566
gtttcaccca tcggagctct gtacccacca ccagcaccgg ggtggtcagc gaggagccat     60
tcacactgaa cttcaccatc aacaacctgc gctacatggc ggacatgggc caacccggct    120
ccctcaagtt caacatcaca gacaacgtca tgaagcacct gctcagtcct ttgttccaga    180
ggagcagcct gggtgcacgg tacacaggct gcagggtcat cgcactaagg tctgtgaaga    240
acggtgctga gacacgggtg gacctcctct gcacctacct gcagcccctc agcggcccag    300
gtctgcctat caagcaggtg ttccatgagc tgagccagca gacccatggc atcacccggc    360
tgggccccta ctctctggac aaagacagcc tctaccttaa cg                       402

<210> SEQ ID NO 567
<211> LENGTH: 450
<212> TYPE: DNA
<213> ORGANISM: Homo sapiens

<400> SEQUENCE: 567
gttacaatga acctggtcta gatgagcctc ctacaactcc caagccagcc accacattcc     60
tgcctcctct gtcagaagcc acaacagcca tggggtacca cctgaagacc ctcacactca    120
acttcaccat ctccaatctc cagtattcac cagatatggg caagggctca gctacattca    180
actccaccga gggggtcctt cagcacctgc tcagacccct tgttccagaag agcagcatgg    240 gccccttcta cttgggttgc caactgatct ccctcaggcc tgagaaggat ggggcagcca    300
ctggtgtgga caccacctgc acctaccacc ctgaccctgt gggccccggg ctggacatac    360
agcagcttta ctgggagctg agtcagctga cccatggtgt cacccaactg ggcttctatg    420
tcctggacag ggatagcctc ttcatcaatg                                     450

<210> SEQ ID NO 568
<211> LENGTH: 1060
<212> TYPE: DNA
<213> ORGANISM: Homo sapiens
<220> FEATURE:
<221> NAME/KEY: misc_feature
<222> LOCATION: 406,742,801
<223> OTHER INFORMATION: n = A,T,C or G

<400> SEQUENCE: 568
gctatgcacc ccagaattta tcaatccggg gcgagtacca gataaatttc cacattgtca     60
actggaacct cagtaatcca gaccccacat cctcagagta catcaccctg ctgagggaca    120
tccaggacaa ggtcaccaca ctctacaaag gcagtcaact acatgacaca ttccgcttct    180
gcctggtcac caacttgacg atggactccg tgttggtcac tgtcaaggca ttgttctcct    240
ccaatttgga ccccagcctg gtggagcaag tctttctaga taagaccctg aatgcctcat    300
tccattggct gggctccacc taccagttgg tggacatcca tgtgacagaa atggagtcat    360
cagtttatca accaacaagc agctccagca cccagcactt ctaccygaat ttcaccatca    420
```

| | |
|---|---|
| ccaacctacc atattcccag acaaagccc agccaggcac caccaattac cagaggaaca | 480 |
| aaaggaatat tgaggatgcg ctcaaccaac tcttccgaaa cagcagcatc aagagttatt | 540 |
| tttctgactg tcaagtttca acattcaggt ctgtccccaa caggcaccac accggggtgg | 600 |
| actccctgtg taacttctcg ccactggctc ggagagtaga cagagttgcc atctatgagg | 660 |
| aatttctgcg gatgacccgg aatggtaccc agctgcagaa cttcaccctg gacaggagca | 720 |
| gtgtccttgt ggatgggtat tytcccaaca gaaatgagcc cttaactggg aattctgacc | 780 |
| ttcccttctg ggctgtcatc ytcatcggct tggcaggact cctgggactc atcacatgcc | 840 |
| tgatctgcgg tgtcctggtg accacccgcc ggcggaagag ggaaggagaa tacaacgtcc | 900 |
| agcaacagtg cccaggctac taccagtcac acctagacct ggaggatctg caatgactgg | 960 |
| aacttgccgg tgcctggggt gcctttcccc agccagggt ccaaagaagc ttggctgggg | 1020 |
| cagaaataaa ccatattggt cggacacaaa aaaaaaaaa | 1060 |

<210> SEQ ID NO 569
<211> LENGTH: 10622
<212> TYPE: DNA
<213> ORGANISM: Homo sapiens
<220> FEATURE:
<221> NAME/KEY: misc_feature
<222> LOCATION: 1,691,1164,1165,1730,2015,2149,2785,3044,3163,
    4483,4632,4825,4841,4849,4883,4915,4932,4947,6355,
    6370,7716,8210,9131,9968,10304,10363
<223> OTHER INFORMATION: n = A,T,C or G

<400> SEQUENCE: 569

| | |
|---|---|
| ncatcccccag ctcgaacagc agccacagtc ccattcatgg tgccattcac cctcaacttc | 60 |
| aactcatcac caacctgcag tacgaggagg acatgcggca cctggttcca ggaagttcaa | 120 |
| cgcgcacaga gagagaactg cagggtcgtg ctcaaaccct agatcaggaa tagcagtctg | 180 |
| gaatacctct attcaggctg cagactagcc tcactcaggc cagagaagga tagctcagcc | 240 |
| acggcagtgg atgccatctg cacacatcgc cctgaccctg aagacctcgg actggacaga | 300 |
| gagcgactgt actgggagct gagcaatctg acaaatggca tccaggagct gggcccctac | 360 |
| accctggacc ggaacagtct ctatgtcaat ggtttcaccc atcgaagctc tatgcccacc | 420 |
| accagcactc ctgggacctc cacagtggat gtgggaacct cagggactcc atcctccagc | 480 |
| cccagcccca cgactgctgg ccctctcctg atgccgttca ccctcaactt caccatcacc | 540 |
| aacctgcagt acgaggagga catgcgtcgc actggctcca ggaagttcaa caccatggag | 600 |
| agtgtcctgc agggtctgct caagcccttg ttcaagaaca ccagtgttgg ccctctgtac | 660 |
| tctggctgca gattgacctt gctcaggccc ragaaagatg gggcagccac tggagtggat | 720 |
| gccatctgca cccaccgcct tgaccccaaa agccctggac tcaacaggga gcagctgtac | 780 |
| tgggagctaa gcaaactgac caatgacatt gaagagctgg cccctacac cctggacagg | 840 |
| aacagtctct atgtcaatgg tttcacccat cagagctctg tgtccaccac cagcactcct | 900 |
| gggacctcca cagtggatct cagaacctca gtgactccat cctccctctc cagccccaca | 960 |
| attatggctg ctggccctct cctggtacca ttcaccctca acttcaccat caccaacctg | 1020 |
| cagtatgggg aggacatggg tcaccctggc tccaggaagt tcaacaccac agagagggtc | 1080 |
| ctgcagggtc tgcttggtcc catattcaag aacaccagtg ttggccctct gtactctggc | 1140 |
| tgcagactga cctctctcag gtcyragaag gatggagcag ccactggagt ggatgccatc | 1200 |
| tgcatccatc atcttgaccc caaaagccct ggactcaaca gagagcggct gtactgggag | 1260 |
| ctgagccaac tgaccaatgg catcaaagag ctgggcccct acaccctgga caggaacagt | 1320 |

```
ctctatgtca atgctgctgg ccctctcctg gtgctgttca ccctcaactt caccatcacc    1380
aacctgaagt atgaggagga catgcatcgc cctggctcca ggaagttcaa caccactgag    1440
agggtcctgc agactctgcg tggtcctatg ttcaagaaca ccagtggtgg ccttctgtac    1500
tctggctgca gactgacctt gctcaggtcc gagaaggatg gagcagccac tggagtggat    1560
gccatctgca cccaccgtct tgaccccaaa agccctggag tggacaggga gcagctatac    1620
tgggagctga gccagctgac caatggcatc aaagagctgg gccctacac cctggacagg    1680 aacagtctct atgtcaatgg tttcacccat cggacctctg tgcccaccas cagcactcct    1740
gggacctcca cagtggacct tggaacctca gggactccat tctccctccc aagcccgca    1800 actgctggcc ctctcctggt gctgttcacc ctcaacttca ccatcaccaa cctgaagtat    1860
gaggaggaca tgcatcgccc tggctccagg aagttcaaca ccactgagag ggtcctgcag    1920
actctgcttg gtcctatgtt caagaacacc agtgttggcc ttctgtactc tggctgcaga    1980
ctgaccttgc tcaggtccga aaggatgga gcagycactg gagtggatgc catctgcacc    2040
caccgtcttg accccaaaag ccctggagtg gacagggagc agctatactg ggagctgagc    2100
cagctgacca atggcatcaa agagctgggc cctacaccc tggacaggma cagtctctat    2160
gtcaatggtt tcacccattg gatccctgtg cccaccagca gcactcctgg gacctccaca    2220
gtggaccttg ggtcagggac tccatcctcc ctccccagcc cacaactgc tggccctctc    2280 ctggtgccat tcaccctcaa cttcaccatc accaacctgc agtacgagga ggacatgcat    2340
cacccaggct ccaggaagtt caacaccacg gagcgggtcc tgcagggtct gcttggtccc    2400
atgttcaaga acaccagtgt cggccttctg tactctggct gcagactgac cttgctcagg    2460
cctgagaaga atggggcagc cactggaatg gatgccatct gcagccaccg tcttgacccc    2520
aaaagccctg gactcaacag agagcagctg tactgggagc tgagccagct gacccatggc    2580
atcaaagagc tgggcccct acccctggac aggcacagtc tctatgtcaa tggtttcacc    2640
cattggatcc ctgtgcccac cagcagcact cctgggacct ccacagtgga ccttgggtca    2700
gggactccat cctccctccc cagccccaca actgctggcc ctctcctggt gccgttcacc    2760
ctcaacttca ccatcaccaa cctgragtac gaggaggaca tgcattgccc tggctccagg    2820
aagttcaaca ccacagagag agtcctgcag agtctgcttg gtcccatgtt caagaacacc    2880
agtgttggcc ctctgtactc tggctgcaga ctgaccttgc tcaggtccga aaggatgga    2940 gcagccactg gagtggatgc catctgcacc caccgtcttg accccaaaag ccctggagtg    3000
gacagggagc agctatactg ggagctgagc cagctgacca atgscatcaa agagctgggt    3060
ccctacaccc tggacagcaa cagtctctat gtcaatggtt tcacccatca gacctctgcg    3120
cccaacacca gcactcctgg gacctccaca gtggaccttg ggwcctcagg gactccatcc    3180
tccctcccca gccctacatc tgctggccct tcctggtgc cattcaccct caacttcacc    3240
atcaccaacc tgcagtacga ggaggacatg catcacccag gctccaggaa gttcaacacc    3300
acggagcggg tcctgcaggg tctgcttggt cccatgttca agaacaccag tgtcggcctt    3360
ctgtactctg gctgcagact gaccttgctc aggcctgaga gaatggggc agccactgga    3420 atggatgcca tctgcagcca ccgtcttgac cccaaaagcc ctggactcaa cagagagcag    3480
ctgtactggg agctgagcca gctgacccat ggcatcaaag agctgggccc ctacaccctg    3540
gacaggaaca gtctctatgt caatggtttc acccatcgga ctctgtggc ccccaccagc    3600 actcctggga cctccacagt ggaccttggg acctcaggga ctccatcctc cctccccagc    3660
```

```
cccacaacag ctgttcctct cctggtgccg ttcaccctca actttaccat caccaatctg   3720
cagtatgggg aggacatgcg tcaccctggc tccaggaagt tcaacaccac agagagggtc   3780
ctgcagggtc tgcttggtcc cttgttcaag aactccagtg tcggccctct gtactctggc   3840
tgcagactga tctctctcag gtctgagaag gatgggcag ccactggagt ggatgccatc    3900
tgcacccacc accttaaccc tcaaagccct ggactggaca gggagcagct gtactggcag   3960
ctgagccaga tgaccaatgg catcaaagag ctgggcccct acaccctgga ccggaacagt   4020
ctctacgtca atggtttcac ccatcggagc tctgggctca ccaccagcac tccttggact   4080
tccacagttg accttggaac ctcagggact ccatccccg tccccagccc cacaactgct    4140
ggccctctcc tggtgccatt caccctaaac ttcaccatca caacctgca gtatgaggag    4200 gacatgcatc gccctggatc taggaagttc aacgccacag agagggtcct gcagggtctg   4260
cttagtccca tattcaagaa ctccagtgtt ggccctctgt actctggctg cagactgacc   4320
tctctcaggc ccgagaagga tggggcagca actggaatgg atgctgtctg cctctaccac   4380
cctaatccca aaagacctgg gctggacaga gagcagctgt actgggagct aagccagctg   4440
acccacaaca tcactgagct gggccccgtac agcctggaca ggsacagtct ctatgtcaat   4500
ggtttcaccc atcagaactc tgtgcccacc accagtactc ctgggacctc cacagtgtac   4560
tgggcaacca ctgggactcc atcctccttc ccggccaca cagagcctgg ccctctcctg    4620
ataccattca cwttcaactt taccatcacc aacctgcatt atgaggaaaa catgcaacac   4680
cctggttcca ggaagttcaa caccacggag agggttctgc agggtctgct cacgcccttg   4740
ttcaagaaca ccagtgttgg ccctctgtac tctggctgca gactgacctt gctcagacct   4800
gagaagcagg aggcagccac tggartggac accatctgta yccaccgcst tgatcccatc   4860
ggacctggac tggacagaga gcrgctatac tgggagctga gccagctgac ccacrgcatc   4920
acagagctgg gmccctacac cctggayagg gacagtctct atgtcaatgg cttcaacct    4980 tggagctctg tgccaaccac cagcactcct gggacctcca cagtgcacct ggcaacctct   5040
gggactccat cctccctgcc tggccacaca gcccctgtcc ctctcttgat accattcacc   5100
ctcaacttta ccatcaccaa cctgcattat gaagaaaaca tgcaacaccc tggttccagg   5160
aagttcaaca ccacggagag ggttctgcag ggtctgctca gcccttgtt caagagcacc    5220 agcgttggcc ctctgtactc tggctgcaga ctgaccttgc tcagacctga gaaacatggg   5280
gcagccactg gagtggacgc catctgcacc ctccgccttg atcccactgg tcctggactg   5340
gacagagagc ggctatactg ggagctgagc cagctgacca cagcgttac agagctgggc    5400 ccctacaccc tggacaggga cagtctctat gtcaatggct tcacccatcg agctctgtg    5460 ccaaccacca gtattcctgg gacctctgca gtgcacctgg aaacctctgg gactccagcc   5520
tccctccctg ccacacagc ccctggccct ctcctggtgc cattcaccct caacttcact    5580
atcaccaacc tgcagtatga ggaggacatg cgtcaccctg gttccaggaa gttcaacacc   5640
acggagagag tcctgcaggg tctgctcaag cccttgttca agagcaccag tgttggccct   5700
ctgtactctg gctgcagact gaccttgctc aggcctgaaa acgtggggc agccaccggc    5760 gtggacacca tctgcactca ccgccttgac cctctaaacc ctggactgga cagagagcag   5820
ctatactggg agctgagcaa actgacctgt ggcatcatcg agctgggccc ctacctcctg   5880
gacagaggca gtctctatgt caatggtttc acccatcgga ctttgtgcc catcaccagc    5940 actcctggga cctccacagt acacctagga acctctgaaa ctccatcctc cctacctaga   6000
cccatagtgc ctggccctct cctggtgcca ttcaccctca acttcaccat caccaacttg   6060
```

```
cagtatgagg aggccatgcg acaccctggc tccaggaagt tcaataccac ggagagggtc    6120
ctacagggtc tgctcaggcc cttgttcaag aataccagta tcggccctct gtactccagc    6180
tgcagactga ccttgctcag gccagagaag acaaggcag ccaccagagt ggatgccatc    6240
tgtacccacc accctgaccc tcaaagccct ggactgaaca gagagcagct gtactgggag    6300
ctgagccagc tgacccacgg catcactgag ctgggcccct cacccctgga caggsacagt    6360
ctctatgtcr atggtttcac tcattggagc cccataccaa ccaccagcac tcctgggacc    6420
tccatagtga acctgggaac ctctgggatc ccaccttccc tccctgaaac tacagccacc    6480
ggccctctcc tggtgccatt cacactcaac ttcaccatca ctaacctaca gtatgaggag    6540
aacatgggtc accctggctc caggaagttc aacatcacgg agagtgttct gcagggtctg    6600
ctcaagccct tgttcaagag caccagtgtt ggccctctgt attctggctg cagactgacc    6660
ttgctcaggc ctgagaagga cggagtagcc accagagtgg acgccatctg cacccaccgc    6720
cctgaccca aaatccctgg gctagacaga cagcagctat actgggagct gagccagctg    6780
acccacagca tcactgagct gggacccctac accctggata gggacagtct ctatgtcaat    6840
ggtttcaccc agcggagctc tgtgcccacc accagcactc ctgggacttt cacagtacag    6900
ccggaaacct ctgagactcc atcatccctc cctggcccca cagccactgg ccctgtcctg    6960
ctgccattca ccctcaattt taccatcatt aacctgcagt atgaggagga catgcatcgc    7020
cctggctcca ggaagttcaa caccacggag agggtccttc agggtctgct tatgcccttg    7080
ttcaagaaca ccagtgtcag ctctctgtac tctggttgca gactgacctt gctcaggcct    7140
gagaaggatg ggcagccac cagagtggat gctgtctgca cccatcgtcc tgaccccaaa    7200
agccctggac tggacagaga gcggctgtac tggaagctga ccagctgac ccacggcatc    7260
actgagctgg ccctacac cctggacagg cacagtctct atgtcaatgg tttcacccat    7320
cagagctcta tgacgaccac cagaactcct gataccctcca caatgcacct ggcaacctcg    7380
agaactccag cctccctgtc tggacctacg accgccagcc ctctcctggt gctattcaca    7440
attaacttca ccatcactaa cctgcggtat gaggagaaca tgcatcaccc tggctctaga    7500
aagtttaaca ccacggagag agtccttcag ggtctgctca ggcctgtgtt caagaacacc    7560
agtgttggcc ctctgtactc tggctgcaga ctgaccttgc tcaggcccaa gaaggatggg    7620
gcagccacca aagtggatgc catctgcacc taccgccctg atcccaaaag ccctggactg    7680
gacagagagc agctatactg ggagctgagc cagctracc acagcatcac tgagctgggc    7740
ccctacaccc tggacaggga cagtctctat gtcaatggtt tcacacagcg gagctctgtg    7800
cccaccacta gcattcctgg gacccccaca gtggacctgg aacatctgg gactccagtt    7860
tctaaacctg gtccctcggc tgccagccct ctcctggtgc tattcactct caacttcacc    7920
atcaccaacc tgcggtatga ggagaacatg cagcaccctg ctccaggaa gttcaacacc    7980
acggagaggg tccttcaggg cctgctcagg tccctgttca agagcaccag tgttggccct    8040
ctgtactctg gctgcagact gactttgctc aggcctgaaa aggatgggac agccactgga    8100
gtggatgcca tctgcaccca ccacctgac cccaaaagcc taggctgga cagagagcag    8160
ctgtattggg agctgagcca gctgacccac aatatcactg agctgggccm ctatgccctg    8220
gacaacgaca gcctctttgt caatggtttc actcatcgga gctctgtgtc caccaccagc    8280
actcctggga cccccacagt gtatctggga gcatctaaga ctccagcctc gatatttggc    8340
ccttcagctg ccagccatct cctgatacta ttcaccctca acttcaccat cactaacctg    8400
```

```
cggtatgagg agaacatgtg gcctggctcc aggaagttca acactacaga gagggtcctt    8460
cagggcctgc taaggccctt gttcaagaac accagtgttg gccctctgta ctctggctgc    8520
aggctgacct tgctcaggcc agagaaagat ggggaagcca ccggagtgga tgccatctgc    8580
acccaccgcc ctgaccccac aggccctggg ctggacagag agcagctgta tttggagctg    8640
agccagctga cccacagcat cactgagctg gcccctaca cactggacag ggacagtctc     8700
tatgtcaatg gtttcaccca tcggagctct gtacccacca ccagcaccgg ggtggtcagc    8760
gaggagccat tcacactgaa cttcaccatc aacaacctgc gctacatggc ggacatgggc    8820
caacccggct ccctcaagtt caacatcaca gacaacgtca tgaagcacct gctcagtcct    8880
ttgttccaga ggagcagcct gggtgcacgg tacacaggct gcagggtcat cgcactaagg    8940
tctgtgaaga acggtgctga cacggggtg gacctcctct gcacctacct gcagcccctc     9000
agcggcccag gtctgcctat caagcaggtg ttccatgagc tgagccagca gacccatggc    9060
atcacccggc tgggccccta ctctctggac aaagacagcc tctaccttaa cggttacaat    9120
gaacctggtc yagatgagcc tcctacaact cccaagccag ccaccacatt cctgcctcct    9180
ctgtcagaag ccacaacagc catggggtac caccctgaaga ccctcacact caacttcacc    9240
atctccaatc tccagtattc accagatatg ggcaagggct cagctacatt caactccacc    9300
gagggggtcc ttcagcacct gctcagaccc ttgttccaga agagcagcat gggcccttc     9360 tacttgggtt gccaactgat ctccctcagg cctgagaagg atggggcagc cactggtgtg    9420
gacaccacct gcacctacca ccctgaccct gtgggcccg gctggacat acagcagctt      9480 tactgggagc tgagtcagct gacccatggt gtcacccaac tgggcttcta tgtcctggac    9540
agggatagcc tcttcatcaa tggctatgca ccccagaatt tatcaatccg ggcgagtac    9600 cagataaatt tccacattgt caactggaac ctcagtaatc cagaccccac atcctcagag    9660
tacatcaccc tgctgaggga catccaggac aaggtcacca cactctacaa aggcagtcaa    9720
ctacatgaca cattccgctt ctgcctggtc accaacttga cgatggactc cgtgttggtc    9780
actgtcaagg cattgttctc ctccaatttg gaccccagcc tggtggagca agtctttcta    9840
gataagaccc tgaatgcctc attccattgg ctgggctcca cctaccagtt ggtggacatc    9900
catgtgacag aaatggagtc atcagtttat caaccaacaa gcagctccag cacccagcac    9960
ttctaccyga atttcaccat caccaaccta ccatattccc aggacaaagc ccagccaggc   10020
accaccaatt accagaggaa caaaaggaat attgaggatg cgctcaacca actcttccga   10080
aacagcagca tcaagagtta ttttctgac tgtcaagttt caacattcag gtctgtcccc    10140
aacaggcacc acaccggggt ggactccctg tgtaacttct cgccactggc tcggagagta   10200
gacagagttg ccatctatga ggaatttctg cggatgaccc ggaatggtac ccagctgcag   10260
aacttcaccc tggacaggag cagtgtcctt gtggatgggt attytcccaa cagaaatgag   10320
cccttaactg ggaattctga ccttcccttc tgggctgtca tcytcatcgg cttggcagga   10380
ctcctgggac tcatcacatg cctgatctgc ggtgtcctgg tgaccacccg ccggcggaag   10440
aaggaaggag aatacaacgt ccagcaacag tgcccaggct actaccagtc acacctagac   10500
ctggaggatc tgcaatgact ggaacttgcc ggtgcctggg gtgcctttcc cccagccagg   10560
gtccaaagaa gcttggctgg ggcagaaata aaccatattg gtcggacaca aaaaaaaaaa   10620
aa                                                                  10622
```

<210> SEQ ID NO 570
<211> LENGTH: 469

```
<212> TYPE: DNA
<213> ORGANISM: Homo sapiens
<220> FEATURE:
<221> NAME/KEY: misc_feature
<222> LOCATION: 71,92,93,120,124,168,178,218,230,300,
      321,350,387,412,414,415,422,423,451
<223> OTHER INFORMATION: n = A,T,C or G

<400> SEQUENCE: 570
gtttcaccca tcggagctct gtgcccacca ccagcactcc tgggacctcc acagtggacc    60
tgggaacctc wgggactcca tcctccctcc cyrgccccac agctgctggc cctctcctgr   120
tgcyattcac cctcaacttc accatcacca acctgcagta tgaggagrac atgcatcrcc   180
ctggctccag gaagttcaac accacggaga gggtcctkca gggtctgcty aggtcccttg   240
ttcaagaaca ccagtgttgg ccctctgtac tctggctgca gactgacctt gctcaggccy   300
gagaaggatg gggcagccac yggagtggat gccatctgca cccaccgccy tgaccccaaa   360
agccctggac tggacagaga gcagctrtac tgggagctga ccagctgac cmayrgcatc    420 amwgagctgg ccctacac cctggacagg racagtctct atgtcaatg                 469

<210> SEQ ID NO 571
<211> LENGTH: 130
<212> TYPE: PRT
<213> ORGANISM: Homo sapiens
<220> FEATURE:
<221> NAME/KEY: variant
<222> LOCATION: 69,107,110
<223> OTHER INFORMATION: Xaa = Any amino acid

<400> SEQUENCE: 571

His Pro Gln Leu Glu Gln Gln Pro Gln Ser His Ser Trp Cys His Ser
 1               5                  10                  15

Pro Ser Thr Ser Thr His His Gln Pro Ala Val Arg Gly Gly His Ala
                20                  25                  30

Ala Pro Gly Ser Arg Lys Phe Asn Ala His Arg Glu Arg Thr Ala Gly
            35                  40                  45

Ser Cys Ser Asn Pro Arg Ser Gly Ile Ala Val Trp Asn Thr Ser Ile
        50                  55                  60

Gln Ala Ala Asp Xaa Pro His Ser Gly Gln Arg Arg Ile Ala Gln Pro
    65                  70                  75                  80

Arg Gln Trp Met Pro Ser Ala His Ile Ala Leu Thr Leu Lys Thr Ser
                85                  90                  95

Asp Trp Thr Glu Ser Asp Cys Thr Gly Ser Xaa Ala Ile Xaa Gln Met
               100                 105                 110

Ala Ser Arg Ser Trp Ala Pro Thr Pro Trp Thr Gly Thr Val Ser Met
           115                 120                 125

Ser Met
    130

<210> SEQ ID NO 572
<211> LENGTH: 130
<212> TYPE: PRT
<213> ORGANISM: Homo sapiens
<220> FEATURE:
<221> NAME/KEY: variant
<222> LOCATION: 1,58,78,92,94
<223> OTHER INFORMATION: Xaa = Any amino acid

<400> SEQUENCE: 572

Xaa Ile Pro Ser Ser Asn Ser Ser His Ser Pro Ile His Gly Ala Ile
 1               5                  10                  15
```

```
His Pro Gln Leu Gln Leu Ile Thr Asn Leu Gln Tyr Glu Glu Asp Met
            20                  25                  30

Arg His Leu Val Pro Gly Ser Ser Thr Arg Thr Glu Arg Glu Leu Gln
        35                  40                  45

Gly Arg Ala Gln Thr Leu Asp Gln Glu Xaa Gln Ser Gly Ile Pro Leu
    50                  55                  60

Phe Arg Leu Gln Thr Ser Leu Thr Gln Ala Arg Glu Gly Xaa Leu Ser
65                  70                  75                  80

His Gly Ser Gly Cys His Leu His Thr Ser Pro Xaa Pro Xaa Arg Pro
                85                  90                  95

Arg Thr Gly Gln Arg Ala Thr Val Leu Gly Ala Glu Gln Ser Asp Lys
            100                 105                 110

Trp His Pro Gly Ala Gly Pro Leu His Pro Gly Pro Glu Gln Ser Leu
        115                 120                 125

Cys Gln
    130

<210> SEQ ID NO 573
<211> LENGTH: 130
<212> TYPE: PRT
<213> ORGANISM: Homo sapiens
<220> FEATURE:
<221> NAME/KEY: variant
<222> LOCATION: 1,54
<223> OTHER INFORMATION: Xaa = Any amino acid

<400> SEQUENCE: 573

Xaa Ser Pro Ala Arg Thr Ala Ala Thr Val Pro Phe Met Val Pro Phe
                5                   10                  15

Thr Leu Asn Phe Asn Ser Ser Pro Thr Cys Ser Thr Arg Thr Cys
            20                  25                  30

Gly Thr Trp Phe Gln Glu Val Gln Arg Ala Gln Arg Glu Asn Cys Arg
        35                  40                  45

Val Val Leu Lys Pro Xaa Ile Arg Asn Ser Ser Leu Glu Tyr Leu Tyr
    50                  55                  60

Ser Gly Cys Arg Leu Ala Ser Leu Arg Pro Glu Lys Asp Ser Ser Ala
65                  70                  75                  80

Thr Ala Val Asp Ala Ile Cys Thr His Arg Pro Asp Pro Glu Asp Leu
                85                  90                  95

Gly Leu Asp Arg Glu Arg Leu Tyr Trp Glu Leu Ser Asn Leu Thr Asn
            100                 105                 110

Gly Ile Gln Glu Leu Gly Pro Tyr Thr Leu Asp Arg Asn Ser Leu Tyr
        115                 120                 125

Val Asn
    130

<210> SEQ ID NO 574
<211> LENGTH: 156
<212> TYPE: PRT
<213> ORGANISM: Homo sapiens
<220> FEATURE:
<221> NAME/KEY: variant
<222> LOCATION: 101
<223> OTHER INFORMATION: Xaa = Any amino acid

<400> SEQUENCE: 574

Gly Phe Thr His Arg Ser Ser Met Pro Thr Thr Ser Thr Pro Gly Thr
                5                   10                  15
```

Ser Thr Val Asp Val Gly Thr Ser Gly Thr Pro Ser Ser Ser Pro Ser
            20                  25                  30

Pro Thr Thr Ala Gly Pro Leu Leu Met Pro Phe Thr Leu Asn Phe Thr
        35                  40                  45

Ile Thr Asn Leu Gln Tyr Glu Glu Asp Met Arg Arg Thr Gly Ser Arg
    50                  55                  60

Lys Phe Asn Thr Met Glu Ser Val Leu Gln Gly Leu Lys Pro Leu
65                  70                  75                  80

Phe Lys Asn Thr Ser Val Gly Pro Leu Tyr Ser Gly Cys Arg Leu Thr
                85                  90                  95

Leu Leu Arg Pro Xaa Lys Asp Gly Ala Ala Thr Gly Val Asp Ala Ile
            100                 105                 110

Cys Thr His Arg Leu Asp Pro Lys Ser Pro Gly Leu Asn Arg Glu Gln
        115                 120                 125

Leu Tyr Trp Glu Leu Ser Lys Leu Thr Asn Asp Ile Glu Glu Leu Gly
    130                 135                 140

Pro Tyr Thr Leu Asp Arg Asn Ser Leu Tyr Val Asn
145                 150                 155

<210> SEQ ID NO 575
<211> LENGTH: 158
<212> TYPE: PRT
<213> ORGANISM: Homo sapiens
<220> FEATURE:
<221> NAME/KEY: variant
<222> LOCATION: 103
<223> OTHER INFORMATION: Xaa = Any amino acid

<400> SEQUENCE: 575

Gly Phe Thr His Gln Ser Ser Val Ser Thr Thr Ser Thr Pro Gly Thr
                5                   10                  15

Ser Thr Val Asp Leu Arg Thr Ser Val Thr Pro Ser Ser Leu Ser Ser
            20                  25                  30

Pro Thr Ile Met Ala Ala Gly Pro Leu Leu Val Pro Phe Thr Leu Asn
        35                  40                  45

Phe Thr Ile Thr Asn Leu Gln Tyr Gly Glu Asp Met Gly His Pro Gly
    50                  55                  60

Ser Arg Lys Phe Asn Thr Thr Glu Arg Val Leu Gln Gly Leu Leu Gly
65                  70                  75                  80

Pro Ile Phe Lys Asn Thr Ser Val Gly Pro Leu Tyr Ser Gly Cys Arg
                85                  90                  95

Leu Thr Ser Leu Arg Ser Xaa Lys Asp Gly Ala Ala Thr Gly Val Asp
            100                 105                 110

Ala Ile Cys Ile His His Leu Asp Pro Lys Ser Pro Gly Leu Asn Arg
        115                 120                 125

Glu Arg Leu Tyr Trp Glu Leu Ser Gln Leu Thr Asn Gly Ile Lys Glu
    130                 135                 140

Leu Gly Pro Tyr Thr Leu Asp Arg Asn Ser Leu Tyr Val Asn
145                 150                 155

<210> SEQ ID NO 576
<211> LENGTH: 122
<212> TYPE: PRT
<213> ORGANISM: Homo sapiens

<400> SEQUENCE: 576

Ala Ala Gly Pro Leu Leu Val Leu Phe Thr Leu Asn Phe Thr Ile Thr
                5                   10                  15

```
Asn Leu Lys Tyr Glu Glu Asp Met His Arg Pro Gly Ser Arg Lys Phe
             20                  25                  30

Asn Thr Thr Glu Arg Val Leu Gln Thr Leu Arg Gly Pro Met Phe Lys
         35                  40                  45

Asn Thr Ser Gly Gly Leu Leu Tyr Ser Gly Cys Arg Leu Thr Leu Leu
     50                  55                  60

Arg Ser Glu Lys Asp Gly Ala Ala Thr Gly Val Asp Ala Ile Cys Thr
65                  70                  75                  80

His Arg Leu Asp Pro Lys Ser Pro Gly Val Asp Arg Glu Gln Leu Tyr
             85                  90                  95

Trp Glu Leu Ser Gln Leu Thr Asn Gly Ile Lys Glu Leu Gly Pro Tyr
         100                 105                 110

Thr Leu Asp Arg Asn Ser Leu Tyr Val Asn
    115                 120

<210> SEQ ID NO 577
<211> LENGTH: 156
<212> TYPE: PRT
<213> ORGANISM: Homo sapiens
<220> FEATURE:
<221> NAME/KEY: variant
<222> LOCATION: 11,106,151
<223> OTHER INFORMATION: Xaa = Any amino acid

<400> SEQUENCE: 577

Gly Phe Thr His Arg Thr Ser Val Pro Thr Xaa Ser Thr Pro Gly Thr
                 5                  10                  15

Ser Thr Val Asp Leu Gly Thr Ser Gly Thr Pro Phe Ser Leu Pro Ser
             20                  25                  30

Pro Ala Thr Ala Gly Pro Leu Leu Val Leu Phe Thr Leu Asn Phe Thr
         35                  40                  45

Ile Thr Asn Leu Lys Tyr Glu Glu Asp Met His Arg Pro Gly Ser Arg
     50                  55                  60

Lys Phe Asn Thr Thr Glu Arg Val Leu Gln Thr Leu Leu Gly Pro Met
65                  70                  75                  80

Phe Lys Asn Thr Ser Val Gly Leu Leu Tyr Ser Gly Cys Arg Leu Thr
             85                  90                  95

Leu Leu Arg Ser Glu Lys Asp Gly Ala Xaa Thr Gly Val Asp Ala Ile
         100                 105                 110

Cys Thr His Arg Leu Asp Pro Lys Ser Pro Gly Val Asp Arg Glu Gln
     115                 120                 125

Leu Tyr Trp Glu Leu Ser Gln Leu Thr Asn Gly Ile Lys Glu Leu Gly
130                 135                 140

Pro Tyr Thr Leu Asp Arg Xaa Ser Leu Tyr Val Asn
145                 150                 155

<210> SEQ ID NO 578
<211> LENGTH: 155
<212> TYPE: PRT
<213> ORGANISM: Homo sapiens

<400> SEQUENCE: 578

Gly Phe Thr His Trp Ile Pro Val Pro Thr Ser Ser Thr Pro Gly Thr
                 5                  10                  15

Ser Thr Val Asp Leu Gly Ser Gly Thr Pro Ser Ser Leu Pro Ser Pro
             20                  25                  30

Thr Thr Ala Gly Pro Leu Leu Val Pro Phe Thr Leu Asn Phe Thr Ile
```

```
                35                  40                  45
Thr Asn Leu Gln Tyr Glu Glu Asp Met His His Pro Gly Ser Arg Lys
 50                  55                  60

Phe Asn Thr Thr Glu Arg Val Leu Gln Gly Leu Leu Gly Pro Met Phe
 65                  70                  75                  80

Lys Asn Thr Ser Val Gly Leu Leu Tyr Ser Gly Cys Arg Leu Thr Leu
                 85                  90                  95

Leu Arg Pro Glu Lys Asn Gly Ala Ala Thr Gly Met Asp Ala Ile Cys
                100                 105                 110

Ser His Arg Leu Asp Pro Lys Ser Pro Gly Leu Asn Arg Glu Gln Leu
            115                 120                 125

Tyr Trp Glu Leu Ser Gln Leu Thr His Gly Ile Lys Glu Leu Gly Pro
130                 135                 140

Tyr Thr Leu Asp Arg His Ser Leu Tyr Val Asn
145                 150                 155

<210> SEQ ID NO 579
<211> LENGTH: 155
<212> TYPE: PRT
<213> ORGANISM: Homo sapiens
<220> FEATURE:
<221> NAME/KEY: variant
<222> LOCATION: 52,138
<223> OTHER INFORMATION: Xaa = Any amino acid

<400> SEQUENCE: 579

Gly Phe Thr His Trp Ile Pro Val Pro Thr Ser Ser Thr Pro Gly Thr
                  5                  10                  15

Ser Thr Val Asp Leu Gly Ser Gly Thr Pro Ser Ser Leu Pro Ser Pro
                 20                  25                  30

Thr Thr Ala Gly Pro Leu Leu Val Pro Phe Thr Leu Asn Phe Thr Ile
             35                  40                  45

Thr Asn Leu Xaa Tyr Glu Glu Asp Met His Cys Pro Gly Ser Arg Lys
 50                  55                  60

Phe Asn Thr Thr Glu Arg Val Leu Gln Ser Leu Leu Gly Pro Met Phe
 65                  70                  75                  80

Lys Asn Thr Ser Val Gly Pro Leu Tyr Ser Gly Cys Arg Leu Thr Leu
                 85                  90                  95

Leu Arg Ser Glu Lys Asp Gly Ala Ala Thr Gly Val Asp Ala Ile Cys
                100                 105                 110

Thr His Arg Leu Asp Pro Lys Ser Pro Gly Val Asp Arg Glu Gln Leu
            115                 120                 125

Tyr Trp Glu Leu Ser Gln Leu Thr Asn Xaa Ile Lys Glu Leu Gly Pro
130                 135                 140

Tyr Thr Leu Asp Ser Asn Ser Leu Tyr Val Asn
145                 150                 155

<210> SEQ ID NO 580
<211> LENGTH: 156
<212> TYPE: PRT
<213> ORGANISM: Homo sapiens
<220> FEATURE:
<221> NAME/KEY: variant
<222> LOCATION: 23
<223> OTHER INFORMATION: Xaa = Any amino acid

<400> SEQUENCE: 580

Gly Phe Thr His Gln Thr Ser Ala Pro Asn Thr Ser Pro Gly Thr
                  5                  10                  15
```

-continued

Ser Thr Val Asp Leu Gly Xaa Ser Gly Thr Pro Ser Ser Leu Pro Ser
            20                  25                  30

Pro Thr Ser Ala Gly Pro Leu Leu Val Pro Phe Thr Leu Asn Phe Thr
        35                  40                  45

Ile Thr Asn Leu Gln Tyr Glu Glu Asp Met His His Pro Gly Ser Arg
    50                  55                  60

Lys Phe Asn Thr Thr Glu Arg Val Leu Gln Gly Leu Leu Gly Pro Met
65                  70                  75                  80

Phe Lys Asn Thr Ser Val Gly Leu Leu Tyr Ser Gly Cys Arg Leu Thr
                85                  90                  95

Leu Leu Arg Pro Glu Lys Asn Gly Ala Ala Thr Gly Met Asp Ala Ile
            100                 105                 110

Cys Ser His Arg Leu Asp Pro Lys Ser Pro Gly Leu Asn Arg Glu Gln
        115                 120                 125

Leu Tyr Trp Glu Leu Ser Gln Leu Thr His Gly Ile Lys Glu Leu Gly
    130                 135                 140

Pro Tyr Thr Leu Asp Arg Asn Ser Leu Tyr Val Asn
145                 150                 155

<210> SEQ ID NO 581
<211> LENGTH: 156
<212> TYPE: PRT
<213> ORGANISM: Homo sapiens

<400> SEQUENCE: 581

Gly Phe Thr His Arg Ser Ser Val Ala Pro Thr Ser Thr Pro Gly Thr
                5                   10                  15

Ser Thr Val Asp Leu Gly Thr Ser Gly Thr Pro Ser Ser Leu Pro Ser
            20                  25                  30

Pro Thr Thr Ala Val Pro Leu Leu Val Pro Phe Thr Leu Asn Phe Thr
        35                  40                  45

Ile Thr Asn Leu Gln Tyr Gly Glu Asp Met Arg His Pro Gly Ser Arg
    50                  55                  60

Lys Phe Asn Thr Thr Glu Arg Val Leu Gln Gly Leu Leu Gly Pro Leu
65                  70                  75                  80

Phe Lys Asn Ser Ser Val Gly Pro Leu Tyr Ser Gly Cys Arg Leu Ile
                85                  90                  95

Ser Leu Arg Ser Glu Lys Asp Gly Ala Ala Thr Gly Val Asp Ala Ile
            100                 105                 110

Cys Thr His His Leu Asn Pro Gln Ser Pro Gly Leu Asp Arg Glu Gln
        115                 120                 125

Leu Tyr Trp Gln Leu Ser Gln Met Thr Asn Gly Ile Lys Glu Leu Gly
    130                 135                 140

Pro Tyr Thr Leu Asp Arg Asn Ser Leu Tyr Val Asn
145                 150                 155

<210> SEQ ID NO 582
<211> LENGTH: 156
<212> TYPE: PRT
<213> ORGANISM: Homo sapiens
<220> FEATURE:
<221> NAME/KEY: variant
<222> LOCATION: 151
<223> OTHER INFORMATION: Xaa = Any amino acid

<400> SEQUENCE: 582

Gly Phe Thr His Arg Ser Ser Gly Leu Thr Thr Ser Thr Pro Trp Thr

```
              5               10              15
Ser Thr Val Asp Leu Gly Thr Ser Gly Thr Pro Ser Pro Val Pro Ser
            20              25              30

Pro Thr Thr Ala Gly Pro Leu Leu Val Pro Phe Thr Leu Asn Phe Thr
            35              40              45

Ile Thr Asn Leu Gln Tyr Glu Glu Asp Met His Arg Pro Gly Ser Arg
            50              55              60

Lys Phe Asn Ala Thr Glu Arg Val Leu Gln Gly Leu Leu Ser Pro Ile
 65             70              75              80

Phe Lys Asn Ser Ser Val Gly Pro Leu Tyr Ser Gly Cys Arg Leu Thr
            85              90              95

Ser Leu Arg Pro Glu Lys Asp Gly Ala Ala Thr Gly Met Asp Ala Val
            100             105             110

Cys Leu Tyr His Pro Asn Pro Lys Arg Pro Gly Leu Asp Arg Glu Gln
            115             120             125

Leu Tyr Trp Glu Leu Ser Gln Leu Thr His Asn Ile Thr Glu Leu Gly
            130             135             140

Pro Tyr Ser Leu Asp Arg Xaa Ser Leu Tyr Val Asn
145             150             155

<210> SEQ ID NO 583
<211> LENGTH: 156
<212> TYPE: PRT
<213> ORGANISM: Homo sapiens
<220> FEATURE:
<221> NAME/KEY: variant
<222> LOCATION: 109,114,117,128,139
<223> OTHER INFORMATION: Xaa = Any amino acid

<400> SEQUENCE: 583

Gly Phe Thr His Gln Asn Ser Val Pro Thr Thr Ser Thr Pro Gly Thr
              5               10              15

Ser Thr Val Tyr Trp Ala Thr Thr Gly Thr Pro Ser Ser Phe Pro Gly
            20              25              30

His Thr Glu Pro Gly Pro Leu Leu Ile Pro Phe Thr Phe Asn Phe Thr
            35              40              45

Ile Thr Asn Leu His Tyr Glu Glu Asn Met Gln His Pro Gly Ser Arg
            50              55              60

Lys Phe Asn Thr Thr Glu Arg Val Leu Gln Gly Leu Leu Thr Pro Leu
 65             70              75              80

Phe Lys Asn Thr Ser Val Gly Pro Leu Tyr Ser Gly Cys Arg Leu Thr
            85              90              95

Leu Leu Arg Pro Glu Lys Gln Glu Ala Ala Thr Gly Xaa Asp Thr Ile
            100             105             110

Cys Xaa His Arg Xaa Asp Pro Ile Gly Pro Gly Leu Asp Arg Glu Xaa
            115             120             125

Leu Tyr Trp Glu Leu Ser Gln Leu Thr His Xaa Ile Thr Glu Leu Gly
            130             135             140

Pro Tyr Thr Leu Asp Arg Asp Ser Leu Tyr Val Asn
145             150             155

<210> SEQ ID NO 584
<211> LENGTH: 156
<212> TYPE: PRT
<213> ORGANISM: Homo sapiens

<400> SEQUENCE: 584
```

```
Gly Phe Asn Pro Trp Ser Ser Val Pro Thr Thr Ser Thr Pro Gly Thr
                 5                  10                  15

Ser Thr Val His Leu Ala Thr Ser Gly Thr Pro Ser Ser Leu Pro Gly
             20                  25                  30

His Thr Ala Pro Val Pro Leu Leu Ile Pro Phe Thr Leu Asn Phe Thr
         35                  40                  45

Ile Thr Asn Leu His Tyr Glu Glu Asn Met Gln His Pro Gly Ser Arg
     50                  55                  60

Lys Phe Asn Thr Thr Glu Arg Val Leu Gln Gly Leu Leu Lys Pro Leu
 65                  70                  75                  80

Phe Lys Ser Thr Ser Val Gly Pro Leu Tyr Ser Gly Cys Arg Leu Thr
                 85                  90                  95

Leu Leu Arg Pro Glu Lys His Gly Ala Ala Thr Gly Val Asp Ala Ile
            100                 105                 110

Cys Thr Leu Arg Leu Asp Pro Thr Gly Pro Gly Leu Asp Arg Glu Arg
        115                 120                 125

Leu Tyr Trp Glu Leu Ser Gln Leu Thr Asn Ser Val Thr Glu Leu Gly
    130                 135                 140

Pro Tyr Thr Leu Asp Arg Asp Ser Leu Tyr Val Asn
145                 150                 155
```

<210> SEQ ID NO 585
<211> LENGTH: 156
<212> TYPE: PRT
<213> ORGANISM: Homo sapiens

<400> SEQUENCE: 585

```
Gly Phe Thr His Arg Ser Ser Val Pro Thr Thr Ser Ile Pro Gly Thr
                 5                  10                  15

Ser Ala Val His Leu Glu Thr Ser Gly Thr Pro Ala Ser Leu Pro Gly
             20                  25                  30

His Thr Ala Pro Gly Pro Leu Leu Val Pro Phe Thr Leu Asn Phe Thr
         35                  40                  45

Ile Thr Asn Leu Gln Tyr Glu Glu Asp Met Arg His Pro Gly Ser Arg
     50                  55                  60

Lys Phe Asn Thr Thr Glu Arg Val Leu Gln Gly Leu Leu Lys Pro Leu
 65                  70                  75                  80

Phe Lys Ser Thr Ser Val Gly Pro Leu Tyr Ser Gly Cys Arg Leu Thr
                 85                  90                  95

Leu Leu Arg Pro Glu Lys Arg Gly Ala Ala Thr Gly Val Asp Thr Ile
            100                 105                 110

Cys Thr His His Arg Leu Asp Pro Leu Asn Pro Gly Leu Asp Arg Glu Gln
        115                 120                 125

Leu Tyr Trp Glu Leu Ser Lys Leu Thr Cys Gly Ile Ile Glu Leu Gly
    130                 135                 140

Pro Tyr Leu Leu Asp Arg Gly Ser Leu Tyr Val Asn
145                 150                 155
```

<210> SEQ ID NO 586
<211> LENGTH: 156
<212> TYPE: PRT
<213> ORGANISM: Homo sapiens
<220> FEATURE:
<221> NAME/KEY: variant
<222> LOCATION: 151,156
<223> OTHER INFORMATION: Xaa = Any amino acid

<400> SEQUENCE: 586

```
Gly Phe Thr His Arg Asn Phe Val Pro Ile Thr Ser Thr Pro Gly Thr
            5                   10                  15

Ser Thr Val His Leu Gly Thr Ser Glu Thr Pro Ser Ser Leu Pro Arg
            20                  25                  30

Pro Ile Val Pro Gly Pro Leu Leu Val Pro Phe Thr Leu Asn Phe Thr
            35                  40                  45

Ile Thr Asn Leu Gln Tyr Glu Glu Ala Met Arg His Pro Gly Ser Arg
            50                  55                  60

Lys Phe Asn Thr Thr Glu Arg Val Leu Gln Gly Leu Leu Arg Pro Leu
65                  70                  75                  80

Phe Lys Asn Thr Ser Ile Gly Pro Leu Tyr Ser Ser Cys Arg Leu Thr
            85                  90                  95

Leu Leu Arg Pro Glu Lys Asp Lys Ala Ala Thr Arg Val Asp Ala Ile
            100                 105                 110

Cys Thr His His Pro Asp Pro Gln Ser Pro Gly Leu Asn Arg Glu Gln
            115                 120                 125

Leu Tyr Trp Glu Leu Ser Gln Leu Thr His Gly Ile Thr Glu Leu Gly
            130                 135                 140

Pro Tyr Thr Leu Asp Arg Xaa Ser Leu Tyr Val Xaa
145                 150                 155

<210> SEQ ID NO 587
<211> LENGTH: 156
<212> TYPE: PRT
<213> ORGANISM: Homo sapiens

<400> SEQUENCE: 587

Gly Phe Thr His Trp Ser Pro Ile Pro Thr Thr Ser Thr Pro Gly Thr
            5                   10                  15

Ser Ile Val Asn Leu Gly Thr Ser Gly Ile Pro Pro Ser Leu Pro Glu
            20                  25                  30

Thr Thr Ala Thr Gly Pro Leu Leu Val Pro Phe Thr Leu Asn Phe Thr
            35                  40                  45

Ile Thr Asn Leu Gln Tyr Glu Glu Asn Met Gly His Pro Gly Ser Arg
            50                  55                  60

Lys Phe Asn Ile Thr Glu Ser Val Leu Gln Gly Leu Leu Lys Pro Leu
65                  70                  75                  80

Phe Lys Ser Thr Ser Val Gly Pro Leu Tyr Ser Gly Cys Arg Leu Thr
            85                  90                  95

Leu Leu Arg Pro Glu Lys Asp Gly Val Ala Thr Arg Val Asp Ala Ile
            100                 105                 110

Cys Thr His Arg Pro Asp Pro Lys Ile Pro Gly Leu Asp Arg Gln Gln
            115                 120                 125

Leu Tyr Trp Glu Leu Ser Gln Leu Thr His Ser Ile Thr Glu Leu Gly
            130                 135                 140

Pro Tyr Thr Leu Asp Arg Asp Ser Leu Tyr Val Asn
145                 150                 155

<210> SEQ ID NO 588
<211> LENGTH: 156
<212> TYPE: PRT
<213> ORGANISM: Homo sapiens

<400> SEQUENCE: 588

Gly Phe Thr Gln Arg Ser Ser Val Pro Thr Thr Ser Thr Pro Gly Thr
            5                   10                  15
```

```
Phe Thr Val Gln Pro Glu Thr Ser Glu Thr Pro Ser Ser Leu Pro Gly
            20                  25                  30

Pro Thr Ala Thr Gly Pro Val Leu Leu Pro Phe Thr Leu Asn Phe Thr
        35                  40                  45

Ile Ile Asn Leu Gln Tyr Glu Glu Asp Met His Arg Pro Gly Ser Arg
    50                  55                  60

Lys Phe Asn Thr Thr Glu Arg Val Leu Gln Gly Leu Leu Met Pro Leu
65                  70                  75                  80

Phe Lys Asn Thr Ser Val Ser Ser Leu Tyr Ser Gly Cys Arg Leu Thr
                85                  90                  95

Leu Leu Arg Pro Glu Lys Asp Gly Ala Ala Thr Arg Val Asp Ala Val
            100                 105                 110

Cys Thr His Arg Pro Asp Pro Lys Ser Pro Gly Leu Asp Arg Glu Arg
        115                 120                 125

Leu Tyr Trp Lys Leu Ser Gln Leu Thr His Gly Ile Thr Glu Leu Gly
    130                 135                 140

Pro Tyr Thr Leu Asp Arg His Ser Leu Tyr Val Asn
145                 150                 155

<210> SEQ ID NO 589
<211> LENGTH: 156
<212> TYPE: PRT
<213> ORGANISM: Homo sapiens

<400> SEQUENCE: 589

Gly Phe Thr His Gln Ser Ser Met Thr Thr Arg Thr Pro Asp Thr
                5                  10                  15

Ser Thr Met His Leu Ala Thr Ser Arg Thr Pro Ala Ser Leu Ser Gly
            20                  25                  30

Pro Thr Thr Ala Ser Pro Leu Leu Val Leu Phe Thr Ile Asn Phe Thr
        35                  40                  45

Ile Thr Asn Leu Arg Tyr Glu Glu Asn Met His His Pro Gly Ser Arg
    50                  55                  60

Lys Phe Asn Thr Thr Glu Arg Val Leu Gln Gly Leu Leu Arg Pro Val
65                  70                  75                  80

Phe Lys Asn Thr Ser Val Gly Pro Leu Tyr Ser Gly Cys Arg Leu Thr
                85                  90                  95

Leu Leu Arg Pro Lys Lys Asp Gly Ala Ala Thr Lys Val Asp Ala Ile
            100                 105                 110

Cys Thr Tyr Arg Pro Asp Pro Lys Ser Pro Gly Leu Asp Arg Glu Gln
        115                 120                 125

Leu Tyr Trp Glu Leu Ser Gln Leu Thr His Ser Ile Thr Glu Leu Gly
    130                 135                 140

Pro Tyr Thr Leu Asp Arg Asp Ser Leu Tyr Val Asn
145                 150                 155

<210> SEQ ID NO 590
<211> LENGTH: 156
<212> TYPE: PRT
<213> ORGANISM: Homo sapiens
<220> FEATURE:
<221> NAME/KEY: variant
<222> LOCATION: 145
<223> OTHER INFORMATION: Xaa = Any amino acid

<400> SEQUENCE: 590

Gly Phe Thr Gln Arg Ser Ser Val Pro Thr Thr Ser Ile Pro Gly Thr
```

-continued

```
                  5                   10                  15
Pro Thr Val Asp Leu Gly Thr Ser Gly Thr Pro Val Ser Lys Pro Gly
                 20                  25                  30

Pro Ser Ala Ala Ser Pro Leu Leu Val Leu Phe Thr Leu Asn Phe Thr
                 35                  40                  45

Ile Thr Asn Leu Arg Tyr Glu Glu Asn Met Gln His Pro Gly Ser Arg
                 50                  55                  60

Lys Phe Asn Thr Thr Glu Arg Val Leu Gln Gly Leu Leu Arg Ser Leu
 65                  70                  75                  80

Phe Lys Ser Thr Ser Val Gly Pro Leu Tyr Ser Gly Cys Arg Leu Thr
                 85                  90                  95

Leu Leu Arg Pro Glu Lys Asp Gly Thr Ala Thr Gly Val Asp Ala Ile
                100                 105                 110

Cys Thr His His Pro Asp Pro Lys Ser Pro Arg Leu Asp Arg Glu Gln
                115                 120                 125

Leu Tyr Trp Glu Leu Ser Gln Leu Thr His Asn Ile Thr Glu Leu Gly
                130                 135                 140

Xaa Tyr Ala Leu Asp Asn Asp Ser Leu Phe Val Asn
145                 150                 155

<210> SEQ ID NO 591
<211> LENGTH: 155
<212> TYPE: PRT
<213> ORGANISM: Homo sapiens

<400> SEQUENCE: 591

Gly Phe Thr His Arg Ser Ser Val Ser Thr Thr Ser Thr Pro Gly Thr
                  5                  10                  15

Pro Thr Val Tyr Leu Gly Ala Ser Lys Thr Pro Ala Ser Ile Phe Gly
                 20                  25                  30

Pro Ser Ala Ala Ser His Leu Leu Ile Leu Phe Thr Leu Asn Phe Thr
                 35                  40                  45

Ile Thr Asn Leu Arg Tyr Glu Glu Asn Met Trp Pro Gly Ser Arg Lys
                 50                  55                  60

Phe Asn Thr Thr Glu Arg Val Leu Gln Gly Leu Leu Arg Pro Leu Phe
 65                  70                  75                  80

Lys Asn Thr Ser Val Gly Pro Leu Tyr Ser Gly Cys Arg Leu Thr Leu
                 85                  90                  95

Leu Arg Pro Glu Lys Asp Gly Glu Ala Thr Gly Val Asp Ala Ile Cys
                100                 105                 110

Thr His Arg Pro Asp Pro Thr Gly Pro Gly Leu Asp Arg Glu Gln Leu
                115                 120                 125

Tyr Leu Glu Leu Ser Gln Leu Thr His Ser Ile Thr Glu Leu Gly Pro
                130                 135                 140

Tyr Thr Leu Asp Arg Asp Ser Leu Tyr Val Asn
145                 150                 155

<210> SEQ ID NO 592
<211> LENGTH: 134
<212> TYPE: PRT
<213> ORGANISM: Homo sapiens

<400> SEQUENCE: 592

Gly Phe Thr His Arg Ser Ser Val Pro Thr Thr Ser Thr Gly Val Val
                  5                  10                  15

Ser Glu Glu Pro Phe Thr Leu Asn Phe Thr Ile Asn Asn Leu Arg Tyr
```

```
                    20                  25                  30

Met Ala Asp Met Gly Gln Pro Gly Ser Leu Lys Phe Asn Ile Thr Asp
            35                  40                  45

Asn Val Met Lys His Leu Leu Ser Pro Leu Phe Gln Arg Ser Ser Leu
        50                  55                  60

Gly Ala Arg Tyr Thr Gly Cys Arg Val Ile Ala Leu Arg Ser Val Lys
65                  70                  75                  80

Asn Gly Ala Glu Thr Arg Val Asp Leu Leu Cys Thr Tyr Leu Gln Pro
                85                  90                  95

Leu Ser Gly Pro Gly Leu Pro Ile Lys Gln Val Phe Glu Leu Ser
            100                 105                 110

Gln Gln Thr His Gly Ile Thr Arg Leu Gly Pro Tyr Ser Leu Asp Lys
        115                 120                 125

Asp Ser Leu Tyr Leu Asn
    130
```

<210> SEQ ID NO 593
<211> LENGTH: 150
<212> TYPE: PRT
<213> ORGANISM: Homo sapiens
<220> FEATURE:
<221> NAME/KEY: variant
<222> LOCATION: 7
<223> OTHER INFORMATION: Xaa = Any amino acid

<400> SEQUENCE: 593

```
Gly Tyr Asn Glu Pro Gly Xaa Asp Glu Pro Pro Thr Thr Pro Lys Pro
                5                   10                  15

Ala Thr Thr Phe Leu Pro Pro Leu Ser Glu Ala Thr Thr Ala Met Gly
            20                  25                  30

Tyr His Leu Lys Thr Leu Thr Leu Asn Phe Thr Ile Ser Asn Leu Gln
        35                  40                  45

Tyr Ser Pro Asp Met Gly Lys Gly Ser Ala Thr Phe Asn Ser Thr Glu
    50                  55                  60

Gly Val Leu Gln His Leu Leu Arg Pro Leu Phe Gln Lys Ser Ser Met
65                  70                  75                  80

Gly Pro Phe Tyr Leu Gly Cys Gln Leu Ile Ser Leu Arg Pro Glu Lys
                85                  90                  95

Asp Gly Ala Ala Thr Gly Val Asp Thr Thr Cys Thr Tyr His Pro Asp
            100                 105                 110

Pro Val Gly Pro Gly Leu Asp Ile Gln Gln Leu Tyr Trp Glu Leu Ser
        115                 120                 125

Gln Leu Thr His Gly Val Thr Gln Leu Gly Phe Tyr Val Leu Asp Arg
    130                 135                 140

Asp Ser Leu Phe Ile Asn
145                 150
```

<210> SEQ ID NO 594
<211> LENGTH: 318
<212> TYPE: PRT
<213> ORGANISM: Homo sapiens
<220> FEATURE:
<221> NAME/KEY: variant
<222> LOCATION: 136,248,268
<223> OTHER INFORMATION: Xaa = Any amino acid

<400> SEQUENCE: 594

```
Gly Tyr Ala Pro Gln Asn Leu Ser Ile Arg Gly Glu Tyr Gln Ile Asn
                5                   10                  15
```

-continued

Phe His Ile Val Asn Trp Asn Leu Ser Asn Pro Asp Pro Thr Ser Ser
            20                  25                  30

Glu Tyr Ile Thr Leu Leu Arg Asp Ile Gln Asp Lys Val Thr Thr Leu
        35                  40                  45

Tyr Lys Gly Ser Gln Leu His Asp Thr Phe Arg Phe Cys Leu Val Thr
    50                  55                  60

Asn Leu Thr Met Asp Ser Val Leu Val Thr Val Lys Ala Leu Phe Ser
65                  70                  75                  80

Ser Asn Leu Asp Pro Ser Leu Val Glu Gln Val Phe Leu Asp Lys Thr
                85                  90                  95

Leu Asn Ala Ser Phe His Trp Leu Gly Ser Thr Tyr Gln Leu Val Asp
            100                 105                 110

Ile His Val Thr Glu Met Glu Ser Val Tyr Gln Pro Thr Ser Ser
        115                 120                 125

Ser Ser Thr Gln His Phe Tyr Xaa Asn Phe Thr Ile Thr Asn Leu Pro
    130                 135                 140

Tyr Ser Gln Asp Lys Ala Gln Pro Gly Thr Thr Asn Tyr Gln Arg Asn
145                 150                 155                 160

Lys Arg Asn Ile Glu Asp Ala Leu Asn Gln Leu Phe Arg Asn Ser Ser
                165                 170                 175

Ile Lys Ser Tyr Phe Ser Asp Cys Gln Val Ser Thr Phe Arg Ser Val
            180                 185                 190

Pro Asn Arg His His Thr Gly Val Asp Ser Leu Cys Asn Phe Ser Pro
        195                 200                 205

Leu Ala Arg Arg Val Asp Arg Val Ala Ile Tyr Glu Glu Phe Leu Arg
    210                 215                 220

Met Thr Arg Asn Gly Thr Gln Leu Gln Asn Phe Thr Leu Asp Arg Ser
225                 230                 235                 240

Ser Val Leu Val Asp Gly Tyr Xaa Pro Asn Arg Asn Glu Pro Leu Thr
                245                 250                 255

Gly Asn Ser Asp Leu Pro Phe Trp Ala Val Ile Xaa Ile Gly Leu Ala
            260                 265                 270

Gly Leu Leu Gly Leu Ile Thr Cys Leu Ile Cys Gly Val Leu Val Thr
        275                 280                 285

Thr Arg Arg Arg Lys Lys Glu Gly Glu Tyr Asn Val Gln Gln Gln Cys
    290                 295                 300

Pro Gly Tyr Tyr Gln Ser His Leu Asp Leu Glu Asp Leu Gln
305                 310                 315

<210> SEQ ID NO 595
<211> LENGTH: 3451
<212> TYPE: PRT
<213> ORGANISM: Homo sapiens
<220> FEATURE:
<221> NAME/KEY: VARIANT
<222> LOCATION: 177, 335, 523, 618, 663, 875, 961, 1001, 1441, 1555,
    1560, 1563, 1574, 1585, 2065, 2070, 2683, 2990, 3269, 3381, 3401
<223> OTHER INFORMATION: Xaa = Any Amino Acid

<400> SEQUENCE: 595

Ile Arg Asn Ser Ser Leu Glu Tyr Leu Tyr Ser Gly Cys Arg Leu Ala
1               5                   10                  15

Ser Leu Arg Pro Glu Lys Asp Ser Ser Ala Thr Ala Val Asp Ala Ile
            20                  25                  30

Cys Thr His Arg Pro Asp Pro Glu Asp Leu Gly Leu Asp Arg Glu Arg
        35                  40                  45

-continued

```
Leu Tyr Trp Glu Leu Ser Asn Leu Thr Asn Gly Ile Gln Glu Leu Gly
 50                  55                  60

Pro Tyr Thr Leu Asp Arg Asn Ser Leu Tyr Val Asn Gly Phe Thr His
 65                  70                  75                  80

Arg Ser Ser Met Pro Thr Thr Ser Thr Pro Gly Thr Ser Thr Val Asp
                 85                  90                  95

Val Gly Thr Ser Gly Thr Pro Ser Ser Pro Ser Pro Thr Thr Ala
                100                 105                 110

Gly Pro Leu Leu Met Pro Phe Thr Leu Asn Phe Thr Ile Thr Asn Leu
                115                 120                 125

Gln Tyr Glu Glu Asp Met Arg Arg Thr Gly Ser Arg Lys Phe Asn Thr
130                 135                 140

Met Glu Ser Val Leu Gln Gly Leu Leu Lys Pro Leu Phe Lys Asn Thr
145                 150                 155                 160

Ser Val Gly Pro Leu Tyr Ser Gly Cys Arg Leu Thr Leu Leu Arg Pro
                165                 170                 175

Xaa Lys Asp Gly Ala Ala Thr Gly Val Asp Ala Ile Cys Thr His Arg
                180                 185                 190

Leu Asp Pro Lys Ser Pro Gly Leu Asn Arg Glu Gln Leu Tyr Trp Glu
                195                 200                 205

Leu Ser Lys Leu Thr Asn Asp Ile Glu Glu Leu Gly Pro Tyr Thr Leu
                210                 215                 220

Asp Arg Asn Ser Leu Tyr Val Asn Gly Phe Thr His Gln Ser Ser Val
225                 230                 235                 240

Ser Thr Thr Ser Thr Pro Gly Thr Ser Thr Val Asp Leu Arg Thr Ser
                245                 250                 255

Val Thr Pro Ser Ser Leu Ser Ser Pro Thr Ile Met Ala Ala Gly Pro
                260                 265                 270

Leu Leu Val Pro Phe Thr Leu Asn Phe Thr Ile Thr Asn Leu Gln Tyr
                275                 280                 285

Gly Glu Asp Met Gly His Pro Gly Ser Arg Lys Phe Asn Thr Thr Glu
290                 295                 300

Arg Val Leu Gln Gly Leu Leu Gly Pro Ile Phe Lys Asn Thr Ser Val
305                 310                 315                 320

Gly Pro Leu Tyr Ser Gly Cys Arg Leu Thr Ser Leu Arg Ser Xaa Lys
                325                 330                 335

Asp Gly Ala Ala Thr Gly Val Asp Ala Ile Cys Ile His His Leu Asp
                340                 345                 350

Pro Lys Ser Pro Gly Leu Asn Arg Glu Arg Leu Tyr Trp Glu Leu Ser
                355                 360                 365

Gln Leu Thr Asn Gly Ile Lys Glu Leu Gly Pro Tyr Thr Leu Asp Arg
370                 375                 380

Asn Ser Leu Tyr Val Asn Ala Ala Gly Pro Leu Leu Val Leu Phe Thr
385                 390                 395                 400

Leu Asn Phe Thr Ile Thr Asn Leu Lys Tyr Glu Glu Asp Met His Arg
                405                 410                 415

Pro Gly Ser Arg Lys Phe Asn Thr Thr Glu Arg Val Leu Gln Thr Leu
                420                 425                 430

Arg Gly Pro Met Phe Lys Asn Thr Ser Gly Gly Leu Leu Tyr Ser Gly
                435                 440                 445

Cys Arg Leu Thr Leu Leu Arg Ser Glu Lys Asp Gly Ala Ala Thr Gly
450                 455                 460
```

-continued

```
Val Asp Ala Ile Cys Thr His Arg Leu Asp Pro Lys Ser Pro Gly Val
465                 470                 475                 480

Asp Arg Glu Gln Leu Tyr Trp Glu Leu Ser Gln Leu Thr Asn Gly Ile
                485                 490                 495

Lys Glu Leu Gly Pro Tyr Thr Leu Asp Arg Asn Ser Leu Tyr Val Asn
            500                 505                 510

Gly Phe Thr His Arg Thr Ser Val Pro Thr Xaa Ser Thr Pro Gly Thr
        515                 520                 525

Ser Thr Val Asp Leu Gly Thr Ser Gly Thr Pro Phe Ser Leu Pro Ser
    530                 535                 540

Pro Ala Thr Ala Gly Pro Leu Leu Val Leu Phe Thr Leu Asn Phe Thr
545                 550                 555                 560

Ile Thr Asn Leu Lys Tyr Glu Glu Asp Met His Arg Pro Gly Ser Arg
                565                 570                 575

Lys Phe Asn Thr Thr Glu Arg Val Leu Gln Thr Leu Leu Gly Pro Met
            580                 585                 590

Phe Lys Asn Thr Ser Val Gly Leu Leu Tyr Ser Gly Cys Arg Leu Thr
        595                 600                 605

Leu Leu Arg Ser Glu Lys Asp Gly Ala Xaa Thr Gly Val Asp Ala Ile
    610                 615                 620

Cys Thr His Arg Leu Asp Pro Lys Ser Pro Gly Val Asp Arg Glu Gln
625                 630                 635                 640

Leu Tyr Trp Glu Leu Ser Gln Leu Thr Asn Gly Ile Lys Glu Leu Gly
                645                 650                 655

Pro Tyr Thr Leu Asp Arg Xaa Ser Leu Tyr Val Asn Gly Phe Thr His
            660                 665                 670

Trp Ile Pro Val Pro Thr Ser Ser Thr Pro Gly Thr Ser Thr Val Asp
        675                 680                 685

Leu Gly Ser Gly Thr Pro Ser Ser Leu Pro Ser Pro Thr Thr Ala Gly
    690                 695                 700

Pro Leu Leu Val Pro Phe Thr Leu Asn Phe Thr Ile Thr Asn Leu Gln
705                 710                 715                 720

Tyr Glu Glu Asp Met His His Pro Gly Ser Arg Lys Phe Asn Thr Thr
                725                 730                 735

Glu Arg Val Leu Gln Gly Leu Leu Gly Pro Met Phe Lys Asn Thr Ser
            740                 745                 750

Val Gly Leu Leu Tyr Ser Gly Cys Arg Leu Thr Leu Leu Arg Pro Glu
        755                 760                 765

Lys Asn Gly Ala Ala Thr Gly Met Asp Ala Ile Cys Ser His Arg Leu
    770                 775                 780

Asp Pro Lys Ser Pro Gly Leu Asn Arg Glu Gln Leu Tyr Trp Glu Leu
785                 790                 795                 800

Ser Gln Leu Thr His Gly Ile Lys Glu Leu Gly Pro Tyr Thr Leu Asp
                805                 810                 815

Arg His Ser Leu Tyr Val Asn Gly Phe Thr His Trp Ile Pro Val Pro
            820                 825                 830

Thr Ser Ser Thr Pro Gly Thr Ser Thr Val Asp Leu Gly Ser Gly Thr
        835                 840                 845

Pro Ser Ser Leu Pro Ser Pro Thr Thr Ala Gly Pro Leu Leu Val Pro
    850                 855                 860

Phe Thr Leu Asn Phe Thr Ile Thr Asn Leu Xaa Tyr Glu Glu Asp Met
865                 870                 875                 880

His Cys Pro Gly Ser Arg Lys Phe Asn Thr Thr Glu Arg Val Leu Gln
```

-continued

```
                885                 890                 895
Ser Leu Leu Gly Pro Met Phe Lys Asn Thr Ser Val Gly Pro Leu Tyr
            900                 905                 910
Ser Gly Cys Arg Leu Thr Leu Leu Arg Ser Glu Lys Asp Gly Ala Ala
            915                 920                 925
Thr Gly Val Asp Ala Ile Cys Thr His Arg Leu Asp Pro Lys Ser Pro
            930                 935                 940
Gly Val Asp Arg Glu Gln Leu Tyr Trp Glu Leu Ser Gln Leu Thr Asn
945                 950                 955                 960
Xaa Ile Lys Glu Leu Gly Pro Tyr Thr Leu Asp Ser Asn Ser Leu Tyr
                965                 970                 975
Val Asn Gly Phe Thr His Gln Thr Ser Ala Pro Asn Thr Ser Thr Pro
            980                 985                 990
Gly Thr Ser Thr Val Asp Leu Gly Xaa Ser Gly Thr Pro Ser Ser Leu
            995                 1000                1005
Pro Ser Pro Thr Ser Ala Gly Pro Leu Leu Val Pro Phe Thr Leu Asn
            1010                1015                1020
Phe Thr Ile Thr Asn Leu Gln Tyr Glu Glu Asp Met His His Pro Gly
1025                1030                1035                1040
Ser Arg Lys Phe Asn Thr Thr Glu Arg Val Leu Gln Gly Leu Leu Gly
                1045                1050                1055
Pro Met Phe Lys Asn Thr Ser Val Gly Leu Leu Tyr Ser Gly Cys Arg
            1060                1065                1070
Leu Thr Leu Leu Arg Pro Glu Lys Asn Gly Ala Ala Thr Gly Met Asp
            1075                1080                1085
Ala Ile Cys Ser His Arg Leu Asp Pro Lys Ser Pro Gly Leu Asn Arg
            1090                1095                1100
Glu Gln Leu Tyr Trp Glu Leu Ser Gln Leu Thr His Gly Ile Lys Glu
1105                1110                1115                1120
Leu Gly Pro Tyr Thr Leu Asp Arg Asn Ser Leu Tyr Val Asn Gly Phe
                1125                1130                1135
Thr His Arg Ser Ser Val Ala Pro Thr Ser Thr Pro Gly Thr Ser Thr
            1140                1145                1150
Val Asp Leu Gly Thr Ser Gly Thr Pro Ser Ser Leu Pro Ser Pro Thr
            1155                1160                1165
Thr Ala Val Pro Leu Leu Val Pro Phe Thr Leu Asn Phe Thr Ile Thr
            1170                1175                1180
Asn Leu Gln Tyr Gly Glu Asp Met Arg His Pro Gly Ser Arg Lys Phe
1185                1190                1195                1200
Asn Thr Thr Glu Arg Val Leu Gln Gly Leu Leu Gly Pro Leu Phe Lys
                1205                1210                1215
Asn Ser Ser Val Gly Pro Leu Tyr Ser Gly Cys Arg Leu Ile Ser Leu
            1220                1225                1230
Arg Ser Glu Lys Asp Gly Ala Ala Thr Gly Val Asp Ala Ile Cys Thr
            1235                1240                1245
His His Leu Asn Pro Gln Ser Pro Gly Leu Asp Arg Glu Gln Leu Tyr
            1250                1255                1260
Trp Gln Leu Ser Gln Met Thr Asn Gly Ile Lys Glu Leu Gly Pro Tyr
1265                1270                1275                1280
Thr Leu Asp Arg Asn Ser Leu Tyr Val Asn Gly Phe Thr His Arg Ser
                1285                1290                1295
Ser Gly Leu Thr Thr Ser Thr Pro Trp Thr Ser Thr Val Asp Leu Gly
            1300                1305                1310
```

-continued

```
Thr Ser Gly Thr Pro Ser Pro Val Pro Ser Pro Thr Thr Ala Gly Pro
        1315                1320                1325

Leu Leu Val Pro Phe Thr Leu Asn Phe Thr Ile Thr Asn Leu Gln Tyr
        1330                1335                1340

Glu Glu Asp Met His Arg Pro Gly Ser Arg Lys Phe Asn Ala Thr Glu
1345                1350                1355                1360

Arg Val Leu Gln Gly Leu Leu Ser Pro Ile Phe Lys Asn Ser Ser Val
                1365                1370                1375

Gly Pro Leu Tyr Ser Gly Cys Arg Leu Thr Ser Leu Arg Pro Glu Lys
                1380                1385                1390

Asp Gly Ala Ala Thr Gly Met Asp Ala Val Cys Leu Tyr His Pro Asn
                1395                1400                1405

Pro Lys Arg Pro Gly Leu Asp Arg Glu Gln Leu Tyr Trp Glu Leu Ser
        1410                1415                1420

Gln Leu Thr His Asn Ile Thr Glu Leu Gly Pro Tyr Ser Leu Asp Arg
1425                1430                1435                1440

Xaa Ser Leu Tyr Val Asn Gly Phe Thr His Gln Asn Ser Val Pro Thr
                1445                1450                1455

Thr Ser Thr Pro Gly Thr Ser Thr Val Tyr Trp Ala Thr Gly Thr
                1460                1465                1470

Pro Ser Ser Phe Pro Gly His Thr Glu Pro Gly Pro Leu Leu Ile Pro
        1475                1480                1485

Phe Thr Phe Asn Phe Thr Ile Thr Asn Leu His Tyr Glu Glu Asn Met
        1490                1495                1500

Gln His Pro Gly Ser Arg Lys Phe Asn Thr Thr Glu Arg Val Leu Gln
1505                1510                1515                1520

Gly Leu Leu Thr Pro Leu Phe Lys Asn Thr Ser Val Gly Pro Leu Tyr
                1525                1530                1535

Ser Gly Cys Arg Leu Thr Leu Leu Arg Pro Glu Lys Gln Glu Ala Ala
        1540                1545                1550

Thr Gly Xaa Asp Thr Ile Cys Xaa His Arg Xaa Asp Pro Ile Gly Pro
        1555                1560                1565

Gly Leu Asp Arg Glu Xaa Leu Tyr Trp Glu Leu Ser Gln Leu Thr His
        1570                1575                1580

Xaa Ile Thr Glu Leu Gly Pro Tyr Thr Leu Asp Arg Asp Ser Leu Tyr
1585                1590                1595                1600

Val Asn Gly Phe Asn Pro Trp Ser Ser Val Pro Thr Thr Ser Thr Pro
                1605                1610                1615

Gly Thr Ser Thr Val His Leu Ala Thr Ser Gly Thr Pro Ser Ser Leu
        1620                1625                1630

Pro Gly His Thr Ala Pro Val Pro Leu Leu Ile Pro Phe Thr Leu Asn
        1635                1640                1645

Phe Thr Ile Thr Asn Leu His Tyr Glu Glu Asn Met Gln His Pro Gly
        1650                1655                1660

Ser Arg Lys Phe Asn Thr Thr Glu Arg Val Leu Gln Gly Leu Leu Lys
1665                1670                1675                1680

Pro Leu Phe Lys Ser Thr Ser Val Gly Pro Leu Tyr Ser Gly Cys Arg
                1685                1690                1695

Leu Thr Leu Leu Arg Pro Glu Lys His Gly Ala Ala Thr Gly Val Asp
                1700                1705                1710

Ala Ile Cys Thr Leu Arg Leu Asp Pro Thr Gly Pro Gly Leu Asp Arg
        1715                1720                1725
```

```
Glu Arg Leu Tyr Trp Glu Leu Ser Gln Leu Thr Asn Ser Val Thr Glu
    1730                1735                1740
Leu Gly Pro Tyr Thr Leu Asp Arg Asp Ser Leu Tyr Val Asn Gly Phe
1745                1750                1755                1760
Thr His Arg Ser Ser Val Pro Thr Thr Ser Ile Pro Gly Thr Ser Ala
                1765                1770                1775
Val His Leu Glu Thr Ser Gly Thr Pro Ala Ser Leu Pro Gly His Thr
            1780                1785                1790
Ala Pro Gly Pro Leu Leu Val Pro Phe Thr Leu Asn Phe Thr Ile Thr
        1795                1800                1805
Asn Leu Gln Tyr Glu Glu Asp Met Arg His Pro Gly Ser Arg Lys Phe
    1810                1815                1820
Asn Thr Thr Glu Arg Val Leu Gln Gly Leu Leu Lys Pro Leu Phe Lys
1825                1830                1835                1840
Ser Thr Ser Val Gly Pro Leu Tyr Ser Gly Cys Arg Leu Thr Leu Leu
                1845                1850                1855
Arg Pro Glu Lys Arg Gly Ala Ala Thr Gly Val Asp Thr Ile Cys Thr
            1860                1865                1870
His Arg Leu Asp Pro Leu Asn Pro Gly Leu Asp Arg Glu Gln Leu Tyr
        1875                1880                1885
Trp Glu Leu Ser Lys Leu Thr Cys Gly Ile Ile Glu Leu Gly Pro Tyr
    1890                1895                1900
Leu Leu Asp Arg Gly Ser Leu Tyr Val Asn Gly Phe Thr His Arg Asn
1905                1910                1915                1920
Phe Val Pro Ile Thr Ser Thr Pro Gly Thr Ser Val His Leu Gly
                1925                1930                1935
Thr Ser Glu Thr Pro Ser Ser Leu Pro Arg Pro Ile Val Pro Gly Pro
            1940                1945                1950
Leu Leu Val Pro Phe Thr Leu Asn Phe Thr Ile Thr Asn Leu Gln Tyr
        1955                1960                1965
Glu Glu Ala Met Arg His Pro Gly Ser Arg Lys Phe Asn Thr Thr Glu
    1970                1975                1980
Arg Val Leu Gln Gly Leu Leu Arg Pro Leu Phe Lys Asn Thr Ser Ile
1985                1990                1995                2000
Gly Pro Leu Tyr Ser Ser Cys Arg Leu Thr Leu Leu Arg Pro Glu Lys
                2005                2010                2015
Asp Lys Ala Ala Thr Arg Val Asp Ala Ile Cys Thr His His Pro Asp
            2020                2025                2030
Pro Gln Ser Pro Gly Leu Asn Arg Glu Gln Leu Tyr Trp Glu Leu Ser
        2035                2040                2045
Gln Leu Thr His Gly Ile Thr Glu Leu Gly Pro Tyr Thr Leu Asp Arg
    2050                2055                2060
Xaa Ser Leu Tyr Val Xaa Gly Phe Thr His Trp Ser Pro Ile Pro Thr
2065                2070                2075                2080
Thr Ser Thr Pro Gly Thr Ser Ile Val Asn Leu Gly Thr Ser Gly Ile
                2085                2090                2095
Pro Pro Ser Leu Pro Glu Thr Thr Ala Thr Gly Pro Leu Leu Val Pro
            2100                2105                2110
Phe Thr Leu Asn Phe Thr Ile Thr Asn Leu Gln Tyr Glu Glu Asn Met
        2115                2120                2125
Gly His Pro Gly Ser Arg Lys Phe Asn Ile Thr Glu Ser Val Leu Gln
    2130                2135                2140
Gly Leu Leu Lys Pro Leu Phe Lys Ser Thr Ser Val Gly Pro Leu Tyr
```

-continued

```
                2145                2150                2155                2160

Ser Gly Cys Arg Leu Thr Leu Leu Arg Pro Glu Lys Asp Gly Val Ala
            2165                2170                2175

Thr Arg Val Asp Ala Ile Cys Thr His Arg Pro Asp Pro Lys Ile Pro
            2180                2185                2190

Gly Leu Asp Arg Gln Gln Leu Tyr Trp Glu Leu Ser Gln Leu Thr His
            2195                2200                2205

Ser Ile Thr Glu Leu Gly Pro Tyr Thr Leu Asp Arg Asp Ser Leu Tyr
            2210                2215                2220

Val Asn Gly Phe Thr Gln Arg Ser Ser Val Pro Thr Thr Ser Thr Pro
2225                2230                2235                2240

Gly Thr Phe Thr Val Gln Pro Glu Thr Ser Glu Thr Pro Ser Ser Leu
            2245                2250                2255

Pro Gly Pro Thr Ala Thr Gly Pro Val Leu Leu Pro Phe Thr Leu Asn
            2260                2265                2270

Phe Thr Ile Ile Asn Leu Gln Tyr Glu Glu Asp Met His Arg Pro Gly
            2275                2280                2285

Ser Arg Lys Phe Asn Thr Thr Glu Arg Val Leu Gln Gly Leu Leu Met
            2290                2295                2300

Pro Leu Phe Lys Asn Thr Ser Val Ser Ser Leu Tyr Ser Gly Cys Arg
2305                2310                2315                2320

Leu Thr Leu Leu Arg Pro Glu Lys Asp Gly Ala Ala Thr Arg Val Asp
            2325                2330                2335

Ala Val Cys Thr His Arg Pro Asp Pro Lys Ser Pro Gly Leu Asp Arg
            2340                2345                2350

Glu Arg Leu Tyr Trp Lys Leu Ser Gln Leu Thr His Gly Ile Thr Glu
            2355                2360                2365

Leu Gly Pro Tyr Thr Leu Asp Arg His Ser Leu Tyr Val Asn Gly Phe
            2370                2375                2380

Thr His Gln Ser Ser Met Thr Thr Arg Thr Pro Asp Thr Ser Thr
2385                2390                2395                2400

Met His Leu Ala Thr Ser Arg Thr Pro Ala Ser Leu Ser Gly Pro Thr
            2405                2410                2415

Thr Ala Ser Pro Leu Leu Val Leu Phe Thr Ile Asn Phe Thr Ile Thr
            2420                2425                2430

Asn Leu Arg Tyr Glu Glu Asn Met His Pro Gly Ser Arg Lys Phe
            2435                2440                2445

Asn Thr Thr Glu Arg Val Leu Gln Gly Leu Leu Arg Pro Val Phe Lys
            2450                2455                2460

Asn Thr Ser Val Gly Pro Leu Tyr Ser Gly Cys Arg Leu Thr Leu Leu
2465                2470                2475                2480

Arg Pro Lys Lys Asp Gly Ala Ala Thr Lys Val Asp Ala Ile Cys Thr
            2485                2490                2495

Tyr Arg Pro Asp Pro Lys Ser Pro Gly Leu Asp Arg Glu Gln Leu Tyr
            2500                2505                2510

Trp Glu Leu Ser Gln Leu Thr His Ser Ile Thr Glu Leu Gly Pro Tyr
            2515                2520                2525

Thr Leu Asp Arg Asp Ser Leu Tyr Val Asn Gly Phe Thr Gln Arg Ser
            2530                2535                2540

Ser Val Pro Thr Thr Ser Ile Pro Gly Thr Pro Thr Val Asp Leu Gly
2545                2550                2555                2560

Thr Ser Gly Thr Pro Val Ser Lys Pro Gly Pro Ser Ala Ala Ser Pro
            2565                2570                2575
```

```
Leu Leu Val Leu Phe Thr Leu Asn Phe Thr Ile Thr Asn Leu Arg Tyr
            2580                2585                2590

Glu Glu Asn Met Gln His Pro Gly Ser Arg Lys Phe Asn Thr Thr Glu
            2595                2600                2605

Arg Val Leu Gln Gly Leu Leu Arg Ser Leu Phe Lys Ser Thr Ser Val
            2610                2615                2620

Gly Pro Leu Tyr Ser Gly Cys Arg Leu Thr Leu Leu Arg Pro Glu Lys
2625                2630                2635                2640

Asp Gly Thr Ala Thr Gly Val Asp Ala Ile Cys Thr His His Pro Asp
            2645                2650                2655

Pro Lys Ser Pro Arg Leu Asp Arg Glu Gln Leu Tyr Trp Glu Leu Ser
            2660                2665                2670

Gln Leu Thr His Asn Ile Thr Glu Leu Gly Xaa Tyr Ala Leu Asp Asn
            2675                2680                2685

Asp Ser Leu Phe Val Asn Gly Phe Thr His Arg Ser Ser Val Ser Thr
            2690                2695                2700

Thr Ser Thr Pro Gly Thr Pro Thr Val Tyr Leu Gly Ala Ser Lys Thr
2705                2710                2715                2720

Pro Ala Ser Ile Phe Gly Pro Ser Ala Ala Ser His Leu Leu Ile Leu
            2725                2730                2735

Phe Thr Leu Asn Phe Thr Ile Thr Asn Leu Arg Tyr Glu Glu Asn Met
            2740                2745                2750

Trp Pro Gly Ser Arg Lys Phe Asn Thr Thr Glu Arg Val Leu Gln Gly
            2755                2760                2765

Leu Leu Arg Pro Leu Phe Lys Asn Thr Ser Val Gly Pro Leu Tyr Ser
            2770                2775                2780

Gly Cys Arg Leu Thr Leu Leu Arg Pro Glu Lys Asp Gly Glu Ala Thr
2785                2790                2795                2800

Gly Val Asp Ala Ile Cys Thr His Arg Pro Asp Pro Thr Gly Pro Gly
            2805                2810                2815

Leu Asp Arg Glu Gln Leu Tyr Leu Glu Leu Ser Gln Leu Thr His Ser
            2820                2825                2830

Ile Thr Glu Leu Gly Pro Tyr Thr Leu Asp Arg Asp Ser Leu Tyr Val
            2835                2840                2845

Asn Gly Phe Thr His Arg Ser Ser Val Pro Thr Thr Ser Thr Gly Val
            2850                2855                2860

Val Ser Glu Glu Pro Phe Thr Leu Asn Phe Thr Ile Asn Asn Leu Arg
2865                2870                2875                2880

Tyr Met Ala Asp Met Gly Gln Pro Gly Ser Leu Lys Phe Asn Ile Thr
            2885                2890                2895

Asp Asn Val Met Lys His Leu Leu Ser Pro Leu Phe Gln Arg Ser Ser
            2900                2905                2910

Leu Gly Ala Arg Tyr Thr Gly Cys Arg Val Ile Ala Leu Arg Ser Val
            2915                2920                2925

Lys Asn Gly Ala Glu Thr Arg Val Asp Leu Leu Cys Thr Tyr Leu Gln
            2930                2935                2940

Pro Leu Ser Gly Pro Gly Leu Pro Ile Lys Gln Val Phe His Glu Leu
2945                2950                2955                2960

Ser Gln Gln Thr His Gly Ile Thr Arg Leu Gly Pro Tyr Ser Leu Asp
            2965                2970                2975

Lys Asp Ser Leu Tyr Leu Asn Gly Tyr Asn Glu Pro Gly Xaa Asp Glu
            2980                2985                2990
```

```
Pro Pro Thr Thr Pro Lys Pro Ala Thr Thr Phe Leu Pro Pro Leu Ser
        2995                3000                3005

Glu Ala Thr Thr Ala Met Gly Tyr His Leu Lys Thr Leu Thr Leu Asn
        3010                3015                3020

Phe Thr Ile Ser Asn Leu Gln Tyr Ser Pro Asp Met Gly Lys Gly Ser
3025            3030                3035                3040

Ala Thr Phe Asn Ser Thr Glu Gly Val Leu Gln His Leu Leu Arg Pro
        3045                3050                3055

Leu Phe Gln Lys Ser Ser Met Gly Pro Phe Tyr Leu Gly Cys Gln Leu
        3060                3065                3070

Ile Ser Leu Arg Pro Glu Lys Asp Gly Ala Ala Thr Gly Val Asp Thr
        3075                3080                3085

Thr Cys Thr Tyr His Pro Asp Pro Val Gly Pro Gly Leu Asp Ile Gln
        3090                3095                3100

Gln Leu Tyr Trp Glu Leu Ser Gln Leu Thr His Gly Val Thr Gln Leu
3105            3110                3115                3120

Gly Phe Tyr Val Leu Asp Arg Asp Ser Leu Phe Ile Asn Gly Tyr Ala
        3125                3130                3135

Pro Gln Asn Leu Ser Ile Arg Gly Glu Tyr Gln Ile Asn Phe His Ile
        3140                3145                3150

Val Asn Trp Asn Leu Ser Asn Pro Asp Pro Thr Ser Ser Glu Tyr Ile
        3155                3160                3165

Thr Leu Leu Arg Asp Ile Gln Asp Lys Val Thr Thr Leu Tyr Lys Gly
3170            3175                3180

Ser Gln Leu His Asp Thr Phe Arg Phe Cys Leu Val Thr Asn Leu Thr
3185            3190                3195                3200

Met Asp Ser Val Leu Val Thr Val Lys Ala Leu Phe Ser Ser Asn Leu
        3205                3210                3215

Asp Pro Ser Leu Val Glu Gln Val Phe Leu Asp Lys Thr Leu Asn Ala
        3220                3225                3230

Ser Phe His Trp Leu Gly Ser Thr Tyr Gln Leu Val Asp Ile His Val
        3235                3240                3245

Thr Glu Met Glu Ser Ser Val Tyr Gln Pro Thr Ser Ser Ser Ser Thr
        3250                3255                3260

Gln His Phe Tyr Xaa Asn Phe Thr Ile Thr Asn Leu Pro Tyr Ser Gln
3265            3270                3275                3280

Asp Lys Ala Gln Pro Gly Thr Thr Asn Tyr Gln Arg Asn Lys Arg Asn
        3285                3290                3295

Ile Glu Asp Ala Leu Asn Gln Leu Phe Arg Asn Ser Ser Ile Lys Ser
        3300                3305                3310

Tyr Phe Ser Asp Cys Gln Val Ser Thr Phe Arg Ser Val Pro Asn Arg
        3315                3320                3325

His His Thr Gly Val Asp Ser Leu Cys Asn Phe Ser Pro Leu Ala Arg
        3330                3335                3340

Arg Val Asp Arg Val Ala Ile Tyr Glu Glu Phe Leu Arg Met Thr Arg
        3345                3350                3355                3360

Asn Gly Thr Gln Leu Gln Asn Phe Thr Leu Asp Arg Ser Ser Val Leu
        3365                3370                3375

Val Asp Gly Tyr Xaa Pro Asn Arg Asn Glu Pro Leu Thr Gly Asn Ser
        3380                3385                3390

Asp Leu Pro Phe Trp Ala Val Ile Xaa Ile Gly Leu Ala Gly Leu Leu
        3395                3400                3405

Gly Leu Ile Thr Cys Leu Ile Cys Gly Val Leu Val Thr Thr Arg Arg
```

-continued

```
              3410                3415                3420
Arg Lys Lys Glu Gly Glu Tyr Asn Val Gln Gln Gln Cys Pro Gly Tyr
3425                3430                3435                3440

Tyr Gln Ser His Leu Asp Leu Glu Asp Leu Gln
            3445                3450

<210> SEQ ID NO 596
<211> LENGTH: 156
<212> TYPE: PRT
<213> ORGANISM: Homo sapiens

<400> SEQUENCE: 596

Gly Phe Thr His Arg Ser Ser Val Pro Thr Thr Ser Thr Pro Gly Thr
1               5                   10                  15

Ser Thr Val Asp Leu Gly Thr Ser Gly Thr Pro Ser Ser Leu Pro Ser
            20                  25                  30

Pro Thr Ala Ala Gly Pro Leu Leu Val Pro Phe Thr Leu Asn Phe Thr
        35                  40                  45

Ile Thr Asn Leu Gln Tyr Glu Glu Asp Met His His Pro Gly Ser Arg
    50                  55                  60

Lys Phe Asn Thr Thr Glu Arg Val Leu Gln Gly Leu Leu Gly Pro Leu
65                  70                  75                  80

Phe Lys Asn Thr Ser Val Gly Pro Leu Tyr Ser Gly Cys Arg Leu Thr
                85                  90                  95

Leu Leu Arg Pro Glu Lys Asp Gly Ala Ala Thr Gly Val Asp Ala Ile
            100                 105                 110

Cys Thr His Arg Leu Asp Pro Lys Ser Pro Gly Leu Asp Arg Glu Gln
        115                 120                 125

Leu Tyr Trp Glu Leu Ser Gln Leu Thr His Gly Ile Thr Glu Leu Gly
    130                 135                 140

Pro Tyr Thr Leu Asp Arg Asp Ser Leu Tyr Val Asn
145                 150                 155

<210> SEQ ID NO 597
<211> LENGTH: 28
<212> TYPE: PRT
<213> ORGANISM: Artificial Sequence
<220> FEATURE:
<223> OTHER INFORMATION: Peptide that correspond to the extracellular
      domain of O772P molecule.

<400> SEQUENCE: 597

Lys Ser Tyr Phe Ser Asp Cys Gln Val Ser Thr Phe Arg Ser Val Pro
1               5                   10                  15

Asn Arg His His Thr Gly Val Asp Ser Leu Cys Asn
            20                  25

<210> SEQ ID NO 598
<211> LENGTH: 28
<212> TYPE: PRT
<213> ORGANISM: Artificial Sequence
<220> FEATURE:
<223> OTHER INFORMATION: Peptide that correspond to the extracellular
      domain of O772P molecule.

<400> SEQUENCE: 598

Phe Ser Pro Leu Ala Arg Arg Val Asp Arg Val Ala Ile Tyr Glu Glu
1               5                   10                  15

Phe Leu Arg Met Thr Arg Asn Gly Thr Gln Leu Gln
            20                  25
```

```
<210> SEQ ID NO 599
<211> LENGTH: 28
<212> TYPE: PRT
<213> ORGANISM: Artificial Sequence
<220> FEATURE:
<223> OTHER INFORMATION: Peptide that correspond to the extracellular
      domain of O772P molecule.

<400> SEQUENCE: 599

Thr Leu Asp Arg Ser Ser Val Leu Val Asp Gly Tyr Phe Pro Asn Arg
 1               5                  10                  15

Asn Glu Pro Leu Thr Gly Asn Ser Asp Leu Pro Phe
            20                  25

<210> SEQ ID NO 600
<211> LENGTH: 20
<212> TYPE: PRT
<213> ORGANISM: Homo sapiens

<400> SEQUENCE: 600

Met Ala Ser Leu Gly Gln Ile Leu Phe Trp Ser Ile Ile Ser Ile Ile
 1               5                  10                  15

Ile Ile Leu Ala
            20

<210> SEQ ID NO 601
<211> LENGTH: 20
<212> TYPE: PRT
<213> ORGANISM: Homo sapiens

<400> SEQUENCE: 601

Ile Ile Ile Leu Ala Gly Ala Ile Ala Leu Ile Ile Gly Phe Gly Ile
 1               5                  10                  15

Ser Gly Arg His
            20

<210> SEQ ID NO 602
<211> LENGTH: 20
<212> TYPE: PRT
<213> ORGANISM: Homo sapiens

<400> SEQUENCE: 602

Ile Ser Gly Arg His Ser Ile Thr Val Thr Thr Val Ala Ser Ala Gly
 1               5                  10                  15

Asn Ile Gly Glu
            20

<210> SEQ ID NO 603
<211> LENGTH: 20
<212> TYPE: PRT
<213> ORGANISM: Homo sapiens

<400> SEQUENCE: 603

Gly Asn Ile Gly Glu Asp Gly Ile Leu Ser Cys Thr Phe Glu Pro Asp
 1               5                  10                  15

Ile Lys Leu Ser
            20

<210> SEQ ID NO 604
<211> LENGTH: 20
<212> TYPE: PRT
<213> ORGANISM: Homo sapiens
```

-continued

<400> SEQUENCE: 604

Asp Ile Lys Leu Ser Asp Ile Val Ile Gln Trp Leu Lys Glu Gly Val
1               5                   10                  15

Leu Gly Leu Val
            20

<210> SEQ ID NO 605
<211> LENGTH: 20
<212> TYPE: PRT
<213> ORGANISM: Homo sapiens

<400> SEQUENCE: 605

Val Leu Gly Leu Val His Glu Phe Lys Glu Gly Lys Asp Glu Leu Ser
1               5                   10                  15

Glu Gln Asp Glu
            20

<210> SEQ ID NO 606
<211> LENGTH: 20
<212> TYPE: PRT
<213> ORGANISM: Homo sapiens

<400> SEQUENCE: 606

Ser Glu Gln Asp Glu Met Phe Arg Gly Arg Thr Ala Val Phe Ala Asp
1               5                   10                  15

Gln Val Ile Val
            20

<210> SEQ ID NO 607
<211> LENGTH: 20
<212> TYPE: PRT
<213> ORGANISM: Homo sapiens

<400> SEQUENCE: 607

Asp Gln Val Ile Val Gly Asn Ala Ser Leu Arg Leu Lys Asn Val Gln
1               5                   10                  15

Leu Thr Asp Ala
            20

<210> SEQ ID NO 608
<211> LENGTH: 21
<212> TYPE: PRT
<213> ORGANISM: Homo sapiens

<400> SEQUENCE: 608

Val Gln Leu Thr Asp Ala Gly Thr Tyr Lys Cys Tyr Ile Ile Thr Ser
1               5                   10                  15

Lys Gly Lys Gly Asn
            20

<210> SEQ ID NO 609
<211> LENGTH: 20
<212> TYPE: PRT
<213> ORGANISM: Homo sapiens

<400> SEQUENCE: 609

Lys Gly Lys Gly Asn Ala Asn Leu Glu Tyr Lys Thr Gly Ala Phe Ser
1               5                   10                  15

Met Pro Glu Val
            20

-continued

```
<210> SEQ ID NO 610
<211> LENGTH: 20
<212> TYPE: PRT
<213> ORGANISM: Homo sapiens

<400> SEQUENCE: 610

Ser Met Pro Glu Val Asn Val Asp Tyr Asn Ala Ser Ser Glu Thr Leu
1               5                   10                  15

Arg Cys Glu Ala
            20

<210> SEQ ID NO 611
<211> LENGTH: 20
<212> TYPE: PRT
<213> ORGANISM: Homo sapiens

<400> SEQUENCE: 611

Leu Arg Cys Glu Ala Pro Arg Trp Phe Pro Gln Pro Thr Val Val Trp
1               5                   10                  15

Ala Ser Gln Val
            20

<210> SEQ ID NO 612
<211> LENGTH: 20
<212> TYPE: PRT
<213> ORGANISM: Homo sapiens

<400> SEQUENCE: 612

Trp Ala Ser Gln Val Asp Gln Gly Ala Asn Phe Ser Glu Val Ser Asn
1               5                   10                  15

Thr Ser Phe Glu
            20

<210> SEQ ID NO 613
<211> LENGTH: 20
<212> TYPE: PRT
<213> ORGANISM: Homo sapiens

<400> SEQUENCE: 613

Asn Thr Ser Phe Glu Leu Asn Ser Glu Asn Val Thr Met Lys Val Val
1               5                   10                  15

Ser Val Leu Tyr
            20

<210> SEQ ID NO 614
<211> LENGTH: 20
<212> TYPE: PRT
<213> ORGANISM: Homo sapiens

<400> SEQUENCE: 614

Val Ser Val Leu Tyr Asn Val Thr Ile Asn Asn Thr Tyr Ser Cys Met
1               5                   10                  15

Ile Glu Asn Asp
            20

<210> SEQ ID NO 615
<211> LENGTH: 20
<212> TYPE: PRT
<213> ORGANISM: Homo sapiens

<400> SEQUENCE: 615

Met Ile Glu Asn Asp Ile Ala Lys Ala Thr Gly Asp Ile Lys Val Thr
```

```
                1               5                  10                 15

Glu Ser Glu Ile
            20

<210> SEQ ID NO 616
<211> LENGTH: 20
<212> TYPE: PRT
<213> ORGANISM: Homo sapiens

<400> SEQUENCE: 616

Thr Glu Ser Glu Ile Lys Arg Arg Ser His Leu Gln Leu Leu Asn Ser
  1               5                  10                 15

Lys Ala Ser Leu
            20

<210> SEQ ID NO 617
<211> LENGTH: 20
<212> TYPE: PRT
<213> ORGANISM: Homo sapiens

<400> SEQUENCE: 617

Ser Lys Ala Ser Leu Cys Val Ser Ser Phe Phe Ala Ile Ser Trp Ala
  1               5                  10                 15

Leu Leu Pro Ile
            20

<210> SEQ ID NO 618
<211> LENGTH: 20
<212> TYPE: PRT
<213> ORGANISM: Homo sapiens

<400> SEQUENCE: 618

Ser Ser Phe Phe Ala Ile Ser Trp Ala Leu Leu Pro Leu Ser Pro Tyr
  1               5                  10                 15

Leu Met Leu Lys
            20

<210> SEQ ID NO 619
<211> LENGTH: 30
<212> TYPE: DNA
<213> ORGANISM: Artificial Sequence
<220> FEATURE:
<223> OTHER INFORMATION: PCR primer

<400> SEQUENCE: 619
cagaagctta tggcttccct ggggcagact                                       30

<210> SEQ ID NO 620
<211> LENGTH: 31
<212> TYPE: DNA
<213> ORGANISM: Artificial Sequence
<220> FEATURE:
<223> OTHER INFORMATION: PCR primer

<400> SEQUENCE: 620
cagcggccgc ttattttagc atcaggtaag g                                     31

<210> SEQ ID NO 621
<211> LENGTH: 849
<212> TYPE: DNA
<213> ORGANISM: Rhesus Monkey

<400> SEQUENCE: 621
```

```
atggcttccc tggggcagat cctcttctgg agcataatta gcatcatctt tattctggct      60
ggagcaattg cactcatcat tggctttggt atttcaggga gacactccat cacagtcact     120
actgttgcct cagctgggaa cattgggag gatggaatcc tgagctgcac ttttgaacct      180
gacatcaaac tttctgatat cgtgatacaa tggctgaagg aaggtgttat aggcttggtc     240
catgagttca agaaggcaa agatgagctg tcggagcagg atgaaatgtt cagaggccgg      300
acagcagtgt ttgctgatca agtgatagtt ggcaatgcct ctctgcggct gaaaaatgta     360
caacttacag acgctggcac ctacaaatgt acatcatca cttctaaagg caaggggaat      420
gctaaccttg agtataaaac tggagccttc agcatgccag aggtgaatgt ggactataac     480
gccagctcag agaccttgcg gtgtgaggct ccccgatggt tcccccagcc cacagtggtc     540
tgggcatccc aagttgacca gggagccaac ttctcggaag tctccaatac cagctttgag     600
ctgaactctg agaatgtgac catgaaggtt gtgtctgtgc tatacaatgt tacgatcaac     660
aacacatact cctgtatgat tgaaaatgac attgccaaag caacagggga tatcaaagtg     720
acagaatctg agatcaaaag acggagtcac ctacagctgc taaactcaaa ggcttctctg     780
tgtgtctctt ctttccttgc catcagctgg gcacttctgc ctctcgcccc ttacctgatg     840
ctaaaataa                                                             849

<210> SEQ ID NO 622
<211> LENGTH: 1399
<212> TYPE: DNA
<213> ORGANISM: Mus musculus
<220> FEATURE:
<221> NAME/KEY: misc_feature
<222> LOCATION: 1093,1130,1134,1233
<223> OTHER INFORMATION: n = A,T,C or G

<400> SEQUENCE: 622
cccgcgtccg cggacgcgtg gggcagcagg caggcagctc cactcaccaa aatctggccc      60
cacacacagc aggactgtgg gaaggaactc cctctccatg gcttccttgg ggcagatcat     120
cttttggagt attattaaca tcatcatcat cctggctggg gccatcgcac tcatcattgg     180
ctttggcatt tcaggcaagc acttcatcac ggtcacgacc ttcacctcag ctggaaacat     240
tggagaggac gggacccctga gctgcacttt tgaacctgac atcaaactca acggcatcgt     300
catccagtgg ctgaaagaag gcatcaaagg tttggtccac gagttcaaag aaggcaaaga     360
cgacctctca cagcagcatg agatgttcag aggccgcaca gcagtgtttg ctgatcaggt     420
ggtagttggc aatgcttccc tgagactgaa aaacgtgcag ctcacggatg ctggcaccta     480
cacatgttac atccgcacct caaaaggcaa agggaatgca aaccttgagt ataagaccgg     540
agccttcagt atgccagaga taatgtggga ctataatgcc agttcagaga gtttacgctg     600
cgaggctcct cggtggttcc cccagcccac agtggcctgg gcatctcaag tcgaccaagg     660
agccaatttc tcagaagtct ccaacaccag ctttgagttg aactctgaga atgtgaccat     720
gaaggtcgta tctgtgctct acaatgtcac aatcaacaac acatactcct gtatgattga     780
aaacgacatt gccaaagcca ccggggacat caaagtgaca gattcagagg tcaaaaggcg     840
aagtcagctg cagttgctga actctgggcc ttccccgtgt gttttttctt ctgcctttgt     900
ggctggctgg gcactcctat ctctctcctg ttgcctgatg ctaagatgag gggccctggc     960
tacacaaaag catgcaacgt tgctggtcca acagaatccc ggagaactac agaaatattt    1020
tcctcaagac atgacctagt tttatatttt tagaagaaga tgaaatcatg tctagaagtc    1080
tggagagagc agncaggacc aagatgtgga aggaaaacaa aagtaacccn cagnccccc    1140
```

```
cgatcggaac aagatggacc tagaaaataa ttcaaccaaa ctagagtata ctaagtgtgc    1200
tgttacaatg tgtgtagggt aggtgtcctc ccmcatctca ggggcctccc ctggtccccc    1260
agctcctgag ttaggatggg ctgttatgat gtccctctga aggttcctgg atggttccta    1320
ctgccatata ctcattttat attcagccca ttaaaccata gtgaatgcta aaaaaaaaa    1380 aaaaaaaaaa aaaaaaaa                                                  1399
```

<210> SEQ ID NO 623
<211> LENGTH: 282
<212> TYPE: PRT
<213> ORGANISM: Rhesus Monkey

<400> SEQUENCE: 623

```
Met Ala Ser Leu Gly Gln Ile Leu Phe Trp Ser Ile Ile Ser Ile Ile
                 5                  10                  15

Phe Ile Leu Ala Gly Ala Ile Ala Leu Ile Ile Gly Phe Gly Ile Ser
             20                  25                  30

Gly Arg His Ser Ile Thr Val Thr Thr Val Ala Ser Ala Gly Asn Ile
         35                  40                  45

Gly Glu Asp Gly Ile Leu Ser Cys Thr Phe Glu Pro Asp Ile Lys Leu
     50                  55                  60

Ser Asp Ile Val Ile Gln Trp Leu Lys Glu Gly Val Ile Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
            260                 265                 270

Leu Pro Leu Ala Pro Tyr Leu Met Leu Lys
        275                 280
```

```
<210> SEQ ID NO 624
<211> LENGTH: 283
<212> TYPE: PRT
<213> ORGANISM: Mus musculus

<400> SEQUENCE: 624

Met Ala Ser Leu Gly Gln Ile Ile Phe Trp Ser Ile Ile Asn Ile Ile
                 5                  10                  15

Ile Ile Leu Ala Gly Ala Ile Ala Leu Ile Ile Gly Phe Gly Ile Ser
             20                  25                  30

Gly Lys His Phe Ile Thr Val Thr Thr Phe Thr Ser Ala Gly Asn Ile
             35                  40                  45

Gly Glu Asp Gly Thr Leu Ser Cys Thr Phe Glu Pro Asp Ile Lys Leu
     50                  55                  60

Asn Gly Ile Val Ile Gln Trp Leu Lys Glu Gly Ile Lys Gly Leu Val
 65                  70                  75                  80

His Glu Phe Lys Glu Gly Lys Asp Asp Leu Ser Gln Gln His Glu Met
                 85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
            115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Val Ala Gly Trp Ala
            260                 265                 270

Leu Leu Ser Leu Ser Cys Cys Leu Met Leu Arg
            275                 280
```

US 7,888,477 B2

OVARIAN CANCER-ASSOCIATED ANTIBODIES AND KITS

BACKGROUND OF THE INVENTION

1. Field of the Invention

The present invention relates generally to therapy and diagnosis of cancer, such as ovarian cancer. The invention is more specifically related to polypeptides, comprising at least a portion of an ovarian tumor protein, and to polynucleotides encoding such polypeptides. Such polypeptides and polynucleotides are useful in pharmaceutical compositions, e.g., vaccines, and other compositions for the diagnosis and treatment of ovarian cancer.

2. Description of the Related Art

Cancer is a significant health problem throughout the world. Although advances have been made in detection and therapy of cancer, no vaccine or other universally successful method for prevention and/or treatment is currently available. Current therapies, which are generally based on a combination of chemotherapy or surgery and radiation, continue to prove inadequate in many patients.

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

In spite of considerable research into therapies for these and other cancers, ovarian cancer remains difficult to diagnose and treat effectively. Accordingly, there is a need in the art for improved methods for detecting and treating such cancers. The present invention fulfills these needs and further provides other related advantages.

BRIEF SUMMARY OF THE INVENTION

In one aspect, the present invention provides polynucleotide compositions comprising a sequence selected from the group consisting of:

(a) sequences provided in SEQ ID NOs: 1-311, 313-387, 391, 457, 460-477, 512-570 and 619-622;

(b) complements of the sequences provided in SEQ ID NOs: 1-311, 313-387, 391, 457, 460-477, 512-570 and 619-622;

(c) sequences consisting of at least 20, 25, 30, 35, 40, 45, 50, 75 and 100 contiguous residues of a sequence provided in SEQ ID NOs: 1-311, 313-387, 391, 457, 460-477, 512-570 and 619-622;

(d) sequences that hybridize to a sequence provided in SEQ ID NOs: 1-311, 313-387, 391, 457, 460-477, 512-570 and 619-622, under moderate or highly stringent conditions;

(e) sequences having at least 75%, 80%, 85%, 90%, 95%, 96%, 97%, 98% or 99% identity to a sequence of SEQ ID NOs: 1-311, 313-387, 391, 457, 460-477, 512-570 and 619-622;

(f) degenerate variants of a sequence provided in SEQ ID NOs: 1-311, 313-387, 391, 457, 460-477, 512-570 and 619-622.

In one preferred embodiment, the polynucleotide compositions of the invention are expressed in at least about 20%, more preferably in at least about 30%, and most preferably in at least about 50% of ovarian tumors samples tested, at a level that is at least about 2-fold, preferably at least about 5-fold, and most preferably at least about 10-fold higher than that for normal tissues.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NOs: 312, 388-389, 392-455, 458-459, 478-511, 571-618 and 623-624.

In certain preferred embodiments, the polypeptides and/or polynucleotides of the present invention are immunogenic, i.e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NOs: 312, 388-389, 392-455, 458-459, 478-511, and 571-618 and 623-624 or a polypeptide sequence encoded by a polynucleotide sequence set forth in SEQ ID NOs: 1-311, 313-387, 391, 457, 460-477, 512-570 and 619-622.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with ovarian cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with ovarian cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably an ovarian cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample, e.g., tumor sample, serum sample, etc., obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE SEVERAL VIEWS OF THE DRAWINGS

FIGS. 1A-1S (SEQ ID NO:1-71) depict partial sequences of polynucleotides encoding representative secreted ovarian carcinoma antigens.

FIGS. 2A-2C depict full insert sequences for three of the clones of FIG. 1. FIG. 2A shows the sequence designated O7E (11731; SEQ ID NO:72), FIG. 2B shows the sequence designated O9E (11785; SEQ ID NO:73) and FIG. 2C shows the sequence designated O8E (13695; SEQ ID NO:74).

FIG. 3 presents results of microarray expression analysis of the ovarian carcinoma sequence designated O8E.

FIG. 4 presents a partial sequence of a polynucleotide (designated 3g; SEQ ID NO:75) encoding an ovarian carcinoma sequence that is a splice fusion between the human T-cell leukemia virus type I oncoprotein TAX and osteonectin.

FIG. 5 presents the ovarian carcinoma polynucleotide designated 3f (SEQ ID NO:76).

FIG. 6 presents the ovarian carcinoma polynucleotide designated 6b (SEQ ID NO:77).

FIGS. 7A and 7B present the ovarian carcinoma polynucleotides designated 8e (SEQ ID NO:78) and 8h (SEQ ID NO:79).

FIG. 8 presents the ovarian carcinoma polynucleotide designated 12c (SEQ ID NO:80).

FIG. 9 presents the ovarian carcinoma polynucleotide designated 12h (SEQ ID NO:81).

FIG. 10 depicts results of microarray expression analysis of the ovarian carcinoma sequence designated 3f.

FIG. 11 depicts results of microarray expression analysis of the ovarian carcinoma sequence designated 6b.

FIG. 12 depicts results of microarray expression analysis of the ovarian carcinoma sequence designated 8e.

FIG. 13 depicts results of microarray expression analysis of the ovarian carcinoma sequence designated 12c.

FIG. 14 depicts results of microarray expression analysis of the ovarian carcinoma sequence designated 12h.

FIGS. 15A-15E2 depict partial sequences of additional polynucleotides encoding representative secreted ovarian carcinoma antigens (SEQ ID NO:82-310).

FIG. 23 shows the ELISA analysis of anti-O8E rabbit sera.

FIG. 24 shows the ELISA analysis of affinity purified rabbit anti-08E polyclonal antibody.

FIG. 25 is a graph determining antibody internalization of anti-O8E mAb showing that mAbs against amino acids 61-80 induces ligand internalization.

BRIEF DESCRIPTION OF THE SEQUENCE IDENTIFIERS

Figure 16:
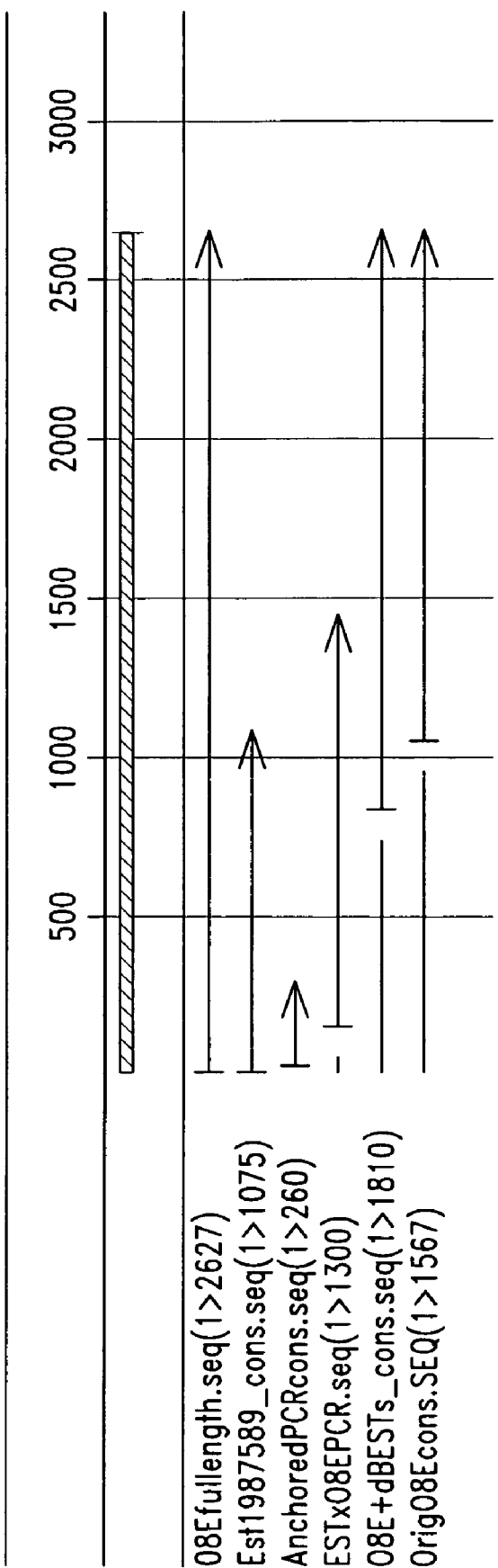
FIG. 16 is a diagram illustrating the location of various partial O8E sequences within the full length sequence.

SEQ ID NO:1-71 are ovarian carcinoma antigen polynucleotides shown in FIGS. 1A-1S.

SEQ ID NO:72-74 are ovarian carcinoma antigen polynucleotides shown in FIGS. 2A-2C.

SEQ ID NO:75 is the ovarian carcinoma polynucleotide 3g (FIG. 4).

SEQ ID NO:76 is the ovarian carcinoma polynucleotide 3f (FIG. 5).

SEQ ID NO:77 is the ovarian carcinoma polynucleotide 6b (FIG. 6).

SEQ ID NO:78 is the ovarian carcinoma polynucleotide 8e (FIG. 7A).

SEQ ID NO:79 is the ovarian carcinoma polynucleotide 8h (FIG. 7B).

SEQ ID NO:80 is the ovarian carcinoma polynucleotide 12e (FIG. 8).

SEQ ID NO:81 is the ovarian carcinoma polynucleotide 12h (FIG. 9).

SEQ ID NO:82-310 are ovarian carcinoma antigen polynucleotides shown in FIGS. 15A-15EEE.

SEQ ID NO:311 is a full length sequence of ovarian carcinoma polynucleotide O772P.

SEQ ID NO:312 is the O772P amino acid sequence.

SEQ ID NO:313-384 are ovarian carcinoma antigen polynucleotides.

SEQ ID NO:385 represents the cDNA sequence of a form of the clone O772P, designated 21013.

SEQ ID NO:386 represents the cDNA sequence of a form of the clone O772P, designated 21003.

SEQ ID NO:387 represents the cDNA sequence of a form of the clone O772P, designated 21008.

SEQ ID NOs:388 is the amino acid sequence corresponding to SEQ ID NO:385.

SEQ ID NOs:389 is the amino acid sequence corresponding to SEQ ID NO:386.

SEQ ID NOs:390 is the amino acid sequence corresponding to SEQ ID NO:387.

SEQ ID NO:391 is a full length sequence of ovarian carcinoma polynucleotide O8E.

SEQ ID NO:392-393 are protein sequences encoded by O8E.

SEQ ID NO:394-415 are peptide sequences corresponding to the O8E antibody epitopes.

SEQ ID NO:416-435 are potential HLA-A2 10-mer binding peptides predicted using the full length open-reading frame from O8E.

SEQ ID NO:436-455 are potential HLA-A2 9-mer binding peptides predicted using the full length open-reading frame from O8E.

SEQ ID NO:456 is a truncated nucleotide sequence of the full length Genbank sequence showing homology to O772P SEQ ID NO:457 is the full length Genbank sequence showing significant homology to O772P SEQ ID NO:458 is a protein encoding a truncated version of the full length Genbank sequence showing homology to O772P SEQ ID NO:459 is the full length protein sequence from Genbank showing significant homology to the protein sequence for O772P SEQ ID NO:460 encodes a unique N-terminal portion of O772P contained in residues 1-70.

SEQ ID NO:461 contains unique sequence and encodes residues 1-313 of SEQ ID NO: 456.

SEQ ID NO:462 is the hypothetical sequence for clone O772P.

SEQ ID NO:463 is the cDNA sequence for clone FLJ14303.

SEQ ID NO:464 is a partial cDNA sequence for clone O772P.

SEQ ID NO:465 is a partial cDNA sequence for clone O772P.

SEQ ID NO:466 is a partial cDNA sequence for clone O772P.

SEQ ID NO:467 is a partial cDNA sequence for clone O772P.

SEQ ID NO:468 is a partial cDNA sequence for clone O772P.

SEQ ID NO:469 is a partial cDNA sequence for clone O772P.

SEQ ID NO:470 is a partial cDNA sequence for clone O772P.

SEQ ID NO:471 is a partial cDNA sequence for clone O772P.

SEQ ID NO:472 is a partial cDNA sequence for clone O772P.

SEQ ID NO:473 is a partial cDNA sequence for clone O772P.

SEQ ID NO:474 is a partial cDNA sequence for clone O772P.

SEQ ID NO:475 is a partial cDNA sequence for clone O772P.

SEQ ID NO:476 is a partial cDNA sequence for clone O772P.

SEQ ID NO:477 represents the novel 5'-end of the ovarian tumor antigen O772P.

SEQ ID NO:478 is the amino acid sequence encoded by SEQ ID NO:462.

SEQ ID NO:479 is the amino acid sequence encoded by SEQ ID NO:463.

SEQ ID NO:480 is a partial amino acid sequence encoded by SEQ ID NO:472.

SEQ ID NO:481 is a partial amino acid sequence encoded by a possible open reading frame of SEQ ID NO:471.

SEQ ID NO:482 is a partial amino acid sequence encoded by a second possible open reading frame of SEQ ID NO:471.

SEQ ID NO:483 is a partial amino acid sequence encoded by SEQ ID NO:467.

SEQ ID NO:484 is a partial amino acid sequence encoded by a possible open reading frame of SEQ ID NO:466.

SEQ ID NO:485 is a partial amino acid sequence encoded by a second possible open reading frame of SEQ ID NO:466.

SEQ ID NO:486 is a partial amino acid sequence encoded by SEQ ID NO:465.

SEQ ID NO:487 is a partial amino acid sequence encoded by SEQ ID NO:464.

SEQ ID NO:488 represents the extracellular, transmembrane and cytoplasmic regions of O772P.

SEQ ID NO:489 represents the predicted extracellular domain of O772P.

SEQ ID NO:490 represents the amino acid sequence of peptide #2 which corresponds to an O772P specific antibody epitope.

SEQ ID NO:491 represents the amino acid sequence of peptide #6 which corresponds to an O772P specific antibody epitope.

SEQ ID NO:492 represents the amino acid sequence of peptide #7 which corresponds to an O772P specific antibody epitope.

SEQ ID NO:493 represents the amino acid sequence of peptide #8 which corresponds to an O772P specific antibody epitope.

SEQ ID NO:494 represents the amino acid sequence of peptide #9 which corresponds to an O772P specific antibody epitope.

SEQ ID NO:495 represents the amino acid sequence of peptide #11 which corresponds to an O772P specific antibody epitope.

SEQ ID NO:496 represents the amino acid sequence of peptide #13 which corresponds to an O772P specific antibody epitope.

SEQ ID NO:497 represents the amino acid sequence of peptide #22 which corresponds to an O772P specific antibody epitope.

SEQ ID NO:498 represents the amino acid sequence of peptide #24 which corresponds to an O772P specific antibody epitope.

SEQ ID NO:499 represents the amino acid sequence of peptide #27 which corresponds to an O772P specific antibody epitope.

SEQ ID NO:500 represents the amino acid sequence of peptide #40 which corresponds to an O772P specific antibody epitope.

SEQ ID NO:501 represents the amino acid sequence of peptide #41 which corresponds to an O772P specific antibody epitope.

SEQ ID NO:502 represents the amino acid sequence of peptide #47 which corresponds to an O772P specific antibody epitope.

SEQ ID NO:503 represents the amino acid sequence of peptide #50 which corresponds to an O772P specific antibody epitope.

SEQ ID NO:504 represents the amino acid sequence of peptide #51 which corresponds to an O772P specific antibody epitope.

SEQ ID NO:505 represents the amino acid sequence of peptide #52 which corresponds to an O772P specific antibody epitope.

SEQ ID NO:506 represents the amino acid sequence of peptide #53 which corresponds to an O772P specific antibody epitope.

SEQ ID NO:507 represents the amino acid sequence of peptide #58 which corresponds to an O772P specific antibody epitope.

SEQ ID NO:508 represents the amino acid sequence of peptide #59 which corresponds to an O772P specific antibody epitope.

SEQ ID NO:509 represents the amino acid sequence of peptide #60 which corresponds to an O772P specific antibody epitope.

SEQ ID NO:510 represents the amino acid sequence of peptide #61 which corresponds to an O772P specific antibody epitope.

SEQ ID NO:511 represents the amino acid sequence of peptide #71 which corresponds to an O772P specific antibody epitope.

SEQ ID NO:512 (O772P repeat1) represents an example of a cDNA sequence corresponding to repeat number 21 from the 5' variable region of O772P.

SEQ ID NO:513 (O772P repeat2) represents an example of a cDNA sequence corresponding to repeat number 20 from the 5' variable region of O772P.

SEQ ID NO:514 (O772P repeat3) represents an example of a cDNA sequence corresponding to repeat number 19 from the 5' variable region of O772P.

SEQ ID NO:515 (O772P repeat4) represents an example of a cDNA sequence corresponding to repeat number 18 from the 5' variable region of O772P.

SEQ ID NO:516 (O772P repeat5) represents an example of a cDNA sequence corresponding to repeat number 17 from the 5' variable region of O772P.

SEQ ID NO:517 (HB repeat1) represents an example of a cDNA sequence corresponding to repeat number 21 from the 5' variable region of O772P.

SEQ ID NO:518 (HB repeat2) represents an example of a cDNA sequence corresponding to repeat number 20 from the 5' variable region of O772P.

SEQ ID NO:519 (HB repeat3) represents an example of a cDNA sequence corresponding to repeat number 19 from the 5' variable region of O772P.

SEQ ID NO:520 (HB repeat4) represents an example of a cDNA sequence corresponding to repeat number 18 from the 5' variable region of O772P.

SEQ ID NO:521 (HB repeat5) represents an example of a cDNA sequence corresponding to repeat number 17 from the 5' variable region of O772P.

SEQ ID NO:522 (HB repeat6 5'-end) represents an example of a cDNA sequence corresponding to repeat number 16 from the 5' variable region of O772P.

SEQ ID NO:523 (1043400.1 repeat1) represents an example of a cDNA sequence corresponding to repeat number 9 from the 5' variable region of O772P.

SEQ ID NO:524 (1043400.1 repeat2) represents an example of a cDNA sequence corresponding to repeat number 10 from the 5' variable region of O772P.

SEQ ID NO:525 (1043400.1 repeat3) represents an example of a cDNA sequence corresponding to repeat No. 10/11 from the 5' variable region of O772P.

SEQ ID NO:526 (1043400.1 repeat4) represents an example of a cDNA sequence corresponding to repeat number 11 from the 5' variable region of O772P.

SEQ ID NO:527 (1043400.1 repeat5) represents an example of a cDNA sequence corresponding to repeat number 14 from the 5' variable region of O772P.

SEQ ID NO:528 (1043400.1 repeat6) represents an example of a cDNA sequence corresponding to repeat number 17 from the 5' variable region of O772P.

SEQ ID NO:529 (1043400.3 repeat1) represents an example of a cDNA sequence corresponding to repeat number 20 from the 5' variable region of O772P.

SEQ ID NO:530 (1043400.3 repeat2) represents an example of a cDNA sequence corresponding to repeat number 21 from the 5' variable region of O772P.

SEQ ID NO:531 (1043400.5 repeat1) represents an example of a cDNA sequence corresponding to repeat number 8 from the 5' variable region of O772P.

SEQ ID NO:532 (1043400.5 repeat2) represents an example of a cDNA sequence corresponding to repeat number 9 from the 5' variable region of O772P, in addition containing intron sequence.

SEQ ID NO:533 (1043400.5 repeat2) represents an example of a cDNA sequence corresponding to repeat number 9 from the 5' variable region of O772P.

SEQ ID NO:534 (1043400.8 repeat1) represents an example of a cDNA sequence corresponding to repeat number 17 from the 5' variable region of O772P.

SEQ ID NO:535 (1043400.8 repeat2) represents an example of a cDNA sequence corresponding to repeat number 18 from the 5' variable region of O772P.

SEQ ID NO:536 (1043400.8 repeat3) represents an example of a cDNA sequence corresponding to repeat number 19 from the 5' variable region of O772P.

SEQ ID NO:537 (1043400.9 repeat1) represents an example of a cDNA sequence corresponding to repeat number 4 from the 5' variable region of O772P.

SEQ ID NO:538 (1043400.9 repeat2) represents an example of a cDNA sequence corresponding to repeat number 5 from the 5' variable region of O772P.

SEQ ID NO:539 (1043400.9 repeat3) represents an example of a cDNA sequence corresponding to repeat number 7 from the 5' variable region of O772P.

SEQ ID NO:540 (1043400.9 repeat4) represents an example of a cDNA sequence corresponding to repeat number 8 from the 5' variable region of O772P.

SEQ ID NO:541 (1043400.11 repeat1) represents an example of a cDNA sequence corresponding to repeat number 1 from the 5' variable region of O772P.

SEQ ID NO:542 (1043400.11 repeat2) represents an example of a cDNA sequence corresponding to repeat number 2 from the 5' variable region of O772P.

SEQ ID NO:543 (1043400.11 repeat3) represents an example of a cDNA sequence corresponding to repeat number 3 from the 5' variable region of O772P.

SEQ ID NO:544 (1043400.11 repeat4) represents an example of a cDNA sequence corresponding to repeat number 11 from the 5' variable region of O772P.

SEQ ID NO:545 (1043400.11 repeat5) represents an example of a cDNA sequence corresponding to repeat number 12 from the 5' variable region of O772P.

SEQ ID NO:546 (1043400.12 repeat1) represents an example of a cDNA sequence corresponding to repeat number 20 from the 5' variable region of O772P.

SEQ ID NO:547 (PB repeata) represents an example of a cDNA sequence corresponding to repeat number 1 from the 5' variable region of O772P.

SEQ ID NO:548 (PB repeatB) represents an example of a cDNA sequence corresponding to repeat number 2 from the 5' variable region of O772P.

SEQ ID NO:549 (PB repeatE) represents an example of a cDNA sequence corresponding to repeat number 3 from the 5' variable region of O772P.

SEQ ID NO:550 (PB repeatG) represents an example of a cDNA sequence corresponding to repeat number 4 from the 5' variable region of O772P.

SEQ ID NO:551 (PB repeatC) represents an example of a cDNA sequence corresponding to repeat number 4 from the 5' variable region of O772P.

SEQ ID NO:552 (PB repeatH) represents an example of a cDNA sequence corresponding to repeat number 6 from the 5' variable region of O772P.

SEQ ID NO:553 (PB repeatj) represents an example of a cDNA sequence corresponding to repeat number 7 from the 5' variable region of O772P.

SEQ ID NO:554 (PB repeatk) represents an example of a cDNA sequence corresponding to repeat number 8 from the 5' variable region of O772P.

SEQ ID NO:555 (PB repeatD) represents an example of a cDNA sequence corresponding to repeat number 9 from the 5' variable region of O772P.

SEQ ID NO:556 (PB repeatI) represents an example of a cDNA sequence corresponding to repeat number 10 from the 5' variable region of O772P.

SEQ ID NO:557 (PB repeatM) represents an example of a cDNA sequence corresponding to repeat number 11 from the 5' variable region of O772P.

SEQ ID NO:558 (PB repeat9) represents an example of a cDNA sequence corresponding to repeat number 12 from the 5' variable region of O772P.

SEQ ID NO:559 (PB repeat8.5) represents an example of a cDNA sequence corresponding to repeat number 13 from the 5' variable region of O772P.

SEQ ID NO:560 (PB repeat8) represents an example of a cDNA sequence corresponding to repeat number 14 from the 5' variable region of O772P.

SEQ ID NO:561 (PB repeat7) represents an example of a cDNA sequence corresponding to repeat number 15 from the 5' variable region of O772P.

SEQ ID NO:562 (PB repeat6) represents an example of a cDNA sequence corresponding to repeat number 16 from the 5' variable region of O772P.

SEQ ID NO:563 (PB repeat5) represents an example of a cDNA sequence corresponding to repeat number 17 from the 5' variable region of O772P.

SEQ ID NO:564 (PB repeat4) represents an example of a cDNA sequence corresponding to repeat number 18 from the 5' variable region of O772P.

SEQ ID NO:565 (PB repeat3) represents an example of a cDNA sequence corresponding to repeat number 19 from the 5' variable region of O772P.

SEQ ID NO:566 (PB repeat2) represents an example of a cDNA sequence corresponding to repeat number 20 from the 5' variable region of O772P.

SEQ ID NO:567 (PB repeat1) represents an example of a cDNA sequence corresponding to repeat number 21 from the 5' variable region of O772P.

SEQ ID NO:568 represents the cDNA sequence form the 3' constant region.

SEQ ID NO:569 represents a cDNA sequence containing the consensus sequences of the 21 repeats, the 3' constant region and the 3' untranslated region.

SEQ ID NO:570 represents the cDNA sequence of the consensus repeat sequence.

SEQ ID NO:571 represents the consensus amino acid sequence of one potential open reading frame of repeat number 1 from the 5' variable region of O772P.

SEQ ID NO:572 represents the consensus amino acid sequence of a second potential open reading frame of repeat number 1 from the 5' variable region of O772P.

SEQ ID NO:573 represents the consensus amino acid sequence of a third potential open reading frame of repeat number 1 from the 5' variable region of O772P.

SEQ ID NO:574 represents the consensus amino acid sequence of repeat number 2 from the 5' variable region of O772P.

SEQ ID NO:575 represents the consensus amino acid sequence of repeat number 3 from the 5' variable region of O772P.

SEQ ID NO:576 represents the consensus amino acid sequence of repeat number 4 from the 5' variable region of O772P.

SEQ ID NO:577 represents the consensus amino acid sequence of repeat number 5 from the 5' variable region of O772P.

SEQ ID NO:578 represents the consensus amino acid sequence of repeat number 6 from the 5' variable region of O772P.

SEQ ID NO:579 represents the consensus amino acid sequence of repeat number 7 from the 5' variable region of O772P.

SEQ ID NO:580 represents the consensus amino acid sequence of repeat number 8 from the 5' variable region of O772P.

SEQ ID NO:581 represents the consensus amino acid sequence of repeat number 9 from the 5' variable region of O772P.

SEQ ID NO:582 represents the consensus amino acid sequence of repeat number 10 from the 5' variable region of O772P.

SEQ ID NO:583 represents the consensus amino acid sequence of repeat number 11 from the 5' variable region of O772P.

SEQ ID NO:584 represents the consensus amino acid sequence of repeat number 12 from the 5' variable region of O772P.

SEQ ID NO:585 represents the consensus amino acid sequence of repeat number 13 from the 5' variable region of O772P.

SEQ ID NO:586 represents the consensus amino acid sequence of repeat number 14 from the 5' variable region of O772P.

SEQ ID NO:587 represents the consensus amino acid sequence of repeat number 15 from the 5' variable region of O772P.

SEQ ID NO:588 represents the consensus amino acid sequence of repeat number 16 from the 5' variable region of O772P.

SEQ ID NO:589 represents the consensus amino acid sequence of repeat number 17 from the 5' variable region of O772P.

SEQ ID NO:590 represents the consensus amino acid sequence of repeat number 18 from the 5' variable region of O772P.

SEQ ID NO:591 represents the consensus amino acid sequence of repeat number 19 from the 5' variable region of O772P.

SEQ ID NO:592 represents the consensus amino acid sequence of repeat number 20 from the 5' variable region of O772P.

SEQ ID NO:593 represents the consensus amino acid sequence of repeat number 21 from the 5' variable region of O772P.

SEQ ID NO:594 represents the amino acid sequence of the 3' constant region.

SEQ ID NO:595 represents an amino acid sequence containing the consensus sequences of the 21 repeats and the 3' constant region.

SEQ ID NO:596 represents the amino acid sequence of the consensus repeat sequence.

SEQ ID NO:597 represents the amino acid sequence for Peptide #1, a 30-mer peptide that corresponds to the predicted extracellular domain of O772P.

SEQ ID NO:598 represents the amino acid sequence for Peptide #2, a 30-mer peptide that corresponds to the predicted extracellular domain of O772P.

SEQ ID NO:599 represents the amino acid sequence for Peptide #3, a 30-mer peptide that corresponds to the predicted extracellular domain of O772P.

SEQ ID NO:600 represents the amino acid sequence of Peptide #1 from O8E, which corresponds to amino acids 1-20.

SEQ ID NO:601 represents the amino acid sequence of Peptide #2 from O8E, which corresponds to amino acids 16-35.

SEQ ID NO:602 represents the amino acid sequence of Peptide #3 from O8E, which corresponds to amino acids 31-50.

SEQ ID NO:603 represents the amino acid sequence of Peptide #4 from O8E, which corresponds to amino acids 46-65.

SEQ ID NO:604 represents the amino acid sequence of Peptide #5 from O8E, which corresponds to amino acids 61-80.

SEQ ID NO:605 represents the amino acid sequence of Peptide #6 from O8E, which corresponds to amino acids 76-95.

SEQ ID NO:606 represents the amino acid sequence of Peptide #7 from O8E, which corresponds to amino acids 91-110.

SEQ ID NO:607 represents the amino acid sequence of Peptide #8 from O8E, which corresponds to amino acids 106-125.

SEQ ID NO:608 represents the amino acid sequence of Peptide #9 from O8E, which corresponds to amino acids 120-140.

SEQ ID NO:609 represents the amino acid sequence of Peptide #10 from O8E, which corresponds to amino acids 136-155.

SEQ ID NO:610 represents the amino acid sequence of Peptide #11 from O8E, which corresponds to amino acids 151-170.

SEQ ID NO:611 represents the amino acid sequence of Peptide #12 from O8E, which corresponds to amino acids 166-185.

SEQ ID NO:612 represents the amino acid sequence of Peptide #13 from O8E, which corresponds to amino acids 181-200.

SEQ ID NO:613 represents the amino acid sequence of Peptide #14 from O8E, which corresponds to amino acids 196-215.

SEQ ID NO:614 represents the amino acid sequence of Peptide #15 from O8E, which corresponds to amino acids 211-230.

SEQ ID NO:615 represents the amino acid sequence of Peptide #16 from O8E, which corresponds to amino acids 225-245.

SEQ ID NO:616 represents the amino acid sequence of Peptide #17 from O8E, which corresponds to amino acids 241-260.

SEQ ID NO:617 represents the amino acid sequence of Peptide #18 from O8E, which corresponds to amino acids 256-275.

SEQ ID NO:618 represents the amino acid sequence of Peptide #19 from O8E, which corresponds to amino acids 263-282.

SEQ ID NO:619 is the DNA sequence for the O8E PCR primer, O8E-UP1.

SEQ ID NO:620 is the DNA sequence for the O8E reverse PCR primer designated O8E-DN1.

SEQ ID NO:621 is a DNA sequence corresponding to the O8E Rhesus orthologs.

SEQ ID NO:622 is a DNA sequence corresponding to the O8E mouse ortholog.

SEQ ID NO:623 is an amino acid sequence corresponding to the O8E Rhesus orthologs.

SEQ ID NO:624 is an amino acid sequence corresponding to the O8E mouse ortholog.

DETAILED DESCRIPTION OF THE INVENTION

U.S. patents, U.S. patent application publications, U.S. patent applications, foreign patents, foreign patent applications and non-patent publications referred to in this specification and/or listed in the Application Data Sheet, are incorporated herern by reference, in their entirety.

The present invention is directed generally to compositions and their use in the therapy and diagnosis of cancer, particularly ovarian cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" "is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NOs: 1-311, 313-387, 391, 457, 460-477, 512-570 and 619-622, or a sequence that hybridizes under moderately stringent conditions, or, alternatively, under highly stringent conditions, to a polynucleotide sequence set forth in any one of SEQ ID NOs: 1-311, 313-387, 391, 457, 460-477, 512-570 and 619-622. Certain other illustrative polypeptides of the invention comprise amino acid sequences as set forth in any one of SEQ ID NOs: 312, 388-389, 392-455, 458-459, 478-511, and 571-618.

The polypeptides of the present invention are sometimes herein referred to as ovarian tumor proteins or ovarian tumor polypeptides, as an indication that their identification has been based at least in part upon their increased levels of expression in ovarian tumor samples. Thus, an "ovarian tumor polypeptide" or "ovarian tumor protein," refers generally to a polypeptide sequence of the present invention, or a polynucleotide sequence encoding such a polypeptide, that is expressed in a substantial proportion of ovarian tumor samples, for example preferably greater than about 20%, more preferably greater than about 30%, and most preferably greater than about 50% or more of ovarian tumor samples tested, at a level that is at least two fold, and preferably at least five fold, greater than the level of expression in normal tissues, as determined using a representative assay provided herein. A ovarian tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with ovarian cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1-30 amino acids, preferably 5-15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NOs: 312, 388-389, 392-455, 458-459, 478-511, and 571-618, or those encoded by a polynucleotide sequence set forth in a sequence of SEQ ID NOs: 1-311, 313-387, 391, 457, 460-477, 512-570 and 619-622.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provided by the present invention are immunologically reactive with an antibody and/or T-cell that reacts with a full-length polypeptide specifically set forth herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1-30 amino acids, preferably 5-15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., (1978) *A model of evolutionary change in proteins—Matrices for detecting distant relationships*. In Dayhoff, M. O. (ed.) *Atlas of Protein Sequence and Structure*, National Biomedical Research Foundation, Washington D.C. Vol. 5, Suppl. 3, pp. 345-358; Hein J. (1990) *Unified Approach to Alignment and Phylogenes*, pp. 626-645 *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Saitou, N. Nei, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a xenogeneic polypeptide that comprises an polypeptide having substantial sequence identity, as described above, to the human polypeptide (also termed autologous antigen) which served as a reference polypeptide, but which xenogeneic polypeptide is derived from a different, non-human species. One skilled in the art will recognize that "self" antigens are often poor stimulators of CD8+ and CD4+ T-lymphocyte responses, and therefore efficient immunotherapeutic strategies directed against tumor polypeptides require the development of methods to overcome immune tolerance to particular self tumor polypeptides. For example, humans immunized with prostase protein from a xenogeneic (non human) origin are capable of mounting an immune response against the counterpart human protein, e.g., the human prostase tumor protein present on human tumor cells. Accordingly, the present invention provides methods for purifying the xenogeneic form of the tumor proteins set forth herein, such as the polypeptides set forth in SEQ ID NOs: 312, 388-389, 392-455, 458-459, 478-511, and 571-618, or those encoded by polynucleotide sequences set forth in SEQ ID NOs: 1-311, 313-387, 391, 457, 460-477, 512-570 and 619-622.

Therefore, one aspect of the present invention provides xenogeneic variants of the polypeptide compositions described herein. Such xenogeneic variants generally encompassed by the present invention will typically exhibit at least about 70%, 75%, 80%, 85%, 90%, 91%, 92%, 93%, 94%, 95%, 96%, 97%, 98%, or 99% or more identity along their lengths, to a polypeptide sequences set forth herein.

More particularly, the invention is directed to mouse, rat, monkey, porcine and other non-human polypeptides which can be used as xenogeneic forms of human polypeptides set forth herein, to induce immune responses directed against tumor polypeptides of the invention.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.,* 336:86-91, 1997).

In one preferred embodiment, the immunological fusion partner is derived from a *Mycobacterium* sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158,585; see also, Skeiky et al., *Infection and Immun.* 67:3998-4007 (1999), incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion polypeptide. A repeat portion is found in the C-terminal region starting at residue 178. A particularly preferred repeat portion incorporates residues 188-305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of CD4$^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NOs: 1-311, 313-387, 391, 457, 460-477, 512-570 and 619-622, complements of a polynucleotide sequence set forth in any one of SEQ ID NOs: 1-311, 313-387, 391, 457, 460-477, 512-570 and 619-622, and degenerate variants of a polynucleotide sequence set forth in any one of SEQ ID NOs: 1-311, 313-387, 391, 457, 460-477, 512-570 and 619-622. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NOs: 1-311, 313-387, 391, 457, 460-477, 512-570 and 619-622, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising or consisting of various lengths of contiguous stretches of sequence identical to or complementary to one or more of the sequences disclosed herein. For example, polynucleotides are provided by this invention that comprise or consist of at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of the disclosed sequence or at both ends of the disclosed sequence.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Nat. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise or consist of a sequence region of at least about a 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. Nos. 5,739,119 and 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science 1988 Jun. 10; 240(4858):1544-6; Vasanthakumar and Ahmed, Cancer Commun. 1989; 1(4):225-32; Peris et al., Brain Res Mol Brain Res. 1998 Jun. 15; 57(2):310-20; U.S. Pat. Nos. 5,801,154; 5,789,573; 5,718,709 and 5,610,288). Antisense constructs have also been described that inhibit and can be used to treat a variety of abnormal cellular proliferations, e.g., cancer (U.S. Pat. Nos. 5,747,470; 5,591,317 and 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389-402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 Jul. 15; 25(14):2730-6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, *Proc. Natl. Acad. Sci. USA.* 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J. Mol. Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., *Proc. Nat. Acad. Sci. USA.* 1992 Aug. 15; 89(16):7305-9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; Neurospora VS RNA ribozyme motif is described by Collins (Saville and Collins, Cell. 1990 May 18; 61(4):685-96; Saville and Collins, *Proc. Natl. Acad. Sci. USA,* 88(19):8826-30 (Oct. 1, 1991); Collins and Olive, *Biochemistry* 32(11): 2795-9 (Mar. 23, 1993); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431-37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 15(6):224-9 (June 1997)). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 254(5037):1497-500 (Dec. 6, 1991); Hanvey et al., *Science* 258(5087):1481-5 (Nov. 27, 1992); Hyrup and Nielsen, *Bioorg. Med. Chem.* 4(1):5-23 (January 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., *Bioorg. Med. Chem.* 3(4):437-45 (April 1995)). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., *Bioorg Med Chem* 3(4):437-45 (April 1995); Petersen et al., *J Pept Sci* 1(3):175-83 (May-June 1995); Orum et al., *Biotechniques* 19(3):472-80 (September 1995); Footer et al., *Biochemistry.* 1996 Aug. 20; 35(33):10673-9; Griffith et al., *Nucleic Acids Res* 23(15):3003-8 (Aug. 11, 1995); Pardridge et al., *Proc. Natl. Acad. Sci. USA.* 92(12):5592-6 (Jun. 6, 1995); Boffa et al., *Proc. Natl. Acad. Sci. USA.* 92(6):1901-5 (Mar. 14, 1995); Gambacorti-Passerini et al., *Blood* 88(4):1411-7 (Aug. 15, 1996); Armitage et al., *Proc. Natl. Acad. Sci. USA.* 94(23): 12320-5 (Nov. 11, 1997); Seeger et al., *Biotechniques* 23(3): 512-7 (September 1997)). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (*Anal Chem* 65(24):3545-9 (Dec. 15, 1993) and Jensen et al. (Biochemistry. 1997 Apr. 22; 36(16):5072-7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614-10619, 1996 and Heller et al., *Proc. Natl. Acad. Sci. USA* 94:2150-2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GENBANK®. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids Res. Symp. Ser.* 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202-204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring. Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as pBLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264: 5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or Trichoplusia larvae in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.– or aprt.sup.– cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263-281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as ovarian cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) *Nature* 349: 293-299; Lobuglio et al. (1989) *Proc. Nat. Acad. Sci. USA* 86:4220-4224; Shaw et al. (1987) *J. Immunol.* 138:4534-4538; and Brown et al. (1987) *Cancer Res.* 47:3577-3583), rodent CDRs grafted into a human supporting FR prior to fusion with an appropriate human antibody constant domain (Riechmann et al. (1988) *Nature* 332:323-327; Verhoeyen et al. (1988) *Science* 239:1534-1536; and Jones et al. (1986) *Nature* 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) *Ann. Rev. Biochem.* 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml-100 µg/ml, preferably 200 ng/ml-25 µg/ml) for 3-7 days will typically result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

T Cell Receptor Compositions

The T cell receptor (TCR) consists of 2 different, highly variable polypeptide chains, termed the T-cell receptor α and β chains, that are linked by a disulfide bond (Janeway, Travers, Walport. Immunobiology. Fourth Ed., 148-159. Elsevier Science Ltd/Garland Publishing. 1999). The α/β heterodimer complexes with the invariant CD3 chains at the cell membrane. This complex recognizes specific antigenic peptides bound to MHC molecules. The enormous diversity of TCR specificities is generated much like immunoglobulin diversity, through somatic gene rearrangement. The β chain genes contain over 50 variable (V), 2 diversity (D), over 10 joining (J) segments, and 2 constant region segments (C). The α chain genes contain over 70 V segments, and over 60 J segments but no D segments, as well as one C segment. During T cell development in the thymus, the D to J gene rearrangement of the β chain occurs, followed by the V gene segment rearrangement to the DJ. This functional VDJβ exon is transcribed and spliced to join to a Cβ. For the α chain, a Vα gene segment rearranges to a Jα gene segment to create the functional exon that is then transcribed and spliced to the Cα. Diversity is further increased during the recombination process by the random addition of P and N-nucleotides between the V, D, and J segments of the b chain and between the V and J segments in the α chain (Janeway, Travers, Walport. Immunobiology. Fourth Ed., 98 and 150. Elsevier Science Ltd/Garland Publishing. 1999).

The present invention, in another aspect, provides TCRs specific for a polypeptide disclosed herein, or for a variant or derivative thereof. In accordance with the present invention, polynucleotide and amino acid sequences are provided for the V-J or V-D-J junctional regions or parts thereof for the alpha and beta chains of the T-cell receptor which recognize tumor polypeptides described herein. In general, this aspect of the invention relates to T-cell receptors which recognize or bind tumor polypeptides presented in the context of MHC. In a preferred embodiment the tumor antigens recognized by the T-cell receptors comprise a polypeptide of the present invention. For example, cDNA encoding a TCR specific for a ovarian tumor peptide can be isolated from T cells specific for a tumor polypeptide using standard molecular biological and recombinant DNA techniques.

This invention further includes the T-cell receptors or analogs thereof having substantially the same function or activity as the T-cell receptors of this invention which recognize or bind tumor polypeptides. Such receptors include, but are not limited to, a fragment of the receptor, or a substitution, addition or deletion mutant of a T-cell receptor provided herein. This invention also encompasses polypeptides or peptides that are substantially homologous to the T-cell receptors provided herein or that retain substantially the same activity. The term "analog" includes any protein or polypeptide having an amino acid residue sequence substantially identical to the T-cell receptors provided herein in which one or more residues, preferably no more than 5 residues, more preferably no more than 25 residues have been conservatively substituted with a functionally similar residue and which displays the functional aspects of the T-cell receptor as described herein.

The present invention further provides for suitable mammalian host cells, for example, non-specific T-cells, that are transfected with a polynucleotide encoding TCRs specific for a polypeptide described herein, thereby rendering the host cell specific for the polypeptide. The α and β chains of the TCR may be contained on separate expression vectors or alternatively, on a single expression vector that also contains an internal ribosome entry site (IRES) for cap-independent translation of the gene downstream of the IRES. Said host cells expressing TCRs specific for the polypeptide may be used, for example, for adoptive immunotherapy of ovarian cancer as discussed further below.

In further aspects of the present invention, cloned TCRs specific for a polypeptide recited herein may be used in a kit for the diagnosis of ovarian cancer. For example, the nucleic acid sequence or portions thereof, of tumor-specific TCRs can be used as probes or primers for the detection of expression of the rearranged genes encoding the specific TCR in a biological sample. Therefore, the present invention further provides for an assay for detecting messenger RNA or DNA encoding the TCR specific for a polypeptide.

Pharmaceutical Compositions

In additional embodiments, the present invention concerns formulation of one or more of the polynucleotide, polypeptide, T-cell, TCR, and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, TCR, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143-198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as *Bacillus-Calmette-Guerrin*) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) *BioTechniques* 7:980-990; Miller, A. D. (1990) *Human Gene Therapy* 1:5-14; Scarpa et al. (1991) *Virology* 180:849-852; Burns et al. (1993) *Proc. Natl. Acad. Sci. USA* 90:8033-8037; and Boris-Lawrie and Temin (1993) *Cur. Opin. Genet. Develop.* 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) *J. Virol.* 57:267-274; Bett et al. (1993) *J. Virol.* 67:5911-5921; Mittereder et al. (1994) *Human Gene Therapy* 5:717-729; Seth et al. (1994) *J. Virol.* 68:933-940; Barr et al. (1994) *Gene Therapy* 1:51-58; Berkner, K. L. (1988) *BioTechniques* 6:616-629; and Rich et al. (1993) *Human Gene Therapy* 4:461-476).

Various adeno-associated virus (MV) vector systems have also been developed for polynucleotide delivery. MV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) *Molec. Cell. Biol.* 8:3988-3996; Vincent et al. (1990) *Vaccines* 90 (Cold Spring Harbor Laboratory Press); Carter, B. J. (1992) *Current Opinion in Biotechnology* 3:533-539; Muzyczka, N. (1992) *Current Topics in Microbiol. and Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, *Proc. Nat. Acad. Sci. USA* 87:6743-6747 (1990); Fuerst et al., *Proc. Natl. Acad. Sci. USA* 83:8122-8126 (1986).

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843, 723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. *J. Biol. Chem.* 268:6866-6869 (1993) and Wagner et al., *Proc. Natl. Acad. Sci. USA* 89:6099-6103 (1992), can also be used for gene delivery under the invention.

Additional illustrative information on these and other known viral-based delivery systems can be found, for example, in Fisher-Hoch et al., *Proc. Natl. Acad. Sci. USA* 86:317-321, 1989; Flexner et al., *Ann. N.Y. Acad. Sci.* 569: 86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell, TCR, and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{-A-R,} \qquad (I)$$

wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (ie., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245-251,1998) and have been shown to be effective as a physiological adjuvant for eliciting prophylactic or therapeutic antitumor immunity (see Timmerman and Levy, *Ann. Rev. Med.* 50:507-529,1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peri-tumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

In another illustrative embodiment, calcium phosphate core particles are employed as carriers, vaccine adjuvants, or as controlled release matrices for the compositions of this invention. Exemplary calcium phosphate particles are disclosed, for example, in published patent application No. WO/0046147.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410-4; Hwang et al., Crit Rev Ther Drug Carrier Syst 1998; 15(3):243-84; U.S. Pat. Nos. 5,641,515; 5,580,579 and 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially nontoxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. Nos. 5,756,353 and 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J. Biol. Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm. 1998 March; 45(2): 149-55; Zambaux et al. J Controlled Release. 1998 Jan. 2; 50(1-3):31-40; and U.S. Pat. No. 5,145,684.

Cancer Therapeutic Methods

Immunologic approaches to cancer therapy are based on the recognition that cancer cells can often evade the body's defenses against aberrant or foreign cells and molecules, and that these defenses might be therapeutically stimulated to regain the lost ground, e.g., pgs. 623-648 in Klein, Immunology (Wiley-Interscience, New York, 1982). Numerous recent observations that various immune effectors can directly or indirectly inhibit growth of tumors has led to renewed interest in this approach to cancer therapy, e.g., Jager, et al., Oncology 2001; 60(1):1-7; Renner, et al., Ann Hematol 2000 December; 79(12):651-9.

Four-basic cell types whose function has been associated with antitumor cell immunity and the elimination of tumor cells from the body are: i) B-lymphocytes which secrete immunoglobulins into the blood plasma for identifying and labeling the nonself invader cells; ii) monocytes which secrete the complement proteins that are responsible for lysing and processing the immunoglobulin-coated target invader cells; iii) natural killer lymphocytes having two mechanisms for the destruction of tumor cells, antibody-dependent cellular cytotoxicity and natural killing; and iv) T-lymphocytes possessing antigen-specific receptors and having the capacity to recognize a tumor cell carrying complementary marker molecules (Schreiber, H., 1989, in Fundamental Immunology (ed). W. E. Paul, pp. 923-955).

Cancer immunotherapy generally focuses on inducing humoral immune responses, cellular immune responses, or both. Moreover, it is well established that induction of $CD4^+$ T helper cells is necessary in order to secondarily induce either antibodies or cytotoxic $CD8^+$ T cells. Polypeptide antigens that are selective or ideally specific for cancer cells, particularly ovarian cancer cells, offer a powerful approach for inducing immune responses against ovarian cancer, and are an important aspect of the present invention.

Therefore, in further aspects of the present invention, the pharmaceutical compositions described herein may be used to stimulate an immune response against cancer, particularly for the immunotherapy of ovarian cancer. Within such methods, the pharmaceutical compositions described herein are administered to a patient, typically a warm-blooded animal, preferably a human. A patient may or may not be afflicted with cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Monoclonal antibodies may be labeled with any of a variety of labels for desired selective usages in detection, diagnostic assays or therapeutic applications (as described in U.S. Pat. Nos. 6,090,365; 6,015,542; 5,843,398; 5,595,721; and 4,708,930, hereby incorporated by reference in their entirety as if each was incorporated individually). In each case, the binding of the labelled monoclonal antibody to the determinant site of the antigen will signal detection or delivery of a particular therapeutic agent to the antigenic determinant on the non-normal cell. A further object of this invention is to provide the specific monoclonal antibody suitably labelled for achieving such desired selective usages thereof.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more ovarian tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of antigen that binds to the agent in the biological sample.

Polynucleotide primers and probes may be used to detect the level of mRNA encoding a tumor protein, which is also indicative of the presence or absence of a cancer. In general, a tumor sequence should be present at a level that is at least two-fold, preferably three-fold, and more preferably five-fold or higher in tumor tissue than in normal tissue of the same type from which the tumor arose. Expression levels of a particular tumor sequence in tissue types different from that in which the tumor arose are irrelevant in certain diagnostic embodiments since the presence of tumor cells can be confirmed by observation of predetermined differential expression levels, e.g., 2-fold, 5-fold, etc, in tumor tissue to expression levels in normal tissue of the same type.

Other differential expression patterns can be utilized advantageously for diagnostic purposes. For example, in one aspect of the invention, overexpression of a tumor sequence in tumor tissue and normal tissue of the same type, but not in other normal tissue types, e.g., PBMCs, can be exploited diagnostically. In this case, the presence of metastatic tumor cells, for example in a sample taken from the circulation or some other tissue site different from that in which the tumor arose, can be identified and/or confirmed by detecting expression of the tumor sequence in the sample, for example using RT-PCR analysis. In many instances, it will be desired to enrich for tumor cells in the sample of interest, e.g., PBMCs, using cell capture or other like techniques.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above. The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2-9 days (typically 4 days) at 37° C. with polypeptide (e.g., 5-25 µg/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis.

Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10-40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.,* 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another aspect of the present invention, cell capture technologies may be used in conjunction, with, for example, real-time PCR to provide a more sensitive tool for detection of metastatic cells expressing ovarian tumor antigens. Detection of ovarian cancer cells in biological samples, e.g., bone marrow samples, peripheral blood, and small needle aspiration samples is desirable for diagnosis and prognosis in ovarian cancer patients.

Immunomagnetic beads coated with specific monoclonal antibodies to surface cell markers, or tetrameric antibody complexes, may be used to first enrich or positively select cancer cells in a sample. Various commercially available kits may be used, including Dynabeads® Epithelial Enrich (Dynal Biotech, Oslo, Norway), StemSep™ (StemCell Technologies, Inc., Vancouver, BC), and RosetteSep (StemCell Technologies). A skilled artisan will recognize that other methodologies and kits may also be used to enrich or positively select desired cell populations. Dynabeads® Epithelial Enrich contains magnetic beads coated with mAbs specific for two glycoprotein membrane antigens expressed on normal and neoplastic epithelial tissues. The coated beads may be added to a sample and the sample then applied to a magnet, thereby capturing the cells bound to the beads. The unwanted cells are washed away and the magnetically isolated cells eluted from the beads and used in further analyses.

RosetteSep can be used to enrich cells directly from a blood sample and consists of a cocktail of tetrameric antibodies that targets a variety of unwanted cells and crosslinks them to glycophorin A on red blood cells (RBC) present in the sample, forming rosettes. When centrifuged over Ficoll, targeted cells pellet along with the free RBC. The combination of antibodies in the depletion cocktail-determines which cells will be removed and consequently which cells will be recovered. Antibodies that are available include, but are not limited to: CD2, CD3, CD4, CD5, CD8, CD10, CD11b, CD14, CD15, CD16, CD19, CD20, CD24, CD25, CD29, CD33, CD34, CD36, CD38, CD41, CD45, CD45RA, CD45RO, CD56, CD66B, CD66e, HLA-DR, IgE, and TCRαβ.

Additionally, it is contemplated in the present invention that mAbs specific for ovarian tumor antigens can be generated and used in a similar manner. For example, mAbs that bind to tumor-specific cell surface antigens may be conjugated to magnetic beads, or formulated in a tetrameric antibody complex, and used to enrich or positively select metastatic ovarian tumor cells from a sample. Once a sample is enriched or positively selected, cells may be lysed and RNA isolated. RNA may then be subjected to RT-PCR analysis using ovarian tumor-specific primers in a real-time PCR assay as described herein. One skilled in the art will recognize that enriched or selected populations of cells may be analyzed by other methods (e.g., in situ hybridization or flow cytometry).

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24-72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLES

Example 1

Identification of Representative Ovarian Carcinoma Protein cDNAs

This Example illustrates the identification of cDNA molecules encoding ovarian carcinoma proteins.

Anti-SCID mouse sera (generated against sera from SCID mice carrying late passage ovarian carcinoma) was precleared of E. coli and phage antigens and used at a 1:200 dilution in a serological expression screen. The library screened was made from a SCID-derived human ovarian tumor (OV9334) using a directional RH oligo(dT) priming cDNA library construction kit and the AScreen vector (Novagen). A bacteriophage lambda screen was employed. Approximately 400,000 pfu of the amplified OV9334 library were screened.

196 positive clones were isolated. Certain sequences that appear to be novel are provided in FIGS. 1A-1S and SEQ ID NO:1 to 71. Three complete insert sequences are shown in FIGS. 2A-2C (SEQ ID NO:72 to 74). Other clones having known sequences are presented in FIGS. 15A-15EEE (SEQ ID NO:82 to 310). Database searches identified the following sequences that were substantially identical to the sequences presented in FIGS. 15A-15EEE.

Figure 3:
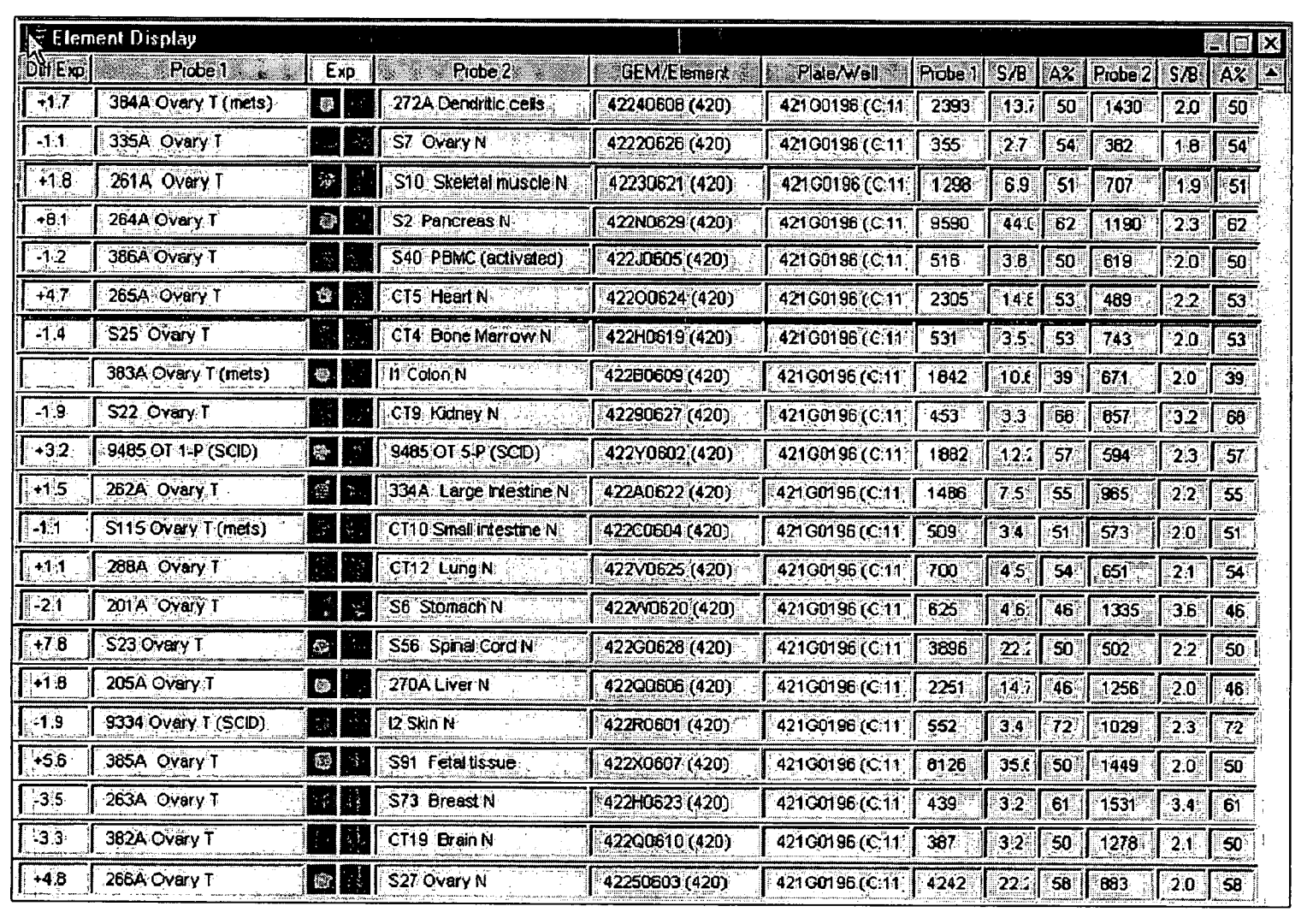

These clones were further characterized using microarray technology to determine mRNA expression levels in a variety of tumor and normal tissues. Such analyses were performed using a Synteni (Palo Alto, Calif.) microarray, according to the manufacturer's instructions. PCR amplification products were arrayed on slides, with each product occupying a unique location in the array. mRNA was extracted from the tissue sample to be tested, reverse transcribed and fluorescent-labeled cDNA probes were generated. The microarrays were probed with the labeled cDNA probes and the slides were scanned to measure fluorescence intensity. Data was analyzed using Synteni's provided GEMtools software. The results for one clone (13695, also referred to as O8E) are shown in FIG. 3.

Example 2

Identification of Ovarian Carcinoma cDNAs Using Microarray Technology

This Example illustrates the identification of ovarian carcinoma polynucleotides by PCR subtraction and microarray analysis. Microarrays of cDNAs were analyzed for ovarian tumor-specific expression using a Synteni (Palo Alto, Calif.) microarray, according to the manufacturer's instructions (and essentially as described by Schena et al., *Proc. Natl. Acad. Sci. USA* 93:10614-10619, 1996 and Heller et al., *Proc. Natl. Acad. Sci. USA* 94:2150-2155, 1997).

A PCR subtraction was performed using a tester comprising cDNA of four ovarian tumors (three of which were metastatic tumors) and a driver of cDNA form five normal tissues (adrenal gland, lung, pancreas, spleen and brain). cDNA fragments recovered from this subtraction were subjected to DNA microarray analysis where the fragments were PCR amplified, adhered to chips and hybridized with fluorescently labeled probes derived from mRNAs of human ovarian tumors and a variety of normal human tissues. In this analysis, the slides were scanned and the fluorescence intensity was measured, and the data were analyzed using Synteni's GEMtools software. In general, sequences showing at least a 5-fold increase in expression in tumor cells (relative to normal cells) were considered ovarian tumor antigens. The fluorescent results were analyzed and clones that displayed increased expression in ovarian tumors were further characterized by DNA sequencing and database searches to determine the novelty of the sequences.

Using such assays, an ovarian tumor antigen was identified that is a splice fusion between the human T-cell leukemia virus type I oncoprotein TAX (see Jin et al., *Cell* 93:81-91, 1998) and an extracellular matrix protein called osteonectin. A splice junction sequence exists at the fusion point. The sequence of this clone is presented in FIG. 4 and SEQ ID NO:75. Osteonectin, unspliced and unaltered, was also identified from such assays independently.

Further clones identified by this method are referred to herein as 3f, 6b, 8e, 8h, 12c and 12h. Sequences of these clones are shown in FIGS. 5 to 9 and SEQ ID NO:76 to 81. Microarray analyses were performed as described above, and are presented in FIGS. 10 to 14. A full length sequence encompassing clones 3f, 6b, 8e and 12h was obtained by screening an ovarian tumor (SCID-derived) cDNA library. This 2996 base pair sequence (designated O772P) is presented in SEQ ID NO:311, and the encoded 914 amino acid protein sequence is shown in SEQ ID NO:312. PSORT analysis indicates a Type 1a transmembrane protein localized to the plasma membrane.

In addition to certain of the sequences described above, this screen identified the following sequences which are described in detail in Table 2:

TABLE 2

| Sequence | Comments |
| --- | --- |
| OV4vG11 (SEQ ID NO: 313) | human clone 1119D9 on chromosome 20p12 |
| OV4vB11 (SEQ ID NO: 314) | human UWGC: y14c094 from chromosome 6p21 |
| OV4vD9 (SEQ ID NO: 315) | human clone 1049G16 chromosome 20q12-13.2 |
| OV4vD5 (SEQ ID NO: 316) | human KIAA0014 gene |
| OV4vC2 (SEQ ID NO: 317) | human KIAA0084 gene |
| OV4vF3 (SEQ ID NO: 318) | human chromosome 19 cosmid R31167 |
| OV4VC1 (SEQ ID NO: 319) | Novel |
| OV4vH3 (SEQ ID NO: 320) | Novel |
| OV4vD2 (SEQ IDNO: 321) | novel |
| O815P (SEQ ID NO: 322) | novel |
| OV4vC12 (SEQ ID NO: 323) | novel |
| OV4vA4 (SEQ ID NO: 324) | novel |
| OV4vA3 (SEQ ID NO: 325) | novel |
| OV4v2A5 (SEQ ID NO: 326) | novel |
| O819P (SEQ ID NO: 327) | novel |
| O818P (SEQ ID NO: 328) | novel |
| O817P (SEQ ID NO: 329) | novel |
| O816P (SEQ ID NO: 330) | novel |
| Ov4vC5 (SEQ ID NO: 331) | novel |
| 21721 (SEQ ID NO: 332) | human lumican |
| 21719 (SEQ ID NO: 333) | human retinoic acid-binding protein II |
| 21717 (SEQ ID NO: 334) | human26S proteasome ATPase subunit |
| 21654 (SEQ ID NO: 335) | human copine I |
| 21627 (SEQ ID NO: 336) | human neuron specific gamma-2 enolase |
| 21623 (SEQ ID NO: 337) | human geranylgeranyl transferase II |
| 21621 (SEQ ID NO: 338) | human cyclin-dependent protein kinase |
| 21616 (SEQ ID NO: 339) | human prepro-megakaryocyte potentiating factor |
| 21612 (SEQ ID NO: 340) | human UPH1 |
| 21558 (SEQ ID NO: 341) | human RalGDS-like 2 (RGL2) |
| 21555 (SEQ ID NO: 342) | human autoantigen P542 |
| 21548 (SEQ ID NO: 343) | human actin-related protein (ARP2) |
| 21462 (SEQ ID NO: 344) | human huntingtin interacting protein |
| 21441 (SEQ ID NO: 345) | human 90K product (tumor associated antigen) |
| 21439 (SEQ ID NO: 346) | human guanine nucleotide regulator protein (tim1) |
| 21438 (SEQ ID NO: 347) | human Ku autoimmune (p70/p80) antigen |
| 21237 (SEQ ID NO: 348) | human S-laminin |
| 21436 (SEQ ID NO: 349) | human ribophorin I |
| 21435 (SEQ ID NO: 350) | human cytoplasmic chaperonin hTRiC5 |
| 21425 (SEQ ID NO: 351) | humanEMX2 |
| 21423 (SEQ ID NO: 352) | human p87/p89 gene |
| 21419 (SEQ ID NO: 353) | human HPBRII-7 |
| 21252 (SEQ ID NO: 354) | human T1-227H |
| 21251 (SEQ ID NO: 355) | human cullin I |
| 21247 (SEQ ID NO: 356) | kunitz type protease inhibitor (KOP) |
| 21244-1 (SEQ ID NO: 357) | human protein tyrosine phosphatase receptor F (PTPRF) |
| 21718 (SEQ ID NO: 358) | human LTR repeat |
| OV2-90 (SEQ ID NO: 359) | novel |
| Human zinc finger (SEQ ID NO: 360) | |
| Human polyA binding protein (SEQ ID NO: 361) | |
| Human pleitrophin (SEQ ID NO: 362) | |
| Human PAC clone 278C19 (SEQ ID NO: 363) | |
| Human LLRep3 (SEQ ID NO: 364) | |
| Human Kunitz type protease inhib (SEQ ID NO: 365) | |
| Human KIAA0106 gene (SEQ ID NO: 366) | |
| Human keratin (SEQ ID NO: 367) | |
| Human HIV-1TAR (SEQ ID NO: 368) | |
| Human glia derived nexin (SEQ ID NO: 369) | |
| Human fibronectin (SEQ ID NO: 370) | |
| Human ECMproBM40 (SEQ ID NO: 371) | |
| Human collagen (SEQ ID NO: 372) | |
| Human alpha enolase (SEQ ID NO: 373) | |
| Human aldolase (SEQ ID NO: 374) | |
| Human transf growth factor BIG H3 (SEQ ID NO: 375) | |
| Human SPARC osteonectin (SEQ ID NO: 376) | |
| Human SLP1 leucocyte protease (SEQ ID NO: 377) | |
| Human mitochondrial ATP synth (SEQ ID NO: 378) | |

TABLE 2-continued

| Sequence | Comments |
| --- | --- |
| Human DNA seq clone 461P17 (SEQ ID NO: 379) | |
| Human dbpB pro Y box (SEQ ID NO: 380) | |
| Human 40 kDa keratin (SEQ ID NO: 381) | |
| Human arginosuccinate synth (SEQ ID NO: 382) | |
| Human acidic ribosomal phosphoprotein (SEQ ID NO: 383) | |
| Human colon carcinoma laminin binding pro (SEQ ID NO: 384) | |

This screen further identified multiple forms of the clone O772P, referred to herein as 21013, 21003 and 21008. PSORT analysis indicates that 21003 (SEQ ID NO:386; translated as SEQ ID NO:389) and 21008 (SEQ ID NO:387; translated as SEQ ID NO:390) represent Type 1a transmembrane protein forms of O772P. 21013 (SEQ ID NO:385; translated as SEQ ID NO:388) appears to be a truncated form of the protein and is predicted by PSORT analysis to be a secreted protein.

Additional sequence analysis resulted in a full length clone for O8E (2627 bp, which agrees with the message size observed by Northern analysis; SEQ ID NO:391). This nucleotide sequence was obtained as follows: the original O8E sequence (OrigO8Econs) was found to overlap by 33 nucleotides with a sequence from an EST clone (IMAGE#1987589). This clone provided 1042 additional nucleotides upstream of the original O8E sequence. The link between the EST and O8E was confirmed by sequencing multiple PCR fragments generated from an ovary primary tumor library using primers to the unique EST and the O8E sequence (ESTxO8EPCR). Full length status was further indicated when anchored PCR from the ovary tumor library gave several clones (AnchoredPCR cons) that all terminated upstream of the putative start methionine, but failed to yield any additional sequence information. FIG. 16 presents a diagram that illustrates the location of each partial sequence within the full length O8E sequence.

Two protein sequences may be translated from the full length O8E. For "a" (SEQ ID NO:393) begins with a putative start methionine. A second form "b" (SEQ ID NO:392) includes 27 additional upstream residues to the 5' end of the nucleotide sequence.

Example 3

This example discloses the identification and characterization of antibody epitopes recognized by the O8E polyclonal anti-sera.

Rabbit anti-sera was raised against E. coli derived O8E recombinant protein and tested for antibody epitope recognition against 20 or 21 mer peptides that correspond to the O8E amino acid sequence. Peptides spanning amino acid regions 31 to 65, 76 to 110, 136 to 200 and 226 to 245 of the full length O8E protein were recognized by an acid eluted peak and/or a salt eluted peak from affinity purified anti-O8E sera. Thus, the corresponding amino acid sequences of the above peptides constitute the antibody epitopes recognized by affinity purified anti-O8E antibodies.

ELISA analysis of anti-O8E rabbit sera is shown in FIG. 23, and ELISA analysis of affinity purified rabbit anti-O8E polyclonal antibody is shown in FIG. 24.

Figure 17:
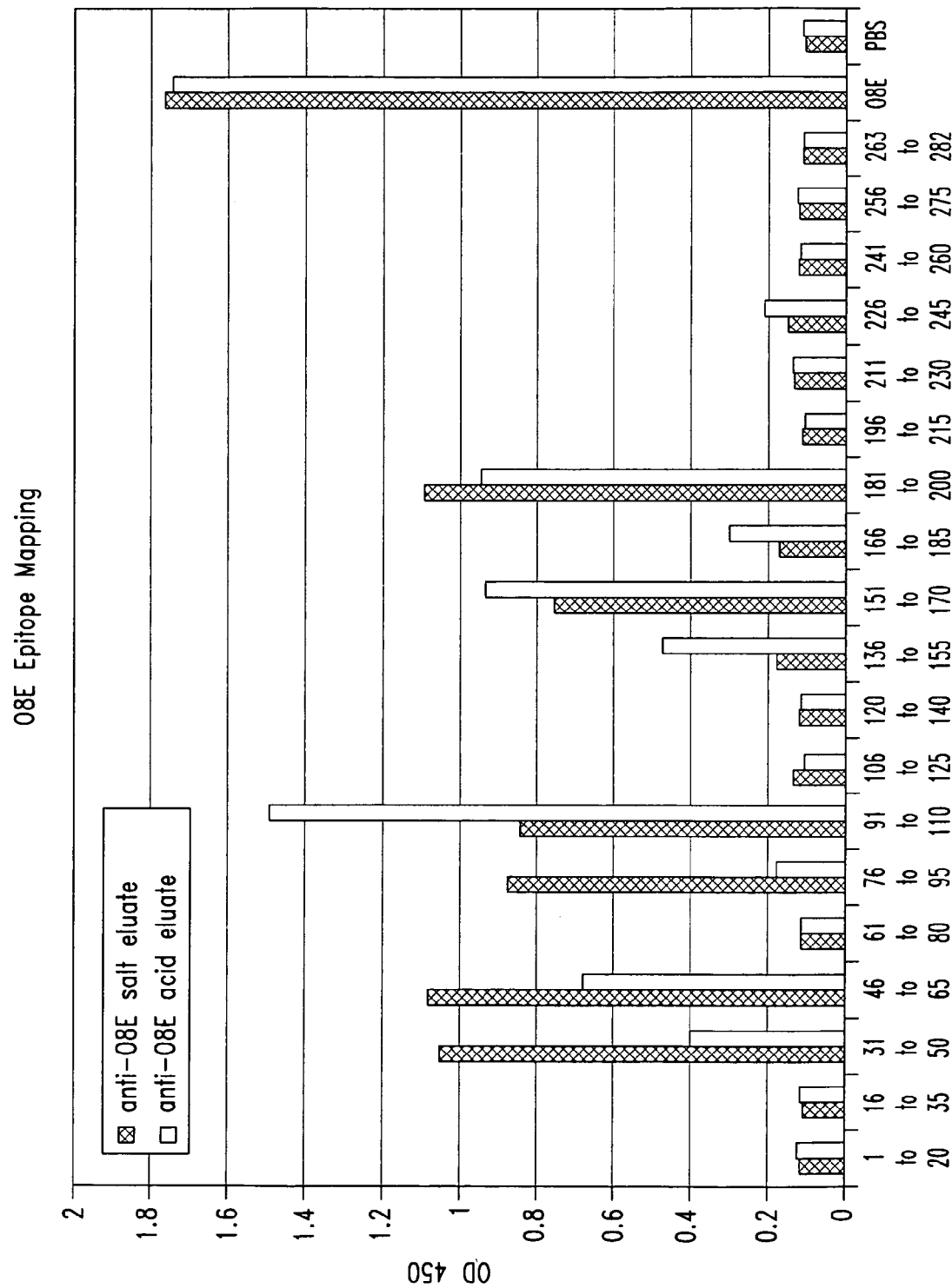
FIG. 17 is a graph illustrating the results of epitope mapping studies on O8E protein.

For epitope mapping, 20 or 21 mer peptides corresponding to the O8E protein were synthesized. For antibody affinity purification, rabbit anti-O8E sera was run over an O8E-sepharose column, then antibody was eluted with a salt buffer containing 0.5 M NaCl and 20 mM $PO_4$, followed by an acid elution step using 0.2 M Glycine, pH 2.3. Purified antibody was neutralized by the addition of 1M Tris, pH 8 and buffer exchanged into phosphate buffered saline (PBS). For enzyme linked immunosorbant assay (ELISA) analysis, O8E peptides and O8E recombinant protein were coated onto 96 well flat bottom plates at 2 µg/ml for 2 hours at room temperature (RT). Plates were then washed 5 times with PBS+0.1% Tween 20 and blocked with PBS+1% bovine serum albumin (BSA) for 1 hour. Affinity purified anti-O8E antibody, either an acid or salt eluted fraction, was then added to the wells at 1 µg/ml and incubated at RT for 1 hr. Plates were again washed, followed by the addition of donkey anti-rabbit-Ig-horseradish peroxidase (HRP) antibody for 1 hour at RT. Plates were washed, then developed by the addition of the chromagenic substrate 3, 3', 5, 5'-tetramethylbenzidine (TMB) (described by Bos et al., J. of Immunoassay 2:187-204 (1981); available from Sigma (St. Louis, MO)). The reaction was incubated 15 minutes at RT and then stopped by the addition of 1 N $H_2SO_4$. Plates were read at an optical density of 450 (OD450) in an automated plate reader. The sequences of peptides corresponding to the O8E antibody epitopes are disclosed herein as SEQ ID NO: 394-415. Antibody epitopes recognized by the O8E polyclonal anti-sera are disclosed herein in FIG. 17.

Example 4

This example discloses IHC analysis of O8E expression in ovarian cancer tissue samples.

For immunohistochemistry studies, paraffin-embedded formalin fixed ovarian cancer tissue was sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (anti-O8E rabbit affinity purified polyclonal antibody) was added to each section for 25 min followed by a 25 min incubation with an anti-rabbit biotinylated antibody. Endogenous peroxidase activity was blocked by three 1.5 min incubations with hydrogen peroxidase. The avidin biotin complex/horse radish peroxidase system was used along with DAB chromogen to visualize antigen expression. Slides were counterstained with hematoxylin. One (papillary serous carcinoma) of six ovarian cancer tissue sections displayed O8E immunoreactivity. Upon optimization of the staining conditions, 4/5 ovarian cancer samples stained positive using the O8E polyclonal antibody. O8E expression was localized to the plasma membrane.

Six ovarian cancer tissues were analyzed with the anti-O8E rabbit polyclonal antibody. One (papillary serous carcinoma) of six ovarian cancer tissue samples stained positive for O8E expression. O8E expression was localized to the surface membrane.

Example 5

This example discloses O8E peptides that are predicted to bind HLA-A2 and to be immunogenic for CD8 T cell responses in humans.

Potential HLA-A2 binding peptides of O8E were predicted by using the full-length open-reading frame (ORF) from O8E and running it through "Episeek," a program used to predict MHC binding peptides. The program used is based on the algorithm published by Parker, K. C. et al., J. Immunol. 152 (1):163-175 (1994) (incorporated by reference herein in its entirety). 10-mer and 9-mer peptides predicted to bind HLA-0201 are disclosed herein as SEQ ID NO: 416-435 and SEQ ID NO: 436-455, respectively.

Example 6

This example discloses O8E cell surface expression measured by fluoresence activated cell sorting.

Figure 18:
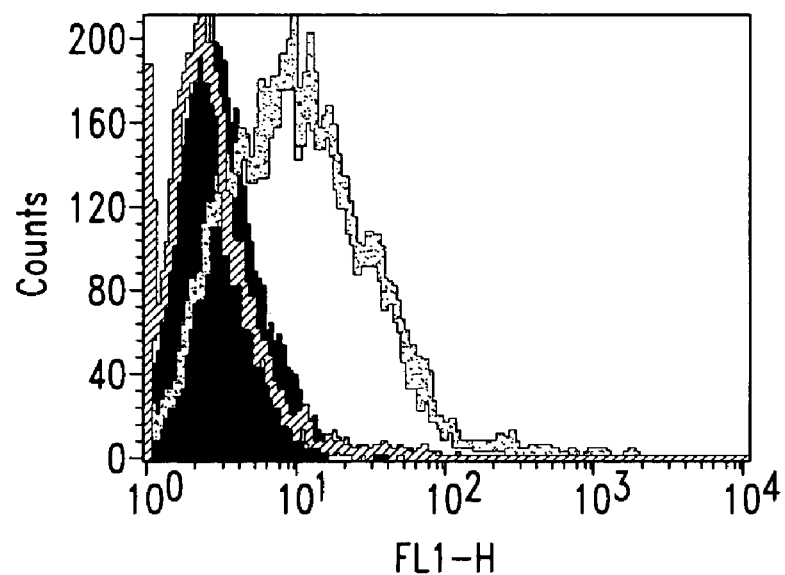
FIG. 18 is graph of a fluorescence activated cell sorting (FACS) analysis of O8E cell surface expression.
Figure 19:
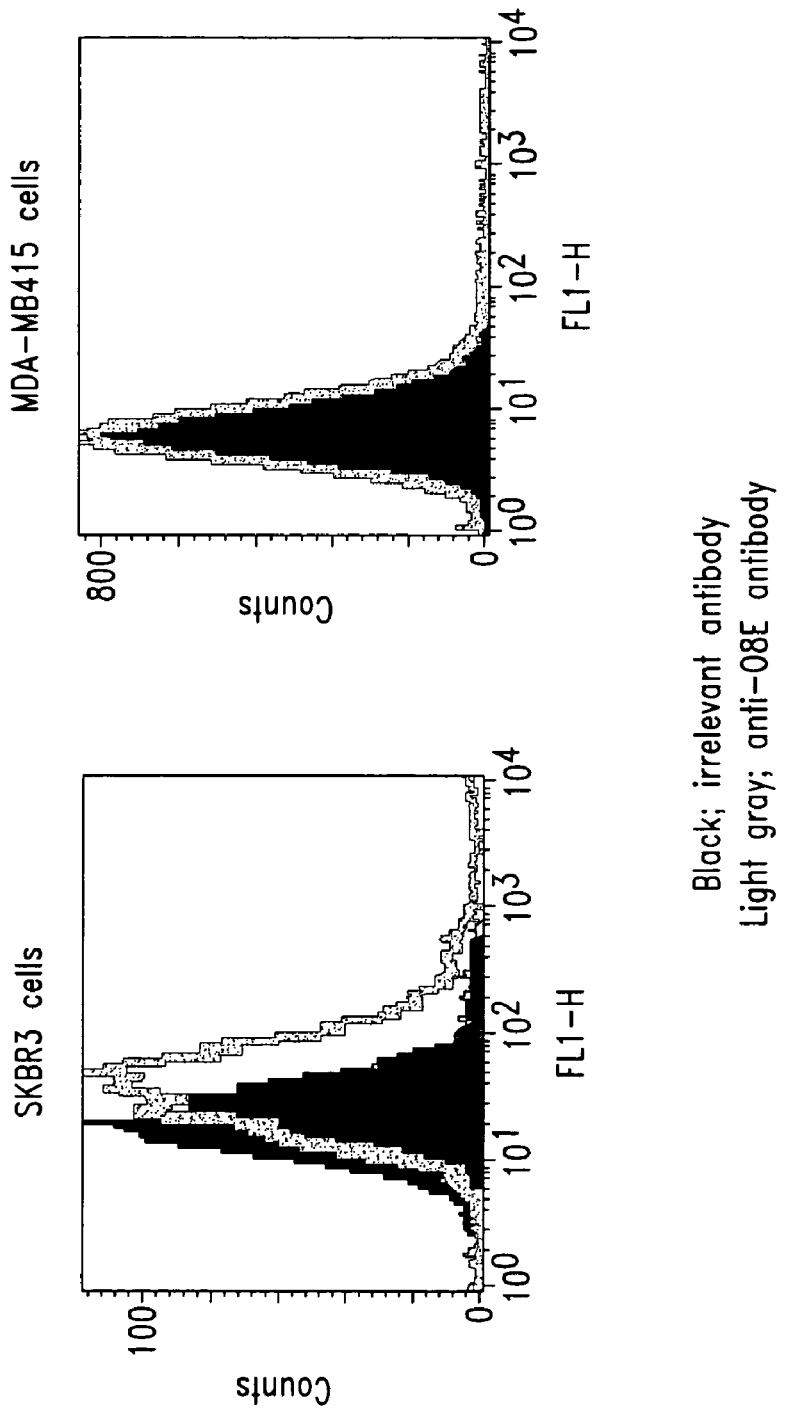
FIG. 19 is graph of a FACS analysis of O8E cell surface expression.

For FACS analysis, cells were washed with ice cold staining buffer (PBS/1% BSA/azide). Next, the cells were incubated for 30 minutes on ice with 10 micrograms/ml of affinity purified rabbit anti-B305D polyclonal antibody. The cells were washed 3 times with staining buffer and then incubated with a 1:100 dilution of a goat anti-rabbit Ig (H+L)-FITC reagent (Southern Biotechnology) for 30 minutes on ice. Following 3 washes, the cells were resuspended in staining buffer containing prodium iodide, a vital stain that allows for identification of permeable cells, and analyzed by FACS. O8E surface expression was confirmed on SKBR3 breast cancer cells and HEK293 cells that stably overexpress the cDNA for O8E. Neither MB415 cells nor HEK293 cells stably transfected with a control irrelevant plasmid DNA showed surface expression of O8E (FIGS. 18 and 19).

Example 7

This example further evaluates the expression and surface localization of O8E.

For expression and purification of antigen used for immunization, O8E expressed in an *E. coli* recombinant expression system was grown overnight in LB Broth with the appropriate antibiotics at 37° C. in a shaking incubator. The next morning, 10 ml of the overnight culture was added to 500 ml of 2×YT plus appropriate antibiotics in a 2L-baffled Erlenmeyer flask. When the Optical Density (at 560 nanometers) of the culture reached 0.4-0.6 the cells were induced with IPTG (1 mM). 4 hours after induction with IPTG the cells were harvested by centrifugation. The cells were then washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For protein that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10-20 column volumes of the solubilization buffer. The antigen was then eluted from the column using 8M urea, 10 mM tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. This material was then evaluated for acceptable purity as determined by SDS-PAGE or HPLC, concentration as determined by Lowry assay or Amino Acid Analysis, identity as determined by amino terminal protein sequence, and endotoxin level as determined by the Limulus (LAL) assay. The proteins were then vialed after filtration through a 0.22 micron filter and the antigens were frozen until needed for immunization.

For generation of polyclonal anti-sera, 400 micrograms of each prostate antigen was combined with 100 micrograms of muramyldipeptide (MDP). Equal volume of Incomplete Freund's Adjuvant (IFA) was added and then mixed. Every four weeks animals were boosted with 100 micrograms of antigen mixed with an equal volume of IFA. Seven days following each boost the animal was bled. Sera was generated by incubating the blood at 4° C. for 12-24 hours followed by centrifugation.

For characterization of polyclonal antisera, 96 well plates were coated with antigen by incubating with 50 microliters (typically 1 microgram) at 4° C. for 20 hrs. 250 microliters of BSA blocking buffer was added to the wells and incubated at RT for 2 hrs. Plates were washed 6 times with PBS/0.01% tween. Anti-O8E rabbit sera or affinity purified anti-O8e antibody was diluted in PBS. Fifty microliters of diluted antibody was added to each well and incubated at RT for 30 min. Plates were washed as described above before 50 microliters of goat anti-rabbit horse radish peroxidase (HRP) at a 1:10000 dilution was added and incubated at RT for 30 min. Plates were washed as described above and 100 microliters of TMB microwell Peroxidase Substrate was added to each well. Following a 15 minute incubation in the dark at room temperature the calorimetric reaction was stopped with 100 microliters of 1N H2SO4 and read immediately at 450 nm. All polyclonal antibodies showed immunoreactivity to the O8E antigen.

For recombinant expression in mammalian HEK293 cells, full length O8E cDNA was subcloned into the mammalian expression vectors pcDNA3.1+ and pCEP4 (Invitrogen) which were modified to contain His and FLAG epitope tags, respectively. These constructs were transfected into HEK293 cells (ATCC) using Fugene 6 reagent (Roche). Briefly, HEK293 cells were plated at a density of 100,000 cells/ml in DMEM (Gibco) containing 10% FBS (Hyclone) and grown overnight. The following day, 2 ul of Fugene6 was added to 100 ul of DMEM containing no FBS and incubated for 15 minutes at room temperature. The Fugene6/DMEM mixture was then added to 1 ug of O8E/pCEP4 or O8E/pcDNA3.1 plasmid DNA and incubated for 15 minutes at room temperature. The Fugene/DNA mix was then added to the HEK293 cells and incubated for 48-72 hrs at 37° C. with 7% CO2. Cells were rinsed with PBS then collected and pelleted by centrifugation. For Western blot analysis, whole cell lysates were generated by incubating the cells in Triton-X100 containing lysis buffer for 30 minutes on ice. Lysates were then cleared by centrifugation at 10,000 rpm for 5 minutes at 4 C. Samples were diluted with SDS-PAGE loading buffer containing beta-mercaptoethanol, then boiled for 10 minutes prior to loading the SDS-PAGE gel. Protein was transferred to nitrocellulose and probed using anti-O8E rabbit polyclonal sera #2333L at a dilution of 1:750. The blot was revealed with a goat anti-rabbit Ig coupled to HRP followed by incubation in ECL substrate.

For FACS analysis, cells were washed further with ice cold staining buffer (PBS+1% BSA+Azide). Next, the cells were incubated for 30 minutes on ice with 10 ug/ml of Protein A purified anti-O8E polyclonal sera. The cells were washed 3 times with staining buffer and then incubated with a 1:100 dilution of a goat anti-rabbit Ig(H+L)-FITC reagent (Southern Biotechnology) for 30 minutes on ice. Following 3 washes, the cells were resuspended in staining buffer containing Propidium Iodide (PI), a vital stain that allows for the identification of permeable cells, and analyzed by FACS.

Figure 20:
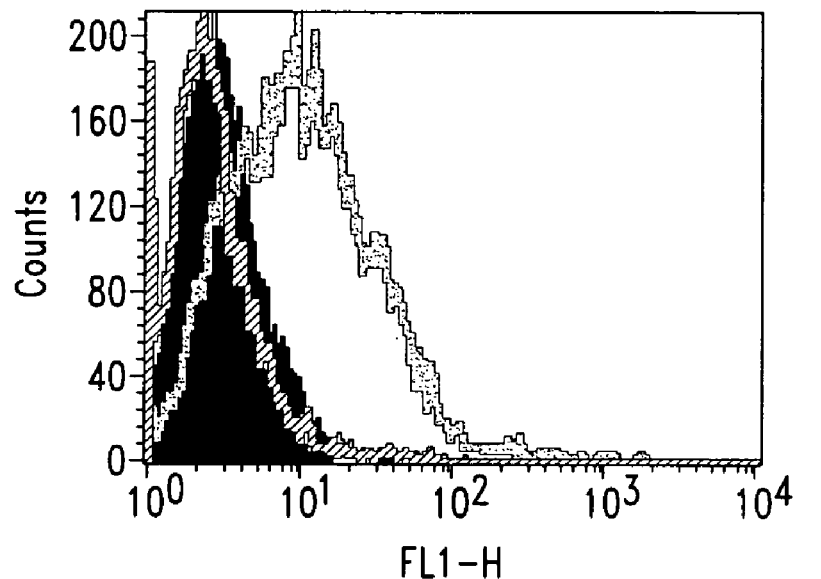
FIG. 20 shows FACS analysis results for O8E transfected HEK293 cells demonstrating cell surface expression of O8E.
Figure 21:
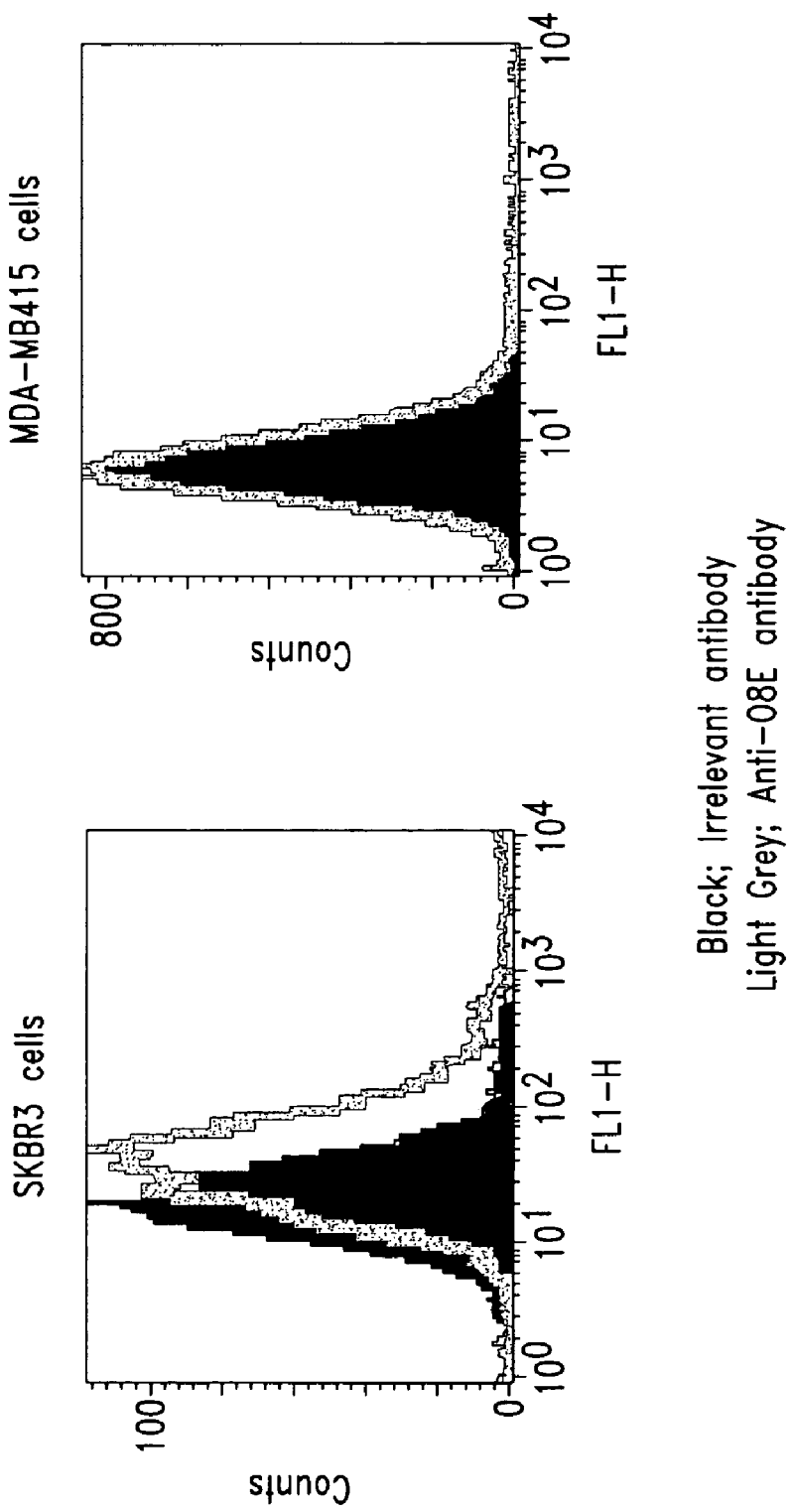
FIG. 21 shows FACS analysis results for SKBR3 breast tumor cells demonstrating cell surface expression of O8E.
Figure 22:
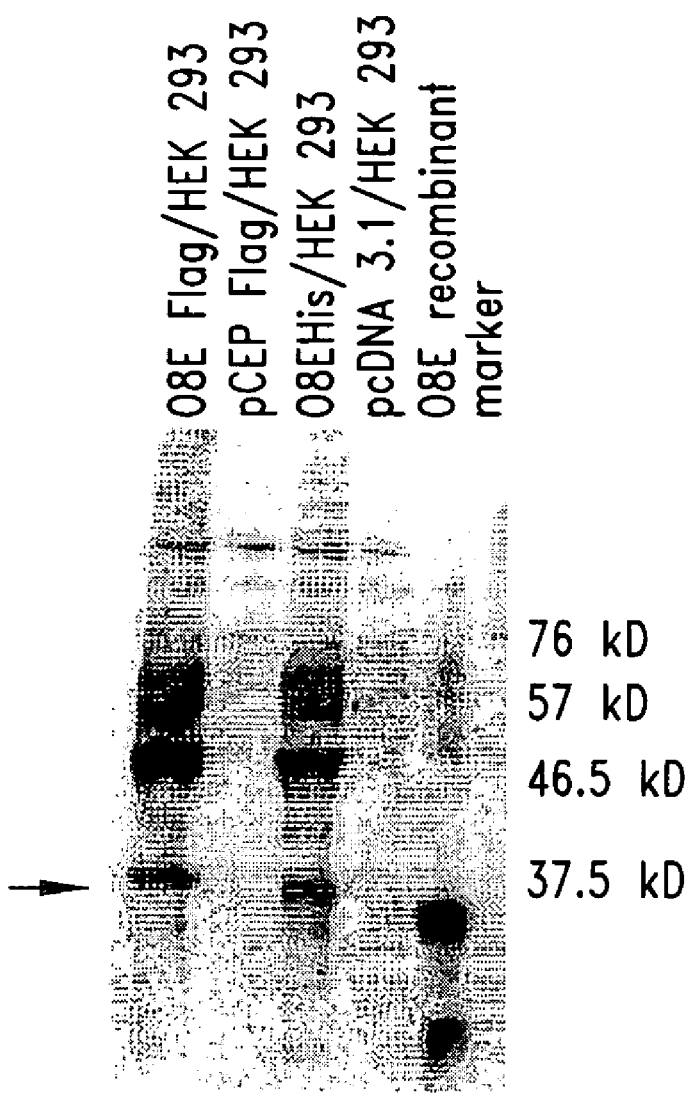
FIG. 22 shows O8E expression in HEK 293 cells. The cells were probed with anti-O8E rabbit polyclonal antisera #2333L.

From these experiments, the results of which are illustrated in FIGS. 20-21, O8E expression was detected on the surface of transfected HEK293 cells and SKBR3 cells by FACS analysis using rabbit anti-O8E sera. Expression was also detected in transfected HEK293 cell lysates by Western blot analysis (FIG. 22).

Example 8

Generation and Characterization of Anti-O8E mAbs

Mouse monoclonal antibodies were raised against *E. coli* derived O8E proteins as follows. A/J mice were immunized intraperitoneally (IP) with Complete Freund's Adjuvant (CFA) containing 50 µg recombinant O8E, followed by a subsequent IP boost with Incomplete Freund's Adjuvant (IFA) containing 10 µg recombinant O8E protein. Three days prior to removal of the spleens, the mice were immunized intravenously with approximately 50 µg of soluble O8E recombinant protein. The spleen of a mouse with a positive titer to O8E was removed, and a single-cell suspension made and used for fusion to SP2/0 myeloma cells to generate B cell hybridomas. The supernatants from the hybrid clones were tested by ELISA for specificity to recombinant O8E, and epitope mapped using peptides that spanned the entire O8E sequence. The mAbs were also tested by flow cytometry for their ability to detect O8E on the surface of cells stably transfected with O8E and on the surface of a breast tumor cell line.

For ELISA analysis, 96 well plates were coated with either recombinant O8E protein or overlapping 20-mer peptides spanning the entire O8E molecule at a concentration of either 1-2 µg/ml or 10 µg/ml, respectively. After coating, the plates were washed 5 times with washing buffer (PBS+0.1% Tween-20) and blocked with PBS containing 0.5% BSA, 0.4% Tween-20. Hybrid supernatants or purified mAbs were then added and the plates incubated for 60 minutes at room temperature. The plates were washed 5 times with washing buffer and the secondary antibody, donkey-anti mouse Ig linked to horseradish peroxidase (HRP)(Jackson ImmunoResearch), was added for 60 minutes. The plates were again washed 5 times in washing buffer, followed by the addition of the peroxidase substrate. Of the hybridoma clones generated, 15 secreted mAbs that recognized the entire O8E protein. Epitope mapping revealed that of these 15 clones, 14 secreted mAbs that recognized the O8E amino acid residues 61-80 and one clone secreted a mAb that recognized amino acid residues 151-170.

For flow cytometric analysis, HEK293 cells which had been stably transfected with O8E and SKBR3 cells which express O8E mRNA, were harvested and washed in flow staining buffer (PBS+1% BSA+Azide). The cells were incubated with the supernatant from the mAb hybrids for 30 minutes on ice followed by 3 washes with staining buffer. The cells were incubated with goat-anti mouse Ig-FITC for 30 minutes on ice, followed by three washes with staining buffer before being resuspended in wash buffer containing propidium iodide. Flow cytometric analysis revealed that 15/15 mAbs were able to detect O8E protein expressed on the surface of O8E-transfected HEK293 cells. 6/6 mAbs tested on SKBR3 cells were able to recognize surface expressed O8E.

Example 9

Extended DNA and Protein Sequence Analysis of Sequence O772P

A full-length sequence encompassing clones 3f, 6b, 8e, and 12 was obtained by screening an ovarian tumor (SCID-derived) cDNA library described in detail in Example 2. This 2996 base pair sequence, designated O772P, is presented in SEQ ID NO: 311, and the encoded 914 amino acid protein sequence is shown in SEQ ID NO: 312. The DNA sequence O772P was searched against public databases including Genbank and showed a significant hit to Genbank Accession number AK024365 (SEQ ID NO: 457). This Genbank sequence was found to be 3557 base pairs in length and encodes a protein 1156 amino acids in length (SEQ ID NO: 459). A truncated version of this sequence, residues 25-3471, in which residue 25 corresponds to the first ATG initiation codon in the Genbank sequence, (SEQ ID NO: 456), encodes a protein that is 1148 amino acids in length (SEQ ID NO: 458). The published DNA sequence (SEQ ID NO: 457) differs from O772P in that it has a 5 base pair insertion corresponding to bases 958-962 of SEQ ID NO: 457. This insertion results in a frame shift such that SEQ ID NO: 457 encodes an additional N-terminal protein sequence relative to O772P (SEQ ID NO: 312). In addition, O772P encodes a unique N-terminal portion contained in residues 1-79 (SEQ ID NO: 460). The N-terminal portion of SEQ ID NO: 456, residues 1-313, also contains unique sequence and is listed as SEQ ID NO: 461.

Example 10

The Generation of Polyclonal Antibodies for Immunohistochemistry and Flow Cytometric Analysis of the Cell Associated Expression Pattern of Molecule O772P The O772P molecule was identified in Examples 2 and 9 of this application. To evaluate the subcellular localization and specificity of antigen expression in various tissues, polyclonal antibodies were generated against O772P. To produce these antibodies, O772P-1 (amino acids 44-772 of SEQ ID NO:312) and O772P-2 (477-914 of SEQ ID NO:312) were expressed in an *E. coli* recombinant expression system and grown overnight at 37° C. in LB Broth. The following day, 10 ml of the overnight culture was added to 500 ml of 2×YT containing the appropriate antibiotics. When the optical density of the cultures (560 nanometers) reached 0.4-0.6 the cells were induced with IPTG. Following induction, the cells were harvested, washed, lysed and run through a French Press at a pressure of 16000 psi. The cells were then centrifuged and the pellet checked by SDS-PAGE for the partitioning of the recombinant protein. For proteins that localize to the cell pellet, the pellet was resuspended in 10 mM Tris, pH 8.0, 1% CHAPS and the inclusion body pellet washed and centrifuged. The washed inclusion body was solubilized with either 8M urea or 6M guanidine HCL containing 10 mM Tris, pH 8.0, plus 10 mM imidazole. The solubilized protein was then added to 5 ml of nickel-chelate resin (Qiagen) and incubated for 45 minutes at room temperature.

Following the incubation, the resin and protein mixture was poured through a column and the flow through collected.

The column was washed with 10-20 column volumes of buffer and the antigen eluted using 8M urea, 10 mM Tris, pH 8.0, and 300 mM imidazole and collected in 3 ml fractions. SDS-PAGE was run to determine which fractions to pool for further purification. As a final purification step, a strong anion exchange resin was equilibrated with the appropriate buffer and the pooled fractions were loaded onto the column. Each antigen was eluted from the column with an increasing salt gradient. Fractions were collected and analyzed by a SDS-PAGE to determine which fractions from the column to pool. The pooled fractions were dialyzed against 10 mM Tris, pH 8.0, and the resulting protein was submitted for quality control for final release. The release criteria were: (a) purity as determined by SDS-PAGE or HPLC, (b) concentration as determined by Lowry assay or Amino Acid Analysis, (c) identity as determined by amino terminal protein, and (d) endotoxin levels as determined by the Limulus (LAL) assay. The proteins were then filtered through a 0.22 µM filter and frozen until needed for immunizations.

To generate polyclonal antisera, 400 µg of O772P-1 or O772P-2 was combined with 100 µg of muramyldipeptide (MDP). The rabbits were immunized every 4 weeks with 100 µg of antigen mixed with an equal volume of Incomplete Freund's Adjuvant (IFA). Seven days following each boost, the animals were bled and sera was generated by incubating the blood at 4° C. for 12-24 hours followed by centrifugation.

To characterize the antisera, 96 well plates were coated with antigen followed by blocking with BSA. Rabbit sera was diluted in PBS and added to each well. The plates were then washed, and goat anti-rabbit horseradish peroxidase (HRP). The plates were again washed and TMB microwell Peroxidase Substrate was added. Following this incubation, the colormetric reaction was stopped and the plates read immediately at 450 nm. All polyclonal antibodies showed immunoreactivity to the appropriate antigen.

Immunohistochemistry analysis of O772P expression was performed on paraffin-embedded formalin fixed tissue. O772P was found to be expressed in normal ovary and ovarian tumor, but not in normal heart, kidney, colon, lung or liver. Additionally, immunohistochemistry and flow cytometric analysis indicates that O772P is a plasma membrane-associated molecule. O772P contains 1 plasma transmembrane domain predicted to be encoded by amino acids 859-880. The N-terminus of O772P is extracellular and is encoded by amino acids 1-859, while the C-terminus is intracellular. Sequence analysis shows that there are 17 potential N-linked glycosylation sites.

Example 11

O772P is Expressed on the Surface of Primary Ovarian Tumor Cells

For recombinant expression in mammalian cells, the O772P-21008 (SEQ ID NO:387) and O772P full length cDNA (SEQ ID NO:311 encoding the protein of SEQ ID NO:312) were subcloned into mammalian expression vectors pBIB or pCEP4 respectively. These constructs were transfected into HEK293 cells using Fugene 6 (Roche). The HEK cells were then plated at a density of 100,000 cells/ml in DMEM containing fetal bovine serum (FBS) and grown overnight. The following day, 2 µl of Fugene 6 was added to 100 µl of DMEM, which contained no FBS, and incubated for 15 minutes at room temperature. The Fugene 6/DMEM mixture was then added to 1 µg of O772P/pBIB or O772P/pCEP4 plasmid DNA and incubated for an additional 15 minutes at room temperature. The Fugene 6/DNA mix was then added to the HEK293 cells and incubated for 48-72 hours at 37° C. with 7% $CO_2$. The cells were rinsed and pelleted by centrifugation.

For Western Blot analysis, whole cell lysates were generated by incubating the cells in lysis buffer followed by clarification by centrifugation. The samples were diluted and run on SDS-PAGE. The gel was then transferred to nitrocellulose and probed using purified anti-O772P-2 rabbit polyclonal antibody. The blot was revealed with a goat anti-rabbit Ig coupled to HRP followed by incubation in ECL substrate. Western Blot analysis revealed that O772P-21008 could be detected in HEK293 cells that had been transfected with O772P.

To determine the cell expression profile of O772P in cells, primary ovarian tumor cells were grown in SCID mice. The cells were retrieved from the mice and analyzed by flow cytometry. Briefly, cells washed in cold staining buffer containing PBS, 1% BSA, and Na Azide. The cells were incubated for 30 minutes with 10 µg/ml of purified anti-O772P-1 and O772P-2 polyclonal sera. Following this incubation, the cells were washed three times in staining buffer and incubated with goat anti-rabbit Ig (H+L) conjugated to FITC (Southern Biotechnology). The cells were washed and resuspended in staining buffer containing Propidium Iodide (PI), a vital stain that identifies non-viable cells. The cells were then analyzed using Fluorescence Activated Cell Sorting (FACS). FACS analysis revealed that O772P was present on the cells surface. Surface expression of O772P on tumor cells allows for immune targeting by therapeutic antibodies.

Example 12

Functional Characterization of Anti-O8E Monoclonal Antibodies

Mouse monoclonal antibodies (mAb) raised against *E. coli* derived O8E, as described in Example 8, were tested for their ability to promote O8E antigen internalization. Internalization of the antibody was determined using an in vitro cytotoxicity assay. Briefly, HEK293 and O8E/HEK transfected cells were plated into 96 well plates containing DME plus 10% heat-inactivated FBS in the presence of 50 ng/well of purified anti-O8E or control antibodies. The isotype of the anti-O8E mabs are as follows: 11A6-IgG1/kappa, 15C6-IgG2b/kappa, 18A8-IgG2b/kappa, and 14F1-IgG2a/kappa. W6/32 is a pan anti-human MHC class I mouse monoclonal antibody that serves as a positive control, and two irrelevant mAbs, Ir-Pharm and Ir-Crxa were included as negative controls. Following incubation with the O8E specific antibodies or the relevant controls antibodies, the mAb-zap, a goat anti-mouse Ig-saporin conjugated secondary antibody (Advanced Targeting Systems) was added at a concentration of 100 ng/ml to half of the wells, and the plates were incubated for 48 to 72 hours at 37° C. in a 7% $CO_2$ incubator. This assay takes advantage of the toxic nature of saporin, a ribozyme inactivating protein, which when internalized has a cytotoxic effect. Following incubation with the mAb-zap, internalization was quantitated by the addition of MTS reagent, followed by reading the OD490 of the plate on a microplate ELISA reader. FIG. 25 depicts the results from these assays. The top panel represents HEK cells that have not been transfected with O8E and therefore O8E antibody should not bind and be internalized. Levels of proliferation were the same in all samples whether they were incubated with or without the mAb-zap, with the exception of the positive control Ab, W6/32. The lower panel represents cells that have been transfected with O8E and therefore should bind O8E specific antibodies. Antibodies from the hybridomas 11H6, 14F1, and 15C6, which recognize the amino acids 61-80 of O8E were able to promote internalization of the O8E surface protein as measured by decreased levels of proliferation due to the toxic nature of the mAb-zap (See FIG. 25). The antibody generated by the hybridoma 18A8, which recognizes amino acids 151-170 of O8E, was unable to promote internalization as determined by normal levels of proliferation either in the absence or presence of the mAb-zap.

Example 13

Characterization of the Ovarian Tumor Antigen, O772P

The cDNA and protein sequences for multiple forms of the ovarian tumor antigen O772P have been described in the above (e.g., Examples 2 and 9). A Genbank search indicated that O772P has a high degree of similarity with FLJ14303 (Accession # AK024365; SEQ ID NO:457 and 463). Protein sequences corresponding to O772P and FLJ14303 are disclosed in SEQ ID NO:478 and 479, respectively. FLJ14303 was identical to the majority of O772P, with much of the 3'-end showing 100% homology. However, the 5'-end of FLJ14303 was found to extend further 5' than O772P. In addition, FLJ14303 contained a 5 bp insert (SEQ ID NO:457) resulting in a frame shift of the amino-terminus protein sequence such that FLJ14303 utilizes a different starting methionine than O772P and therefore encodes a different protein. This insertion was present in the genomic sequence and seen in all EST clones that showed identity to this region, suggesting that FLJ14303 (SEQ ID NO:457) represents a splice variant of O772P, with an ORF that contains an extended and different amino-terminus. The additional 5'-nucleotide sequence included repeat sequences that were identified during the genomic mapping of O772P. The 5'-end of O772P and the corresponding region of FLJ14303 showed between 90-100% homology. Taken together, this suggests that O772P and FLJ14303 are different splice variants of the same gene, with different unique repeat sequences being spliced into the 5'-end of the gene.

The identification of an additional ten or more repeat sequences within the same region of chromosome 19, indicates that there may be many forms of O772P, each with a different 5'-end, due to differential splicing of different repeat sequences. Northern blot analysis of O772P demonstrated multiple O772P-hybridizing transcripts of different sizes, some in excess 10 kb.

Upon further analysis, 13 additional O772P-related sequences were identified, the cDNA and amino acid sequences of which are described in Table 3.

TABLE 3

| SEQ ID NO: | Description | Transmembrane Domains |
|---|---|---|
| 464 | LS #1043400.1 (cDNA) | nd |
| 465 | LS #1043400.10 (cDNA) | 0 |
| 466 | LS #1043400.11 (cDNA) | 2 |
| 467 | LS #1043400.12 (cDNA) | 2 |
| 468 | LS #1043400.2 (cDNA) | nd |
| 469 | LS #1043400.3 (cDNA) | |
| 470 | LS #1043400.5 (cDNA) | nd |
| 471 | LS #1043400.8 (cDNA) | 1 |
| 472 | LS #1043400.9 (cDNA) | 0 |
| 473 | LS #1043400.6 (cDNA) | nd |
| 474 | LS #1043400.7 (cDNA) | nd |
| 475 | LS #1043400.4 (cDNA) | nd |
| 476 | LS #1397610.1 (cDNA) | 0 |

TABLE 3-continued

| SEQ ID NO: | Description | Transmembrane Domains |
|---|---|---|
| 477 | 1043400.10 Novel 5' (cDNA) | — |
| 480 | LS #1043400.9 (amino acid) | — |
| 481 | LS #1043400.8B (amino acid) Contains a transmembrane domain | — |
| 482 | LS #1043400.8A (amino acid) | — |
| 483 | LS #1043400.12 (amino acid) Contains a transmembrane domain | — |
| 484 | LS #1043400.11B (amino acid) Contains a transmembrane domain | — |
| 485 | LS #1043400.11A (amino acid) | — |
| 486 | LS #1043400.10 (amino acid) | — |
| 487 | LS #1043400.1 (amino acid) | — | nd = not determined

Initially it appeared that these sequences represented overlapping and/or discrete sequences of O772P splice forms that were capable of encoding polypeptides unique to the specific splice forms of O772P. However, nucleotide alignment of these sequences failed to identify any identical regions within the repeat elements. This indicates that the sequences may represent different specific regions of a single O772P gene, one that contains 16 or more repeat domains, all of which form a single linear transcript. The 5'-end of sequence LS #1043400.10 (Table 2; SEQ ID NO:465) is unique to both O772P and FLJ14303 and contains no repeat elements, indicating that this sequence may represent the 5'-end of O772P.

Previously, transmembrane prediction analysis had indicated that O772P contained between 1 and 3 transmembrane spanning domains. This was verified by the use of immunohistochemistry and flow cytometry, which demonstrated the existence of a plasma membrane-associated molecule representing O772P. However, immunohistochemistry also indicated the presence of secreted form(s) of O772P, possibly resulting from an alternative splice form of O772P or from a post-translational cleavage event. Analysis of several of the sequences presented in Table 2 showed that sequences 1043400B.12, 1043400.8B, and 1043400.11B all contained transmembrane regions, while 1043400.8A, 1043400.10, 1043400.1, 1043400.11A, and 1043400.9 were all lacking transmembrane sequences, suggesting that these proteins may be secreted.

Analysis indicates a part of O772P is expressed and/or retained on the plasma membrane, making O772P an attractive target for directing specific immunotherapies, e.g., therapeutic antibodies, against this protein. The predicted extracellular domain of O772P is disclosed in SEQ ID NO:489 and secretion of O772P is likely to occur as a result of a cleavage event within the sequence:

SLVEQVFLD
KTLNASFHWLGSTYQLVDIHVTEMESSVYQP.

Proteolytic cleavage is most likely to occur at the Lysine (K) at position 10 of SEQ ID NO:489. The extracellular, transmembrane, and cytoplasmic regions of O772P are all disclosed in SEQ ID NO:488:

Extracellular:
SLVEQVFLDKTLNASFHWLGSTYQLVDIHVTEMESSVYQPTSSSSTQHFY

LNFTITNLPYSQDKAQPGTTNYQRNKRNIEDALNQLFRNSSIKSYFSDCQ

VSTFRSVPNRHHTGVDSLCNFSPLARRVDRVAIYEEFLRMTRNGTQLQNF

-continued

TLDRSSVLVDGYFPNRNEPLTGNSDLPF

Transmembrane:
WAVILIGLAGLLGLITCLICGVLVTT

Cytoplasmic:
RRRKKEGEYNVQQQCPGYYQSHLDLEDLQ

Example 14

Immunohistochemistry (IHC) Analysis of O8E Expression in Ovarian Cancer and Normal Tissues In order to determine which tissues express the ovarian cancer antigen O8E, IHC analysis was performed on a diverse range of tissue sections using both polyclonal and monoclonal antibodies specific for O8E. The generation of O8E specific polyclonal antibodies is described in detail in Example 8. The monoclonal antibodies used for staining were 11A6 and 14F1, both of which are specific for amino acids 61-80 of O8E and 18A8, which recognizes amino acids 151-170 of O8E (see Example 12 for details on generation).

To perform staining, tissue samples were fixed in formalin solution for 12-24 hours and embedded in paraffin before being sliced into 8 micron sections. Steam heat induced epitope retrieval (SHEIR) in 0.1M sodium citrate buffer (pH 6.0) was used for optimal staining conditions. Sections were incubated with 10% serum/PBS for 5 minutes. Primary antibody was then added to each section for 25 minutes followed by 25 minutes of incubation with either anti-rabbit or anti-mouse biotinylated antibody. Endogenous peroxidase activity was blocked by three 1.5 minute incubations with hydrogen peroxidase. The avidin biotin complex/horse radish peroxidase (ABC/HRP) system was used along with DAB chromogen to visualize the antigen expression. Slides were counterstained with hematoxylin to visualize the cell nuclei.

Results using rabbit affinity purified polyclonal antibody to O8E (a.a. 29-283; for details on the generation of this Ab, see Example 3) are presented in Table 3. Results using the three monoclonal antibodies are presented in Table 4.

TABLE 4

Immunohistochemistry analysis of O8E using polyclonal antibodies

| Tissue | O8E Expression |
| --- | --- |
| Ovarian Cancer | Positive |
| Breast Cancer | Positive |
| Normal Ovary | Positive |
| Normal Breast | Positive |
| Blood Vessel | Positive |
| Kidney | Negative |
| Lung | Negative |
| Colon | Negative |
| Liver | Negative |
| Heart | Negative |

TABLE 5

Immunohistochemistry analysis of O8E using monoclonal antibodies

| Normal Tissue | 11A6 | | 18A8 | | 14F1 | |
| --- | --- | --- | --- | --- | --- | --- |
|  | Endothelial | Epithelial | Endothelial | Epithelial | Endothelial | Epithelial |
| Skin | 2 | 2 | 0 | 0 | 1 | 1 |
| Skin | 1 | 1 | 0 | 0 | 1 | 1 |
| Breast | 0 | 1 | n/a | n/a | 1 | 1 |
| Colon | 0 | 0 | 0 | 0 | 0 | 0 |
| Jejunum | 0 | 0 | 0 | 0 | 0 | 0 |
| Colon | 0 | 0 | 0 | 0 | 0 | 0 |
| Colon | 0 | 0 | 0 | 0 | 0 | 0 |
| Ovary | 0 | 0 | 0 | 0 | 1 | 0 |
| Colon | 0 | 0 | 0 | 0 | 0 | 1 |
| Liver | 0 | 0 | 0 | 0 | 1 | 2 |
| Skin | 0 | 0 | 0 | 0 | 1 | 0 |
| Duodenum and Pancreas | 0 | 0 | 0 | 0 | 0 | 0 |
| Appendix | 0 | 0 | 0 | 0 | 0 | 0 |
| Ileum | 0 | 0 | 0 | 0 | 0 | 0 |

0 = no staining,
1 = light staining,
2 = moderate staining,
n/a = not available

Example 15

Epitope Mapping of O772P Polyclonal Antibodies

To perform epitope mapping of O772P, peptides were generated, the sequences of which were derived from the sequence of O772P. These peptides were 15 mers that overlapped by 5 amino acids and were generated via chemical synthesis on membrane supports. The peptides were covalently bound to Whatman 50 cellulose support by their C-terminus with the N-terminus unbound. In order to determine epitope specificity, the membranes were wet with 100% ethanol for 1 minute, and then blocked for 16 hours in TBS/Tween/Triton buffer (50 mM Tris, 137 mM NaCl, 2.7 mM KCl, 0.5% BSA, 0.05% Tween 20, 0.05% Triton X-100, pH 7.5). The peptides were then probed with 2 O772P specific antibodies, O772P-1 (amino acids 44-772 of SEQ ID NO:312) and O772P-2 (477-914 of SEQ ID NO:312; see Example 10 for details of antibody generation), as well as irrelevant rabbit antibodies for controls. The antibodies were diluted to 1 µg/ml and incubated with the membranes for 2 hours at room temperature. The membranes were then washed for 30 minutes in TBS/Tween/Triton buffer, prior to being incubated with a 1:10,000 dilution of HRP-conjugated anti-rabbit secondary antibody for 2 hours. The membranes were again washed for 30 minutes in TBS/Tween/Triton and anti-peptide reactivity was visualized using ECL. Specific epitope binding specificity for each of the O772P-polyclonal antibodies is described in Table 6.

TABLE 6

| SEQ ID NO: | Peptide # | Anti-O772P1 | Anti-O772P2 | Peptide Sequence |
|---|---|---|---|---|
| 490 | 2 | *** | – | TCGMRRTCSTLAPGS |
| 491 | 6 | * | */– | CRLTLLRPEKDGTAT |
| 492 | 7 | * | – | DGTATGVDAICTHHP |
| 493 | 8 | – | – | CTHHPDPKSPRLDRE |
| 494 | 9 | *** | *** | RLDREQLYWELSQLT |
| 495 | 11 | */– | – | LGPYALDNDSLFVNG |
| 496 | 13 | **** | – | SVSTTSTPGTPTYVL |
| 497 | 22 | – | – | LRPEKDGEATGVDAI |
| 498 | 24 | ** | */– | DPTGPGLDREQLYLE |
| 499 | 27 | */– | – | LDRDSLYVNGFTHRS |
| 500 | 40 | */– | – | GPYSLDKDSLYLNGY |
| 501 | 41 | – | – | YLNGYNEPGPDEPPT |
| 502 | 47 | *** | *** | ATFNSTEGVLQHLLR |
| 503 | 50 | – | *** | QLISLRPEKDGAATG |
| 504 | 51 | – | ** | GAATGVDTTCTYHPD |
| 505 | 52 | – | */– | TYHPDPVGPGLDIQQ |
| 506 | 53 | – | * | LDIQQLYWELSQLTH |
| 507 | 58 | – | * | HIVNWNLSNPDPTSS |
| 508 | 59 | – | * | DPTSSEYITLLRDIQ |
| 509 | 60 | – | * | LRDIQDKVTTLYKGS |
| 510 | 61 | – | *** | LYKGSQLHDTFRFCL |
| 511 | 71 | – | ** | DKAQPGTTNYQRNKR |

* = relative reactive level, –; no binding, ****; maximal binding

Example 16

Identification of a Novel N-Terminal Repeat Structure Associated with O772P

Various O772P cDNA and protein forms have been identified and characterized as detailed above (e.g., Examples 1, 2, 9, and 14). Importantly, O772P RNA and protein have been demonstrated to be over-expressed in ovarian cancer tissue relative to normal tissues and thus represents an attractive target for ovarian cancer diagnostic and therapeutic applications.

Using bioinformatic analysis of open reading frames (ORFs) from genomic nucleotide sequence identified previously as having homology with O772P, multiple nucleotide repeat sequences were identified in the 5' region of the gene encoding the O772P protein. A number of these repeat sequences were confirmed by RT-PCR using primers specific for the individual repeats. Fragments which contained multiple repeats were amplified from cDNA, thus confirming the presence of specific repeats and allowing an order of these repeats to be established.

Unexpectedly, when various sets of O772P sequences derived from different database and laboratory sources were analyzed, at least 20 different repeat structures, each having substantial levels of identity with each other (see Table 6), were identified in the 5' region of the O772P gene and the corresponding N-terminal region of the O772P protein. Each repeat comprises a contiguous open reading frame encoding a polypeptide unit that is capable of being spliced to one or more other repeats such that concatomers of the repeats are formed in differing numbers and orders. Interestingly, other molecules have been described in the scientific literature that have repeating structural domains analogous to those described herein for O772P. For example, the mucin family of proteins, which are the major glycoprotein component of the mucous which coats the surfaces of cells lining the respiratory, digestive and urogenital tracts, have been shown to be composed of tandemly repeated sequences that vary in number, length and amino acid sequence from one mucin to another (Perez-Vilar and Hill, J. Biol. Chem. 274(45):31751-31754, 1999).

The various identified repeat structures set forth herein are expected to give rise to multiple forms of O772P, most likely by alternative splicing. The cDNA sequences of the identified repeats are set forth in SEQ ID NOs:513-540, 542-546, and 548-567. The encoded amino acid sequences of the repeats are set forth in SEQ ID NOs:574-593. In many instances these amino acid sequences represent consensus sequences that were derived from the alignment of more than one experimentally derived sequence.

Each of these splice forms is capable of encoding a unique O772P protein with multiple repeat domains attached to a constant carboxy terminal protein portion of O772P that contains a trans membrane region. The cDNA sequence of the O772P constant region is set forth in SEQ ID NO:568 and the encoded amino acid sequence is set forth in SEQ ID NO:594.

All of the available O772P sequences that were obtained were broken down into their identifiable repeats and these sequences were compared using the Clustal method with weighted residue weight table (MegAlign software within DNASTAR sequence analysis package) to identify the relationship between the repeat sequences. Using this information, the ordering data provided by the RT-PCR, and sequence alignments (automatic and manual) using SeqMan (DNASTAR), one illustrative consensus full length O772P contig was identified comprising 20 distinct repeat units. The cDNA for this O772P cDNA contig is set forth in SEQ ID NO:569 and the encoded amino acid sequence is set forth in SEQ ID NO:595. This form of the O772P protein includes the following consensus repeat structures in the following order:

SEQ ID NO:572-SEQ ID NO:574-SEQ ID NO:575-SEQ ID NO:576-SEQ ID NO:577-SEQ ID NO:578-SEQ ID NO:579-SEQ ID NO:580-SEQ ID NO:581-SEQ ID NO:582-SEQ ID NO:583-SEQ ID NO:584-SEQ ID NO:585-SEQ ID NO:586-SEQ ID NO:587-SEQ ID NO:588-SEQ ID NO:589-SEQ ID NO:590-SEQ ID NO:591-SEQ ID NO:592-SEQ ID NO:593.

SEQ ID NO:595, therefore, represents one illustrative full-length consensus sequence for the O772P protein. As discussed above, however, based on current knowledge of this protein and based upon scientific literature describing proteins containing analogous repeating structures, many other forms of O772P are expected to exist with either more or less repeats. In addition, many forms of O772P are expected to have differing arrangements, e.g., different orders, of these N-terminal repeat structures. The existence of multiple forms of O772P having differing numbers of repeats is supported by Northern analysis of O772P. In this study, Northern hybridization of a O772P-specific probe resulted in a smear of multiple O772P-hybridizing transcripts, some in excess 10 kb.

Thus, the variable repeat region of the O772 protein can be illustratively represented by the structure Xn—Y, wherein X comprises a repeat structure having at least 50% identity with the consensus repeat sequence set forth in SEQ ID NO:596; n is the number of repeats present in the protein and is expected to typically be a integer from 1 to about 35; Y comprise the O772P constant region sequence set forth in SEQ ID NO:594 or sequences having at least 80% identity with SEQ ID NO:594. Each X present in the Xn repeat region of the O772 molecule is different.

To determine the consensus sequences of each of the 20 repeat regions, sequences that were experimentally determined for a discrete repeat region were aligned and a consensus sequence determined. In addition to determining the consensus sequences for individual repeat regions, a consensus repeat sequence was also determined. This sequence was obtained by aligning the 20 individual consensus sequences. Variability of the repeats was determined by aligning the consensus amino acid sequences from each of the individual repeat regions with the over all repeat consensus sequence. Identity data is presented in Table 6.

TABLE 7

Percent identities of Repeat Sequences with Reference to the Consensus Repeat Sequence

| Repeat Number (amino acid) | SEQ ID NO: | Percent Identity to Consensus Repeat Sequence |
|---|---|---|
| 2 | 574 | 88 |
| 3 | 575 | 84 |
| 4 | 576 | 88 |
| 5 | 577 | 89 |
| 6 | 578 | 93 |
| 7 | 579 | 90 |
| 8 | 580 | 91 |
| 9 | 581 | 88 |
| 10 | 582 | 85 |
| 11 | 583 | 86 |
| 12 | 584 | 87 |
| 13 | 585 | 87 |
| 14 | 586 | 89 |
| 15 | 587 | 89 |
| 16 | 588 | 89 |
| 17 | 589 | 83 |
| 18 | 590 | 84 |
| 19 | 591 | 83 |
| 20 | 592 | 57 |
| 21 | 593 | 68 |

Example 17

Generation and Characterization of Anti-O772P Monoclonal Antibodies

Monoclonal antibodies were generated against the O772P-2 protein, specifically amino acid residues 447-914 of SEQ ID NO:312. To produce these antibodies, A/J mice were immunized i.p. with 50 µg of recombinant O772P-2 (rO772P-2) mixed with Complete Freud's Adjuvant, followed by a second immunization with 10 µg of rO772P-2 in Incomplete Freud's Adjuvant. Three days prior to the animals being sacrificed, the mice were immunized i.v. with 50 µg of soluble rO772P-2 protein. The spleens from mice with positive titers of O772P-2 were harvested, and a single cell suspension was made and used for fusion to SP2/0 myeloma cells to generate B cell hybridomas.

The supernatants from the resulting hybrid clones were tested by ELISA for specificity to the rO772P-2 protein. Briefly, 96 well plates were coated with rO772P-2 or with one of three 30 mer peptides, which corresponded to the extracellualr domain of the O772P protein. Sequences corresponding to these peptides are disclosed in SEQ ID NO:597-599. The rO772P protein or peptides were coated at a concentration of 1-2 µg/ml and 10 µg/ml, respectively, and allowed to incubate for 60 minutes at room temperature. Following coating, the plates were washed five times with PBS containing 0.1% Tween-20, and then blocked with PBS containing 0.5% BSA and 0.4% Tween-20 for 1-2 hours at room temperature. Following the addition of the hybridoma supernatants the plates were again incubated for 60 minutes at room temperature. The plates were then washed as above and donkey-anti-mouse Ig-HRP linked secondary antibody (Jackson ImmunoResearch) was added and incubated for 60 minutes at room temperature, followed by a final wash. TMB peroxidase substrate was then added and incubated for 5-15 minutes at room temperature in the dark. The reaction was stopped by the addition of 1N $H_2SO_4$ and the optical density was read at 450 nm. Epitope mapping using ELISA revealed that there was 1 hybridoma that recognized peptide #1 (SEQ ID NO:597).

The hybrid supernatants were also tested using flow cytometry to determine if they were capable of recognizing surface expressed epitopes of the O772P protein. Briefly, transiently transfected O772P-08/HEK293, O772P-3rpt/HEK293, O772P-7rpt/HEK293 cells were harvested and washed, followed by incubation with the hybridoma supernatants on ice for 30 minutes. The cells were then washed in staining buffer (1×PBS, 0.5% BSA and 0.01% sodium azide), followed by incubation with goat-anti-mouse Ig-FITC for 30 minutes on ice. The cells were again washed, and resuspended in staining buffer containing 1% propidium iodide (to determine cell viability). The cells were then analyzed for surface expression of the mAbs. Flow cytometry analysis revealed that the 3 of the hybridomas tested were able to detect O772P protein expressed in the surface of O772P-transfected HEK293 cells.

Example 18

Characterization of Human Anti-O8E Monoclonal Antibodies

Monoclonal antibodies (mAb) were generated against the O8E protein, the amino acid sequence of which is disclosed in SEQ ID NO:392. To produce these mAbs, Medarex mice were i.p. immunized repeatedly with multiple forms if recombinant O8E antigens, including O8E protein produced using E. coli, O8E plasmid DNA and O8E expressing CHO-1 cells. Spleens from mice with positive titers to O8E were collected and used for fusion to myeloma cells in order to generate B cell hybrids. The supernatants from the resulting hybrids were tested by ELISA for specificity to O8E recombinant protein as well as being tested by flow cytometry for recognition of surface expressed epitopes of the O8E protein and in internalization assays.

For ELISA analysis, 96 well plates were coated with recombinant O8E (rO8E) protein or with pools of 5 overlapping 20-mer peptides that span the entire O8E molecule (peptides 1-19, the sequences of which are disclosed in SEQ ID NOs:600-618). Recombinant proteins and peptides were coated at a concentration of 1-2 µg/ml and 10 µg/ml, respectively, and then allowed to incubate for 60 minutes at room temperature. After coating, the plates were washed five times with PBS containing 0.1% Tween-20 and then blocked with PBS containing 0.5% BSA and 0.4% Tween-20 for 1-2 hours at room temperature. Following the addition of the hybridoma supernatants, the plates were incubated for 60 minutes at room temperature. The plates were washed as above and mouse anti-human IgG-HRP linked secondary antibody was added and incubated for 60 minutes at room temperature, followed by a final washing as above. TMB peroxidase substrate was added and incubated for 5-15 minutes at room temperature in the dark. The reaction was stopped by the addition of 1N $H_2SO_4$ and the OD was read at 450 nm. Hybridoma 7F5 was shown to react with peptides 11-15, corresponding to amino acids 151-230. No other hybridoma demonstrated reactivity against the O8E specific peptides. Results from this study are presented in Table 7, column 2.

For flow cytometric analysis, HEK293 cells stably transfected with O8E or SKBR3 cells, which naturally express O8E, were harvested and washed, then incubated with the hybridoma supernatants for 30 minutes on ice. Following this incubation, the cells were washed with staining buffer (1×PBS, 0.5% BSA, and 0.01% sodium azide). Next, mouse anti-human kappa-FITC was added to the cells and allowed to incubate for 30 minutes on ice. Again, the cells were washed followed by resuspension in wash buffer containing 1% propidium iodide. The cells were then subjected to flow cytometric analysis. Results from these experiments are presented in Table 8, column 3.

For internalization assays, $1\times10^3$ SKBR3 cells/well were plated into 96 well plates containing DME plus 10% heat inactivated fetal bovine serum in the presence of 50 ng/well of human anti-O8E hybridoma supernatants or a control antibody. A mouse anti-human Ig-saporin conjugated secondary antibody was then added at various concentrations to the wells, and the plates were incubated for 4 days at 37° C. in a 7% $CO_2$ incubator. To measure any decreases in the amount of proliferation MTS (20 µl/ml: Promega) was added to the cells for 1 to 2 hours. Proliferation was then measured by reading the OD490 of the plate. The majority of the hybridomas tested were internalized resulting in a decrease in the amount of proliferation detected. The results from these studies are summarized in Table 8, column 6. These findings indicate that the hybridomas can be used to deliver toxins, either directly or indirectly conjugated to the anti-O8E antibodies, to cells that express O8E on their cell surface. This allows for the specific targeting and death of cells that express the ovarian tumor antigen, O8E.

TABLE 8

Summary of anti-O8E hybridoma data

| Clone | ELISA (O8E Ag) | Facs* | HEK (MFI) | O8E/HEK (MFI) | SKBR3 % death |
|---|---|---|---|---|---|
| 7H4 | − | + | 2.29 | 96.08 | 50 |
| 9C10 | − | + | 2.85 | 105.98 | 40 |
| 12B9 | − | + | 2.22 | 113.63 | 12 |
| 6F9 | − | + | 4.78 | 100.36 | 25 |
| 11C11 | − | nt | 2.44 | 26.64 | 20 |
| 2A7 | + | + | 2.52 | 153.61 | 25 |
| 5A7 | + | + | 2.45 | 22.76 | 25 |
| 14D2 | − | + | 3.92 | 55.45 | 15 |
| 12B10 | − | + | 2.21 | 23.74 | 40 |
| 12E.1 | + | + | 2.27 | 10.87 | 50 |
| 6E.2 | − | + | 2.45 | 31.89 | 12 |
| 2G6 | − | + | 2.43 | 86.7 | 30.7 |
| 3C7 | − | + | 2.61 | 112.2 | 5.6 |
| 3D8 | − | + | 2.47 | 105.02 | 24.2 |
| 4B8 | − | + | 2.74 | 128 | 29.6 |
| 4G5 | − | + | 2.64 | 68.56 | 14.1 |
| 8D5 | − | + | 2.55 | 131.99 | 8.2 |
| 8G9 | − | + | 2.64 | 123.4 | 18 |
| 9A5 | − | + | 2.43 | 89.43 | 12.3 |
| 9B6 | − | + | 2.51 | 175.81 | 16.3 |
| 14A4 | − | + | 2.52 | 197.33 | 4.5 |
| 18H6 | − | + | 2.58 | 90.29 | −16.2 |
| 19C9 | − | + | 2.44 | 47.11 | −14.1 |
| 20E8 | − | + | 2.51 | 111.2 | −14.9 |
| 21B9 | − | + | 2.46 | 137.36 | −2.2 |
| 22G5 | − | + | 2.88 | 54.66 | 16.3 |
| 23F9 | − | + | 2.53 | 30.02 | 13.5 |
| 24C2 | − | + | 2.59 | 57.9 | 24 |
| 2A7.G4 | − | + | 2.45 | 42.87 | 40.5 |
| 2A7.G7 | + | + | 2.48 | 47.28 | 46.4 |
| 2A7.H5 | + | + | 2.47 | 43.57 | 37 |
| 2A7.H8 | + | + | 2.42 | 45.76 | 40 |
| 2A7.D12 | + | + | 2.67 | 51.83 | 44.3 |
| 1E9 | − | + | 2.67 | 26.14 | 68.5 |
| 2A2 | − | + | 2.59 | 156.82 | 49.4 |
| 2D4 | − | + | 2.56 | 115.79 | 50 |
| 2E4 | − | + | 2.54 | 32.5 | 58.1 |
| 2F9 | − | + | 2.46 | 92.78 | 59.5 |
| 4C7 | − | + | nt | nt | nt |
| 5C6 | − | + | 2.54 | 88.19 | 64.2 |
| 5H5 | − | + | 2.66 | 100.82 | 52 |
| 6F1 | − | + | 2.45 | 57.81 | 49.8 |
| 7H12 | − | + | 2.56 | 172 | 45 |
| 8A10 | − | + | 2.41 | 16.47 | 58.3 |
| 8B7 | − | + | nt | nt | nt |
| 9E11 | − | + | nt | nt | nt |

TABLE 8-continued

Summary of anti-O8E hybridoma data

| Clone | ELISA (O8E Ag) | Facs* | HEK (MFI) | O8E/HEK (MFI) | SKBR3 % death |
|---|---|---|---|---|---|
| 10D4 | – | + | nt | nt | nt |
| 10G7 | – | + | 2.5 | 3.04 | 59.1 |
| 11H8 | – | + | 2.43 | 5.22 | 9 |
| 13A4 | – | + | 2.45 | 53.58 | 37.5 |

MFI = mean fluorescence intensity;
Facs = fluorescence activated cells sorter Internalization assay - 1% death = average OD (+) toxin/average OD (–) toxins × 100

Example 19

Immunohistochemical Analysis Ovarian Cancer Using Human Anti-O8E Monoclonal Antibodies Anti-O8E immunoreactivity was tested in breast cancer, ovarian cancer and normal tissues. In order to perform this analysis, paraffin embedded formalin fixed tissues were sliced into 8 micron sections. Steam heat induced epitope retrieval (SHIER) in 0.1 M sodium, citrate buffer (pH 6.0) was used for optimal staining conditions. Sections were incubated in PBS containing 10% serum for 5 minutes. Primary O8E mAb (described in detail in Example 18) was then added to each section for 25 minutes followed by a 25 minute incubation with an anti-mouse biotinylated antibody. Endogenous peroxidase was blocked by three 1.5 minute incubations with hydrogen peroxidase. The avidin biotin complex/horse radish peroxidase (ABC/HRP) system was used along with DAB chromogen to visualize antigen expression. Slides were counterstained with hematoxylin.

O8E expression was detected in the majority of ovarian tumor samples but not in normal ovary. O8E expression was also observed in breast cancer samples and at very low levels in normal breast. Of the normal tissues tested (blood vessel, heart, liver, kidney, colon, stomach, skin and lung), only stomach and skin tested positive.

Example 20

Expression of O8E Orthologs

The identification and characterization of related forms of the ovarian specific antigen O8E has been described above, one representative DNA sequence for which is set forth in SEQ ID NO:391, encoding amino acid sequences set forth in SEQ ID NOs:392-393. O8E is a plasma membrane associated protein that is over-expressed in ovarian and other cancers. In this example, O8E orthologs from monkey and mouse are identified.

For the cloning of the Rhesus monkey O8E, a PCR primer set was designed using the human O8E open reading frame sequence. The O8E forward primer, designated O8E-UP1, 5'CAGMGCTTATGGCTTCCCTGGGGCAGACT-3' (SEQ ID NO:619) corresponds to the first 21 nucleotides of the human O8E ORF including the start codon, with a HindIII restriction site added at the 5'-end. The O8E reverse primer, designated O8E-DN1, 5'CAGCGGCCGCTTATTTTAG-CATCAGGTAAGG-3' (SEQ ID NO:620) corresponds to the last 21 nucleotides of the human O8E ORF including the stop codon, with a NotI restriction site added to the 5'-end. The monkey O8E was then amplified from Rhesus monkey placenta cDNA sample using the above-described primer set and cloned into pCEP4 mammalian expression vector. Sequence analysis showed that the O8E sequence derived from the Rhesus (rhO8E) cDNA demonstrated 97.9% identity at the cDNA level and 98.2% identity at the protein level when compared to human O8E. Representative protein and cDNA sequences are disclosed in SEQ ID NOs: 623 and 621, respectively.

For the cloning of the mouse O8E cDNA, the moue EST database was searched using the human O8E sequence. This search resulted in the identification of several mouse ESTs that shared greater than 80% identity to the human O8E cDNA sequence. Three of the mouse EST clones were obtained and sequenced. One clone, 557246, (Genebank Accession number AA117088) contained the full-length cDNA insert for the mouse O8E in a mammalian expression vector, pCMV-SPORT2. Sequence analysis showed that the mouse O8E (rmO8E) shared 82.7% identity at the cDNA level and 86.6% identity at the protein level with human O8E. Representative protein and cDNA sequences are disclosed in SEQ ID NOs:624 and 622, respectively.

Example 21

Characterization of the Expression Profile of O8E Orthologs

This example demonstrates that mAbs generated against human O8E were capable of recognizing cells transfected with either Rhesus O8E or mouse O8E.

For expression of the O8E orthologs, HEK293 cells were plated at a density of 250,000 cells/well in DMEM containing 10% FBS and incubated for 4 hours. At the end of the incubation period, 2 μl of Lipofectamine 2000 (Invitrogen) was added to 50 μl of Optimen 1 (Invitrogen) containing no FBS and incubated for 5 minutes at room temperature. In a different tube 50 μl of Optimen 1 was mixed with ~1.0 μg of pCEP4 vector, pCEP/rhesus monkey O8E, or pCMV-Spert2/mouse O8E plasmid DNA and the mixture was transferred to the Lipofectamine 2000/Optimen mix. The combined mixture was incubated for 20 minutes at room temperature and then transferred to the HEK293 cells containing 2 ml of fresh DMEM containing 10% FBS. The transformed HEK293 cells were incubated for approximately 72 hours at 37° C. with 7% $CO_2$.

For Fluorescence Activated Cell Sorting (FACS) analysis, cells were collected and washed with ice cold staining buffer (PBS containing 1% BSA and Azide). HEK293/human O8E stable transfectants were used as a positive control for the FACS analysis. The cells were incubated for 45 minutes at room temperature with human mAbs generated against the human O8E protein (identified in Example 18) then washed 2 times with staining buffer followed by incubation with 20 μl of anti-human IgG-FITC reagent (Pharminigen) for 30 minutes ay room temperature. Following 2 washes, the cells were resuspended in staining buffer containing Propidium Iodide (PI), a vital stain that allows for identification of dead cells, and analyzed by FACS.

Cells transfected with human O8E, monkey O8E and mouse O8E demonstrated O8E specific staining with all human O8E mAbs tested. The results of this study are summarized in Table 9.

TABLE 9

Summary of O8E Staining Using Cells Expressing
Human O8E, Mouse O8E, and Rhesus O8E Orthologs

| | Geometric Mean Fluorescent Intensity (GeoMFI) | | | |
|---|---|---|---|---|
| Human mAb | HEK293-pCEP4 | HEK293-huO8E | HEK293-rmO8E | HEK293-mO8E |
| Human IgG (control) | 24.45 | 24.88 | 38.96 | 49.65 |
| 1G11 | 26.40 | 275.60 | 301.06 | 300.97 |
| 2A7 | 26.35 | 419.46 | 474.83 | 448.04 |
| 2D4 | 28.57 | 352.71 | 416.72 | 436.11 |
| 2F9 | 28.51 | 381.29 | 446.81 | 426.47 |
| 5A4 | 27.08 | 77.78 | 72.64 | 141.51 |
| 5C6 | 31.47 | 395.61 | 464.40 | 377.79 |
| 5H5 | 32.58 | 220.14 | 302.87 | 323.77 |
| 6F1 | 27.01 | 214.72 | 211.47 | 157.42 |
| 6F9 | 29.22 | 241.65 | 272.48 | 212.39 |
| 7H12 | 27.48 | 365.52 | 416.14 | 403.88 |
| 7H4 | 27.58 | 279.54 | 333.76 | 305.97 |
| 8A10 | 29.59 | 371.75 | 438.83 | 402.82 |
| 9B6 | 26.04 | 267.77 | 442.83 | 415.75 |
| 9C10 | 28.34 | 260.90 | 273.98 | 113.19 |
| 12B10 | 25.38 | 199.61 | 258.99 | 99.53 |
| 12B9 | 23.26 | 272.40 | 284.54 | 116.58 |
| 12E1 | 25.74 | 302.00 | 68.24 | 47.49 |
| 13A12 | 27.03 | 172.35 | 196.80 | 99.19 |
| 13D8 | 25.03 | 386.35 | 462.70 | 430.94 |
| 14A4 | 27.45 | 408.81 | 471.49 | 440.18 |
| 14D2 | 27.58 | 243.74 | 295.29 | 212.84 |
| 15C8 | 30.12 | 392.47 | 448.20 | 440.61 |
| 18H6 | 26.27 | 160.84 | 222.63 | 213.72 |

Example 22

Analysis of cDNA Expression Using Real-Time PCR

Real-time PCR (see Gibson et al., *Genome Research* 6:995-1001, 1996; Heid et al., *Genome Research* 6:986-994, 1996) is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR is performed, for example, using a Perkin Elmer/Applied Biosystems (Foster City, Calif.) 7700 Prism instrument. Matching primers and fluorescent probes are designed for genes of interest using, for example, the primer express program provided by Perkin Elmer/Applied Biosystems (Foster City, Calif.). Optimal concentrations of primers and probes are initially determined by those of ordinary skill in the art, and control (e.g., β-actin) primers and probes are obtained commercially from, for example, Perkin Elmer/Applied Biosystems (Foster City, Calif.). To quantitate the amount of specific RNA in a sample, a standard curve is generated using a plasmid containing the gene of interest. Standard curves are generated using the Ct values determined in the real-time PCR, which are related to the initial cDNA concentration used in the assay. Standard dilutions ranging from $10$-$10^6$ copies of the gene of interest are generally sufficient. In addition, a standard curve is generated for the control sequence. This permits standardization of initial RNA content of a tissue sample to the amount of control for comparison purposes.

An alternative real-time PCR procedure can be carried out as follows: The first-strand cDNA to be used in the quantitative real-time PCR is synthesized from 20 μg of total RNA that is first treated with DNase I (e.g., Amplification Grade, Gibco BRL Life Technology, Gaitherburg, Md.), using Superscript Reverse Transcriptase (RT) (e.g., Gibco BRL Life Technology, Gaitherburg, Md.). Real-time PCR is performed, for example, with a GeneAmp™ 5700 sequence detection system (PE Biosystems, Foster City, Calif.). The 5700 system uses SYBR™ green, a fluorescent dye that only intercalates into double stranded DNA, and a set of gene-specific forward and reverse primers. The increase in fluorescence is monitored during the whole amplification process. The optimal concentration of primers is determined using a checkerboard approach and a pool of cDNAs from ovarian tumors is used in this process. The PCR reaction is performed in 25 μl volumes that include 2.5 μl of SYBR green buffer, 2 μl of cDNA template and 2.5 μl each of the forward and reverse primers for the gene of interest. The cDNAs used for RT reactions are diluted approximately 1:10 for each gene of interest and 1:100 for the β-actin control. In order to quantitate the amount of specific cDNA (and hence initial mRNA) in the sample, a standard curve is generated for each run using the plasmid DNA containing the gene of interest. Standard curves are generated using the Ct values determined in the real-time PCR which are related to the initial cDNA concentration used in the assay. Standard dilution ranging from $20$-$2 \times 10^6$ copies of the gene of interest are used for this purpose. In addition, a standard curve is generated for β-actin ranging from 200 fg-2000 fg. This enables standardization of the initial RNA content of a tissue sample to the amount of β-actin for comparison purposes. The mean copy number for each group of tissues tested is normalized to a constant amount of β-actin, allowing the evaluation of the over-expression levels seen with each of the genes.

Example 23

Peptide Priming of T-Helper Lines

Generation of CD4$^+$ T helper lines and identification of peptide epitopes derived from tumor-specific antigens that are capable of being recognized by CD4$^+$ T cells in the context of HLA class II molecules, is carried out as follows:

Fifteen-mer peptides overlapping by 10 amino acids, derived from a tumor-specific antigen, are generated using standard procedures. Dendritic cells (DC) are derived from PBMC of a normal donor using GM-CSF and IL-4 by standard protocols. CD4$^+$ T cells are generated from the same donor as the DC using MACS beads (Miltenyi Biotec, Auburn, Calif.) and negative selection. DC are pulsed overnight with pools of the 15-mer peptides, with each peptide at a final concentration of 0.25 μg/ml. Pulsed DC are washed and plated at $1 \times 10^4$ cells/well of 96-well V-bottom plates and purified CD4$^+$ T cells are added at $1 \times 10^5$/well. Cultures are supplemented with 60 ng/ml IL-6 and 10 ng/ml IL-12 and incubated at 37° C. Cultures are restimulated as above on a weekly basis using DC generated and pulsed as above as antigen presenting cells, supplemented with 5 ng/ml IL-7 and 10 U/ml IL-2. Following 4 in vitro stimulation cycles, resulting CD4$^+$ T cell lines (each line corresponding to one well) are tested for specific proliferation and cytokine production in

Example 24

Generation of Tumor-Specific CTL Lines Using In Vitro Whole-Gene Priming

Using in vitro whole-gene priming with tumor antigen-vaccinia infected DC (see, for example, Yee et al, *The Journal of Immunology,* 157(9):4079-86, 1996), human CTL lines are derived that specifically recognize autologous fibroblasts transduced with a specific tumor antigen, as determined by interferon-γ ELISPOT analysis. Specifically, dendritic cells (DC) are differentiated from monocyte cultures derived from PBMC of normal human donors by growing for five days in RPMI medium containing 10% human serum, 50 ng/ml human GM-CSF and 30 ng/ml human IL-4. Following culture, DC are infected overnight with tumor antigen-recombinant vaccinia virus at a multiplicity of infection (M.O.I) of five, and matured overnight by the addition of 3 μg/ml CD40 ligand. Virus is then inactivated by UV irradiation. CD8+T cells are isolated using a magnetic bead system, and priming cultures are initiated using standard culture techniques. Cultures are restimulated every 7-10 days using autologous primary fibroblasts retrovirally transduced with previously identified tumor antigens. Following four stimulation cycles, CD8+T cell lines are identified that specifically produce interferon-γ when stimulated with tumor antigen-transduced autologous fibroblasts. Using a panel of HLA-mismatched B-LCL lines transduced with a vector expressing a tumor antigen, and measuring interferon-γ production by the CTL lines in an ELISPOT assay, the HLA restriction of the CTL lines is determined.

From the foregoing it will be appreciated that, although specific embodiments of the invention have been described herein for purposes of illustration, various modifications may be made without deviating from the spirit and scope of the invention. Accordingly, the invention is not limited except as by the appended claims.

---

What is claimed:

1. An isolated antibody or antigen binding fragment thereof, which specifically binds to the O8E polypeptide of SEQ ID NO: 392 at an amino acid sequence selected from the group consisting of SEQ ID NOs: 396-400, 403-406, 409 and 413-415.

2. An isolated antibody or antigen binding fragment thereof, which specifically binds to the O8E polypeptide of SEQ ID NO: 392 at an amino acid sequence selected from the group consisting of SEQ ID NOs: 398, 414 and 415.

3. An antibody or antigen binding fragment of any one of claims 1 or 2, wherein the antibody or antigen binding fragment is conjugated to a toxin.

4. An antibody or antigen binding fragment of claim 3, wherein the toxin is selected from the group consisting of a ricin toxin, abrin toxin, diptheria toxin, cholera toxin, gelonin toxin, Pseudomonas exotoxin, Shigella toxin, and pokeweed antiviral protein.

5. An antibody or antigen binding fragment of any one of claims 1 or 2, wherein the antibody or antigen binding fragment is a human antibody or antigen binding fragment.

6. A composition comprising at least one antibody or antigen binding fragment of any one of claims 1 or 2 and a physiologically acceptable carrier.

7. A diagnostic kit comprising at least one antibody or antigen binding fragment of any one of claims 1 or 2 and a detection reagent.

8. A diagnostic kit of claim 7, wherein the detection reagent comprises a reporter group.

9. A method for making an antibody comprising immunizing a mammal with a peptide having an amino acid sequence selected from any one of SEQ ID NOs: 396-400, 403-406, 409 and 413-415.

* * * * *